United States Patent
Duan et al.

(10) Patent No.: US 9,458,171 B2
(45) Date of Patent: Oct. 4, 2016

(54) PYRROLIDINYL SULFONE RORγ MODULATORS

(71) Applicant: BRISTOL-MYERS SQUIBB COMPANY, Princeton, NJ (US)

(72) Inventors: Jingwu Duan, Yardley, PA (US); T. G. Murali Dhar, Newtown, PA (US); Bin Jiang, Norristown, PA (US); Zhonghui Lu, King of Prussia, PA (US); Hai-Yun Xiao, Belle Mead, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 14/590,233

(22) Filed: Jan. 6, 2015

(65) Prior Publication Data

US 2015/0191483 A1    Jul. 9, 2015

Related U.S. Application Data

(60) Provisional application No. 61/923,896, filed on Jan. 6, 2014.

(51) Int. Cl.

| | | |
|---|---|---|
| C07D 417/14 | (2006.01) | |
| C07D 471/10 | (2006.01) | |
| C07D 493/04 | (2006.01) | |
| C07D 207/12 | (2006.01) | |
| C07D 207/16 | (2006.01) | |
| C07D 401/06 | (2006.01) | |
| C07D 401/12 | (2006.01) | |
| C07D 403/04 | (2006.01) | |
| C07D 403/06 | (2006.01) | |
| C07D 405/06 | (2006.01) | |
| C07D 417/06 | (2006.01) | |
| C07D 487/04 | (2006.01) | |
| C07D 403/12 | (2006.01) | |
| C07D 401/14 | (2006.01) | |
| C07D 413/14 | (2006.01) | |
| C07D 405/12 | (2006.01) | |
| C07D 407/12 | (2006.01) | |
| C07D 407/14 | (2006.01) | |
| C07D 409/12 | (2006.01) | |
| C07D 413/12 | (2006.01) | |
| C07D 417/12 | (2006.01) | |
| C07D 487/10 | (2006.01) | |

(52) U.S. Cl.
CPC .......... *C07D 493/04* (2013.01); *C07D 207/12* (2013.01); *C07D 207/16* (2013.01); *C07D 401/06* (2013.01); *C07D 401/12* (2013.01); *C07D 401/14* (2013.01); *C07D 403/04* (2013.01); *C07D 403/06* (2013.01); *C07D 403/12* (2013.01); *C07D 405/06* (2013.01); *C07D 405/12* (2013.01); *C07D 407/12* (2013.01); *C07D 407/14* (2013.01); *C07D 409/12* (2013.01); *C07D 413/12* (2013.01); *C07D 413/14* (2013.01); *C07D 417/06* (2013.01); *C07D 417/12* (2013.01); *C07D 417/14* (2013.01); *C07D 471/10* (2013.01); *C07D 487/04* (2013.01); *C07D 487/10* (2013.01)

(58) Field of Classification Search
CPC ........................... C07D 417/14; C07D 471/10
See application file for complete search history.

(56) References Cited

FOREIGN PATENT DOCUMENTS

| | | |
|---|---|---|
| WO | WO 02/081435 | 10/2002 |
| WO | WO 2013/092939 | 6/2013 |
| WO | WO 2013/169588 | 11/2013 |
| WO | WO 2014/028669 | 2/2014 |
| WO | PCT/US2015/010084 | 1/2015 |
| WO | PCT/US2015/010085 | 1/2015 |
| WO | PCT/US2015/010090 | 1/2015 |

OTHER PUBLICATIONS

Cancer and Metastasis Reviews (1998), 17(1), 91-106.*
Science (1999), vol. 286, 531-537.*
Cancer [online], [retrieved on Jul. 6, 2007]. Retrieved from the internet, URL http://www.nlm.nih.gov/medlineplus/cancer.html>.*
Cancer [online], [retrieved on Jul. 6, 2007]. Retrieved from the internet, URL; http://en.wikipedia.orglwikilCancer.*
Lupus [online], retrieved from internet on Mar. 21, 2016. http://www.nytimes.com/health/guides/disease/system-lupus-erythematosus/overview.html.*

* cited by examiner

*Primary Examiner* — Shawquia Jackson
(74) *Attorney, Agent, or Firm* — Elliott Korsen

(57) ABSTRACT

Described are RORγ modulators of the formula (I),

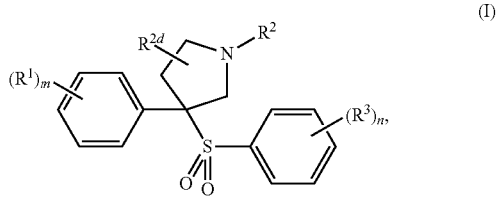

or stereoisomers, tautomers, pharmaceutically acceptable salts, solvates, or prodrugs thereof, wherein all substituents are defined herein. Also provided are pharmaceutical compositions comprising the same. Such compounds and compositions are useful in methods for modulating RORγ activity in a cell and methods for treating a subject suffering from a disease or disorder in which the subject would therapeutically benefit from modulation of RORγ activity, for example, autoimmune and/or inflammatory disorders.

14 Claims, No Drawings

PYRROLIDINYL SULFONE RORγ MODULATORS

CROSS-REFERENCE TO RELATED APPLICATIONS

This application claims the benefit of U.S. Provisional Application No. 61/923,896, filed Jan. 6, 2014, the disclosure of which is incorporated herein by reference in its entirety.

FIELD OF THE INVENTION

This invention relates to modulators of the retinoid-related orphan receptor RORγ and methods for using such modulators. The compounds described herein can be particularly useful for diagnosing, preventing, or treating a variety of diseases and disorders in humans and animals. Exemplary disorders include, but are not limited to, psoriasis, rheumatoid arthritis, inflammatory bowel disease, Crohn's disease, ulcerative colitis, acute graft-versus-host disease, psoriatic arthritis, ankylosing spondylitis and multiple sclerosis.

BACKGROUND OF THE INVENTION

The retinoid-related orphan receptors RORα, RORβ, and RORγ play an important role in numerous biological processes including organ development, immunity, metabolism, and circadian rhythms. See, for example, Dussault et al. in Mech. Dev. (1998) vol. 70, 147-153; Andre et al. in EMBO J. (1998) vol. 17, 3867-3877; Sun et al. in Science (2000) vol. 288, 2369-2373; and Jetten in Nucl. Recept. Signal. (2009) vol. 7, 1-32.

RORγ is expressed in several tissues including the thymus, kidney, liver, and muscle. Two isoforms of RORγ have been identified: RORγ1 and RORγ2 (also known, respectively, as RORγ and RORγt). See, for example, Hirose et al. in Biochem. Biophys. Res. Commun. (1994) vol. 205, 1976-1983; Oritz et al. in Mol. Endocrinol. (1995) vol. 9, 1679-1691; and He et al. in Immunity (1998) vol. 9, 797-806. Expression of RORγt is restricted to lymphoid cell types including CD4+CD8+ thymocytes, IL-17 producing T helper (Th17) cells, lymphoid tissue inducer (LTi) cells, and γδ cells. RORγt is essential for the development of lymph nodes and Peyer's patches and for the normal differentiation of Th17, γδ, and LTi cells. See, for example, Sun et al. in Science (2000) vol. 288, 2369-2373; Ivanov et al. in Cell (2006) vol. 126, 1121-1133; Eberl et al. in Nat. Immunol. (2004) vol. 5, 64-73; Ivanov et al. in Semin. Immunol. (2007) vol. 19, 409-417; and Cua and Tato in Nat. Rev. Immunol. (2010) vol. 10, 479-489.

Proinflammatory cytokines such as IL-17A (also referred to as IL-17), IL-17F, and IL-22 produced by Th17 cells and other RORγ+ lymphocytes activate and direct the immune response to extracellular pathogens. See, for example, Ivanov et al. in Semin. Immunol. (2007) vol. 19: 409-417; and Marks and Craft in Semin. Immunol. (2009) vol. 21, 164-171. RORγ directly regulates IL-17 transcription and disruption of RORγ in mice attenuates IL-17 production. See, for example, Ivanov et al. in Cell (2006) vol. 126, 1121-1133.

Dysregulated production of IL-17 has been implicated in several human autoimmune and inflammatory diseases including multiple sclerosis, rheumatoid arthritis, psoriasis, inflammatory bowel disease (IBD), and asthma. See, for example, Lock et al. in Nat. Med. (2002) vol. 8, 500-508; Tzartos et al. in Am. J. Pathol. (2008) vol. 172, 146-155; Kotake et al. in J. Clin. Invest. (1999) vol. 103, 1345-1352; Kirkham et al. in Arthritis Rheum. (2006) vol. 54, 1122-1131; Lowes et al. in J. Invest. Dermatol. (2008) vol. 128, 1207-1211; Leonardi et al. in N. Engl. J. Med. (2012) vol. 366, 1190-1199; Fujino et al. in Gut (2003) vol. 52, 65-70; Seiderer et al. in Inflamm. Bowel Dis. (2008) vol. 14, 437-445; Wong et al. in Clin. Exp. Immunol. (2001) vol. 125, 177-183; and Agache et al. in Respir. Med. (2010) 104: 1131-1137. In murine models of these diseases, inhibition of IL-17 function by neutralizing antibodies or genetic disruption of IL-17 or IL-17 receptor ameliorates the disease course or clinical symptoms. See, for example, Hu et al. in Ann. N.Y. Acad. Sci. (2011) vol. 1217, 60-76.

Disruption of RORγ in mice also attenuates disease progression or severity in animal models of autoimmunity and inflammation including experimental autoimmune encephalomyelitis (EAE), imiquimod induced psoriasis, colitis, and allergic airway disease. See, for example, Ivanov et al. in Cell (2006) vol. 126, 1121-1133; Yang et al. in Immunity (2008) vol. 28, 29-39; Pantelyushin et al. in J. Clin. Invest. (2012) vol. 122, 2252-2256; Leppkes et al. in Gastroenterology (2009) vol. 136, 257-267; and Tilley et al. in J. Immunol. (2007) vol. 178, 3208-3218.

Each of the references in this Background section is hereby incorporated herein by reference in its entirety for all purposes.

Therapeutic agents exist to treat a variety of inflammatory and autoimmune diseases, but there still remains a significant unmet medical need in these therapeutic areas. Given the role of IL-17 in human disease and the validation of IL-17 and RORγ as targets in murine disease models, compounds capable of modulating RORγt activity are contemplated to provide a therapeutic benefit in the treatment of multiple immune and inflammatory disorders.

SUMMARY OF THE INVENTION

In one aspect, the invention comprises compounds of the formula (I),

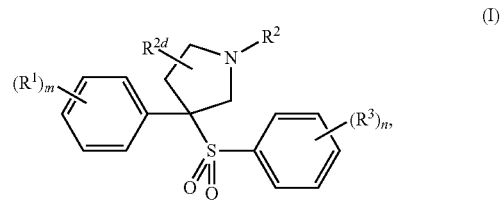

or pharmaceutically acceptable salts thereof, wherein all substituents are defined herein. The invention includes stereoisomers, tautomers, pharmaceutically acceptable salts, solvates, or prodrugs thereof.

In another aspect, the invention comprises pharmaceutical compositions comprising a compound according to formula (I), stereoisomeric form or pharmaceutically acceptable salt, as described herein, and a pharmaceutically acceptable carrier, excipient, or diluent.

In another aspect, the invention comprises methods for antagonizing RORγ in a cell comprising contacting the cell with an effective amount of a compound according to formula (I), stereoisomeric form or pharmaceutically acceptable salt, as described herein. This aspect may be conducted in vitro or in vivo.

In another aspect, the invention comprises methods for treating a subject suffering from a disease or disorder modulated by RORγ, the method comprising administering to a subject a therapeutically effective amount of compound according to formula (I), stereoisomeric form, pharmaceutically acceptable salt or pharmaceutical composition as described herein.

In another aspect, the invention comprises a method for treating a disease or disorder selected from an inflammatory disease or disorder, an autoimmune disease or disorder, an allergic disease or disorder, a metabolic disease or disorder, and/or cancer in a subject, the method comprising administering to the subject a therapeutically effective amount of compound according to formula (I), or a stereoisomeric form, pharmaceutically acceptable salt or pharmaceutical composition as described herein.

DETAILED DESCRIPTION OF THE INVENTION

In one aspect, the invention comprises compounds of formula (I),

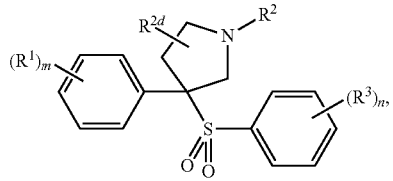

(I)

stereoisomers, tautomers, pharmaceutically acceptable salts, solvates, or prodrugs thereof, wherein:

$R^1$ is selected from H, halo, $C_{1-6}$ alkyl substituted with 0-3 $R^{1a}$ and —$(CR^{2e}R^{2f})$r-3-14 membered carbocycle substituted with 0-3 $R^{1a}$;

$R^{1a}$ is, independently at each occurrence, hydrogen, =O, halo, $CF_3$, $OCF_3$, CN, $NO_2$, —$(CR^{2e}R^{2f})$r-$OR^b$, —$(CR^{2e}R^{2f})$r-$S(O)_pR^b$, —$(CR^{2e}R^{2f})$r-$C(O)R^b$, —$(CR^{2e}R^{2f})$r-$C(O)OR^b$, —$(CR^{2e}R^{2f})$r-$OC(O)R^b$, —$(CR^{2e}R^{2f})$r-$NR^{11}R^{11}$, —$(CR^{2e}R^{2f})$r-$C(O)NR^{11}R^{11}$, —$(CR^{2e}R^{2f})$r-$NR^bC(O)R^c$, —$(CR^{2e}R^{2f})$r-$NR^bC(O)OR^c$, —$NR^bC(O)NR^{11}R^{11}$, —$S(O)_pNR^{11}R^{11}$, —$NR^bS(O)_pR^c$, $C_{1-6}$ alkyl substituted with 0-3 $R^a$, $C_{1-6}$ haloalkyl, $C_{2-6}$ alkenyl substituted with 0-3 $R^a$, $C_{2-6}$ alkynyl substituted with 0-3 $R^a$, —$(CR^{2e}R^{2f})$r-3-14 membered carbocycle substituted with 0-3 $R^a$, or —$(CR^{2e}R^{2f})$r-5-7 membered heterocycle comprising carbon atoms, and 1-4 heteroatoms selected from N, O, and $S(O)_p$ substituted with 0-3 $R^a$;

$R^2$ is selected from hydrogen, —$(CR^{2e}R^{2f})$r-$C(O)R^{2d}$, —$(CR^{2e}R^{2f})$r-$C(O)OR^{2b}$, —$(CR^{2e}R^{2f})$r-$C(O)NR^{11}R^{11}$, —$(CR^{2e}R^{2f})$r-$S(O)_2R^{2c}$, $C_{1-6}$ alkyl substituted with 0-3 $R^{2a}$, $C_{2-6}$ alkenyl substituted with 0-3 $R^{2a}$, —$(CR^{2e}R^{2f})$r-3-10 membered carbocycle substituted with 0-3 $R^a$, and —$(CR^{2e}R^{2f})$r-4-7 membered heterocycle comprising carbon atoms, and 1-4 heteroatoms selected from N, O, and $S(O)_p$ substituted with 0-3 $R^a$;

$R^{2a}$ is, independently at each occurrence, hydrogen, =O, halo, $OCF_3$, CN, $NO_2$, —$(CR^{2e}R^{2f})$r-$OR^b$, —$(CR^{2e}R^{2f})$r-$S(O)_pR^b$, —$(CR^{2e}R^{2f})$r-$C(O)Rb$, —$(CR^{2e}R^{2f})$r-$C(O)OR^b$, —$(CR^{2e}R^{2f})$r-$OC(O)R^b$, —$(CR^{2e}R^{2f})$r-$NR^{11}R^{11}$, —$(CR^{2e}R^{2f})$r-$C(O)NR^{11}R^{11}$, —$(CR^{2e}R^{2f})$r-$NR^bC(O)R^c$, —$(CR^{2e}R^{2f})$r-$NR^bC(O)OR^c$, —$NR^bC(O)NR^{11}R^{11}$, —$S(O)_p$ $NR^{11}R^{11}$, —$NR^bS(O)_pR^c$, $C_{1-6}$ alkyl substituted with 0-3 $R^a$, $C_{1-6}$ haloalkyl, $C_{2-6}$ alkenyl substituted with 0-3 $R^a$, $C_{2-6}$ alkynyl substituted with 0-3 $R^a$, —$(CR^{2e}R^{2f})$r-3-14 membered carbocycle substituted with 0-3 $R^a$, or —$(CR^{2e}R^{2f})$r-4-7 membered heterocycle comprising carbon atoms, and 1-4 heteroatoms selected from N, O, and $S(O)_p$ substituted with 0-3 $R^a$;

$R^{2b}$ is, independently at each occurrence, hydrogen, $CF_3$, —$(CR^{2e}R^{2f})_qOR^b$, —$(CR^{2e}R^{2f})_qS(O)pR^b$, —$(CR^{2e}R^{2f})$r-$C(O)R^{1d}$, —$(CR^{2e}R^{2f})$r-$C(O)OR^b$, —$(CR^{2e}R^{2f})_qOC(O)R^b$, —$(CR^{2e}R^{2f})_q$ $NR^{11}R^{11}$, —$(CR^{2e}R^{2f})$r-$C(O)NR^{11}R^{11}$, —$(CR^{2e}R^{2f})qNR^bC(O)R^{1c}$, —$(CR^{2e}R^{2f})qNR^bC(O)OR^c$, —$(CR^{2e}R^{2f})$ $qNR^bC(O)NR^{11}R^{11}$, —$(CR^{2e}R^{2f})_qS(O)_2$ $NR^{11}R^{11}$, —$(CR^{2e}R^{2f})_qNR^bS(O)_2R^c$, $C_{1-6}$ alkyl substituted with 0-2 $R^a$, $C_{1-6}$ haloalkyl, —$(CR^{2e}R^{2f})$r-3-14 membered carbocycle substituted with 0-3 $R^a$, or —$(CR^{2e}R^{2f})$r-5-7 membered heterocycle comprising carbon atoms and 1-4 heteroatoms selected from N, O, and $S(O)p$ substituted with 0-2 $R^a$;

$R^{2c}$ is independently at each occurrence, hydrogen, $C_{1-6}$ alkyl substituted with 0-3 $R^a$, $C_{2-6}$ alkenyl substituted with 0-3 $R^a$, $C_{3-10}$ cycloalkyl substituted with 0-3 $R^a$, $C_{6-10}$ aryl substituted with 0-3 $R^a$, or —$(CR^{2e}R^{2f})$r-5-10 membered heterocycle containing 1-4 heteroatoms selected from N, O, and $S(O)_p$, substituted with 0-3 $R^a$;

$R^{2d}$ is, independently at each occurrence, hydrogen, $C_{1-6}$ alkyl substituted with 0-2 $R^d$, $C_{1-6}$ haloalkyl, $C(O)NR^{11}R^{11}$, —$(CR^{2e}R^{2f})$r-$C_{3-10}$ cycloalkyl substituted with 0-3 $R^d$, —$(CR^{2e}R^{2f})$r-phenyl substituted with 0-2 $R^a$, or a —$(CR^{2e}R^{2f})$r-4-10 membered heterocycle where the heterocycle may be fused, bridged or spirocyclic, containing 1-4 heteroatoms selected from N, O, and $S(O)_p$, substituted with 0-3 $R^a$;

$R^{2e}$ and $R^{2f}$ are, independently at each occurrence, hydrogen, halogen or $C_{1-6}$ alkyl;

$R^3$ is selected from hydrogen, halo, $N_3$, CN, —$(CR^{2e}R^{2f})$r-$OR^{3b}$, —$(CR^{2e}R^{2f})$r-$NR^{11}R^{11}$, $C_{1-6}$ alkyl substituted with 0-3 $R^{3a}$, $C_{3-10}$ cycloalkyl substituted with 0-3 $R^{3a}$; and phenyl substituted with 0-3 $R^{3a}$, or 4-10 membered heterocycle containing 1-4 heteroatoms selected from N, O, and $S(O)_p$, substituted with 0-3 $R^{1a}$, or two $R^3$ located on adjacent carbon atoms link to form a 5-7 membered carbocycle or a 5-7 membered heterocycle comprising carbon atoms and 1-4 heteroatom selected from N, O and $S(O)p$, both optionally substituted with 0-3 $R^{3a}$;

$R^{3a}$ is, independently at each occurrence, hydrogen, =O, halo, $OCF_3$, $OCHF_2$, $CF_3$, $CHF_2$, CN, $NO_2$, —$(CR^{2e}R^{2f})$r-$OR^b$, —$(CR^{2e}R^{2f})$r-$S(O)pR^b$, —$(CR^{2e}R^{2f})$r-$C(O)R^b$, —$(CR^{2e}R^{2f})$r-$C(O)OR^b$, —$(CR^{2e}R^{2f})$r-$OC(O)R^b$, —$(CR^{2e}R^{2f})$r-$NR^{11}R^{11}$, —$(CR^{2e}R^{2f})$r-$C(O)NR^{11}R^{11}$, —$(CR^{2e}R^{2f})$r-$NR^bC(O)R^c$, —$(CR^{2e}R^{2f})$r-$NR^bC(O)OR^c$, —$NR^bC(O)NR^{11}R^{11}$, —$S(O)_pNR^{11}R^{11}$, —$NR^bS(O)_pR^c$, $C_{1-6}$ alkyl substituted with 0-3 $R^a$, $C_{2-6}$ alkenyl substituted with 0-3 $R^a$, $C_{2-6}$ alkynyl substituted with 0-3 $R^a$, $C_{1-6}$ haloalkyl, —$(CR^{2e}R^{2f})$r-3-14 membered carbocycle substituted with 0-3 $R^a$, or —$(CR^{2e}R^{2f})$r-5-10 membered heterocycle comprising carbon atoms and 1-4 heteroatoms selected from N, O, and $S(O)_p$ substituted with 0-3 $R^a$;

$R^{3b}$ is, independently at each occurrence, hydrogen, $CF_3$, —$(CR^{2e}R^{2f})qOR^b$, —$(CR^{2e}R^{2f})qS(O)pR^b$, —$(CR^{2e}R^{2f})$r-$C(O)R^{1d}$, —$(CR^{2e}R^{2f})$r-$C(O)OR^b$, —$(CR^{2e}R^{2f})_qOC(O)R^b$, —$(CR^{2e}R^{2f})_q$ $NR^{11}R^{11}$, —$(CR^{2e}R^{2f})$r-$C(O)NR^{11}R^{11}$, —$(CR^{2e}R^{2f})qNR^bC(O)R^{1c}$, —$(CR^{2e}R^{2f})qNR^bC(O)OR^c$, —$(CR^{2e}R^{2f})qNR^bC(O)NR^{11}R^{11}$, —$(CR^{2e}R^{2f})_qS(O)_2$ $NR^{11}R^{11}$, —$(CR^{2e}R^{2f})qNR^bS(O)_2R^c$, $C_{1-6}$ alkyl substituted with 0-3 $R^a$, $C_{1-6}$ haloalkyl, —$(CR^{2e}R^{2f})$r-3-14 membered carbocycle substituted with 0-3 $R^a$, or —$(CR^{2e}R^{2f})$r-5-7 membered heterocycle comprising carbon atoms and 1-4 heteroatoms selected from N, O, and S(O)$_p$ substituted with 0-3 R$^a$;

R$^{11}$ is, independently at each occurrence, hydrogen, C$_{1-6}$ alkyl substituted with 0-3 R$^f$, CF$_3$, C$_{3-10}$ cycloalkyl substituted with 0-3 R$^f$, —(CR$^{2e}$R$^{2f}$)r-phenyl substituted with 0-3 R$^d$, or —(CR$^{2e}$R$^{2f}$)r-5-7 membered heterocycle comprising carbon atoms and 1-4 heteroatoms selected from N, O, and S(O)$_p$ substituted with 0-3 R$^d$;

or one R$^{11}$ and a second R$^{11}$, both attached to the same nitrogen atom, combine to form a heterocycle comprising carbon atoms and 1-4 heteroatoms selected from N, O, and S(O)$_p$ substituted with 0-3 R$^d$;

R$^a$ is, independently at each occurrence, hydrogen, =O, halo, OCF$_3$, CF$_3$, CHF$_2$, CN, NO$_2$, —(CR$^{2e}$R$^{2f}$)r-OR$^b$, —(CR$^{2e}$R$^{2f}$)r-S(O)pR$^b$, —(CR$^{2e}$R$^{2f}$)r-C(O)R$^b$, —(CR$^{2e}$R$^{2f}$)r-C(O)OR$^b$, —(CR$^{2e}$R$^{2f}$)r-OC(O)R$^b$, —(CR$^{2e}$R$^{2f}$)r-NR$^{11}$R$^{11}$, —(CR$^{2e}$R$^{2f}$)r-C(O)NR$^{11}$R$^{11}$, —(CR$^{2e}$R$^{2f}$)r-NR$^b$C(O)R$^c$, —(CR$^{2e}$R$^{2f}$)r-NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, C$_{1-6}$ alkyl substituted with 0-3 R$^f$, C$_{1-6}$ haloalkyl, C$_{2-6}$ alkenyl substituted with 0-3 R$^a$, C$_{2-6}$ alkynyl substituted with 0-3 R$^a$, —(CR$^{2e}$R$^{2f}$)r-3-14 membered carbocycle, or —(CR$^{2e}$R$^{2f}$)r-5-7 membered heterocycle comprising carbon atoms and 1-4 heteroatoms selected from N, O, and S(O)$_p$ substituted with 0-3 R$^f$;

R$^b$ is, independently at each occurrence, hydrogen, C$_{1-6}$ alkyl substituted with 0-3 R$^d$, C$_{1-6}$ haloalkyl, C$_{3-6}$ cycloalkyl substituted with 0-3 R$^d$, —(CR$^{2e}$R$^{2f}$)r-5-7 membered heterocycle comprising carbon atoms and 1-4 heteroatoms selected from N, O, and S(O)$_p$ substituted with 0-3 R$^f$, or —(CR$^{2e}$R$^{2f}$)r-6-10 membered carbocycle substituted with 0-3 R$^d$;

R$^c$ is, independently at each occurrence, C$_{1-6}$ alkyl substituted with 0-3 R$^f$, —(CR$^{2e}$R$^{2f}$)r-C$_{3-6}$ cycloalkyl substituted with 0-3 R$^f$, or —(CR$^{2e}$R$^{2f}$)r-phenyl substituted with 0-3 R$^f$;

R$^d$ is, independently at each occurrence, hydrogen, =O, halo, OCF$_3$, CF$_3$, CN, NO$_2$, —OR$^e$, —(CR$^{2e}$R$^{2f}$)r-C(O)R$^c$, —NR$^e$R$^e$, —NR$^e$C(O)OR$^c$, C(O)NR$^e$R$^e$, —NR$^e$C(O)R$^c$, CO$_2$R$^C$, —NR$^e$SO$_2$R$^c$, SO$_2$R$^c$, C$_{1-6}$ alkyl substituted with 0-3 R$^f$, C$_{3-6}$ cycloalkyl substituted with 0-3 R$^f$, —(CR$^{2e}$R$^{2f}$)r-phenyl substituted with 0-3 R$^f$ or —(CR$^{2e}$R$^{2f}$)r-5-7 membered heterocycle comprising carbon atoms and 1-4 heteroatoms selected from N, O, and S(O)$_p$ substituted with 0-3 R$^f$;

R$^e$ is, independently at each occurrence, selected from hydrogen, C(O)NR$^f$R$^f$, C$_{1-6}$ alkyl, C$_{3-6}$ cycloalkyl, or —(CR$^{2e}$R$^{2f}$)r-phenyl substituted with 0-3 R$^f$;

R$^f$ is, independently at each occurrence, hydrogen, =O, halo, CN, NH$_2$, NH(C$_{1-6}$ alkyl), N(C$_{1-6}$ alkyl)$_2$, SO$_2$(C$_{1-6}$ alkyl), CO$_2$H, CO$_2$(C$_{1-6}$ alkyl), OH, C$_{3-6}$ cycloalkyl, CF$_3$ or O(C$_{1-6}$ alkyl);

or R$^f$ is, independently at each occurrence, an optionally substituted —(CR$^{2e}$R$^{2f}$)r-5-10 membered heterocycle comprising carbon atoms and 1-4 heteroatoms selected from N, O, and S(O)$_p$, phenyl or C$_{3-6}$ cycloalkyl, each group optionally substituted with halo, CN, CF$_3$, C$_{1-6}$ alkyl or O(C$_{1-6}$ alkyl);

m and n are independently selected from 0, 1, 2 and 3;

p and q, independently at each occurrence, are 0, 1, or 2; and r is 0, 1, 2, 3, or 4.

In another aspect, there is provided a compound of Formula (I), or stereoisomers, tautomers, pharmaceutically acceptable salts, solvates, or prodrugs thereof, wherein:

R$^1$ is halo, phenyl substituted with 0-3 R$^{1a}$, or C$_{1-6}$ alkyl substituted with 0-3 R$^{1a}$; and R$^{1a}$ is, independently at each occurrence, hydrogen, CF$_3$, halo, C$_{1-6}$ alkyl substituted with 0-3 R$^a$, —(CR$^{2e}$R$^{2f}$)r-OR$^b$, and —(CR$^{2e}$R$^{2f}$)r-phenyl substituted with 0-3 R$^a$.

In another aspect, there is provided a compound of Formula (I), or stereoisomers, tautomers, pharmaceutically acceptable salts, solvates, or prodrugs thereof, wherein:

R$^2$ is hydrogen, SO$_2$R$^{2c}$, C$_{1-6}$ alkyl substituted with 0-3 R$^{2a}$, CO$_2$R$^{2b}$, —C(O)R$^{2d}$, —C(O)NR$^{11}$R$^{11}$; or a 5-7 membered heterocycle comprising carbon atoms, and 1-4 heteroatoms selected from N, O, and S(O)$_p$ substituted with 0-3 R$^a$, R$^{2a}$ is hydrogen or C$_{1-6}$ alkyl substituted with 0-3 R$^a$;

R$^{2b}$ is hydrogen, C$_{1-6}$ alkyl substituted with 0-3 R$^a$, C$_{3-6}$ cycloalkyl substituted with 0-3 R$^a$, —(CR$^{2e}$R$^{2f}$)r-5-7 membered heterocycle comprising carbon atoms and 1-4 heteroatoms selected from N, O, and S(O)$_p$ substituted with 0-3 R$^a$, or —(CR$^{2e}$R$^{2f}$)r-phenyl substituted with 0-3 R$^a$;

R$^{2c}$ is, independently at each occurrence, hydrogen, C$_{1-6}$ alkyl substituted with 0-3 R$^a$, C$_{2-6}$ alkenyl substituted with 0-3 R$^a$, C$_{3-10}$ cycloalkyl substituted with 0-3 R$^a$, C$_{6-10}$ aryl substituted with 0-3 R$^a$, or —(CR$^{2e}$R$^{2f}$)r-5-10-membered heterocycle containing 1-4 heteroatoms selected from N, O, and S(O)$_p$, substituted with 0-3 R$^a$; and R$^{2d}$ is, independently at each occurrence, hydrogen, C$_{1-6}$ alkyl substituted with 0-3 R$^d$, C$_{1-6}$ haloalkyl, C(O)NR$^{11}$R$^{11}$, C$_{3-6}$ cycloalkyl substituted with 0-2 R$^d$ (Preferably, cycloalkyl is cyclobutyl, cyclohexyl, or cyclopentyl substituted with 0-2 R$^d$), —(CR$^{2e}$R$^{2f}$)r-phenyl substituted with 0-2 R$^a$, or a 4-10 membered heterocycle containing 1-4 heteroatoms selected from N, O, and S(O)$_p$, substituted with 0-3 R$^a$. Preferably, the heterocycle is furyl, morpholinyl, piperidinyl, piperazinyl, tetrahydropyranyl, aziridinyl, pyrrolidinyl, pyrrolyl, pyridyl, or benzoisothiazolyl, each substituted with 0-3 R$^a$.

In another aspect, there is provided a compound of Formula (I), or stereoisomers, tautomers, pharmaceutically acceptable salts, solvates, or prodrugs thereof, wherein:

R$^3$ is hydrogen, halo, N$_3$, CN, OR$^{3b}$, —NH$_2$, NH(C$_{1-6}$ alkyl), N(C$_{1-6}$ alkyl)$_2$, C$_{1-6}$ alkyl substituted with 0-3 R$^{3a}$ or C$_{3-10}$ cycloalkyl substituted with 0-3 R$^{1a}$;

R$^{3a}$ is, independently at each occurrence, hydrogen, =O, halo, OCF$_3$, OCHF$_2$, CF$_3$, CHF$_2$, CN, NO$_2$, —(CR$^{2e}$R$^{2f}$)r-OR$^b$, —(CR$^{2e}$R$^{2f}$)r-S(O)pR$^b$, —(CR$^{2e}$R$^{2f}$)r-C(O)R$^b$, —(CR$^{2e}$R$^{2f}$)r-C(O)OR$^b$, —(CR$^{2e}$R$^{2f}$)r-OC(O)R$^b$, —(CR$^{2e}$R$^{2f}$)r-NR$^{11}$R$^{11}$, —(CR$^{2e}$R$^{2f}$)r-C(O)NR$^{11}$R$^{11}$, —(CR$^{2e}$R$^{2f}$)r-NR$^b$C(O)R$^c$, —(CR$^{2e}$R$^{2f}$)r-NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, C$_{1-6}$ alkyl substituted with 0-3 R$^a$, C$_{2-6}$ alkenyl substituted with 0-3 R$^a$, C$_{2-6}$ alkynyl substituted with 0-3 R$^a$, C$_{1-6}$ haloalkyl, —(CR$^{2e}$R$^{2f}$)r-3-14 membered carbocycle substituted with 0-3 R$^a$, or —(CR$^{2e}$R$^{2f}$)r-5-10 membered heterocycle comprising carbon atoms and 1-4 heteroatoms selected from N, O, and S(O)$_p$ substituted with 0-3 R$^a$; and R$^{3b}$ is, independently at each occurrence, hydrogen, C$_{1-6}$ alkyl substituted with 0-3 R$^a$ or phenyl substituted with 0-3 R$^a$.

In another aspect, there is provided a compound having the following formula:

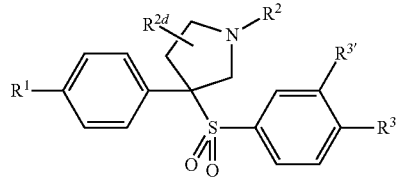

or stereoisomers, tautomers, pharmaceutically acceptable salts, solvates, or prodrugs thereof, wherein:

$R^1$ is halo, phenyl substituted with 0-3 $R^{1a}$, or $C_{1-6}$ alkyl substituted with 0-3 $R^{1a}$;

$R^{1a}$ is, independently at each occurrence, hydrogen, $CF_3$, halo, $C_{1-6}$ alkyl substituted with 0-3 $R^a$, —$(CR^{2e}R^{2f})$r-$OR^b$, and —$(CR^{2e}R^{2f})$r-phenyl substituted with 0-3 $R^a$;

$R^2$ is hydrogen, $SO_2R^{2c}$, $C_{1-6}$ alkyl substituted with 0-3 $R^{2a}$, $CO_2R^{2b}$, —$C(O)R^{2d}$, —$C(O)NR^{11}R^{11}$; or a 5-7 membered heterocycle comprising carbon atoms, and 1-4 heteroatoms selected from N, O, and $S(O)_p$ substituted with 0-3 $R^a$, $R^{2a}$ is hydrogen or $C_{1-6}$ alkyl substituted with 0-3 $R^a$, $R^{2b}$ is hydrogen, $C_{1-6}$ alkyl substituted with 0-3 $R^a$ (Me, Et, tBu), $C_{3-6}$ cycloalkyl substituted with 0-3 $R^a$, —$(CR^{2e}R^{2f})$r-5-7 membered heterocycle comprising carbon atoms and 1-4 heteroatoms selected from N, O, and $S(O)_p$ substituted with 0-3 $R^a$, or —$(CR^{2e}R^{2f})$r-phenyl substituted with 0-3 $R^a$;

$R^{2e}$ is independently at each occurrence hydrogen, $C_{1-6}$ alkyl substituted with 0-3 $R^a$, $C_{2-6}$ alkenyl substituted with 0-3 $R^a$, $C_{3-10}$ cycloalkyl substituted with 0-3 $R^a$, $C_{6-10}$ aryl substituted with 0-3 $R^a$, or a —$(CR^{2e}R^{2f})$r-5-10 membered heterocycle containing 1-4 heteroatoms selected from N, O, and $S(O)_p$, substituted with 0-3 $R^a$;

$R^{2d}$ is, independently at each occurrence, hydrogen, $C_{1-6}$ alkyl substituted with 0-3 $R^d$ (Me), $C_{1-6}$ haloalkyl, $C(O)NR^{11}R^{11}$, $C_{3-6}$ cycloalkyl substituted with 0-2 $R^d$, —$(CR^{2e}R^{2f})$r-phenyl substituted with 0-2 $R^a$, or 4-10 membered heterocycle containing 1-4 heteroatoms selected from N, O, and $S(O)_p$, substituted with 0-3 $R^a$;

$R^3$ and $R^{3'}$ are, independently selected from hydrogen, halo, $N_3$, CN, $OR^{3b}$, —$NH_2$, $NH(C_{1-6}$ alkyl), $N(C_{1-6}$ alkyl$)_2$, $C_{1-6}$ alkyl substituted with 0-3 $R^{3a}$ and $C_{3-10}$ cycloalkyl substituted with 0-3 $R^{3a}$;

$R^{3a}$ is, independently at each occurrence, hydrogen, =O, halo, $OCF_3$, $OCHF_2$, $CF_3$, $CHF_2$, CN, $NO_2$, —$(CR^{2e}R^{2f})$r-$OR^b$, —$(CR^{2e}R^{2f})$r-$S(O)_pR^b$, —$(CR^{2e}R^{2f})$r-$C(O)R^b$, —$(CR^{2e}R^{2f})$r-$C(O)OR^b$, —$(CR^{2e}R^{2f})$r-$OC(O)R^b$, —$(CR^{2e}R^{2f})$r-$NR^{11}R^{11}$, —$(CR^{2e}R^{2f})$r-$C(O)NR^{11}R^{11}$, —$(CR^{2e}R^{2f})$r-$NR^bC(O)R^c$, —$(CR^{2e}R^{2f})$r-$NR^bC(O)OR^c$, —$NR^bC(O)NR^{11}R^{11}$, —$S(O)_pNR^{11}R^{11}$, —$NR^bS(O)_pR^c$, $C_{1-6}$ alkyl substituted with 0-3 $R^a$, $C_{2-6}$ alkenyl substituted with 0-3 $R^a$, $C_{2-6}$ alkynyl substituted with 0-3 $R^a$, $C_{1-6}$ haloalkyl, —$(CR^{2e}R^{2f})$r-3-14 membered carbocycle substituted with 0-3 $R^a$, or —$(CR^{2e}R^{2f})$r-5-10 membered heterocycle comprising carbon atoms and 1-4 heteroatoms selected from N, O, and $S(O)_p$ substituted with 0-3 $R^a$; and $R^{3b}$ is, independently at each occurrence, hydrogen, $C_{1-6}$ alkyl substituted with 0-3 $R^a$ or phenyl substituted with 0-3 $R^a$;

$R^{11}$ is, independently at each occurrence, hydrogen, $C_{1-6}$ alkyl substituted with 0-3 $R^f$, $CF_3$, $C_{3-10}$ cycloalkyl substituted with 0-3 $R^f$, —$(CR^{2e}R^{2f})$r-phenyl substituted with 0-3 $R^d$, or —$(CR^{2e}R^{2f})$r-5-7 membered heterocycle comprising carbon atoms and 1-4 heteroatoms selected from N, O, and $S(O)p$ substituted with 0-3 $R^d$;

or one $R^{11}$ and a second $R^{11}$, both attached to the same nitrogen atom, combine to form a heterocycle comprising carbon atoms and 1-4 heteroatoms selected from N, O, and $S(O)_p$ substituted with 0-3 $R^d$;

$R^a$ is, independently at each occurrence, hydrogen, =O, halo, $OCF_3$, $CF_3$, $CHF_2$, CN, $NO_2$, —$(CR^{2e}R^{2f})$r-$OR^b$, —$(CR^{2e}R^{2f})$r-$S(O)pR^b$, —$(CR^{2e}R^{2f})$r-$C(O)R^b$, —$(CR^{2e}R^{2f})$r-$C(O)OR^b$, —$(CR^{2e}R^{2f})$r-$OC(O)R^b$, —$(CR^{2e}R^{2f})$r-$NR^{11}R^{11}$, —$(CR^{2e}R^{2f})$r-$C(O)NR^{11}R^{11}$, —$(CR^{2e}R^{2f})$r-$NR^bC(O)R^c$, —$(CR^{2e}R^{2f})$r-$NR^bC(O)OR^c$, —$NR^bC(O)NR^{11}R^{11}$, —$S(O)_pNR^{11}R^{11}$, —$NR^bS(O)_pR^c$, $C_{1-6}$ alkyl substituted with 0-3 $R^f$, $C_{1-6}$ haloalkyl, $C_{2-6}$ alkenyl substituted with 0-3 $R^a$, $C_{2-6}$ alkynyl substituted with 0-3 $R^a$, —$(CR^{2e}R^{2f})$r-3-14 membered carbocycle, or —$(CR^{2e}R^{2f})$r-5-7 membered heterocycle comprising carbon atoms and 1-4 heteroatoms selected from N, O, and $S(O)_p$ substituted with 0-3 $R^f$;

$R^b$ is, independently at each occurrence, hydrogen, $C_{1-6}$ alkyl substituted with 0-3 $R^d$, $C_{1-6}$ haloalkyl, $C_{3-6}$ cycloalkyl substituted with 0-3 $R^d$, —$(CR^{2e}R^{2f})$r-5-7 membered heterocycle comprising carbon atoms and 1-4 heteroatoms selected from N, O, and $S(O)_p$substituted with 0-3 $R^f$, or —$(CR^{2e}R^{2f})$r-6-10 carbocycle substituted with 0-3 $R^d$;

$R^c$ is, independently at each occurrence, $C_{1-6}$ alkyl substituted with 0-3 $R^f$, $(CR^{2e}R^{2f})$r-$C_{3-6}$ cycloalkyl substituted with 0-3 $R^f$, or —$(CR^{2e}R^{2f})$r-phenyl substituted with 0-3 $R^f$;

$R^d$ is, independently at each occurrence, hydrogen, =O, halo, $OCF_3$, $CF_3$, CN, $NO_2$, —$OR^e$, —$(CR^{2e}R^{2f})$r-$C(O)R^c$, —$NR^eR^e$, —$NR^eC(O)OR^c$, $C(O)NR^eR^e$, —$NR^eC(O)R^c$, $CO_2R^C$, —$NR^eSO_2R^c$, $SO_2R^c$, $C_{1-6}$ alkyl substituted with 0-3 $R^f$, $C_{3-6}$ cycloalkyl substituted with 0-3 $R^f$, —$(CR^{2e}R^{2f})$r-phenyl substituted with 0-3 $R^f$ or —$(CR^{2e}R^{2f})$r-5-7 membered heterocycle comprising carbon atoms and 1-4 heteroatoms selected from N, O, and $S(O)p$ substituted with 0-3 $R^f$;

$R^e$ is, independently at each occurrence, selected from hydrogen, $C(O)NR^fR^f$, $C_{1-6}$ alkyl, $C_{3-6}$ cycloalkyl, and —$(CR^{2e}R^{2f})$r-phenyl substituted with 0-3 $R^f$;

$R^f$ is, independently at each occurrence, hydrogen, =O, halo, CN, $NH_2$, $NH(C_{1-6}$ alkyl), $N(C_{1-6}$ alkyl$)_2$, $SO_2(C_{1-6}$ alkyl), $CO_2H$, $CO_2(C_{1-6}$ alkyl), OH, $C_{3-6}$ cycloalkyl, $CF_3$, or $O(C_{1-6}$ alkyl);

or $R^f$ is, independently at each occurrence, an optionally substituted —$(CR^{2e}R^{2f})$r-5-10 membered heteroaryl comprising carbon atoms and 1-4 heteroatoms selected from N, O, and S, phenyl or $C_{3-6}$ cycloalkyl, each group optionally substituted with halo, CN, $CF_3$, $C_{1-6}$ alkyl or $O(C_{1-6}$ alkyl);

p and q, independently at each occurrence, are 0, 1, or 2; and r is 0, 1, or 2.

In another aspect, there is provided a compound of the following formula, or tautomers, pharmaceutically acceptable salts, solvates, or prodrugs thereof, having the formula:

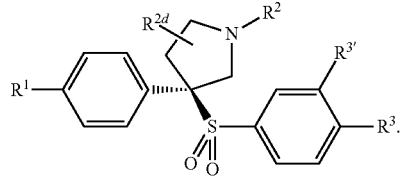

In another aspect, there is provided a compound of Formula (I), or stereoisomers, tautomers, pharmaceutically acceptable salts, solvates, or prodrugs thereof, wherein $R^1$ is

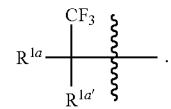

In another aspect, there is provided a compound of Formula (I), or stereoisomers, tautomers, pharmaceutically acceptable salts, solvates, or prodrugs thereof, wherein $R^1$ is

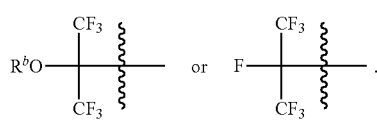
In another aspect, there is provided a compound of Formula (I), or stereoisomers, tautomers, pharmaceutically acceptable salts, solvates, or prodrugs thereof, wherein $R^1$ is:
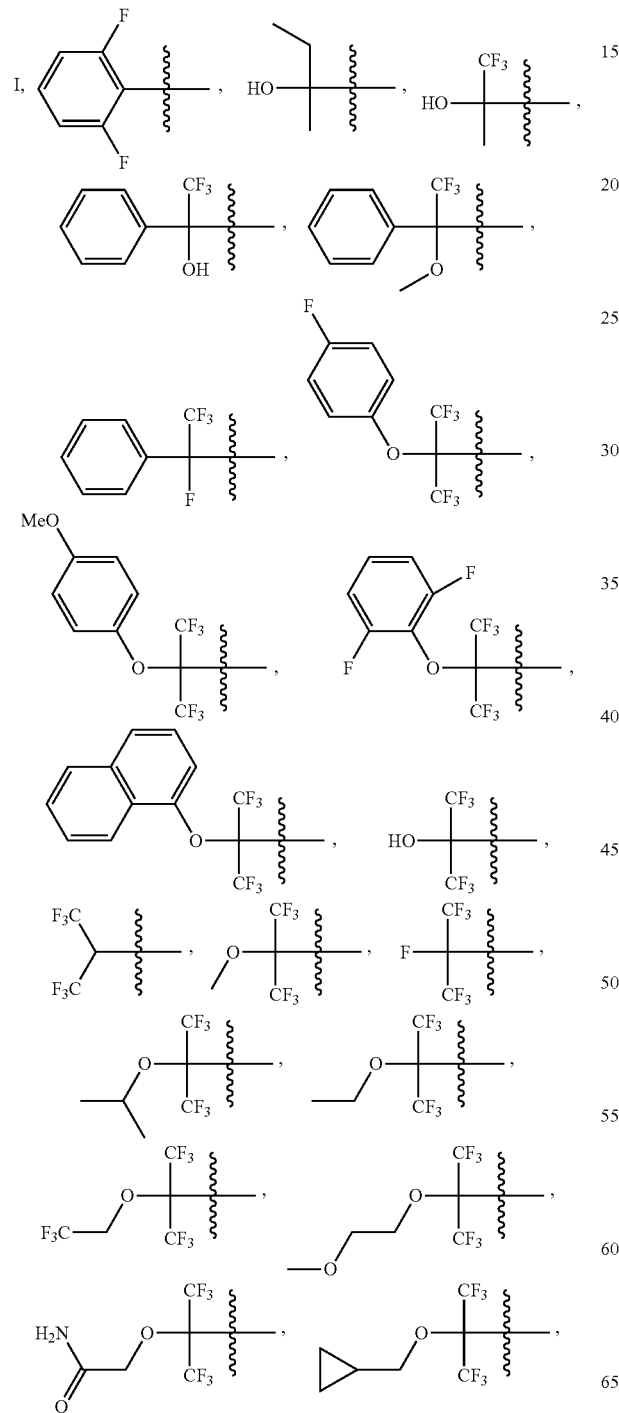
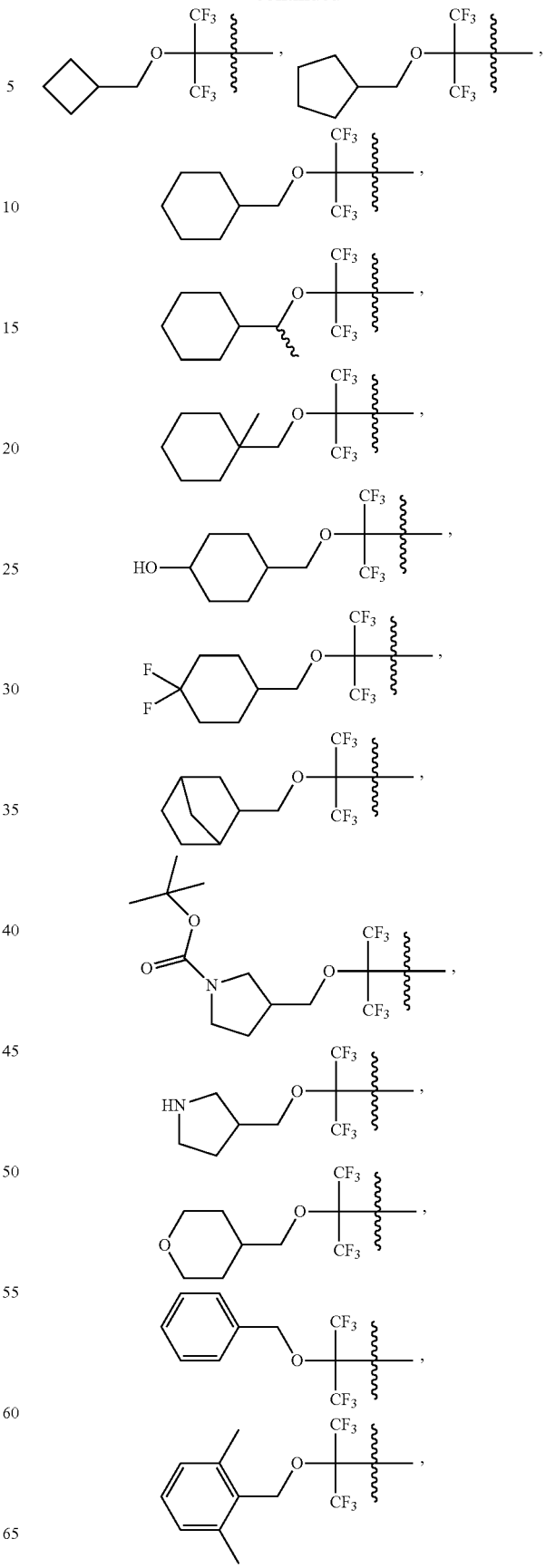

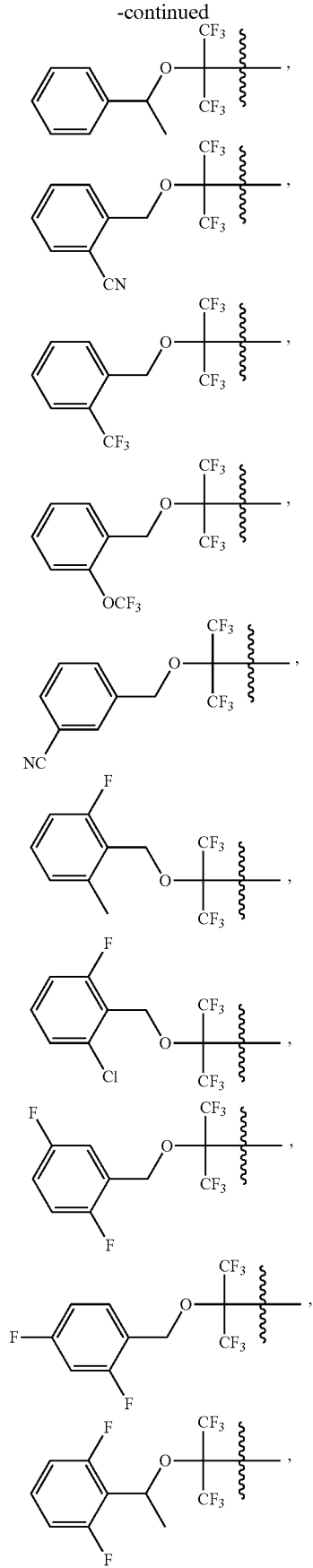
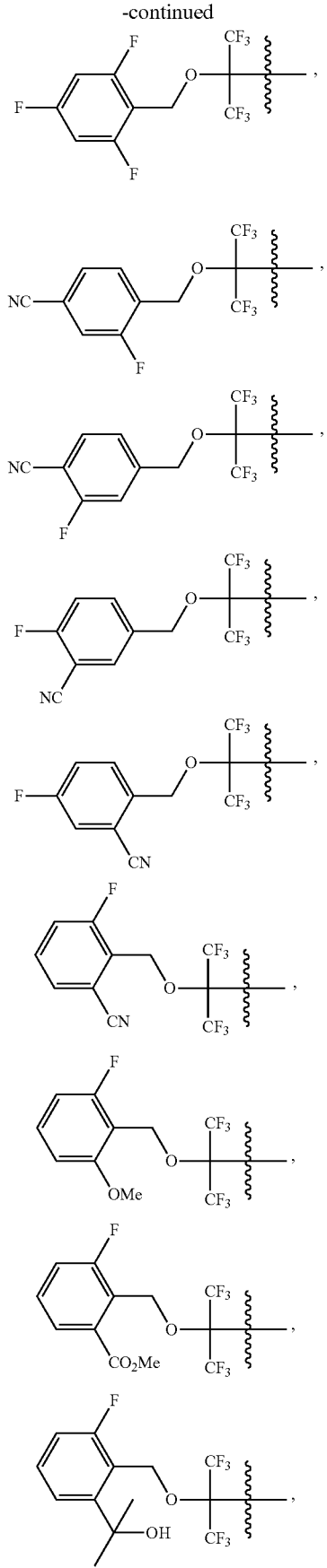

-continued

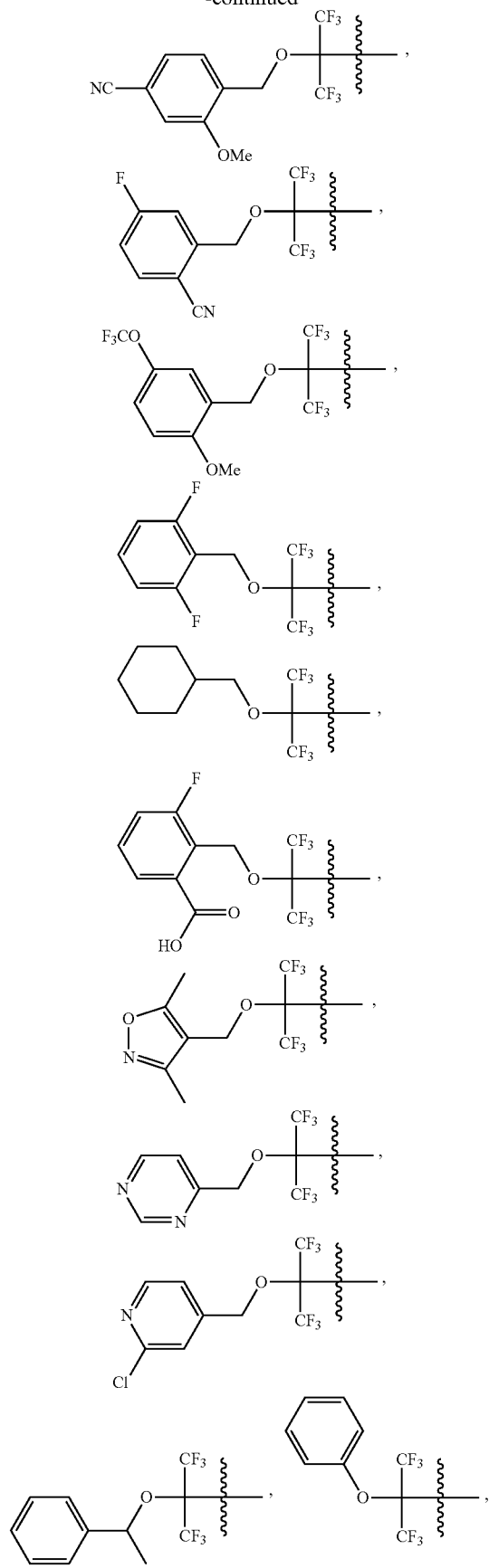

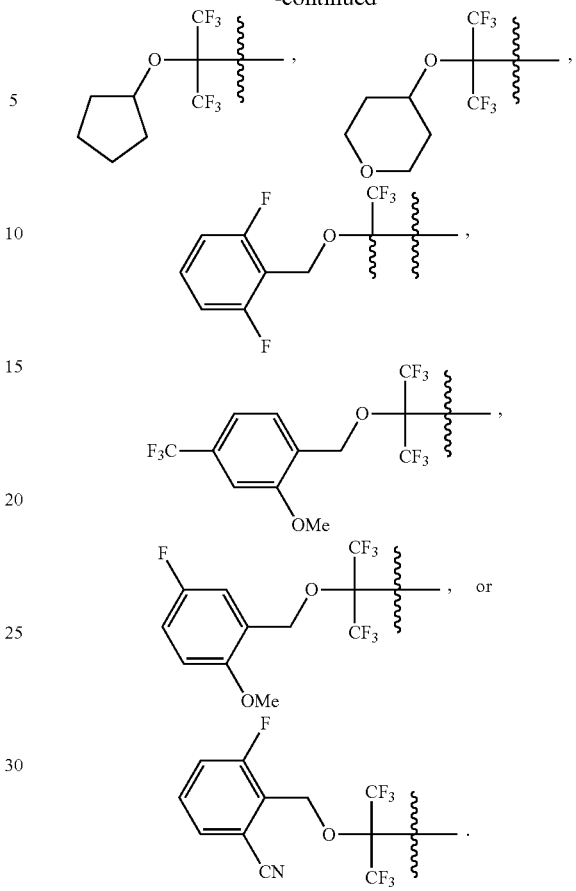

In another aspect, there is provided a compound of Formula (I), or stereoisomers, tautomers, pharmaceutically acceptable salts, solvates, or prodrugs thereof, wherein $R^2$ is $CO_2R^{2b}$, —C(O)$R^{2d}$, or C(O)N$R^{11}R^{11}$.

In another aspect, there is provided a compound of Formula (I), or stereoisomers, tautomers, pharmaceutically acceptable salts, solvates, or prodrugs thereof, wherein $R^2$ is:

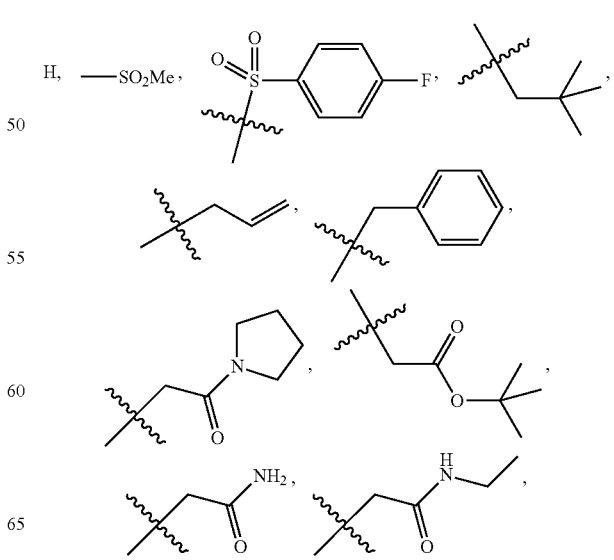

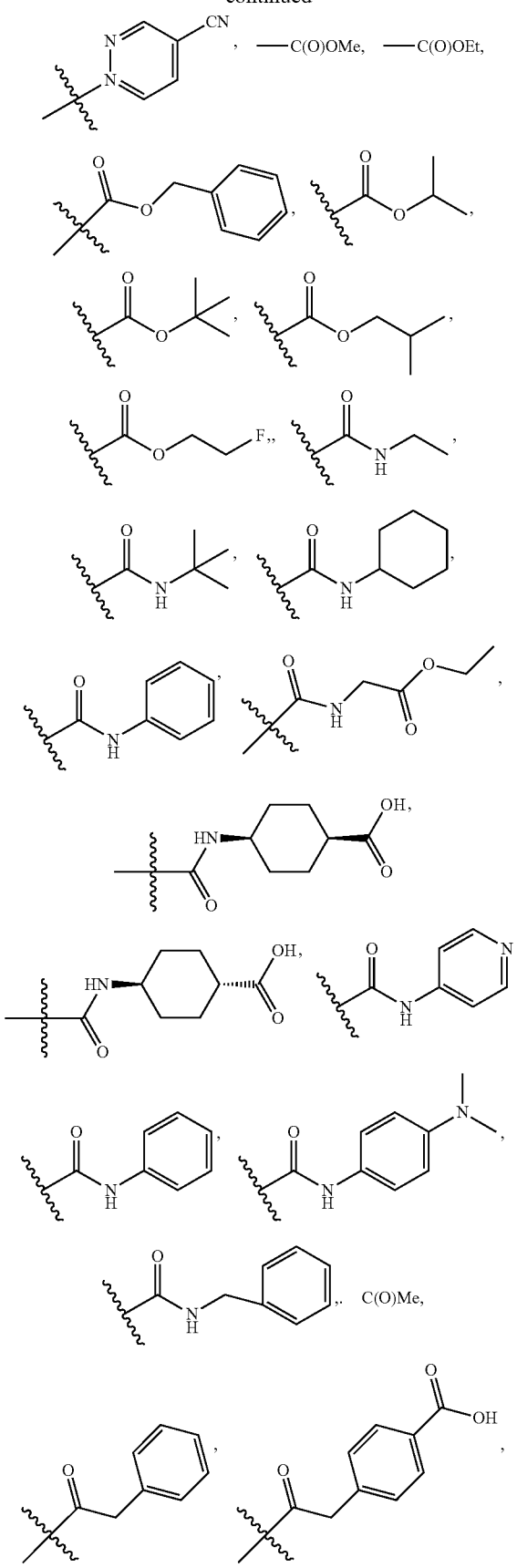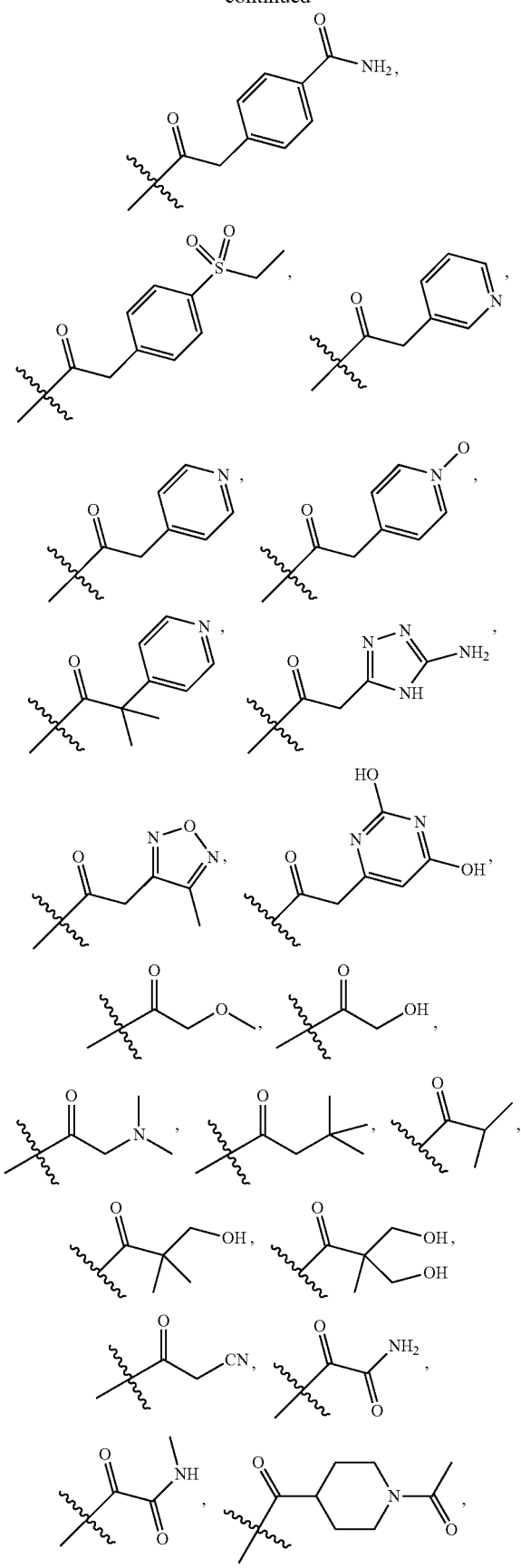

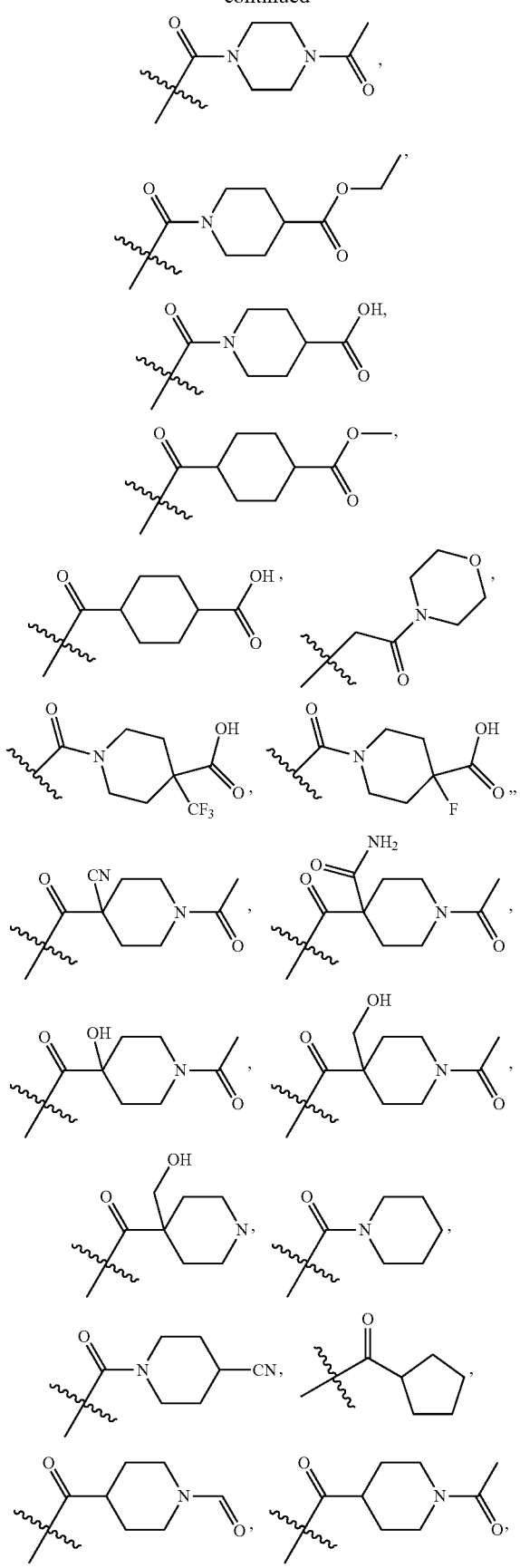
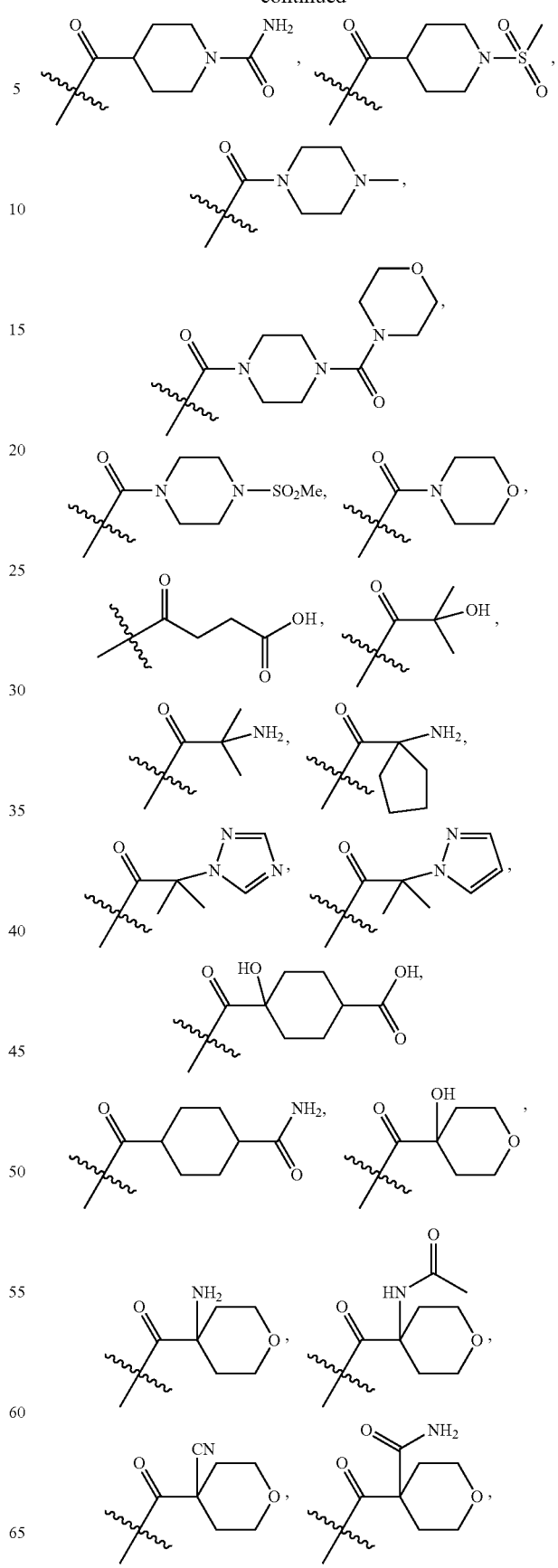

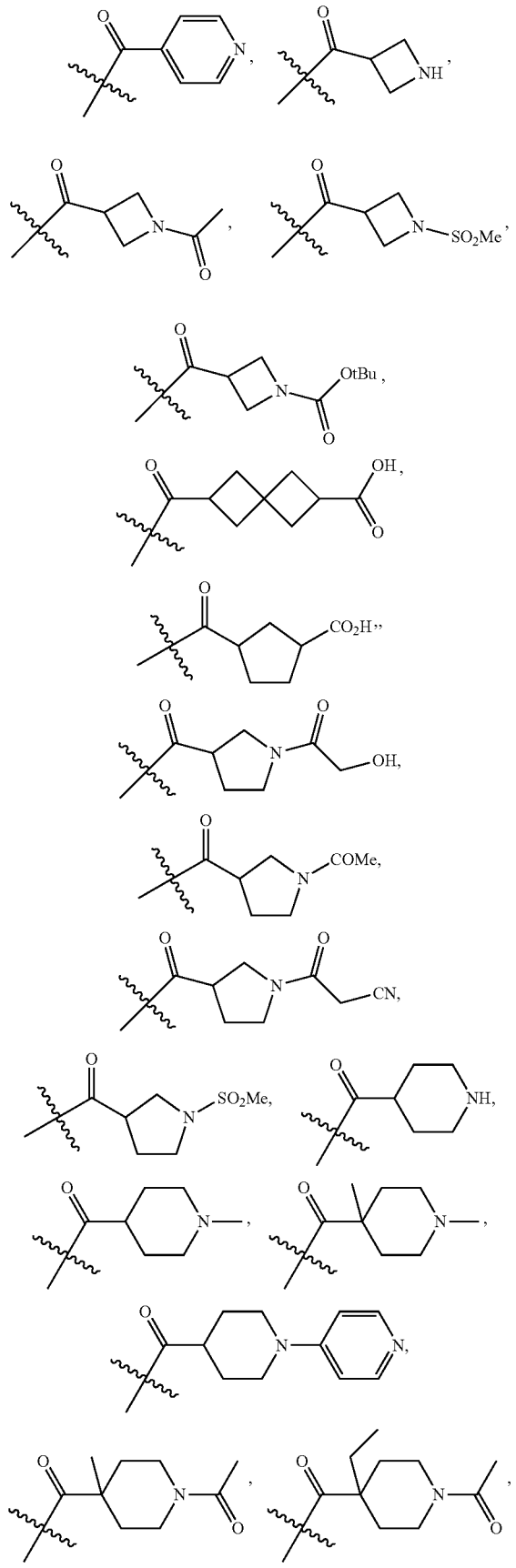
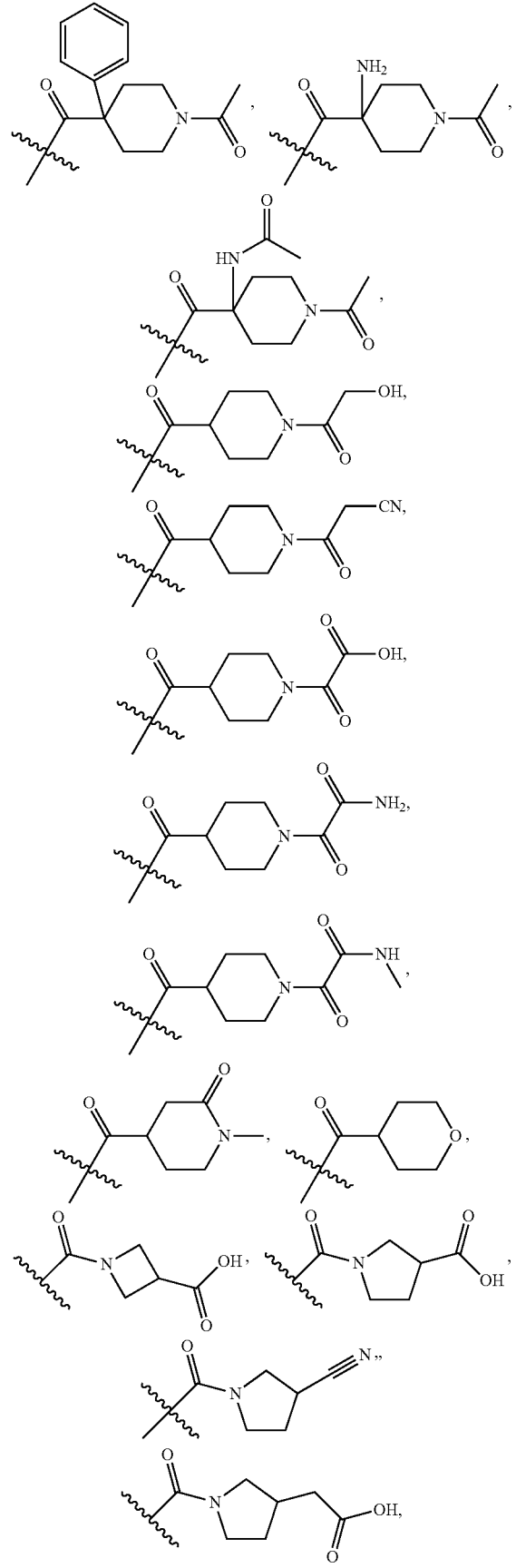

-continued
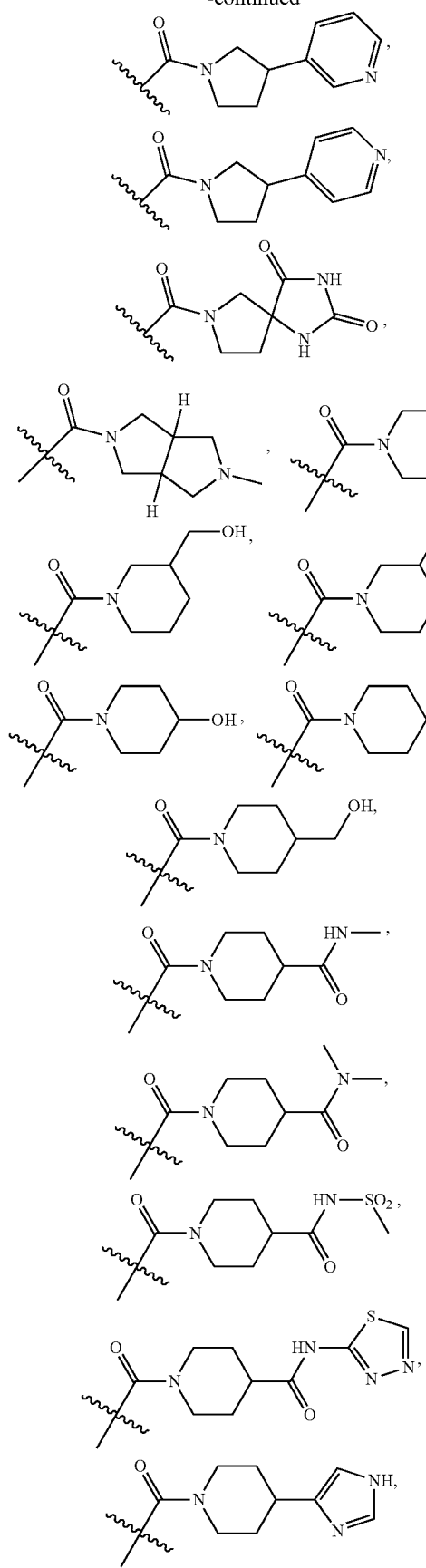
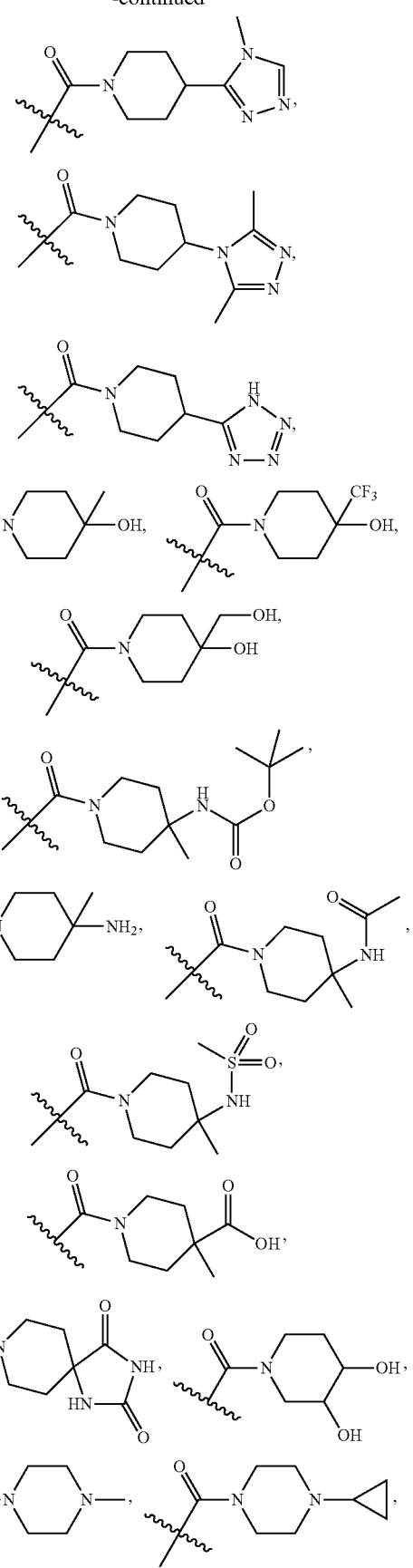

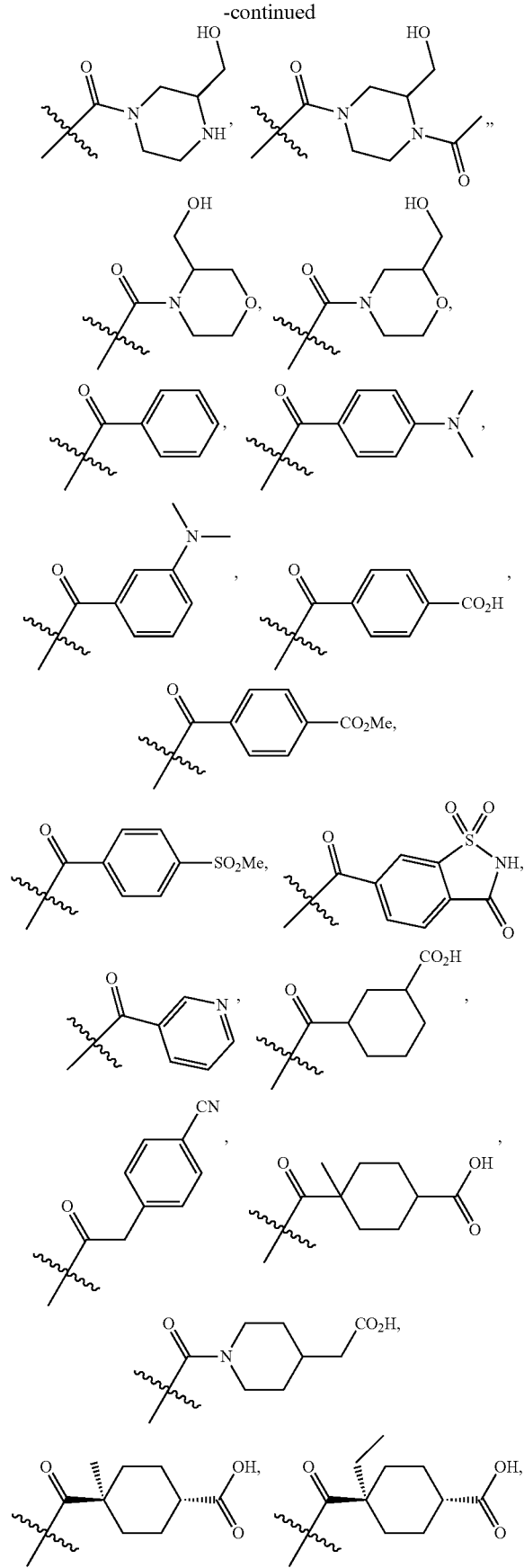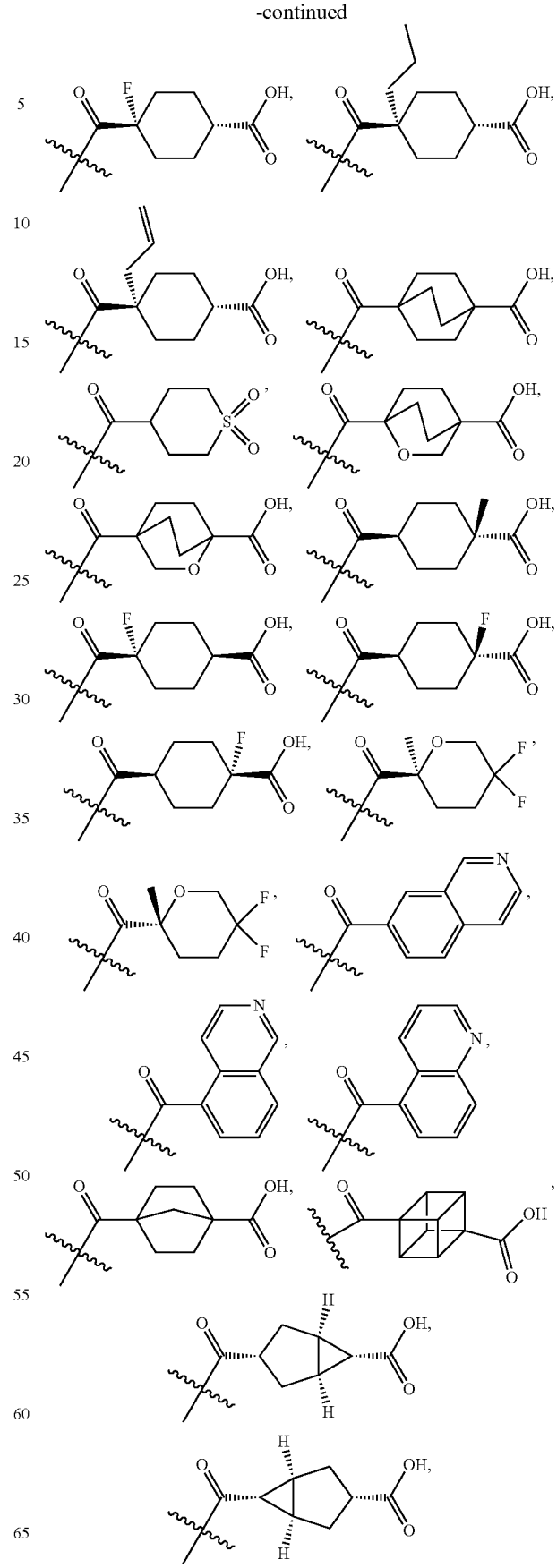

-continued
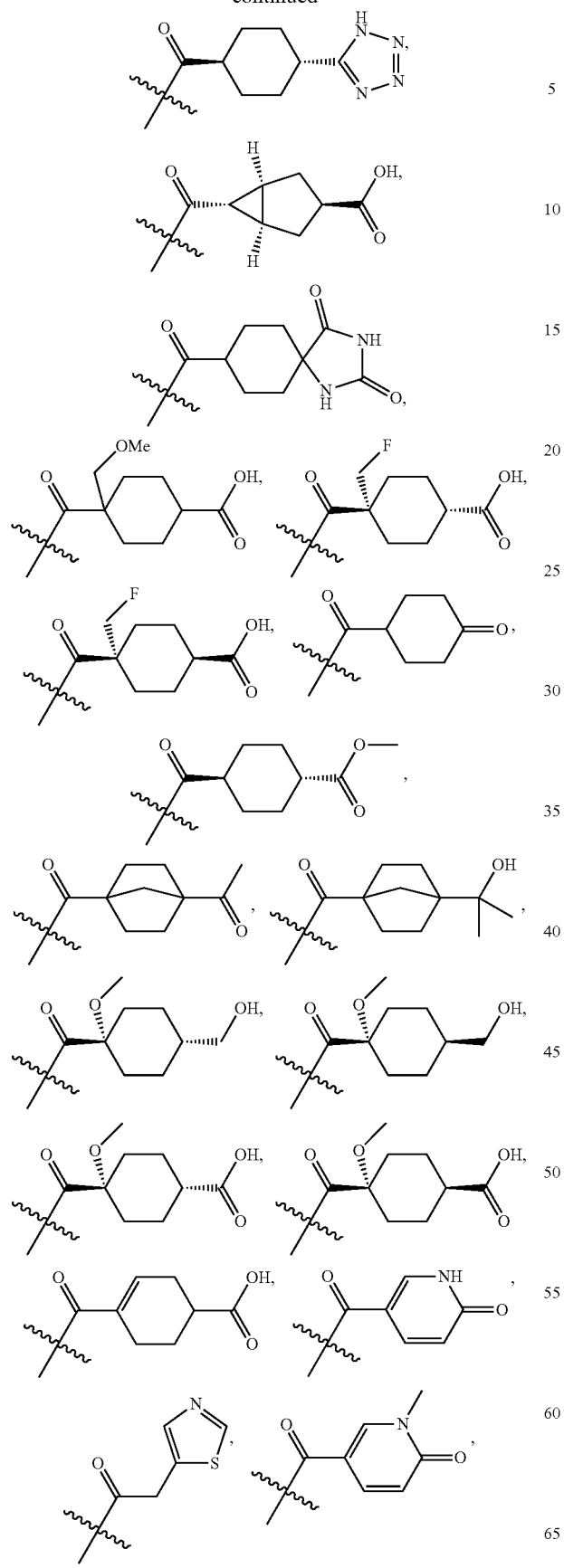
-continued
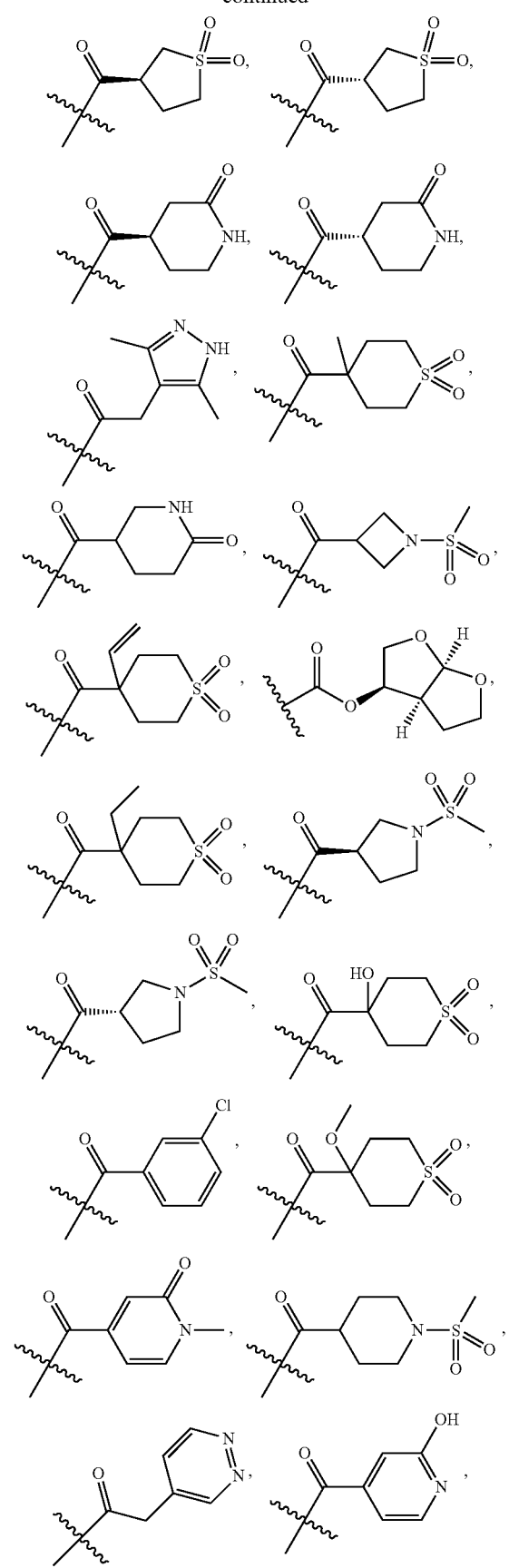

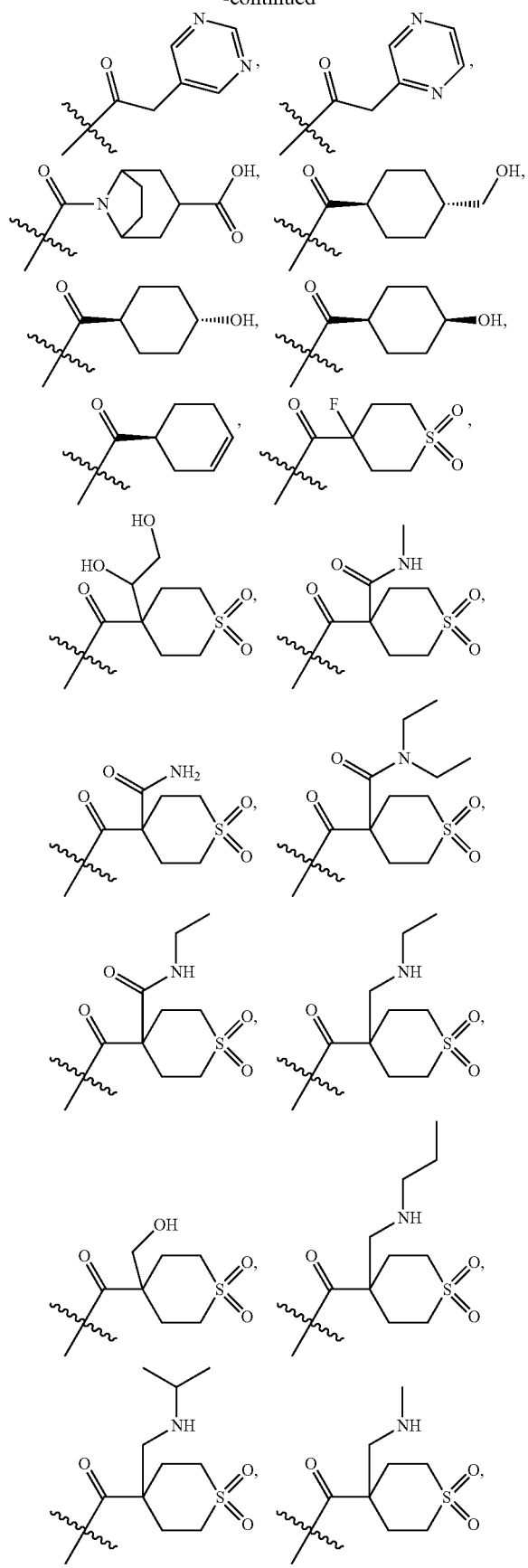
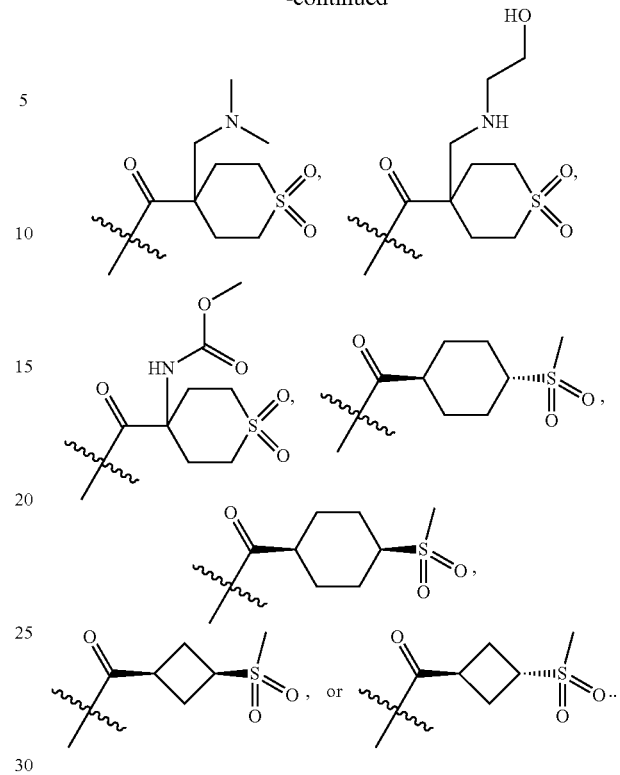

In another aspect, there is provided a compound of formula (I) having the following structure:

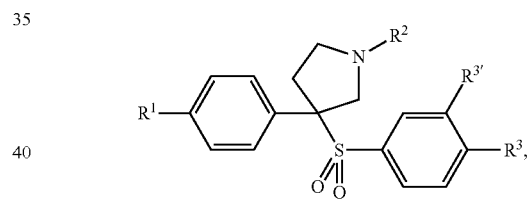

or stereoisomers, tautomers, pharmaceutically acceptable salts, solvates, or prodrugs thereof, wherein $R^3$ and $R^{3'}$ are, independently, hydrogen, halo, $N_3$, CN, —O(phenyl), —$NH_2$, $NH(C_{1-6}$ alkyl), $N(C_{1-6}$ alkyl$)_2$, $C_{1-6}$ alkyl or $C_{3-6}$ cycloalkyl. Preferably, $R^3$ is F, H, OMe, $NH_2$, $N_3$, CN, OPh, cyclopropyl, or $CH_3$, and $R^{3'}$ is hydrogen or $CH_3$.

In another aspect, there is provided a compound selected from the exemplified examples within the scope of the first aspect, or a pharmaceutically acceptable salt, tautomer or stereoisomer thereof.

In another aspect, there is provided a compound selected from any subset list of compounds within the scope of any of the above aspects.

In another embodiment, the invention provides a pharmaceutical composition, comprising a pharmaceutically acceptable carrier and a therapeutically effective amount of at least one of the compounds of the invention or a stereoisomer, a tautomer, a pharmaceutically acceptable salt, or a solvate thereof.

In another embodiment, the invention provides a process for making a compound of the invention or a stereoisomer, a tautomer, a pharmaceutically acceptable salt, or a solvate thereof.

In another embodiment, the invention provides a compound of the present invention for use in therapy.

In another embodiment, the invention provides a combined preparation of a compound of the present invention and additional therapeutic agent(s) for simultaneous, separate or sequential use in therapy.

In another embodiment, the invention provides a compound of the present invention for use in treating diseases (or a method of treating diseases) in which inflammation is a component including, without limitation, diseases such as psoriasis, rheumatoid arthritis, inflammatory bowel disease, Crohn's disease, ulcerative colitis, acute graft-versus-host disease, psoriatic arthritis, ankylosing spondylitis and multiple sclerosis.

The following are definitions of terms used in this specification and appended claims. The initial definition provided for a group or term herein applies to that group or term throughout the specification and claims, individually or as part of another group, unless otherwise indicated.

Compounds of this invention may have one or more asymmetric centers. Unless otherwise indicated, all chiral (enantiomeric and diastereomeric) and racemic forms of compounds of the present invention are included in the present invention. Many geometric isomers of olefins, C=N double bonds, and the like can also be present in the compounds, and all such stable isomers are contemplated in the present invention. Cis and trans geometric isomers of the compounds of the present invention are described and may be isolated as a mixture of isomers or as separated isomeric forms. The present compounds can be isolated in optically active or racemic forms. It is well known in the art how to prepare optically active forms, such as by resolution of racemic forms or by synthesis from optically active starting materials. All chiral (enantiomeric and diastereomeric) and racemic forms and all geometric isomeric forms of a structure are intended, unless the specific stereochemistry or isomer form is specifically indicated.

When any variable (e.g., $R^3$) occurs more than one time in any constituent or formula for a compound, its definition at each occurrence is independent of its definition at every other occurrence. Thus, for example, if a group is shown to be substituted with 0-2 $R^3$, then said group may optionally be substituted with up to two $R^3$ groups and $R^3$ at each occurrence is selected independently from the definition of $R^3$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

In cases wherein there are nitrogen atoms (e.g., amines) on compounds of the present invention, these can be converted to N-oxides by treatment with an oxidizing agent (e.g., MCPBA and/or hydrogen peroxides) to afford other compounds of this invention. Thus, all shown and claimed nitrogen atoms are considered to cover both the shown nitrogen and its N-oxide (N→O) derivative.

In accordance with a convention used in the art,

is used in structural formulas herein to depict the bond that is the point of attachment of the moiety or substituent to the core or backbone structure.

A dash "-" that is not between two letters or symbols is used to indicate a point of attachment for a substituent. For example, —CONH$_2$ is attached through the carbon atom.

The term "optionally substituted" in reference to a particular moiety of the compound of Formula I (e.g., an optionally substituted heteroaryl group) refers to a moiety having 0, 1, 2, or more substituents. For example, "optionally substituted alkyl" encompasses both "alkyl" and "substituted alkyl" as defined below. It will be understood by those skilled in the art, with respect to any group containing one or more substituents, that such groups are not intended to introduce any substitution or substitution patterns that are sterically impractical, synthetically non-feasible and/or inherently unstable.

As used herein, the term "at least one chemical entity" is interchangeable with the term "a compound."

As used herein, the term "alkyl" or "alkylene" is intended to include both branched and straight-chain saturated aliphatic hydrocarbon groups having the specified number of carbon atoms. For example, "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$-$C_6$ alkyl" denotes alkyl having 1 to 6 carbon atoms. Alkyl groups can be unsubstituted or substituted so that one or more of its hydrogens are replaced by another chemical group. Example alkyl groups include, but are not limited to, methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like.

"Alkenyl" or "alkenylene" is intended to include hydrocarbon chains of either straight or branched configuration and having one or more double carbon-carbon bonds that may occur in any stable point along the chain. For example, "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3-pentenyl, 4-pentenyl, 2-hexenyl, 3-hexenyl, 4-hexenyl, 5-hexenyl, 2-methyl-2-propenyl, 4-methyl-3-pentenyl, and the like.

"Alkynyl" or "alkynylene" is intended to include hydrocarbon chains of either straight or branched configuration and having one or more triple carbon-carbon bonds that may occur in any stable point along the chain. For example, "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, hexynyl and the like.

One skilled in the field will understand that, when the designation "CO$_2$" is used herein, this is intended to refer to the group

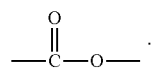

When the term "alkyl" is used together with another group, such as in "arylalkyl", this conjunction defines with more specificity at least one of the substituents that the substituted alkyl will contain. For example, "arylalkyl" refers to a substituted alkyl group as defined above where at least one of the substituents is an aryl, such as benzyl. Thus, the term aryl($C_{0-4}$)alkyl includes a substituted lower alkyl having at least one aryl substituent and also includes an aryl directly bonded to another group, i.e., aryl($C_0$)alkyl. The term "heteroarylalkyl" refers to a substituted alkyl group as defined above where at least one of the substituents is a heteroaryl.

When reference is made to a substituted alkenyl, alkynyl, alkylene, alkenylene, or alkynylene group, these groups are substituted with one to three substituents as defined above for substituted alkyl groups.

The term "alkoxy" refers to an oxygen atom substituted by alkyl or substituted alkyl, as defined herein. For example, the term "alkoxy" includes the group —O—$C_{1-6}$alkyl such as methoxy, ethoxy, propoxy, isopropoxy, n-butoxy, sec-butoxy, tert-butoxy, pentoxy, 2-pentyloxy, isopentoxy, neopentoxy, hexoxy, 2-hexoxy, 3-hexoxy, 3-methylpentoxy, and the like. "Lower alkoxy" refers to alkoxy groups having one to four carbons.

It should be understood that the selections for all groups, including for example, alkoxy, thioalkyl, and aminoalkyl, will be made by one skilled in the field to provide stable compounds.

The term "substituted", as used herein, means that any one or more hydrogens on the designated atom or group is replaced with a selection from the indicated group, provided that the designated atom's normal valence is not exceeded. When a substituent is oxo, or keto, (i.e., =O) then 2 hydrogens on the atom are replaced. Keto substituents are not present on aromatic moieties. Unless otherwise specified, substituents are named into the core structure. For example, it is to be understood that when (cycloalkyl)alkyl is listed as a possible substituent, the point of attachment of this substituent to the core structure is in the alkyl portion. Ring double bonds, as used herein, are double bonds that are formed between two adjacent ring atoms (e.g., C=C, C=N, or N=N).

Combinations of substituents and/or variables are permissible only if such combinations result in stable compounds or useful synthetic intermediates. A stable compound or stable structure is meant to imply a compound that is sufficiently robust to survive isolation from a reaction mixture to a useful degree of purity, and subsequent formulation into an efficacious therapeutic agent. It is preferred that the presently recited compounds do not contain a N-halo, $S(O)_2H$, or $S(O)H$ group.

The term "cycloalkyl" refers to cyclized alkyl groups, including mono-, bi- or poly-cyclic ring systems. $C_{3-7}$ cycloalkyl is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, norbornyl, and the like. As used herein, "carbocycle" or "carbocyclic residue" is intended to mean any stable 3, 4, 5, 6, or 7-membered monocyclic or bicyclic or 7-, 8-, 9-, 10-, 11-, 12-, or 13-membered bicyclic or tricyclic ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane, [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, and phenyl. When the term "carbocycle" is used, it is intended to include "aryl". A bridged ring occurs when one or more carbon atoms link two non-adjacent carbon atoms. Preferred bridges are one or two carbon atoms. It is noted that a bridge always converts a monocyclic ring into a bicyclic ring. When a ring is bridged, the substituents recited for the ring may also be present on the bridge.

The term "aryl" refers to monocyclic or bicyclic aromatic hydrocarbon groups having 6 to 12 carbon atoms in the ring portion, such as phenyl, and naphthyl groups, each of which may be substituted.

Accordingly, in compounds of formula I, the term "cycloalkyl" includes cyclopropyl, cyclobutyl, cyclopentyl, cyclohexyl, cycloheptyl, bicyclooctyl, etc., as well as the following ring systems:

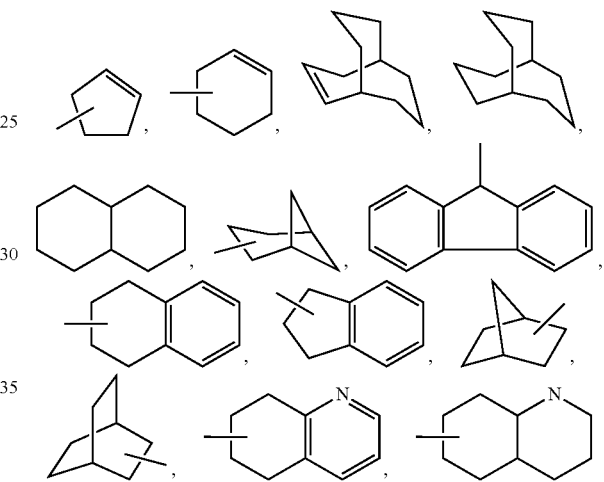

and the like, which optionally may be substituted at any available atoms of the ring(s).

Preferred cycloalkyl groups include cyclopropyl, cyclopentyl, cyclohexyl, and

The term "halo" or "halogen" refers to chloro, bromo, fluoro and iodo.

The term "haloalkyl" means a substituted alkyl having one or more halo substituents. For example, "haloalkyl" includes mono, di, and trifluoromethyl.

The term "haloalkoxy" means an alkoxy group having one or more halo substituents. For example, "haloalkoxy" includes $OCF_3$.

Thus, examples of aryl groups include:

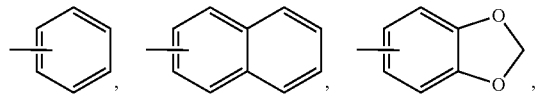

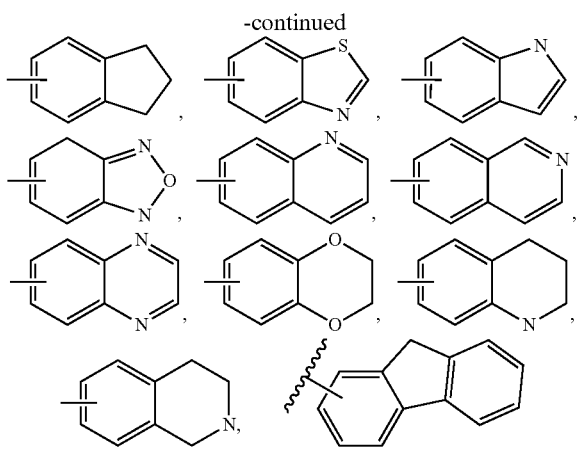

(fluorenyl) and the like, which optionally may be substituted at any available carbon or nitrogen atom. A preferred aryl group is optionally-substituted phenyl.

The terms "heterocycle", "heterocycloalkyl", "heterocyclo", "heterocyclic", or "heterocyclyl" may be used interchangeably and refer to substituted and unsubstituted 3- to 7-membered monocyclic groups, 7- to 11-membered bicyclic groups, and 10- to 15-membered tricyclic groups, in which at least one of the rings has at least one heteroatom (O, S or N), said heteroatom containing ring preferably having 1, 2, or 3 heteroatoms selected from O, S, and N. Each ring of such a group containing a heteroatom can contain one or two oxygen or sulfur atoms and/or from one to four nitrogen atoms provided that the total number of heteroatoms in each ring is four or less, and further provided that the ring contains at least one carbon atom. The nitrogen and sulfur atoms may optionally be oxidized and the nitrogen atoms may optionally be quaternized. The fused rings completing the bicyclic and tricyclic groups may contain only carbon atoms and may be saturated, partially saturated, or fully unsaturated. The heterocyclo group may be attached at any available nitrogen or carbon atom. As used herein the terms "heterocycle", "heterocycloalkyl", "heterocyclo", "heterocyclic", and "heterocyclyl" include "heteroaryl" groups, as defined below.

In addition to the heteroaryl groups described below, exemplary monocyclic heterocycle groups include azetidinyl, pyrrolidinyl, oxetanyl, imidazolinyl, oxazolidinyl, isoxazolinyl, thiazolidinyl, isothiazolidinyl, tetrahydrofuranyl, piperidyl, piperazinyl, 2-oxopiperazinyl, 2-oxopiperidyl, 2-oxopyrrolodinyl, 2-oxoazepinyl, azepinyl, 1-pyridonyl, 4-piperidonyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl and the like. Exemplary bicyclic heterocyclo groups include quinuclidinyl. Additional monocyclic heterocyclyl groups include

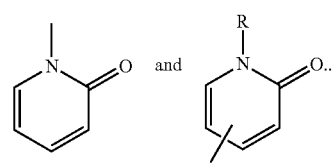

The term "heteroaryl" refers to substituted and unsubstituted aromatic 5- or 6-membered monocyclic groups, 9- or 10-membered bicyclic groups, and 11- to 14-membered tricyclic groups which have at least one heteroatom (O, S or N) in at least one of the rings, said heteroatom-containing ring preferably having 1, 2, or 3 heteroatoms selected from O, S, and N. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. As valence allows, if said further ring is cycloalkyl or heterocyclo it is additionally optionally substituted with =O (oxo).

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl and the like.

Exemplary bicyclic heteroaryl groups include indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridyl, dihydroisoindolyl, tetrahydroquinolinyl and the like.

Exemplary tricyclic heteroaryl groups include carbazolyl, benzindolyl, phenanthrollinyl, acridinyl, phenanthridinyl, xanthenyl and the like.

In compounds of formula I, preferred heteroaryl groups include

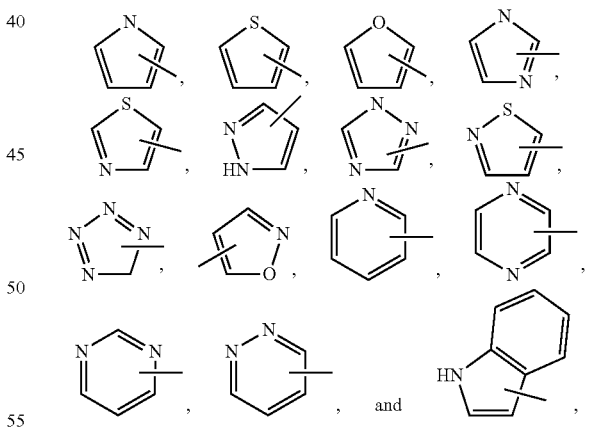

and the like, which optionally may be substituted at any available carbon or nitrogen atom.

Unless otherwise indicated, when reference is made to a specifically-named aryl (e.g., phenyl), cycloalkyl (e.g., cyclohexyl), heterocyclo (e.g., pyrrolidinyl, piperidinyl, and morpholinyl) or heteroaryl (e.g., tetrazolyl, imidazolyl, pyrazolyl, triazolyl, thiazolyl, and furyl) the reference is intended to include rings having 0 to 3, preferably 0 to 2, substituents selected from those recited above for the aryl, cycloalkyl, heterocyclo and/or heteroaryl groups, as appropriate.

The terms "carbocycle, carbocyclyl or "carbocyclic" refers to a saturated or unsaturated monocyclic or bicyclic ring in which all atoms of all rings are carbon. Thus, the term includes cycloalkyl and aryl rings. Monocyclic carbocycles have 3 to 6 ring atoms, still more typically 5 or 6 ring atoms. Bicyclic carbocycles have 7 to 12 ring atoms, e.g., arranged as a bicyclo[4,5], [5,5], [5,6] or [6,6] system, or 9 or 10 ring atoms arranged as a bicyclo[5,6] or [6,6] system. Examples of mono- and bicyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, phenyl and naphthyl. The carbocyclic ring may be substituted in which case the substituents are selected from those recited above for cycloalkyl and aryl groups.

The term "heteroatoms" shall include oxygen, sulfur and nitrogen.

When the term "unsaturated" is used herein to refer to a ring or group, the ring or group may be fully unsaturated or partially unsaturated.

Throughout the specification, groups and substituents thereof may be chosen by one skilled in the field to provide stable moieties and compounds and compounds useful as pharmaceutically-acceptable compounds and/or intermediate compounds useful in making pharmaceutically-acceptable compounds.

The compounds of formula I may exist in a free form (with no ionization) or can form salts which are also within the scope of this invention. Unless otherwise indicated, reference to an inventive compound is understood to include reference to the free form and to salts thereof. The term "salt(s)" denotes acidic and/or basic salts formed with inorganic and/or organic acids and bases. In addition, the term "salt(s) may include zwitterions (inner salts), e.g., when a compound of formula I, contains both a basic moiety, such as an amine or a pyridine or imidazole ring, and an acidic moiety, such as a carboxylic acid. Pharmaceutically acceptable (i.e., non-toxic, physiologically acceptable) salts are preferred, such as, for example, acceptable metal and amine salts in which the cation does not contribute significantly to the toxicity or biological activity of the salt. However, other salts may be useful, e.g., in isolation or purification steps which may be employed during preparation, and thus, are contemplated within the scope of the invention. Salts of the compounds of the formula I may be formed, for example, by reacting a compound of the formula I with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts include ammonium salts, alkali metal salts such as sodium, lithium, and potassium salts; alkaline earth metal salts such as calcium and magnesium salts; barium, zinc, and aluminum salts; salts with organic bases (for example, organic amines) such as trialkylamines such as triethylamine, procaine, dibenzylamine, N-benzyl-β-phenethylamine, 1-ephenamine, N,N'-dibenzylethylenediamine, dehydroabietylamine, N-ethylpiperidine, benzylamine, dicyclohexylamine or similar pharmaceutically acceptable amines and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others. Preferred salts include monohydrochloride, hydrogensulfate, methanesulfonate, phosphate or nitrate salts.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 18th Edition, Mack Publishing Company, Easton, Pa. (1990), the disclosure of which is hereby incorporated by reference.

All stereoisomers of the compounds of the instant invention are contemplated, either in admixture or in pure or substantially pure form. Stereoisomers may include compounds which are optical isomers through possession of one or more chiral atoms, as well as compounds which are optical isomers by virtue of limited rotation about one or more bonds (atropisomers). The definition of compounds according to the invention embraces all the possible stereoisomers and their mixtures. It very particularly embraces the racemic forms and the isolated optical isomers having the specified activity. The racemic forms can be resolved by physical methods, such as, for example, fractional crystallization, separation or crystallization of diastereomeric derivatives or separation by chiral column chromatography. The individual optical isomers can be obtained from the racemates from the conventional methods, such as, for example, salt formation with an optically active acid followed by crystallization.

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

Prodrugs and solvates of the inventive compounds are also contemplated. The term "prodrug" denotes a compound which, upon administration to a subject, undergoes chemical conversion by metabolic or chemical processes to yield a compound of the formula I, and/or a salt and/or solvate thereof. Any compound that will be converted in vivo to provide the bioactive agent (i.e., the compound for formula I) is a prodrug within the scope and spirit of the invention. For example, compounds containing a carboxy group can form physiologically hydrolyzable esters which serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkylbenzyl, 4-methoxybenzyl, indanyl, phthalyl, methoxymethyl, $C_{1-6}$alkanoyloxy-$C_{1-6}$alkyl, e.g., acetoxymethyl, pivaloyloxymethyl or propionyloxymethyl, $C_{1-6}$alkoxycarbonyloxy-$C_{1-6}$alkyl, e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl and other well known physiologically hydrolyzable esters used, for example, in the penicillin and cephalosporin arts. Such esters may be prepared by conventional techniques known in the art.

Various forms of prodrugs are well known in the art. For examples of such prodrug derivatives, see:
a) Bundgaard, H., ed., *Design of Prodrugs*, Elsevier (1985), and Widder, K. et al., eds., *Methods in Enzymology*, 112:309-396, Academic Press (1985);
b) Bundgaard, H., Chapter 5, "Design and Application of Prodrugs", Krosgaard-Larsen, P. et al., eds., *A Textbook of Drug Design and Development*, pp. 113-191, Harwood Academic Publishers (1991); and
c) Bundgaard, H., *Adv. Drug Deliv. Rev.*, 8:1-38 (1992), each of which is incorporated herein by reference.

Compounds of the formula I and salts thereof may exist in their tautomeric form, in which hydrogen atoms are transposed to other parts of the molecules and the chemical bonds between the atoms of the molecules are consequently rearranged. It should be understood that the all tautomeric forms, insofar as they may exist, are included within the invention. Additionally, inventive compounds may have trans and cis isomers.

It should further be understood that solvates (e.g., hydrates) of the compounds of Formula I are also with the scope of the present invention. Methods of solvation are generally known in the art.

Another aspect of the invention is a pharmaceutical composition including a compound, stereoisomeric form, pharmaceutical salt, solvate or hydrate as described herein. The pharmaceutical compositions described herein generally comprise a combination of a compound described herein and a pharmaceutically acceptable carrier, diluent, or excipient. Such compositions are substantially free of non-pharmaceutically acceptable components, i.e., contain amounts of non-pharmaceutically acceptable components lower than permitted by U.S. regulatory requirements at the time of filing this application. In some embodiments of this aspect, if the compound is dissolved or suspended in water, the composition further optionally comprises an additional pharmaceutically acceptable carrier, diluent, or excipient. In other embodiments, the pharmaceutical compositions described herein are solid pharmaceutical compositions (e.g., tablet, capsules, etc.).

These compositions can be prepared in a manner well known in the pharmaceutical art, and can be administered by a variety of routes, depending upon whether local or systemic treatment is desired and upon the area to be treated. Administration may be topical (including ophthalmic and to mucous membranes including intranasal, vaginal and rectal delivery), pulmonary (e.g., by inhalation or insufflation of powders or aerosols, including by nebulizer; intratracheal, intranasal, epidermal and transdermal), ocular, oral or parenteral. Methods for ocular delivery can include topical administration (eye drops), subconjunctival, periocular or intravitreal injection or introduction by balloon catheter or ophthalmic inserts surgically placed in the conjunctival sac. Parenteral administration includes intravenous, intraarterial, subcutaneous, intraperitoneal or intramuscular injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Also, pharmaceutical compositions can contain, as the active ingredient, one or more of the compounds described herein above in combination with one or more pharmaceutically acceptable carriers. In making the compositions described herein, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions described herein can be formulated so as to provide quick, sustained or delayed release of the active ingredient after administration to the subject by employing procedures known in the art.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual subject, the severity of the subject's symptoms, and the like.

For preparing solid compositions such as tablets, the principal active ingredient is mixed with a pharmaceutical excipient to form a solid preformulation composition containing a homogeneous mixture of a compound described herein. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, 0.1 to about 500 mg of the active ingredient of a compound described herein.

The tablets or pills can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The amount of compound or composition administered to a subject will vary depending upon what is being administered, the purpose of the administration, such as prophylaxis or therapy, the state of the subject, the manner of administration, and the like. In therapeutic applications, compositions can be administered to a subject already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the subject, and the like.

The compositions administered to a subject can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the compounds can vary according to, for example, the particular use for which the treatment is made, the manner of administration of the compound, the health and condition of the subject, and the judgment of the prescribing physician. The proportion or concentration of a compound described herein in a pharmaceutical composition can vary depending upon a number of factors including dosage, chemical characteristics (e.g., hydrophobicity), and the route of administration. For example, the compounds described herein can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular subject, the relative biological efficacy of the compound selected, formulation of the excipient, and its route of administration. Effective doses can be extrapolated from dose-response curves derived from in vitro or animal model test systems.

The compounds of the present invention are useful to prevent, diagnose, and treat various medical disorders in humans or animals. The compounds are used to inhibit or reduce one or more activities associated with RORγ receptors, relative to RORγ receptors in the absence of the same compounds. Thus, in one aspect of the invention, a method for treating a disease or disorder selected from an autoimmune disease or disorder, asthma, an allergic disease or disorder, a metabolic disease or disorder, and cancer in a subject comprises administering to the subject a therapeutically effective amount of compound according to formula (I), stereoisomeric form, N-oxide, pharmaceutically acceptable salt, solvate, hydrate or pharmaceutical composition as described herein. See, e.g., L. A. Solt et al., "Action of RORs and their ligands in (patho)physiology," *Trends Endocrinol Metab.*, preprint available online Jul. 11, 2012 at http://www.sciencedirect.com/science/article/pii/S1043276012000926; M. S. Maddur et al., "Th17 cells: biology, pathogenesis of autoimmune and inflammatory diseases, and therapeutic strategies," *Am. J. Pathol.* 2012 July; 181(1):8-18; and A. M. Jetten, "Retinoid-related orphan receptors (RORs): critical roles in development, immunity, circadian rhythm, and cellular metabolism," *Nucl. Recept. Signal.* 2009; 7:e003, each of which is hereby incorporated herein by reference in its entirety, as well as the references discussed in the Background section. In certain embodiments, the autoimmune disease or disorder is selected from rheumatoid arthritis, ankylosing spondylitis, psoriasis and psoriatic arthritis, multiple sclerosis, inflammatory bowel diseases and lupus. In certain embodiments, the allergic disease or disorder is selected from allergic rhinitis and dermatitis. In certain embodiments, the metabolic disease or disorder is selected from obesity, obesity-induced insulin resistance and type II diabetes.

In certain embodiments, the disease or disorder is rheumatoid arthritis. See, e.g., L. A. Solt et al., referenced above, as well as the references discussed in the Background section.

In other embodiments, the disease or disorder is multiple sclerosis. See, e.g., L. Codarri et al., "RORγt drives production of the cytokine GM-CSF in helper T cells, which is essential for the effector phase of autoimmune neuroinflammation," *Nat. Immunol.,* 2011 June; 12(6):560-7, which is hereby incorporated herein by reference in its entirety, as well as the references discussed in the Background section.

In other embodiments, the disease or disorder is ankylosing spondylitis. See, e.g., E. Toussirot, "The IL23/Th17 pathway as a therapeutic target in chronic inflammatory diseases," *Inflamm. Allergy Drug Targets,* 2012 April; 11(2): 159-68, which is hereby incorporated herein by reference in its entirety, as well as the references discussed in the Background section.

In other embodiments, the disease or disorder is inflammatory bowel disease. See, e.g., M. Leppkes et al., "ROR-gamma-expressing Th17 cells induce murine chronic intestinal inflammation via redundant effects of IL-17A and IL-17F," Gastroenterology, 2009 January; 136(1):257-67, which is hereby incorporated herein by reference in its entirety, as well as the references discussed in the Background section.

In other embodiments, the disease or disorder is lupus. See, e.g., K. Yoh et al., "Overexpression of RORγt under control of the CD2 promoter induces polyclonal plasmacytosis and autoantibody production in transgenic mice," *Eur. J. Immunol.,* 2012 August; 42(8):1999-2009, which is hereby incorporated herein by reference in its entirety, as well as the references discussed in the Background section.

In other embodiments, the disease or disorder is psoriasis. See, e.g., S. Pantelyushin et al., "RORγt+ innate lymphocytes and γδ T cells initiate psoriasiform plaque formation in mice," *J. Clin. Invest.,* 2012 Jun. 1; 122(6):2252-6; and S. P. Raychaudhuri, "Role of IL-17 in Psoriasis and Psoriatic Arthritis," Clin. Rev. Allergy Immunol., preprint available online Feb. 24, 2012 at http://rd.springer.com/article/10.1007/s12016-012-8307-1 (PubMed PMID: 22362575), each of which is hereby incorporated herein by reference in its entirety, as well as the references discussed in the Background section.

In other embodiments, the disease or disorder is psoriatic arthritis. See, e.g., S. P. Raychaudhuri, referenced above, as well as the references discussed in the Background section.

In other embodiments, the disease or disorder is graft-vs.-host disease (GVHD). Y. Yu et al., "Prevention of GVHD while sparing GVL effect by targeting Th1 and Th17 transcription factorT-bet and RORγt in mice," *Blood,* 2011 Nov. 3; 118(18):5011-20, which is hereby incorporated herein by reference in its entirety, as well as the references discussed in the Background section.

In other embodiments, the disease or disorder is autoimmune uveitis. See, e.g., R. Horai et al., "Cytokines in autoimmune uveitis," *J. Interferon Cytokine Res.,* 2011 October; 31(10):733-44, which is hereby incorporated herein by reference in its entirety, as well as the references discussed in the Background section.

In other embodiments, the disease or disorder is obesity and/or insulin resistance. See, e.g., B. Meissburger et al., "Adipogenesis and insulin sensitivity in obesity are regulated by retinoid-related orphan receptor gamma," *EMBO Mol. Med.,* 2011 November; 3(11):637-51, which is hereby incorporated herein by reference in its entirety, as well as the references discussed in the Background section.

In other embodiments, the disease or disorder is melanoma. See, e.g., Purwar R, et al. Robust tumor immunity to melanoma mediated by interleukin-9-producing T cells. Nat. Med., 2012 July:18:1248-53, which is hereby incorporated herein by reference in its entirety, as well as the references discussed in the Background section.

In certain aspects, the medical disorder being diagnosed, treated, or prevented by use of the presently disclosed compounds can be, for example, an autoimmune disorder. In other embodiments, the disorder being diagnosed, treated or prevented by use of the presently disclosed compounds can be an inflammatory disorder. For example, in certain embodiments, the disorder is selected from arthritis, diabetes, multiple sclerosis, uveitis, rheumatoid arthritis, psoriasis, asthma, bronchitis, allergic rhinitis, chronic obstructive pulmonary disease, atherosclerosis, *H. pylori* infection and inflammatory bowel disease. In other embodiments, the disorder is selected from Crohn's disease, ulcerative colitis, sprue and food allergies. In other embodiments, the disorder is experimental autoimmune encephalomyelitis, imiquimod-induced psoriasis, colitis or allergic airway disease.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician.

In certain embodiments, a therapeutically effective amount can be an amount suitable for (1) preventing the disease; for example, preventing a disease, condition or disorder in an individual who may be predisposed to the disease, condition or disorder but does not yet experience or display the pathology or symptomatology of the disease; (2) inhibiting the disease; for example, inhibiting a disease, condition or disorder in an individual who is experiencing or displaying the pathology or symptomatology of the disease, condition or disorder; or (3) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

As used here, the terms "treatment" and "treating" means (i) ameliorating the referenced disease state, for example, ameliorating a disease, condition or disorder in an individual who is experiencing or displaying the pathology or symptomatology of the disease, condition or disorder (i.e., reversing or improving the pathology and/or symptomatology) such as decreasing the severity of disease; (ii) eliciting the biological or medicinal response that is being sought in a tissue, system, animal, individual or human by a researcher, veterinarian, medical doctor or other clinician; or (iii) inhibiting the referenced disease state; for example, inhibiting a disease, condition or disorder in an individual who is experiencing or displaying the pathology or symptomatology of the disease, condition or disorder.

Methods of Preparation

The compounds of the present invention may be synthesized by many methods available to those skilled in the art of organic chemistry. General synthetic schemes for preparing compounds of the present invention are described below. These schemes are illustrative and are not meant to limit the possible techniques one skilled in the art may use to prepare the compounds disclosed herein. Different methods to prepare the compounds of the present invention will be evident to those skilled in the art. Additionally, the various steps in the synthesis may be performed in an alternate sequence in order to give the desired compound or compounds. Examples of compounds of the present invention prepared by methods described in the general schemes are given in the preparations and examples section set out hereinafter. Preparation of homochiral examples may be carried out by techniques known to one skilled in the art. For example, homochiral compounds may be prepared by separation of racemic products by chiral phase preparative HPLC. Alternatively, the example compounds may be prepared by methods known to give enantiomerically enriched products.

Scheme 1 illustrates a general synthesis of compound 10. Appropriately functionalized benzyl halide 1 can be reacted with functionalized thiophenol 2 using a base such as potassium carbonate or sodium hydroxide in a solvent such as tetrahydrofuran, ethanol or N,N-dimethylformamide to provide sulfide intermediate 3. Oxidation of 3 to sulfone 4 can be accomplished with mCPBA or other oxidant such as oxone and sodium tungstate. Alternatively, sulfone 4 can be synthesized in one-step by treating 1 with sodium benzenesulfinate 5 in a solvent such as N,N-dimethylformamide. Upon treatment with n-butyllithium, the resulting anion derivative of 4 can be reacted with Eschenmoser's salt (dimethylmethylideneammonium iodide) to yield amine derivative 6, which can be converted to vinyl sulfone 7 after heating in acetic anhydride and toluene. Vinyl sulfone 7 can also be synthesized directly from 4 by heating with N,N,N',N'-tetramethylmethylenediamine and acetic anhydride in N,N-dimethylformamide. From vinyl sulfone 7, pyrrolidine 8 can be synthesized by reaction with N-(methoxymethyl)-N-(trimethylsilylmethyl)benzylamine using trifluoroacetic acid as a catalyst.

Removal of the benzyl group in 8 can be achieved with palladium(II) hydroxide-catalyzed hydrogenolysis in a solvent such as methanol or ethanol. Alternatively, benzylamine 8 can be converted to a Cbz-protected intermediate using benzyl chloroformate. Subsequently, palladium(II) hydroxide-catalyzed hydrogenolysis would provide the same amine intermediate 9. Benzylamine 8 can also be reacted with 1-chloroethyl chloroformate to give the desired intermediate 9 directly, after methanolic workup to decompose the 1-chloroethyl carbamate intermediate. Finally, functionalization of the penultimate intermediate 9 can be achieved using various well known transformations such as alkylation reaction with alkyl halide and a base such as Hunig's base, reductive alkylation with aldehyde/ketone and a reducing reagent such as sodium triacetoxyborohydride, coupling reaction with carboxylic acid using an activating agent such as BOP or HOBt/EDC, and other acylation reactions using acid chloride, anhydride, chloroformate, isocyanate, and sulfonyl chloride. Optionally, enantiomers of 8, 9 and 10 can be separated using chiral HPLC and, if necessary, each enantiomer carried forward individually to provide product 10 in homochiral form.

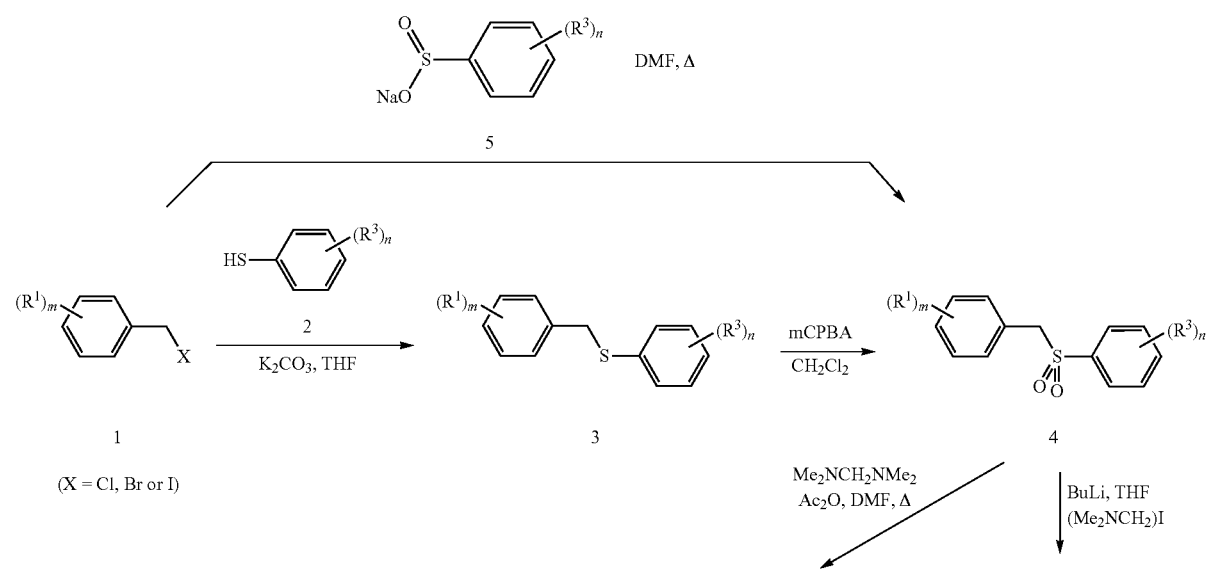

Scheme 1

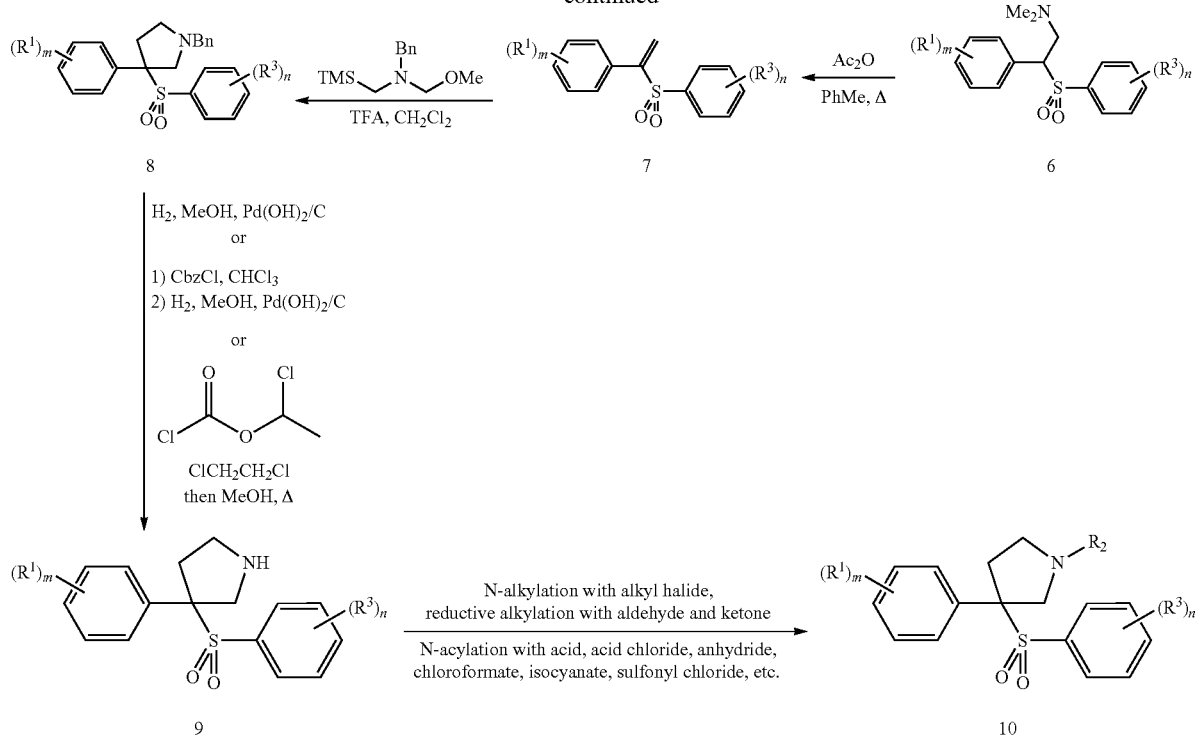

Scheme 2 illustrates a synthesis of a series of compounds 18 where R¹ is 1,1,1,3,3,3-hexafluoro-2-hydroxypropan-2-yl group. Commercially available 1,1,1,3,3,3-hexafluoro-2-(p-tolyl)propan-2-ol (11) can be selectively brominated with N-bromosuccinimide in refluxing carbon tetrachloride using AIBN as radical initiator to yield bromide 12. Reaction of 12 with sodium benzenesulfinate 5 in a solvent such as N,N-dimethylformamide could lead to sulfone product 13. The hydroxyl group in 13 can be protected as a benzyl ether using conditions such as benzyl bromide and potassium carbonate in N,N-dimethylformamide. Vinyl sulfone 15 can be synthesized from 14 by heating with N,N,N',N'-tetramethylmethylenediamine and acetic anhydride in N,N-dimethylformamide. From vinyl sulfone 15, pyrrolidine 16 can be synthesized by reaction with N-(methoxymethyl)-N-(trimethylsilylmethyl)benzylamine using trifluoroacetic acid as a catalyst. At this stage, the racemic 16 can be taken forward to final products, or resolved using chiral HPLC and each enantiomer taken forward separately. Palladium(II) hydroxide-catalyzed hydrogenolysis of 16 could cleave both benzyl ether and benzylamine to provide amino alcohol 17, which can be converted to final compound 18 following previously described conditions.

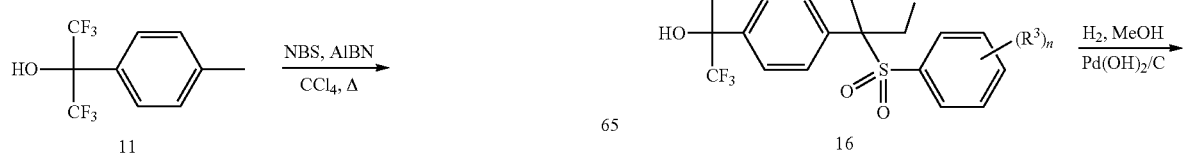

-continued

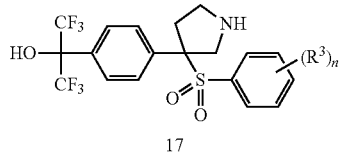

17

N-alkylation with alkyl halide, reductive alkylation with aldehyde and ketone

N-acylation with acids, acid chloride chloroformate, isocyanate, sulfonyl chloride, etc.

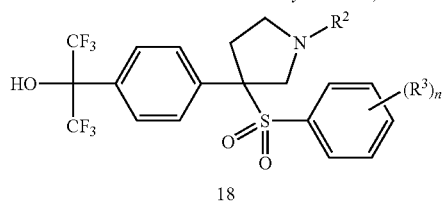

18

Compound 18 can also be useful intermediate for further derivatization (Scheme 3). For example, it can be alkylated with $R^{1a}$-halide (chloride, bromide or iodide) under basic conditions such as potassium carbonate or sodium hydride to give 19. Alternatively, compound 19 can be synthesized from 18 and alcohol $R^{1a}$—OH using Mitsunobu conditions involving an azodicarboxylate such as DEAD and a phosphine ligand such as triphenylphosphine or tributylphosphine. The hydroxyl group in 18 can also be replaced with a fluoro group using (diethylamino)sulfur trifluoride (DAST) to give perfluoroisopropyl analogue 20. In addition, the OH group in 18 can be arylated with diphenyliodonium iodide 21 using a base such as potassium methoxide or sodium hydride to give phenyl ether 22. All transformation in Scheme 3 can also be carried out on suitably protected pyrrolidine 18 ($R^2$=protecting group such as Bn, Boc or Cbz). Subsequent deprotection and chemical manipulation to install $R^2$ group would complete the synthesis.

Iodide 23, prepared from the sequence outlined in Scheme 1, can be a useful intermediate for further diversification to prepare 25, 27 and 28 (Scheme 4). It can be reacted with aryl/heteroaryl boronic acid (or ester) 24 under well-known Suzuki coupling conditions using a catalyst such as palladium tetrakis(triphenylphosphine) or Pd(dppf)Cl$_2$ to give compound 25. Compound 25 can also be obtained using Stille coupling conditions using aryl/heteroaryltin in place of the boronic acid 24. Iodide 23 can also be treated with tert-butyllithium or ethylmagensium bromide to produce the corresponding aryllithium or arylmagnesium species, which can react with ketone 26 to produce alcohol 27. Compound 27 can in turn be converted to ether 28 using previously described conditions. All transformation in Scheme 4 can also be performed on suitably protected pyrrolidine 23 ($R^2$=protecting group such as Bn, Boc or Cbz). Subsequent deprotection and chemical manipulation to install $R^2$ group would complete the synthesis.

Scheme 3

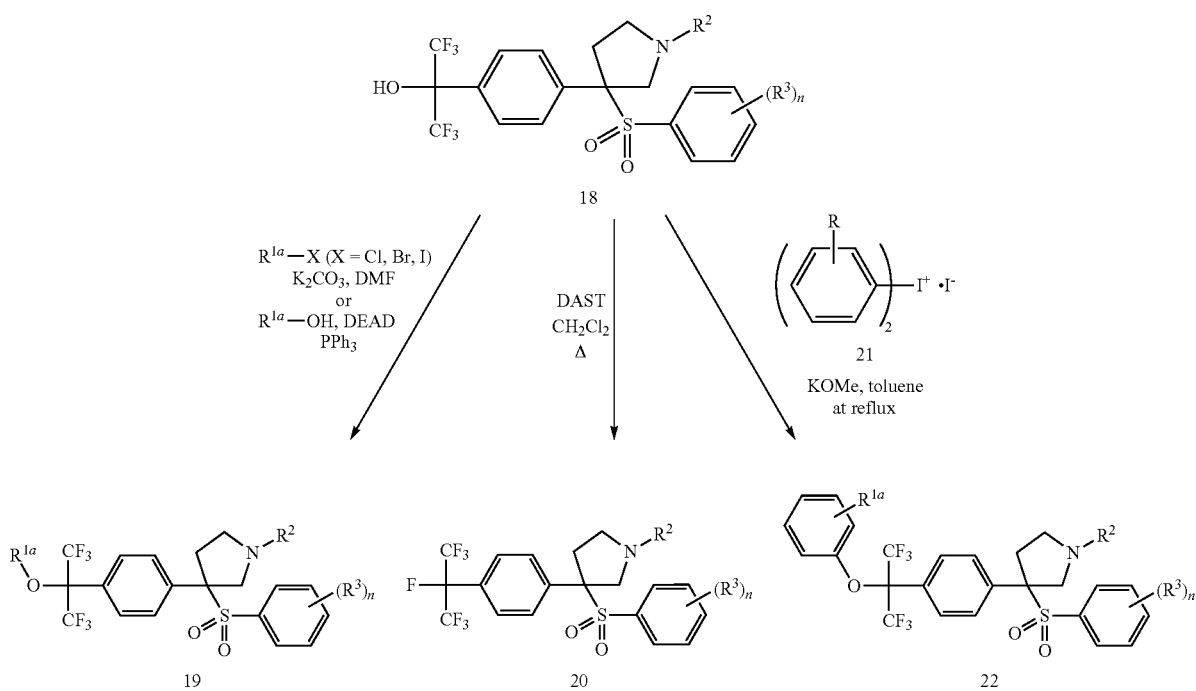

Scheme 4

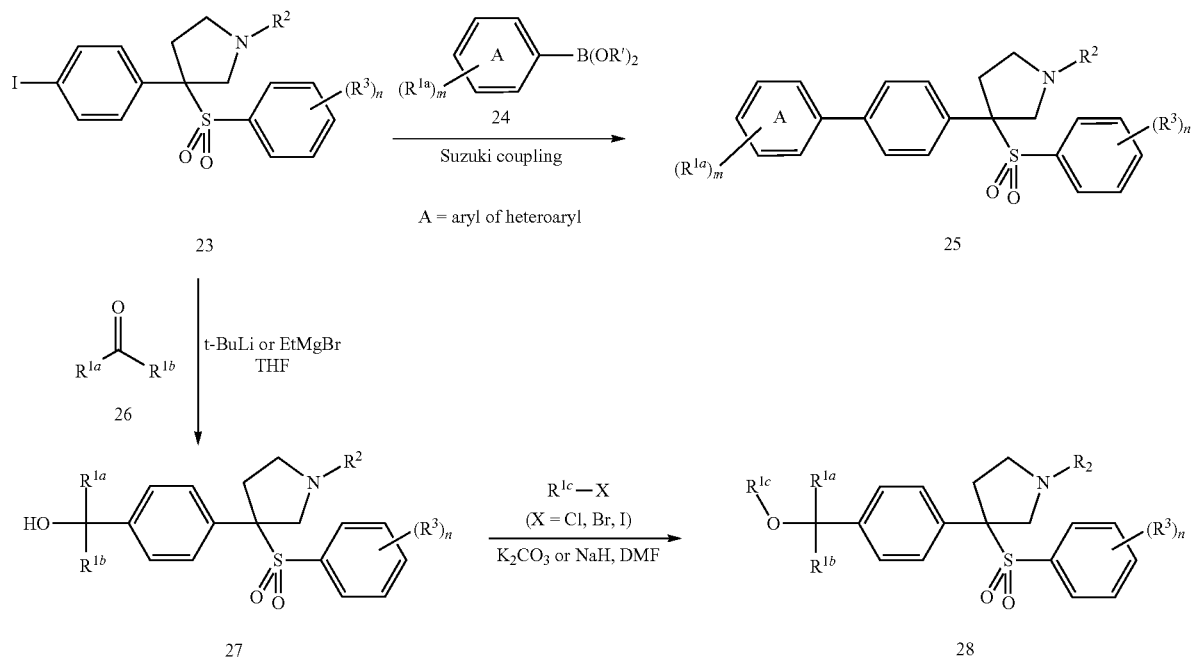

EXAMPLES

The following examples illustrate the particular and preferred embodiments of the present invention and do not limit the scope of the present invention. Chemical abbreviations and symbols as well as scientific abbreviations and symbols have their usual and customary meanings unless otherwise specified. Additional abbreviations employed in the Examples and elsewhere in this application are defined above. Common intermediates are generally useful for the preparation of more than one Example and are identified sequentially (e.g., Intermediate 1, Intermediate 2, etc.) and are abbreviated as Int. 1, Int. 2, etc. Compounds of the Examples are identified by the example and step in which they were prepared (e.g., "1-A" denotes the Example 1, step A), or by the example only where the compound is the title compound of the example (for example, "1" denotes the title compound of Example 1). In some instances alternate preparations of intermediates or examples are described. Frequently chemists skilled in the art of synthesis may devise alternative preparations which may be desirable based on one or more considerations such as shorter reaction time, less expensive starting materials, ease of operation, amenable to catalysis, avoidance of toxic reagents, accessibility of specialized instrumentation, and decreased number of linear steps, etc. The intent of describing alternative preparations is to further enable the preparation of the examples of this invention. In some instances some functional groups in the outlined examples and claims may be replaced by well known bioisosteric replacements known in the art, for example, replacement of a carboxylic acid group with a tetrazole or a phosphate moiety.

HPLC Conditions

Condition A:
Column: YMC Combiscreen ODS-A 4.6×50 mm (4 min.); Linear gradient of 0 to 100% solvent B over 4 min with 1 min hold at 100% B; UV visualization at 220 nm; Solvent A=10% MeOH, 90% $H_2O$, 0.2% $H_3PO_4$; Solvent B=90% MeOH, 10% $H_2O$, 0.2% $H_3PO_4$; Flow: 4 mL/min.

Condition B:
Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min.

Condition C:
Column: Waters Acquity UPLC BEH C18, 2.1×50 mm, 1.7-μm particles; Mobile Phase A: 5:95 acetonitrile:water with 0.05% TFA; Mobile Phase B: 95:5 acetonitrile: water with 0.05% TFA; Temperature: 50° C.; Gradient: 0-100% B over 3 minutes, then a 0.75-minute hold at 100% B; Flow: 1.11 mL/min.

Condition D:
Column: XBridge Phenyl, 4.6×150 mm, 3.5 micron; Mobile Phase A: 5:95 acetonitrile:water with 0.05% TFA; Mobile Phase B: 95:5 acetonitrile:water with 0.05% TFA; Gradient: 10-100% B over 25 minutes, then a 5-minute hold at 100% B; Flow: 1 mL/min.

Condition E:
Column: ZORBAX CN, 4.6×150 mm, 5 micron; Mobile Phase A: 5:95 acetonitrile:water with 10 mM ammonium acetate; Mobile Phase B: 95:5 acetonitrile:water with 10 mM ammonium acetate; Gradient: 10-100% B over 25 minutes, then a 5-minute hold at 100% B; Flow: 1 mL/min.

Condition F:
Column: SUNFIRE C18, 4.6×150 mm, 3.5 micron; Mobile Phase A: 5:95 acetonitrile:water with 0.05% TFA; Mobile Phase B: 95:5 acetonitrile:water with 0.05% TFA; Gradient: 10-100% B over 25 minutes, then a 5-minute hold at 100% B; Flow: 1 mL/min.

Condition G:
Column: Ascentis Express C18 (4.6×50) mm, 2.7 μm; Mobile Phase A: 5:95 acetonitrile:water with 10 mM ammonium acetate; Mobile Phase B: 95:5 acetonitrile:water with 10 mM ammonium acetate; Temperature: 45° C.; Gradient: 0-100% B over 4 minutes; Flow: 4.00 mL/min.
Condition H:
Column: Ascentis Express C18 (2.1×50) mm, 2.7 μm; Mobile Phase A: 5:95 acetonitrile:water with 10 mM ammonium acetate; Mobile Phase B: 95:5 acetonitrile:water with 10 mM ammonium acetate; Gradient: 0-100% B over 3.4 minutes; Flow: 1.11 mL/min.
Condition I:
Waters Acquity UPLC BEH C18 (2.1×50) mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 2-98% B over 1 minutes, then a 0.5-minute hold at 98% B; Flow: 0.80 mL/min.
Condition J:
Column: XBridge Phenyl, 3.0×150 mm, 3.5 micron; Mobile Phase A: 5:95 acetonitrile:water with 0.05% TFA; Mobile Phase B: 95:5 acetonitrile:water with 0.05% TFA; Gradient: 10-100% B over 12 minutes, then a 3-minute hold at 100% B; Flow: 1 mL/min.
Condition K:
Column: Phenomenex Kinetex, C18 (2.1×50) mm, 2.6 micron; Mobile Phase A: 10:90 acetonitrile:water with 0.1% TFA; Mobile Phase B: 90:10 acetonitrile:water with 0.1% TFA; Gradient: 0-100% B over 1.5 minutes, then a 0.5-minute hold at 100% B; Flow: 1 mL/min.
Condition L:
Column: SUNFIRE C18, 3.0×150 mm, 3.5 micron; Mobile Phase A: 5:95 acetonitrile:water with 0.05% TFA; Mobile Phase B: 95:5 acetonitrile:water with 0.05% TFA; Gradient: 10-100% B over 12 minutes, then a 3-minute hold at 100% B; Flow: 1 mL/min.

Intermediates 1 and 2

4-(ethoxycarbonyl)-1-hydroxycyclohexanecarboxylic acid

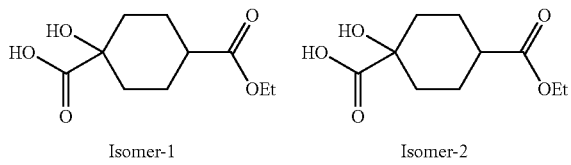 [SMILES: CCOC(=O)C1CCC(O)(C(=O)O)CC1 ; CCOC(=O)C1CCC(O)(C(=O)O)CC1]

Isomer-1        Isomer-2

Step A: ethyl 4-hydroxy-4-vinylcyclohexanecarboxylate

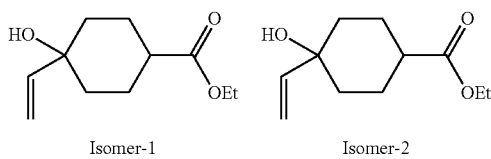

Isomer-1        Isomer-2

Cerium(III) chloride (3.04 g, 12.34 mmol) was added to a solution of ethyl 4-oxocyclohexanecarboxylate (2.10 g, 12.34 mmol) in tetrahydrofuran (20 mL). After 30 min at ambient temperature, the mixture was cooled down to −78° C. and added 1.0 M tetrahydrofuran solution of vinylmagnesium bromide (12.34 mL, 12.34 mmol) dropwise over 10 min. The resultant mixture was stirred at −78° C. for 30 min and warmed up to 0° C. for 1 h. The mixture was quenched with saturated ammonium chloride (10 mL), diluted with ethyl acetate (100 mL), washed with water (10 mL), brine (10 mL), dried (magnesium sulfate), filtered and concentrated under reduced pressure. Silica gel chromatography, eluting with 0-15% ethyl acetate in hexanes, gave the desired ethyl 4-hydroxy-4-vinylcyclohexanecarboxylate isomer-1 as the first eluent off the column (530 mg, 22% yield). 1H NMR (400 MHz, CDCl$_3$) δ ppm 5.94 (dd, J=17.4, 10.8 Hz, 1H), 5.26 (dd, J=17.3, 1.2 Hz, 1H), 5.04 (dd, J=10.8, 1.1 Hz, 1H), 4.16 (dq, J=18.3, 7.1 Hz, 2H), 2.94-2.64 (m, 1H), 2.55-2.41 (m, 2H), 2.41-2.15 (m, 2H), 2.04 (ddd, J=14.6, 9.8, 4.8 Hz, 1H), 1.93-1.77 (m, 2H), 1.74-1.65 (m, 1H), 1.40-1.06 (m, 3H). It also gave the desired ethyl 4-hydroxy-4-vinylcyclohexanecarboxylate isomer-2 as the second eluent off the column (790 mg, 32% yield). 1H NMR (400 MHz, CDCl$_3$) δ ppm 6.03 (dd, J=17.4, 10.8 Hz, 1H), 5.60-5.22 (m, 1H), 5.14 (dd, J=10.8, 1.1 Hz, 1H), 4.13 (q, J=7.2 Hz, 2H), 2.44 (tt, J=8.4, 4.2 Hz, 1H), 2.08-1.88 (m, 2H), 1.89-1.66 (m, 4H), 1.61-1.52 (m, 2H), 1.34-1.08 (m, 3H).

Step B: ethyl 4-formyl-4-hydroxycyclohexanecarboxylate

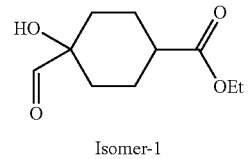 [SMILES: CCOC(=O)C1CCC(O)(C=O)CC1]

Isomer-1

Ozone was bubbled into a solution of ethyl 4-hydroxy-4-vinylcyclohexanecarboxylate isomer-1 (310 mg, 1.564 mmol) in dichloromethane (10 mL) at −78° C. until the mixture turned into blue color. Ozone was removed and bubbled with nitrogen until the blue color disappeared. The mixture was added dimethyl sulfide (0.231 mL, 3.13 mmol) and stirred at room temperature for 15 h. After evaporation of organic solvents, the residue was purified by silica gel chromatography, eluting with 0-50% ethyl acetate in hexanes, to give the desired ethyl 4-formyl-4-hydroxycyclohexanecarboxylate isomer-1 (126 mg, 40% yield). 1H NMR (400 MHz, CDCl$_3$) δ ppm 9.51 (s, 1H), 4.24-4.06 (m, 2H), 2.97 (s, 1H), 2.43-2.12 (m, 1H), 2.09-1.78 (m, 4H), 1.78-1.50 (m, 4H), 1.32-1.18 (m, 3H).

Step C: 4-(ethoxycarbonyl)-1-hydroxycyclohexanecarboxylic acid

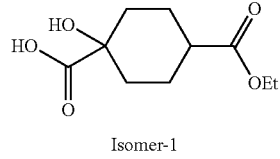 [SMILES: CCOC(=O)C1CCC(O)(C(=O)O)CC1]

Isomer-1

Sodium dihydrogen phosphate (162 mg, 1.348 mmol) and sodium chlorite (244 mg, 2.70 mmol) were added to a mixture of ethyl 4-formyl-4-hydroxycyclohexanecarboxylate isomer-1 (180 mg, 0.899 mmol) and 2.0 M tetrahydrofuran solution of 2-methylbut-2-ene (4.49 mL, 8.99 mmol) in tert-butanol (6 mL) and water (1.2 mL). The resultant mixture was stirred at room temperature for 15 h. After evaporation of organic solvents, the residue was diluted with dichloromethane (10 ml) and extracted with 0.5 N aqueous sodium hydroxide (2×10 mL). The combined aqueous layer was acidified to pH 2-3 with 1 N aqueous hydrochloric acid, diluted with ethyl acetate (100 mL), washed with brine (10 mL), dried (magnesium sulfate), filtered and concentrated under reduced pressure to provide the desired 4-(ethoxycarbonyl)-1-hydroxycyclohexanecarboxylic acid isomer-1 as crude material (120 mg). It was used without further purification. LC/MS (M−1): 215.3; LC retention time: 1.07 min (analytical HPLC Method I); 1HNMR (400 MHz, CDCl$_3$) δ ppm 4.14 (quin, J=7.0 Hz, 2H), 2.42-2.22 (m, 1H), 1.99-1.67 (m, 8H), 1.31-1.18 (m, 3H).

Step D: 4-(ethoxycarbonyl)-1-hydroxycyclohexanecarboxylic acid

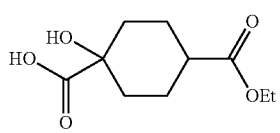

Isomer-2

Following similar procedures as Steps B and C, ethyl 4-hydroxy-4-vinylcyclohexanecarboxylate isomer-2 (320 mg, 1.614 mmol, from Step A) was converted to the desired 4-(ethoxycarbonyl)-1-hydroxycyclohexanecarboxylic acid isomer-2 as crude material (230 mg). It was used without further purification. LC/MS (M−1): 215.4; LC retention time: 1.04 min (analytical HPLC Method I); $^1$HNMR (400 MHz, CDCl$_3$) δ ppm 4.24-4.09 (m, 2H), 2.64-2.54 (m, 1H), 2.00-1.83 (m, 6H), 1.67-1.57 (m, 2H), 1.31-1.11 (m, 3H).

Intermediates 3 and 4

(1s,4s)-4-((benzyloxy)carbonyl)-1-methylcyclohexanecarboxylic acid & (1r,4r)-4-((benzyloxy)carbonyl)-1-methylcyclohexanecarboxylic acid

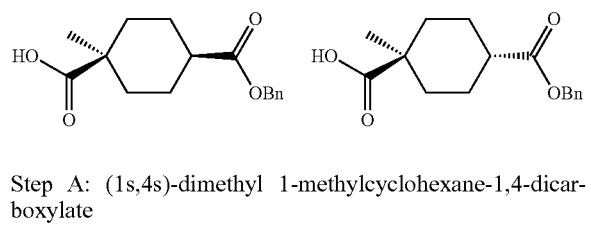

Step A: (1s,4s)-dimethyl 1-methylcyclohexane-1,4-dicarboxylate

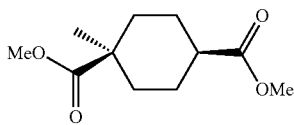

A 2.5 M hexanes solution of butyllithium (3.78 mL, 9.44 mmol) was added to another solution of diisopropylamine (1.345 mL, 9.44 mmol) in tetrahydrofuran (30 mL) at −78° C. and stirred at 0° C. for 30 min. The mixture was cooled down to −78° C. and added a solution of (1r,4r)-dimethyl cyclohexane-1,4-dicarboxylate (1.80 g, 8.99 mmol) in tetrahydrofuran (10 mL) dropwise over 10 min. The resultant mixture was stirred at −78° C. for 30 min and added iodomethane (0.562 mL, 8.99 mmol). The mixture was warmed up to room temperature and stirred for 2 h. After quenching with saturated ammonium chloride (5 mL), the mixture was diluted with ethyl acetate (300 mL), washed with water (30 mL), brine (30 mL), dried (magnesium sulfate), filtered and concentrated under reduced pressure. Silica gel chromatography, eluting with 0-20% ethyl acetate in hexanes, gave the desired (1s,4s)-dimethyl 1-methylcyclohexane-1,4-dicarboxylate (1.51 g, 78% yield). 1H NMR (400 MHz, CDCl$_3$) δ ppm 3.74-3.57 (m, 6H), 2.35-2.16 (m, 2H), 1.95-1.82 (m, 2H), 1.80-1.71 (m, 1H), 1.67-1.59 (m, 1H), 1.55-1.38 (m, 2H), 1.23-1.18 (m, 1H), 1.16 (s, 3H).

Step B: dimethyl 1-methylcyclohexane-1,4-dicarboxylate

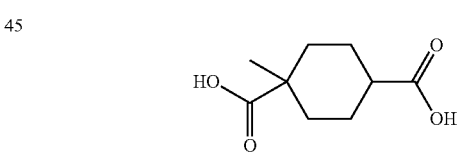

A 2.5 M hexanes solution of butyllithium (2.96 mL, 7.40 mmol) was added to another solution of diisopropylamine (1.055 mL, 7.40 mmol) in tetrahydrofuran (20 mL) at −78° C. and stirred at 0° C. for 30 min. The mixture was cooled down to −78° C. and added a solution of (1s,4s)-dimethyl 1-methylcyclohexane-1,4-dicarboxylate (1.51 g, 7.05 mmol) in tetrahydrofuran (5 mL). After stirring at −78° C. for 1 h, the mixture was quenched with methanol (2 mL) and warmed to room temperature. The mixture was diluted with ethyl acetate (100 mL), washed with water (10 mL), brine (10 mL), dried (magnesium sulfate), filtered and concentrated under reduced pressure. Silica gel chromatography, eluting with 0-20% ethyl acetate in hexanes, gave the desired dimethyl 1-methylcyclohexane-1,4-dicarboxylate as a 2 to 3 mixture of two isomers (1.25 g, 83% yield). 1H NMR showed two sets of signals for the cis and trans isomers.

Step C: 1-methylcyclohexane-1,4-dicarboxylic acid

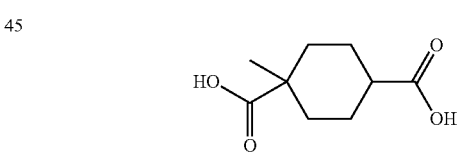

A 1 N aqueous solution of lithium hydroxide (13.72 mL, 13.72 mmol) was added to a mixture of dimethyl 1-methylcyclohexane-1,4-dicarboxylate (490 mg, 2.287 mmol) in tetrahydrofuran (20 mL). After stirring at ambient temperature for 48 h, the mixture was acidified to pH 2-3 with 1 N aqueous hydrochloric acid. After evaporation of organic solvents, the residue was treated with ethyl acetate (100 mL), washed with water (10 mL), brine (10 mL), dried (magnesium sulfate), filtered and concentrated under reduced pressure to give the desired 1-methylcyclohexane-1,4-dicarboxylic acid as crude material (400 mg, 94% yield). It was used without further purification. LC/MS (M−1): 185.3; LC retention time: 0.17 min (analytical HPLC Method I); 1H NMR showed two sets of signals for the cis and trans isomers.

Step D: (1s,4s)-4-((benzyloxy)carbonyl)-1-methylcyclohexanecarboxylic acid & (1r,4r)-4-((benzyloxy)carbonyl)-1-methylcyclohexanecarboxylic acid

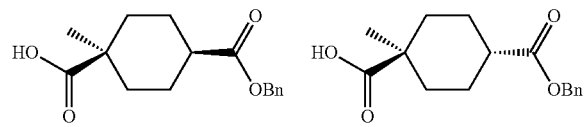 [SMILES: C[C@]1(C(=O)O)CC[C@@H](C(=O)OCc2ccccc2)CC1 ; C[C@]1(C(=O)O)CC[C@H](C(=O)OCc2ccccc2)CC1]

N,N-dimethylformamide (0.1 mL) was added to a solution of 1-methylcyclohexane-1,4-dicarboxylic acid (400 mg, 2.148 mmol) and oxalyl chloride (1.128 mL, 12.89 mmol) in dichloromethane (10 mL). After stirring at ambient temperature for 2 h, the mixture was concentrated under reduced pressure. The residue was dissolved in dichloromethane (10 mL), added pyridine (1.390 mL, 17.19 mmol) and cooled down to 0° C. The mixture was added a solution of benzyl alcohol (0.223 mL, 2.148 mmol) in dichloromethane (2 mL). After stirring at ambient temperature for 1 h, the mixture was diluted with dichloromethane (100 mL), washed with 1N aqueous hydrogen chloride (40 mL), brine (40 mL), dried (magnesium sulfate), filtered and concentrated under reduced pressure. Silica gel chromatography, eluting with 0-5% methanol in dichloromethane, gave the desired 4-((benzyloxy)carbonyl)-1-methylcyclohexanecarboxylic acid as a mixture of two isomers (410 mg, 69% yield). It was further separated by chiral OJ-H column (0.46×25 cm, 5 μm), CO$_2$/methanol (90/10), 40° C., 100 bars to afford the desired (1s,4s)-4-((benzyloxy)carbonyl)-1-methylcyclohexanecarboxylic acid as the first eluent off the column (160 mg). LC/MS (M−1): 275.3; LC retention time: 1.27 min (analytical HPLC Method I); 1H NMR (400 MHz, CDCl$_3$) δ ppm 7.65-6.95 (m, 5H), 5.10 (s, 2H), 2.51-2.21 (m, 3H), 1.93 (dd, J=14.0, 3.0 Hz, 2H), 1.77-1.47 (m, 2H), 1.23 (s, 3H), 1.19-0.80 (m, 2H). It also afforded the desired (1r,4r)-4-((benzyloxy)carbonyl)-1-methylcyclohexanecarboxylic acid as the second eluent off the column (130 mg). LC/MS (M−1): 275.3; LC retention time: 1.15 min (analytical HPLC Method I); 1H NMR (400 MHz, CDCl$_3$) δ ppm 7.63-7.24 (m, 5H), 5.11 (s, 2H), 2.41 (dd, J=8.1, 4.2 Hz, 1H), 2.02-1.74 (m, 6H), 1.74-1.43 (m, 2H), 1.23 (s, 3H).

Intermediate 5

(1s,4s)-4-(tert-butoxycarbonyl)-1-fluorocyclohexanecarboxylic acid

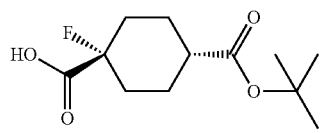 [SMILES: CC(C)(C)OC(=O)[C@H]1CC[C@](F)(C(=O)O)CC1]

Step A: (1s,4s)-dimethyl 1-fluorocyclohexane-1,4-dicarboxylate

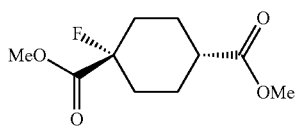 [SMILES: COC(=O)[C@H]1CC[C@](F)(C(=O)OC)CC1]

A 2.5 M hexanes solution of butyllithium (4.07 mL, 10.16 mmol) was added to another solution of diisopropylamine (1.448 mL, 10.16 mmol) in tetrahydrofuran (30 mL) at −78° C. and stirred at 0° C. for 30 min. The mixture was cooled down to −78° C. and added a solution of (1r,4r)-dimethyl cyclohexane-1,4-dicarboxylate (1.85 g, 9.24 mmol) in tetrahydrofuran (15 mL) dropwise over 10 min. The resultant mixture was stirred at −78° C. for 30 min and added a solution of N-fluorobenzenesulfonimide (3.06 g, 9.70 mmol) in tetrahydrofuran (15 mL). The mixture was warmed up to room temperature and stirred for 2 h. After quenching with saturated ammonium chloride (20 mL), the mixture was diluted with ethyl acetate (300 mL), washed with water (30 mL), brine (30 mL), dried (magnesium sulfate), filtered and concentrated under reduced pressure. Silica gel chromatography, eluting with 0-10% ethyl acetate in hexanes, gave the desired (1s,4s)-dimethyl 1-fluorocyclohexane-1,4-dicarboxylate as the second eluent off the column (330 mg, 16% yield, minor isomer). 1H NMR (400 MHz, CDCl$_3$) δ ppm 3.76 (s, 3H), 3.66 (s, 3H), 2.44-2.29 (m, 1H), 2.26-1.73 (m, 8H).

Step B: (1s,4s)-1-fluorocyclohexane-1,4-dicarboxylic acid

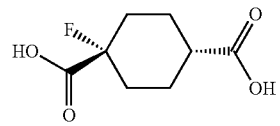

A 1 N aqueous solution of lithium hydroxide (4.95 mL, 4.95 mmol) was added to a mixture of (1s,4s)-dimethyl 1-fluorocyclohexane-1,4-dicarboxylate (180 mg, 0.825 mmol) in tetrahydrofuran (6 mL). After stirring at ambient temperature for 15 h, the mixture was acidified to pH 2-3 with 1 N aqueous hydrochloric acid. After evaporation of organic solvents, the residue was treated with ethyl acetate (100 mL), washed with water (10 mL), brine (10 mL), dried (magnesium sulfate), filtered and concentrated under reduced pressure to give the desired (1s,4s)-1-fluorocyclohexane-1,4-dicarboxylic acid as crude material (142 mg, 91% yield). It was used without further purification. 1H NMR (400 MHz, CD$_3$OD) δ ppm 2.55-2.33 (m, 1H), 2.33-2.11 (m, 1H), 2.10-1.80 (m, 5H), 1.72 (qd, J=12.6, 3.6 Hz, 2H).

Step C: (1s,4s)-4-(tert-butoxycarbonyl)-1-fluorocyclohexanecarboxylic acid

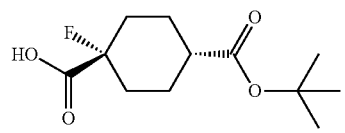 [SMILES: CC(C)(C)OC(=O)[C@H]1CC[C@](F)(C(=O)O)CC1]

N,N-dimethylpyridin-4-amine (9.64 mg, 0.079 mmol) was added to a solution of (1s,4s)-1-fluorocyclohexane-1,4-dicarboxylic acid (50 mg, 0.263 mmol) and di-tert-butyl dicarbonate (0.073 mL, 0.316 mmol) in tert-butanol (2 mL). After stirring at ambient temperature for 15 h, the mixture was treated with ethyl acetate (60 mL), washed with 0.2 N aqueous hydrogen chloride (5 mL), water (5 mL), brine (5 mL), dried (magnesium sulfate), filtered and concentrated under reduced pressure to give the desired (1s,4s)-4-(tert-butoxycarbonyl)-1-fluorocyclohexanecarboxylic acid as crude material (55 mg). It was used without further purification. LC/MS (M−1): 244.9; LC retention time: 0.94 min (analytical HPLC Method I).

Intermediate 6

(1r,4r)-4-((benzyloxy)carbonyl)-4-methylcyclohexanecarboxylic acid

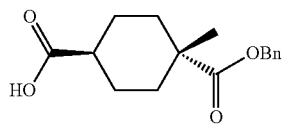 [SMILES: C[C@]1(C(=O)OCc2ccccc2)CC[C@H](C(=O)O)CC1]

Step A: 4-(tert-butoxycarbonyl)-1-methylcyclohexanecarboxylic acid

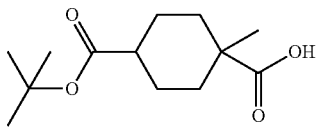

N,N-dimethylpyridin-4-amine (49.2 mg, 0.403 mmol) was added to a solution of 1-methylcyclohexane-1,4-dicarboxylic acid (250 mg, 1.343 mmol, from intermediate 3 Step C) and di-tert-butyl dicarbonate (0.468 mL, 2.104 mmol) in tert-butanol (8 mL). After stirring at ambient temperature for 15 h, the mixture was treated with ethyl acetate (100 mL), washed with 0.2 N aqueous hydrogen chloride (10 mL), water (10 mL), brine (10 mL), dried (magnesium sulfate), filtered and concentrated under reduced pressure to give the desired 4-(tert-butoxycarbonyl)-1-methylcyclohexanecarboxylic acid as crude material (310 mg). It was used without further purification. 1H NMR showed two sets of signals for the cis and trans isomers.
Step B: (1r,4r)-1-benzyl 4-tert-butyl 1-methylcyclohexane-1,4-dicarboxylate

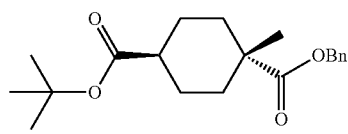 [SMILES: CC(C)(C)OC(=O)[C@H]1CC[C@](C)(C(=O)OCc2ccccc2)CC1]

Potassium carbonate (214 mg, 1.548 mmol) was added to a solution of 4-(tert-butoxycarbonyl)-1-methylcyclohexanecarboxylic acid (250 mg, 1.032 mmol) and benzyl bromide (0.184 mL, 1.548 mmol) in N,N-dimethylformamide (2 mL). After stirring at ambient temperature for 15 h, the mixture was treated with ethyl acetate (100 mL), washed with saturated ammonium chloride (10 mL), water (10 mL), brine (10 mL), dried (magnesium sulfate), filtered and concentrated under reduced pressure. Silica gel chromatography, eluting with 0-5% ethyl acetate in hexanes, gave the desired 1-benzyl 4-tert-butyl 1-methylcyclohexane-1,4-dicarboxylate as a mixture of two isomers (300 mg). It was further separated by chiral AD column (0.46×25 cm, 5 µm), CO₂/methanol (90/10), 40° C., 100 bars to afford the desired (1r,4r)-1-benzyl 4-tert-butyl 1-methylcyclohexane-1,4-dicarboxylate as the second eluent off the column (130 mg, 38% yield). 1H NMR (400 MHz, CDCl₃) δ ppm 7.43-7.27 (m, 5H), 5.12 (s, 2H), 2.30-2.12 (m, 1H), 1.91-1.76 (m, 2H), 1.76-1.53 (m, 6H), 1.44 (s, 9H), 1.22 (s, 3H).
Step C: (1r,4r)-4-((benzyloxy)carbonyl)-4-methylcyclohexanecarboxylic acid

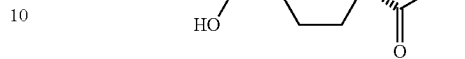

Trifluoroacetic acid (0.33 mL, 4.28 mmol) was added to a solution of (1r,4r)-1-benzyl 4-tert-butyl 1-methylcyclohexane-1,4-dicarboxylate (20 mg, 0.060 mmol) in dichloromethane (2 mL). After stirring at ambient temperature for 1 h, the mixture was concentrated under reduced pressure to give the desired (1r,4r)-4-((benzyloxy)carbonyl)-4-methylcyclohexanecarboxylic acid (16 mg, 96% yield). LC/MS (M+23): 299.2; LC retention time: 0.89 min (analytical HPLC Method C); 1H NMR (400 MHz, CD₃OD) δ ppm 7.74-7.06 (m, 5H), 5.14 (s, 2H), 2.45-2.31 (m, 1H), 1.93-1.68 (m, 7H), 1.68-1.60 (m, 1H), 1.22 (s, 3H).

Intermediate 7

(1r,4r)-1-fluorocyclohexane-1,4-dicarboxylic acid

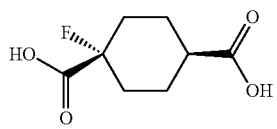

Step A: (1r,4r)-dimethyl 1-fluorocyclohexane-1,4-dicarboxylate

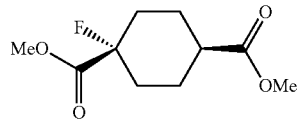 [SMILES: COC(=O)[C@H]1CC[C@@](F)(C(=O)OC)CC1]

A 2.5 M hexanes solution of butyllithium (4.07 mL, 10.16 mmol) was added to another solution of diisopropylamine (1.448 mL, 10.16 mmol) in tetrahydrofuran (30 mL) at −78° C. and stirred at 0° C. for 30 min. The mixture was cooled down to −78° C. and added a solution of (1r,4r)-dimethyl cyclohexane-1,4-dicarboxylate (1.85 g, 9.24 mmol) in tetrahydrofuran (15 mL) dropwise over 10 min. The resultant mixture was stirred at −78° C. for 30 min and added a solution of N-fluorobenzenesulfonimide (3.06 g, 9.70 mmol) in tetrahydrofuran (15 mL). The mixture was warmed up to room temperature and stirred for 2 h. After quenching with saturated ammonium chloride (20 mL), the mixture was diluted with ethyl acetate (300 mL), washed with water (30 mL), brine (30 mL), dried (magnesium sulfate), filtered and concentrated under reduced pressure. Silica gel chromatography, eluting with 0-10% ethyl acetate in hexanes, gave the desired (1r,4r)-dimethyl 1-fluorocyclohexane-1,4-dicarboxylate as the first eluent off the column (940 mg, 47% yield, major isomer). 1H NMR (400 MHz, CDCl₃) δ ppm 3.74 (s, 3H), 3.67 (s, 3H), 2.60 (t, J=4.7 Hz, 1H), 2.15-1.72 (m, 8H).

Step B: (1r,4r)-1-fluorocyclohexane-1,4-dicarboxylic acid

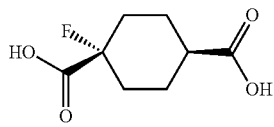 [SMILES: O=C(O)[C@H]1CC[C@@](F)(C(=O)O)CC1]

A 1 N aqueous solution of lithium hydroxide (7.52 mL, 7.52 mmol) was added to a mixture of (1r,4r)-dimethyl 1-fluorocyclohexane-1,4-dicarboxylate (205 mg, 0.939 mmol) in THF (8 mL). After stirring at ambient temperature for 15 h, the mixture was acidified to pH 2-3 with 1 N aqueous hydrochloric acid. After evaporation of organic solvents, the residue was treated with ethyl acetate (100 mL), washed with water (10 mL), brine (10 mL), dried (magnesium sulfate), filtered and concentrated under reduced pressure to give the desired (1r,4r)-1-fluorocyclohexane-1,4-dicarboxylic acid as crude material (170 mg, 95% yield). It was used without further purification. 1H NMR (400 MHz, CD$_3$OD) δ ppm 2.61 (t, J=4.6 Hz, 1H), 2.24-1.94 (m, 5H), 1.93-1.74 (m, 4H).

Intermediate 8

(1r,4r)-4-((benzyloxy)carbonyl)-4-ethylcyclohexanecarboxylic acid

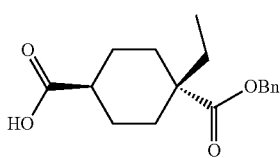 [SMILES: CC[C@]1(C(=O)OCc2ccccc2)CC[C@H](C(=O)O)CC1]

Step A: Dimethyl 4-vinylcyclohex-1-ene-1,4-dicarboxylate

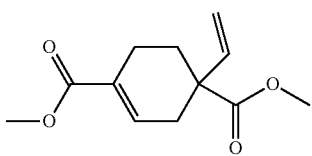

To a stirred solution of methyl 3-hydroxy-2-methylenebutanoate (2.56 g, 21.13 mmol) in DCM (150 mL) at 0° C. under inert atmosphere was added TEA (11.78 mL, 85 mmol) followed by methanesulfonyl Chloride (2.14 mL, 27.5 mmol). The reaction mixture was allowed to reach room temperature and stirring was continued. After 12 h, the reaction mixture was quenched with water (50 mL) and extracted with DCM (3×50 mL). The combined organic layer was washed with 1.5 N HCl (2×50 mL) followed by 50 mL saturated brine solution, dried over anhydrous sodium sulphate, filtered and concentrated under reduced pressure to get crude as pale yellow liquid (3.7 gm). The crude was purified by ISCO Combi-Flash chromatogram (24 g Red-Sep Silica column was used; eluted with 5-7% EtOAc in Pet Ether) to yield dimethyl 4-vinylcyclohex-1-ene-1,4-dicarboxylate (1.9 g, 8.47 mmol, 40.1% yield) as colorless liquid. $^1$H NMR (300 MHz, CDCl$_3$): δ ppm 6.97 (m, 1H), 5.89 (dd, J=18, 9 Hz, 1H), 5.02-5.20 (m, 2H), 3.73 (s, 3H), 3.69 (s, 3H), 2.92-2.72 (m, 1H), 2.45-2.25 (m, 3H), 2.20-2.02 (m, 1H), 1.92-1.72 (m, 1H).

Step B: (1r,4r)-dimethyl 1-ethylcyclohexane-1,4-dicarboxylate

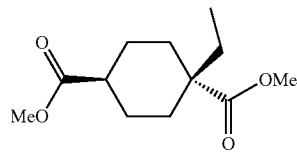 [SMILES: CC[C@]1(C(=O)OC)CC[C@H](C(=O)OC)CC1]

To a solution of dimethyl 4-vinylcyclohex-1-ene-1,4-dicarboxylate (1 g, 4.46 mmol) in DCM (100 mL) was added CRABTREE'S CATALYST (0.072 g, 0.089 mmol). The solution was stirred under hydrogen atmosphere (Bladder pressure). The progress of the reaction was monitored by $^1$H-NMR. After 24 h it showed a proton signal at δ 6.9 ppm to indicate the reaction is not completed. Another portion of CRABTREE'S CATALYST (0.072 g, 0.089 mmol) was again added to the reaction mixture and stirring was continued for another 24 hours. After completion, DCM was completely evaporated from the reaction mixture under reduced pressure to yield brownish gummy-solid crude (1.2 g). To the crude was added 30 mL diethyl-ether & stirred for 5 min, yellowish solids were precipitated out from the solution. The solution was filtered & the solids were washed twice with 15 mL diethyl-ether. Combined ether solution was evaporated to yield crude yellow liquid (1.1 gm). The material thus obtained was purified by ISCO Combi-Flash Silica column chromatogram (12 g Red-Sep Silica column was used; eluted with 5% EtOAc in Pet Ether) to yield (1r,4r)-dimethyl 1-ethylcyclohexane-1,4-dicarboxylate (1 g, 4.38 mmol, 98% yield) as colorless liquid. $^1$H NMR (300 MHz, CDCl$_3$): δ ppm 3.69 (s, 6H), 2.52-2.28 (m, 1H), 1.90-1.50 (m, 10H), 0.82 (t, J=3.9 Hz, 3H).

Step C: ((1r,4r)-1-ethylcyclohexane-1,4-diyl-1)dimethanol

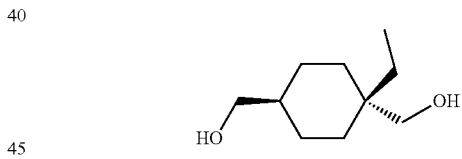

A Toluene (25 mL) solution of (1r,4r)-dimethyl 1-ethylcyclohexane-1,4-dicarboxylate (200 mg, 0.876 mmol) was cooled to −78° C. under argon atmosphere. To the above solution, was slowly (drop-wise over 10 min) added DIBAL-H (4.38 mL, 4.38 mmol). After complete addition, it was allowed to reach room temperature and stirred for 1 h. Progress of the reaction was monitored by TLC (using 10% EtOAc in Hexanes). After complete conversion, the reaction mixture was cooled to 0° C. and slowly quenched with saturated solution of ammonium chloride (~5 mL). The mixture was further diluted with 30 mL of ammonium chloride solution and extracted with 3×30 mL EtOAc. Combined Organic layer was separated out, washed with brine (40 mL), dried over sodium sulphate and concentrated under reduced pressure to yield colorless liquid of ((1r,4r)-1-ethylcyclohexane-1,4-diyl)dimethanol (150 mg, 0.871 mmol, 99% yield). $^1$H NMR (300 MHz, CDCl$_3$): δ ppm 3.52-3.45 (m, 2H), 3.35-3.29 (m, 2H), 1.67-1.50 (m, 3H), 1.43 (q, J=7.6 Hz, 2H), 1.28-1.05 (m, 6H), 0.79 (t, J=7.6 Hz, 3H).

Step D: (1r,4r)-1-ethylcyclohexane-1,4-dicarboxylic acid

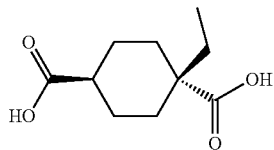

To a solution of ((1r,4r)-1-ethylcyclohexane-1,4-diyl)dimethanol (150 mg, 0.871 mmol) in Acetone (15 mL) at 0° C. was slowly added freshly prepared chromic acid solution [prepared by adding $H_2SO_4$ (0.278 mL, 5.22 mmol) to a cold solution of sodiumdichromate.$2H_2O$ (1038 mg, 3.48 mmol) in 5 mL water at 0° C. with stirring for 10 min]. The resulting reaction mixture was stirred at room temperature for 3 h. Reaction monitored by TLC. After completion of the reaction, acetone was evaporated under reduced pressure and the remaining aqueous portion was extracted with 3×10 mL EtOAc. The combined Organic layer (slight reddish in color) was repeatedly washed with Brine (15 mL in each wash) until the organic layer became colorless. The colorless organic layer was then dried over sodium-sulphate and concentrated to yield white solids of (1r,4r)-1-ethylcyclohexane-1,4-dicarboxylic acid (117 mg, 0.584 mmol, 67.1% yield). $^1$H NMR (400 MHz, DMSO-d6): δ ppm 12.08 (br-s, 2H), 2.35-2.24 (m, 1H), 1.73-1.57 (m, 6H), 1.55-1.40 (m, 4H), 0.75 (t, J=8.0 Hz, 3H).

Step E: (1r,4r)-4-(tert-butoxycarbonyl)-1-ethylcyclohexanecarboxylic acid

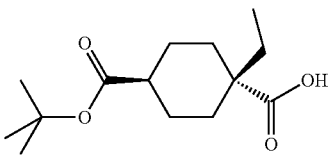 [SMILES: CC[C@]1(C(=O)O)CC[C@H](C(=O)OC(C)(C)C)CC1]

Boc$_2$O (0.139 mL, 0.599 mmol) and DMAP (7.32 mg, 0.060 mmol) was added to a solution of (1r,4r)-1-ethylcyclohexane-1,4-dicarboxylic acid (120 mg, 0.599 mmol) in t-BuOH (0.23 mL) The mixture was stirred at 25° C. for 3 h. t-BuOH was evaporated from the mixture and the remaining gummy material was diluted with 15 mL water. The aqueous mixture was extracted with 3×10 mL EtOAc. Combined Organic layer was separated out, washed with brine (20 mL), dried over sodium sulphate and concentrated under reduced pressure to yield light yellowish gummy solids (115 mg) of crude product, which was purified by Preparative HPLC to yield white solids of pure (1r,4r)-4-(tert-butoxycarbonyl)-1-ethylcyclohexanecarboxylic acid (59.33 mg, 0.231 mmol, 38.5% yield). $^1$H NMR (400 MHz, DMSO-d6): δ ppm 12.10 (s, 1H), 2.25-2.30 (m, 1H), 1.45-1.80 (m, 10H), 1.39 (s, 9H), 0.74 (t, J=7.6 Hz, 3H). LCMS (ELSD): Method Info: ACN/$H_2O$ with NH$_4$COOH, Ascentis Express C18 (50×2.1 mm-2.7 μm), gradient=4 min; 98.73% product @ RT=2.04 min [ADC1 A, ADC1 CHANNEL A]; MS (ES): m/z=255.2 [M−1; −Ve mode]. HPLC purity (ELSD): Method Info: 95/05 to 05/95 $H_2O$/CH$_3$CN; 0.05% TFA, flow=1 mL/min, gradient=30 min, Xbridge-Phenyl 3.5 μm 150×4.6 mm: RT=14.00 min; 99.81% purity.

Step F: (1r,4r)-1-benzyl 4-tert-butyl 1-ethylcyclohexane-1,4-dicarboxylate

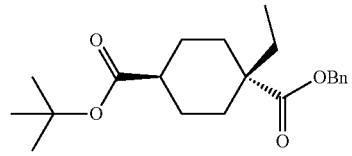 [SMILES: CC[C@]1(C(=O)OCc2ccccc2)CC[C@H](C(=O)OC(C)(C)C)CC1]

Potassium carbonate (20.2 mg, 0.146 mmol) was added to a solution of (1r,4r)-4-(tert-butoxycarbonyl)-1-ethylcyclohexanecarboxylic acid (25 mg, 0.098 mmol) and benzyl bromide (0.017 mL, 0.146 mmol) in N,N-dimethylformamide (0.5 mL). After stirring at ambient temperature for 15 h, the mixture was treated with ethyl acetate (60 mL), washed with saturated ammonium chloride (5 mL), water (5 mL), brine (5 mL), dried (magnesium sulfate), filtered and concentrated under reduced pressure. Silica gel chromatography, eluting with 0-5% ethyl acetate in hexanes, gave the desired (1r,4r)-1-benzyl 4-tert-butyl 1-ethylcyclohexane-1,4-dicarboxylate (29 mg, 86% yield). 1H NMR (400 MHz, CDCl$_3$) δ ppm 7.56-7.23 (m, 5H), 5.12 (s, 2H), 2.43-2.13 (m, 1H), 1.89-1.53 (m, 10H), 1.44 (s, 9H), 0.76 (t, J=7.5 Hz, 3H).

Step G: (1r,4r)-4-((benzyloxy)carbonyl)-4-ethylcyclohexanecarboxylic acid

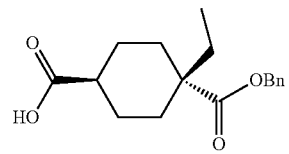 [SMILES: CC[C@]1(C(=O)OCc2ccccc2)CC[C@H](C(=O)O)CC1]

Trifluoroacetic acid (0.30 mL, 3.89 mmol) was added to a solution of (1r,4r)-1-benzyl 4-tert-butyl 1-ethylcyclohexane-1,4-dicarboxylate (29 mg, 0.084 mmol) in dichloromethane (1 mL). After stirring at ambient temperature for 1 h, the mixture was concentrated under reduced pressure to give the desired (1r,4r)-4-((benzyloxy)carbonyl)-4-ethylcyclohexanecarboxylic acid (24 mg, 99% yield). LC/MS (M+23): 313.2; LC retention time: 0.94 min (analytical HPLC Method C); 1H NMR (400 MHz, CD$_3$OD) δ ppm 7.81-7.14 (m, 5H), 5.13 (s, 2H), 2.63-2.23 (m, 1H), 1.98-1.58 (m, 10H), 0.75 (t, J=7.6 Hz, 3H).

Intermediate 9

(1r,4r)-4-(methoxycarbonyl)bicyclo[2.2.1]heptane-1-carboxylic acid

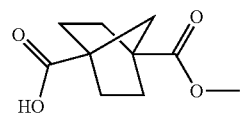

Step A: (1r,4r)-dimethyl bicyclo[2.2.1]heptane-1,4-dicarboxylate

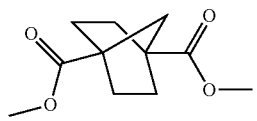

A 2.5 M hexanes solution of butyllithium (2.74 mL, 6.85 mmol) was added to another solution of diisopropylamine (0.976 mL, 6.85 mmol) in tetrahydrofuran (15 mL) at −78° C. and stirred at 0° C. for 30 min. The mixture was cooled down to −78° C. and added a solution of (1R,3S)-dimethyl cyclopentane-1,3-dicarboxylate (510 mg, 2.74 mmol) in tetrahydrofuran (2 mL) dropwise over 5 min. The resultant mixture was stirred at −78° C. for 30 min and added a solution of 1-bromo-2-chloroethane (589 mg, 4.11 mmol) in tetrahydrofuran (2 mL). The mixture was warmed up to room temperature and stirred for 2 h. After quenching with saturated ammonium chloride (5 mL), the mixture was diluted with ethyl acetate (100 mL), washed with water (10 mL), brine (10 mL), dried (magnesium sulfate), filtered and concentrated under reduced pressure. Silica gel chromatography, eluting with 0-10% ethyl acetate in hexanes, gave the desired (1r,4r)-dimethyl bicyclo[2.2.1]heptane-1,4-dicarboxylate (425 mg, 73% yield). 1H NMR (400 MHz, CDCl$_3$) δ ppm 3.69-3.56 (m, 6H), 2.00 (m, 4H), 1.88 (s, 2H), 1.69-1.60 (m, 4H).

Step B: (1r,4r)-4-(methoxycarbonyl)bicyclo[2.2.1]heptane-1-carboxylic acid

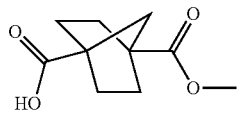

A solution of sodium hydroxide (80 mg, 2.002 mmol) in methanol (1 mL) was added to a mixture of (1r,4r)-dimethyl bicyclo[2.2.1]heptane-1,4-dicarboxylate (425 mg, 2.002 mmol) in tetrahydrofuran (15 mL). After stirring at ambient temperature for 15 h, organic solvents were removed under reduced pressure. The residue was dissolved in water (10 mL), acidified to pH 2-3 with 1 N aqueous hydrochloric acid and extracted with ethyl acetate (3×30 mL). The combined organic layer was washed with water (10 mL), brine (10 mL), dried (magnesium sulfate), filtered and concentrated under reduced pressure to give the desired (1r,4r)-4-(methoxycarbonyl)bicyclo[2.2.1]heptane-1-carboxylic acid as crude material (310 mg, 78% yield). It was used without further purification. 1H NMR (400 MHz, CDCl$_3$) δ ppm 3.70 (s, 3H), 2.13-2.00 (m, 4H), 1.95 (s, 2H), 1.77-1.60 (m, 4H).

Intermediate 10

(1r,4r)-4-(1H-tetrazol-5-yl)cyclohexanecarboxylic acid

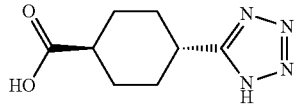 [SMILES: O=C(O)[C@H]1CC[C@H](c2nnn[nH]2)CC1]

Step A: (1r,4r)-methyl 4-carbamoylcyclohexanecarboxylate

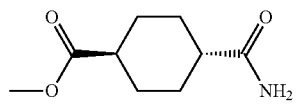

A mixture of (1r,4r)-4-(methoxycarbonyl)cyclohexanecarboxylic acid (560 mg, 3.01 mmol), BOP (1397 mg, 3.16 mmol) and 30% aqueous ammonia (0.868 mL, 12.03 mmol) in N,N-dimethylformamide (10 mL) was stirred at room temperature for 2 h. The mixture was diluted with ethyl acetate (200 mL), washed with water (20 mL), brine (20 mL), dried (magnesium sulfate), filtered and concentrated under reduced pressure to give the desired (1r,4r)-methyl 4-carbamoylcyclohexanecarboxylate as crude material (530 mg, 95% yield). It was used without further purification. LC/MS (M+1): 186.2; LC retention time: 0.84 min (analytical HPLC Method C); 1H NMR (400 MHz, CDCl$_3$) δ ppm 3.67 (s, 3H), 2.40-2.22 (m, 1H), 2.21-1.96 (m, 5H), 1.88-1.84 (m, 2H), 1.57-1.42 (m, 4H).

Step B: (1r,4r)-methyl 4-cyanocyclohexanecarboxylate

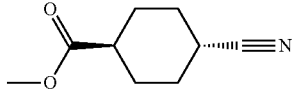

Trifluoroacetic acid anhydride (2.379 mL, 16.84 mmol) was added to a solution of (1r,4r)-methyl 4-carbamoylcyclohexanecarboxylate (520 mg, 2.81 mmol) in pyridine (1.817 mL, 22.46 mmol) at 0° C. After stirring at ambient temperature for 2 h, the mixture was diluted with dichloromethane (100 mL), washed with 1N aqueous hydrogen chloride (10 mL), water (10 mL), brine (10 mL), dried (magnesium sulfate), filtered and concentrated under reduced pressure. Silica gel chromatography, eluting with 0-20% ethyl acetate in hexanes, gave the desired (1r,4r)-methyl 4-cyanocyclohexanecarboxylate (320 mg, 68% yield). 1H NMR (400 MHz, CDCl$_3$) δ ppm 3.70 (br. s, 3H), 2.64-2.32 (m, 2H), 2.26-1.97 (m, 4H), 1.72-1.39 (m, 4H).

Step C: (1r,4r)-methyl 4-(1H-tetrazol-5-yl)cyclohexanecarboxylate

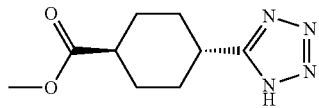

A mixture of (1r,4r)-methyl 4-cyanocyclohexanecarboxylate (150 mg, 0.897 mmol) and azidotributyltin (0.737 mL, 2.69 mmol) in 1,4-dioxane (0.8 mL) and N-methylpyrrolidone (0.2 mL) was heated to 200° C. under microwave for 1 h. The mixture was diluted with ethyl acetate (100 mL), washed with water (10 mL), brine (10 mL), dried (magnesium sulfate), filtered and concentrated under reduced pressure. Silica gel chromatography, eluting with 0-10% methanol in dichloromethane, gave the desired (1r,4r)-methyl 4-(1H-tetrazol-5-yl)cyclohexanecarboxylate (95 mg, 50% yield). LC/MS (M+1): 211.1; LC retention time: 0.56 min (analytical HPLC Method C).

Step D: (1r,4r)-4-(1H-tetrazol-5-yl)cyclohexanecarboxylic acid

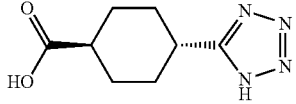 [SMILES: O=C(O)[C@H]1CC[C@H](c2nnn[nH]2)CC1]

A 1N aqueous solution of lithium hydroxide (1.808 mL, 1.808 mmol) was added to a mixture of (1r,4r)-methyl 4-(1H-tetrazol-5-yl)cyclohexanecarboxylate (95 mg, 0.452 mmol) in tetrahydrofuran (4 mL). After stirring at ambient temperature for 15 h, tetrahydrofuran was removed under reduced pressure. The residue was diluted with water (5 mL), acidified to pH 2-3 with 1 N aqueous hydrochloric acid and extracted with ethyl acetate (3×30 mL). The combined organic layer was washed with water (10 mL), brine (10 mL), dried (magnesium sulfate), filtered and concentrated under reduced pressure to give the desired (1r,4r)-4-(1H-tetrazol-5-yl)cyclohexanecarboxylic acid as crude material (85 mg, 96% yield). It was used without further purification. LC/MS (M+1): 197.2; LC retention time: 0.46 min (analytical HPLC Method C); 1H NMR (400 MHz, CD$_3$OD) δ ppm 3.13-2.98 (m, 1H), 2.40 (t, J=3.4 Hz, 1H), 2.23-2.14 (m, 4H), 1.70-1.59 (m, 4H).

Intermediate 11

4-((benzyloxy)carbonyl)-2-oxabicyclo[2.2.2]octane-1-carboxylic acid

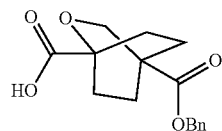

Step A: benzyl 1-vinyl-2-oxabicyclo[2.2.2]octane-4-carboxylate

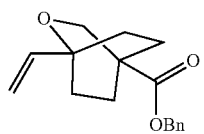 [SMILES: C=CC12CCC(C(=O)OCc3ccccc3)(CC1)CO2]

Potassium carbonate (1.775 g, 12.84 mmol) was added to a solution of benzyl 1-vinyl-2-oxabicyclo[2.2.2]octane-4-carboxylate (780 mg, 4.28 mmol, prepared following literature procedure, WO2013003383) and benzyl bromide (0.764 mL, 6.42 mmol) in N,N-dimethylformamide (10 mL). After stirring at ambient temperature for 15 h, the mixture was treated with ethyl acetate (200 mL), washed with saturated ammonium chloride (20 mL), water (20 mL), brine (20 mL), dried (magnesium sulfate), filtered and concentrated under reduced pressure. Silica gel chromatography, eluting with 0-10% ethyl acetate in hexanes, gave the desired benzyl 1-vinyl-2-oxabicyclo[2.2.2]octane-4-carboxylate (990 mg, 85% yield). LC/MS (M+1): 273.1; LC retention time: 1.03 min (analytical HPLC Method C); 1H NMR (400 MHz, CDCl$_3$) δ ppm 7.48-7.28 (m, 5H), 5.81 (dd, J=17.5, 10.9 Hz, 1H), 5.16 (dd, J=17.5, 1.3 Hz, 1H), 5.11 (s, 2H), 5.03 (dd, J=11.0, 1.3 Hz, 1H), 4.06 (t, J=1.3 Hz, 2H), 2.09-1.85 (m, 6H), 1.81-1.67 (m, 2H).

Step B: benzyl 1-formyl-2-oxabicyclo[2.2.2]octane-4-carboxylate

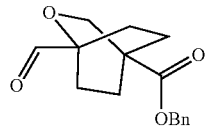 [SMILES: O=CC12CCC(C(=O)OCc3ccccc3)(CC1)CO2]

Ozone was bubbled into a solution of benzyl 1-vinyl-2-oxabicyclo[2.2.2]octane-4-carboxylate (505 mg, 1.854 mmol) in dichloromethane (10 mL) at −78° C. until the mixture turned into blue color. Ozone was removed and bubbled with nitrogen until the blue color disappeared. The mixture was added dimethyl sulfide (0.274 mL, 3.71 mmol) and stirred at room temperature for 15 h. The mixture was diluted with dichloromethane (100 mL), washed with water (10 mL), brine (10 mL), dried (magnesium sulfate), filtered and concentrated under reduced pressure to give the desired benzyl 1-formyl-2-oxabicyclo[2.2.2]octane-4-carboxylate as crude material (530 mg). It was used without further purification. 1H NMR (400 MHz, CDCl$_3$) δ ppm 9.56 (s, 1H), 7.60-7.25 (m, 5H), 5.10 (s, 2H), 4.09 (s, 2H), 2.13-1.69 (m, 8H).

Step C: 4-((benzyloxy)carbonyl)-2-oxabicyclo[2.2.2]octane-1-carboxylic acid

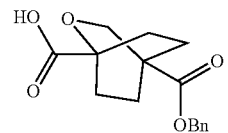

Sodium dihydrogen phosphate (334 mg, 2.78 mmol) and sodium chlorite (503 mg, 5.57 mmol) were added to a mixture of benzyl 1-formyl-2-oxabicyclo[2.2.2]octane-4-carboxylate (509 mg, 1.856 mmol) and 2.0 M tetrahydrofuran solution of 2-methylbut-2-ene (9.28 mL, 18.56 mmol) in tert-butanol (30 mL) and water (10 mL). The resultant mixture was stirred at room temperature for 15 h. After evaporation of organic solvents, the residue was treated with water (30 ml) and extracted with ethyl acetate (3×50 mL). The combined organic layer washed with brine (10 mL), dried (magnesium sulfate), filtered and concentrated under reduced pressure to provide the desired 4-((benzyloxy)carbonyl)-2-oxabicyclo[2.2.2]octane-1-carboxylic acid as crude material (460 mg, 85% yield). It was used without further purification. LC/MS (M+1): 291.1; LC retention time: 0.81 min (analytical HPLC Method C); $^1$HNMR (400 MHz, CD$_3$OD) δ ppm 7.54-7.18 (m, 5H), 5.13 (s, 2H), 4.04 (s, 2H), 2.22-1.86 (m, 8H), 1.54-1.17 (m, 1H), 0.98-0.80 (m, 1H).

Intermediate 12

1-(methoxycarbonyl)-2-oxabicyclo[2.2.2]octane-4-carboxylic acid

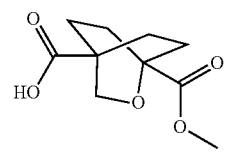

Step A: 4-benzyl 1-methyl 2-oxabicyclo[2.2.2]octane-1,4-dicarboxylate

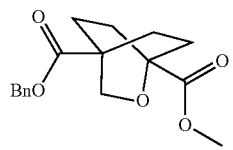 [SMILES: COC(=O)C12CCC(C(=O)OCc3ccccc3)(CC1)CO2]

A 0.6 M hexanes solution of trimethylsilyldiazomethane (1.722 mL, 1.033 mmol) was added to a mixture of 4-((benzyloxy)carbonyl)-2-oxabicyclo[2.2.2]octane-1-carboxylic acid (150 mg, 0.517 mmol, intermediate 11) in toluene (8 mL) and methanol (2 mL). After stirring at ambient temperature for 1 h, the mixture was concentrated under reduced pressure. Silica gel chromatography, eluting with 0-40% ethyl acetate in hexanes, gave the desired 4-benzyl 1-methyl 2-oxabicyclo[2.2.2]octane-1,4-dicarboxylate (130 mg, 83% yield). LC/MS (M+1): 305.1; LC retention time: 0.92 min (analytical HPLC Method C); 1H NMR (400 MHz, CD$_3$OD) δ ppm 7.46-7.17 (m, 5H), 5.09 (s, 2H), 4.08 (s, 2H), 3.73 (s, 3H), 2.19-1.86 (m, 8H).

Step B: 1-(methoxycarbonyl)-2-oxabicyclo[2.2.2]octane-4-carboxylic acid

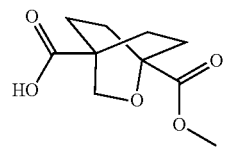

A mixture of 4-benzyl 1-methyl 2-oxabicyclo[2.2.2]octane-1,4-dicarboxylate (130 mg, 0.427 mmol) and 10% palladium on carbon (45.5 mg, 0.043 mmol) in methanol (10 mL) was hydrogenated under 40 psi hydrogen using a Parr Shaker for 2 h. The mixture was filtered to remove the catalyst. The filtrate was concentrated to give the desired 1-(methoxycarbonyl)-2-oxabicyclo[2.2.2]octane-4-carboxylic acid (90 mg, 98% yield). LC/MS (M+1): 215.1; LC retention time: 0.55 min (analytical HPLC Method C); $^1$H NMR (400 MHz, CD$_3$OD) δ ppm 4.04 (s, 2H), 3.73 (s, 3H), 2.19-1.91 (m, 8H).

Intermediate 13

4-(tert-butoxycarbonyl)-1-(methoxymethyl)cyclohexanecarboxylic acid

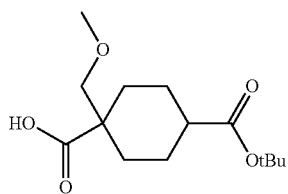 [SMILES: COCC1(C(=O)O)CCC(C(=O)OC(C)(C)C)CC1]

Step A: (1s,4s)-dimethyl 1-(methoxymethyl)cyclohexane-1,4-dicarboxylate

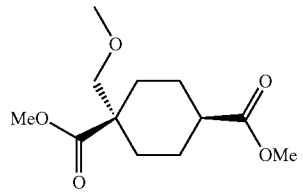 [SMILES: COC[C@]1(C(=O)OC)CC[C@@H](C(=O)OC)CC1]

A 2.5 M hexanes solution of butyllithium (2.088 mL, 5.22 mmol) was added to another solution of diisopropylamine (0.744 mL, 5.22 mmol) in tetrahydrofuran (20 mL) at −78° C. and stirred at 0° C. for 30 min. The mixture was cooled down to −78° C. and added a solution of dimethyl cyclohexane-1,4-dicarboxylate (950 mg, 4.74 mmol) in tetrahydrofuran (10 mL) dropwise over 10 min. The resultant mixture was stirred at −78° C. for 30 min and added bromo(methoxy)methane (652 mg, 5.22 mmol). The mixture was warmed up to room temperature and stirred for 2 h. After quenching with saturated ammonium chloride (10 mL), the mixture was diluted with ethyl acetate (300 mL), washed with water (30 mL), brine (30 mL), dried (magnesium sulfate), filtered and concentrated under reduced pressure. Silica gel chromatography, eluting with 0-10% ethyl acetate in hexanes, gave the desired (1s,4s)-dimethyl 1-(methoxymethyl)cyclohexane-1,4-dicarboxylate (310 mg, 27% yield). 1H NMR (400 MHz, CDCl$_3$) δ ppm 3.69 (s, 3H), 3.63 (s, 3H), 3.30 (s, 2H), 3.28 (s, 3H), 2.34-2.22 (m, 2H), 1.98-1.84 (m, 2H), 1.76 (m, 1H), 1.59-1.38 (m, 3H), 1.22 (m, 2H).

Step B: dimethyl 1-(methoxymethyl)cyclohexane-1,4-dicarboxylate

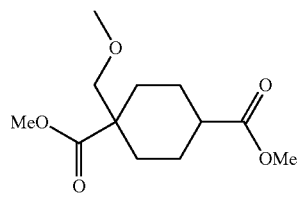 [SMILES: COCC1(C(=O)OC)CCC(C(=O)OC)CC1]

A 2.5 M hexanes solution of butyllithium (0.486 mL, 1.216 mmol) was added to another solution of diisopropylamine (0.173 mL, 1.216 mmol) in tetrahydrofuran (10 mL) at −78° C. and stirred at 0° C. for 30 min. The mixture was cooled down to −78° C. and added a solution of (1s,4s)-dimethyl 1-(methoxymethyl)cyclohexane-1,4-dicarboxylate (270 mg, 1.105 mmol) in tetrahydrofuran (5 mL). After stirring at −78° C. for 1 h, the mixture was quenched with methanol (2 mL) and warmed to room temperature. The mixture was diluted with ethyl acetate (100 mL), washed with water (10 mL), brine (10 mL), dried (magnesium sulfate), filtered and concentrated under reduced pressure. Silica gel chromatography, eluting with 0-10% ethyl acetate in hexanes, gave the desired dimethyl 1-(methoxymethyl) cyclohexane-1,4-dicarboxylate as a 1 to 1 mixture of two isomers (203 mg, 75% yield). 1H NMR showed two sets of signals for the cis and trans isomers.

Step C: 1-(methoxymethyl)cyclohexane-1,4-dicarboxylic acid

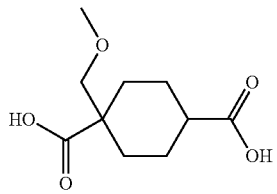

A 1 N aqueous solution of lithium hydroxide (6.58 mL, 6.58 mmol) was added to a mixture of dimethyl 1-(methoxymethyl)cyclohexane-1,4-dicarboxylate (201 mg, 0.823 mmol) in THF (10 mL) and heated to 50° C. for 15 h. After cooling down to room temperature, the mixture was acidified to pH 2-3 with 1 N aqueous hydrochloric acid. After evaporation of organic solvents, the residue was treated with ethyl acetate (100 mL), washed with water (10 mL), brine (10 mL), dried (magnesium sulfate), filtered and concentrated under reduced pressure to give the desired 1-(methoxymethyl)cyclohexane-1,4-dicarboxylic acid as crude material (170 mg, 96% yield). It was used without further purification. 1H NMR showed two sets of signals for the cis and trans isomers.

Step D: 4-(tert-butoxycarbonyl)-1-(methoxymethyl)cyclohexanecarboxylic acid

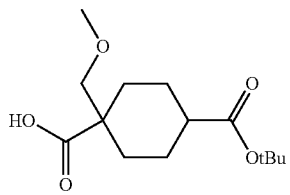 [SMILES: COCC1(C(=O)O)CCC(C(=O)OC(C)(C)C)CC1]

N,N-dimethylpyridin-4-amine (28.8 mg, 0.236 mmol) was added to a solution of 1-(methoxymethyl)cyclohexane-1,4-dicarboxylic acid (170 mg, 0.786 mmol) and di-tert-butyl dicarbonate (0.201 mL, 0.865 mmol) in tert-butanol (3 mL). After stirring at ambient temperature for 15 h, the mixture was treated with ethyl acetate (60 mL), washed with 0.2 N aqueous hydrogen chloride (5 mL), water (5 mL), brine (5 mL), dried (magnesium sulfate), filtered and concentrated under reduced pressure to give the desired 4-(tert-butoxycarbonyl)-1-(methoxymethyl)cyclohexanecarboxylic acid as crude material (130 mg). It was used without further purification. 1H NMR indicated that it's not clean.

Intermediate 14

1-(fluoromethyl)-4-(methoxycarbonyl)cyclohexanecarboxylic acid

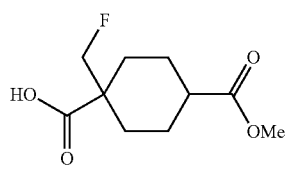

Step A: benzyl 1-(fluoromethyl)-4-(((trifluoromethyl)sulfonyl)oxy)cyclohex-3-enecarboxylate

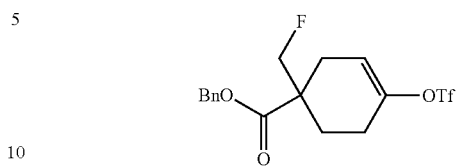

A 0.5 M toluene solution of potassium bis(trimethylsilyl)amide (7.74 mL, 3.87 mmol) was added to a mixture of benzyl 1-(fluoromethyl)-4-oxocyclohexanecarboxylate (930 mg, 3.52 mmol) and 1,1,1-trifluoro-N-phenyl-N-((trifluoromethyl)sulfonyl)methanesulfonamide (1.38 g, 3.87 mmol) in tetrahydrofuran (20 mL) at −78° C. dropwise over 10 min. The resultant mixture was warmed up to 0° C. and stirred for 30 min. It was cooled down to −78° C. and quenched with saturated ammonium chloride (10 mL). The mixture was warmed to room temperature, diluted with ethyl acetate (200 mL), washed with water (20 mL), brine (20 mL), dried (magnesium sulfate), filtered and concentrated under reduced pressure. Silica gel chromatography, eluting with 0-10% ethyl acetate in hexanes, gave the desired benzyl 1-(fluoromethyl)-4-(((trifluoromethyl)sulfonyl)oxy)cyclohex-3-enecarboxylate (910 mg, 65% yield). LC/MS (M+18): 414.3; LC retention time: 1.08 min (analytical HPLC Method C); 1H NMR (400 MHz, CDCl$_3$) δ ppm 7.50-7.30 (m, 5H), 5.76 (t, J=4.0 Hz, 1H), 5.45-4.94 (m, 2H), 4.66-4.34 (m, 2H), 2.92-2.68 (m, 1H), 2.50-2.14 (m, 4H), 1.97-1.85 (m, 1H).

Step B: 4-benzyl 1-methyl 4-(fluoromethyl)cyclohex-1-ene-1,4-dicarboxylate

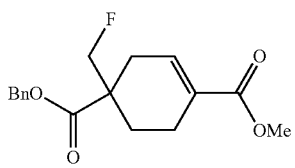 [SMILES: COC(=O)C1=CCC(CF)(C(=O)OCc2ccccc2)CC1]

A mixture of benzyl 1-(fluoromethyl)-4-(((trifluoromethyl)sulfonyl)oxy)cyclohex-3-enecarboxylate (380 mg, 0.959 mmol), Hunig's Base (0.502 mL, 2.88 mmol) and palladium tetrakis (55.4 mg, 0.048 mmol) in methanol (2 mL) and N,N-dimethylformamide (4 mL) was degassed and exchanged with carbon monoxide in a sealed vial. The mixture was stirred at 50° C. under 1 atmosphere of carbon monoxide for 20 h. After cooling down to room temperature, the mixture was diluted with ethyl acetate (100 mL), washed with water (10 mL), brine (10 mL), dried (magnesium sulfate), filtered and concentrated under reduced pressure. Silica gel chromatography, eluting with 0-15% ethyl acetate in hexanes, gave the desired 4-benzyl 1-methyl 4-(fluoromethyl)cyclohex-1-ene-1,4-dicarboxylate (120 mg, 41% yield). LC/MS (M+1): 307.2; LC retention time: 0.98 min (analytical HPLC Method C); 1H NMR (400 MHz, CDCl$_3$) δ ppm 7.49-7.27 (m, 5H), 7.06-6.84 (m, 1H), 5.16 (d, J=1.1 Hz, 2H), 4.70-4.28 (m, 2H), 3.73 (s, 3H), 2.80 (dt, J=18.5, 2.0 Hz, 1H), 2.42-2.17 (m, 3H), 2.10-1.93 (m, 1H), 1.78 (dd, J=13.6, 7.8 Hz, 1H).

Step C: 1-(fluoromethyl)-4-(methoxycarbonyl)cyclohexanecarboxylic acid

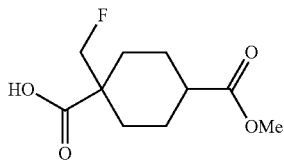

A mixture of 4-benzyl 1-methyl 4-(fluoromethyl)cyclohex-1-ene-1,4-dicarboxylate (80 mg, 0.261 mmol) and 10% palladium on carbon (27.8 mg, 0.026 mmol) in ethanol (10 mL) was hydrogenated under 40 psi hydrogen using a Parr Shaker for 15 h. The mixture was filtered to remove the catalyst. The filtrate was concentrated to give the desired 1-(fluoromethyl)-4-(methoxycarbonyl)cyclohexanecarboxylic acid (56 mg, 98% yield). LC/MS (M+18): 236.1; LC retention time: 0.92 min (analytical HPLC Method I); 1H NMR (400 MHz, CDCl$_3$) δ ppm 4.81-4.15 (m, 2H), 3.84-3.55 (m, 3H), 2.52-2.15 (m, 2H), 2.12-1.50 (m, 5H), 1.49-1.05 (m, 2H).

Example 1

1-benzyl-3-(4-(2-(benzyloxy)-1,1,1,3,3,3-hexafluoropropan-2-yl)phenyl)-3-((4-fluorophenyl)sulfonyl)pyrrolidine Step A: 2-(4-(bromomethyl)phenyl)-1,1,1,3,3,3-hexafluoropropan-2-ol

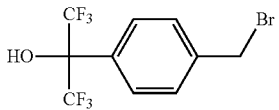

N-Bromosuccinimide (13.79 g, 77 mmol) and 2,2'-azobis(2-methylpropionitrile) (0.025 g, 0.155 mmol) were added to a solution of 1,1,1,3,3,3-hexafluoro-2-(p-tolyl)propan-2-ol (20.00 g, 77 mmol) in carbon tetrachloride (80 mL). The resulting suspension was heated to reflux under nitrogen for 4 h, cooled to room temperature and filtered through a celite pad. The filter cake was rinsed with ether and the filtrate was concentrated under reduced pressure. The residue was treated with ether (100 mL) and hexanes (50 mL), stirred for 15 min and filtered. The filtrate was concentrated under reduced pressure and dried under vacuum to give crude product as tan liquid (27.07 g). 1H NMR analysis showed a 69:15:16 molar ratio of the desired 2-(4-(bromomethyl)phenyl)-1,1,1,3,3,3-hexafluoropropan-2-ol, unreacted 1,1,1,3,3,3-hexafluoro-2-(p-tolyl)propan-2-ol and 2-(4-(dibromomethyl)phenyl)-1,1,1,3,3,3-hexafluoropropan-2-ol. The mixture was used without further purification, assuming ~70% purity of the desired 2-(4-(bromomethyl)phenyl)-1,1,1,3,3,3-hexafluoropropan-2-ol.

Step B: 1,1,1,3,3,3-hexafluoro-2-(4-((phenylsulfonyl)methyl)phenyl)propan-2-ol

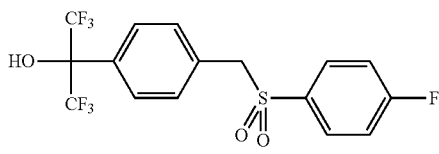

Sodium 4-fluorobenzenesulfinate (12.62 g, 69.3 mmol) was added in small portions to a stirred solution of 2-(4-(bromomethyl)phenyl)-1,1,1,3,3,3-hexafluoropropan-2-ol (20.00 g, ~70% pure from Step A) in N,N-dimethylformamide (80 mL). The mixture warmed up slightly during the addition. After 6 h at ambient temperature, the mixture was diluted with ethyl acetate (1 L), washed with water (3×200 mL), brine (100 mL), dried (magnesium sulfate), filtered and concentrated under reduced pressure. The residue was dissolved in dichloromethane (40 mL), triturated with hexanes (400 mL), stirred for 30 min and filtered. The filter cake was washed with hexanes (100 mL) and dried under vacuum to give 1,1,1,3,3,3-hexafluoro-2-(4-((phenylsulfonyl)methyl)phenyl)propan-2-ol as white solid (14.84 g, 82% yield). LC/MS (M+23): 439.2; 1H NMR (400 MHz, CDCl$_3$) δ ppm 7.64 (d, J=8.1 Hz, 2H), 7.62-7.54 (m, 2H), 7.20 (d, J=8.6 Hz, 2H), 7.15-7.06 (m, 2H), 4.34 (s, 2H), 3.59 (s, 1H).

Step C: 1-(2-(benzyloxy)-1,1,1,3,3,3-hexafluoropropan-2-yl)-4-(4-fluorophenyl)sulfonyl)methyl)benzene

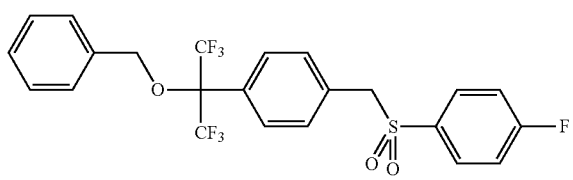 [SMILES: O=S(=O)(Cc1ccc(C(OCc2ccccc2)(C(F)(F)F)C(F)(F)F)cc1)c1ccc(F)cc1]

A mixture of 1,1,1,3,3,3-hexafluoro-2-(4-(((4-fluorophenyl)sulfonyl)methyl)phenyl)propan-2-ol (14.84 g, 35.6 mmol), benzyl bromide (6.71 g, 39.2 mmol) and potassium carbonate (14.78 g, 107 mmol) in N,N-dimethylformamide (150 mL) was stirred under nitrogen for 16 h at room temperature. The mixture was quenched with saturated ammonium chloride (100 mL), diluted with ethyl acetate (800 mL), washed with water (2×200 mL), brine (50 mL), dried (magnesium sulfate), filtered and concentrated under reduced pressure. The residue was dissolved in toluene (40 mL), triturated with hexanes (500 mL), stirred for 30 min and filtered. The filter cake was washed with hexanes (100 mL) and dried under vacuum to give first batch of 1-(2-(benzyloxy)-1,1,1,3,3,3-hexafluoropropan-2-yl)-4-(((4-fluorophenyl)sulfonyl)methyl)benzene as yellow solid (14.239 g). The filtrate was concentrated. Silica gel chromatography, eluting with 5-30% ethyl acetate in hexanes, gave the second batch of the desired product as white solid (1.480 g). The combined yield of the product is 87%. LC/MS (M+18): 524.3; LC retention time: 4.486 min (analytical HPLC Method A); 1H NMR (400 MHz, CDCl$_3$) δ ppm 7.67-7.60 (m, 2H), 7.56 (d, J=8.1 Hz, 2H), 7.45-7.31 (m, 5H), 7.23 (d, J=8.6 Hz, 2H), 7.11 (t, J=8.6 Hz, 2H), 4.62 (s, 2H), 4.34 (s, 2H).

Step D: 1-[2-(benzyloxy)-1,1,1,3,3,3-hexafluoropropan-2-yl]-4-[1-(4-fluorobenzenesulfonyl)ethenyl]benzene

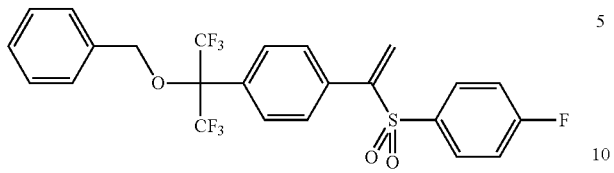

N,N,N',N'-tetramethylmethanediamine (15.34 mL, 112 mmol) and acetic anhydride (10.61 mL, 112 mmol) were added to a solution of 1-(2-(benzyloxy)-1,1,1,3,3,3-hexafluoropropan-2-yl)-4-(((4-fluorophenyl)sulfonyl)methyl)benzene (14.239 g, 28.1 mmol) and N,N,N',N'-tetramethylmethanediamine (15.34 mL, 112 mmol) in N,N-dimethylformamide (140 mL) at room temperature. The reaction flask was equipped with a condenser, placed in a 60° C. oil bath and stirred under nitrogen for 15 h. Additional N,N,N',N'-tetramethylmethanediamine (15.34 mL, 112 mmol) and acetic anhydride (10.61 mL, 112 mmol) were added. After another 8 h at 60° C., more acetic anhydride (10.61 mL, 112 mmol) was added. After 4 h at 60° C., the mixture was diluted with ethyl acetate (1.2 L), washed with saturated sodium bicarbonate (3×200 mL), water (200 mL), brine (200 mL), dried (magnesium sulfate), filtered and concentrated under reduced pressure. Silica gel chromatography, eluting with 2-25% ethyl acetate in hexanes, gave the desired 1-[2-(benzyloxy)-1,1,1,3,3,3-hexafluoropropan-2-yl]-4-[1-(4-fluorobenzenesulfonyl)ethenyl]benzene as colorless viscous oil (8.062 g, 55% yield). LC/MS (M+23): 541.2; LC retention time: 4.606 min (analytical HPLC Method A); $^1$H NMR (400 MHz, CDCl$_3$) δ ppm 7.74-7.66 (m, 2H), 7.56 (d, J=8.4 Hz, 2H), 7.47-7.32 (m, 7H), 7.14-7.03 (m, 2H), 6.66 (s, 1H), 6.03 (s, 1H), 4.61 (s, 2H).

Step E: 1-benzyl-3-(4-(2-(benzyloxy)-1,1,1,3,3,3-hexafluoropropan-2-yl)phenyl)-3-((4-fluorophenyl)sulfonyl)pyrrolidine

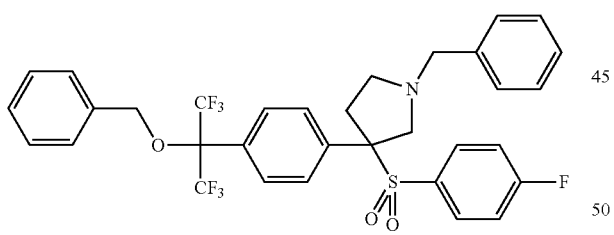

A 0.2 M dichloromethane solution of trifluoroacetic acid (3.11 mL, 0.622 mmol) was added dropwise to a solution of 1-(2-(benzyloxy)-1,1,1,3,3,3-hexafluoropropan-2-yl)-4-(1-((4-fluorophenyl)sulfonyl)vinyl)benzene (8.062 g, 15.55 mmol) and N-benzyl-1-methoxy-N-((trimethylsilyl)methyl)methanamine (7.38 g, 31.1 mmol) in dichloromethane (50 mL) at 0° C. After stirring under nitrogen at 0° C. for 10 min and at room temperature for 1 h, the resulting mixture was diluted with ethyl acetate (400 mL), washed with saturated sodium bicarbonate (2×50 mL) and brine (50 mL), dried (magnesium sulfate), filtered and concentrated under reduced pressure. Silica gel chromatography, eluting with 5-40% ethyl acetate in hexanes, gave Example 1 as off-white solid (9.721 g, 96% yield). LC/MS (M+1): 652.1; LC retention time: 4.196 min (analytical HPLC Method A); $^1$H NMR (400 MHz, CDCl$_3$) δ ppm 7.50 (d, J=8.4 Hz, 2H), 7.44-7.20 (m, 14H), 7.00-6.86 (m, 2H), 4.63 (s, 2H), 3.77-3.62 (m, 3H), 3.28 (d, J=11.0 Hz, 1H), 3.09-2.87 (m, 2H), 2.78 (td, J=8.1, 4.3 Hz, 1H), 2.61-2.46 (m, 1H).

Example 2

(R)-1-benzyl-3-(4-(2-(benzyloxy)-1,1,1,3,3,3-hexafluoropropan-2-yl)phenyl)-3-((4-fluorophenyl)sulfonyl)pyrrolidine

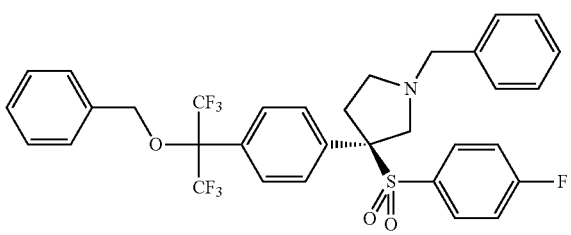 [SMILES: O=S(=O)(c1ccc(F)cc1)[C@@]1(c2ccc(C(OCc3ccccc3)(C(F)(F)F)C(F)(F)F)cc2)CCN(Cc2ccccc2)C1]

1-Benzyl-3-(4-(2-(benzyloxy)-1,1,1,3,3,3-hexafluoropropan-2-yl)phenyl)-3-((4-fluorophenyl)sulfonyl)pyrrolidine (9.72 g, from Example 1) was separated into its homochiral components using a chiral OJ-H column, 15% methanol with 0.1% diethylamine in CO2, 35° C., 100 bars to afford (S)-1-benzyl-3-(4-(2-(benzyloxy)-1,1,1,3,3,3-hexafluoropropan-2-yl)phenyl)-3-((4-fluorophenyl)sulfonyl)pyrrolidine (4.065 g) as the first eluent off the column and (R)-1-benzyl-3-(4-(2-(benzyloxy)-1,1,1,3,3,3-hexafluoropropan-2-yl)phenyl)-3-((4-fluorophenyl)sulfonyl)pyrrolidine (Example 2, 4.177 g) as the second eluent off the column. Spectroscopic data for Example 2: LC/MS (M+1): 652.0; LC retention time: 4.145 min (analytical HPLC Method A); 1H NMR (500 MHz, CDCl$_3$) δ ppm 7.50 (d, J=8.3 Hz, 2H), 7.44-7.21 (m, 14H), 6.99-6.90 (m, 2H), 4.63 (s, 2H), 3.77-3.62 (m, 3H), 3.28 (d, J=11.1 Hz, 1H), 3.07-2.98 (m, 1H), 2.97-2.89 (m, 1H), 2.78 (td, J=8.2, 4.4 Hz, 1H), 2.59-2.49 (m, 1H).

Example 3

(R)-1,1,1,3,3,3-hexafluoro-2-(4-(3-((4-fluorophenyl)sulfonyl)pyrrolidin-3-yl)phenyl)propan-2-ol

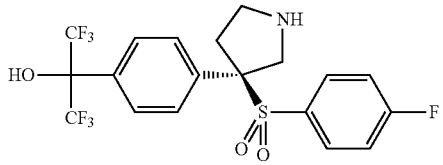 [SMILES: O=S(=O)(c1ccc(F)cc1)[C@@]1(c2ccc(C(O)(C(F)(F)F)C(F)(F)F)cc2)CCNC1]

A mixture of (R)-1-benzyl-3-(4-(2-(benzyloxy)-1,1,1,3,3,3-hexafluoropropan-2-yl)phenyl)-3-((4-fluorophenyl)sulfonyl)pyrrolidine (4.18 g, 6.41 mmol, from Example 2), 1 M aqueous hydrochloric acid (12.83 mL, 12.83 mmol) and 20% palladium hydroxide on carbon (1.126 g, 1.604 mmol) in methanol (40 mL) was hydrogenated under 40 psi hydrogen using a Parr Shaker for 15 h. The mixture was filtered to remove the catalyst. The filtrate was concentrated to give (R)-1,1,1,3,3,3-hexafluoro-2-(4-(3-((4-fluorophenyl)sulfonyl)pyrrolidin-3-yl)phenyl)propan-2-ol hydrochloride salt (3.22 g, 98% yield) as off-white solid. LC/MS (M+1): 472.0; LC retention time: 3.246 min (analytical HPLC Method A); 1H NMR (500 MHz, CD₃OD) δ ppm 7.68 (d, J=8.3 Hz, 2H), 7.41-7.31 (m, 2H), 7.26-7.18 (m, 2H), 7.16-7.07 (m, 2H), 4.53 (d, J=13.6 Hz, 1H), 3.96 (d, J=13.6 Hz, 1H), 3.89 (ddd, J=11.6, 9.8, 7.8 Hz, 1H), 3.66 (ddd, J=11.7, 9.4, 3.6 Hz, 1H), 3.40-3.32 (m, 1H), 2.78 (dt, J=14.8, 9.7 Hz, 1H).

Example 4

(S)-1,1,1,3,3,3-hexafluoro-2-(4-(3-((4-fluorophenyl)sulfonyl)pyrrolidin-3-yl)phenyl)propan-2-ol

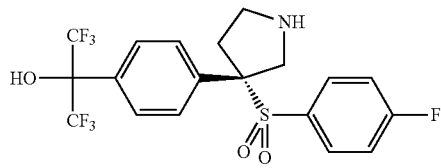 [SMILES: O=S(=O)(c1ccc(F)cc1)[C@]1(c2ccc(C(O)(C(F)(F)F)C(F)(F)F)cc2)CCNC1]

Following conditions similar to Example 3, (S)-1-benzyl-3-(4-(2-(benzyloxy)-1,1,1,3,3,3-hexafluoropropan-2-yl)phenyl)-3-((4-fluorophenyl)sulfonyl)pyrrolidine (4.050 g, 6.22 mmol, from Example 2) was converted to (S)-1,1,1,3,3,3-hexafluoro-2-(4-(3-((4-fluorophenyl)sulfonyl)pyrrolidin-3-yl)phenyl)propan-2-ol hydrochloride salt (3.143 g). LC/MS (M+1): 472.0; LC retention time: 3.250 min (analytical HPLC Method A); ¹H NMR (500 MHz, CD₃OD) δ ppm 7.67 (d, J=8.6 Hz, 2H), 7.39-7.32 (m, 2H), 7.25-7.18 (m, 2H), 7.17-7.10 (m, 2H), 4.53 (d, J=13.3 Hz, 1H), 3.97 (d, J=13.3 Hz, 1H), 3.89 (ddd, J=11.4, 9.8, 7.9 Hz, 1H), 3.71-3.62 (m, 1H), 3.40-3.32 (m, 1H), 2.79 (dt, J=14.8, 9.7 Hz, 1H).

Example 5

1,1,1,3,3,3-hexafluoro-2-(4-(3-((4-fluorophenyl)sulfonyl)pyrrolidin-3-yl)phenyl)propan-2-ol

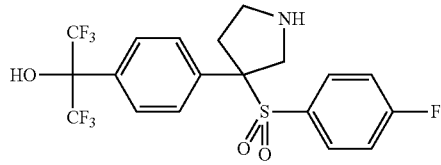 [SMILES: O=S(=O)(c1ccc(F)cc1)C1(c2ccc(C(O)(C(F)(F)F)C(F)(F)F)cc2)CCNC1]

Following conditions similar to Example 3, 1-benzyl-3-(4-(2-(benzyloxy)-1,1,1,3,3,3-hexafluoropropan-2-yl)phenyl)-3-((4-fluorophenyl)sulfonyl)pyrrolidine (0.674 g, 1.034 mmol, Example 1) was converted to 1,1,1,3,3,3-hexafluoro-2-(4-(3-((4-fluorophenyl)sulfonyl)pyrrolidin-3-yl)phenyl)propan-2-ol hydrochloride salt (480 mg). LC/MS (M+1): 472.0; LC retention time: 1.528 min (analytical HPLC Method B); 1H NMR (500 MHz, 1:1 mixture of CDCl₃—CD₃OD) δ ppm 7.63 (d, J=8.4 Hz, 2H), 7.24 (dd, J=8.2, 5.2 Hz, 2H), 7.16 (d, J=8.4 Hz, 2H), 7.03 (t, J=8.4 Hz, 2H), 4.83-4.72 (m, 1H), 4.14 (d, J=13.9 Hz, 1H), 3.50-3.40 (m, 1H), 3.16-2.99 (m, 2H), 2.59-2.48 (m, 1H).

Example 6

1-benzyl-3-(4-(2-((2,6-difluorobenzyl)oxy)-1,1,1,3,3,3-hexafluoropropan-2-yl)phenyl)-3-((4-fluorophenyl)sulfonyl)pyrrolidine Step A: 1,3-difluoro-2-(((1,1,1,3,3,3-hexafluoro-2-(4-(((4-fluorophenyl)sulfonyl)methyl)phenyl)propan-2-yl)oxy)methyl)benzene

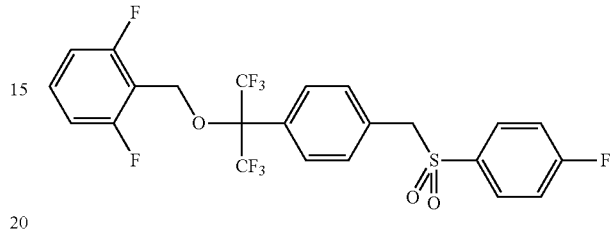

A mixture of 1,1,1,3,3,3-hexafluoro-2-(4-(((4-fluorophenyl)sulfonyl)methyl)phenyl)propan-2-ol (12.625 g, 30.3 mmol, from Step B of Example 1), 2-(bromomethyl)-1,3-difluorobenzene (6.59 g, 31.8 mmol) and potassium carbonate (12.57 g, 91 mmol) in N,N-dimethylformamide (120 mL) was stirred under nitrogen at room temperature for 22 h. The mixture was quenched with saturated ammonium chloride (100 mL), diluted with ethyl acetate (800 mL), washed with water (3×100 mL), brine (50 mL), dried (magnesium sulfate), filtered and concentrated under reduced pressure. The residue was treated with dichloromethane (20 mL) and toluene (40 mL), sonicated, triturated with hexanes (500 mL), stirred for 15 min and filtered. The filter cake was washed with hexanes (100 mL) and dried under vacuum to give first batch of 1,3-difluoro-2-(((1,1,1,3,3,3-hexafluoro-2-(4-(((4-fluorophenyl)sulfonyl)methyl)phenyl)propan-2-yl)oxy)methyl)benzene as white solid (14.881 g). The filtrate was concentrated. Silica gel chromatography, eluting with 5-30% ethyl acetate in hexanes, gave second batch of the desired product as white solid (0.735 g). The combined amount of the product is 15.616 g (95% yield). LC/MS (M+18): 560.2; LC retention time: 4.460 min (analytical HPLC Method A); 1H NMR (400 MHz, CDCl₃) δ ppm 7.68-7.57 (m, 4H), 7.37 (tt, J=8.4, 6.4 Hz, 1H), 7.28-7.21 (m, 2H), 7.15-7.07 (m, 2H), 7.01-6.91 (m, 2H), 4.68 (s, 2H), 4.36 (s, 2H).

Step B: 1,3-difluoro-2-(((1,1,1,3,3,3-hexafluoro-2-(4-(1-((4-fluorophenyl)sulfonyl)vinyl)phenyl)propan-2-yl)oxy)methyl)benzene

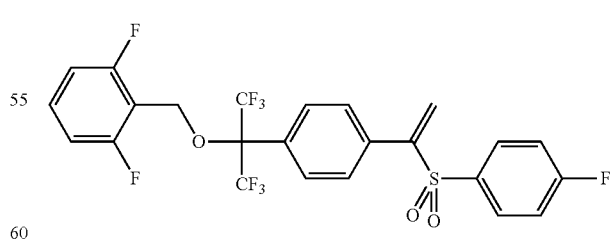

Acetic anhydride (10.35 mL, 110 mmol) was added to a solution of 1,3-difluoro-2-(((1,1,1,3,3,3-hexafluoro-2-(4-(((4-fluorophenyl)sulfonyl)methyl)phenyl)propan-2-yl)oxy)methyl)benzene (14.88 g, 27.4 mmol) and N,N,N',N'-tetramethylmethanediamine (14.97 mL, 110 mmol) in N,N-dimethylformamide (140 mL) at room temperature. The reaction flask was equipped with a condenser, placed in a 60° C. oil bath and stirred under nitrogen for 5 h. Additional N,N,N',N'-tetramethylmethanediamine (14.97 mL, 110 mmol) and acetic anhydride (10.35 mL, 110 mmol) were added dropwise and the mixture stirred at 60° C. for 15 h. Additional acetic anhydride (5 mL) was added. After another 1 h at 60° C., the mixture was diluted with ethyl acetate (1.2 L), washed with saturated sodium bicarbonate (3×200 mL), water (200 mL), brine (200 mL), dried (magnesium sulfate), filtered and concentrated under reduced pressure. Silica gel chromatography, eluting with 5-25% ethyl acetate in hexanes, gave impure 1,3-difluoro-2-(((1,1,1,3,3,3-hexafluoro-2-(4-(1-((4-fluorophenyl)sulfonyl)vinyl)phenyl)propan-2-yl)oxy)methyl)benzene as tan solid (8.834 g). This material was taken to the next reaction without further purification.

Step C: 1-benzyl-3-(4-{2-[(2,6-difluorophenyl)methoxy]-1,1,1,3,3,3-hexafluoropropan-2-yl}phenyl)-3-(4-fluorobenzenesulfonyl)pyrrolidine

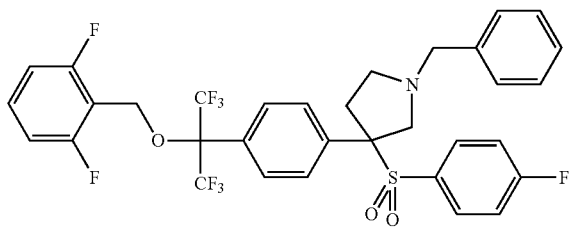 [SMILES: O=S(=O)(c1ccc(F)cc1)C1(c2ccc(C(OCc3c(F)cccc3F)(C(F)(F)F)C(F)(F)F)cc2)CCN(Cc2ccccc2)C1]

A 0.2 M dichloromethane solution of trifluoroacetic acid (3.55 mL, 0.710 mmol) was added dropwise to a solution of impure 1,3-difluoro-2-(((1,1,1,3,3,3-hexafluoro-2-(4-(1-((4-fluorophenyl)sulfonyl)vinyl)phenyl)propan-2-yl)oxy)methyl)benzene (9.840 g) and N-benzyl-1-methoxy-N-((trimethylsilyl)methyl)methanamine (8.43 g, 35.5 mmol) in dichloromethane (60 mL) at 0° C. The resulting mixture was stirred under nitrogen at 0° C. for 10 min and at room temperature for 1 h. The mixture was then diluted with ethyl acetate (600 mL), washed with saturated sodium bicarbonate (2×100 mL) and brine (50 mL), dried (magnesium sulfate), filtered and concentrated under reduced pressure. Silica gel chromatography, eluting with 5-40% ethyl acetate in hexanes, gave impure 1-benzyl-3-(4-{2-[(2,6-difluorophenyl)methoxy]-1,1,1,3,3,3-hexafluoropropan-2-yl}phenyl)-3-(4-fluorobenzenesulfonyl)pyrrolidine as off-white solid (11.86 g). This material was taken to the next step without purification.

A small sample of the material above (18 mg) was purified via preparative LC/MS with the following conditions: Column: Waters XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 45-100% B over 20 minutes, then a 5-minute hold at 100% B; Flow: 25 mL/min. Fractions containing the desired product were combined and dried via centrifugal evaporation to give Example 6 (8.3 mg). LC/MS (M+1): 688.2; LC retention time: 2.74 min (analytical HPLC Method B); 1H NMR (500 MHz, 1:1 mixture of CDCl$_3$—CD$_3$OD) δ ppm 7.58 (d, J=8.4 Hz, 2H), 7.51-7.40 (m, 1H), 7.38-7.25 (m, 9H), 7.03 (dt, J=11.4, 8.2 Hz, 4H), 4.79-4.65 (m, 3H), 3.81-3.64 (m, 3H), 3.12-3.04 (m, 1H), 3.03-2.94 (m, 1H), 2.82 (td, J=8.2, 4.5 Hz, 1H), 2.63 (dt, J=14.0, 7.1 Hz, 1H).

Example 7 tert-butyl 3-(4-(2-((2,6-difluorobenzyl)oxy)-1,1,1,3,3,3-hexafluoropropan-2-yl)phenyl)-3-((4-fluorophenyl)sulfonyl)pyrrolidine-1-carboxylate

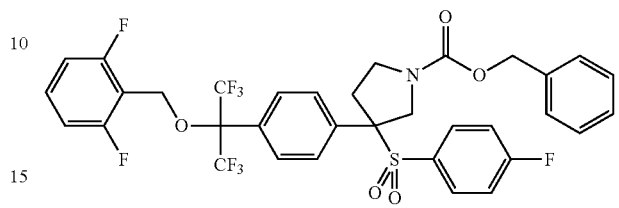

Benzyl chloroformate (4.92 mL, 34.5 mmol) was added to a solution of impure 1-benzyl-3-(4-(2-((2,6-difluorobenzyl)oxy)-1,1,1,3,3,3-hexafluoropropan-2-yl)phenyl)-3-((4-fluorophenyl)sulfonyl)pyrrolidine (11.86 g, from Step C of Example 6) in chloroform (150 mL). The resulting solution was stirred under nitrogen for 36 h. Additional benzyl chloroformate (2.5 mL) was added. After 4 h at 60° C., the mixture was concentrated. Silica gel chromatography, eluting with 5-50% ethyl acetate in hexanes, separated the desired product. The middle fractions of the product peak were combined to afford Example 7 as white solid (7.50 g, 57% yield over 3 steps). LC/MS (M+1): 732.0; LC retention time: 4.781 min (analytical HPLC Method A); 1H NMR (400 MHz, CDCl$_3$) δ ppm 7.58 (d, J=7.9 Hz, 2H), 7.48-7.29 (m, 7H), 7.28-7.23 (m, 1H), 7.20 (d, J=8.6 Hz, 2H), 7.03-6.84 (m, 4H), 5.30-5.11 (m, 2H), 4.76-4.59 (m, 3H), 3.99-3.80 (m, 2H), 3.68-3.57 (m, 1H), 3.39-3.10 (m, 1H), 2.66-2.49 (m, 1H). The front and back shoulder fractions were combined to give additional product (684 mg), which is less pure.

Example 8

3-(4-(2-((2,6-difluorobenzyl)oxy)-1,1,1,3,3,3-hexafluoropropan-2-yl)phenyl)-3-((4-fluorophenyl)sulfonyl)pyrrolidine

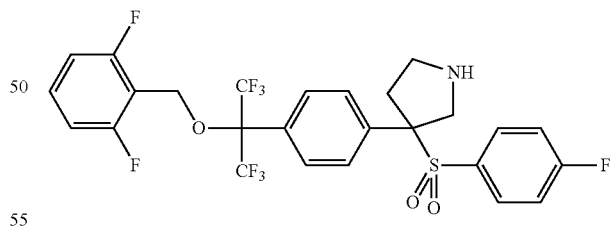

A mixture of benzyl 3-(4-(2-((2,6-difluorobenzyl)oxy)-1,1,1,3,3,3-hexafluoropropan-2-yl)phenyl)-3-((4-fluorophenyl)sulfonyl)pyrrolidine-1-carboxylate (7.500 g, 10.25 mmol, from Example 7), 20% palladium hydroxide on carbon (2.159 g, 3.08 mmol), methanol (160 mL) and ethyl acetate (80 mL) was stirred under balloon pressure hydrogen for 2 h. The mixture was filtered through a celite pad and the filter cake rinsed with methanol-ethyl acetate (1:1 mixture). The filtrate was concentrated, treated with methanol (100 mL), dichloromethane (100 mL), and 4 N HCl in dioxane (5 mL), stirred for 15 min, and filtered with a 0.45 uM Nylon membrane to remove the black impurity particles. The filtrate was concentrated to give 3-(4-(2-((2,6-difluorobenzyl)oxy)-1,1,1,3,3,3-hexafluoropropan-2-yl)phenyl)-3-((4-fluorophenyl)sulfonyl)pyrrolidine hydrochloride as tan solid (6.296 g, 97% yield). LC/MS (M+1): 598.2; LC retention time: 3.946 min (analytical HPLC Method A); $^1$H NMR (400 MHz, CD$_3$OD) δ ppm 7.63 (d, J=8.4 Hz, 2H), 7.51 (tt, J=8.4, 6.5 Hz, 1H), 7.45-7.39 (m, 2H), 7.32 (d, J=8.8 Hz, 2H), 7.23-7.14 (m, 2H), 7.13-7.03 (m, 2H), 4.72 (s, 2H), 4.58 (d, J=13.4 Hz, 1H), 3.99 (d, J=13.4 Hz, 1H), 3.91 (ddd, J=11.6, 9.9, 7.8 Hz, 1H), 3.73-3.62 (m, 1H), 3.40 (ddd, J=14.7, 7.8, 3.0 Hz, 1H), 2.81 (dt, J=14.7, 9.7 Hz, 1H).

Examples 9 and 10

(S)-3-(4-(2-((2,6-difluorobenzyl)oxy)-1,1,1,3,3,3-hexafluoropropan-2-yl)phenyl)-3-((4-fluorophenyl)sulfonyl)pyrrolidine and (R)-3-(4-(2-((2,6-difluorobenzyl)oxy)-1,1,1,3,3,3-hexafluoropropan-2-yl)phenyl)-3-((4-fluorophenyl)sulfonyl)pyrrolidine, respectively

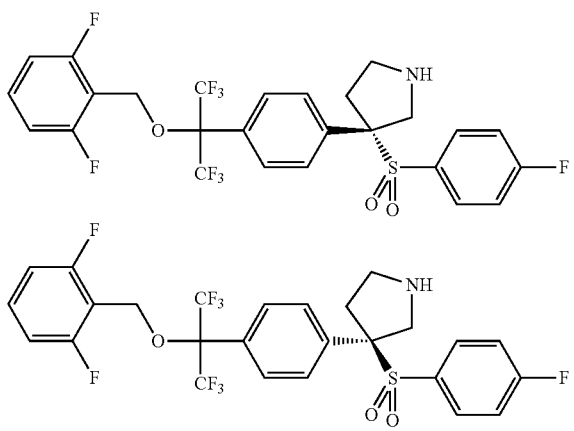

3-(4-(2-((2,6-difluorobenzyl)oxy)-1,1,1,3,3,3-hexafluoropropan-2-yl)phenyl)-3-((4-fluorophenyl)sulfonyl)pyrrolidine hydrochloride (6.29 g, from Example 8) was separated into its homochiral components using a chiral Lux Cellulose-4 (3×25 cm, 5 μm), CO2/methanol (65/35), 40° C., 100 bars to afford (S)-3-(4-(2-((2,6-difluorobenzyl)oxy)-1,1,1,3,3,3-hexafluoropropan-2-yl)phenyl)-3-((4-fluorophenyl)sulfonyl)pyrrolidine (Example 9, 2.94 g) as the first eluent off the column and (R)-3-(4-(2-((2,6-difluorobenzyl)oxy)-1,1,1,3,3,3-hexafluoropropan-2-yl)phenyl)-3-((4-fluorophenyl)sulfonyl)pyrrolidine (Example 10, 2.88 g) as the second eluent off the column. Single crystal X-Ray analysis established that Example 9 has the S configuration. Spectroscopic data for Example 9: LC/MS (M+1): 597.9; LC retention time: 3.945 min (analytical HPLC Method A); $^1$H NMR (500 MHz, CD$_3$OD) δ ppm 7.63 (d, J=8.3 Hz, 2H), 7.56-7.47 (m, 1H), 7.45-7.39 (m, 2H), 7.32 (d, J=8.6 Hz, 2H), 7.22-7.14 (m, 2H), 7.12-7.02 (m, 2H), 4.72 (s, 2H), 4.58 (d, J=13.6 Hz, 1H), 3.98 (d, J=13.6 Hz, 1H), 3.91 (ddd, J=11.5, 9.8, 8.0 Hz, 1H), 3.73-3.62 (m, 1H), 3.44-3.36 (m, J=7.4, 7.4, 3.3 Hz, 1H), 2.81 (dt, J=14.7, 9.7 Hz, 1H). Spectroscopic data for Example 10: LC/MS (M+1): 597.9; LC retention time: 3.968 min (analytical HPLC Method A); $^1$H NMR (500 MHz, CD$_3$OD) δ ppm 7.63 (d, J=8.3 Hz, 2H), 7.51 (tt, J=8.4, 6.6 Hz, 1H), 7.45-7.38 (m, 2H), 7.32 (d, J=8.6 Hz, 2H), 7.22-7.15 (m, 2H), 7.12-7.04 (m, 2H), 4.72 (s, 2H), 4.58 (d, J=13.6 Hz, 1H), 3.98 (d, J=13.6 Hz, 1H), 3.91 (ddd, J=11.6, 9.8, 7.8 Hz, 1H), 3.72-3.62 (m, 1H), 3.40 (ddd, J=14.7, 7.8, 3.3 Hz, 1H), 2.81 (dt, J=14.8, 9.7 Hz, 1H).

Example 11

(R)-1-(4-(3-((4-fluorophenyl)sulfonyl)-3-(4-(1,1,1,3,3,3-hexafluoro-2-hydroxypropan-2-yl)phenyl)pyrrolidine-1-carbonyl)piperidin-1-yl)ethanone

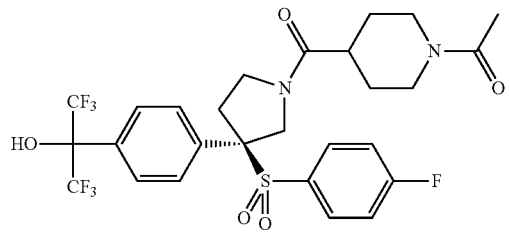 [SMILES: CC(=O)N1CCC(C(=O)N2CC[C@](c3ccc(C(O)(C(F)(F)F)C(F)(F)F)cc3)(S(=O)(=O)c3ccc(F)cc3)C2)CC1]

Hunig's Base (0.258 mL, 1.477 mmol) was added dropwise to a suspension of (R)-1,1,1,3,3,3-hexafluoro-2-(4-(3-((4-fluorophenyl)sulfonyl)pyrrolidin-3-yl)phenyl)propan-2-ol hydrochloride (150 mg, 0.295 mmol, from Example 3) and 1-acetylpiperidine-4-carbonyl chloride (140 mg, 0.738 mmol) in dichloromethane (8 mL). After 1 h at room temperature, the mixture was diluted with ethyl acetate (80 mL), washed with saturated sodium bicarbonate (2×20 mL), water (20 mL) and brine (10 mL), dried (magnesium sulfate), filtered and concentrated under reduced pressure. Silica gel chromatography, eluting with 0-8% methanol in dichloromethane gave Example 11 as white solid (174 mg, 94% yield). LC/MS (M+1): 625.0; LC retention time: 3.780 min (analytical HPLC Method A); 1H NMR showed a mixture of cis and trans amide isomers.

Example 12

(R)-1-(4-(3-((4-fluorophenyl)sulfonyl)-3-(4-(1,1,1,3,3,3-hexafluoro-2-hydroxypropan-2-yl)phenyl)pyrrolidine-1-carbonyl)piperazin-1-yl)ethanone

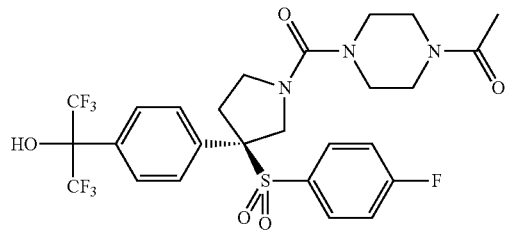 [SMILES: CC(=O)N1CCN(C(=O)N2CC[C@](c3ccc(C(O)(C(F)(F)F)C(F)(F)F)cc3)(S(=O)(=O)c3ccc(F)cc3)C2)CC1]

Hunig's Base (0.413 mL, 2.363 mmol) was added dropwise to a suspension of (R)-1,1,1,3,3,3-hexafluoro-2-(4-(3-((4-fluorophenyl)sulfonyl)pyrrolidin-3-yl)phenyl)propan-2-ol hydrochloride (300 mg, 0.591 mmol, from Example 3) and 4-acetylpiperazine-1-carbonyl chloride (169 mg, 0.886 mmol) in dichloromethane (12 mL). After 1 h at room temperature, the mixture was diluted with ethyl acetate (80 mL), washed with water (2×20 mL) and brine (10 mL), dried (magnesium sulfate), filtered and concentrated under reduced pressure. Silica gel chromatography, eluting with 0-10% methanol in dichloromethane, gave Example 12 as white solid (349 mg, 94% yield). LC/MS (M+1): 626.0; LC retention time: 3.848 min (analytical HPLC Method A); ¹H NMR (500 MHz, 1:1 mixture of CDCl₃—CD₃OD) δ ppm 7.66 (d, J=8.3 Hz, 2H), 7.36-7.26 (m, 2H), 7.17 (d, J=8.9 Hz, 2H), 7.04 (t, J=8.5 Hz, 2H), 4.66 (d, J=12.5 Hz, 1H), 4.03 (d, J=12.5 Hz, 1H), 3.98 (q, J=8.6 Hz, 1H), 3.73-3.54 (m, 5H), 3.48-3.27 (m, 4H), 3.20 (ddd, J=13.7, 7.6, 3.1 Hz, 1H), 2.62 (dt, J=13.9, 8.8 Hz, 1H), 2.15 (s, 3H).

Example 13

(R)-ethyl 1-(3-((4-fluorophenyl)sulfonyl)-3-(4-(1,1,1,3,3,3-hexafluoro-2-hydroxypropan-2-yl)phenyl)pyrrolidine-1-carbonyl)piperidine-4-carboxylate

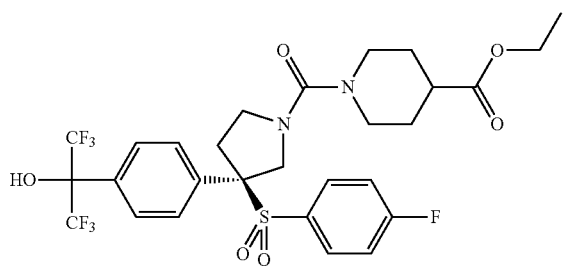 [SMILES: CCOC(=O)C1CCN(C(=O)N2CC[C@](c3ccc(C(O)(C(F)(F)F)C(F)(F)F)cc3)(S(=O)(=O)c3ccc(F)cc3)C2)CC1]

Hunig's Base (0.138 mL, 0.788 mmol) was added dropwise to a suspension of (R)-1,1,1,3,3,3-hexafluoro-2-(4-(3-((4-fluorophenyl)sulfonyl)pyrrolidin-3-yl)phenyl)propan-2-ol hydrochloride (100 mg, 0.197 mmol, from Example 3) and ethyl 1-(chlorocarbonyl)piperidine-4-carboxylate (78 mg, 0.354 mmol) in dichloromethane (4 mL). After 1 h at room temperature, the mixture was directly loaded to silica gel column, eluting with 0-8% methanol in hexanes, to give Example 13 as off-white solid (127 mg, 99% yield). LC/MS (M+1): 655.0; LC retention time: 4.230 min (analytical HPLC Method A); 1H NMR (500 MHz, CDCl₃) δ ppm 7.58 (d, J=8.6 Hz, 2H), 7.32-7.23 (m, 2H), 7.11 (d, J=8.6 Hz, 2H), 6.99-6.92 (m, 2H), 5.02 (br. s., 1H), 4.47 (d, J=12.8 Hz, 1H), 4.21-4.12 (m, 2H), 4.09 (d, J=12.8 Hz, 1H), 3.93 (td, J=9.3, 7.5 Hz, 1H), 3.80-3.68 (m, 2H), 3.52 (td, J=9.3, 3.1 Hz, 1H), 3.20 (ddd, J=13.7, 7.3, 2.9 Hz, 1H), 2.96-2.82 (m, 2H), 2.54-2.42 (m, 2H), 2.00-1.90 (m, 2H), 1.82-1.65 (m, 2H), 1.27 (t, J=7.1 Hz, 3H).

Example 14

(R)-1-(3-((4-fluorophenyl)sulfonyl)-3-(4-(1,1,1,3,3,3-hexafluoro-2-hydroxypropan-2-yl)phenyl)pyrrolidine-1-carbonyl)piperidine-4-carboxylic acid

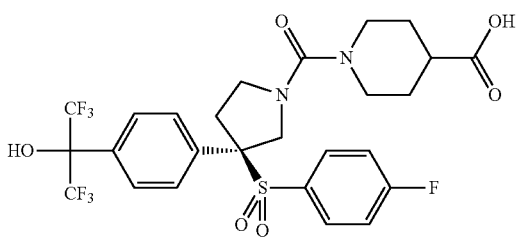 [SMILES: O=C(O)C1CCN(C(=O)N2CC[C@](c3ccc(C(O)(C(F)(F)F)C(F)(F)F)cc3)(S(=O)(=O)c3ccc(F)cc3)C2)CC1]

A mixture of (R)-ethyl 1-(3-((4-fluorophenyl)sulfonyl)-3-(4-(1,1,1,3,3,3-hexafluoro-2-hydroxypropan-2-yl)phenyl)pyrrolidine-1-carbonyl)piperidine-4-carboxylate (13.0 mg, 0.020 mmol, from Example 13), 1 N aqueous sodium hydroxide (0.5 mL), methanol (0.5 mL) and tetrahydrofuran (0.5 mL) was stirred at room temperature for 14 h. The mixture was neutralized to pH~4-5 with 1 N hydrochloric acid. After evaporation of organic solvents, the residue was treated with ethyl acetate (20 mL), washed with water (2×5 mL), brine (5 mL), dried (magnesium sulfate), filtered and concentrated under reduced pressure. The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 0-100% B over 25 minutes, then a 5-minute hold at 100% B; Flow: 20 mL/min. Fractions containing the desired product were combined and dried via centrifugal evaporation to give Example 14 (10.8 mg, 84% yield). LC/MS (M+1): 627.1; LC retention time: 1.43 min (analytical HPLC Method B); 1H NMR (500 MHz, 1:1 mixture of CDCl₃—CD₃OD) δ ppm 7.65 (d, J=8.3 Hz, 2H), 7.40-7.28 (m, 2H), 7.18 (d, J=8.9 Hz, 2H), 7.09-6.98 (m, 2H), 4.59 (d, J=12.5 Hz, 1H), 4.02 (d, J=12.5 Hz, 1H), 3.97-3.88 (m, 1H), 3.80-3.67 (m, 2H), 3.54 (td, J=9.4, 3.6 Hz, 1H), 3.23-3.12 (m, 1H), 2.99-2.87 (m, 2H), 2.67-2.43 (m, 2H), 2.05-1.91 (m, 2H), 1.81-1.64 (m, 2H).

Example 15

(1R,4r)-methyl 4-((R)-3-((4-fluorophenyl)sulfonyl)-3-(4-(1,1,1,3,3,3-hexafluoro-2-hydroxypropan-2-yl)phenyl)pyrrolidine-1-carbonyl)cyclohexanecarboxylate

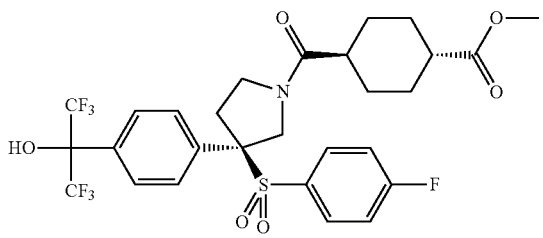 [SMILES: COC(=O)[C@H]1CC[C@H](C(=O)N2CC[C@](c3ccc(C(O)(C(F)(F)F)C(F)(F)F)cc3)(S(=O)(=O)c3ccc(F)cc3)C2)CC1]

Hunig's Base (0.344 mL, 1.969 mmol) was added dropwise to a suspension of (R)-1,1,1,3,3,3-hexafluoro-2-(4-(3-((4-fluorophenyl)sulfonyl)pyrrolidin-3-yl)phenyl)propan-2-ol hydrochloride (200 mg, 0.394 mmol, from Example 3), trans-1,4-cyclohexanedicarboxylic acid monomethyl ester (147 mg, 0.788 mmol) and (benzotriazol-1-yloxy)tris(dimethylamino)phosphonium hexafluorophosphate (348 mg, 0.788 mmol) in dichloromethane (6 mL). After 1 h at room temperature, the mixture was diluted with ethyl acetate (30 mL), washed with sat sodium bicarbonate (2×10 mL), water (10 mL), brine (10 mL), dried (magnesium sulfate), filtered and concentrated under reduced pressure. Silica gel chromatography, eluting with 0-8% methanol in hexanes, gave impure (1R,4r)-methyl 4-((R)-3-((4-fluorophenyl)sulfonyl)-3-(4-(1,1,1,3,3,3-hexafluoro-2-hydroxypropan-2-yl)phenyl)pyrrolidine-1-carbonyl)cyclohexanecarboxylate (326 mg). The material was dissolved in dichloromethane (4 mL), triturated with hexanes (8 mL) and stirred for 15 min. The resulting suspension was filtered and the filter cake washed with dichloromethane-hexanes (1:2, 2×2 mL) to give Example 15 (222 mg, 84% yield). LC/MS (M+1): 640.0; LC retention time: 4.236 min (analytical HPLC Method A); 1H NMR showed a mixture of cis and trans amide isomers.

Example 16

(1R,4r)-4-((R)-3-((4-fluorophenyl)sulfonyl)-3-(4-(1,1,1,3,3,3-hexafluoro-2-hydroxypropan-2-yl)phenyl)pyrrolidine-1-carbonyl)cyclohexanecarboxylic acid

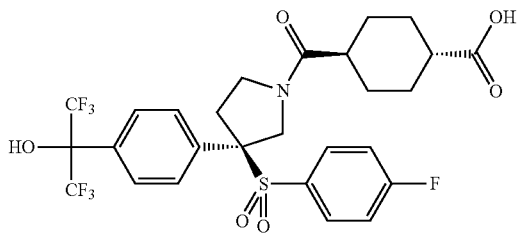 [SMILES: O=C(O)[C@H]1CC[C@H](C(=O)N2CC[C@](c3ccc(C(O)(C(F)(F)F)C(F)(F)F)cc3)(S(=O)(=O)c3ccc(F)cc3)C2)CC1]

A 1 N aqueous solution of sodium hydroxide (1 mL) was added to a mixture of methyl (1R,4r)-methyl 4-((R)-3-((4-fluorophenyl)sulfonyl)-3-(4-(1,1,1,3,3,3-hexafluoro-2-hydroxypropan-2-yl)phenyl)pyrrolidine-1-carbonyl)cyclohexanecarboxylate (15 mg, 0.023 mmol, from Example 15), tetrahydrofuran (1 mL) and methanol (1 mL) at 0° C. The resulting mixture was stirred at 0° C. for 5 min, at room temperature for 30 min, and acidified to pH 2-3 with 1 N hydrochloric acid. After evaporation of organic solvents, the residue was treated with ethyl acetate (10 mL), washed with water (5 mL), brine (5 mL), dried (magnesium sulfate), filtered and concentrated under reduced pressure. The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-100% B over 10 minutes, then a 5-minute hold at 100% B; Flow: 20 mL/min. Fractions containing the desired product were combined and dried via centrifugal evaporation to give Example 16 (12.5 mg, 87% yield). LC/MS (M+1): 626.2; LC retention time: 1.33 min (analytical HPLC Method B); 1H NMR showed a mixture of cis and trans amide isomers.

Example 17

2-(3-(4-(2-((2,6-difluorobenzyl)oxy)-1,1,1,3,3,3-hexafluoropropan-2-yl)phenyl)-3-((4-fluorophenyl)sulfonyl)pyrrolidin-1-yl)pyrimidine-5-carbonitrile

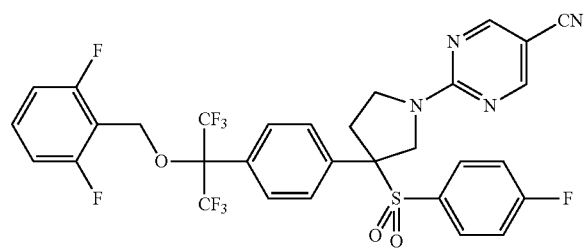 [SMILES: N#Cc1cnc(N2CCC(c3ccc(C(OCc4c(F)cccc4F)(C(F)(F)F)C(F)(F)F)cc3)(S(=O)(=O)c3ccc(F)cc3)C2)nc1]

A mixture of 3-(4-(2-((2,6-difluorobenzyl)oxy)-1,1,1,3,3,3-hexafluoropropan-2-yl)phenyl)-3-((4-fluorophenyl)sulfonyl)pyrrolidine hydrochloride (10 mg, 0.016 mmol, from Example 8), 2-chloropyrimidine-5-carbonitrile (4.40 mg, 0.032 mmol) and potassium carbonate (8.72 mg, 0.063 mmol) in N,N-dimethylformamide (1 mL) in a sealed vial was stirred at 80° C. for 15 h. The mixture was filtered and purified via preparative LC/MS with the following conditions: Column: Waters XBridge C18, 19×100 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 35-100% B over 10 minutes, then a 5-minute hold at 100% B; Flow: 20 mL/min. Fractions containing the desired product were combined and dried via centrifugal evaporation to give Example 17 (8.2 mg, 72% yield). LC/MS (M+1): 701.0; LC retention time: 2.443 min (analytical HPLC Method B); 1H NMR (500 MHz, DMSO-d6) δ ppm 8.87 (d, J=2.5 Hz, 1H), 8.81 (d, J=3.0 Hz, 1H), 7.64-7.53 (m, 3H), 7.48-7.36 (m, 4H), 7.32-7.17 (m, 4H), 5.04 (d, J=13.9 Hz, 1H), 4.71-4.59 (m, 2H), 4.12 (d, J=13.9 Hz, 1H), 3.82-3.68 (m, 2H), 3.31-3.22 (m, 1H), 2.83 (dt, J=14.2, 9.5 Hz, 1H).

Example 18 tert-butyl 2-(3-(4-(2-((2,6-difluorobenzyl)oxy)-1,1,1,3,3,3-hexafluoropropan-2-yl)phenyl)-3-((4-fluorophenyl)sulfonyl)pyrrolidin-1-yl)acetate

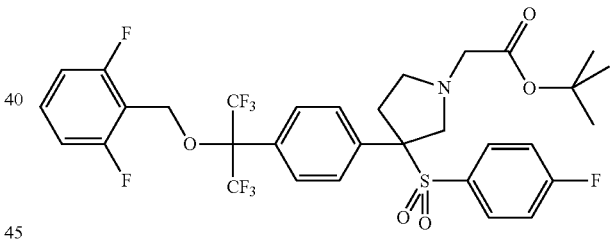

Hunig's Base (0.138 mL, 0.789 mmol) was added to a mixture of 3-(4-(2-((2,6-difluorobenzyl)oxy)-1,1,1,3,3,3-hexafluoropropan-2-yl)phenyl)-3-((4-fluorophenyl)sulfonyl)pyrrolidine hydrochloride (50 mg, 0.079 mmol, from Example 8) and tert-butyl 2-bromoacetate (61.5 mg, 0.315 mmol) in dichloromethane (1 mL). After 17 h at room temperature, the mixture was quenched with ammonium hydroxide (0.05 mL), stirred for 30 min, diluted with ethyl acetate (30 mL), washed with water (2×5 mL) and brine (5 mL), dried (magnesium sulfate), filtered and concentrated under reduced pressure. Silica gel chromatography, eluting with 10-50% ethyl acetate in hexanes, gave Example 18 as colorless liquid (50.7 mg, 86% yield). LC/MS (M+1): 712.1; LC retention time: 4.270 min (analytical HPLC Method A); 1H NMR (400 MHz, CDCl$_3$) δ ppm 7.56 (d, J=8.4 Hz, 2H), 7.43-7.28 (m, 5H), 6.95 (td, J=8.2, 2.5 Hz, 4H), 4.76-4.61 (m, 2H), 3.84-3.66 (m, 2H), 3.47-3.28 (m, 2H), 3.16-3.07 (m, 1H), 3.06-2.92 (m, 2H), 2.65-2.55 (m, 1H), 1.47 (s, 9H).

Example 19

2-(3-(4-(2-((2,6-difluorobenzyl)oxy)-1,1,1,3,3,3-hexafluoropropan-2-yl)phenyl)-3-((4-fluorophenyl)sulfonyl)pyrrolidin-1-yl)-1-morpholinoethanone Step A: 2-(3-(4-(2-((2,6-difluorobenzyl)oxy)-1,1,1,3,3,3-hexafluoropropan-2-yl)phenyl)-3-((4-fluorophenyl)sulfonyl)pyrrolidin-1-yl)acetic acid

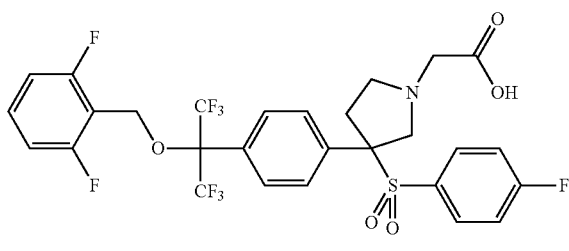 [SMILES: O=C(O)CN1CCC(c2ccc(C(OCc3c(F)cccc3F)(C(F)(F)F)C(F)(F)F)cc2)(S(=O)(=O)c2ccc(F)cc2)C1]

A 4 M dioxane solution of hydrogen chloride (2 mL) was added to a solution of tert-butyl 2-(3-(4-(2-((2,6-difluorobenzyl)oxy)-1,1,1,3,3,3-hexafluoropropan-2-yl)phenyl)-3-((4-fluorophenyl)sulfonyl)pyrrolidin-1-yl)acetate (46.3 mg, 0.065 mmol, from Example 18) in dichloromethane (4 mL). After 2 h at room temperature, additional hydrogen chloride (2 mL) was added. After another 18 h, the reaction was complete. The mixture was concentrated and dried under vacuum to give crude 2-(3-(4-(2-((2,6-difluorobenzyl)oxy)-1,1,1,3,3,3-hexafluoropropan-2-yl)phenyl)-3-((4-fluorophenyl)sulfonyl)pyrrolidin-1-yl)acetic acid hydrochloride, which was used without purification. LC/MS (M+1): 656.0.

Step B: 2-(3-(4-(2-((2,6-difluorobenzyl)oxy)-1,1,1,3,3,3-hexafluoropropan-2-yl)phenyl)-3-((4-fluorophenyl)sulfonyl)pyrrolidin-1-yl)-1-morpholinoethanone

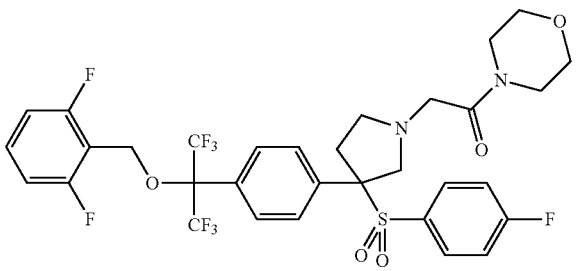 [SMILES: O=C(CN1CCC(c2ccc(C(OCc3c(F)cccc3F)(C(F)(F)F)C(F)(F)F)cc2)(S(=O)(=O)c2ccc(F)cc2)C1)N1CCOCC1]

Hunig's Base (0.014 mL, 0.081 mmol) was added to a mixture of crude 2-(3-(4-(2-((2,6-difluorobenzyl)oxy)-1,1,1,3,3,3-hexafluoropropan-2-yl)phenyl)-3-((4-fluorophenyl)sulfonyl)pyrrolidin-1-yl)acetic acid hydrochloride (25% of the material from Step A, assumed 0.0162 mmol), morpholine (7.06 mg, 0.081 mmol) and (benzotriazol-1-yloxy)tris(dimethylamino)phosphonium hexafluorophosphate (10.75 mg, 0.024 mmol) in dichloromethane (1 mL). After 1 h at room temperature, the mixture was concentrated, treated with methanol (1.5 mL) and filtered. The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 35-100% B over 25 minutes, then a 5-minute hold at 100% B; Flow: 20 mL/min. Fractions containing the desired product were combined and dried via centrifugal evaporation to give Example 19 (6.6 mg, 53% yield over 2 steps). LC/MS (M+1): 725.1; LC retention time: 2.14 min (analytical HPLC Method B); 1H NMR (500 MHz, DMSO-d6) δ ppm 7.64-7.55 (m, 1H), 7.52 (d, J=8.4 Hz, 2H), 7.43 (d, J=8.9 Hz, 2H), 7.38 (dd, J=8.7, 5.2 Hz, 2H), 7.31-7.17 (m, 4H), 4.63 (s, 2H), 3.67 (d, J=10.4 Hz, 1H), 3.55-3.49 (m, 2H), 3.48-3.36 (m, 9H), 2.97-2.87 (m, 1H), 2.79 (t, J=6.2 Hz, 2H), 2.61-2.53 (m, 1H).

Example 20

(R)-1-(3-(4-(2-((2,6-difluorobenzyl)oxy)-1,1,1,3,3,3-hexafluoropropan-2-yl)phenyl)-3-((4-fluorophenyl)sulfonyl)pyrrolidine-1-carbonyl)-4-fluoropiperidine-4-carboxylic acid Step A: (R)-3-(4-(2-((2,6-difluorobenzyl)oxy)-1,1,1,3,3,3-hexafluoropropan-2-yl)phenyl)-3-((4-fluorophenyl)sulfonyl)pyrrolidine-1-carbonyl chloride

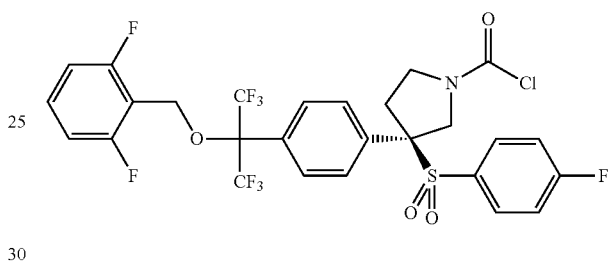

Pyridine (0.230 mL, 2.84 mmol) was added to a cloudy solution of triphosgene (281 mg, 0.946 mmol) in dichloromethane (15 mL) at −78° C. The resulting suspension was stirred at −78° C. for 5 min and at ambient temperature until it became a homogeneous solution (~15 min). A suspension of (R)-3-(4-(2-((2,6-difluorobenzyl)oxy)-1,1,1,3,3,3-hexafluoropropan-2-yl)phenyl)-3-((4-fluorophenyl)sulfonyl)pyrrolidine hydrochloride (300 mg, 0.473 mmol, from Example 10) and pyridine (37.5 mg) in dichloromethane (6 mL) was added to the above solution. The container was rinsed with dichloromethane (2×2 mL) and added. The resulting light brown solution was stirred under nitrogen at room temperature for 15 h. The mixture was diluted with dichloromethane (50 mL), washed with 1 N HCl-brine (1:1 mixture, 2×12 mL), dried (magnesium sulfate), filtered and concentrated under reduced pressure to give (R)-3-(4-(2-((2,6-difluorobenzyl)oxy)-1,1,1,3,3,3-hexafluoropropan-2-yl)phenyl)-3-((4-fluorophenyl)sulfonyl)pyrrolidine-1-carbonyl chloride as tan solid (309 mg, 99% yield). LC/MS (M+18): 677.3.

Step B: (R)-1-(3-(4-(2-((2,6-difluorobenzyl)oxy)-1,1,1,3,3,3-hexafluoropropan-2-yl)phenyl)-3-((4-fluorophenyl)sulfonyl)pyrrolidine-1-carbonyl)-4-fluoropiperidine-4-carboxylic acid

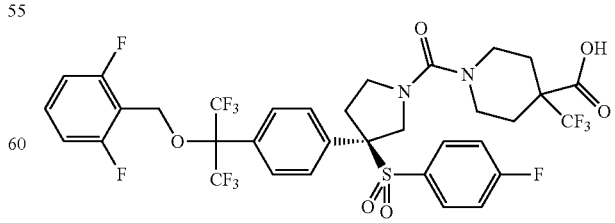

Hunig's Base (0.015 mL, 0.083 mmol) was added to a solution of (R)-3-(4-(2-((2,6-difluorobenzyl)oxy)-1,1,1,3,3,3-hexafluoropropan-2-yl)phenyl)-3-((4-fluorophenyl)sulfonyl)pyrrolidine-1-carbonyl chloride (11 mg, 0.017 mmol) and ethyl 4-fluoropiperidine-4-carboxylate hydrochloride (10.58 mg, 0.050 mmol) in tetrahydrofuran (1 mL). After 1 h at room temperature, LCMS analysis showed that the urea formation was complete. The mixture was diluted with methanol (1 mL) and cooled to 0° C. A 1 N aqueous solution of sodium hydroxide (1 mL) was added. The mixture was stirred at 0° C. for 10 min, at ambient temperature for 30 min and acidified to pH 3-4 with 1 N hydrochloric acid. After evaporation of organic solvents, the residue was diluted with ethyl acetate (20 mL), washed with water (5 mL), brine (5 mL), dried (magnesium sulfate), filtered and concentrated under reduced pressure. The crude material was purified via preparative LC/MS with the following conditions: Column: XBridge C18, 19×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-100% B over 10 minutes, then a 5-minute hold at 100% B; Flow: 20 mL/min. Fractions containing the desired product were combined and dried via centrifugal evaporation to give Example 20 (10.4 mg, 79% yield). LC/MS (M+1): 771.2; LC retention time: 1.77 min (analytical HPLC Method B); 1H NMR (500 MHz, 1:1 mixture of CD$_3$OD-CDCl$_3$) δ ppm 7.60 (t, J=4.0 Hz, 2H), 7.49-7.41 (m, 1H), 7.41-7.36 (m, 2H), 7.29 (d, J=8.6 Hz, 2H), 7.12-6.97 (m, 4H), 4.70 (s, 2H), 4.67-4.60 (m, 1H), 4.07 (d, J=12.8 Hz, 1H), 4.01-3.92 (m, 1H), 3.71 (t, J=12.8 Hz, 2H), 3.59 (td, J=9.4, 3.6 Hz, 1H), 3.28-3.12 (m, 3H), 2.71-2.59 (m, 1H), 2.33-2.09 (m, 2H), 2.04-1.91 (m, 2H).

Example 21

(R)-1-(3-(4-(2-(cyclohexylmethoxy)-1,1,1,3,3,3-hexafluoropropan-2-yl)phenyl)-3-((4-fluorophenyl)sulfonyl)pyrrolidine-1-carbonyl)piperidine-4-carboxylic acid Step A: (R)-ethyl 1-(3-(4-(2-(cyclohexylmethoxy)-1,1,1,3,3,3-hexafluoropropan-2-yl)phenyl)-3-((4-fluorophenyl)sulfonyl)pyrrolidine-1-carbonyl)piperidine-4-carboxylate

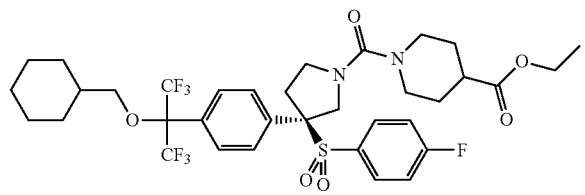 [SMILES: CCOC(=O)C1CCN(C(=O)N2CC[C@](c3ccc(C(OCC4CCCCC4)(C(F)(F)F)C(F)(F)F)cc3)(S(=O)(=O)c3ccc(F)cc3)C2)CC1]

Cyclohexylmethanol (10.47 mg, 0.092 mmol) was added to a solution of (R)-ethyl 1-(3-((4-fluorophenyl)sulfonyl)-3-(4-(1,1,1,3,3,3-hexafluoro-2-hydroxypropan-2-yl)phenyl) pyrrolidine-1-carbonyl)piperidine-4-carboxylate (20 mg, 0.031 mmol, from Example 13), triphenylphosphine (24.04 mg, 0.092 mmol) and N1,N1,N2,N2-tetramethyldiazene-1,2-dicarboxamide (15.78 mg, 0.092 mmol) in toluene (0.5 mL) under nitrogen at room temperature. The reaction vial was purged with nitrogen for 5 min, sealed and stirred at 80° C. for 2.5 h. After cooling to room temperature and evaporation of solvent, the residue was dissolved in methanol (2 mL) and purified by preparative RP-HPLC (20-100% solvent B in 6 min, 20 mL/min, Phenomenex Luna C18 S5 21×100 mm) to give (R)-ethyl 1-(3-(4-(2-(cyclohexylmethoxy)-1,1,1,3,3,3-hexafluoropropan-2-yl)phenyl)-3-((4-fluorophenyl)sulfonyl)pyrrolidine-1-carbonyl)piperidine-4-carboxylate as colorless oil (19.7 mg). LC/MS (M+1): 751.6.

Step B: (R)-1-(3-(4-(2-(cyclohexylmethoxy)-1,1,1,3,3,3-hexafluoropropan-2-yl)phenyl)-3-((4-fluorophenyl)sulfonyl)pyrrolidine-1-carbonyl)piperidine-4-carboxylic acid

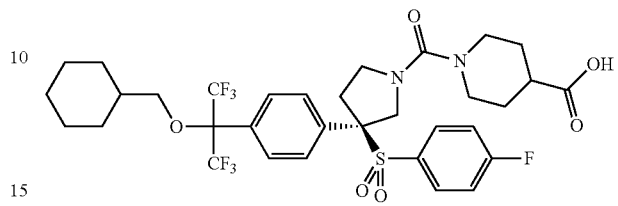

A 1 M aqueous solution of sodium hydroxide (0.25 mL, 0.250 mmol) was added to a solution of (R)-ethyl 1-(3-(4-(2-(cyclohexylmethoxy)-1,1,1,3,3,3-hexafluoropropan-2-yl)phenyl)-3-((4-fluorophenyl)sulfonyl)pyrrolidine-1-carbonyl)piperidine-4-carboxylate (19.7 mg) in methanol (0.25 mL) and tetrahydrofuran (0.25 mL) at room temperature. After 15 h at room temperature, the mixture was neutralized with 1 N hydrochloric acid (0.25 mL), diluted with methanol (1 mL) and filtered. The filtrate was concentrated and purified via preparative LC/MS with the following conditions: Column: Waters XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 35-100% B over 25 minutes, then a 5-minute hold at 100% B; Flow: 20 mL/min. Fractions containing the desired product were combined and dried via centrifugal evaporation to give Example 21 (13.5 mg, 60% yield over 2 steps). LC/MS (M+1): 723.5; LC retention time: 2.24 min (analytical HPLC Method B); 1H NMR (400 MHz, 1:1 mixture of CDCl$_3$—CD$_3$OD) δ ppm 7.50 (d, J=8.4 Hz, 2H), 7.42-7.33 (m, 2H), 7.25 (d, J=8.6 Hz, 2H), 7.08 (t, J=8.6 Hz, 2H), 4.62 (d, J=12.5 Hz, 1H), 4.03 (d, J=12.5 Hz, 1H), 3.98-3.87 (m, 1H), 3.80-3.67 (m, 2H), 3.54 (td, J=9.5, 3.5 Hz, 1H), 3.40-3.34 (m, 2H), 3.26-3.13 (m, 1H), 3.03-2.86 (m, 2H), 2.69-2.47 (m, 2H), 2.04-1.92 (m, 2H), 1.88-1.65 (m, 8H), 1.41-1.16 (m, 3H), 1.11-0.96 (m, 2H).

Example 22

(R)-1-acetyl-4-(3-(4-(2-((2,6-difluorobenzyl)oxy)-1,1,1,3,3,3-hexafluoropropan-2-yl)phenyl)-3-((4-fluorophenyl)sulfonyl)pyrrolidine-1-carbonyl)piperidine-4-carbonitrile Step A: (R)-tert-butyl 4-cyano-4-(3-(4-(2-((2,6-difluorobenzyl)oxy)-1,1,1,3,3,3-hexafluoropropan-2-yl)phenyl)-3-((4-fluorophenyl)sulfonyl)pyrrolidine-1-carbonyl)piperidine-1-carboxylate

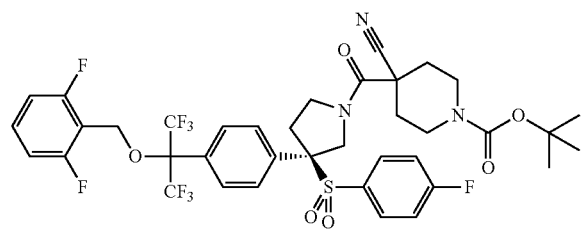 [SMILES: CC(C)(C)OC(=O)N1CCC(C#N)(C(=O)N2CC[C@](c3ccc(C(OCc4c(F)cccc4F)(C(F)(F)F)C(F)(F)F)cc3)(S(=O)(=O)c3ccc(F)cc3)C2)CC1]

Hunig's Base (0.033 mL, 0.189 mmol) was added to a solution of (R)-3-(4-(2-((2,6-difluorobenzyl)oxy)-1,1,1,3,3,3-hexafluoropropan-2-yl)phenyl)-3-((4-fluorophenyl)sulfonyl)pyrrolidine hydrochloride (20 mg, 0.032 mmol, from Example 10), 1-(tert-butoxycarbonyl)-4-cyanopiperidine-4-carboxylic acid (20.06 mg, 0.079 mmol) and HATU (30.0 mg, 0.079 mmol) in N,N-dimethylformamide (1 mL). The resulting solution was stirred at 70° C. for 2 h, cooled to room temperature, diluted with ethyl acetate (25 mL), washed with water (2×5 mL), brine (5 mL), dried (magnesium sulfate), filtered and concentrated under reduced pressure to give the crude (R)-tert-butyl 4-cyano-4-(3-(4-(2-(2,6-difluorobenzyl)oxy)-1,1,1,3,3,3-hexafluoropropan-2-yl)phenyl)-3-((4-fluorophenyl)sulfonyl)pyrrolidine-1-carbonyl)piperidine-1-carboxylate, which was taken to the next reaction without purification. LC/MS (M−56+1): 778.3.
Step B: (R)-4-(3-(4-(2-((2,6-difluorobenzyl)oxy)-1,1,1,3,3,3-hexafluoropropan-2-yl)phenyl)-3-((4-fluorophenyl)sulfonyl)pyrrolidine-1-carbonyl)piperidine-4-carbonitrile

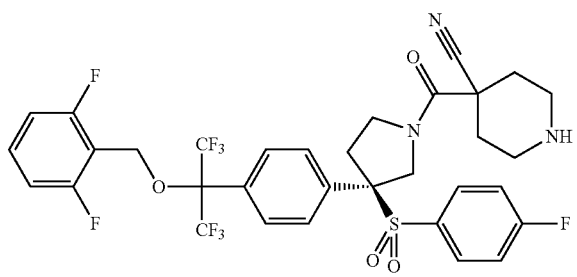 [SMILES: N#CC1(C(=O)N2CC[C@](c3ccc(C(OCc4c(F)cccc4F)(C(F)(F)F)C(F)(F)F)cc3)(S(=O)(=O)c3ccc(F)cc3)C2)CCNCC1]

A mixture of crude (R)-tert-butyl 4-cyano-4-(3-(4-(2-((2,6-difluorobenzyl)oxy)-1,1,1,3,3,3-hexafluoropropan-2-yl)phenyl)-3-((4-fluorophenyl)sulfonyl)pyrrolidine-1-carbonyl)piperidine-1-carboxylate from Step A, 4 N HCl in dioxane (2 mL) and dichloromethane (2 mL) was stirred at room temperature for 2 h. The mixture was concentrated and dried under vacuum overnight to give crude (R)-4-(3-(4-(2-((2,6-difluorobenzyl)oxy)-1,1,1,3,3,3-hexafluoropropan-2-yl)phenyl)-3-((4-fluorophenyl)sulfonyl)pyrrolidine-1-carbonyl)piperidine-4-carbonitrile hydrochloride as brown solid. This material was taken to the next reaction without purification. LC/MS (M+1): 734.4.
Step C: (R)-1-acetyl-4-(3-(4-(2-((2,6-difluorobenzyl)oxy)-1,1,1,3,3,3-hexafluoropropan-2-yl)phenyl)-3-((4-fluorophenyl)sulfonyl)pyrrolidine-1-carbonyl)piperidine-4-carbonitrile

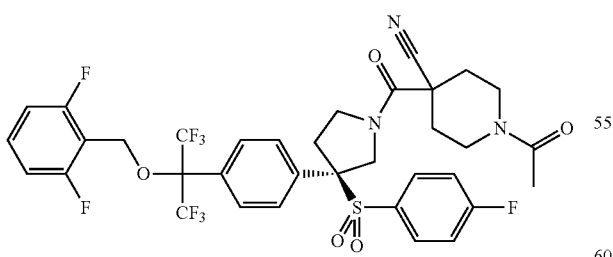

Hunig's Base (0.045 mL, 0.256 mmol) was added to a mixture of crude (R)-4-(3-(4-(2-((2,6-difluorobenzyl)oxy)-1,1,1,3,3,3-hexafluoropropan-2-yl)phenyl)-3-((4-fluorophenyl)sulfonyl)pyrrolidine-1-carbonyl)piperidine-4-carbonitrile hydrochloride from Step B, acetic anhydride (0.012 mL, 0.128 mmol) and dichloromethane (1 mL) at room temperature. The resulting brown solution was stirred at room temperature for 1 h, quenched with ammonium hydroxide (1 drop), stirred for 5 min, filtered and concentrated under reduced pressure. The crude material was purified via preparative LC/MS with the following conditions: Column: Waters XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 35-100% B over 20 minutes, then a 5-minute hold at 100% B; Flow: 20 mL/min. Fractions containing the desired product were combined and dried via centrifugal evaporation to give Example 22 (18.1 mg, 73% yield over two steps). LC/MS (M+1): 776.3; LC retention time: 2.16 (analytical HPLC Method B); 1H NMR showed two sets of signals for some of the protons due to presence of cis and trans amide isomers.

Example 23

(R)-1-acetyl-4-(3-(4-(2-((2,6-difluorobenzyl)oxy)-1,1,1,3,3,3-hexafluoropropan-2-yl)phenyl)-3-((4-fluorophenyl)sulfonyl)pyrrolidine-1-carbonyl)piperidine-4-carboxamide Step A: 1-tert-butyl 4-ethyl 4-carbamoylpiperidine-1,4-dicarboxylate

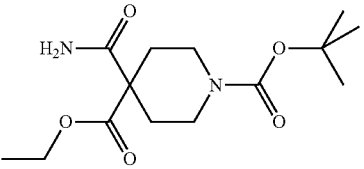 [SMILES: CCOC(=O)C1(C(N)=O)CCN(C(=O)OC(C)(C)C)CC1]

Hunig's Base (0.614 mL, 3.52 mmol) and ammonia (0.377 mL, 2.64 mmol, 7 M solution in methanol) were added to a solution of 1-(tert-butoxycarbonyl)-4-(ethoxycarbonyl)piperidine-4-carboxylic acid (0.265 g, 0.879 mmol, impure from Sinova) and (benzotriazol-1-yloxy)tris(dimethylamino)phosphonium hexafluorophosphate (0.467 g, 1.055 mmol) in N,N-dimethylformamide (5 mL). After 15 h at room temperature, the mixture was diluted with ethyl acetate (80 mL), washed with water (2×20 mL) and brine (20 mL), dried (magnesium sulfate), filtered and concentrated under reduced pressure. Silica gel chromatography, eluting with 0-10% methanol in dichloromethane, gave impure 1-tert-butyl 4-ethyl 4-carbamoylpiperidine-1,4-dicarboxylate as colorless liquid (244 mg), which was taken to the next step without further purification.
Step B: ethyl 4-carbamoylpiperidine-4-carboxylate

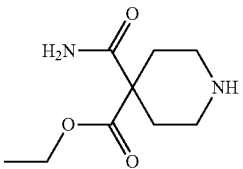

A mixture of impure 1-tert-butyl 4-ethyl 4-carbamoylpiperidine-1,4-dicarboxylate from Step A (244 mg) in 4 N HCl in dioxane (4 mL) and dichloromethane (4 mL) was stirred at room temperature for 2 h, concentrated and dried under vacuum to give impure ethyl 4-carbamoylpiperidine-4-carboxylate hydrochloride as colorless glass. This material was taken to the next step without further purification.

Step C: ethyl 1-acetyl-4-carbamoylpiperidine-4-carboxylate

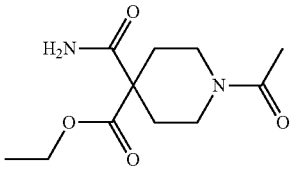 [SMILES: CCOC(=O)C1(C(N)=O)CCN(C(C)=O)CC1]

Hunig's Base (0.614 mL, 3.52 mmol) was added to a mixture of impure ethyl 4-carbamoylpiperidine-4-carboxylate hydrochloride from Step B, acetic anhydride (0.149 mL, 1.582 mmol) and dichloromethane (5 mL). The resulting solution was stirred for 1 h, quenched with ammonium hydroxide (0.05 mL) and directly loaded on a silica gel column. Silica gel chromatography, eluting with 0-10% methanol in dichloromethane, gave ethyl 1-acetyl-4-carbamoylpiperidine-4-carboxylate (118 mg). 1H NMR indicated that the material was still impure.

Step D: 1-acetyl-4-carbamoylpiperidine-4-carboxylic acid

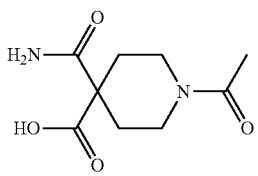

A mixture of impure ethyl 1-acetyl-4-carbamoylpiperidine-4-carboxylate from Step C (118 mg) in tetrahydrofuran (1 mL), methanol (1 mL) and 1 N sodium hydroxide (1 mL) in a sealed vial was stirred at 80° C. for 1 h and at room temperature over the long weekend. The mixture was acidified to pH ~2 with 1 N hydrochloric acid and concentrated under reduced pressure to dryness. The solid residue was treated with methanol (1 mL) and ethyl acetate (4 mL), sonicated for 1 min, stirred for 30 min and filtered. The filtrate was concentrated to give crude 1-acetyl-4-carbamoylpiperidine-4-carboxylic acid as colorless oil (120 mg). 1H NMR showed that the major component is consistent with the desired product, but the material was impure. This material was used in subsequent reaction without purification.

Step E: (R)-1-acetyl-4-(3-(4-(2-((2,6-difluorobenzyl)oxy)-1,1,1,3,3,3-hexafluoropropan-2-yl)phenyl)-3-((4-fluorophenyl)sulfonyl)pyrrolidine-1-carbonyl)piperidine-4-carboxamide

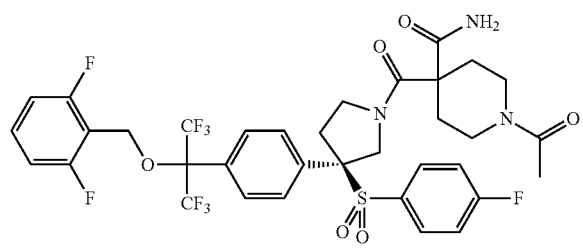 [SMILES: CC(=O)N1CCC(C(N)=O)(C(=O)N2CC[C@](c3ccc(C(OCc4c(F)cccc4F)(C(F)(F)F)C(F)(F)F)cc3)(S(=O)(=O)c3ccc(F)cc3)C2)CC1]

Hunig's Base (0.023 mL, 0.130 mmol) was added to a mixture of (R)-3-(4-(2-((2,6-difluorobenzyl)oxy)-1,1,1,3,3,3-hexafluoropropan-2-yl)phenyl)-3-((4-fluorophenyl)sulfonyl)pyrrolidine hydrochloride (16.5 mg, 0.026 mmol, from Example 10), (benzotriazol-1-yloxy)tris(dimethylamino)phosphonium hexafluorophosphate (28.8 mg, 0.065 mmol) and impure 1-acetyl-4-carbamoylpiperidine-4-carboxylic acid from Step D (16.7 mg) in N,N-dimethylformamide (1 mL). The reaction vial was sealed and stirred at 70° C. for 1 h, cooled to room temperature and filtered. The crude material was purified via preparative LC/MS with the following conditions: Column: Waters XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-65% B over 25 minutes, then a 10-minute hold at 65% B; Flow: 20 mL/min. Fractions containing the desired product were combined and dried via centrifugal evaporation to give Example 23 (9.7 mg, 47% yield). LC/MS (M+1): 794.2; LC retention time: 1.95 (analytical HPLC Method B); 1H NMR showed two sets of signals for some of the protons due to presence of cis and trans amide isomers.

Example 24

(R)-1-(4-(3-(4-(2-((2,6-difluorobenzyl)oxy)-1,1,1,3,3,3-hexafluoropropan-2-yl)phenyl)-3-((4-fluorophenyl)sulfonyl)pyrrolidine-1-carbonyl)-4-hydroxypiperidin-1-yl)ethanone Step A: (R)-tert-butyl 4-(3-(4-(2-((2,6-difluorobenzyl)oxy)-1,1,1,3,3,3-hexafluoropropan-2-yl)phenyl)-3-((4-fluorophenyl)sulfonyl)pyrrolidine-1-carbonyl)-4-hydroxypiperidine-1-carboxylate

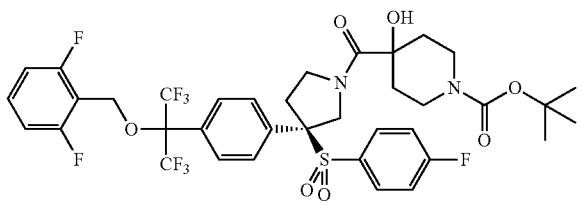 [SMILES: CC(C)(C)OC(=O)N1CCC(O)(C(=O)N2CC[C@](c3ccc(C(OCc4c(F)cccc4F)(C(F)(F)F)C(F)(F)F)cc3)(S(=O)(=O)c3ccc(F)cc3)C2)CC1]

Hunig's Base (0.017 mL, 0.099 mmol) was added to a mixture of (R)-3-(4-(2-((2,6-difluorobenzyl)oxy)-1,1,1,3,3,3-hexafluoropropan-2-yl)phenyl)-3-((4-fluorophenyl)sulfonyl)pyrrolidine hydrochloride (18 mg, 0.028 mmol, from Example 10), (benzotriazol-1-yloxy)tris(dimethylamino)phosphonium hexafluorophosphate (25.1 mg, 0.057 mmol) and 1-(tert-butoxycarbonyl)-4-hydroxypiperidine-4-carboxylic acid (13.93 mg, 0.057 mmol) in N,N-dimethylformamide (1 mL). The reaction vial was sealed and stirred at 70° C. for 2 h. The mixture was diluted with ethyl acetate (25 mL), washed with water (2×5 mL), brine (5 mL), dried (magnesium sulfate), filtered and concentrated under reduced pressure to give crude (R)-tert-butyl 4-(3-(4-(2-((2,6-difluorobenzyl)oxy)-1,1,1,3,3,3-hexafluoropropan-2-yl)phenyl)-3-((4-fluorophenyl)sulfonyl)pyrrolidine-1-carbonyl)-4-hydroxypiperidine-1-carboxylate, which was taken to the next step without further purification. LC/MS (M−56+1): 769.4.

Step B: (R)-(3-(4-(2-((2,6-difluorobenzyl)oxy)-1,1,1,3,3,3-hexafluoropropan-2-yl)phenyl)-3-((4-fluorophenyl)sulfonyl)pyrrolidin-1-yl)(4-hydroxypiperidin-4-yl)methanone

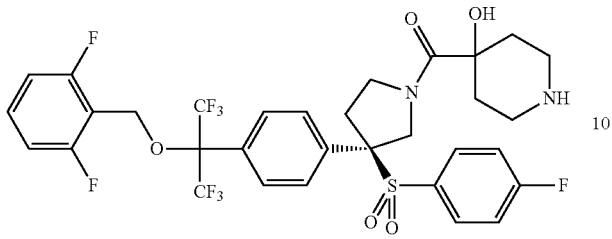

A 4 N dioxane solution of HCl (2 mL) was added to a solution of crude (R)-tert-butyl 4-(3-(4-(2-((2,6-difluorobenzyl)oxy)-1,1,1,3,3,3-hexafluoropropan-2-yl)phenyl)-3-((4-fluorophenyl)sulfonyl)pyrrolidine-1-carbonyl)-4-hydroxypiperidine-1-carboxylate from Step A in dichloromethane (2 mL). After 2 h at room temperature, the mixture was concentrated and dried under vacuum to give the crude (R)-(3-(4-(2-((2,6-difluorobenzyl)oxy)-1,1,1,3,3,3-hexafluoropropan-2-yl)phenyl)-3-((4-fluorophenyl)sulfonyl)pyrrolidin-1-yl)(4-hydroxypiperidin-4-yl)methanone hydrochloride. This material was taken to the next step without purification. LC/MS (M+1): 725.4.

Step C: (R)-1-(4-(3-(4-(2-((2,6-difluorobenzyl)oxy)-1,1,1,3,3,3-hexafluoropropan-2-yl)phenyl)-3-((4-fluorophenyl)sulfonyl)pyrrolidine-1-carbonyl)-4-hydroxypiperidin-1-yl)ethanone

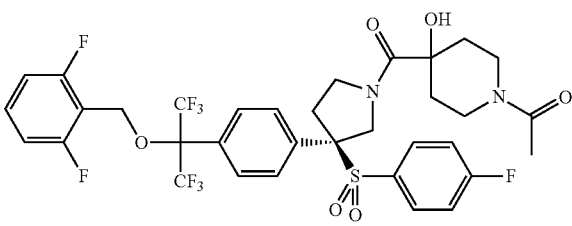 [SMILES: CC(=O)N1CCC(O)(C(=O)N2CC[C@](c3ccc(C(OCc4c(F)cccc4F)(C(F)(F)F)C(F)(F)F)cc3)(S(=O)(=O)c3ccc(F)cc3)C2)CC1]

Hunig's Base (0.017 mL, 0.099 mmol) was added to a suspension of crude (R)-(3-(4-(2-((2,6-difluorobenzyl)oxy)-1,1,1,3,3,3-hexafluoropropan-2-yl)phenyl)-3-((4-fluorophenyl)sulfonyl)pyrrolidin-1-yl)(4-hydroxypiperidin-4-yl)methanone hydrochloride from Step B, (benzotriazol-1-yloxy)tris(dimethylamino)phosphonium hexafluorophosphate (25.1 mg, 0.057 mmol) and acetic acid (3.41 mg, 0.057 mmol) in dichloromethane (1 mL) and N,N-dimethylformamide (0.5 mL). After 1 h at room temperature, the mixture was quenched with ammonium hydroxide (1 drop) and stirred for 10 min. After evaporation of the volatile dichloromethane, the residue was diluted with N,N-dimethylformamide (1 mL) and filtered. The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-100% B over 25 minutes, then a 5-minute hold at 100% B; Flow: 20 mL/min. Fractions containing the desired product were combined and dried via centrifugal evaporation to give Example 24 (13.8 mg, 63% yield over three steps). LC/MS (M+1): 767.2; LC retention time: 2.01 (analytical HPLC Method B); 1H NMR showed two sets of signals for some of the protons due to presence of cis and trans amide isomers.

Example 25

(R)-1-(4-(3-(4-(2-((2,6-difluorobenzyl)oxy)-1,1,1,3,3,3-hexafluoropropan-2-yl)phenyl)-3-((4-fluorophenyl)sulfonyl)pyrrolidone-1-carbonyl)-4-(hydroxymethyl)piperidin-1-yl)ethanone Step A: (R)-tert-butyl 4-(3-(4-(2-((2,6-difluorobenzyl)oxy)-1,1,1,3,3,3-hexafluoropropan-2-yl)phenyl)-3-((4-fluorophenyl)sulfonyl)pyrrolidine-1-carbonyl)-4-(hydroxymethyl)piperidine-1-carboxylate

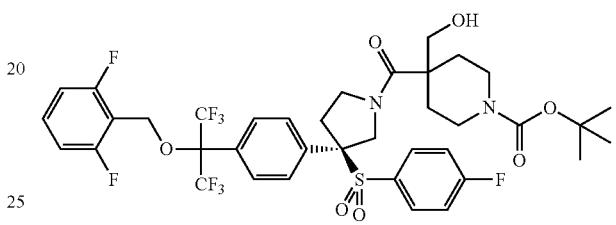

Hunig's Base (0.033 mL, 0.189 mmol) was added to a mixture of (R)-3-(4-(2-((2,6-difluorobenzyl)oxy)-1,1,1,3,3,3-hexafluoropropan-2-yl)phenyl)-3-((4-fluorophenyl)sulfonyl)pyrrolidine hydrochloride (20 mg, 0.032 mmol, from Example 10), 1-(tert-butoxycarbonyl)-4-(hydroxymethyl)-4-piperidinecarboxylic acid (20.45 mg, 0.079 mmol) and HATU (30.0 mg, 0.079 mmol) in N,N-dimethylformamide (1 mL). The reaction vial was sealed and stirred at 75° C. for 3.5 h. The mixture was diluted with ethyl acetate (20 mL), washed with water (2×5 mL), brine (5 mL), dried (magnesium sulfate), filtered and concentrated under reduced pressure to give crude (R)-tert-butyl 4-(3-(4-(2-((2,6-difluorobenzyl)oxy)-1,1,1,3,3,3-hexafluoropropan-2-yl)phenyl)-3-((4-fluorophenyl)sulfonyl)pyrrolidine-1-carbonyl)-4-(hydroxymethyl)piperidine-1-carboxylate, which was taken to the next step without further purification. LC/MS (M+1): 839.6.

Step B: (R)-(3-(4-(2-((2,6-difluorobenzyl)oxy)-1,1,1,3,3,3-hexafluoropropan-2-yl)phenyl)-3-((4-fluorophenyl)sulfonyl)pyrrolidin-1-yl)(4-(hydroxymethyl)piperidin-4-yl)methanone

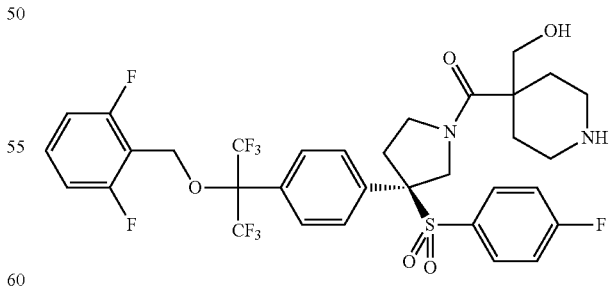

A mixture of crude (R)-tert-butyl 4-(3-(4-(2-((2,6-difluorobenzyl)oxy)-1,1,1,3,3,3-hexafluoropropan-2-yl)phenyl)-3-((4-fluorophenyl)sulfonyl)pyrrolidine-1-carbonyl)-4-(hydroxymethyl)piperidine-1-carboxylate from Step A, 4 N HCl in dioxane (2 mL) and dichloromethane (4 mL) was stirred at room temperature for 3 h. The mixture was concentrated and dried under vacuum to give crude (R)-(3-(4-(2-((2,6-difluorobenzyl)oxy)-1,1,1,3,3,3-hexafluoropropan-2-yl)phenyl)-3-((4-fluorophenyl)sulfonyl)pyrrolidin-1-yl)(4-(hydroxymethyl)piperidin-4-yl)methanone hydrochloride as brown solid. This material was taken to the next step without purification. LC/MS (M+1): 739.5.

Step C: (R)-1-(4-(3-(4-(2-((2,6-difluorobenzyl)oxy)-1,1,1,3,3,3-hexafluoropropan-2-yl)phenyl)-3-((4-fluorophenyl)sulfonyl)pyrrolidine-1-carbonyl)-4-(hydroxymethyl)piperidin-1-yl)ethanone

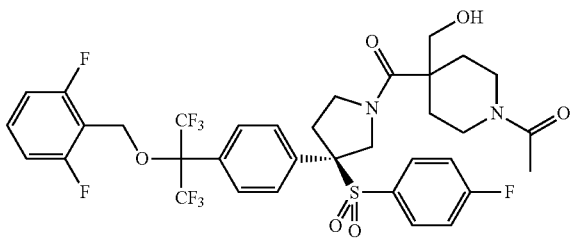 [SMILES: CC(=O)N1CCC(CO)(C(=O)N2CC[C@](c3ccc(C(OCc4c(F)cccc4F)(C(F)(F)F)C(F)(F)F)cc3)(S(=O)(=O)c3ccc(F)cc3)C2)CC1]

Hunig's Base (0.045 mL, 0.256 mmol) was added to a suspension of crude (R)-(3-(4-(2-((2,6-difluorobenzyl)oxy)-1,1,1,3,3,3-hexafluoropropan-2-yl)phenyl)-3-((4-fluorophenyl)sulfonyl)pyrrolidin-1-yl)(4-(hydroxymethyl)piperidin-4-yl)methanone hydrochloride from Step C, acetic acid (7.33 µl, 0.128 mmol) and (benzotriazol-1-yloxy)tris(dimethylamino)phosphonium hexafluorophosphate (18.40 mg, 0.042 mmol) in dichloromethane (1 mL) and tetrahydrofuran (1 mL). After 1 h at room temperature, the mixture was quenched with ammonium hydroxide (2 drops), stirred for 10 min and concentrated under reduced pressure. The crude material was purified via preparative LC/MS with the following conditions: Column: Waters XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 40-80% B over 25 minutes, then a 10-minute hold at 80% B; Flow: 20 mL/min. Fractions containing the desired product were combined and dried via centrifugal evaporation to give Example 25 (12.3 mg, 49% yield over three steps). LC/MS (M+1): 781.4; LC retention time: 2.01 (analytical HPLC Method B); 1H NMR showed two sets of signals for some of the protons due to presence of cis and trans amide isomers.

Example 26

(R)-(3-(4-(2-((2,6-difluorobenzyl)oxy)-1,1,1,3,3,3-hexafluoropropan-2-yl)phenyl)-3-((4-fluorophenyl)sulfonyl)pyrrolidin-1-yl)4-(hydroxymethyl)tetrahydro-2H-pyran-4-yl)methanone Step A: methyl 4-formyltetrahydro-2H-pyran-4-carboxylate

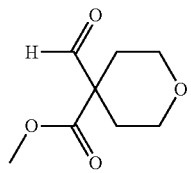

A 1 M toluene solution of diisobutylaluminum hydride (24.73 mL, 24.73 mmol) was added over 10 min to a solution of dimethyl dihydro-2H-pyran-4,4(3H)-dicarboxylate (2.50 g, 12.36 mmol) in dichloromethane (50 mL) at −78° C. After 3 h at −78° C., the mixture was quenched with saturated ammonium chloride (2 mL) and 1 N hydrochloric acid (4 mL). The cold bath was removed and the mixture stirred at ambient temperature for 1 h. The resulting suspension was filtered and the filter cake washed with dichloromethane (50 mL). The filtrate was concentrated and dried under vacuum to give methyl 4-formyltetrahydro-2H-pyran-4-carboxylate as colorless liquid (2.022 g). $^1$H NMR showed that aldehyde proton was present as the main component, but the material was impure. This material was used in the next step without purification.

Step B: methyl 4-(hydroxymethyl)tetrahydro-2H-pyran-4-carboxylate

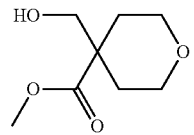

Granular sodium borohydride (0.234 g, 6.18 mmol) was added to a solution of impure methyl 4-formyltetrahydro-2H-pyran-4-carboxylate (2.022 g) from Step A in methanol (10 mL) at 0° C. After 1 h at 0° C., the mixture was quenched with saturated ammonium chloride (10 mL). The methanol was evaporated under reduced pressure. The aqueous residue was diluted with water (10 mL) and extracted with dichloromethane (5×15 mL). The combined extracts were dried (magnesium sulfate), filtered and concentrated under reduced pressure. Silica gel chromatography, eluting with 20-100% ethyl acetate in hexanes, gave methyl 4-(hydroxymethyl)tetrahydro-2H-pyran-4-carboxylate as colorless liquid (1.266 g, 59% yield over two steps). 1H NMR (400 MHz, CDCl3) δ ppm 3.82 (dt, J=12.0, 4.2 Hz, 2H), 3.77 (s, 3H), 3.67 (d, J=6.2 Hz, 2H), 3.60-3.49 (m, 2H), 2.15-1.99 (m, 3H), 1.57 (ddd, J=14.0, 10.0, 4.4 Hz, 2H).

Step C: 4-(hydroxymethyl)tetrahydro-2H-pyran-4-carboxylic acid

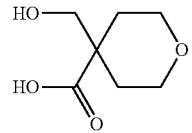 [SMILES: O=C(O)C1(CO)CCOCC1]

A mixture of methyl 4-(hydroxymethyl)tetrahydro-2H-pyran-4-carboxylate (257 mg) and 1 N sodium hydroxide (3 mL) in tetrahydrofuran (3 mL) and methanol (3 mL) in a sealed vial was stirred at 70° C. for 15 h. The resulting mixture was cooled to room temperature, acidified to pH 2-3 with 1 N hydrochloric acid and concentrated under reduced pressure to dryness. The solid residue was treated with ethyl acetate (10 mL) and methanol (1 mL), sonicated for 1 min, stirred for 1 h, and filtered. The filtrate was concentrated and dried under vacuum to give 4-(hydroxymethyl)tetrahydro-2H-pyran-4-carboxylic acid as white solid (226 mg, 95% yield). 1H NMR (400 MHz, CD$_3$OD) δ ppm 3.82 (dt, J=11.6, 3.9 Hz, 2H), 3.58 (s, 2H), 3.54 (td, J=11.5, 2.4 Hz, 2H), 2.07-1.94 (m, 2H), 1.55 (ddd, J=13.9, 11.2, 4.5 Hz, 2H).

Step D: (R)-(3-(4-(2-((2,6-difluorobenzyl)oxy)-1,1,1,3,3,3-hexafluoropropan-2-yl)phenyl)-3-((4-fluorophenyl)sulfonyl)pyrrolidin-1-yl)(4-(hydroxymethyl)tetrahydro-2H-pyran-4-yl)methanone

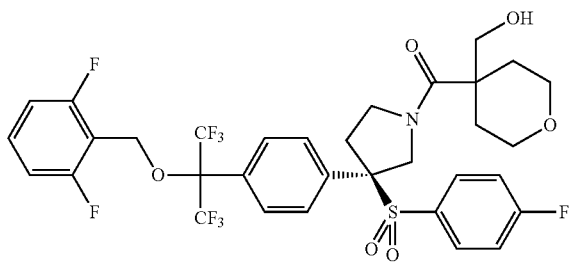 [SMILES: O=C(N1CC[C@](c2ccc(C(OCc3c(F)cccc3F)(C(F)(F)F)C(F)(F)F)cc2)(S(=O)(=O)c2ccc(F)cc2)C1)C1(CO)CCOCC1]

Hunig's Base (0.018 mL, 0.104 mmol) was added to a mixture of (R)-3-(4-(2-((2,6-difluorobenzyl)oxy)-1,1,1,3,3,3-hexafluoropropan-2-yl)phenyl)-3-((4-fluorophenyl)sulfonyl)pyrrolidine hydrochloride (16.5 mg, 0.026 mmol, from Example 27), (benzotriazol-1-yloxy)tris(dimethylamino)phosphonium hexafluorophosphate (20.72 mg, 0.047 mmol) and 4-(hydroxymethyl)tetrahydro-2H-pyran-4-carboxylic acid (7.50 mg, 0.047 mmol) in N,N-dimethylformamide (1 mL). The reaction vial was sealed and stirred at 70° C. for 2 h. The crude material was purified via preparative LC/MS with the following conditions: Column: Waters XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 35-75% B over 25 minutes, then a 10-minute hold at 75% B; Flow: 20 mL/min. Fractions containing the desired product were combined and dried via centrifugal evaporation to give Example 26 (10.5 mg, 54% yield). LC/MS (M+1): 740.2; LC retention time: 2.06 (analytical HPLC Method B); 1H NMR (500 MHz, 1:1 mixture of $CDCl_3$—$CD_3OD$) δ ppm 7.59 (d, J=8.2 Hz, 2H), 7.52-7.43 (m, J=6.8, 6.8 Hz, 1H), 7.37 (dd, J=8.6, 5.0 Hz, 2H), 7.28 (d, J=8.2 Hz, 2H), 7.14-6.99 (m, 4H), 4.70 (br. s., 2H), 4.38 (br. s., 4H), 4.23-4.05 (m, 2H), 3.84 (br. s., 2H), 3.75 (d, J=10.2 Hz, 2H), 3.66 (d, J=9.8 Hz, 2H), 2.84-2.59 (m, 1H), 2.42-2.25 (m, 2H), 1.79-1.53 (m, 2H).

Examples 27 and 28

(R)-2-(((2-(4-(1-(1-acetylpiperidine-4-carbonyl)-3-((4-fluorophenyl)sulfonyl)pyrrolidin-3-yl)phenyl)-1,1,1,3,3,3-hexafluoropropan-2-yl)oxy)methyl)-3-fluorobenzoic acid, and (R)-2-(((2-(4-(1-(1-acetylpiperidine-4-carbonyl)-3-((4-methoxyphenyl)sulfonyl)pyrrolidin-3-yl)phenyl)-1,1,1,3,3,3-hexafluoropropan-2-yl)oxy)methyl)-3-fluorobenzoic acid, respectively

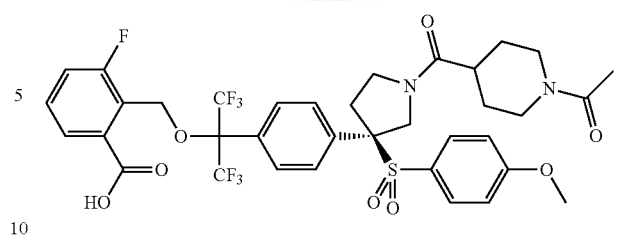

A 1 N aqueous sodium hydroxide solution (0.5 mL) was added to a solution of (R)-methyl 2-(((2-(4-(1-(1-acetylpiperidine-4-carbonyl)-3-((4-fluorophenyl)sulfonyl)pyrrolidin-3-yl)phenyl)-1,1,1,3,3,3-hexafluoropropan-2-yl)oxy)methyl)-3-fluorobenzoate (30 mg, 0.038 mmol) in tetrahydrofuran (0.5 mL) and methanol (0.5 mL). The resulting mixture was stirred at room temperature for two days. LCMS showed that the starting material was consumed and both products were formed in approximately 1:1 ratio. The mixture was neutralized to pH 5 with 1 N hydrochloric acid. After evaporation of organic solvents, the residue was dissolved in ethyl acetate (15 mL), washed with water (5 mL) and brine (5 mL), dried (magnesium sulfate), filtered and concentrated under reduced pressure. The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 25 minutes, then a 0-minute hold at 100% B; Flow: 20 mL/min. Fractions containing the desired product were combined and dried via centrifugal evaporation to give Example 27 (7.8 mg, 25% yield) and Example 28 (7.7 mg, 25% yield). Spectroscopic data for Example 27: LC/MS (M+1): 777.2; LC retention time: 1.41 (analytical HPLC Method B); 1H NMR showed two sets of signals for some of the protons due to presence of cis and trans amide isomers. Spectroscopic data for Example 28: LC/MS (M+1): 789.3; LC retention time: 1.38 (analytical HPLC Method B); $^1$H NMR showed two sets of signals for some of the protons due to presence of cis and trans amide isomers.

Examples 29 and 30

(R)-1-(3-((4-aminophenyl)sulfonyl)-3-(4-(2-((2,6-difluorobenzyl)oxy)-1,1,1,3,3,3-hexafluoropropan-2-yl)phenyl)pyrrolidine-1-carbonyl)piperidine-4-carbonitrile, and (R)-1-(3-((4-azidophenyl)sulfonyl)-3-(4-(2-(2,6-difluorobenzyl)oxy)-1,1,1,3,3,3-hexafluoropropan-2-yl)phenyl)pyrrolidine-1-carbonyl)piperidine-4-carbonitrile

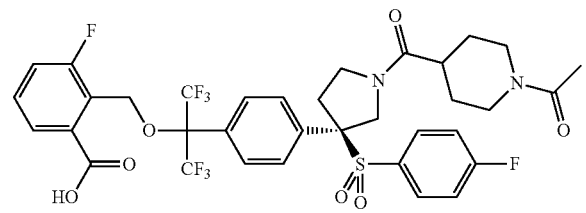

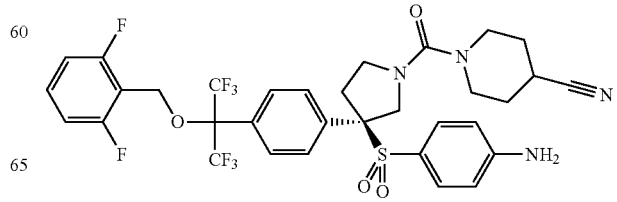

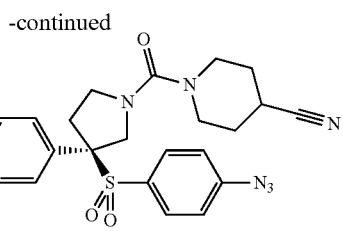

A mixture of (R)-1-(3-(4-(2-((2,6-difluorobenzyl)oxy)-1,1,1,3,3,3-hexafluoropropan-2-yl)phenyl)-3-((4-fluorophenyl)sulfonyl)pyrrolidine-1-carbonyl)piperidine-4-carbonitrile (23.2 mg, 32 mmol) and sodium azide (29.6 mg, 0.455 mmol) in N,N-dimethylformamide (2 mL) in a sealed vial was stirred at 100° C. for 18 h. LCMS analysis showed that the expected tetrazole product was not observed. Instead, two products corresponding to Examples 29 and 30 were formed. The mixture was diluted with ethyl acetate (20 mL), washed with water (5 mL) and brine (5 mL), dried (magnesium sulfate), filtered and concentrated under reduced pressure. The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-100% B over 25 minutes, then a 5-minute hold at 100% B; Flow: 20 mL/min. Fractions containing the desired product were combined and dried via centrifugal evaporation to give Example 29 (5.8 mg, 25% yield) and Example 30 (10.0 mg, 41% yield). Spectroscopic data for Example 29 LC/MS (M+1): 731.1; LC retention time: 2.091 (analytical HPLC Method B); 1H NMR (500 MHz, 1:1 mixture of CDCl$_3$—CD$_3$OD) δ ppm 7.64-7.56 (m, 2H), 7.49-7.38 (m, 1H), 7.29 (d, J=8.6 Hz, 2H), 7.07-6.92 (m, 4H), 6.53-6.42 (m, 2H), 4.71 (s, 2H), 4.56 (d, J=12.5 Hz, 1H), 4.03 (d, J=12.5 Hz, 1H), 3.95-3.84 (m, 1H), 3.61-3.44 (m, 3H), 3.29-3.10 (m, 3H), 2.97 (tt, J=8.2, 4.0 Hz, 1H), 2.59 (dt, J=13.9, 8.9 Hz, 1H), 2.09-1.95 (m, 2H), 1.95-1.79 (m, 2H). Spectroscopic data for Example 30: LC/MS (M+1): 757.3; LC retention time: 2.357 (analytical HPLC Method B); 1H NMR (500 MHz, 1:1 mixture of CDCl$_3$—CD$_3$OD) δ ppm 7.59 (d, J=8.3 Hz, 2H), 7.50-7.41 (m, 1H), 7.36-7.31 (m, 2H), 7.27 (d, J=8.9 Hz, 2H), 7.08-6.92 (m, 4H), 4.69 (s, 2H), 4.67-4.61 (m, 1H), 4.04 (d, J=12.8 Hz, 1H), 4.00-3.90 (m, 1H), 3.63-3.49 (m, 3H), 3.32-3.16 (m, 3H), 3.01-2.94 (m, 1H), 2.63 (dt, J=13.9, 8.9 Hz, 1H), 2.02 (dtd, J=13.7, 7.0, 3.6 Hz, 2H), 1.95-1.81 (m, 2H).

Example 31

(R)-1-(3-((4-cyanophenyl)sulfonyl)-3-(4-(2-((2,6-difluorobenzyl)oxy)-1,1,1,3,3,3-hexafluoropropan-2-yl)phenyl)pyrrolidine-1-carbonyl)piperidine-4-carboxylic acid

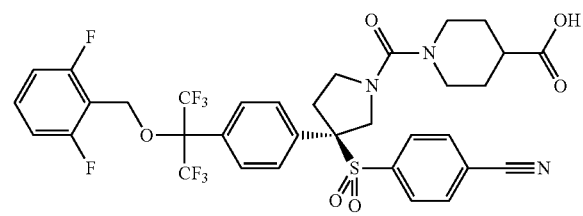 [SMILES: N#Cc1ccc(S(=O)(=O)[C@@]2(c3ccc(C(OCc4c(F)cccc4F)(C(F)(F)F)C(F)(F)F)cc3)CCN(C(=O)N3CCC(C(=O)O)CC3)C2)cc1]

A mixture of (R)-1-(3-(4-(2-((2,6-difluorobenzyl)oxy)-1,1,1,3,3,3-hexafluoropropan-2-yl)phenyl)-3-((4-fluorophenyl)sulfonyl)pyrrolidine-1-carbonyl)piperidine-4-carboxylic acid (12 mg, 0.016 mmol), potassium cyanide (5.19 mg, 0.080 mmol), potassium carbonate (22.04 mg, 0.159 mmol) and N,N-dimethylformamide (1 mL) in a sealed vial was stirred at 90° C. for 40 h. The mixture was filtered and purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 18-100% B over 20 minutes, then a 0-minute hold at 100% B; Flow: 20 mL/min. Fractions containing the desired product were combined and dried via centrifugal evaporation to give Example 31 (9 mg, 70% yield). LC/MS (M+1): 760.3; LC retention time: 1.84 (analytical HPLC Method B); 1H NMR (500 MHz, 1:1 mixture of CDCl$_3$—CD$_3$OD) δ ppm 7.70 (d, J=8.3 Hz, 2H), 7.63-7.57 (m, 2H), 7.53 (d, J=8.3 Hz, 2H), 7.50-7.41 (m, 1H), 7.27 (d, J=8.6 Hz, 2H), 7.03 (t, J=7.9 Hz, 2H), 4.05 (d, J=12.5 Hz, 1H), 4.01-3.92 (m, 1H), 3.83-3.70 (m, 2H), 3.59 (td, J=9.4, 3.1 Hz, 1H), 3.32-3.19 (m, 1H), 3.01-2.91 (m, 2H), 2.66 (dt, J=14.1, 8.7 Hz, 1H), 2.59-2.48 (m, 1H), 2.00 (d, J=13.6 Hz, 2H), 1.83-1.66 (m, 2H), three protons were under the water peak and were not identified.

Example 32

(R)-1-(4-(3-(4-(1,1,1,3,3,3-hexafluoro-2-hydroxypropan-2-yl)phenyl)-3-((4-phenoxyphenyl)sulfonyl)pyrrolidine-1-carbonyl)piperazin-1-yl)ethanone

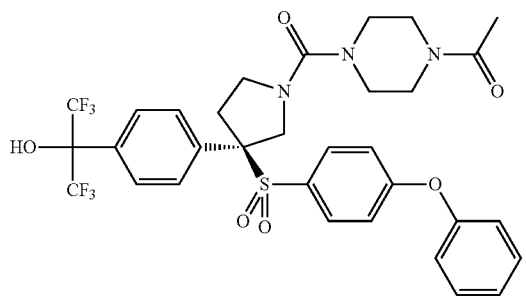 [SMILES: CC(=O)N1CCN(C(=O)N2CC[C@](c3ccc(C(O)(C(F)(F)F)C(F)(F)F)cc3)(S(=O)(=O)c3ccc(Oc4ccccc4)cc3)C2)CC1]

A mixture of (R)-1-(4-(3-((4-fluorophenyl)sulfonyl)-3-(4-(1,1,1,3,3,3-hexafluoro-2-hydroxypropan-2-yl)phenyl)pyrrolidine-1-carbonyl)piperazin-1-yl)ethanone (15 mg, 0.024 mmol), phenol (18.05 mg, 0.192 mmol), potassium carbonate (49.7 mg, 0.360 mmol) and N,N-dimethylformamide (1 mL) in a sealed vial was stirred at 90° C. for 15 h. The mixture was filtered. The crude material was purified via preparative LC/MS with the following conditions: Column: Waters XBridge C18, 19×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-100% B over 10 minutes, then a 5-minute hold at 100% B; Flow: 20 mL/min. Fractions containing the desired product were combined and dried via centrifugal evaporation to give Example 32 (16.1 mg, 96% yield). LC/MS (M+1): 700.2; LC retention time: 1.89 (analytical HPLC Method B); 1H NMR (500 MHz, 1:1 mixture of $CDCl_3$—$CD_3OD$) δ ppm 7.66 (d, J=8.3 Hz, 2H), 7.44 (t, J=7.9 Hz, 2H), 7.29-7.24 (m, 1H), 7.21 (dd, J=12.3, 8.7 Hz, 4H), 7.09-7.01 (m, 2H), 6.83 (d, J=8.9 Hz, 2H), 4.64 (d, J=12.5 Hz, 1H), 4.04 (d, J=12.5 Hz, 1H), 3.96 (q, J=8.8 Hz, 1H), 3.73-3.54 (m, 5H), 3.47-3.27 (m, 4H), 3.19 (ddd, J=10.3, 7.1, 3.6 Hz, 1H), 2.62 (dt, J=14.0, 8.9 Hz, 1H), 2.15 (s, 3H).

Example 33

(R)-1-(3-(4-(2-((2,6-difluorobenzyl)oxy)-1,1,1,3,3,3-hexafluoropropan-2-yl)phenyl)-3-((4-phenoxyphenyl)sulfonyl)pyrrolidine-1-carbonyl)piperidine-4-carboxylic acid

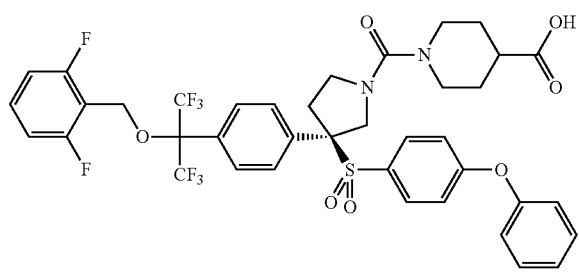 [SMILES: O=C(O)C1CCN(C(=O)N2CC[C@](c3ccc(C(OCc4c(F)cccc4F)(C(F)(F)F)C(F)(F)F)cc3)(S(=O)(=O)c3ccc(Oc4ccccc4)cc3)C2)CC1]

A mixture of (R)-1-(3-(4-(2-((2,6-difluorobenzyl)oxy)-1,1,1,3,3,3-hexafluoropropan-2-yl)phenyl)-3-((4-fluorophenyl)sulfonyl)pyrrolidine-1-carbonyl)piperidine-4-carboxylic acid (12 mg, 0.016 mmol), phenol (12.00 mg, 0.128 mmol), potassium carbonate (33.1 mg, 0.239 mmol) and N,N-dimethylformamide (1 mL) in a sealed vial was stirred at 90° C. for 12 h. The mixture was filtered. The crude material was purified via preparative LC/MS with the following conditions: Column: Waters XBridge C18, 19×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-100% B over 10 minutes, then a 5-minute hold at 100% B; Flow: 20 mL/min. Fractions containing the desired product were combined and dried via centrifugal evaporation to give Example 33 (8.8 mg, 66% yield). LC/MS (M+1): 827.3; LC retention time: 2.17 (analytical HPLC Method B); 1H NMR (500 MHz, 1:1 mixture of $CDCl_3$—$CD_3OD$) δ ppm 7.58 (d, J=8.3 Hz, 2H), 7.47-7.39 (m, 1H), 7.38-7.33 (m, 2H), 7.27 (dd, J=11.9, 8.9 Hz, 4H), 7.22-7.16 (m, 1H), 7.03-6.95 (m, 4H), 6.82 (d, J=8.9 Hz, 2H), 4.65 (s, 2H), 4.58 (d, J=12.8 Hz, 1H), 4.03 (d, J=12.5 Hz, 1H), 3.94-3.85 (m, 1H), 3.71 (dd, J=17.9, 14.0 Hz, 2H), 3.52 (td, J=9.4, 3.3 Hz, 1H), 3.22-3.14 (m, 1H), 2.96-2.86 (m, 2H), 2.60 (dt, J=13.9, 8.7 Hz, 1H), 2.54-2.45 (m, 1H), 2.00-1.90 (m, J=13.6 Hz, 2H), 1.79-1.61 (m, 2H).

Example 34

(R)-2-(3-((4-fluorophenyl)sulfonyl)-3-(4-(perfluoropropan-2-yl)phenyl)pyrrolidin-1-yl)acetamide Step A: (R)-tert-butyl 3-((4-fluorophenyl)sulfonyl)-3-(4-(1,1,1,3,3,3-hexafluoro-2-hydroxypropan-2-yl)phenyl)pyrrolidine-1-carboxylate

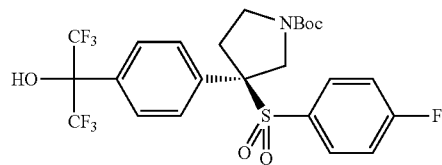

Hunig's base (0.095 mL, 0.546 mmol) was added to a solution of (R)-1,1,1,3,3,3-hexafluoro-2-(4-(3-((4-fluorophenyl)sulfonyl)pyrrolidin-3-yl)phenyl)propan-2-ol (103 mg, 0.219 mmol, from Example 3) and di-t-butyl dicarbonate (0.066 mL, 0.284 mmol) in dichloromethane (2 mL) at room temperature. After stirring for 2 h at room temperature, the mixture was concentrated. Silica gel chromatography, eluting with 20 to 60% ethyl acetate in hexanes, provided (R)-tert-butyl 3-((4-fluorophenyl)sulfonyl)-3-(4-(1,1,1,3,3,3-hexafluoro-2-hydroxypropan-2-yl)phenyl)pyrrolidine-1-carboxylate (120 mg, 96% yield). LC/MS (M−55): 515.9.

Step B: (R)-tert-butyl 3-((4-fluorophenyl)sulfonyl)-3-(4-(perfluoropropan-2-yl)phenyl)pyrrolidine-1-carboxylate

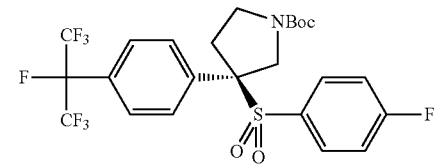 [SMILES: CC(C)(C)OC(=O)N1CC[C@](c2ccc(C(F)(C(F)(F)F)C(F)(F)F)cc2)(S(=O)(=O)c2ccc(F)cc2)C1]

(Diethylamino)sulfur trifluoride (0.277 mL, 2.100 mmol) was added to a mixture of (R)-tert-butyl 3-((4-fluorophenyl)sulfonyl)-3-(4-(1,1,1,3,3,3-hexafluoro-2-hydroxypropan-2-yl)phenyl)pyrrolidine-1-carboxylate (120 mg, 0.210 mmol) in dichloromethane (1 mL) at room temperature. The resultant mixture was heated to 50° C. for 24 h. After cooling to room temperature, the mixture was carefully quenched with methanol (0.5 mL) and concentrated. Silica gel chromatography, eluting with 0 to 40% ethyl acetate in hexanes, provided (R)-tert-butyl 3-((4-fluorophenyl)sulfonyl)-3-(4-(perfluoropropan-2-yl)phenyl)pyrrolidine-1-carboxylate (95 mg, 79% yield). LC/MS (M+18): 591.1; $^1$H NMR (400 MHz, $CDCl_3$) δ ppm 7.58-7.47 (m, 2H), 7.34 (dd, J=8.4, 5.1 Hz, 2H), 7.29-7.13 (m, 2H), 7.11-6.90 (m, 2H), 4.61 (d, J=13.0 Hz, 1H), 3.95-3.81 (m, 1H), 3.80-3.65 (m, 1H), 3.58-3.44 (m, 1H), 3.36-2.96 (m, 1H), 2.62-2.40 (m, 1H), 1.55-1.39 (m, 9H).

Step C: (R)-3-((4-fluorophenyl)sulfonyl)-3-(4-(perfluoropropan-2-yl)phenyl)pyrrolidine

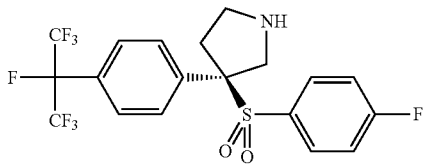 [SMILES: O=S(=O)(c1ccc(F)cc1)[C@@]1(c2ccc(C(F)(C(F)(F)F)C(F)(F)F)cc2)CCNC1]

Trifluoroacetic acid (0.438 mL, 3.31 mmol) was added to a solution of (R)-tert-butyl 3-((4-fluorophenyl)sulfonyl)-3-(4-(perfluoropropan-2-yl)phenyl)pyrrolidine-1-carboxylate (95 mg, 0.166 mmol) in dichloromethane (2 mL) at room temperature. After stirring for 1 h, the mixture was concentrated and dried under vacuum to provide (R)-3-((4-fluorophenyl)sulfonyl)-3-(4-(perfluoropropan-2-yl)phenyl)pyrrolidine trifluoroacetic acid salt (96 mg, 99% yield). LC/MS (M+1): 473.9; $^1$H NMR (400 MHz, CD$_3$OD) δ ppm 7.61 (d, J=8.6 Hz, 2H), 7.44-7.28 (m, 4H), 7.22-7.05 (m, 2H), 4.56 (d, J=13.4 Hz, 1H), 3.99 (d, J=13.6 Hz, 1H), 3.93-3.85 (m, 1H), 3.76-3.62 (m, 1H), 3.44-3.35 (m, 1H), 2.80 (m, 1H).

Step D: (R)-2-(3-((4-fluorophenyl)sulfonyl)-3-(4-(perfluoropropan-2-yl)phenyl)pyrrolidin-1-yl)acetamide

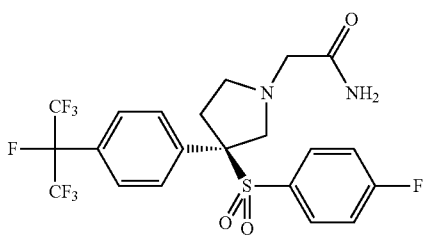 [SMILES: NC(=O)CN1CC[C@](c2ccc(C(F)(C(F)(F)F)C(F)(F)F)cc2)(S(=O)(=O)c2ccc(F)cc2)C1]

Hunig's Base (0.030 mL, 0.170 mmol) was added to a mixture of (R)-3-((4-fluorophenyl)sulfonyl)-3-(4-(perfluoropropan-2-yl)phenyl)pyrrolidine trifluoroacetic acid salt (10 mg, 0.017 mmol) and 2-bromoacetamide (9.39 mg, 0.068 mmol) in dichloromethane (1 mL). The mixture was stirred for 1 h and concentrated. The crude material was purified via preparative LC/MS with the following conditions: Column: Waters XBridge C18, 19×200 mm, 5-μm particles; Mobile Phase A: 5:95 acetonitrile: water with 10-mM ammonium acetate; Mobile Phase B: 95:5 acetonitrile:water with 10-mM ammonium acetate; Gradient: 25-100% B over 20 minutes, then a 5-minute hold at 100% B; Flow: 20 mL/min. Fractions containing the desired product were combined and dried via centrifugal evaporation to provide (R)-2-(3-((4-fluorophenyl)sulfonyl)-3-(4-(perfluoropropan-2-yl)phenyl)pyrrolidin-1-yl)acetamide (5.6 mg, 62% yield). LC/MS (M+1): 531.2; HPLC RT=1.63 min (analytical HPLC Method A); $^1$H NMR (500 MHz, 1:1 mixture of CDCl$_3$—CD$_3$OD) δ ppm 7.52 (d, J=8.6 Hz, 2H), 7.33-7.17 (m, 5H), 7.14-6.86 (m, 2H), 3.99 (d, J=11.1 Hz, 1H), 3.29-3.12 (m, 4H), 2.90-2.77 (m, 1H), 2.71-2.45 (m, 1H).

Example 35

(R)-1-(4-(3-((4-fluorophenyl)sulfonyl)-3-(4-(1,1,1,3,3,3-hexafluoro-2-phenoxypropan-2-yl)phenyl)pyrrolidine-1-carbonyl)piperidin-1-yl)ethanone

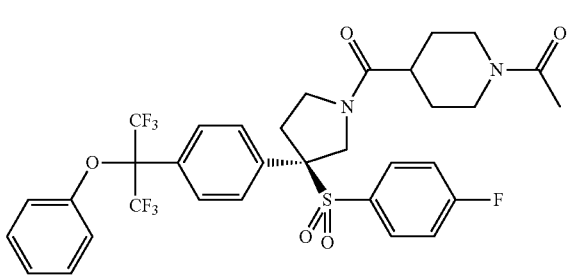 [SMILES: CC(=O)N1CCC(C(=O)N2CC[C@](c3ccc(C(Oc4ccccc4)(C(F)(F)F)C(F)(F)F)cc3)(S(=O)(=O)c3ccc(F)cc3)C2)CC1]

Potassium methoxide (2.53 mg, 0.036 mmol) was added to a mixture of (R)-1-(4-(3-((4-fluorophenyl)sulfonyl)-3-(4-(1,1,1,3,3,3-hexafluoro-2-hydroxypropan-2-yl)phenyl)pyrrolidine-1-carbonyl)piperidin-1-yl)ethanone (15 mg, 0.024 mmol) in toluene (0.5 mL) and tetrahydrofuran (0.5 mL) under nitrogen at room temperature. After stirring for 1 h, the mixture was concentrated. To the crude residue was added toluene (1 ml) followed by diphenyliodonium iodide (11.76 mg, 0.029 mmol). The resultant suspension was heated to reflux for 4 h, cooled to room temperature, quenched with methanol (1 mL) and concentrated. The crude material was purified via preparative HPLC with the following conditions: Column: Waters XBridge C18, 19×100 mm; Mobile Phase A: 10:90 Methanol:water with 0.1% trifluoroacetic acid; Mobile Phase B: 10:90 Water:methanol with 0.1% trifluoroacetic acid; Gradient: 10-100% B over 15 minutes, then a 5-minute hold at 100% B; Flow: 30 mL/min. Fractions containing the desired product were combined and dried under vacuum to provide the title compound (3.3 mg, 20% yield). LC/MS (M+1): 701.0; HPLC RT=4.44 min. (analytical HPLC Method B); $^1$H NMR (400 MHz, 1:1 mixture of CDCl$_3$—CD$_3$OD) δ ppm 7.60 (d, J=8.1 Hz, 2H), 7.49-7.31 (m, 3H), 7.31-7.21 (m, 3H), 7.21-7.06 (m, 3H), 6.84 (d, J=8.1 Hz, 2H), 5.09-4.90 (m, 1H), 4.66-4.46 (m, 1H), 4.23-3.95 (m, 2H), 3.95-3.74 (m, 3H), 3.27-2.96 (m, 2H), 2.85-2.67 (m, 2H), 2.19-2.07 (m, 3H), 2.03-1.83 (m, 1H), 1.83-1.48 (m, 3H).

Example 36

1-(4-(3-(4-(2-((2,6-difluorobenzyl)oxy)-1,1,1,3,3,3-hexafluoropropan-2-yl)phenyl)-3-((3-ethyl-4-fluorophenyl)sulfonyl)pyrrolidine-1-carbonyl)piperazin-1-yl)ethanone Step A: 2-(4-(((3-bromo-4-fluorophenyl)thio)methyl)phenyl)-1,1,1,3,3,3-hexafluoropropan-2-ol

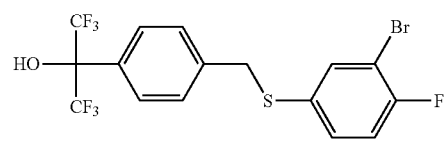 [SMILES: OC(c1ccc(CSc2ccc(F)c(Br)c2)cc1)(C(F)(F)F)C(F)(F)F]

Potassium carbonate (206 mg, 1.492 mmol) was added to a mixture of 3-bromo-4-fluorobenzenethiol (103 mg, 0.497 mmol) and 2-(4-(bromomethyl)phenyl)-1,1,1,3,3,3-hexafluoropropan-2-ol (251 mg, 0.746 mmol, ~70% purity) in tetrahydrofuran (1 mL) at room temperature. The mixture was stirred for 15 h, diluted with ethyl acetate (60 mL), washed with water, brine, dried (magnesium sulfate), filtered and concentrated under reduced pressure to provide crude 2-(4-(((3-bromo-4-fluorophenyl)thio)methyl)phenyl)-1,1,1,3,3,3-hexafluoropropan-2-ol (260 mg). The material was directly taken to the next step without purification. LC/MS (M−1): 463.1.

Step B: 2-(4-(((3-bromo-4-fluorophenyl)sulfonyl)methyl)phenyl)-1,1,1,3,3,3-hexafluoropropan-2-ol

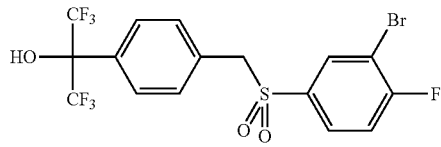 [SMILES: O=S(=O)(Cc1ccc(C(O)(C(F)(F)F)C(F)(F)F)cc1)c1ccc(F)c(Br)c1]

3-Chloroperbenzoic acid (172 mg, 0.994 mmol, 77% pure) was added to a mixture of 2-(4-(((3-bromo-4-fluorophenyl)thio)methyl)phenyl)-1,1,1,3,3,3-hexafluoropropan-2-ol (230 mg) in dichloromethane (5 mL) at room temperature. After stirring for 2 h, the mixture was diluted with ethyl acetate (60 mL), washed with saturated sodium bicarbonate, water, brine, dried (magnesium sulfate), filtered and concentrated under reduced pressure. Silica gel chromatography, eluting with 0 to 50% ethyl acetate in hexanes, provided 2-(4-(((3-bromo-4-fluorophenyl)sulfonyl)methyl)phenyl)-1,1,1,3,3,3-hexafluoropropan-2-ol (130 mg, 53% yield for 2 steps). LC/MS (M−1): 495.0; $^1$H NMR (400 MHz, CDCl$_3$) δ ppm 7.77 (m, 1H), 7.68 (d, J=8.1 Hz, 2H), 7.52 (m, 1H), 7.32-7.19 (m, 2H), 7.15 (t, J=8.3 Hz, 1H), 4.35 (s, 2H).

Step C: 2-(((2-(4-(((3-bromo-4-fluorophenyl)sulfonyl)methyl)phenyl)-1,1,1,3,3,3-hexafluoropropan-2-yl)oxy)methyl)-1,3-difluorobenzene

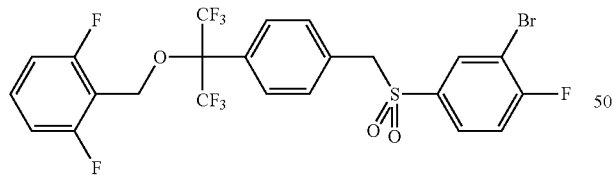

A mixture of 2-(4-(((3-bromo-4-fluorophenyl)sulfonyl)methyl)phenyl)-1,1,1,3,3,3-hexafluoropropan-2-ol (130 mg, 0.263 mmol), 2-(bromomethyl)-1,3-difluorobenzene (65.2 mg, 0.315 mmol) and potassium carbonate (109 mg, 0.788 mmol) in N,N-dimethylformamide (2 mL) was stirred under nitrogen at room temperature for 5 h. Following addition of water (5 mL) and ethyl acetate (60 mL), the mixture was washed with water, brine, dried (magnesium sulfate), filtered and concentrated under reduced pressure. Silica gel chromatography, eluting with 0 to 30% ethyl acetate in hexanes, provided 2-(((2-(4-(((3-bromo-4-fluorophenyl)sulfonyl)methyl)phenyl)-1,1,1,3,3,3-hexafluoropropan-2-yl)oxy)methyl)-1,3-difluorobenzene (130 mg, 80% yield). LC/MS (M−1): 621.1; $^1$H NMR (400 MHz, CDCl$_3$) δ ppm 7.78 (dd, J=6.4, 2.2 Hz, 1H), 7.64 (d, J=8.1 Hz, 2H), 7.57 (m, 1H), 7.43-7.33 (m, 1H), 7.29-7.24 (m, 2H), 7.17 (t, J=8.1 Hz, 1H), 7.10-6.90 (m, 2H), 4.68 (s, 2H), 4.40 (s, 2H).

Step D: 2-(((2-(4-(1-(((3-bromo-4-fluorophenyl)sulfonyl)vinyl)phenyl)-1,1,1,3,3,3-hexafluoropropan-2-yl)oxy)methyl)-1,3-difluorobenzene

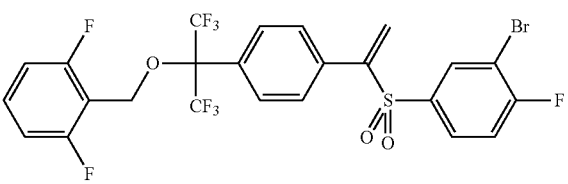 [SMILES: C=C(c1ccc(C(OCc2c(F)cccc2F)(C(F)(F)F)C(F)(F)F)cc1)S(=O)(=O)c1ccc(F)c(Br)c1]

To a mixture of 2-(((2-(4-(((3-bromo-4-fluorophenyl)sulfonyl)methyl)phenyl)-1,1,1,3,3,3-hexafluoropropan-2-yl)oxy)methyl)-1,3-difluorobenzene (90 mg, 0.145 mmol) and N,N,N',N'-tetramethylmethanediamine (89 mg, 0.869 mmol) in N,N-dimethylformamide (0.5 mL) under nitrogen at room temperature was added acetic anhydride (0.082 mL, 0.869 mmol) dropwise over 1 min. The mixture was heated to 65° C. in a sealed tube for 15 h, cooled to room temperature, quenched with saturated sodium bicarbonate (2 mL) and extracted with ethyl acetate (3×10 mL). The combined organic layer was washed with water, brine, dried (magnesium sulfate), filtered and concentrated under reduced pressure. Silica gel chromatography, eluting with 0 to 20% ethyl acetate in hexanes, provided 2-(((2-(4-(1-((3-bromo-4-fluorophenyl)sulfonyl)vinyl)phenyl)-1,1,1,3,3,3-hexafluoropropan-2-yl)oxy)methyl)-1,3-difluorobenzene (65 mg, 70% yield). LC/MS (M+23): 655.3; $^1$H NMR (400 MHz, CDCl$_3$) δ ppm 7.86 (dd, J=6.2, 2.3 Hz, 1H), 7.72-7.57 (m, 3H), 7.52-7.43 (m, 2H), 7.44-7.32 (m, 1H), 7.17-7.08 (m, 1H), 7.00-6.89 (m, 2H), 6.71 (s, 1H), 6.09 (s, 1H), 4.68 (s, 2H).

Step E: 1-benzyl-3-((3-bromo-4-fluorophenyl)sulfonyl)-3-(4-(2-((2,6-difluorobenzyl)oxy)-1,1,1,3,3,3-hexafluoropropan-2-yl)phenyl)pyrrolidine

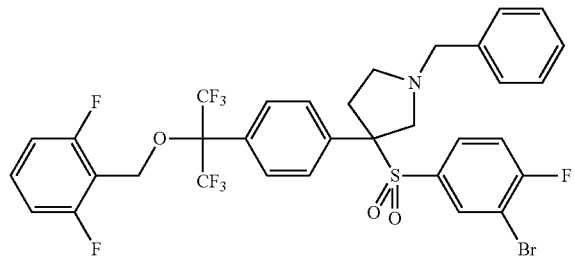 [SMILES: O=S(=O)(c1ccc(F)c(Br)c1)C1(c2ccc(C(OCc3c(F)cccc3F)(C(F)(F)F)C(F)(F)F)cc2)CCN(Cc2ccccc2)C1]

A 0.2 M dichloromethane solution of trifluoroacetic acid (0.021 mL, 4.11 μmol) was added dropwise to a solution of 2-(((2-(4-(1-((3-bromo-4-fluorophenyl)sulfonyl)vinyl)phenyl)-1,1,1,3,3,3-hexafluoropropan-2-yl)oxy)methyl)-1,3-difluorobenzene (65 mg, 0.103 mmol) and N-benzyl-1-methoxy-N-((trimethylsilyl)methyl)methanamine (73.1 mg, 0.308 mmol) in dichloromethane (2 mL) at 0° C. The resulting solution was stirred at 0° C. for 5 min and at ambient temperature for 15 h. After quenching with saturated sodium bicarbonate (1 mL) and diluting with ethyl acetate (30 mL), the mixture was washed with water, brine, dried (magnesium sulfate), filtered and concentrated under reduced pressure. Silica gel chromatography, eluting with 0 to 30% ethyl acetate in hexanes, provided 1-benzyl-3-((3-bromo-4-fluorophenyl)sulfonyl)-3-(4-(2-((2,6-difluorobenzyl)oxy)-1,1,1,3,3,3-hexafluoropropan-2-yl)phenyl)pyrrolidine (30 mg, 38% yield). LC/MS (M+1): 766.3; $^1$H NMR (400 MHz, CD$_3$OD) δ ppm 7.72-7.51 (m, 3H), 7.54-7.44 (m, 2H), 7.41 (d, J=8.8 Hz, 2H), 7.33-7.15 (m, 6H), 7.10-6.84 (m, 2H), 4.71 (s, 2H), 3.75 (d, J=11.2 Hz, 1H), 3.64 (s, 2H), 3.39-3.30 (m, 1H), 3.09-2.97 (m, 1H), 2.89-2.80 (m, 1H), 2.75-2.39 (m, 2H).

Step F: 1-benzyl-3-(4-(2-((2,6-difluorobenzyl)oxy)-1,1,1,3,3,3-hexafluoropropan-2-yl)phenyl)-3-((4-fluoro-3-vinylphenyl)sulfonyl)pyrrolidine

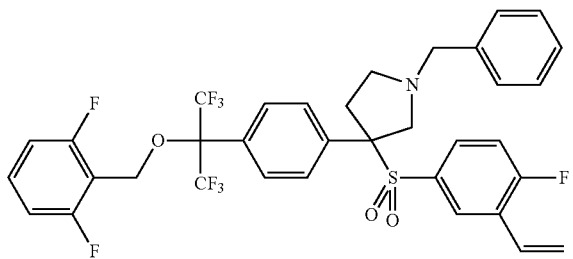 [SMILES: C=Cc1cc(S(=O)(=O)C2(c3ccc(C(OCc4c(F)cccc4F)(C(F)(F)F)C(F)(F)F)cc3)CCN(Cc3ccccc3)C2)ccc1F]

Nitrogen was bubbled into a mixture of 1-benzyl-3-((3-bromo-4-fluorophenyl)sulfonyl)-3-(4-(2-((2,6-difluorobenzyl)oxy)-1,1,1,3,3,3-hexafluoropropan-2-yl)phenyl)pyrrolidine (30 mg, 0.039 mmol), potassium trifluoro(vinyl)borate (10.49 mg, 0.078 mmol), PdCl2(dppf) (5.73 mg, 7.83 μmol) and 2.0 M aqueous potassium phosphate (0.078 mL, 0.157 mmol) in N,N-dimethylformamide (0.7 mL) at room temperature for 3 min. The reaction vial was sealed and heated to 90° C. for 2 h. After cooling to room temperature, ethyl acetate (30 mL) was added. The mixture was washed with water, brine, dried (magnesium sulfate), filtered and concentrated under reduced pressure. Silica gel chromatography, eluting with 0 to 30% ethyl acetate in hexanes, provided 1-benzyl-3-(4-(2-((2,6-difluorobenzyl)oxy)-1,1,1,3,3,3-hexafluoropropan-2-yl)phenyl)-3-((4-fluoro-3-vinylphenyl)sulfonyl)pyrrolidine (22 mg, 79% yield). LC/MS (M+1): 714.3; $^1$H NMR (400 MHz, CDCl$_3$) δ ppm 7.56 (d, J=8.4 Hz, 2H), 7.45-7.14 (m, 10H), 7.02-6.85 (m, 3H), 6.64 (dd, J=17.8, 11.2 Hz, 1H), 5.63 (d, J=17.6 Hz, 1H), 5.36 (d, J=11.2 Hz, 1H), 4.66 (s, 2H), 3.87-3.74 (m, 1H), 3.74-3.63 (m, 2H), 3.30 (d, J=11.0 Hz, 1H), 3.13-2.91 (m, 2H), 2.82 (td, J=8.1, 4.5 Hz, 1H), 2.67-2.44 (m, 1H).

Step G: 3-(4-(2-((2,6-difluorobenzyl)oxy)-1,1,1,3,3,3-hexafluoropropan-2-yl)phenyl)-3-((3-ethyl-4-fluorophenyl)sulfonyl)pyrrolidine

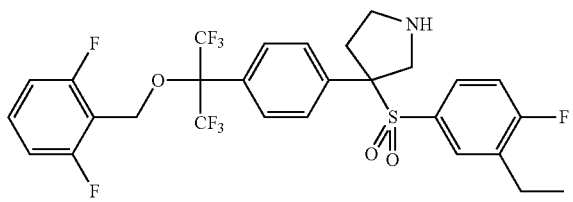 [SMILES: CCc1cc(S(=O)(=O)C2(c3ccc(C(OCc4c(F)cccc4F)(C(F)(F)F)C(F)(F)F)cc3)CCNC2)ccc1F]

A mixture of 1-benzyl-3-(4-(2-((2,6-difluorobenzyl)oxy)-1,1,1,3,3,3-hexafluoropropan-2-yl)phenyl)-3-((4-fluoro-3-vinylphenyl)sulfonyl)pyrrolidine (22 mg, 0.031 mmol), 10% palladium on carbon (32.8 mg, 0.031 mmol) in methanol (5 mL) was stirred under hydrogen at 50 psi for 2 h. After filtration to remove the insoluble catalyst, the filtrate was concentrated to provide 3-(4-(2-((2,6-difluorobenzyl)oxy)-1,1,1,3,3,3-hexafluoropropan-2-yl)phenyl)-3-((3-ethyl-4-fluorophenyl)sulfonyl)pyrrolidine (18 mg, 93% yield). LC/MS (M+1): 626.3; $^1$H NMR (400 MHz, CD$_3$OD) δ ppm 7.64 (d, J=6.6 Hz, 2H), 7.61-7.45 (m, 1H), 7.34 (d, J=7.9 Hz, 3H), 7.29-7.12 (m, 2H), 7.08 (t, J=8.0 Hz, 2H), 4.73 (s, 2H), 4.63-4.49 (m, 1H), 4.04-3.85 (m, 2H), 3.67 (m., 1H), 3.46-3.38 (m, 1H), 2.89-2.69 (m, 1H), 2.56 (q, J=7.2 Hz, 2H), 1.10 (t, J=7.4 Hz, 3H).

Step H: 1-(4-(3-(4-(2-((2,6-difluorobenzyl)oxy)-1,1,1,3,3,3-hexafluoropropan-2-yl)phenyl)-3-((3-ethyl-4-fluorophenyl)sulfonyl)pyrrolidine-1-carbonyl)piperazin-1-yl)ethanone

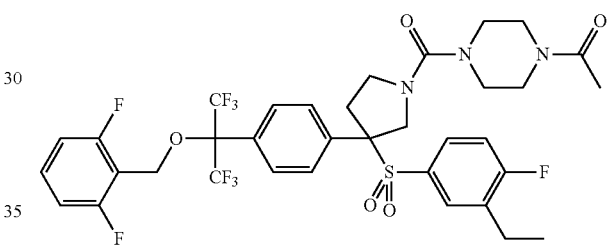

Hunig's Base (10.05 μA, 0.058 mmol) was added to a mixture of 3-(4-(2-((2,6-difluorobenzyl)oxy)-1,1,1,3,3,3-hexafluoropropan-2-yl)phenyl)-3-(((3-ethyl-4-fluorophenyl)sulfonyl)pyrrolidine (9 mg, 0.014 mmol) and 4-acetylpiperazine-1-carbonyl chloride (5.49 mg, 0.029 mmol) in dichloromethane (1 mL) at room temperature. After stirring for 3 h, the mixture was concentrated. The crude material was purified via preparative LC/MS with the following conditions: Column: Waters XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-100% B over 20 minutes, then a 5-minute hold at 100% B; Flow: 20 mL/min. Fractions containing the desired product were combined and dried via centrifugal evaporation to provide to provide 1-(4-(3-(4-(2-((2,6-difluorobenzyl)oxy)-1,1,1,3,3,3-hexafluoropropan-2-yl)phenyl)-3-((3-ethyl-4-fluorophenyl)sulfonyl)pyrrolidine-1-carbonyl)piperazin-1-yl)ethanone (6.8 mg, 60% yield). LC/MS (M+1): 780.4; HPLC RT=2.26 min. (analytical HPLC Method A); $^1$H NMR (500 MHz, DMSO-d$_6$) δ ppm 7.75-7.50 (m, 3H), 7.42 (d, J=8.4 Hz, 1H), 7.37-7.18 (m, 5H), 4.66 (s, 2H), 4.56 (d, J=12.5 Hz, 1H), 3.96 (d, J=12.8 Hz, 1H), 3.77-3.65 (m, 1H), 3.59-3.35 (m, 2H), 3.30-2.98 (m, 6H), 2.66-2.56 (m, 3H), 2.03 (s, 3H), 1.05 (t, J=7.4 Hz, 2H).

Examples 37 and 38

(S)-benzyl 3-((4-fluorophenyl)sulfonyl)-3-(4-iodophenyl)pyrrolidine-1-carboxylate and (R)-benzyl 3-((4-fluorophenyl)sulfonyl)-3-(4-iodophenyl)pyrrolidine-1-carboxylate, respectively

Step A: 1-fluoro-4-((4-iodobenzyl)sulfonyl)benzene

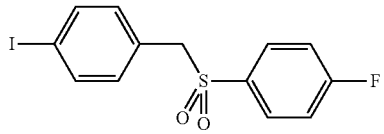 [SMILES: O=S(=O)(Cc1ccc(I)cc1)c1ccc(F)cc1]

Sodium 4-fluorobenzenesulfinate (3.52 g, 19.33 mmol) was added in several portions to a stirred solution of 1-(bromomethyl)-4-iodobenzene (4.10 g, 13.81 mmol) in N,N-dimethylformamide (30 mL). The reaction was slightly exothermic. The resulting suspension was stirred under nitrogen for 15 h, diluted with water (120 mL), stirred for 15 min and filtered. The filter cake was washed with water (3×30 mL) and dried under vacuum to give 1-fluoro-4-((4-iodobenzyl)sulfonyl)benzene as white solid (5.130 g, 99% yield). LC/MS (M+23): 399.1; HPLC RT=3.773 min (analytical HPLC Method A); $^1$H NMR (400 MHz, CDCl$_3$) δ ppm 7.69-7.58 (m, 4H), 7.15 (t, J=8.6 Hz, 2H), 6.87-6.79 (m, 2H), 4.23 (s, 2H).

Step B: 1-fluoro-4-((1-(4-iodophenyl)vinyl)sulfonyl)benzene

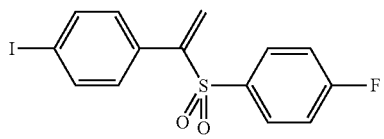 [SMILES: C=C(c1ccc(I)cc1)S(=O)(=O)c1ccc(F)cc1]

To a mixture of 1-fluoro-4-((4-iodobenzyl)sulfonyl)benzene (1.05 g, 2.79 mmol) and N,N,N',N'-tetramethylmethanediamine (1.711 g, 16.75 mmol) in N,N-dimethylformamide (3 mL) under nitrogen at room temperature was added acetic anhydride (1.580 mL, 16.75 mmol) dropwise over 5 min. The mixture was heated to 65° C. in a sealed tube for 72 h. After cooling to room temperature, the mixture was quenched with saturated sodium bicarbonate (20 mL) and extracted with ethyl acetate (2×100 mL). The combined organic layer was washed with water, brine, dried (magnesium sulfate), filtered and concentrated under reduced pressure. Silica gel chromatography, eluting with 0 to 20% ethyl acetate, provided 1-fluoro-4-((1-(4-iodophenyl)vinyl)sulfonyl)benzene (495 mg, 46% yield). LC/MS (M+23): 411.0; $^1$H NMR (400 MHz, CDCl$_3$) δ ppm 7.76-7.60 (m, 4H), 7.18-6.97 (m, 4H), 6.63 (s, 1H), 5.96 (s, 1H).

Step C: 1-benzyl-3-((4-fluorophenyl)sulfonyl)-3-(4-iodophenyl)pyrrolidine

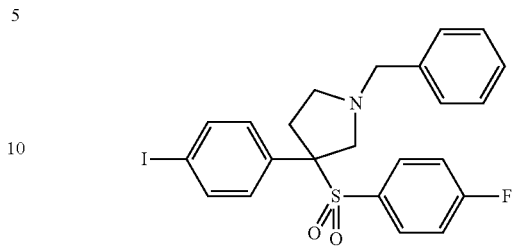

A 0.2 M dichloromethane solution of trifluoroacetic acid (2.86 ml, 0.572 mmol) was added dropwise to a stirred solution of 1-fluoro-4-((1-(4-iodophenyl)vinyl)sulfonyl)benzene (5.55 g, 14.30 mmol) and N-benzyl-1-methoxy-N-((trimethylsilyl)methyl)methanamine (10.18 g, 42.9 mmol) in dichloromethane (70 mL) at 0° C. After 20 min at 0° C. and 16 h at room temperature, the mixture was quenched with saturated sodium bicarbonate (50 mL) and stirred for 30 min. The dichloromethane phase was separated and concentrated. Silica gel chromatography, eluting with 0 to 100% ethyl acetate in hexanes, gave 1-benzyl-3-((4-fluorophenyl)sulfonyl)-3-(4-iodophenyl)pyrrolidine as light yellow oil (8.12 g, 90% pure, 98% yield). LC/MS (M+23): 522.2; HPLC RT=3.431 min. (analytical HPLC Method A); 1H NMR (400 MHz, CDCl$_3$) δ ppm 7.60 (d, J=8.7 Hz, 2H), 7.43-7.38 (m, 2H), 7.35-7.30 (m, 3H), 7.26-7.22 (m, 2H), 7.08-7.01 (m, 2H), 6.90 (d, J=8.7 Hz, 2H), 3.68-3.61 (m, 3H), 3.16 (d, J=11.0 Hz, 1H), 3.02-2.87 (m, 2H), 2.72 (td, J=8.0, 4.5 Hz, 1H), 2.52-2.44 (m, 1H); $^{19}$F NMR (400 MHz, CDCl$_3$) d −103.41.

Step D: benzyl 3-((4-fluorophenyl)sulfonyl)-3-(4-iodophenyl)pyrrolidine-1-carboxylate

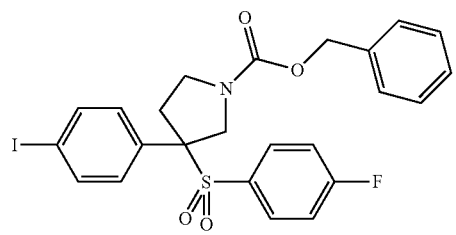 [SMILES: O=C(OCc1ccccc1)N1CCC(c2ccc(I)cc2)(S(=O)(=O)c2ccc(F)cc2)C1]

Benzyl chloroformate (1.315 g, 7.71 mmol) was added to a solution of 1-benzyl-3-((4-fluorophenyl)sulfonyl)-3-(4-iodophenyl)pyrrolidine (2.01 g, 3.86 mmol) in chloroform (20 mL) at room temperature and the resulting mixture was heated to reflux for 3 h. After cooling to room temperature, the mixture was quenched with saturated sodium bicarbonate (20 mL), diluted with ethyl acetate (200 mL), washed with water, brine, dried (magnesium sulfate), filtered and concentrated under reduced pressure. Silica gel chromatography, eluting with 10 to 70% ethyl acetate in hexanes, provided benzyl 3-((4-fluorophenyl)sulfonyl)-3-(4-iodophenyl)pyrrolidine-1-carboxylate (1.70 g, 78% yield). LC/MS (M+1): 565.8; 1H NMR (400 MHz, CDCl$_3$) δ ppm 7.60 (dd, J=8.3, 3.6 Hz, 2H), 7.49-7.29 (m, 7H), 7.13-6.91 (m, 2H), 6.84-6.67 (m, 2H), 5.20-5.07 (m, 2H), 4.59 (m, 1H), 3.99-3.66 (m, 2H), 3.59-3.46 (m, 1H), 3.28-3.01 (m, 1H), 2.60-2.33 (m, 1H).

Step E: (S)-benzyl 3-((4-fluorophenyl)sulfonyl)-3-(4-iodophenyl)pyrrolidine-1-carboxylate and (R)-benzyl 3-((4-fluorophenyl)sulfonyl)-3-(4-iodophenyl)pyrrolidine-1-carboxylate

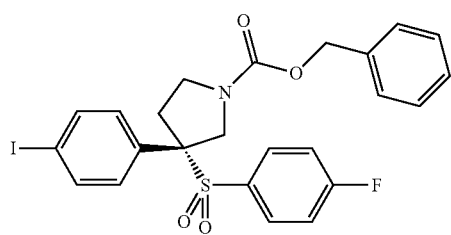

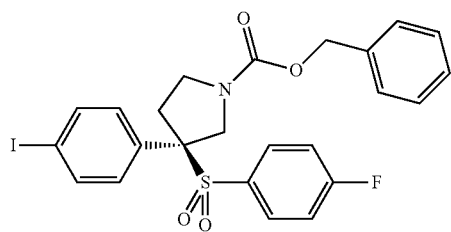

Benzyl 3-((4-fluorophenyl)sulfonyl)-3-(4-iodophenyl)pyrrolidine-1-carboxylate (1.70 g, 3.01 mmol) was separated into its homochiral components using a chiral Chiral OD-H 25×3 cm ID (5 um), 23% methanol in CO₂ to afford (S)-benzyl 3-((4-fluorophenyl)sulfonyl)-3-(4-iodophenyl)pyrrolidine-1-carboxylate (Example 37, 530 mg, 30% yield) as the first eluent off the column and (R)-benzyl 3-((4-fluorophenyl)sulfonyl)-3-(4-iodophenyl)pyrrolidine-1-carboxylate (Example 38, 520 mg, 29% yield) as the second eluent off the column. Analytical data for Example 37: LC/MS (M+1): 565.9; HPLC RT=4.50 min (analytical HPLC Method A); 1H NMR (400 MHz, CD₃OD) δ ppm 7.65 (t, J=8.5 Hz, 2H), 7.53-7.25 (m, 7H), 7.21 (t, J=8.7 Hz, 1H), 7.17-7.04 (m, 1H), 6.93-6.78 (m, 2H), 5.19-5.08 (m, 2H), 4.69 (m, 1H), 3.85 (m, 1H), 3.73-3.62 (m, 1H), 3.59-3.43 (m, 1H), 3.23-3.03 (m, 1H), 2.76-2.42 (m, 1H). Analytical data for Example 38: LC/MS (M+1): 565.9; HPLC RT=4.50 min (analytical HPLC Method A); 1H NMR (400 MHz, CD₃OD) δ ppm 7.65 (t, J=8.5 Hz, 2H), 7.53-7.25 (m, 7H), 7.21 (t, J=8.7 Hz, 1H), 7.17-7.04 (m, 1H), 6.93-6.78 (m, 2H), 5.19-5.08 (m, 2H), 4.69 (m, 1H), 3.85 (m, 1H), 3.73-3.62 (m, 1H), 3.59-3.43 (m, 1H), 3.23-3.03 (m, 1H), 2.76-2.42 (m, 1H).

Example 39

(1R,4r)-4-((R)-3-(2',6'-difluoro-[1,1'-biphenyl]-4-yl)-3-((4-fluorophenyl)sulfonyl)pyrrolidone-1-carbonyl)cyclohexanecarboxylic acid Step A: (R)-1-benzyl-3-((4-fluorophenyl)sulfonyl)-3-(4-iodophenyl)pyrrolidine and (S)-1-benzyl-3-((4-fluorophenyl)sulfonyl)-3-(4-iodophenyl)pyrrolidine

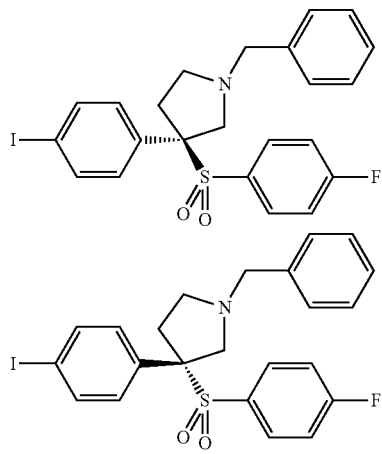

1-Benzyl-3-((4-fluorophenyl)sulfonyl)-3-(4-iodophenyl)pyrrolidine (8.12 g, 14.02 mmol) was separated into its homochiral components using a chiral SFC separation, Chiral AD-H (25×3 cm ID, 5 um), 50% methanol in CO2, to afford (R)-1-benzyl-3-((4-fluorophenyl)sulfonyl)-3-(4-iodophenyl)pyrrolidine (3.13 g, 43% yield) as the first eluent off the column and (S)-1-benzyl-3-((4-fluorophenyl)sulfonyl)-3-(4-iodophenyl)pyrrolidine (1.93 g, 26% yield) as the second eluent off the column. Analytical data for (R)-1-benzyl-3-((4-fluorophenyl)sulfonyl)-3-(4-iodophenyl)pyrrolidine: LC/MS (M+1): 522.2; HPLC RT=3.426 min (analytical HPLC Method A); 1H NMR (400 MHz, CDCl₃) δ ppm 7.60 (d, J=8.4 Hz, 2H), 7.44-7.37 (m, 2H), 7.36-7.21 (m, 5H), 7.08-7.00 (m, 2H), 6.90 (d, J=8.6 Hz, 2H), 3.72-3.60 (m, 3H), 3.16 (d, J=11.0 Hz, 1H), 3.03-2.87 (m, 2H), 2.72 (td, J=8.0, 4.6 Hz, 1H), 2.52-2.42 (m, 1H); 19F NMR (376 MHz, CDCl₃) d -103.41. Analytical data for (S)-1-benzyl-3-((4-fluorophenyl)sulfonyl)-3-(4-iodophenyl)pyrrolidine: LC/MS (M+1): 522.2; HPLC RT=3.420 min (analytical HPLC Method A); 1H NMR (400 MHz, CDCl₃) δ ppm 7.63-7.57 (m, 2H), 7.44-7.37 (m, 2H), 7.36-7.21 (m, 5H), 7.09-6.99 (m, 2H), 6.93-6.87 (m, 2H), 3.72-3.60 (m, 3H), 3.16 (d, J=10.8 Hz, 1H), 3.02-2.86 (m, 2H), 2.72 (td, J=8.0, 4.5 Hz, 1H), 2.52-2.42 (m, 1H); ¹⁹F NMR (376 MHz, CDCl₃) δ ppm -103.41.

Step B: (R)-3-((4-fluorophenyl)sulfonyl)-3-(4-iodophenyl)pyrrolidine

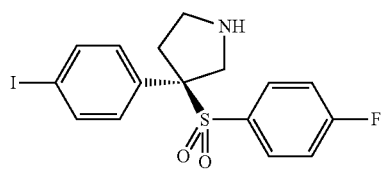 [SMILES: O=S(=O)(c1ccc(F)cc1)[C@@]1(c2ccc(I)cc2)CCNC1]

1-Chloroethyl chloroformate (0.016 mL, 0.147 mmol) was added to a stirred solution of (R)-1-benzyl-3-((4-fluorophenyl)sulfonyl)-3-(4-iodophenyl)pyrrolidine (51 mg, 0.098 mmol) in 1,2-dichloroethane (0.5 mL) at room temperature. After 4 h at 50° C., additional 1-chloroethyl chloroformate (16 uL) was added. After 19 h at 50° C. and 2 h at 90° C., additional 1-chloroethyl chloroformate (32 uL) was added. After another 16 at 90° C., the mixture was cooled to room temperature and concentrated under reduced pressure. The residue was treated with methanol (0.5 mL) and heated to 70° C. for 1 h. The crude material was purified by preparative RP-HPLC (0-100% solvent B in 10 min then isocratic @ 100% until 12 min, 20 mL/min, Phenomenex Luna Axia C18 5 u 30×100 mm; Solvent A: 95% water+5% MeCN+0.05% trifluoroacetic acid; Solvent B: 5% water+95% MeCN+0.05% trifluoroacetic acid) to give (R)-3-((4-fluorophenyl)sulfonyl)-3-(4-iodophenyl)pyrrolidine trifluoroacetic acid salt as white solid (42.5 mg, 80% yield). LC/MS (M+1): 432.2; HPLC RT=3.103 min (analytical HPLC Method A); 1H NMR (400 MHz, CD$_3$OD) δ ppm 7.71-7.65 (m, 2H), 7.47-7.41 (m, 2H), 7.29-7.21 (m, 2H), 6.88-6.82 (m, 2H), 4.46 (d, J=13.4 Hz, 1H), 3.92-3.82 (m, 2H), 3.62 (ddd, J=11.7, 9.5, 3.5 Hz, 1H), 3.26 (td, J=7.2, 3.2 Hz, 1H), 2.70 (dt, J=14.9, 9.6 Hz, 1H).

Step C: (1R,4r)-methyl 4-((R)-3-((4-fluorophenyl)sulfonyl)-3-(4-iodophenyl)pyrrolidine-1-carbonyl)cyclohexanecarboxylate

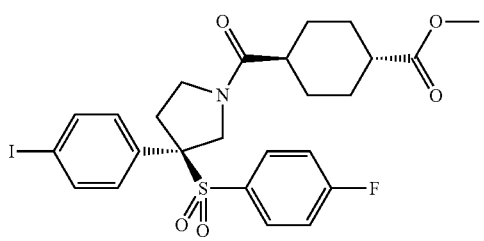 [SMILES: COC(=O)[C@H]1CC[C@H](C(=O)N2CC[C@](c3ccc(I)cc3)(S(=O)(=O)c3ccc(F)cc3)C2)CC1]

Hunig's Base (0.067 mL, 0.385 mmol) was added to a stirred solution of (R)-3-((4-fluorophenyl)sulfonyl)-3-(4-iodophenyl)pyrrolidine trifluoroacetic acid salt (42 mg, 0.077 mmol), (1r,4r)-4-(methoxycarbonyl)cyclohexanecarboxylic acid (15 mg, 0.081 mmol) and (benzotriazol-1-yloxy)tris(dimethylamino)phosphonium hexafluorophosphate (38 mg, 0.086 mmol) in acetonitrile (0.5 mL) at room temperature. After 1 h at room temperature, LCMS analysis showed that the reaction was complete. The crude mixture was purified by silica gel chromatography, eluting with 0-100% ethyl acetate in hexanes, to provide (1R,4r)-methyl 4-((R)-3-((4-fluorophenyl)sulfonyl)-3-(4-iodophenyl)pyrrolidine-1-carbonyl)cyclohexanecarboxylate as white solid (0.0263 g, 57% yield). LC/MS (M+1): 600.3; HPLC RT=4.100 min (analytical HPLC Method A); 1H NMR (400 MHz, CDCl$_3$) δ ppm 7.66-7.58 (m, 2H), 7.40-7.32 (m, 2H), 7.12-7.03 (m, 2H), 6.87-6.74 (m, 2H), 4.75-4.64 (m, 1H), 4.05-3.96 (m, 1H), 3.83-3.76 (m, 1H), 3.73-3.64 (m, 4H), 3.38 (ddd, J=14.0, 7.9, 2.1 Hz, 1H), 2.63-2.27 (m, 2H), 2.19-1.95 (m, 2H), 1.82-1.38 (m, 4H).

Step D: (1R,4r)-methyl 4-((R)-3-(2',6'-difluoro-[1,1'-biphenyl]-4-yl)-3-((4-fluorophenyl)sulfonyl)pyrrolidine-1-carbonyl)cyclohexanecarboxylate

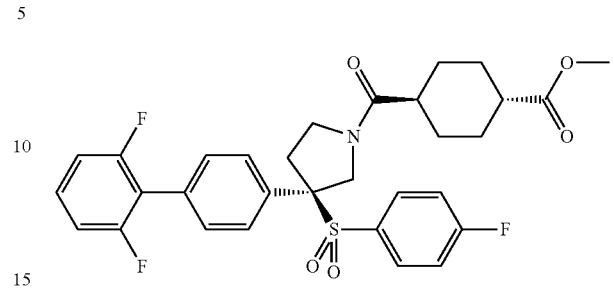

A mixture of (1R,4r)-methyl 4-((R)-3-((4-fluorophenyl)sulfonyl)-3-(4-iodophenyl)pyrrolidine-1-carbonyl)cyclohexanecarboxylate (10 mg, 0.017 mmol), (2,6-difluorophenyl)boronic acid (39.5 mg, 0.250 mmol), Pd2(dba)3.chloroform (1.5 mg, 1.6 mmol), X-Phos (1.591 mg, 3.34 μmol) and aqueous potassium phosphate tribasic (0.042 mL, 0.083 mmol, 2 M solution) was mixed with dioxane (0.5 mL). The vial was immediately degassed by vacuum-N2 refill cycle twice, sealed and heated to 90° C. for 3 h. The crude material was purified by silica gel chromatography, eluting with 0-100% ethyl acetate in hexanes, to provide (1R,4r)-methyl 4-((R)-3-(2',6'-difluoro-[1,1'-biphenyl]-4-yl)-3-((4-fluorophenyl)sulfonyl)pyrrolidine-1-carbonyl)cyclohexanecarboxylate as white solid (10.8 mg). 1H NMR (400 MHz, CDCl3) δ ppm 7.40-7.29 (m, 5H), 7.19-7.09 (m, 2H), 7.07-6.96 (m, 4H), 4.84-4.73 (m, 1H), 4.15-4.03 (m, 1H), 3.94-3.87 (m, 1H), 3.80-3.72 (m, 1H), 3.71-3.68 (m, 3H), 3.52-3.42 (m, 1H), 2.69 (dt, J=14.1, 9.3 Hz, 1H), 2.43-2.32 (m, 2H), 2.16-2.00 (m, 3H), 1.82 (d, J=12.0 Hz, 1H), 1.71-1.60 (m, 2H), 1.54-1.41 (m, 2H).

Step E: (1R,4r)-4-((R)-3-(2',6'-difluoro-[1,1'-biphenyl]-4-yl)-3-((4-fluorophenyl)sulfonyl)pyrrolidine-1-carbonyl)cyclohexanecarboxylic acid

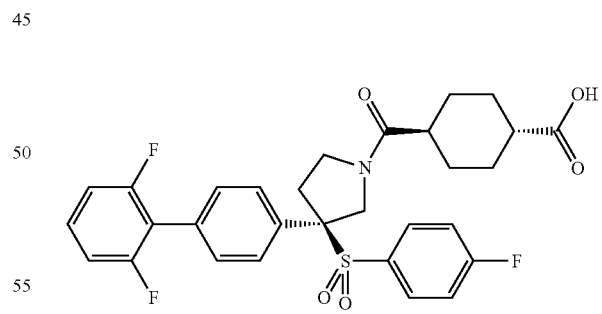

A mixture of (1R,4r)-methyl 4-((R)-3-(2',6'-difluoro-[1,1'-biphenyl]-4-yl)-3-((4-fluorophenyl)sulfonyl)pyrrolidine-1-carbonyl)cyclohexanecarboxylate from Step D, aqueous lithium hydroxide (0.5 mL, 1 N) and tetrahydrofuran (0.5 mL) was stirred at room temperature for 40 min. LCMS analysis showed that the reaction was about 30% complete. Methanol (0.18 mL) and methyl sulfoxide (0.54 mL) were added to help solublize the starting material. After 1 h at room temperature, the reaction was complete. The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile:water with 10-mM ammonium acetate; Gradient: 20-90% B over 20 minutes, then a 7-minute hold at 100% B; Flow: 20 mL/min. Fractions containing the desired product were combined and dried via centrifugal evaporation to give Example 39 (5.1 mg, 53% yield for two steps). LC/MS (M+1): 572.2; HPLC RT=1.48 min (analytical HPLC Method B); 1H NMR (500 MHz, 1:1 mixture of CDCl₃—CD₃OD) δ ppm 7.40-7.30 (m, 5H), 7.21-7.06 (m, 4H), 7.05-6.98 (m, 2H), 4.92-4.78 (m, 1H), 4.20-4.00 (m, 1H), 3.94-3.79 (m, 2H), 3.70-3.33 (m, 1H), 2.80-2.55 (m, 1H), 2.48-1.74 (m, 6H), 1.64-1.39 (m, 4H).

Example 40

(R)-1-(4-(3-((4-fluorophenyl)sulfonyl)-3-(4-(2,2,2-trifluoro-1-hydroxy-1-phenylethyl)phenyl)pyrrolidine-1-carbonyl)piperazin-1-yl)ethanone Step A: (3R)-benzyl-3-((4-fluorophenyl)sulfonyl)-3-(4-(2,2,2-trifluoro-1-hydroxy-1-phenylethyl)phenyl)pyrrolidone-1-carboxylate

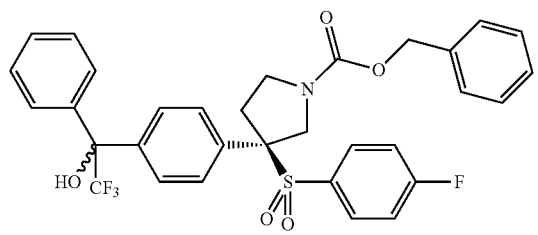

mixture of two diastereomers

A 2.0 M ether solution of isopropylmagnesium chloride (0.106 mL, 0.212 mmol) was added to a solution of (R)-benzyl 3-((4-fluorophenyl)sulfonyl)-3-(4-iodophenyl)pyrrolidine-1-carboxylate (40 mg, 0.071 mmol) in tetrahydrofuran (0.8 mL) at 0° C. After stirring for 30 min at 0° C., 2,2,2-trifluoro-1-phenylethanone (37.0 mg, 0.212 mmol) was added. After stirring at 0° C. for 30 min and at room temperature for 1 h, the mixture was quenched with saturated ammonium chloride (1 mL), diluted with ethyl acetate (40 mL), washed with water, brine, dried (magnesium sulfate), filtered and concentrated under reduced pressure. The residue was purified by silica gel chromatography, eluting with 0 to 40% ethyl acetate in hexanes, to provide (3R)-benzyl 3-((4-fluorophenyl)sulfonyl)-3-(4-(2,2,2-trifluoro-1-hydroxy-1-phenylethyl)phenyl)pyrrolidine-1-carboxylate (30 mg, 69% yield). LC/MS (M+1): 614.0; HPLC RT=4.453 min (analytical HPLC Method A); 1H NMR (400 MHz, CD₃OD) δ ppm 7.54-7.24 (m, 14H), 7.16-7.05 (m, 3H), 7.00 (t, J=8.6 Hz, 1H), 5.20-5.09 (m, 2H), 4.77-4.62 (m, 1H), 3.98-3.80 (m, 1H), 3.81-3.64 (m, 1H), 3.64-3.47 (m, 1H), 3.24-2.97 (m, 1H), 2.69-2.44 (m, 1H).

Step B: 2,2,2-trifluoro-1-(4-((R)-3-((4-fluorophenyl)sulfonyl)pyrrolidin-3-yl)phenyl)-1-phenylethanol

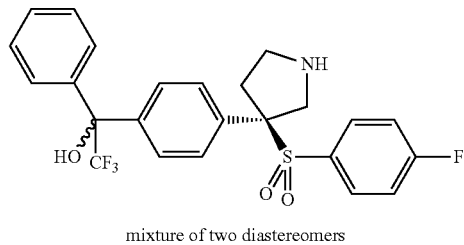 [SMILES: O=S(=O)(c1ccc(F)cc1)[C@@]1(c2ccc(C(O)(c3ccccc3)C(F)(F)F)cc2)CCNC1]

mixture of two diastereomers

A mixture of (R)-benzyl 3-((4-fluorophenyl)sulfonyl)-3-(4-((S)-2,2,2-trifluoro-1-hydroxy-1-phenylethyl)phenyl)pyrrolidine-1-carboxylate (30 mg, 0.049 mmol) and 20% palladium hydroxide on carbon (6.87 mg, 9.78 μmol) and methanol (5 mL) was stirred under hydrogen balloon for 2 h. The mixture was filtered to remove the catalyst. The filtrate was concentrated and dried under vacuum to provide 2,2,2-trifluoro-1-(4-((R)-3-((4-fluorophenyl)sulfonyl)pyrrolidin-3-yl)phenyl)-1-phenylethanol (20 mg, 85% yield). LC/MS (M+1): 480.0; 1H NMR (400 MHz, CDCl₃) δ ppm 7.55-7.27 (m, 8H), 7.22-6.99 (m, 2H), 6.99-6.68 (m, 3H), 4.01-3.64 (m, 1H), 3.34-3.18 (m, 1H), 3.11-2.75 (m, 2H), 2.58-2.42 (m, 1H), 2.15-1.88 (m, 1H).

Step C: (R)-1-(4-(3-((4-fluorophenyl)sulfonyl)-3-(4-(2,2,2-trifluoro-1-hydroxy-1-phenylethyl)phenyl)pyrrolidine-1-carbonyl)piperazin-1-yl)ethanone

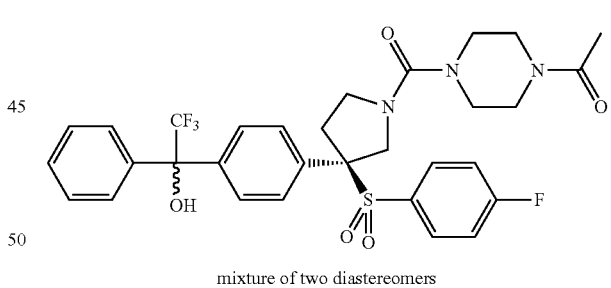

mixture of two diastereomers

Hunig's Base (0.029 mL, 0.167 mmol) was added to a mixture of (S)-2,2,2-trifluoro-1-(4-((R)-3-((4-fluorophenyl)sulfonyl)pyrrolidin-3-yl)phenyl)-1-phenylethanol (20 mg, 0.042 mmol) and 4-acetylpiperazine-1-carbonyl chloride (11.93 mg, 0.063 mmol) in dichloromethane (1 mL) at room temperature. After 2 h at room temperature, the mixture was concentrated and purified by preparative HPLC to provide Example 40 (12 mg, 43% yield). LC/MS (M+1): 634.0; HPLC RT=3.85 min (analytical HPLC Method A); 1H NMR (400 MHz, CD₃OD) δ ppm 7.52-7.44 (m, 2H), 7.44-7.30 (m, 7H), 7.25-6.89 (m, 4H), 4.63 (m, 1H), 4.00 (m, 1H), 3.98-3.84 (m, 1H), 3.76-3.46 (m, 5H), 3.45-3.37 (m, 4H), 3.15 (m, 1H), 2.72-2.55 (m, 1H), 2.13 (s, 3H).

Example 41

(R)-1-(4-(3-((4-fluorophenyl)sulfonyl)-3-(4-(2,2,2-trifluoro-1-methoxy-1-phenylethyl)phenyl)pyrrolidine-1-carbonyl)piperazin-1-yl)ethanone

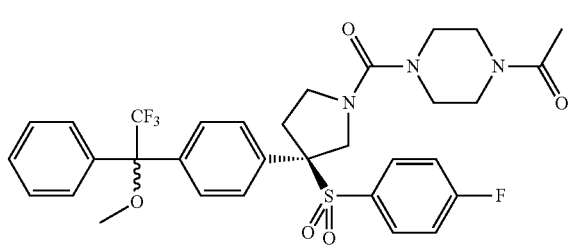

mixture of two diastereomers

Sodium hydride (1.894 mg, 0.047 mmol, 60% suspension in mineral oil) was added to a mixture of 1-(4-((3R)-3-((4-fluorophenyl)sulfonyl)-3-(4-(2,2,2-trifluoro-1-hydroxy-1-phenylethyl)phenyl)pyrrolidine-1-carbonyl)piperazin-1-yl)ethanone (10 mg, 0.016 mmol) and iodomethane (2.96 μl, 0.047 mmol) in N,N-dimethylformamide (1 mL) at room temperature. After stirring for 1 h at room temperature, the mixture was quenched water (1 mL). The crude material was purified via preparative LC/MS with the following conditions: Column: Waters XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-100% B over 20 minutes, then a 5-minute hold at 100% B; Flow: 20 mL/min. Fractions containing the desired product were combined and dried via centrifugal evaporation to give Example 41 (9.1 mg, 89% yield). LC/MS (M+1): 648.2; HPLC RT=2.04 min (analytical HPLC Method B).

Example 42

(R)-1-(4-(3-((4-fluorophenyl)sulfonyl)-3-(4-(1,2,2,2-tetrafluoro-1-phenylethyl)phenyl)pyrrolidine-1-carbonyl)piperazin-1-yl)ethanone

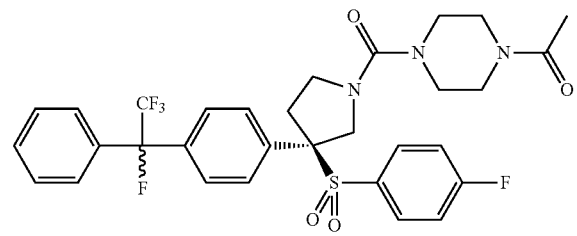

mixture of two diastereomers (Diethylamino)sulfur trifluoride (0.031 mL, 0.237 mmol) was added to a mixture of 1-(4-((3R)-3-(4-fluorophenyl)sulfonyl)-3-(4-(2,2,2-trifluoro-1-hydroxy-1-phenylethyl)phenyl)pyrrolidine-1-carbonyl)piperazin-1-yl)ethanone (15 mg, 0.024 mmol) in dichloromethane (0.5 mL) at room temperature. After stirring for 1 h at room temperature, the mixture was quenched with methanol (0.5 mL) and concentrated. The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile: water with 10-mM ammonium acetate; Gradient: 25-100% B over 25 minutes, then a 5-minute hold at 100% B; Flow: 20 mL/min. Fractions containing the desired product were combined and dried via centrifugal evaporation to provide Example 42. LC/MS (M+1): 636.2; HPLC RT=1.99 min (analytical HPLC Method B). 1H NMR (500 MHz, 1:1 mixture of $CDCl_3$—$CD_3OD$) δ ppm 7.52-7.44 (m, 5H), 7.44-7.25 (m, 4H), 7.16 (d, J=8.3 Hz, 2H), 7.04 (t, J=8.5 Hz, 2H), 4.65 (m, 1H), 4.09-3.85 (m, 2H), 3.72-3.53 (m, 4H), 3.47-3.40 (m, 5H), 3.22-3.11 (m, 1H), 2.61 (m, 1H), 2.15 (s, 3H).

The Examples in TABLE 1 below were prepared in the same manner as outlined in examples above.

TABLE 1

| Ex. No. | Structure | MS (M + 1) | HPLC ret. time (min.) | HPLC method |
|---|---|---|---|---|
| 43 | 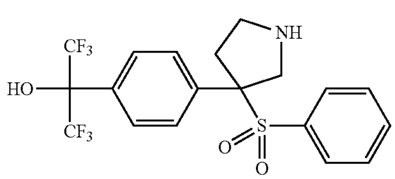 [SMILES: O=S(=O)(c1ccccc1)C1(c2ccc(C(O)(C(F)(F)F)C(F)(F)F)cc2)CCNC1] | 454.1 | 1.302 | B |
| 44 | 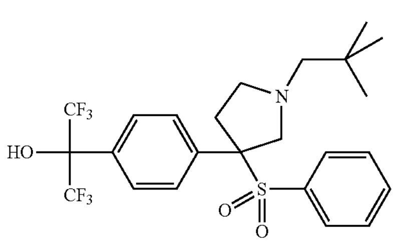 [SMILES: CC(C)(C)CN1CCC(c2ccc(C(O)(C(F)(F)F)C(F)(F)F)cc2)(S(=O)(=O)c2ccccc2)C1] | 524.2 | 2.083 | B |

TABLE 1-continued
| Ex. No. | Structure | MS (M + 1) | HPLC ret. time (min.) | HPLC method |
|---|---|---|---|---|
| 45 | 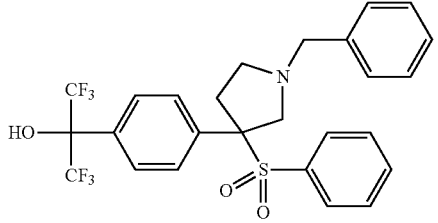 [SMILES: O=S(=O)(c1ccccc1)C1(c2ccc(C(O)(C(F)(F)F)C(F)(F)F)cc2)CCN(Cc2ccccc2)C1] | 544.1 | 1.878 | B |
| 46 | 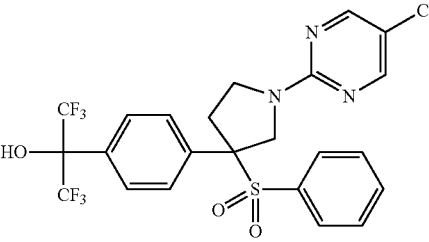 | 557.1 | 1.610 | B |
| 47 | 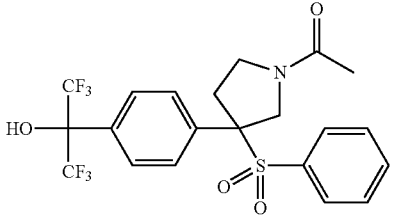 [SMILES: CC(=O)N1CCC(c2ccc(C(O)(C(F)(F)F)C(F)(F)F)cc2)(S(=O)(=O)c2ccccc2)C1] | 496.1 | 1.362 | B |
| 48 | 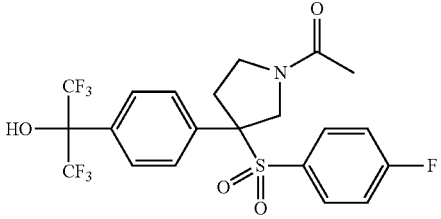 [SMILES: CC(=O)N1CCC(c2ccc(C(O)(C(F)(F)F)C(F)(F)F)cc2)(S(=O)(=O)c2ccc(F)cc2)C1] | 514.0 | 1.42 | C |
| 49 | 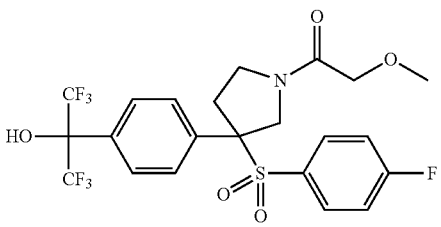 [SMILES: COCC(=O)N1CCC(c2ccc(C(O)(C(F)(F)F)C(F)(F)F)cc2)(S(=O)(=O)c2ccc(F)cc2)C1] | 544.0 | 1.43 | C |
| 50 | 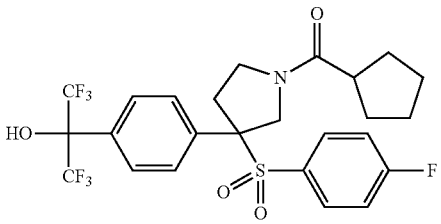 [SMILES: O=C(C1CCCC1)N1CCC(c2ccc(C(O)(C(F)(F)F)C(F)(F)F)cc2)(S(=O)(=O)c2ccc(F)cc2)C1] | 568.1 | 1.68 | C |

TABLE 1-continued

| Ex. No. | Structure | MS (M + 1) | HPLC ret. time (min.) | HPLC method |
|---|---|---|---|---|
| 51 | 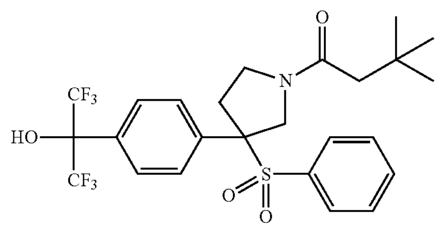 [SMILES: CC(C)(C)CC(=O)N1CCC(c2ccc(C(O)(C(F)(F)F)C(F)(F)F)cc2)(S(=O)(=O)c2ccccc2)C1] | 552.1 | 2.714 | B |
| 52 | 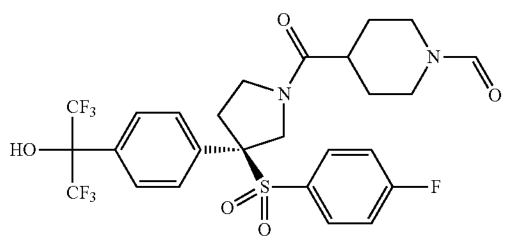 [SMILES: O=CN1CCC(C(=O)N2CC[C@](c3ccc(C(O)(C(F)(F)F)C(F)(F)F)cc3)(S(=O)(=O)c3ccc(F)cc3)C2)CC1] | 611.1 | 1.51 | B |
| 53 | 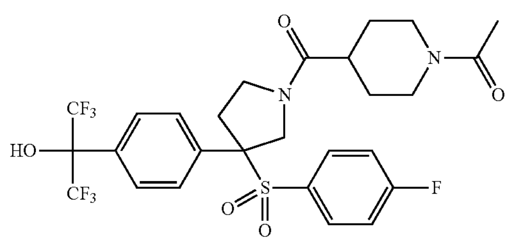 [SMILES: CC(=O)N1CCC(C(=O)N2CCC(c3ccc(C(O)(C(F)(F)F)C(F)(F)F)cc3)(S(=O)(=O)c3ccc(F)cc3)C2)CC1] | 625.1 | 1.638 | A |
| 54 | 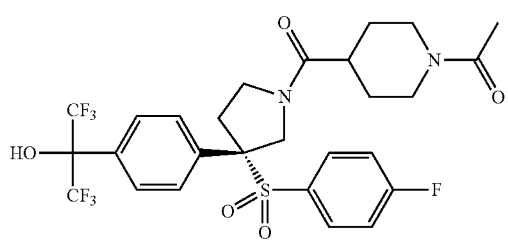 [SMILES: CC(=O)N1CCC(C(=O)N2CC[C@@](c3ccc(C(O)(C(F)(F)F)C(F)(F)F)cc3)(S(=O)(=O)c3ccc(F)cc3)C2)CC1] | 625.0 | 3.780 | A |
| 55 | 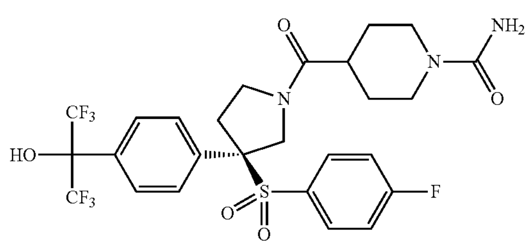 [SMILES: NC(=O)N1CCC(C(=O)N2CC[C@](c3ccc(C(O)(C(F)(F)F)C(F)(F)F)cc3)(S(=O)(=O)c3ccc(F)cc3)C2)CC1] | 626.1 | 1.44 | B |
| 56 | 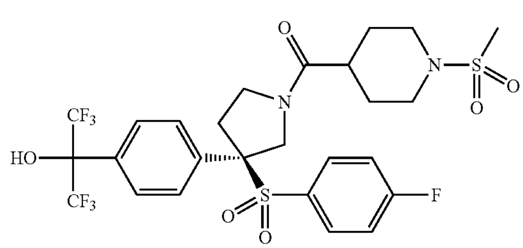 [SMILES: CS(=O)(=O)N1CCC(C(=O)N2CC[C@](c3ccc(C(O)(C(F)(F)F)C(F)(F)F)cc3)(S(=O)(=O)c3ccc(F)cc3)C2)CC1] | 661.2 | 1.61 | B |

TABLE 1-continued
| Ex. No. | Structure | MS (M + 1) | HPLC ret. time (min.) | HPLC method |
|---|---|---|---|---|
| 57 | 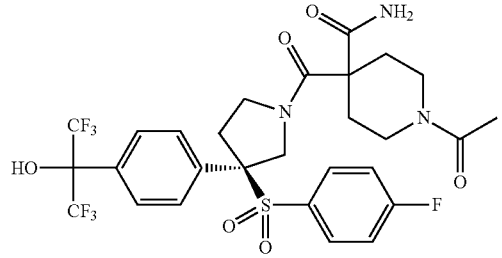 [SMILES: CC(=O)N1CCC(C(N)=O)(C(=O)N2CC[C@](c3ccc(C(O)(C(F)(F)F)C(F)(F)F)cc3)(S(=O)(=O)c3ccc(F)cc3)C2)CC1] | 668.2 | 1.41 | B |
| 58 | 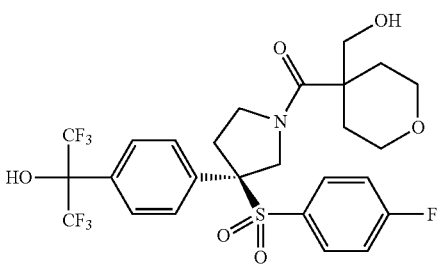 [SMILES: O=C(N1CC[C@](c2ccc(C(O)(C(F)(F)F)C(F)(F)F)cc2)(S(=O)(=O)c2ccc(F)cc2)C1)C1(CO)CCOCC1] | 614.2 | 1.50 | B |
| 59 | 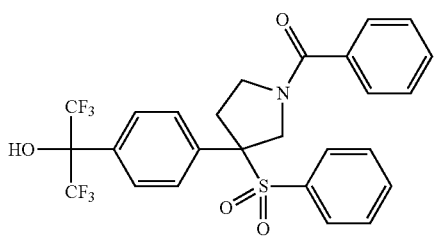 [SMILES: O=C(c1ccccc1)N1CCC(c2ccc(C(O)(C(F)(F)F)C(F)(F)F)cc2)(S(=O)(=O)c2ccccc2)C1] | 558.1 | 1.563 | B |
| 60 | 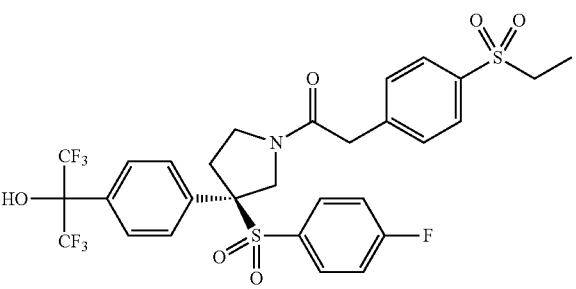 [SMILES: CCS(=O)(=O)c1ccc(CC(=O)N2CC[C@](c3ccc(C(O)(C(F)(F)F)C(F)(F)F)cc3)(S(=O)(=O)c3ccc(F)cc3)C2)cc1] | 682.0 | 1.71 | B |
| 61 | 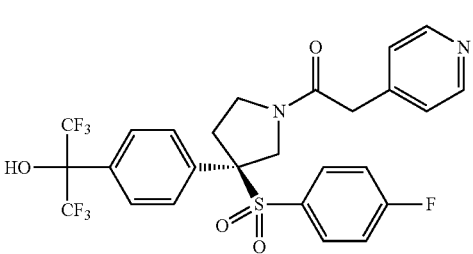 [SMILES: O=C(Cc1ccncc1)N1CC[C@](c2ccc(C(O)(C(F)(F)F)C(F)(F)F)cc2)(S(=O)(=O)c2ccc(F)cc2)C1] | 591.2 | 1.58 | B |
| 62 | 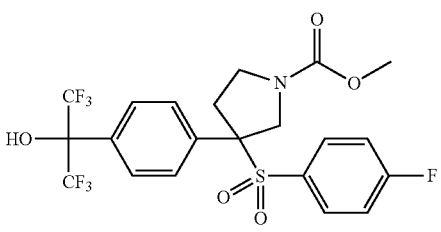 [SMILES: COC(=O)N1CCC(c2ccc(C(O)(C(F)(F)F)C(F)(F)F)cc2)(S(=O)(=O)c2ccc(F)cc2)C1] | 529.9 | 1.80 | C |

TABLE 1-continued

| Ex. No. | Structure | MS (M + 1) | HPLC ret. time (min.) | HPLC method |
|---|---|---|---|---|
| 63 | 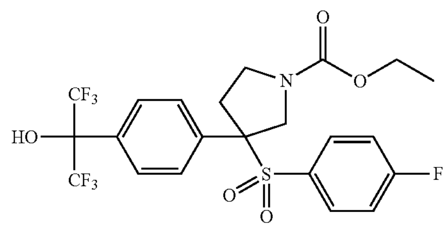 | 544.0 | 1.64 | C |
| 64 | 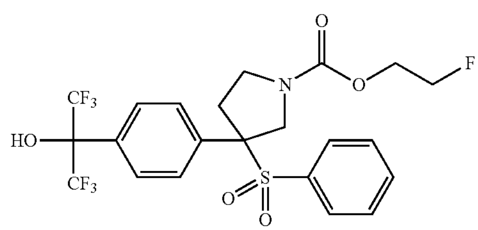 [SMILES: O=C(OCCF)N1CCC(c2ccc(C(O)(C(F)(F)F)C(F)(F)F)cc2)(S(=O)(=O)c2ccccc2)C1] | 544.1 | 1.523 | B |
| 65 | 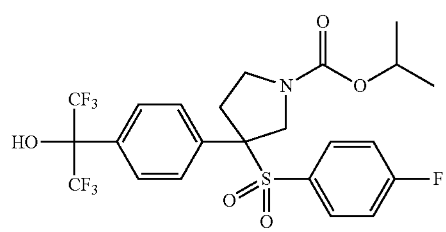 [SMILES: CC(C)OC(=O)N1CCC(c2ccc(C(O)(C(F)(F)F)C(F)(F)F)cc2)(S(=O)(=O)c2ccc(F)cc2)C1] | 558.1 | 1.72 | B |
| 66 | 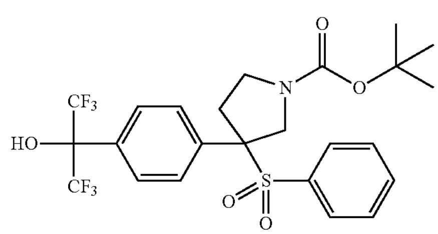 [SMILES: CC(C)(C)OC(=O)N1CCC(c2ccc(C(O)(C(F)(F)F)C(F)(F)F)cc2)(S(=O)(=O)c2ccccc2)C1] | 571.1 (M + 18) | 1.751 | B |
| 67 | 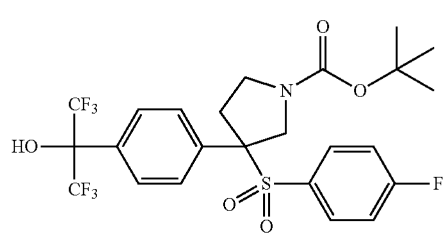 [SMILES: CC(C)(C)OC(=O)N1CCC(c2ccc(C(O)(C(F)(F)F)C(F)(F)F)cc2)(S(=O)(=O)c2ccc(F)cc2)C1] | 516.2 (M − 56 + 1) | 4.311 | A |
| 68 | 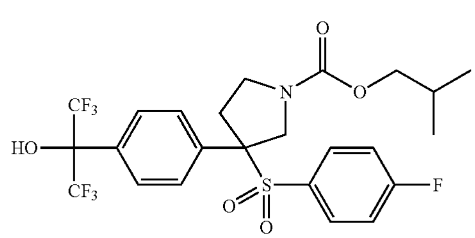 [SMILES: CC(C)COC(=O)N1CCC(c2ccc(C(O)(C(F)(F)F)C(F)(F)F)cc2)(S(=O)(=O)c2ccc(F)cc2)C1] | 572.1 | 1.82 | B |

TABLE 1-continued

| Ex. No. | Structure | MS (M + 1) | HPLC ret. time (min.) | HPLC method |
|---|---|---|---|---|
| 69 | 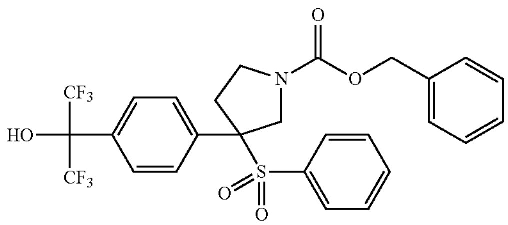 [SMILES: O=C(OCc1ccccc1)N1CCC(c2ccc(C(O)(C(F)(F)F)C(F)(F)F)cc2)(S(=O)(=O)c2ccccc2)C1] | 588.1 | 1.753 | B |
| 70 | 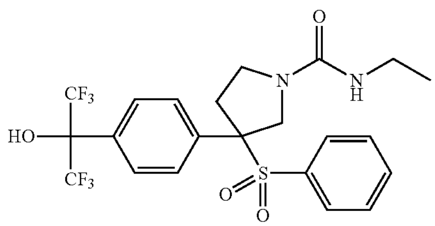 [SMILES: CCNC(=O)N1CCC(c2ccc(C(O)(C(F)(F)F)C(F)(F)F)cc2)(S(=O)(=O)c2ccccc2)C1] | 525.1 | 1.385 | B |
| 71 | 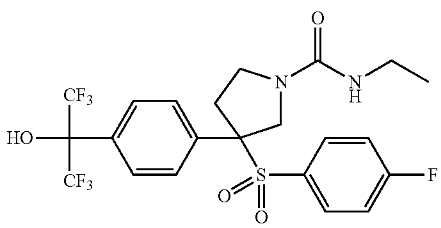 [SMILES: CCNC(=O)N1CCC(c2ccc(C(O)(C(F)(F)F)C(F)(F)F)cc2)(S(=O)(=O)c2ccc(F)cc2)C1] | 543.1 | 1.44 | C |
| 72 | 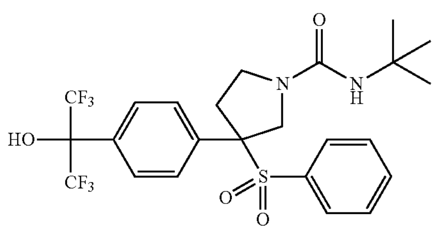 [SMILES: CC(C)(C)NC(=O)N1CCC(c2ccc(C(O)(C(F)(F)F)C(F)(F)F)cc2)(S(=O)(=O)c2ccccc2)C1] | 553.1 | 1.572 | B |
| 73 | 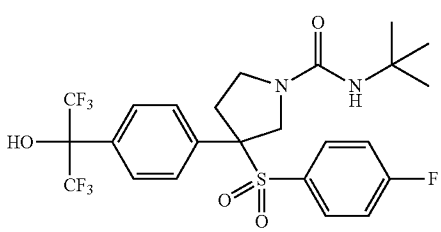 [SMILES: CC(C)(C)NC(=O)N1CCC(c2ccc(C(O)(C(F)(F)F)C(F)(F)F)cc2)(S(=O)(=O)c2ccc(F)cc2)C1] | 571.1 | 1.62 | B |
| 74 | 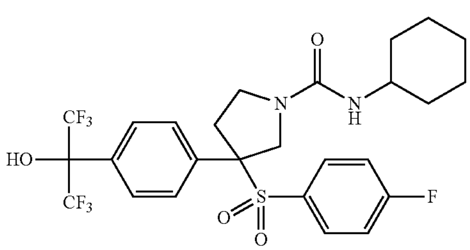 [SMILES: O=C(NC1CCCCC1)N1CCC(c2ccc(C(O)(C(F)(F)F)C(F)(F)F)cc2)(S(=O)(=O)c2ccc(F)cc2)C1] | 597.0 | 1.66 | B |

TABLE 1-continued
| Ex. No. | Structure | MS (M + 1) | HPLC ret. time (min.) | HPLC method |
|---|---|---|---|---|
| 75 | 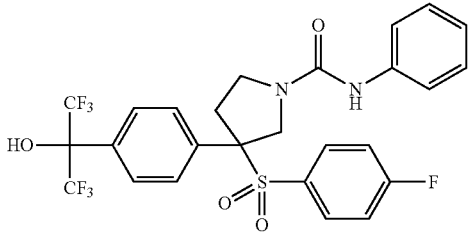 [SMILES: O=C(Nc1ccccc1)N1CCC(c2ccc(C(O)(C(F)(F)F)C(F)(F)F)cc2)(S(=O)(=O)c2ccc(F)cc2)C1] | 591.0 | 1.61 | C |
| 76 | 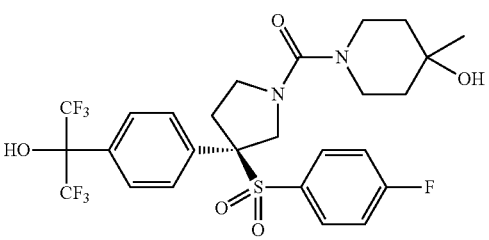 [SMILES: CC1(O)CCN(C(=O)N2CC[C@](c3ccc(C(O)(C(F)(F)F)C(F)(F)F)cc3)(S(=O)(=O)c3ccc(F)cc3)C2)CC1] | 613.1 | 1.75 | B |
| 77 | 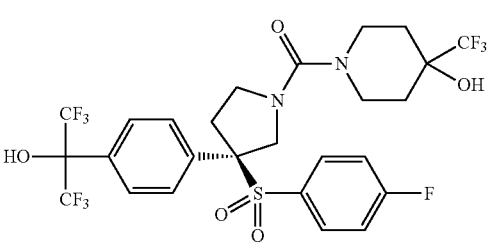 [SMILES: O=C(N1CCC(O)(C(F)(F)F)CC1)N1CC[C@](c2ccc(C(O)(C(F)(F)F)C(F)(F)F)cc2)(S(=O)(=O)c2ccc(F)cc2)C1] | 667.1 | 1.92 | B |
| 78 | 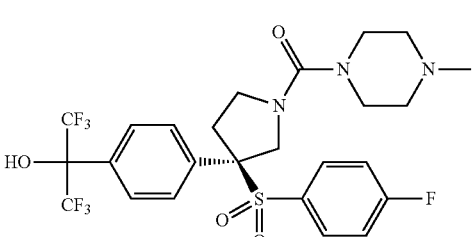 | 598.1 | 1.45 | B |
| 79 | 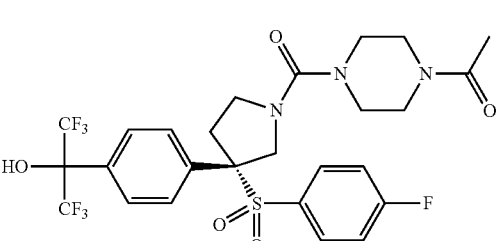 | 626.1 | 1.51 | B |
| 80 | 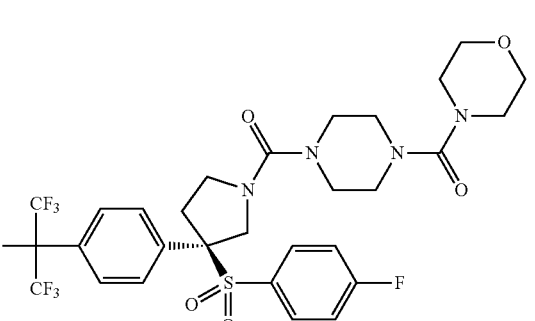 | 696.7 (M) | 1.58 | B |

TABLE 1-continued

| Ex. No. | Structure | MS (M + 1) | HPLC ret. time (min.) | HPLC method |
|---|---|---|---|---|
| 81 | 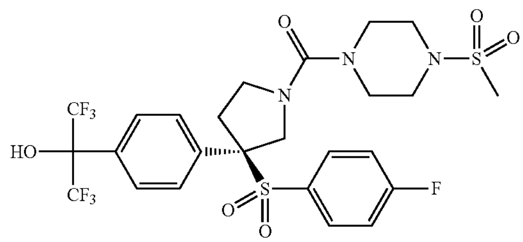 [SMILES: CS(=O)(=O)N1CCN(C(=O)N2CC[C@](c3ccc(C(O)(C(F)(F)F)C(F)(F)F)cc3)(S(=O)(=O)c3ccc(F)cc3)C2)CC1] | 662.2 | 1.64 | B |
| 82 | 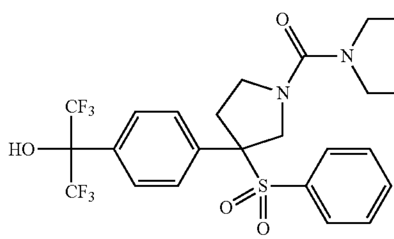 | 567.1 | 1.422 | B |
| 83 | 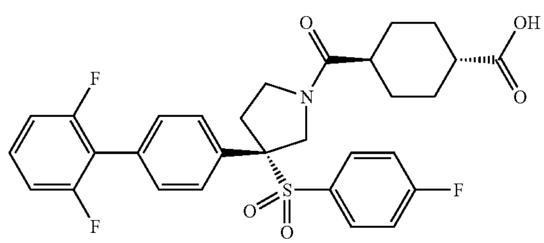 [SMILES: O=C(O)[C@H]1CC[C@H](C(=O)N2CC[C@@](c3ccc(-c4c(F)cccc4F)cc3)(S(=O)(=O)c3ccc(F)cc3)C2)CC1] | 572.2 | 1.48 | B |
| 84 | 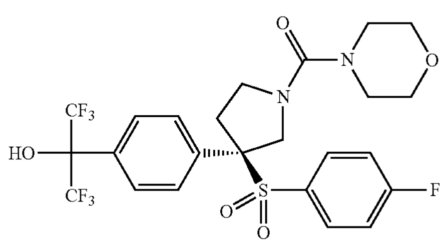 [SMILES: O=C(N1CCOCC1)N1CC[C@](c2ccc(C(O)(C(F)(F)F)C(F)(F)F)cc2)(S(=O)(=O)c2ccc(F)cc2)C1] | 585.1 | 1.62 | B |
| 85 | 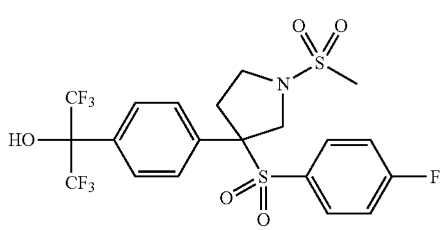 [SMILES: CS(=O)(=O)N1CCC(c2ccc(C(O)(C(F)(F)F)C(F)(F)F)cc2)(S(=O)(=O)c2ccc(F)cc2)C1] | 550.0 | 1.53 | B |
| 86 | 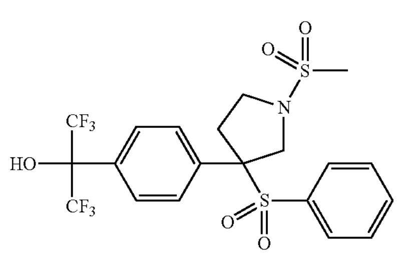 [SMILES: CS(=O)(=O)N1CCC(c2ccc(C(O)(C(F)(F)F)C(F)(F)F)cc2)(S(=O)(=O)c2ccccc2)C1] | 532.1 | 1.473 | B |

TABLE 1-continued

| Ex. No. | Structure | MS (M + 1) | HPLC ret. time (min.) | HPLC method |
|---|---|---|---|---|
| 87 | 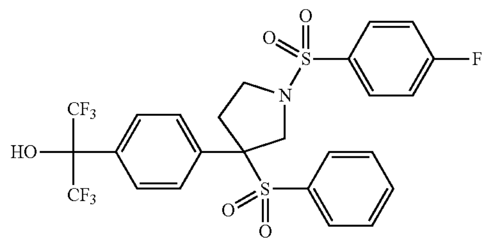 [SMILES: O=S(=O)(c1ccc(F)cc1)N1CCC(c2ccc(C(O)(C(F)(F)F)C(F)(F)F)cc2)(S(=O)(=O)c2ccccc2)C1] | 612.0 | 1.737 | B |
| 88 | 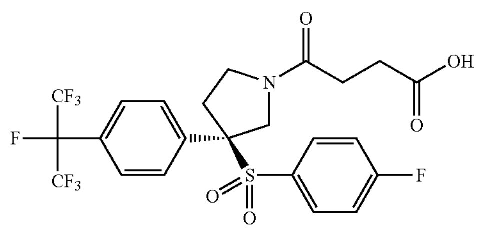 [SMILES: O=C(O)CCC(=O)N1CC[C@](c2ccc(C(F)(C(F)(F)F)C(F)(F)F)cc2)(S(=O)(=O)c2ccc(F)cc2)C1] | 574.2 | 1.56 | B |
| 89 | 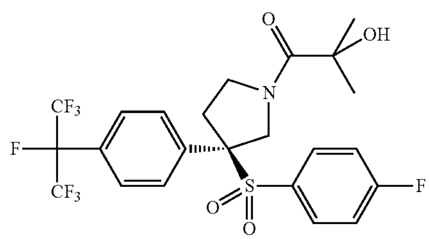 [SMILES: CC(C)(O)C(=O)N1CC[C@](c2ccc(C(F)(C(F)(F)F)C(F)(F)F)cc2)(S(=O)(=O)c2ccc(F)cc2)C1] | 560.2 | 1.98 | B |
| 90 | 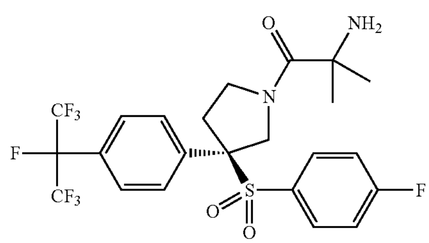 [SMILES: CC(C)(N)C(=O)N1CC[C@](c2ccc(C(F)(C(F)(F)F)C(F)(F)F)cc2)(S(=O)(=O)c2ccc(F)cc2)C1] | 559.2 | 1.67 | B |
| 91 | 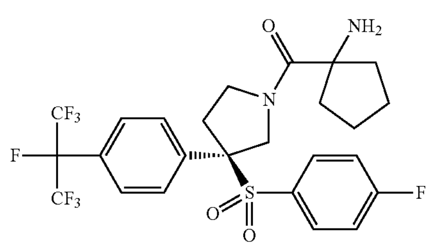 [SMILES: NC1(C(=O)N2CC[C@](c3ccc(C(F)(C(F)(F)F)C(F)(F)F)cc3)(S(=O)(=O)c3ccc(F)cc3)C2)CCCC1] | 585.2 | 1.92 | B |
| 92 | 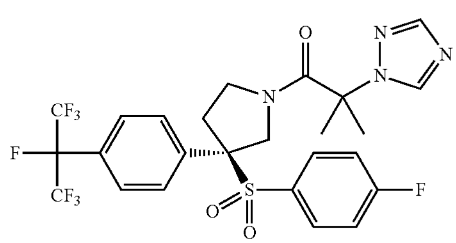 [SMILES: CC(C)(C(=O)N1CC[C@](c2ccc(C(F)(C(F)(F)F)C(F)(F)F)cc2)(S(=O)(=O)c2ccc(F)cc2)C1)n1cncn1] | 611.2 | 1.90 | B |

TABLE 1-continued

| Ex. No. | Structure | MS (M + 1) | HPLC ret. time (min.) | HPLC method |
|---|---|---|---|---|
| 93 | 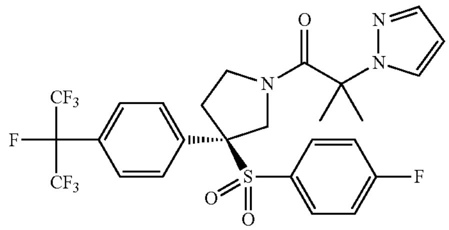 [SMILES: CC(C)(C(=O)N1CC[C@](c2ccc(C(F)(C(F)(F)F)C(F)(F)F)cc2)(S(=O)(=O)c2ccc(F)cc2)C1)n1cccn1] | 610.2 | 2.11 | B |
| 94 | 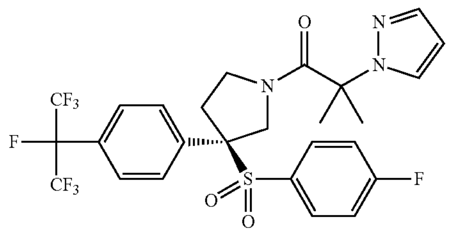 [SMILES: CC(C)(C(=O)N1CC[C@](c2ccc(C(F)(C(F)(F)F)C(F)(F)F)cc2)(S(=O)(=O)c2ccc(F)cc2)C1)n1cccn1] | 640.3 | 1.77 | B |
| 95 | 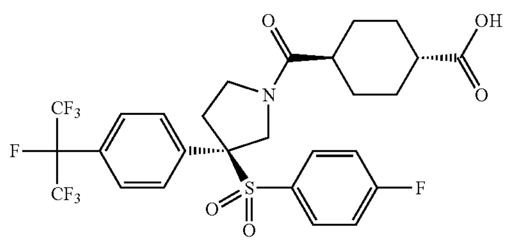 | 628.1 | 1.74 | B |
| 96 | 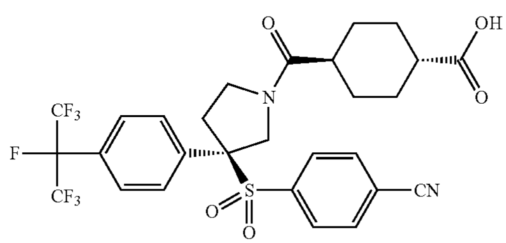 [SMILES: N#Cc1ccc(S(=O)(=O)[C@@]2(c3ccc(C(F)(C(F)(F)F)C(F)(F)F)cc3)CCN(C(=O)[C@H]3CC[C@H](C(=O)O)CC3)C2)cc1] | 635.3 | 1.83 | B |
| 97 | 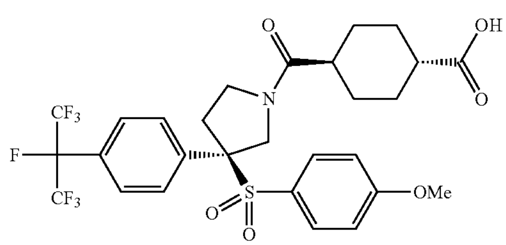 [SMILES: COc1ccc(S(=O)(=O)[C@@]2(c3ccc(C(F)(C(F)(F)F)C(F)(F)F)cc3)CCN(C(=O)[C@H]3CC[C@H](C(=O)O)CC3)C2)cc1] | 640.3 | 1.61 | B |
| 98 | 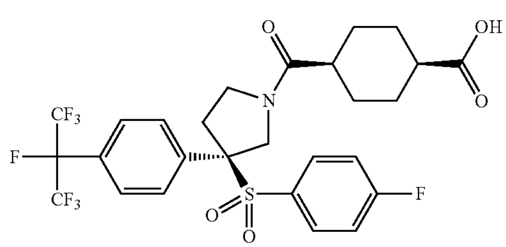 [SMILES: O=C(O)[C@H]1CC[C@@H](C(=O)N2CC[C@](c3ccc(C(F)(C(F)(F)F)C(F)(F)F)cc3)(S(=O)(=O)c3ccc(F)cc3)C2)CC1] | 628.2 | 1.72 | B |

TABLE 1-continued

| Ex. No. | Structure | MS (M + 1) | HPLC ret. time (min.) | HPLC method |
|---|---|---|---|---|
| 99 | 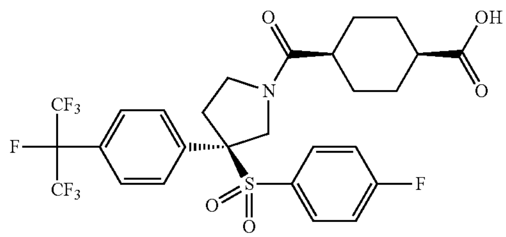 [SMILES: O=C(O)[C@H]1CC[C@@H](C(=O)N2CC[C@](c3ccc(C(F)(C(F)(F)F)C(F)(F)F)cc3)(S(=O)(=O)c3ccc(F)cc3)C2)CC1] | 642.3 | 4.336 | A |
| 100 | 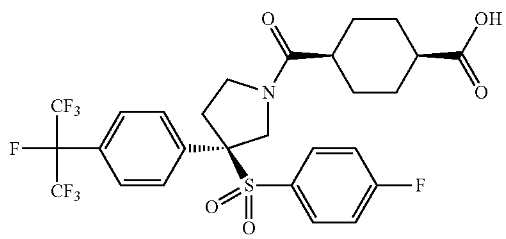 [SMILES: O=C(O)[C@H]1CC[C@@H](C(=O)N2CC[C@](c3ccc(C(F)(C(F)(F)F)C(F)(F)F)cc3)(S(=O)(=O)c3ccc(F)cc3)C2)CC1] | 642.3 | 4.369 | A |
| 101 | diastereomer A | 644.4 | 4.20 | A |
| 102 | diastereomer B | 644.4 | 4.223 | A |
| 103 | 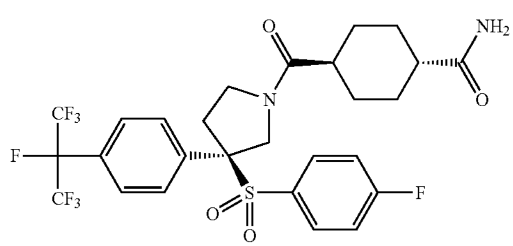 [SMILES: NC(=O)[C@H]1CC[C@H](C(=O)N2CC[C@](c3ccc(C(F)(C(F)(F)F)C(F)(F)F)cc3)(S(=O)(=O)c3ccc(F)cc3)C2)CC1] | 637.3 | 1.84 | B |
| 104 | 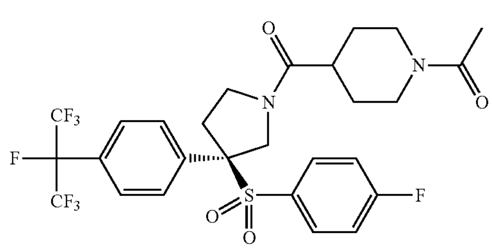 [SMILES: CC(=O)N1CCC(C(=O)N2CC[C@](c3ccc(C(F)(C(F)(F)F)C(F)(F)F)cc3)(S(=O)(=O)c3ccc(F)cc3)C2)CC1] | 627.2 | 2.04 | B |

TABLE 1-continued

| Ex. No. | Structure | MS (M + 1) | HPLC ret. time (min.) | HPLC method |
|---|---|---|---|---|
| 105 | 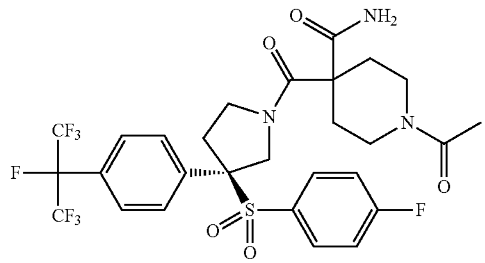 [SMILES: CC(=O)N1CCC(C(N)=O)(C(=O)N2CC[C@](c3ccc(C(F)(C(F)(F)F)C(F)(F)F)cc3)(S(=O)(=O)c3ccc(F)cc3)C2)CC1] | 670.2 | 1.72 | B |
| 106 | 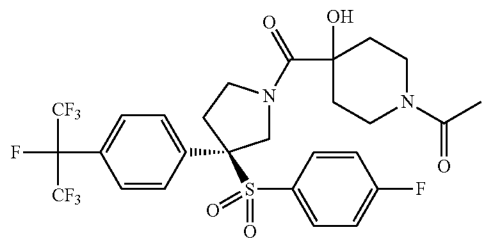 [SMILES: CC(=O)N1CCC(O)(C(=O)N2CC[C@](c3ccc(C(F)(C(F)(F)F)C(F)(F)F)cc3)(S(=O)(=O)c3ccc(F)cc3)C2)CC1] | 643.3 | 1.81 | B |
| 107 | 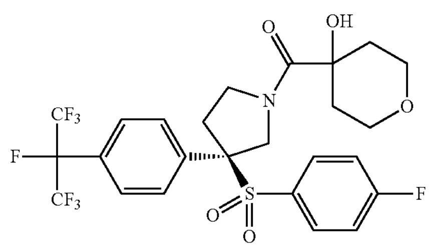 | 602.2 | 1.88 | B |
| 108 | 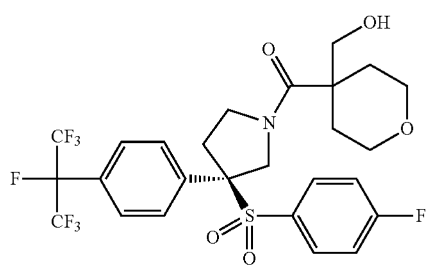 [SMILES: O=C(N1CC[C@](c2ccc(C(F)(C(F)(F)F)C(F)(F)F)cc2)(S(=O)(=O)c2ccc(F)cc2)C1)C1(CO)CCOCC1] | 616.1 | 1.83 | B |
| 109 | 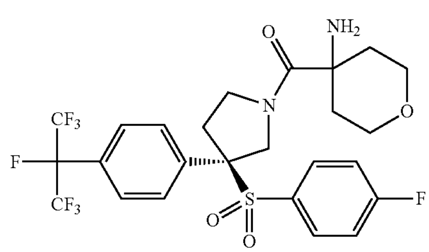 [SMILES: NC1(C(=O)N2CC[C@](c3ccc(C(F)(C(F)(F)F)C(F)(F)F)cc3)(S(=O)(=O)c3ccc(F)cc3)C2)CCOCC1] | 601.2 | 1.88 | B |
| 110 | 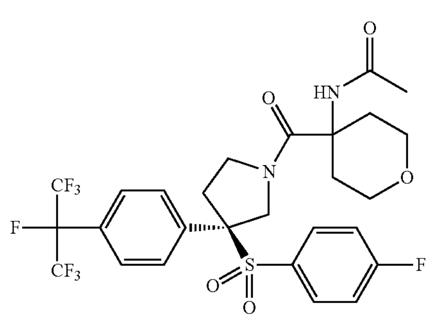 [SMILES: CC(=O)NC1(C(=O)N2CC[C@](c3ccc(C(F)(C(F)(F)F)C(F)(F)F)cc3)(S(=O)(=O)c3ccc(F)cc3)C2)CCOCC1] | 643.3 | 1.80 | B |

TABLE 1-continued

| Ex. No. | Structure | MS (M + 1) | HPLC ret. time (min.) | HPLC method |
|---|---|---|---|---|
| 111 | 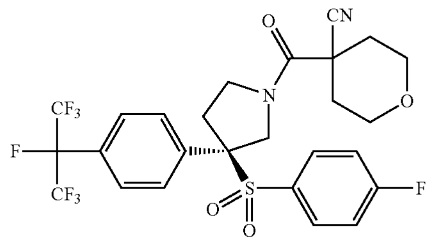 | 611.2 | 2.10 | B |
| 112 | 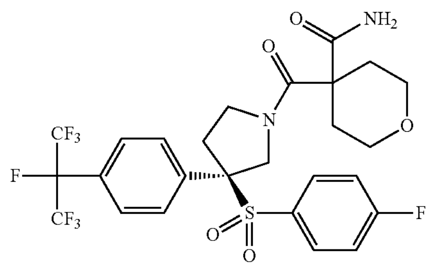 [SMILES: NC(=O)C1(C(=O)N2CC[C@](c3ccc(C(F)(C(F)(F)F)C(F)(F)F)cc3)(S(=O)(=O)c3ccc(F)cc3)C2)CCOCC1] | 629.2 | 1.80 | B |
| 113 | 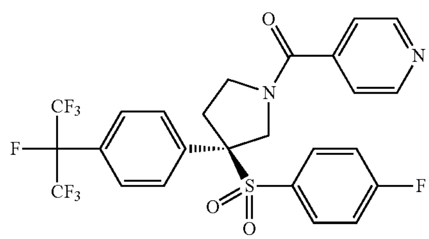 [SMILES: O=C(c1ccncc1)N1CC[C@](c2ccc(C(F)(C(F)(F)F)C(F)(F)F)cc2)(S(=O)(=O)c2ccc(F)cc2)C1] | 579.3 | 1.96 | B |
| 114 | 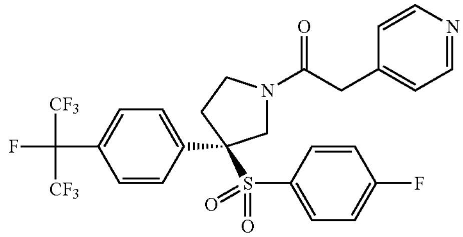 [SMILES: O=C(Cc1ccncc1)N1CC[C@](c2ccc(C(F)(C(F)(F)F)C(F)(F)F)cc2)(S(=O)(=O)c2ccc(F)cc2)C1] | 593.3 | 1.93 | B |
| 115 | 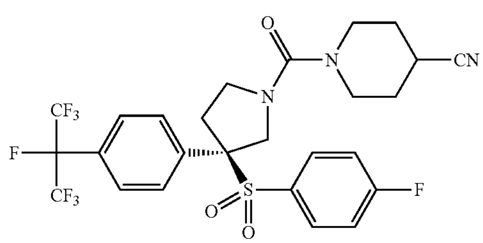 [SMILES: N#CC1CCN(C(=O)N2CC[C@](c3ccc(C(F)(C(F)(F)F)C(F)(F)F)cc3)(S(=O)(=O)c3ccc(F)cc3)C2)CC1] | 609.9 | 4.235 | A |
| 116 | 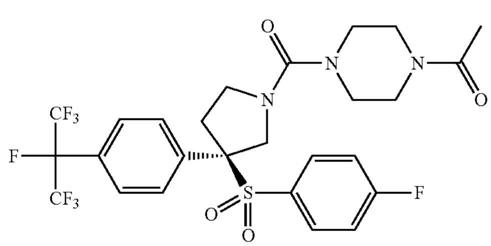 [SMILES: CC(=O)N1CCN(C(=O)N2CC[C@](c3ccc(C(F)(C(F)(F)F)C(F)(F)F)cc3)(S(=O)(=O)c3ccc(F)cc3)C2)CC1] | 628.1 | 1.87 | B |

TABLE 1-continued

| Ex. No. | Structure | MS (M + 1) | HPLC ret. time (min.) | HPLC method |
|---|---|---|---|---|
| 117 | 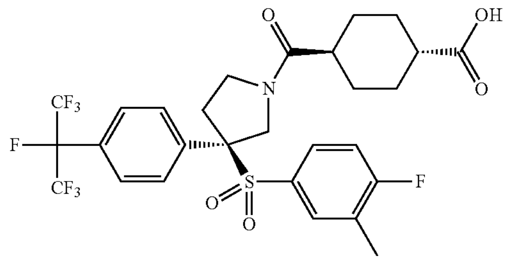 [SMILES: Cc1cc(S(=O)(=O)[C@@]2(c3ccc(C(F)(C(F)(F)F)C(F)(F)F)cc3)CCN(C(=O)[C@H]3CC[C@H](C(=O)O)CC3)C2)ccc1F] | 642.3 | 4.383 | A |
| 118 | 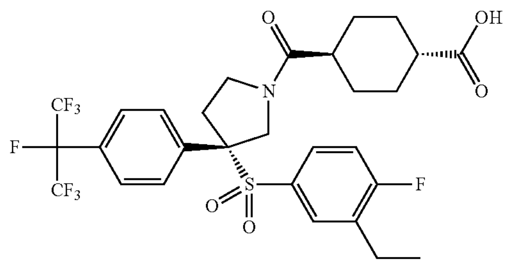 [SMILES: CCc1cc(S(=O)(=O)[C@]2(c3ccc(C(F)(C(F)(F)F)C(F)(F)F)cc3)CCN(C(=O)[C@H]3CC[C@H](C(=O)O)CC3)C2)ccc1F] | 656.4 | 4.480 | A |
| 119 | 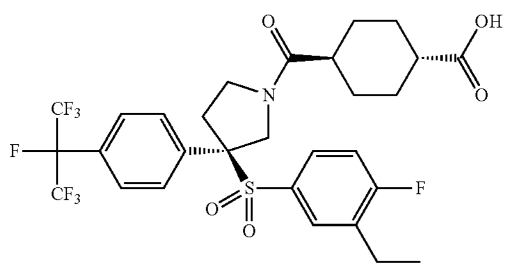 [SMILES: CCc1cc(S(=O)(=O)[C@@]2(c3ccc(C(F)(C(F)(F)F)C(F)(F)F)cc3)CCN(C(=O)[C@H]3CC[C@H](C(=O)O)CC3)C2)ccc1F] | 656.3 | 4.490 | A |
| 120 | 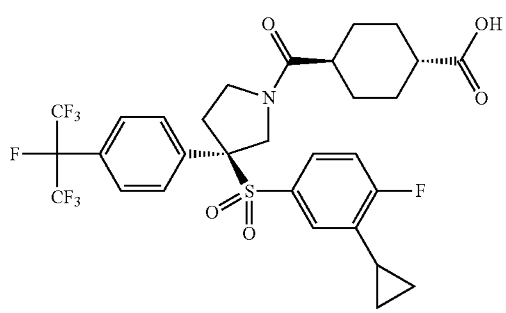 [SMILES: O=C(O)[C@H]1CC[C@H](C(=O)N2CC[C@](c3ccc(C(F)(C(F)(F)F)C(F)(F)F)cc3)(S(=O)(=O)c3ccc(F)c(C4CC4)c3)C2)CC1] | 668.4 | 4.488 | A |
| 121 | 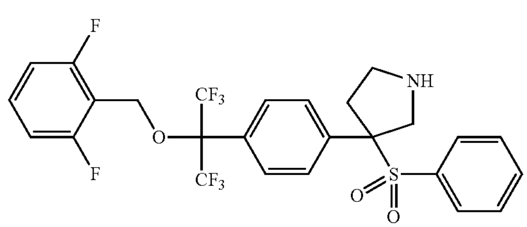 [SMILES: O=S(=O)(c1ccccc1)C1(c2ccc(C(OCc3c(F)cccc3F)(C(F)(F)F)C(F)(F)F)cc2)CCNC1] | 580.2 | 3.846 | A |

TABLE 1-continued

| Ex. No. | Structure | MS (M + 1) | HPLC ret. time (min.) | HPLC method |
|---|---|---|---|---|
| 122 | 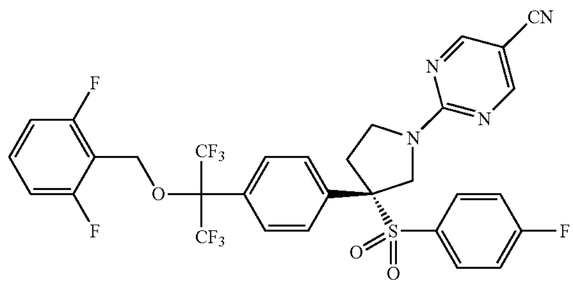 [SMILES: N#Cc1cnc(N2CC[C@@](c3ccc(C(OCc4c(F)cccc4F)(C(F)(F)F)C(F)(F)F)cc3)(S(=O)(=O)c3ccc(F)cc3)C2)nc1] | 701.0 | 2.41 | B |
| 123 | 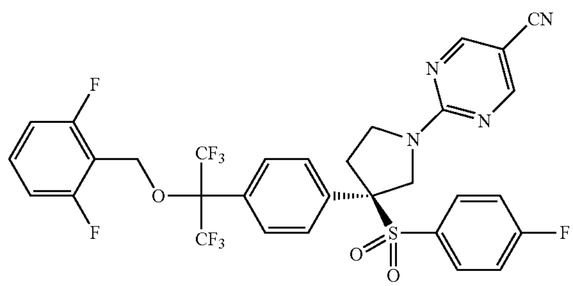 [SMILES: N#Cc1cnc(N2CC[C@](c3ccc(C(OCc4c(F)cccc4F)(C(F)(F)F)C(F)(F)F)cc3)(S(=O)(=O)c3ccc(F)cc3)C2)nc1] | 701.1 | 2.41 | B |
| 124 | 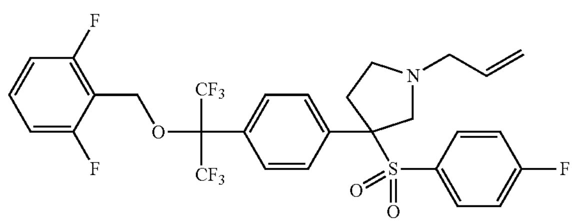 [SMILES: C=CCN1CCC(c2ccc(C(OCc3c(F)cccc3F)(C(F)(F)F)C(F)(F)F)cc2)(S(=O)(=O)c2ccc(F)cc2)C1] | 638.1 | 2.297 | B |
| 125 | 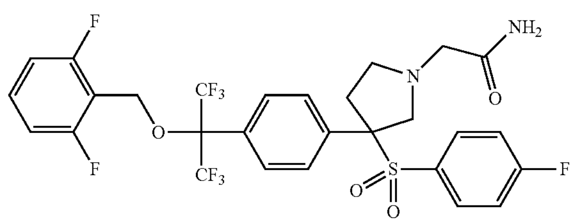 [SMILES: NC(=O)CN1CCC(c2ccc(C(OCc3c(F)cccc3F)(C(F)(F)F)C(F)(F)F)cc2)(S(=O)(=O)c2ccc(F)cc2)C1] | 655.1 | 1.991 | B |
| 126 | 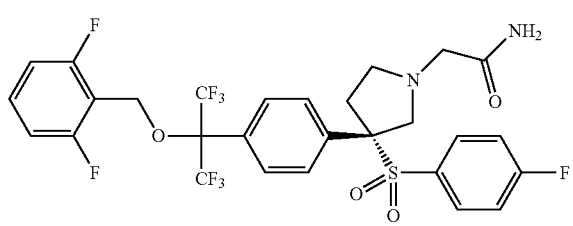 [SMILES: NC(=O)CN1CC[C@@](c2ccc(C(OCc3c(F)cccc3F)(C(F)(F)F)C(F)(F)F)cc2)(S(=O)(=O)c2ccc(F)cc2)C1] | 655.0 | 2.11 | B |
| 127 | 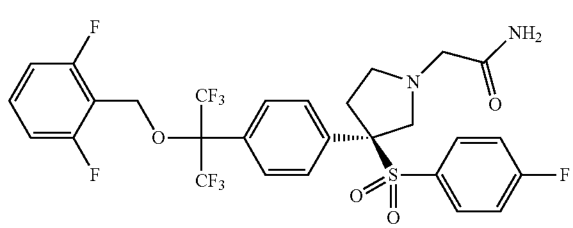 [SMILES: NC(=O)CN1CC[C@](c2ccc(C(OCc3c(F)cccc3F)(C(F)(F)F)C(F)(F)F)cc2)(S(=O)(=O)c2ccc(F)cc2)C1] | 655.1 | 2.11 | B |

TABLE 1-continued

| Ex. No. | Structure | MS (M + 1) | HPLC ret. time (min.) | HPLC method |
|---|---|---|---|---|
| 128 | 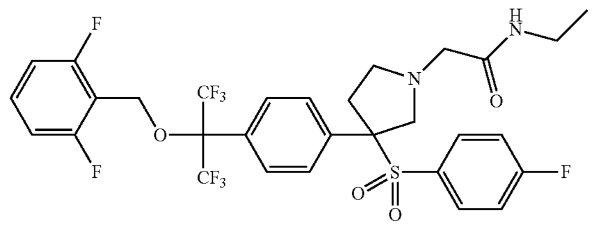 [SMILES: CCNC(=O)CN1CCC(c2ccc(C(OCc3c(F)cccc3F)(C(F)(F)F)C(F)(F)F)cc2)(S(=O)(=O)c2ccc(F)cc2)C1] | 683.1 | 2.21 | B |
| 129 | 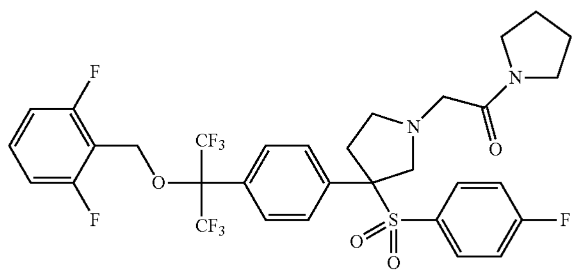 [SMILES: O=C(CN1CCC(c2ccc(C(OCc3c(F)cccc3F)(C(F)(F)F)C(F)(F)F)cc2)(S(=O)(=O)c2ccc(F)cc2)C1)N1CCCC1] | 709.1 | 2.22 | B |
| 130 | 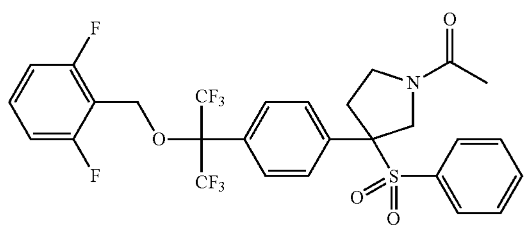 [SMILES: CC(=O)N1CCC(c2ccc(C(OCc3c(F)cccc3F)(C(F)(F)F)C(F)(F)F)cc2)(S(=O)(=O)c2ccccc2)C1] | 622.1 | 2.15 | B |
| 131 | 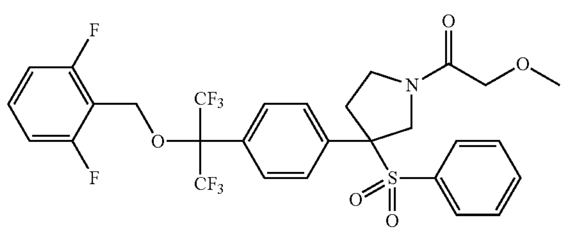 [SMILES: COCC(=O)N1CCC(c2ccc(C(OCc3c(F)cccc3F)(C(F)(F)F)C(F)(F)F)cc2)(S(=O)(=O)c2ccccc2)C1] | 652.1 | 2.16 | C |
| 132 | 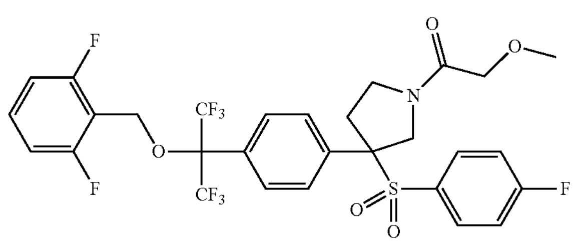 [SMILES: COCC(=O)N1CCC(c2ccc(C(OCc3c(F)cccc3F)(C(F)(F)F)C(F)(F)F)cc2)(S(=O)(=O)c2ccc(F)cc2)C1] | 669.8 | 2.16 | B |
| 133 | 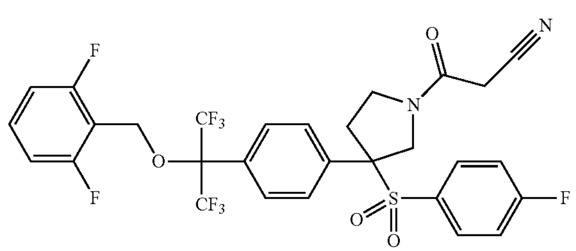 [SMILES: N#CCC(=O)N1CCC(c2ccc(C(OCc3c(F)cccc3F)(C(F)(F)F)C(F)(F)F)cc2)(S(=O)(=O)c2ccc(F)cc2)C1] | 682.1 (M + 18) | 2.11 | B |

TABLE 1-continued

| Ex. No. | Structure | MS (M + 1) | HPLC ret. time (min.) | HPLC method |
|---|---|---|---|---|
| 134 | 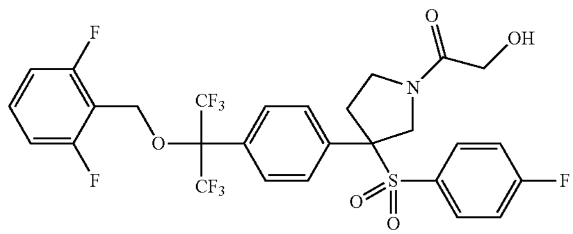 [SMILES: O=C(CO)N1CCC(c2ccc(C(OCc3c(F)cccc3F)(C(F)(F)F)C(F)(F)F)cc2)(S(=O)(=O)c2ccc(F)cc2)C1] | 656.0 | 2.01 | B |
| 135 | 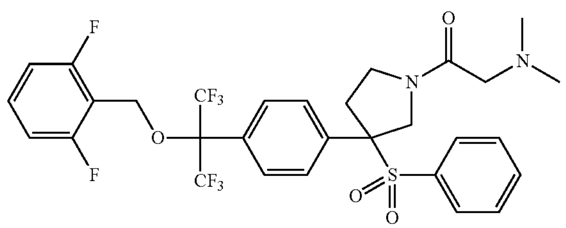 [SMILES: CN(C)CC(=O)N1CCC(c2ccc(C(OCc3c(F)cccc3F)(C(F)(F)F)C(F)(F)F)cc2)(S(=O)(=O)c2ccccc2)C1] | 665.1 | 1.89 | C |
| 136 | 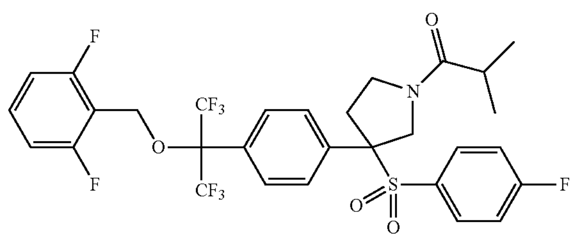 | 667.9 | 2.34 | C |
| 137 | 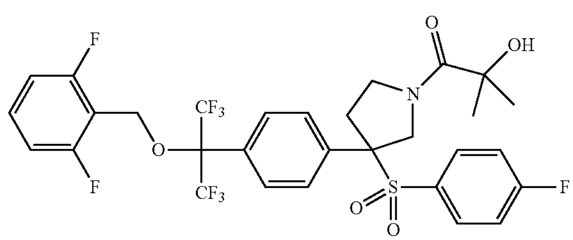 [SMILES: CC(C)(O)C(=O)N1CCC(c2ccc(C(OCc3c(F)cccc3F)(C(F)(F)F)C(F)(F)F)cc2)(S(=O)(=O)c2ccc(F)cc2)C1] | 684.0 | 2.12 | B |
| 138 | 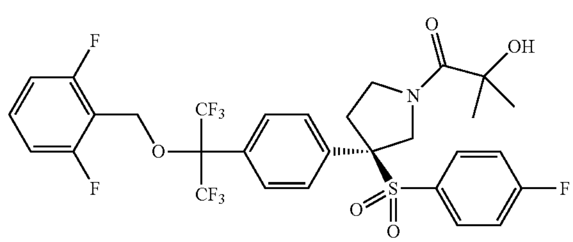 [SMILES: CC(C)(O)C(=O)N1CC[C@](c2ccc(C(OCc3c(F)cccc3F)(C(F)(F)F)C(F)(F)F)cc2)(S(=O)(=O)c2ccc(F)cc2)C1] | 684.2 | 2.17 | B |
| 139 | 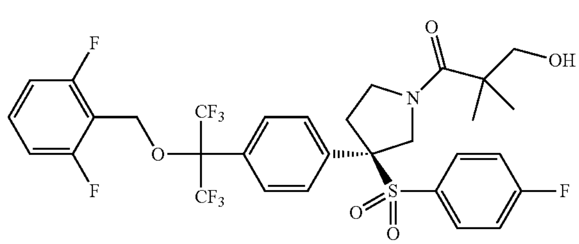 [SMILES: CC(C)(CO)C(=O)N1CC[C@](c2ccc(C(OCc3c(F)cccc3F)(C(F)(F)F)C(F)(F)F)cc2)(S(=O)(=O)c2ccc(F)cc2)C1] | 698.2 | 2.20 | B |

TABLE 1-continued

| Ex. No. | Structure | MS (M + 1) | HPLC ret. time (min.) | HPLC method |
|---|---|---|---|---|
| 140 | 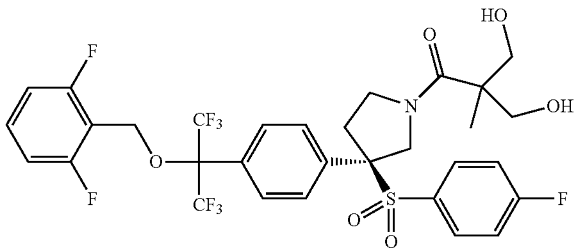 [SMILES: CC(CO)(CO)C(=O)N1CC[C@](c2ccc(C(OCc3c(F)cccc3F)(C(F)(F)F)C(F)(F)F)cc2)(S(=O)(=O)c2ccc(F)cc2)C1] | 714.2 | 2.05 | B |
| 141 | 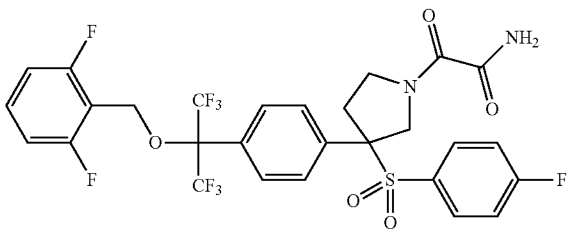 [SMILES: NC(=O)C(=O)N1CCC(c2ccc(C(OCc3c(F)cccc3F)(C(F)(F)F)C(F)(F)F)cc2)(S(=O)(=O)c2ccc(F)cc2)C1] | 686.0 (M + 18) | 2.04 | B |
| 142 | 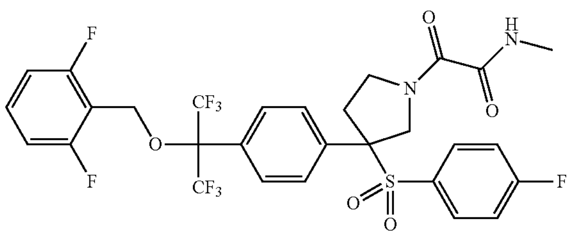 [SMILES: CNC(=O)C(=O)N1CCC(c2ccc(C(OCc3c(F)cccc3F)(C(F)(F)F)C(F)(F)F)cc2)(S(=O)(=O)c2ccc(F)cc2)C1] | 683.0 | 2.239 | B |
| 143 | 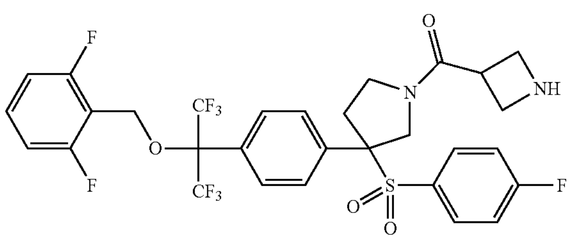 [SMILES: O=C(C1CNC1)N1CCC(c2ccc(C(OCc3c(F)cccc3F)(C(F)(F)F)C(F)(F)F)cc2)(S(=O)(=O)c2ccc(F)cc2)C1] | 681.0 | 1.82 | B |
| 144 | 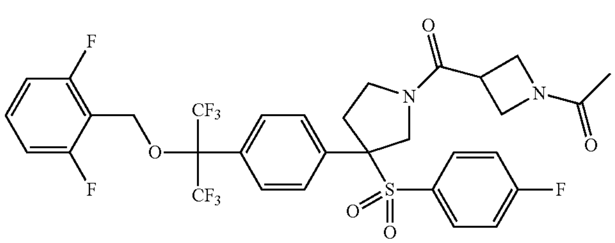 [SMILES: CC(=O)N1CC(C(=O)N2CCC(c3ccc(C(OCc4c(F)cccc4F)(C(F)(F)F)C(F)(F)F)cc3)(S(=O)(=O)c3ccc(F)cc3)C2)C1] | 723.2 | 2.03 | B |
| 145 | 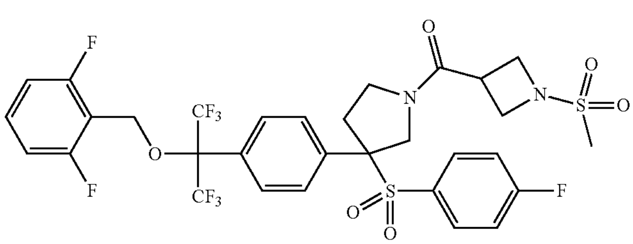 [SMILES: CS(=O)(=O)N1CC(C(=O)N2CCC(c3ccc(C(OCc4c(F)cccc4F)(C(F)(F)F)C(F)(F)F)cc3)(S(=O)(=O)c3ccc(F)cc3)C2)C1] | 759.2 | 2.15 | B |

TABLE 1-continued

| Ex. No. | Structure | MS (M + 1) | HPLC ret. time (min.) | HPLC method |
|---|---|---|---|---|
| 146 | 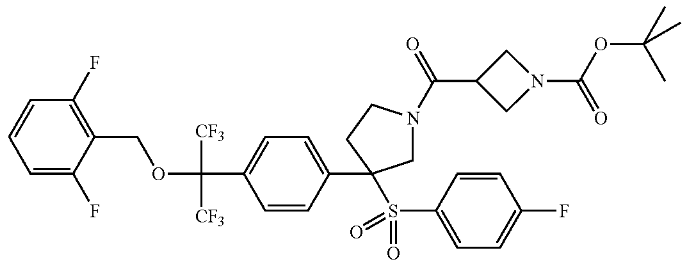 [SMILES: CC(C)(C)OC(=O)N1CC(C(=O)N2CCC(c3ccc(C(OCc4c(F)cccc4F)(C(F)(F)F)C(F)(F)F)cc3)(S(=O)(=O)c3ccc(F)cc3)C2)C1] | 725.0 (M − 56 + 1) | 4.636 | A |
| 147 | mixture of two diastereomers | 764.1 | 2.006 | B |
| 148 | diastereomer A | 764.6 | 4.516 | A |
| 149 | diastereomer B | 764.6 | 4.516 | A |
| 150 | mixture of 2 diastereomers from cis-di-acid | 738.2 | 1.91 | B |

TABLE 1-continued

| Ex. No. | Structure | MS (M + 1) | HPLC ret. time (min.) | HPLC method |
|---|---|---|---|---|
| 151 | 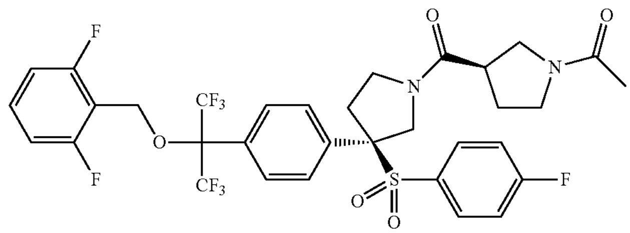 [SMILES: CC(=O)N1CC[C@@H](C(=O)N2CC[C@](c3ccc(C(OCc4c(F)cccc4F)(C(F)(F)F)C(F)(F)F)cc3)(S(=O)(=O)c3ccc(F)cc3)C2)C1] | 737.0 | 2.02 | B |
| 152 | 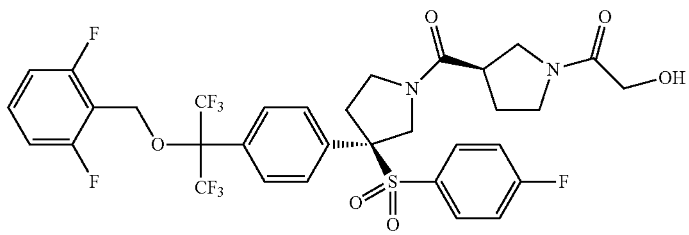 [SMILES: O=C(CO)N1CC[C@@H](C(=O)N2CC[C@](c3ccc(C(OCc4c(F)cccc4F)(C(F)(F)F)C(F)(F)F)cc3)(S(=O)(=O)c3ccc(F)cc3)C2)C1] | 753.2 | 2.16 | B |
| 153 | 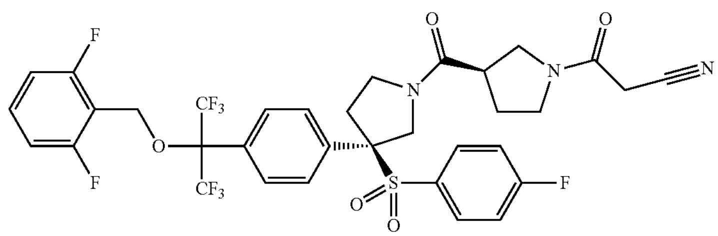 [SMILES: N#CCC(=O)N1CC[C@@H](C(=O)N2CC[C@](c3ccc(C(OCc4c(F)cccc4F)(C(F)(F)F)C(F)(F)F)cc3)(S(=O)(=O)c3ccc(F)cc3)C2)C1] | 762.2 | 2.24 | B |
| 154 | 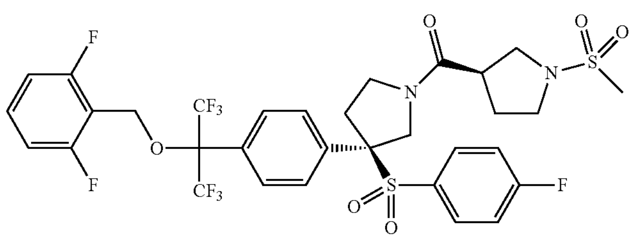 [SMILES: CS(=O)(=O)N1CC[C@@H](C(=O)N2CC[C@](c3ccc(C(OCc4c(F)cccc4F)(C(F)(F)F)C(F)(F)F)cc3)(S(=O)(=O)c3ccc(F)cc3)C2)C1] | 773.0 | 2.13 | B |
| 155 | 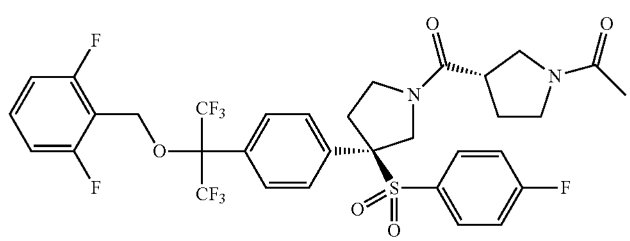 [SMILES: CC(=O)N1CC[C@H](C(=O)N2CC[C@](c3ccc(C(OCc4c(F)cccc4F)(C(F)(F)F)C(F)(F)F)cc3)(S(=O)(=O)c3ccc(F)cc3)C2)C1] | 737.0 | 2.02 | B |
| 156 | 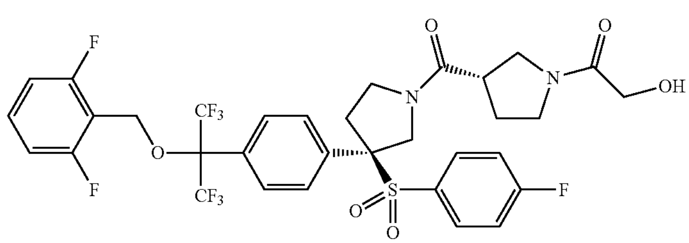 [SMILES: O=C(CO)N1CC[C@H](C(=O)N2CC[C@](c3ccc(C(OCc4c(F)cccc4F)(C(F)(F)F)C(F)(F)F)cc3)(S(=O)(=O)c3ccc(F)cc3)C2)C1] | 753.2 | 2.16 | B |

TABLE 1-continued

| Ex. No. | Structure | MS (M + 1) | HPLC ret. time (min.) | HPLC method |
|---|---|---|---|---|
| 157 | 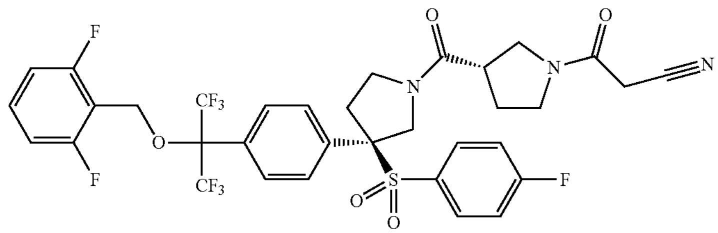 [SMILES: N#CCC(=O)N1CC[C@H](C(=O)N2CC[C@](c3ccc(C(OCc4c(F)cccc4F)(C(F)(F)F)C(F)(F)F)cc3)(S(=O)(=O)c3ccc(F)cc3)C2)C1] | 762.2 | 2.24 | B |
| 158 | 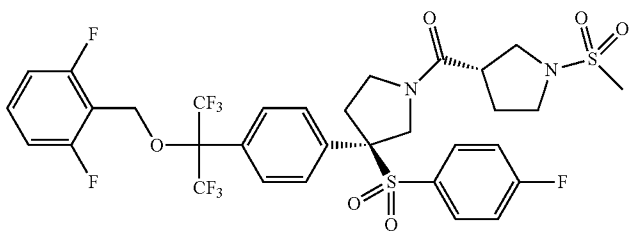 [SMILES: CS(=O)(=O)N1CC[C@H](C(=O)N2CC[C@](c3ccc(C(OCc4c(F)cccc4F)(C(F)(F)F)C(F)(F)F)cc3)(S(=O)(=O)c3ccc(F)cc3)C2)C1] | 773.0 | 2.13 | B |
| 159 | 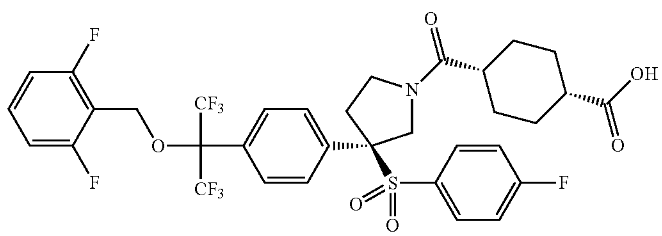 | 752.2 | 2.10 | B |
| 160 | 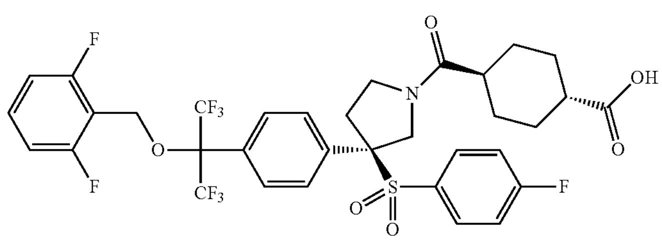 | 752.2 | 2.00 | B |
| 161 | mixture of 2 diastereomers from cis-di-acid | 752.2 | 1.92 | B |
| 162 | 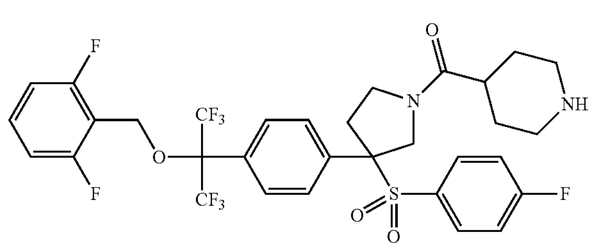 [SMILES: O=C(C1CCNCC1)N1CCC(c2ccc(C(OCc3c(F)cccc3F)(C(F)(F)F)C(F)(F)F)cc2)(S(=O)(=O)c2ccc(F)cc2)C1] | 709.0 | 1.86 | B |

TABLE 1-continued

| Ex. No. | Structure | MS (M + 1) | HPLC ret. time (min.) | HPLC method |
|---|---|---|---|---|
| 163 | 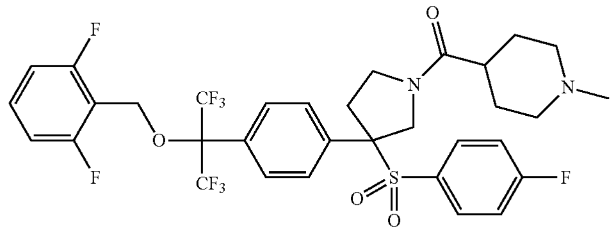 [SMILES: CN1CCC(C(=O)N2CCC(c3ccc(C(OCc4c(F)cccc4F)(C(F)(F)F)C(F)(F)F)cc3)(S(=O)(=O)c3ccc(F)cc3)C2)CC1] | 723.1 | 1.91 | B |
| 164 | 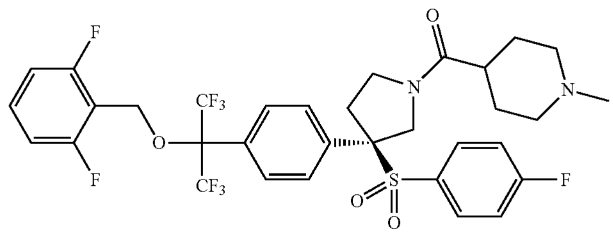 [SMILES: CN1CCC(C(=O)N2CC[C@](c3ccc(C(OCc4c(F)cccc4F)(C(F)(F)F)C(F)(F)F)cc3)(S(=O)(=O)c3ccc(F)cc3)C2)CC1] | 723.3 | 1.95 | B |
| 165 | 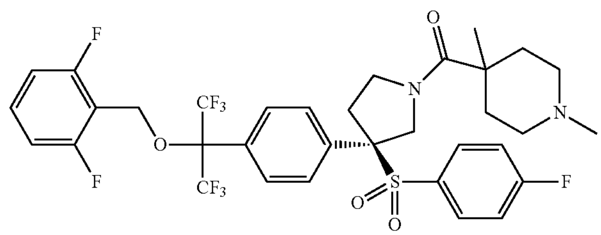 [SMILES: CN1CCC(C)(C(=O)N2CC[C@](c3ccc(C(OCc4c(F)cccc4F)(C(F)(F)F)C(F)(F)F)cc3)(S(=O)(=O)c3ccc(F)cc3)C2)CC1] | 737.3 | 1.96 | B |
| 166 | 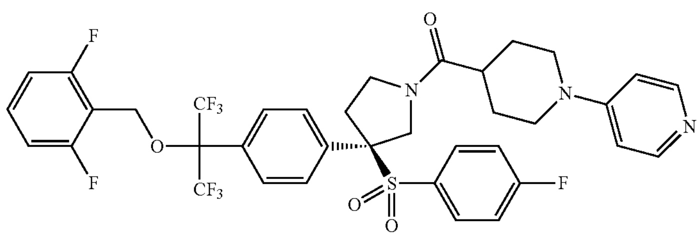 [SMILES: O=C(C1CCN(c2ccncc2)CC1)N1CC[C@](c2ccc(C(OCc3c(F)cccc3F)(C(F)(F)F)C(F)(F)F)cc2)(S(=O)(=O)c2ccc(F)cc2)C1] | 786.3 | 2.05 | B |
| 167 | 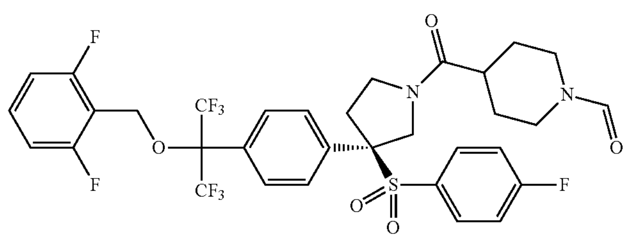 [SMILES: O=CN1CCC(C(=O)N2CC[C@](c3ccc(C(OCc4c(F)cccc4F)(C(F)(F)F)C(F)(F)F)cc3)(S(=O)(=O)c3ccc(F)cc3)C2)CC1] | 737.3 | 2.14 | B |
| 168 | 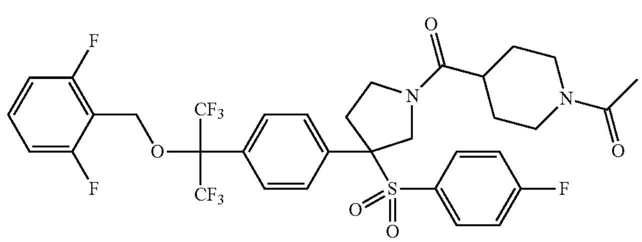 [SMILES: CC(=O)N1CCC(C(=O)N2CCC(c3ccc(C(OCc4c(F)cccc4F)(C(F)(F)F)C(F)(F)F)cc3)(S(=O)(=O)c3ccc(F)cc3)C2)CC1] | 751.1 | 2.001 | B |

TABLE 1-continued

| Ex. No. | Structure | MS (M + 1) | HPLC ret. time (min.) | HPLC method |
|---|---|---|---|---|
| 169 | 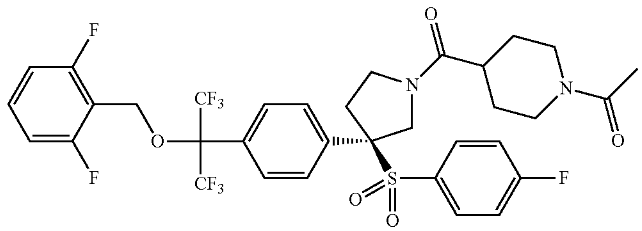 | 751.0 | 4.401 | A |
| 170 | 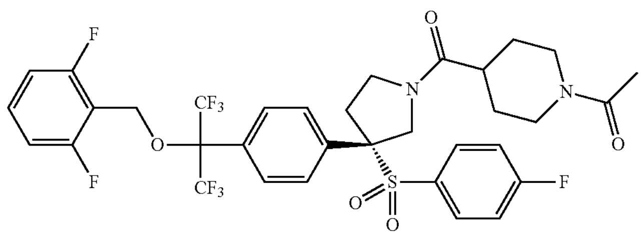 [SMILES: CC(=O)N1CCC(C(=O)N2CC[C@@](c3ccc(C(OCc4c(F)cccc4F)(C(F)(F)F)C(F)(F)F)cc3)(S(=O)(=O)c3ccc(F)cc3)C2)CC1] | 751.0 | 4.386 | A |
| 171 | 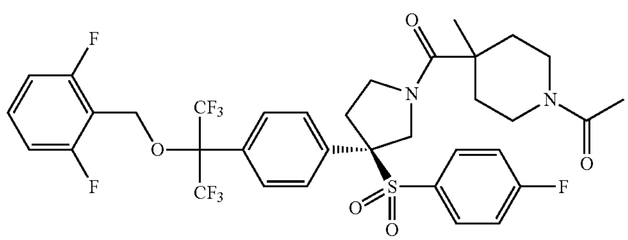 [SMILES: CC(=O)N1CCC(C)(C(=O)N2CC[C@](c3ccc(C(OCc4c(F)cccc4F)(C(F)(F)F)C(F)(F)F)cc3)(S(=O)(=O)c3ccc(F)cc3)C2)CC1] | 765.4 | 2.15 | B |
| 172 | 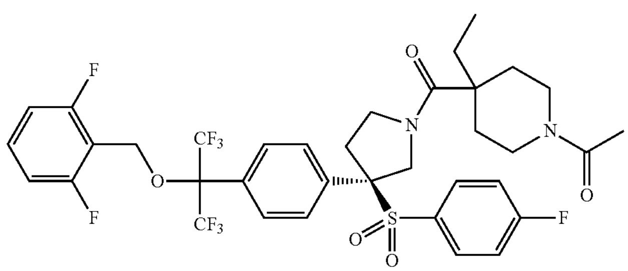 [SMILES: CCC1(C(=O)N2CC[C@](c3ccc(C(OCc4c(F)cccc4F)(C(F)(F)F)C(F)(F)F)cc3)(S(=O)(=O)c3ccc(F)cc3)C2)CCN(C(C)=O)CC1] | 779.3 | 2.30 | B |
| 173 | 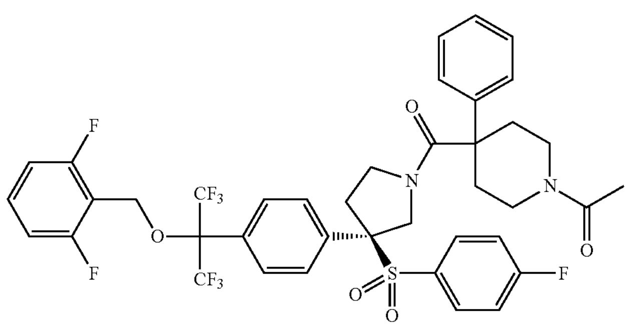 [SMILES: CC(=O)N1CCC(C(=O)N2CC[C@](c3ccc(C(OCc4c(F)cccc4F)(C(F)(F)F)C(F)(F)F)cc3)(S(=O)(=O)c3ccc(F)cc3)C2)(c2ccccc2)CC1] | 827.3 | 2.40 | B |
| 174 | 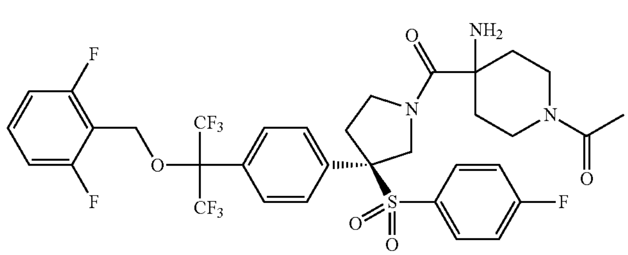 [SMILES: CC(=O)N1CCC(N)(C(=O)N2CC[C@](c3ccc(C(OCc4c(F)cccc4F)(C(F)(F)F)C(F)(F)F)cc3)(S(=O)(=O)c3ccc(F)cc3)C2)CC1] | 766.5 | 1.90 | B |

TABLE 1-continued

| Ex. No. | Structure | MS (M + 1) | HPLC ret. time (min.) | HPLC method |
|---|---|---|---|---|
| 175 | 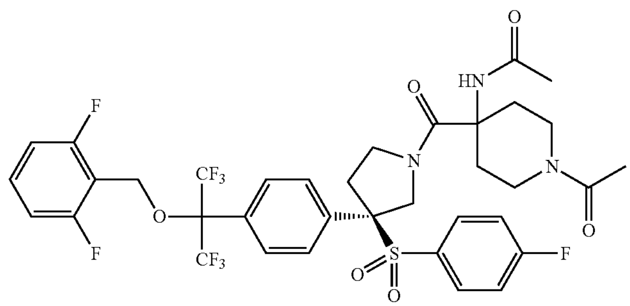 [SMILES: CC(=O)NC1(C(=O)N2CC[C@](c3ccc(C(OCc4c(F)cccc4F)(C(F)(F)F)C(F)(F)F)cc3)(S(=O)(=O)c3ccc(F)cc3)C2)CCN(C(C)=O)CC1] | 808.5 | 2.02 | B |
| 176 | 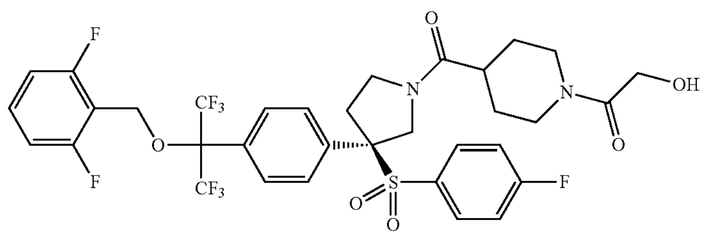 [SMILES: O=C(CO)N1CCC(C(=O)N2CC[C@](c3ccc(C(OCc4c(F)cccc4F)(C(F)(F)F)C(F)(F)F)cc3)(S(=O)(=O)c3ccc(F)cc3)C2)CC1] | 767.3 | 2.16 | B |
| 177 | 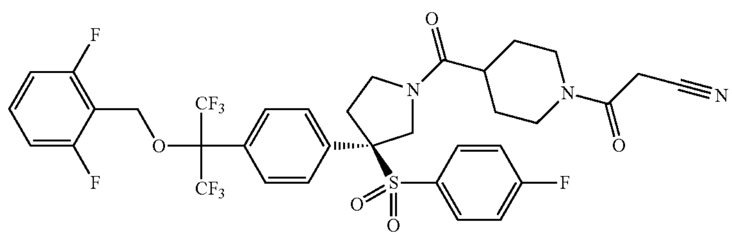 [SMILES: N#CCC(=O)N1CCC(C(=O)N2CC[C@](c3ccc(C(OCc4c(F)cccc4F)(C(F)(F)F)C(F)(F)F)cc3)(S(=O)(=O)c3ccc(F)cc3)C2)CC1] | 776.0 | 2.10 | B |
| 178 | 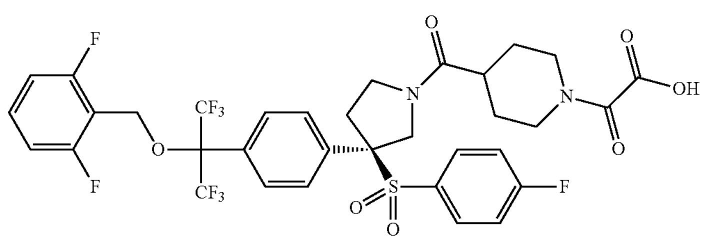 [SMILES: O=C(O)C(=O)N1CCC(C(=O)N2CC[C@](c3ccc(C(OCc4c(F)cccc4F)(C(F)(F)F)C(F)(F)F)cc3)(S(=O)(=O)c3ccc(F)cc3)C2)CC1] | 798.2 (M + 18) | 1.76 | B |
| 179 | 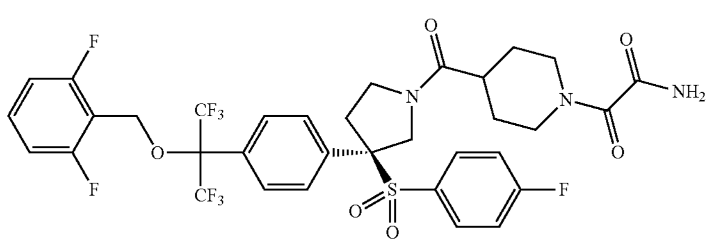 [SMILES: NC(=O)C(=O)N1CCC(C(=O)N2CC[C@](c3ccc(C(OCc4c(F)cccc4F)(C(F)(F)F)C(F)(F)F)cc3)(S(=O)(=O)c3ccc(F)cc3)C2)CC1] | 780.3 | 1.99 | B |
| 180 | 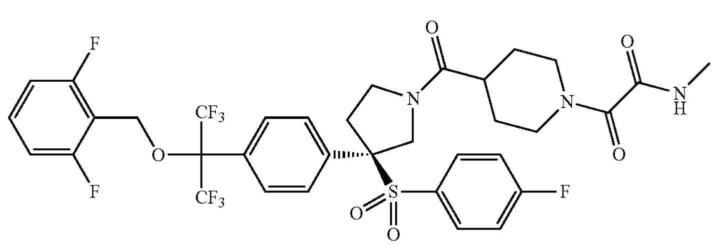 [SMILES: CNC(=O)C(=O)N1CCC(C(=O)N2CC[C@](c3ccc(C(OCc4c(F)cccc4F)(C(F)(F)F)C(F)(F)F)cc3)(S(=O)(=O)c3ccc(F)cc3)C2)CC1] | 794.3 | 2.04 | B |

TABLE 1-continued

| Ex. No. | Structure | MS (M + 1) | HPLC ret. time (min.) | HPLC method |
|---|---|---|---|---|
| 181 | 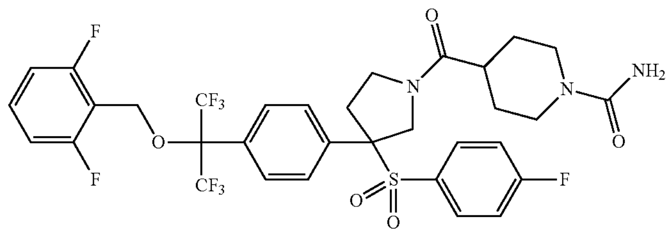 [SMILES: NC(=O)N1CCC(C(=O)N2CCC(c3ccc(C(OCc4c(F)cccc4F)(C(F)(F)F)C(F)(F)F)cc3)(S(=O)(=O)c3ccc(F)cc3)C2)CC1] | 752.0 | 2.078 | B |
| 182 | 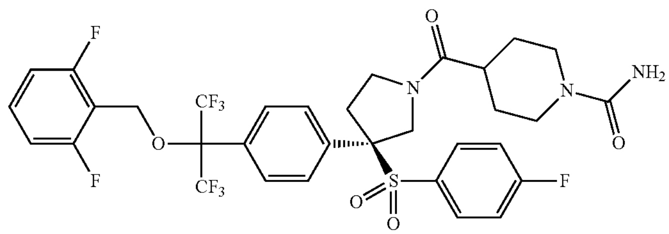 [SMILES: NC(=O)N1CCC(C(=O)N2CC[C@](c3ccc(C(OCc4c(F)cccc4F)(C(F)(F)F)C(F)(F)F)cc3)(S(=O)(=O)c3ccc(F)cc3)C2)CC1] | 752.0 | 1.97 | B |
| 183 | 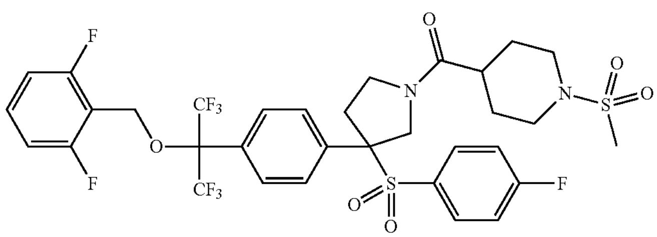 [SMILES: CS(=O)(=O)N1CCC(C(=O)N2CCC(c3ccc(C(OCc4c(F)cccc4F)(C(F)(F)F)C(F)(F)F)cc3)(S(=O)(=O)c3ccc(F)cc3)C2)CC1] | 787.0 | 2.14 | B |
| 184 | 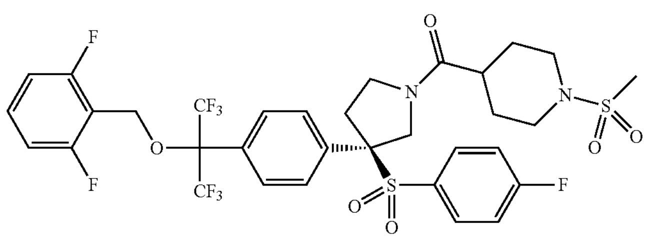 [SMILES: CS(=O)(=O)N1CCC(C(=O)N2CC[C@](c3ccc(C(OCc4c(F)cccc4F)(C(F)(F)F)C(F)(F)F)cc3)(S(=O)(=O)c3ccc(F)cc3)C2)CC1] | 787.0 | 2.15 | B |
| 185 | (mixture of two diastereomers) | 737.3 | 2.13 | B |
| 186 | 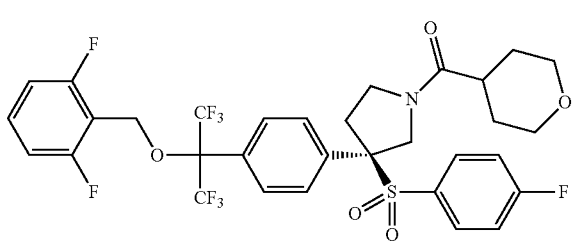 | 710.0 | 2.16 | B |

TABLE 1-continued

| Ex. No. | Structure | MS (M + 1) | HPLC ret. time (min.) | HPLC method |
|---|---|---|---|---|
| 187 | 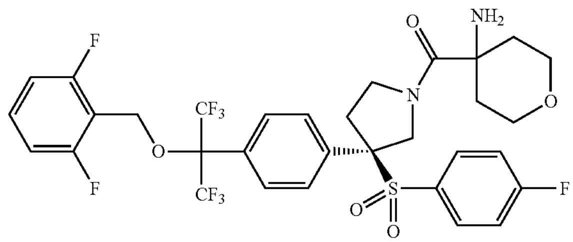 [SMILES: NC1(C(=O)N2CC[C@](c3ccc(C(OCc4c(F)cccc4F)(C(F)(F)F)C(F)(F)F)cc3)(S(=O)(=O)c3ccc(F)cc3)C2)CCOCC1] | 725.4 | 1.96 | B |
| 188 | 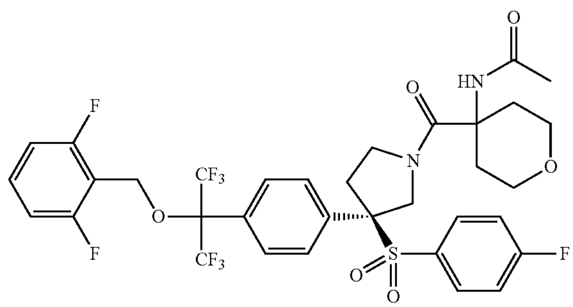 [SMILES: CC(=O)NC1(C(=O)N2CC[C@](c3ccc(C(OCc4c(F)cccc4F)(C(F)(F)F)C(F)(F)F)cc3)(S(=O)(=O)c3ccc(F)cc3)C2)CCOCC1] | 767.5 | 2.07 | B |
| 189 | 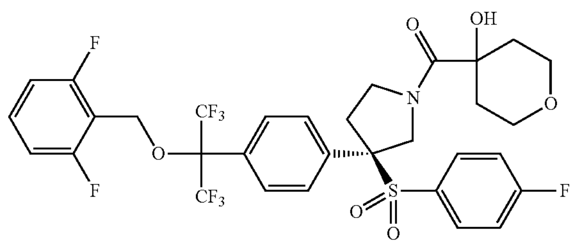 | 726.2 | 2.09 | B |
| 190 | 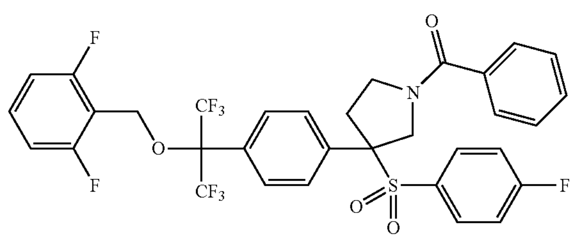 [SMILES: O=C(c1ccccc1)N1CCC(c2ccc(C(OCc3c(F)cccc3F)(C(F)(F)F)C(F)(F)F)cc2)(S(=O)(=O)c2ccc(F)cc2)C1] | 702.0 | 2.43 | B |
| 191 | 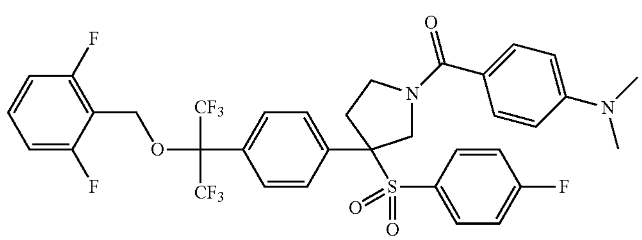 [SMILES: CN(C)c1ccc(C(=O)N2CCC(c3ccc(C(OCc4c(F)cccc4F)(C(F)(F)F)C(F)(F)F)cc3)(S(=O)(=O)c3ccc(F)cc3)C2)cc1] | 745.0 | 2.50 | B |
| 192 | 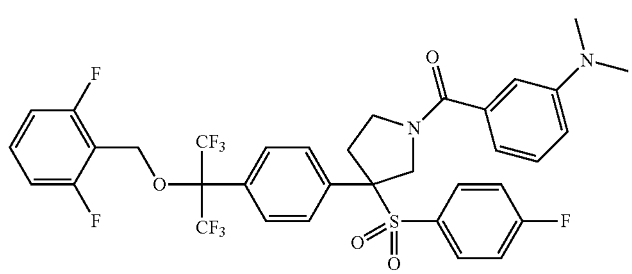 [SMILES: CN(C)c1cccc(C(=O)N2CCC(c3ccc(C(OCc4c(F)cccc4F)(C(F)(F)F)C(F)(F)F)cc3)(S(=O)(=O)c3ccc(F)cc3)C2)c1] | 745.1 | 2.51 | B |

TABLE 1-continued

| Ex. No. | Structure | MS (M + 1) | HPLC ret. time (min.) | HPLC method |
|---|---|---|---|---|
| 193 | 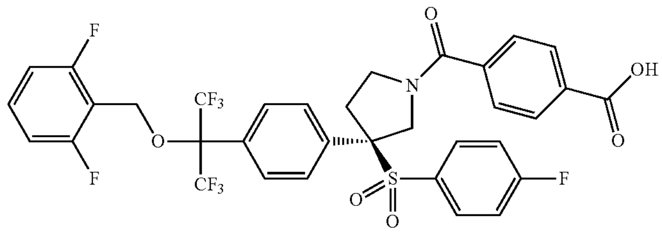 [SMILES: O=C(O)c1ccc(C(=O)N2CC[C@](c3ccc(C(OCc4c(F)cccc4F)(C(F)(F)F)C(F)(F)F)cc3)(S(=O)(=O)c3ccc(F)cc3)C2)cc1] | 746.2 | 1.95 | B |
| 194 | 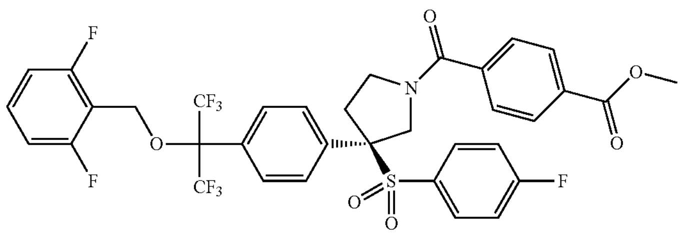 [SMILES: COC(=O)c1ccc(C(=O)N2CC[C@](c3ccc(C(OCc4c(F)cccc4F)(C(F)(F)F)C(F)(F)F)cc3)(S(=O)(=O)c3ccc(F)cc3)C2)cc1] | 760.2 | 2.47 | B |
| 195 | 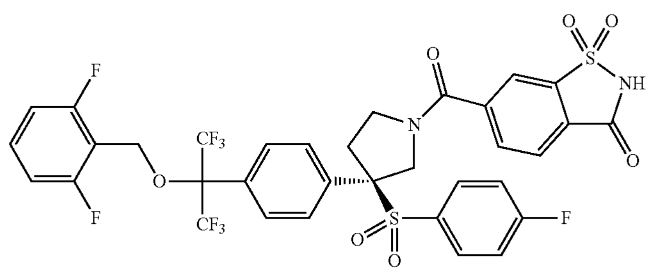 [SMILES: O=C1NS(=O)(=O)c2cc(C(=O)N3CC[C@](c4ccc(C(OCc5c(F)cccc5F)(C(F)(F)F)C(F)(F)F)cc4)(S(=O)(=O)c4ccc(F)cc4)C3)ccc21] | 824.0 (M + 18) | 1.80 | B |
| 196 | 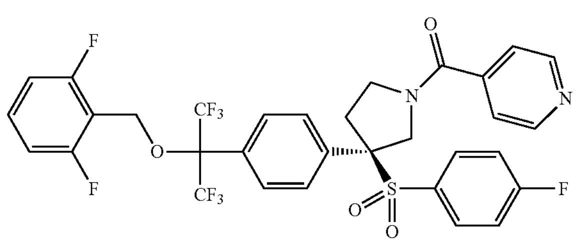 [SMILES: O=C(c1ccncc1)N1CC[C@](c2ccc(C(OCc3c(F)cccc3F)(C(F)(F)F)C(F)(F)F)cc2)(S(=O)(=O)c2ccc(F)cc2)C1] | 703.1 | 2.13 | B |
| 197 | 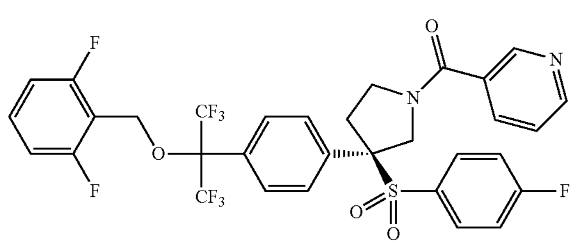 [SMILES: O=C(c1cccnc1)N1CC[C@](c2ccc(C(OCc3c(F)cccc3F)(C(F)(F)F)C(F)(F)F)cc2)(S(=O)(=O)c2ccc(F)cc2)C1] | 703.2 | 2.13 | B |
| 198 | 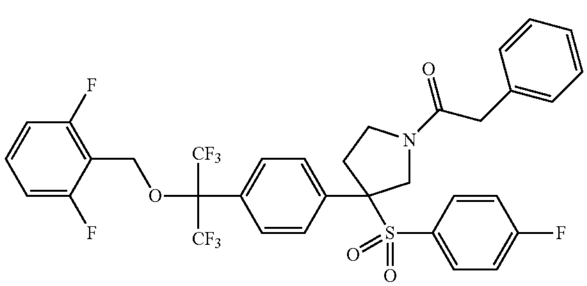 [SMILES: O=C(Cc1ccccc1)N1CCC(c2ccc(C(OCc3c(F)cccc3F)(C(F)(F)F)C(F)(F)F)cc2)(S(=O)(=O)c2ccc(F)cc2)C1] | 715.8 | 2.40 | B |

TABLE 1-continued

| Ex. No. | Structure | MS (M + 1) | HPLC ret. time (min.) | HPLC method |
|---|---|---|---|---|
| 199 | 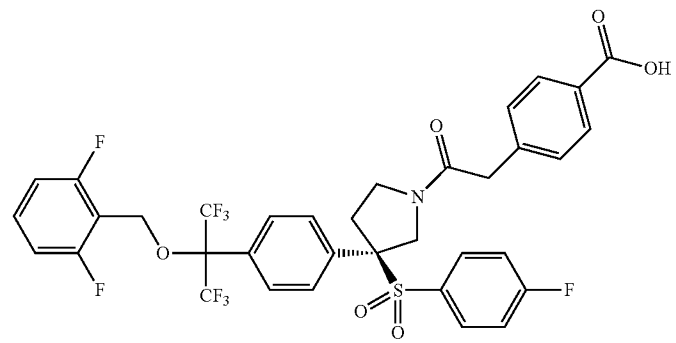 [SMILES: O=C(O)c1ccc(CC(=O)N2CC[C@](c3ccc(C(OCc4c(F)cccc4F)(C(F)(F)F)C(F)(F)F)cc3)(S(=O)(=O)c3ccc(F)cc3)C2)cc1] | 760.2 | 1.90 | B |
| 200 | 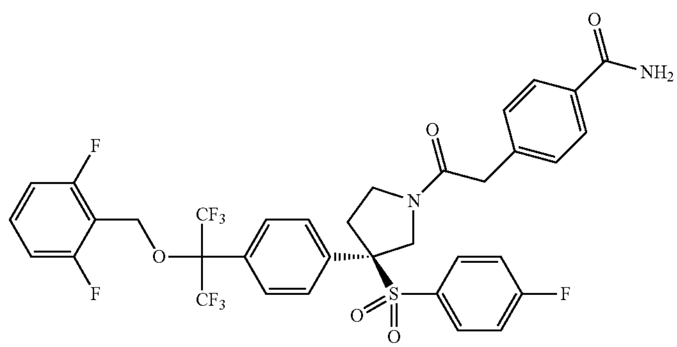 [SMILES: NC(=O)c1ccc(CC(=O)N2CC[C@](c3ccc(C(OCc4c(F)cccc4F)(C(F)(F)F)C(F)(F)F)cc3)(S(=O)(=O)c3ccc(F)cc3)C2)cc1] | 759.2 | 2.13 | B |
| 201 | 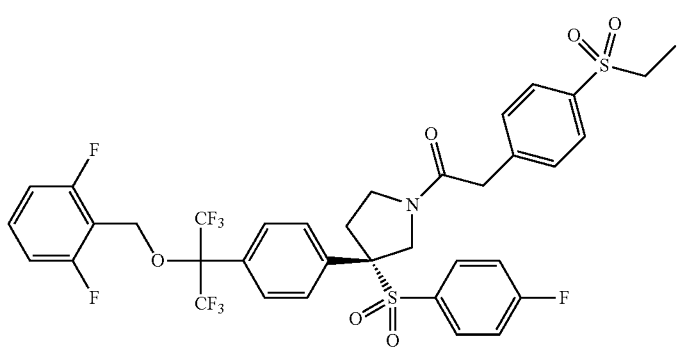 [SMILES: CCS(=O)(=O)c1ccc(CC(=O)N2CC[C@@](c3ccc(C(OCc4c(F)cccc4F)(C(F)(F)F)C(F)(F)F)cc3)(S(=O)(=O)c3ccc(F)cc3)C2)cc1] | 808.1 | 2.24 | B |
| 202 | 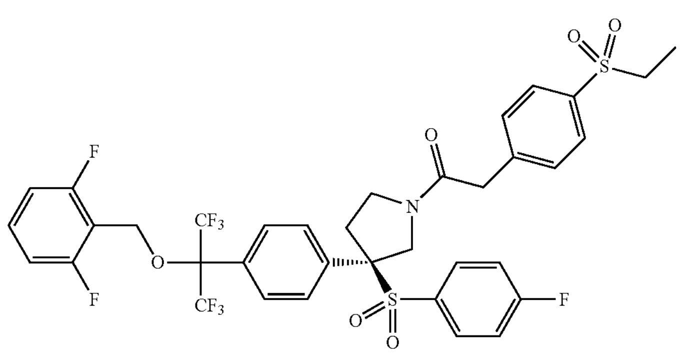 [SMILES: CCS(=O)(=O)c1ccc(CC(=O)N2CC[C@](c3ccc(C(OCc4c(F)cccc4F)(C(F)(F)F)C(F)(F)F)cc3)(S(=O)(=O)c3ccc(F)cc3)C2)cc1] | 808.1 | 2.24 | B |

TABLE 1-continued

| Ex. No. | Structure | MS (M + 1) | HPLC ret. time (min.) | HPLC method |
|---|---|---|---|---|
| 203 | 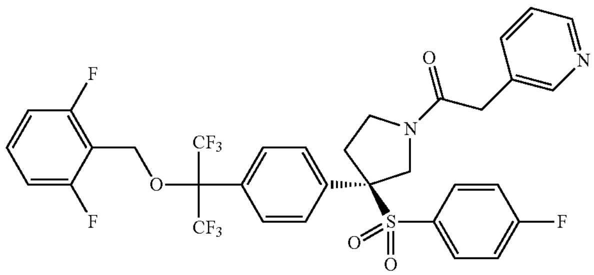 [SMILES: O=C(Cc1cccnc1)N1CC[C@](c2ccc(C(OCc3c(F)cccc3F)(C(F)(F)F)C(F)(F)F)cc2)(S(=O)(=O)c2ccc(F)cc2)C1] | 717.1 | 2.11 | B |
| 204 | 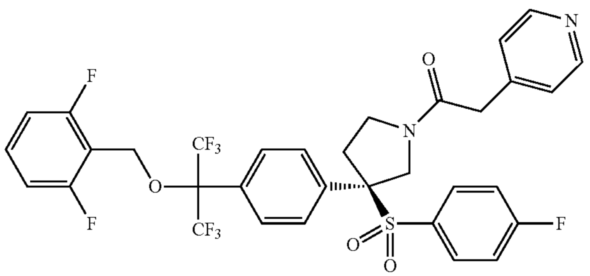 [SMILES: O=C(Cc1ccncc1)N1CC[C@](c2ccc(C(OCc3c(F)cccc3F)(C(F)(F)F)C(F)(F)F)cc2)(S(=O)(=O)c2ccc(F)cc2)C1] | 717.2 | 2.10 | B |
| 205 | 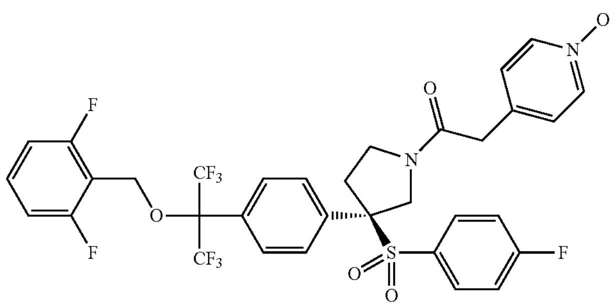 | 733.2 | 2.01 | B |
| 206 | 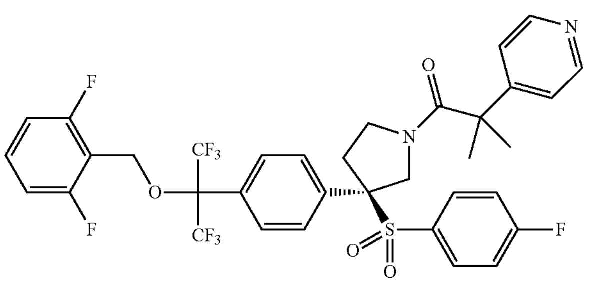 [SMILES: CC(C)(C(=O)N1CC[C@](c2ccc(C(OCc3c(F)cccc3F)(C(F)(F)F)C(F)(F)F)cc2)(S(=O)(=O)c2ccc(F)cc2)C1)c1ccncc1] | 745.2 | 2.30 | B |
| 207 | 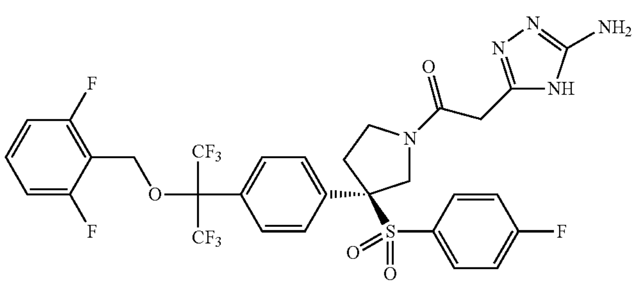 [SMILES: Nc1nnc(CC(=O)N2CC[C@](c3ccc(C(OCc4c(F)cccc4F)(C(F)(F)F)C(F)(F)F)cc3)(S(=O)(=O)c3ccc(F)cc3)C2)[nH]1] | 722.2 | 1.95 | B |

TABLE 1-continued

| Ex. No. | Structure | MS (M + 1) | HPLC ret. time (min.) | HPLC method |
|---|---|---|---|---|
| 208 | 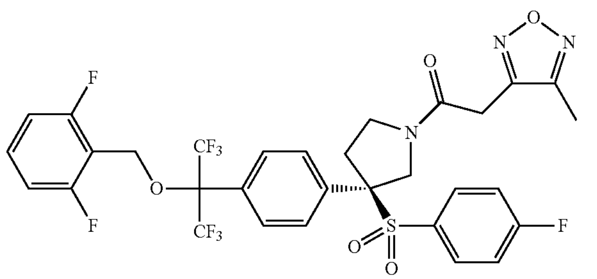 [SMILES: Cc1nonc1CC(=O)N1CC[C@](c2ccc(C(OCc3c(F)cccc3F)(C(F)(F)F)C(F)(F)F)cc2)(S(=O)(=O)c2ccc(F)cc2)C1] | 722.1 | 2.37 | B |
| 209 | 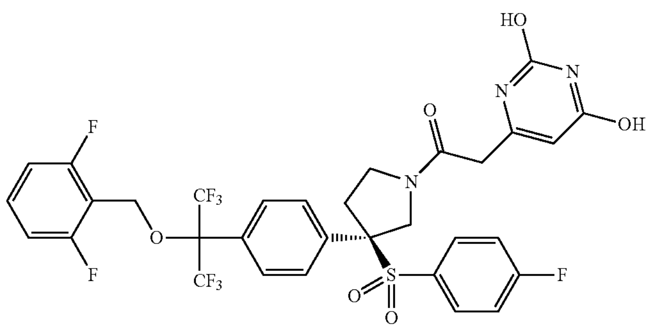 [SMILES: O=C(Cc1cc(O)nc(O)n1)N1CC[C@](c2ccc(C(OCc3c(F)cccc3F)(C(F)(F)F)C(F)(F)F)cc2)(S(=O)(=O)c2ccc(F)cc2)C1] | 750.2 | 2.03 | B |
| 210 | 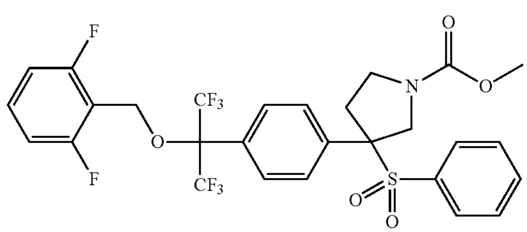 [SMILES: COC(=O)N1CCC(c2ccc(C(OCc3c(F)cccc3F)(C(F)(F)F)C(F)(F)F)cc2)(S(=O)(=O)c2ccccc2)C1] | 638.1 | 2.33 | C |
| 211 | 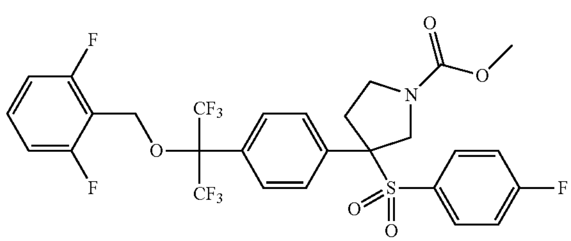 [SMILES: COC(=O)N1CCC(c2ccc(C(OCc3c(F)cccc3F)(C(F)(F)F)C(F)(F)F)cc2)(S(=O)(=O)c2ccc(F)cc2)C1] | 655.8 | 2.34 | B |
| 212 | 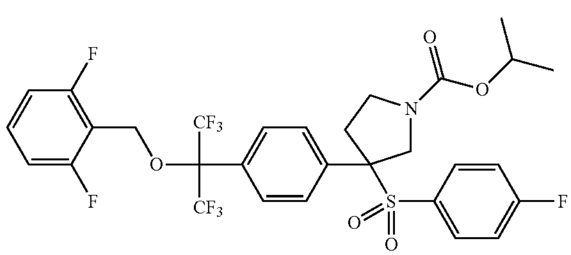 [SMILES: CC(C)OC(=O)N1CCC(c2ccc(C(OCc3c(F)cccc3F)(C(F)(F)F)C(F)(F)F)cc2)(S(=O)(=O)c2ccc(F)cc2)C1] | 683.8 | 2.52 | C |
| 213 | 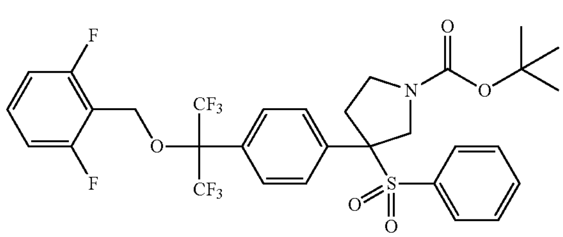 | 697.3 (M + 18) | 4.723 | A |

TABLE 1-continued

| Ex. No. | Structure | MS (M + 1) | HPLC ret. time (min.) | HPLC method |
|---|---|---|---|---|
| 214 | 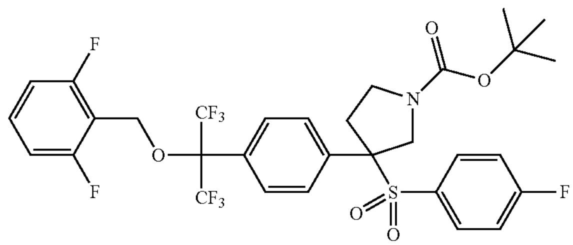 [SMILES: CC(C)(C)OC(=O)N1CCC(c2ccc(C(OCc3c(F)cccc3F)(C(F)(F)F)C(F)(F)F)cc2)(S(=O)(=O)c2ccc(F)cc2)C1] | 642.2 (M − 56 + 1) | 4.753 | A |
| 215 | 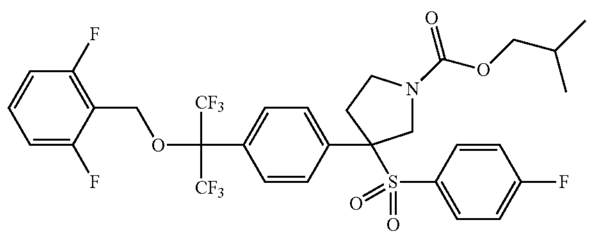 [SMILES: CC(C)COC(=O)N1CCC(c2ccc(C(OCc3c(F)cccc3F)(C(F)(F)F)C(F)(F)F)cc2)(S(=O)(=O)c2ccc(F)cc2)C1] | 697.8 | 2.58 | B |
| 216 | 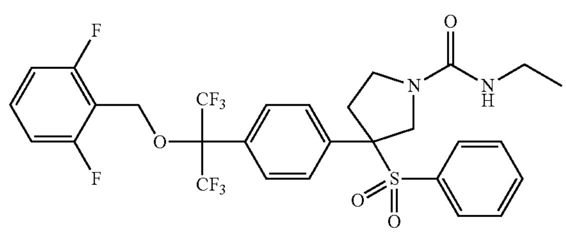 [SMILES: CCNC(=O)N1CCC(c2ccc(C(OCc3c(F)cccc3F)(C(F)(F)F)C(F)(F)F)cc2)(S(=O)(=O)c2ccccc2)C1] | 651.1 | 2.17 | C |
| 217 | 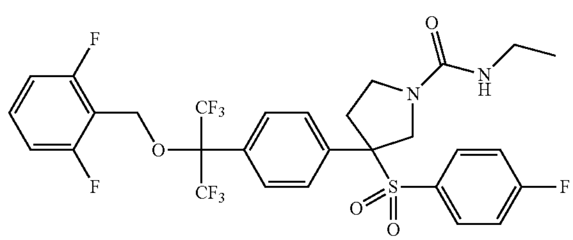 [SMILES: CCNC(=O)N1CCC(c2ccc(C(OCc3c(F)cccc3F)(C(F)(F)F)C(F)(F)F)cc2)(S(=O)(=O)c2ccc(F)cc2)C1] | 668.8 | 2.16 | B |
| 218 | 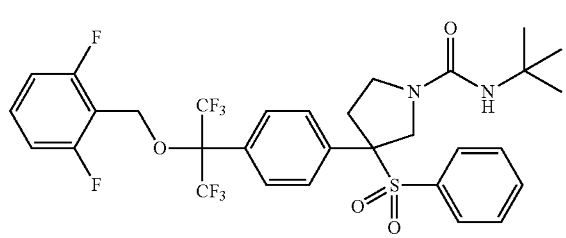 [SMILES: CC(C)(C)NC(=O)N1CCC(c2ccc(C(OCc3c(F)cccc3F)(C(F)(F)F)C(F)(F)F)cc2)(S(=O)(=O)c2ccccc2)C1] | 679.1 | 2.38 | C |
| 219 | 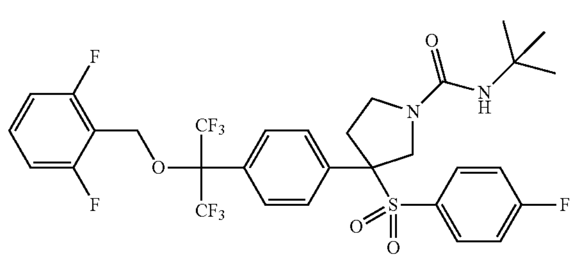 [SMILES: CC(C)(C)NC(=O)N1CCC(c2ccc(C(OCc3c(F)cccc3F)(C(F)(F)F)C(F)(F)F)cc2)(S(=O)(=O)c2ccc(F)cc2)C1] | 696.9 | 2.38 | B |

TABLE 1-continued
| Ex. No. | Structure | MS (M + 1) | HPLC ret. time (min.) | HPLC method |
|---|---|---|---|---|
| 220 | 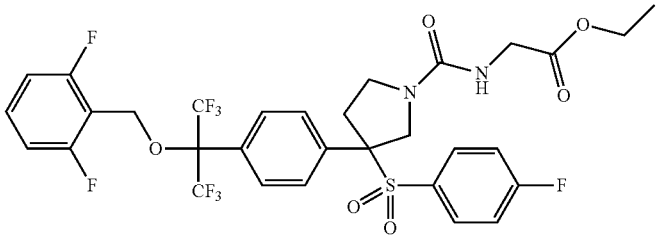 [SMILES: CCOC(=O)CNC(=O)N1CCC(c2ccc(C(OCc3c(F)cccc3F)(C(F)(F)F)C(F)(F)F)cc2)(S(=O)(=O)c2ccc(F)cc2)C1] | 727.0 | 2.25 | C |
| 221 | 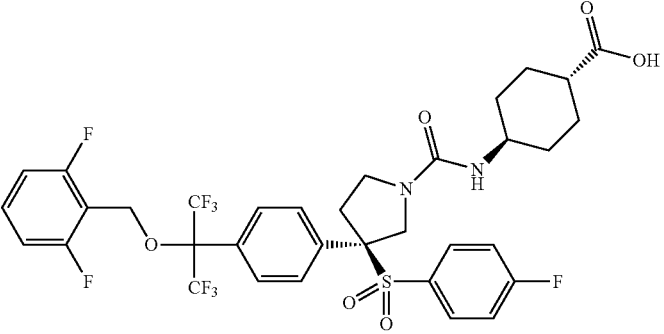 [SMILES: O=C(N[C@H]1CC[C@H](C(=O)O)CC1)N1CC[C@](c2ccc(C(OCc3c(F)cccc3F)(C(F)(F)F)C(F)(F)F)cc2)(S(=O)(=O)c2ccc(F)cc2)C1] | 767.1 | 1.89 | B |
| 222 | 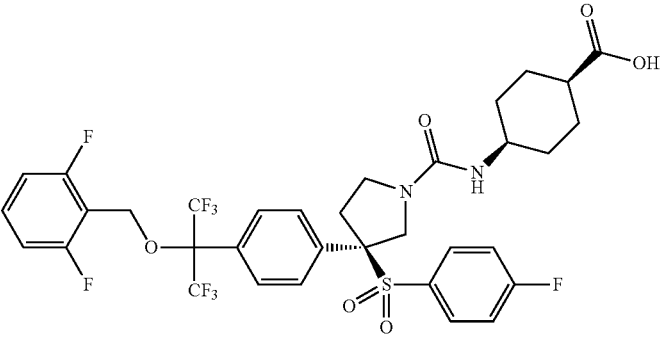 [SMILES: O=C(N[C@H]1CC[C@@H](C(=O)O)CC1)N1CC[C@](c2ccc(C(OCc3c(F)cccc3F)(C(F)(F)F)C(F)(F)F)cc2)(S(=O)(=O)c2ccc(F)cc2)C1] | 767.2 | 1.94 | B |
| 223 | 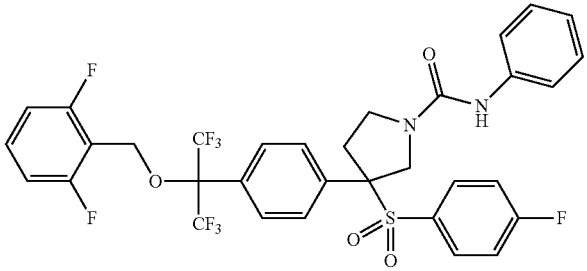 [SMILES: O=C(Nc1ccccc1)N1CCC(c2ccc(C(OCc3c(F)cccc3F)(C(F)(F)F)C(F)(F)F)cc2)(S(=O)(=O)c2ccc(F)cc2)C1] | 716.8 | 2.36 | B |
| 224 | 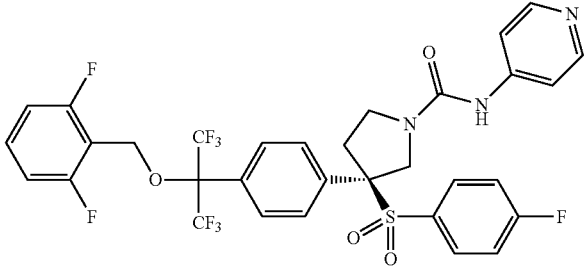 [SMILES: O=C(Nc1ccncc1)N1CC[C@](c2ccc(C(OCc3c(F)cccc3F)(C(F)(F)F)C(F)(F)F)cc2)(S(=O)(=O)c2ccc(F)cc2)C1] | 718.2 | 2.20 | B |

TABLE 1-continued

| Ex. No. | Structure | MS (M + 1) | HPLC ret. time (min.) | HPLC method |
|---|---|---|---|---|
| 225 | 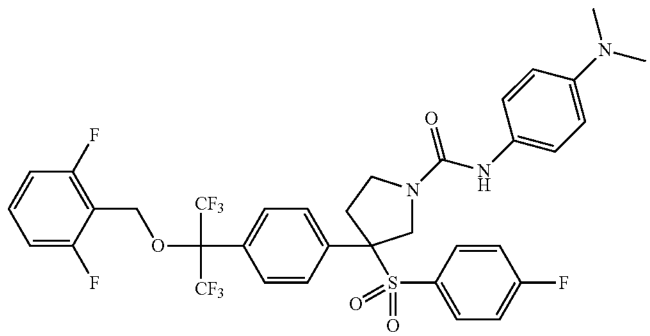 [SMILES: CN(C)c1ccc(NC(=O)N2CCC(c3ccc(C(OCc4c(F)cccc4F)(C(F)(F)F)C(F)(F)F)cc3)(S(=O)(=O)c3ccc(F)cc3)C2)cc1] | 760.0 | 2.02 | C |
| 226 | 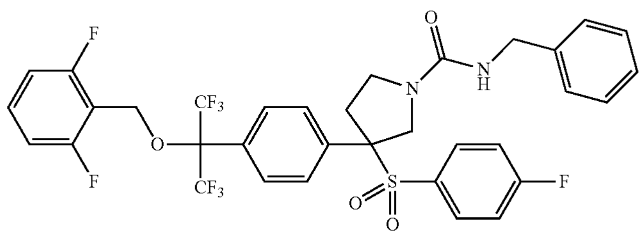 [SMILES: O=C(NCc1ccccc1)N1CCC(c2ccc(C(OCc3c(F)cccc3F)(C(F)(F)F)C(F)(F)F)cc2)(S(=O)(=O)c2ccc(F)cc2)C1] | 731.0 | 2.39 | B |
| 227 | 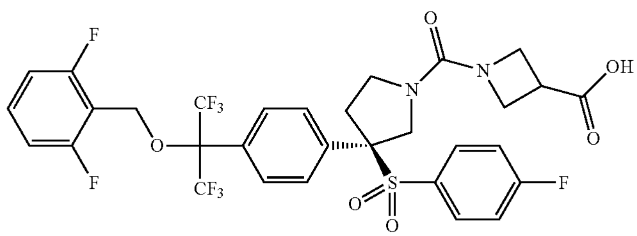 [SMILES: O=C(O)C1CN(C(=O)N2CC[C@](c3ccc(C(OCc4c(F)cccc4F)(C(F)(F)F)C(F)(F)F)cc3)(S(=O)(=O)c3ccc(F)cc3)C2)C1] | 725.1 | 1.755 | B |
| 228 | (mixture of two diastereomers) | 739.2 | 1.77 | B |
| 229 | 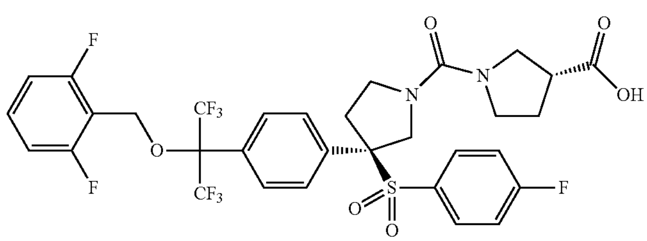 [SMILES: O=C(O)[C@@H]1CCN(C(=O)N2CC[C@](c3ccc(C(OCc4c(F)cccc4F)(C(F)(F)F)C(F)(F)F)cc3)(S(=O)(=O)c3ccc(F)cc3)C2)C1] | 739.1 | 1.75 | B |
| 230 | 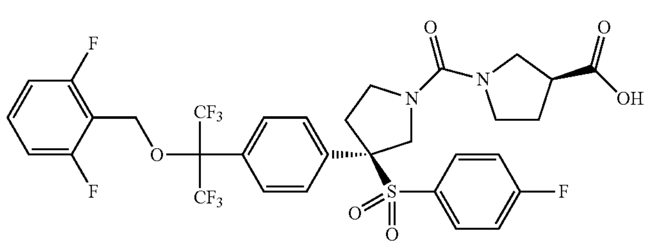 [SMILES: O=C(O)[C@H]1CCN(C(=O)N2CC[C@](c3ccc(C(OCc4c(F)cccc4F)(C(F)(F)F)C(F)(F)F)cc3)(S(=O)(=O)c3ccc(F)cc3)C2)C1] | 739.2 | 1.76 | B |

TABLE 1-continued

| Ex. No. | Structure | MS (M + 1) | HPLC ret. time (min.) | HPLC method |
|---|---|---|---|---|
| 231 | 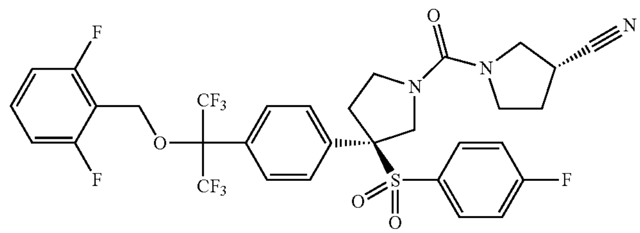 [SMILES: N#C[C@@H]1CCN(C(=O)N2CC[C@](c3ccc(C(OCc4c(F)cccc4F)(C(F)(F)F)C(F)(F)F)cc3)(S(=O)(=O)c3ccc(F)cc3)C2)C1] | 720.2 | 2.28 | B |
| 232 | 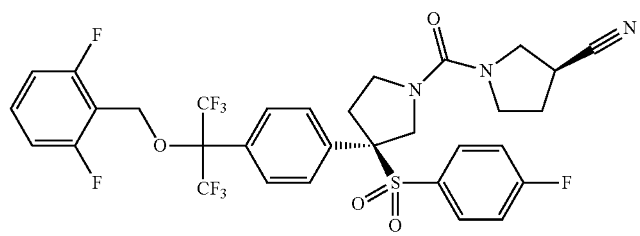 [SMILES: N#C[C@H]1CCN(C(=O)N2CC[C@](c3ccc(C(OCc4c(F)cccc4F)(C(F)(F)F)C(F)(F)F)cc3)(S(=O)(=O)c3ccc(F)cc3)C2)C1] | 720.2 | 2.28 | B |
| 233 | 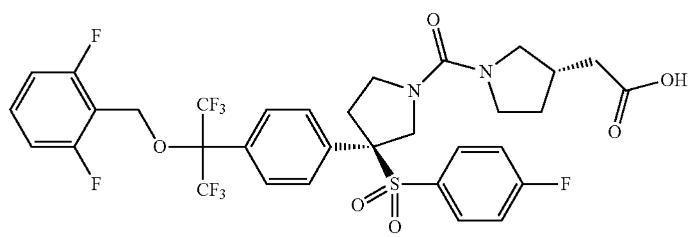 [SMILES: O=C(O)C[C@@H]1CCN(C(=O)N2CC[C@](c3ccc(C(OCc4c(F)cccc4F)(C(F)(F)F)C(F)(F)F)cc3)(S(=O)(=O)c3ccc(F)cc3)C2)C1] | 753.2 | 1.98 | B |
| 234 | 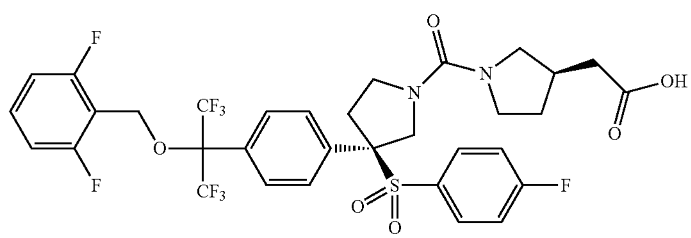 [SMILES: O=C(O)C[C@H]1CCN(C(=O)N2CC[C@](c3ccc(C(OCc4c(F)cccc4F)(C(F)(F)F)C(F)(F)F)cc3)(S(=O)(=O)c3ccc(F)cc3)C2)C1] | 753.2 | 1.92 | B |
| 235 | (mixture of two diastereomers) | 772.3 | 2.20 | B |
| 236 | (mixture of two diastereomers) | 772.3 | 1.98 | B |

TABLE 1-continued
| Ex. No. | Structure | MS (M + 1) | HPLC ret. time (min.) | HPLC method |
|---|---|---|---|---|
| 237 | 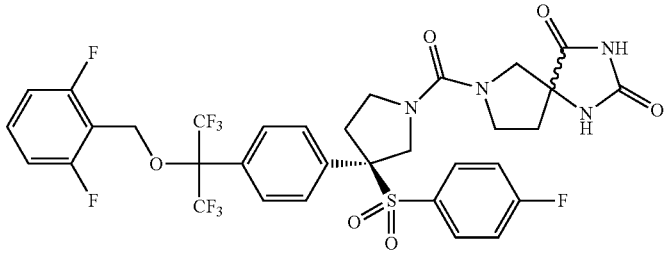<br>(mixture of two diastereomers) | 779.2 | 1.98 | B |
| 238 | 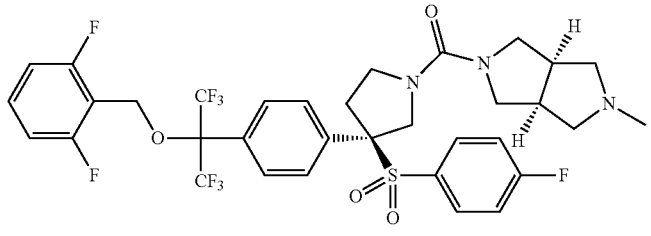 [SMILES: CN1C[C@@H]2CN(C(=O)N3CC[C@](c4ccc(C(OCc5c(F)cccc5F)(C(F)(F)F)C(F)(F)F)cc4)(S(=O)(=O)c4ccc(F)cc4)C3)C[C@@H]2C1] | 750.1 | 2.018 | B |
| 239 | 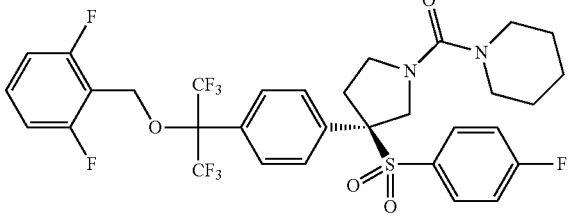 | 709.2 | 2.51 | B |
| 240 | 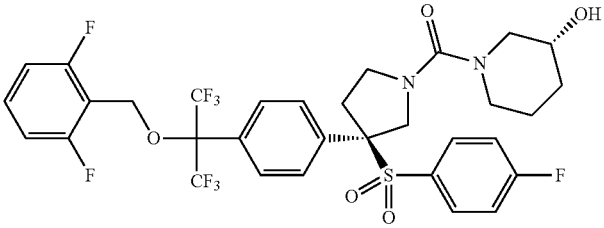 [SMILES: O=C(N1CCC[C@@H](O)C1)N1CC[C@](c2ccc(C(OCc3c(F)cccc3F)(C(F)(F)F)C(F)(F)F)cc2)(S(=O)(=O)c2ccc(F)cc2)C1] | 725.2 | 2.14 | B |
| 241 | 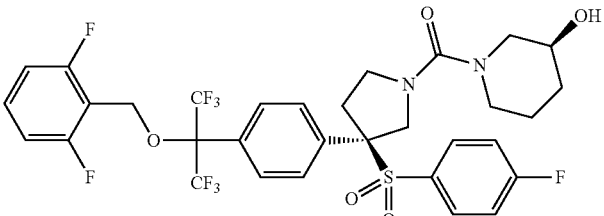 | 725.2 | 2.14 | B |
| 242 | 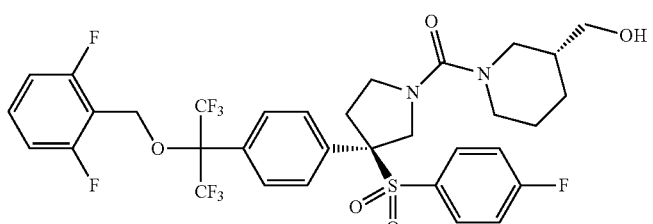 | 739.4 | 2.20 | B |

TABLE 1-continued

| Ex. No. | Structure | MS (M + 1) | HPLC ret. time (min.) | HPLC method |
|---|---|---|---|---|
| 243 | 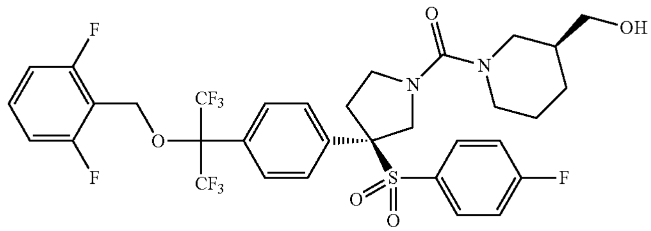 [SMILES: O=C(N1CCC[C@H](CO)C1)N1CC[C@](c2ccc(C(OCc3c(F)cccc3F)(C(F)(F)F)C(F)(F)F)cc2)(S(=O)(=O)c2ccc(F)cc2)C1] | 739.4 | 2.19 | B |
| 244 | (mixture of two diastereomers) | 753.2 | 1.89 | B |
| 245 | 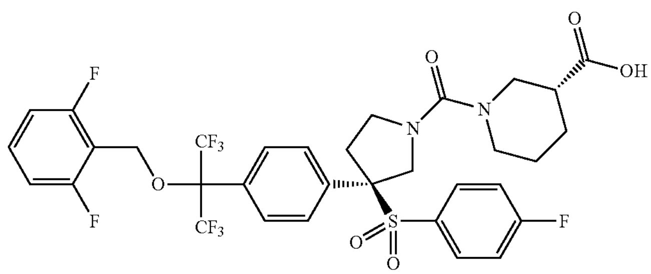 [SMILES: O=C(O)[C@@H]1CCCN(C(=O)N2CC[C@](c3ccc(C(OCc4c(F)cccc4F)(C(F)(F)F)C(F)(F)F)cc3)(S(=O)(=O)c3ccc(F)cc3)C2)C1] | 753.2 | 1.87 | B |
| 246 | 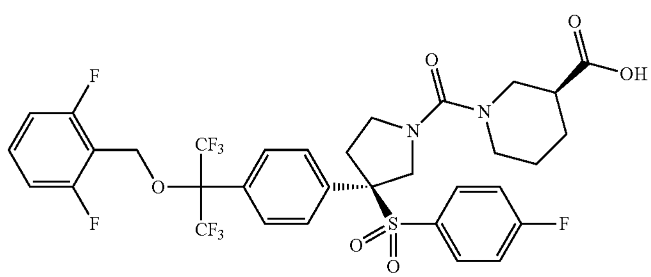 [SMILES: O=C(O)[C@H]1CCCN(C(=O)N2CC[C@](c3ccc(C(OCc4c(F)cccc4F)(C(F)(F)F)C(F)(F)F)cc3)(S(=O)(=O)c3ccc(F)cc3)C2)C1] | 753.2 | 1.81 | B |
| 247 | 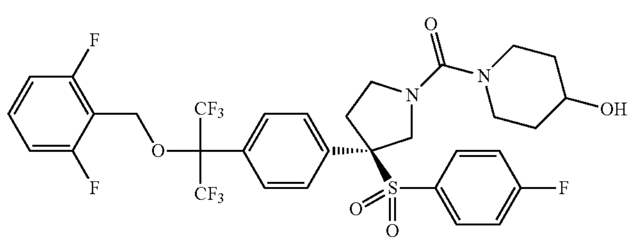 | 725.2 | 2.20 | B |
| 248 | 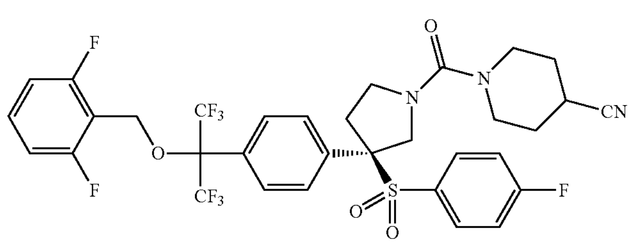 [SMILES: O=C(N1CCC(O)CC1)N1CC[C@](c2ccc(C(OCc3c(F)cccc3F)(C(F)(F)F)C(F)(F)F)cc2)(S(=O)(=O)c2ccc(F)cc2)C1] | 734.3 | 2.32 | B |

TABLE 1-continued

| Ex. No. | Structure | MS (M + 1) | HPLC ret. time (min.) | HPLC method |
|---|---|---|---|---|
| 249 | 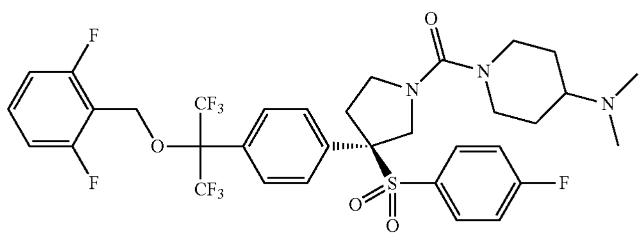 [SMILES: CN(C)C1CCN(C(=O)N2CC[C@](c3ccc(C(OCc4c(F)cccc4F)(C(F)(F)F)C(F)(F)F)cc3)(S(=O)(=O)c3ccc(F)cc3)C2)CC1] | 752.0 | 2.010 | B |
| 250 | 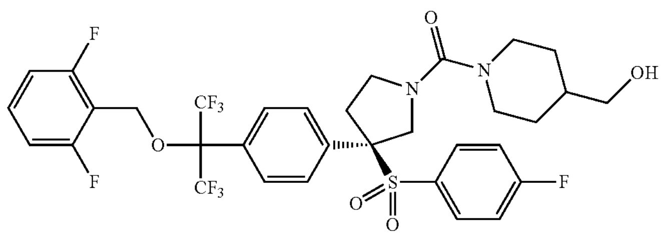 [SMILES: O=C(N1CCC(CO)CC1)N1CC[C@](c2ccc(C(OCc3c(F)cccc3F)(C(F)(F)F)C(F)(F)F)cc2)(S(=O)(=O)c2ccc(F)cc2)C1] | 739.2 | 2.25 | B |
| 251 | 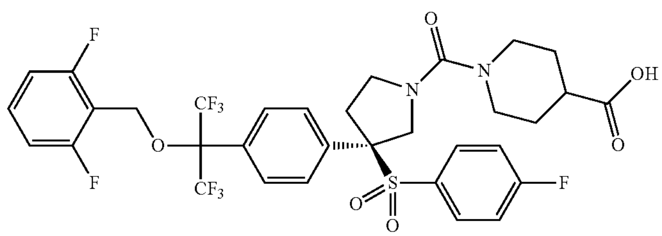 | 753.2 | 1.95 | B |
| 252 | 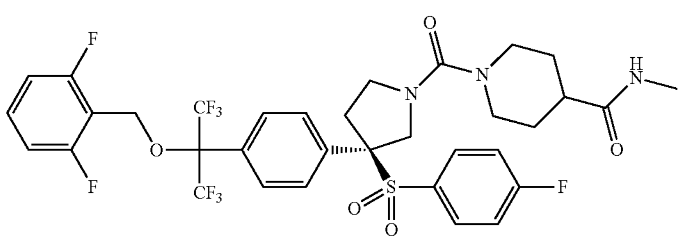 [SMILES: CNC(=O)C1CCN(C(=O)N2CC[C@](c3ccc(C(OCc4c(F)cccc4F)(C(F)(F)F)C(F)(F)F)cc3)(S(=O)(=O)c3ccc(F)cc3)C2)CC1] | 766.2 | 2.19 | B |
| 253 | 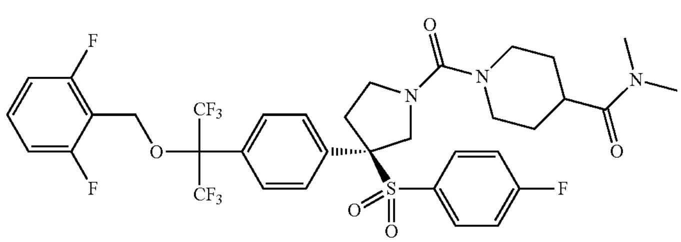 [SMILES: CN(C)C(=O)C1CCN(C(=O)N2CC[C@](c3ccc(C(OCc4c(F)cccc4F)(C(F)(F)F)C(F)(F)F)cc3)(S(=O)(=O)c3ccc(F)cc3)C2)CC1] | 780.3 | 2.27 | B |
| 254 | 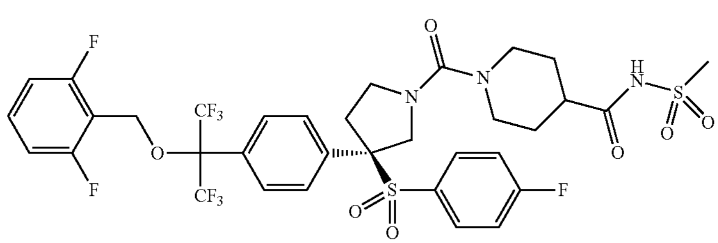 [SMILES: CS(=O)(=O)NC(=O)C1CCN(C(=O)N2CC[C@](c3ccc(C(OCc4c(F)cccc4F)(C(F)(F)F)C(F)(F)F)cc3)(S(=O)(=O)c3ccc(F)cc3)C2)CC1] | 830.4 | 1.84 | B |

TABLE 1-continued

| Ex. No. | Structure | MS (M + 1) | HPLC ret. time (min.) | HPLC method |
|---|---|---|---|---|
| 255 | 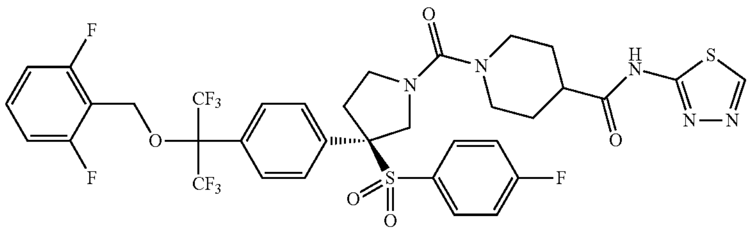 [SMILES: O=C(Nc1nncs1)C1CCN(C(=O)N2CC[C@](c3ccc(C(OCc4c(F)cccc4F)(C(F)(F)F)C(F)(F)F)cc3)(S(=O)(=O)c3ccc(F)cc3)C2)CC1] | 836.2 | 2.21 | B |
| 256 | 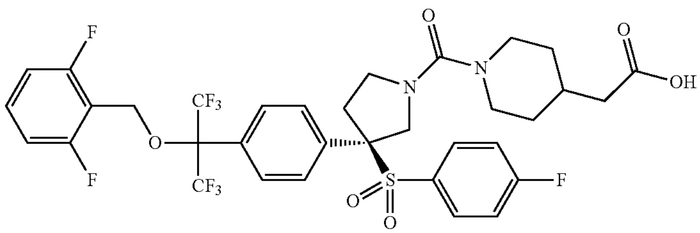 [SMILES: O=C(O)CC1CCN(C(=O)N2CC[C@](c3ccc(C(OCc4c(F)cccc4F)(C(F)(F)F)C(F)(F)F)cc3)(S(=O)(=O)c3ccc(F)cc3)C2)CC1] | 767.2 | 1.88 | B |
| 257 | 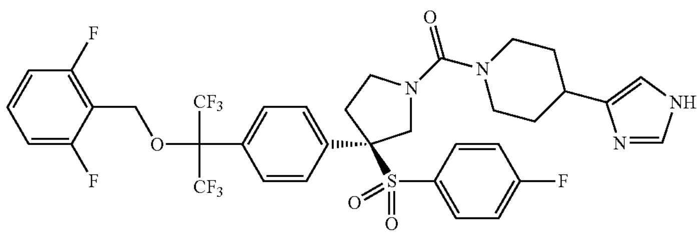 [SMILES: O=C(N1CCC(c2c[nH]cn2)CC1)N1CC[C@](c2ccc(C(OCc3c(F)cccc3F)(C(F)(F)F)C(F)(F)F)cc2)(S(=O)(=O)c2ccc(F)cc2)C1] | 775.4 | 2.08 | B |
| 258 | 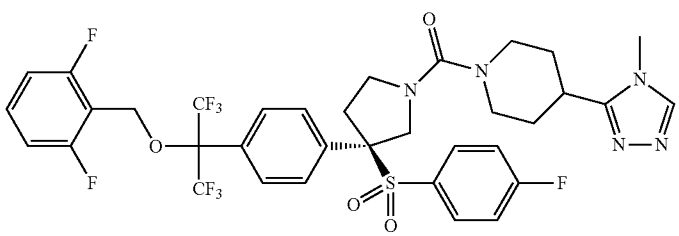 [SMILES: Cn1cnnc1C1CCN(C(=O)N2CC[C@](c3ccc(C(OCc4c(F)cccc4F)(C(F)(F)F)C(F)(F)F)cc3)(S(=O)(=O)c3ccc(F)cc3)C2)CC1] | 790.2 | 2.08 | B |
| 259 | 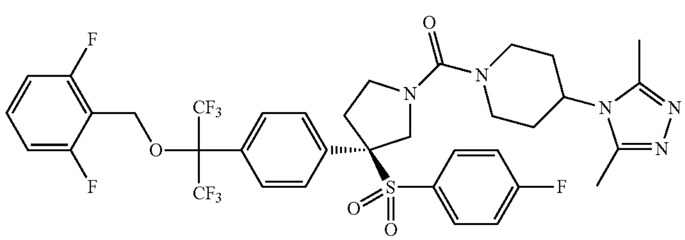 [SMILES: Cc1nnc(C)n1C1CCN(C(=O)N2CC[C@](c3ccc(C(OCc4c(F)cccc4F)(C(F)(F)F)C(F)(F)F)cc3)(S(=O)(=O)c3ccc(F)cc3)C2)CC1] | 804.3 | 2.21 | B |
| 260 | 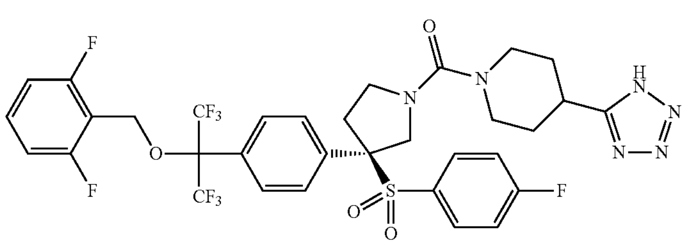 [SMILES: O=C(N1CCC(c2nnn[nH]2)CC1)N1CC[C@](c2ccc(C(OCc3c(F)cccc3F)(C(F)(F)F)C(F)(F)F)cc2)(S(=O)(=O)c2ccc(F)cc2)C1] | 777.3 | 1.88 | B |

TABLE 1-continued

| Ex. No. | Structure | MS (M + 1) | HPLC ret. time (min.) | HPLC method |
|---|---|---|---|---|
| 261 | 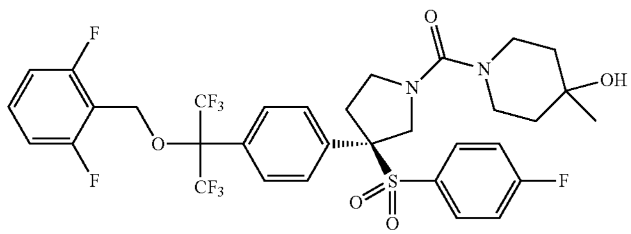 [SMILES: CC1(O)CCN(C(=O)N2CC[C@](c3ccc(C(OCc4c(F)cccc4F)(C(F)(F)F)C(F)(F)F)cc3)(S(=O)(=O)c3ccc(F)cc3)C2)CC1] | 739.2 | 2.28 | B |
| 262 | 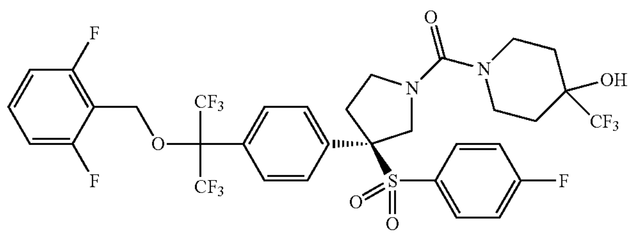 | 793.1 | 2.351 | B |
| 263 | 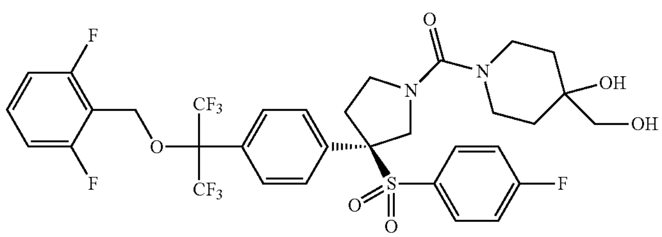 [SMILES: O=C(N1CCC(O)(CO)CC1)N1CC[C@](c2ccc(C(OCc3c(F)cccc3F)(C(F)(F)F)C(F)(F)F)cc2)(S(=O)(=O)c2ccc(F)cc2)C1] | 755.2 | 2.01 | B |
| 264 | 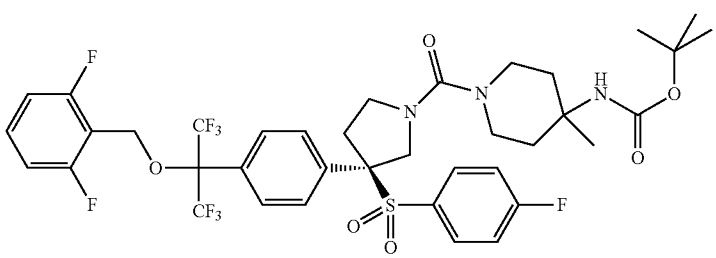 [SMILES: CC1(NC(=O)OC(C)(C)C)CCN(C(=O)N2CC[C@](c3ccc(C(OCc4c(F)cccc4F)(C(F)(F)F)C(F)(F)F)cc3)(S(=O)(=O)c3ccc(F)cc3)C2)CC1] | 838.3 | 2.61 | B |
| 265 | 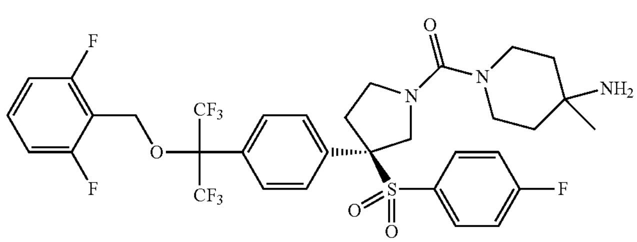 [SMILES: CC1(N)CCN(C(=O)N2CC[C@](c3ccc(C(OCc4c(F)cccc4F)(C(F)(F)F)C(F)(F)F)cc3)(S(=O)(=O)c3ccc(F)cc3)C2)CC1] | 738.2 | 2.02 | B |
| 266 | 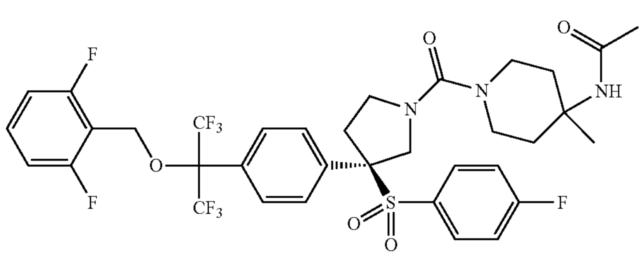 [SMILES: CC(=O)NC1(C)CCN(C(=O)N2CC[C@](c3ccc(C(OCc4c(F)cccc4F)(C(F)(F)F)C(F)(F)F)cc3)(S(=O)(=O)c3ccc(F)cc3)C2)CC1] | 780.2 | 2.26 | B |

TABLE 1-continued

| Ex. No. | Structure | MS (M + 1) | HPLC ret. time (min.) | HPLC method |
|---|---|---|---|---|
| 267 | 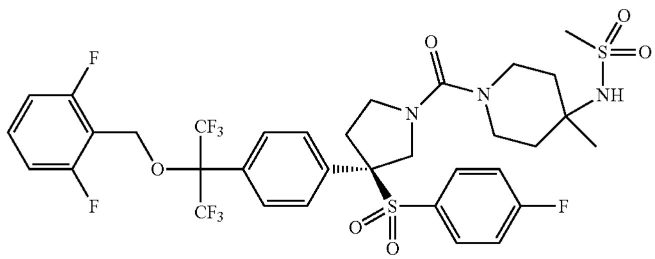 [SMILES: CC1(NS(C)(=O)=O)CCN(C(=O)N2CC[C@](c3ccc(C(OCc4c(F)cccc4F)(C(F)(F)F)C(F)(F)F)cc3)(S(=O)(=O)c3ccc(F)cc3)C2)CC1] | 816.3 | 2.30 | B |
| 268 | 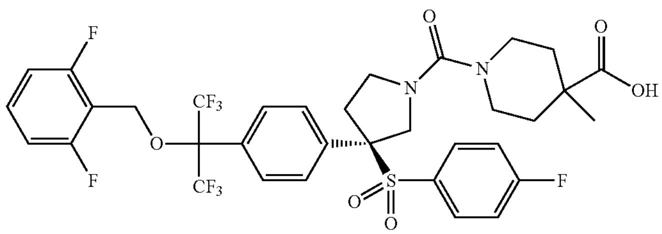 [SMILES: CC1(C(=O)O)CCN(C(=O)N2CC[C@](c3ccc(C(OCc4c(F)cccc4F)(C(F)(F)F)C(F)(F)F)cc3)(S(=O)(=O)c3ccc(F)cc3)C2)CC1] | 767.1 | 2.019 | B |
| 269 | 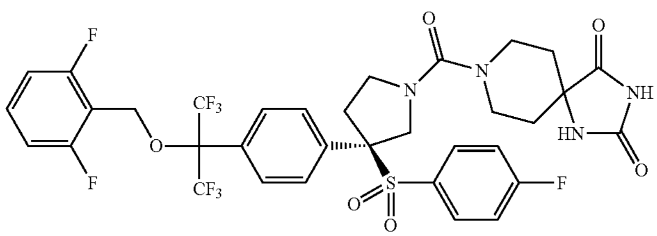 [SMILES: O=C1NC(=O)C2(CCN(C(=O)N3CC[C@](c4ccc(C(OCc5c(F)cccc5F)(C(F)(F)F)C(F)(F)F)cc4)(S(=O)(=O)c4ccc(F)cc4)C3)CC2)N1] | 793.1 | 2.02 | B |
| 270 | two diastereomers from trans-diol | 741.4 | 2.01 | B |
| 271 | 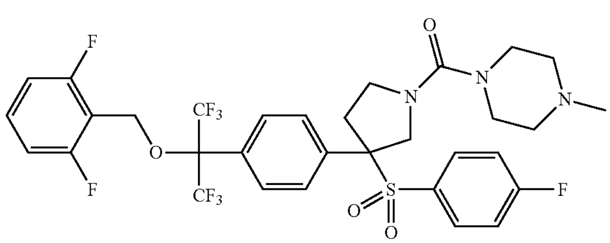 | 724.3 | 2.14 | B |
| 272 | 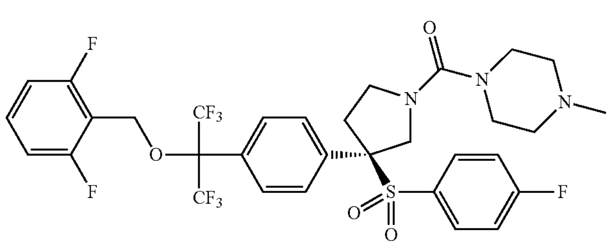 | 724.0 | 4.001 | A |

TABLE 1-continued

| Ex. No. | Structure | MS (M + 1) | HPLC ret. time (min.) | HPLC method |
|---|---|---|---|---|
| 273 | 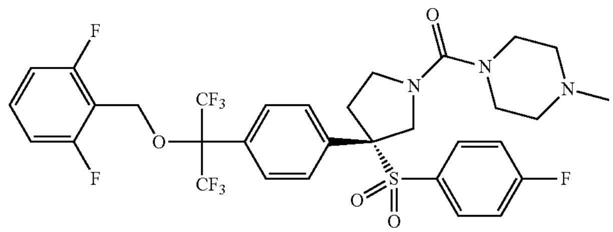 [SMILES: CN1CCN(C(=O)N2CC[C@@](c3ccc(C(OCc4c(F)cccc4F)(C(F)(F)F)C(F)(F)F)cc3)(S(=O)(=O)c3ccc(F)cc3)C2)CC1] | 724.0 | 4.001 | A |
| 274 | 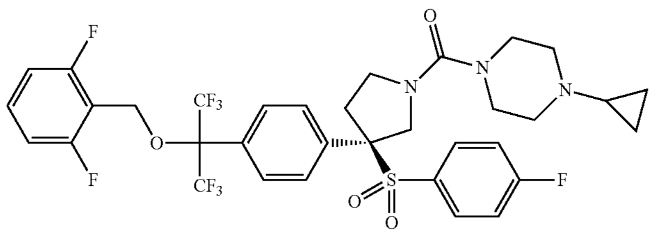 [SMILES: O=C(N1CCN(C2CC2)CC1)N1CC[C@](c2ccc(C(OCc3c(F)cccc3F)(C(F)(F)F)C(F)(F)F)cc2)(S(=O)(=O)c2ccc(F)cc2)C1] | 750.3 | 2.39 | B |
| 275 | 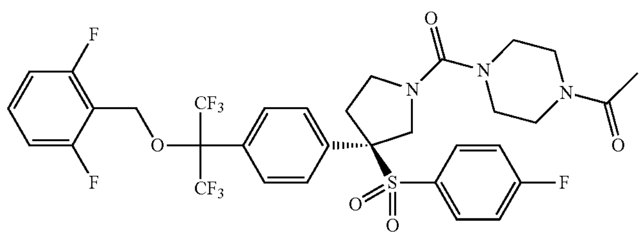 [SMILES: CC(=O)N1CCN(C(=O)N2CC[C@](c3ccc(C(OCc4c(F)cccc4F)(C(F)(F)F)C(F)(F)F)cc3)(S(=O)(=O)c3ccc(F)cc3)C2)CC1] | 752.3 | 2.20 | B |
| 276 | 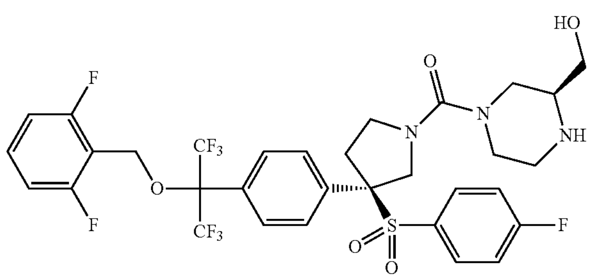 [SMILES: O=C(N1CCN[C@H](CO)C1)N1CC[C@](c2ccc(C(OCc3c(F)cccc3F)(C(F)(F)F)C(F)(F)F)cc2)(S(=O)(=O)c2ccc(F)cc2)C1] | 740.2 | 1.86 | B |
| 277 | 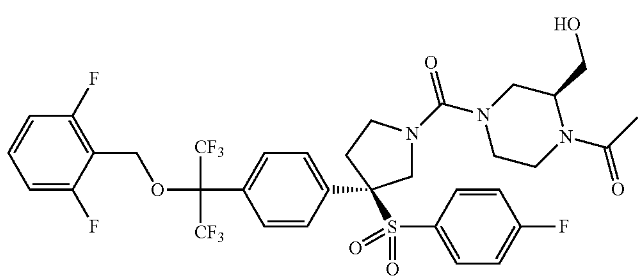 [SMILES: CC(=O)N1CCN(C(=O)N2CC[C@](c3ccc(C(OCc4c(F)cccc4F)(C(F)(F)F)C(F)(F)F)cc3)(S(=O)(=O)c3ccc(F)cc3)C2)C[C@H]1CO] | 782.2 | 2.01 | B |
| 278 | 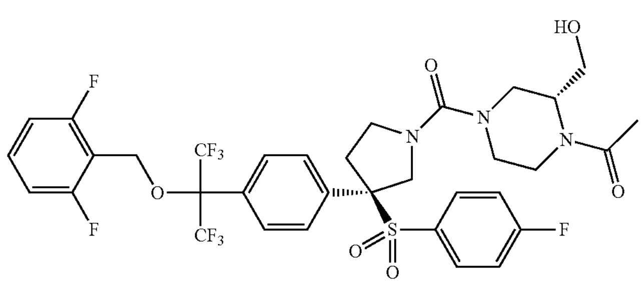 [SMILES: CC(=O)N1CCN(C(=O)N2CC[C@](c3ccc(C(OCc4c(F)cccc4F)(C(F)(F)F)C(F)(F)F)cc3)(S(=O)(=O)c3ccc(F)cc3)C2)C[C@@H]1CO] | 782.4 | 2.06 | B |

TABLE 1-continued

| Ex. No. | Structure | MS (M + 1) | HPLC ret. time (min.) | HPLC method |
|---|---|---|---|---|
| 279 | 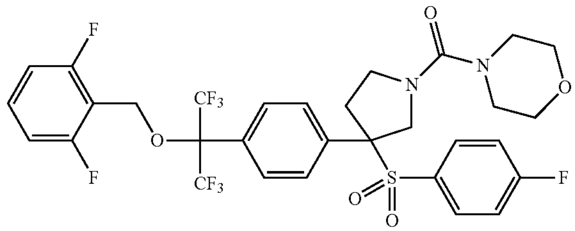 [SMILES: O=C(N1CCOCC1)N1CCC(c2ccc(C(OCc3c(F)cccc3F)(C(F)(F)F)C(F)(F)F)cc2)(S(=O)(=O)c2ccc(F)cc2)C1] | 711.2 | 2.26 | B |
| 280 | 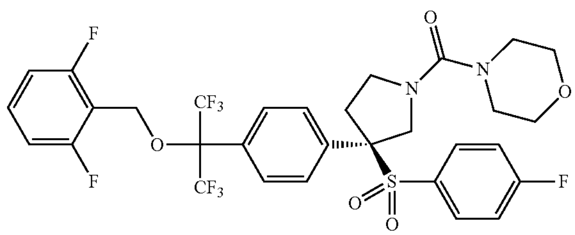 [SMILES: O=C(N1CCOCC1)N1CC[C@](c2ccc(C(OCc3c(F)cccc3F)(C(F)(F)F)C(F)(F)F)cc2)(S(=O)(=O)c2ccc(F)cc2)C1] | 711.1 | 2.19 | B |
| 281 | 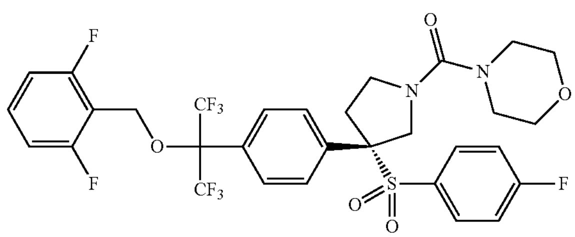 [SMILES: O=C(N1CCOCC1)N1CC[C@@](c2ccc(C(OCc3c(F)cccc3F)(C(F)(F)F)C(F)(F)F)cc2)(S(=O)(=O)c2ccc(F)cc2)C1] | 711.1 | 2.20 | B |
| 282 | (mixture of two diastereomers) | 741.2 | 2.08 | B |
| 283 | 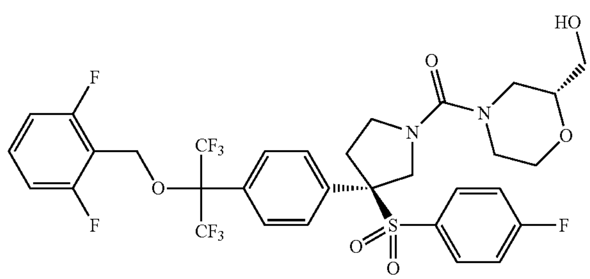 [SMILES: O=C(N1CCO[C@@H](CO)C1)N1CC[C@](c2ccc(C(OCc3c(F)cccc3F)(C(F)(F)F)C(F)(F)F)cc2)(S(=O)(=O)c2ccc(F)cc2)C1] | 741.2 | 2.07 | B |
| 284 | 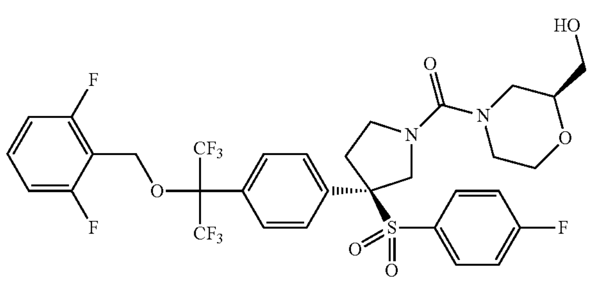 [SMILES: O=C(N1CCO[C@H](CO)C1)N1CC[C@](c2ccc(C(OCc3c(F)cccc3F)(C(F)(F)F)C(F)(F)F)cc2)(S(=O)(=O)c2ccc(F)cc2)C1] | 741.3 | 2.07 | B |

TABLE 1-continued

| Ex. No. | Structure | MS (M + 1) | HPLC ret. time (min.) | HPLC method |
|---|---|---|---|---|
| 285 | 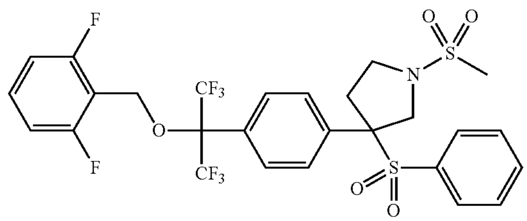 [SMILES: CS(=O)(=O)N1CCC(c2ccc(C(OCc3c(F)cccc3F)(C(F)(F)F)C(F)(F)F)cc2)(S(=O)(=O)c2ccccc2)C1] | 675.0 (M + 18) | 2.28 | B |
| 286 | 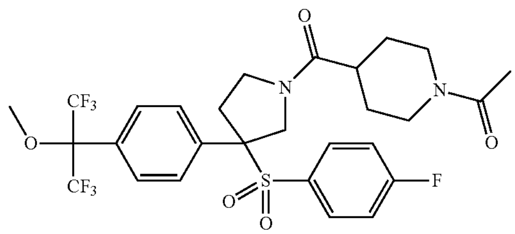 [SMILES: COC(c1ccc(C2(S(=O)(=O)c3ccc(F)cc3)CCN(C(=O)C3CCN(C(C)=O)CC3)C2)cc1)(C(F)(F)F)C(F)(F)F] | 639.2 | 1.90 | B |
| 287 | 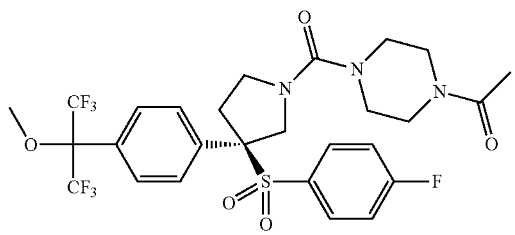 [SMILES: COC(c1ccc([C@]2(S(=O)(=O)c3ccc(F)cc3)CCN(C(=O)N3CCN(C(C)=O)CC3)C2)cc1)(C(F)(F)F)C(F)(F)F] | 640.0 | 1.81 | B |
| 288 | 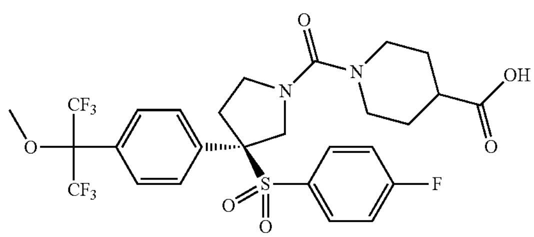 [SMILES: COC(c1ccc([C@]2(S(=O)(=O)c3ccc(F)cc3)CCN(C(=O)N3CCC(C(=O)O)CC3)C2)cc1)(C(F)(F)F)C(F)(F)F] | 641.2 | 1.57 | B |
| 289 | 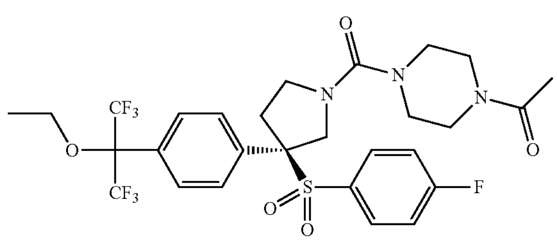 [SMILES: CCOC(c1ccc([C@]2(S(=O)(=O)c3ccc(F)cc3)CCN(C(=O)N3CCN(C(C)=O)CC3)C2)cc1)(C(F)(F)F)C(F)(F)F] | 654.1 | 1.92 | B |
| 290 | 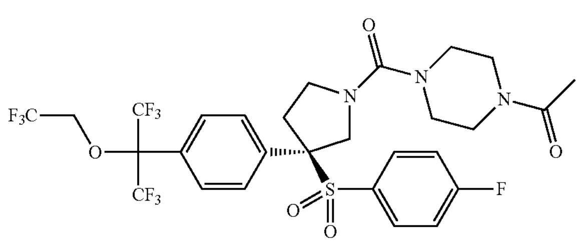 [SMILES: CC(=O)N1CCN(C(=O)N2CC[C@](c3ccc(C(OCC(F)(F)F)(C(F)(F)F)C(F)(F)F)cc3)(S(=O)(=O)c3ccc(F)cc3)C2)CC1] | 708.2 | 1.94 | B |

TABLE 1-continued

| Ex. No. | Structure | MS (M + 1) | HPLC ret. time (min.) | HPLC method |
|---|---|---|---|---|
| 291 | 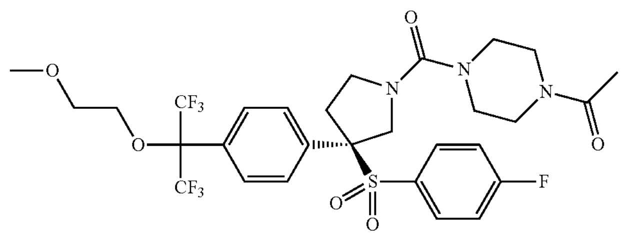 [SMILES: COCCOC(c1ccc([C@]2(S(=O)(=O)c3ccc(F)cc3)CCN(C(=O)N3CCN(C(C)=O)CC3)C2)cc1)(C(F)(F)F)C(F)(F)F] | 684.3 | 1.89 | B |
| 292 | 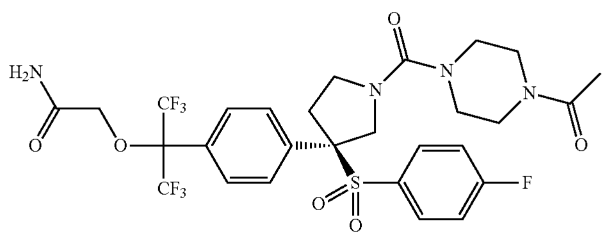 [SMILES: CC(=O)N1CCN(C(=O)N2CC[C@](c3ccc(C(OCC(N)=O)(C(F)(F)F)C(F)(F)F)cc3)(S(=O)(=O)c3ccc(F)cc3)C2)CC1] | 683.0 | 1.42 | B |
| 293 | 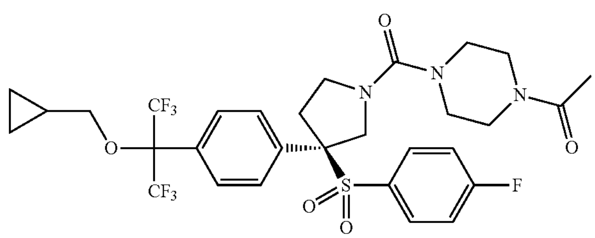 [SMILES: CC(=O)N1CCN(C(=O)N2CC[C@](c3ccc(C(OCC4CC4)(C(F)(F)F)C(F)(F)F)cc3)(S(=O)(=O)c3ccc(F)cc3)C2)CC1] | 680.3 | 2.09 | B |
| 294 | 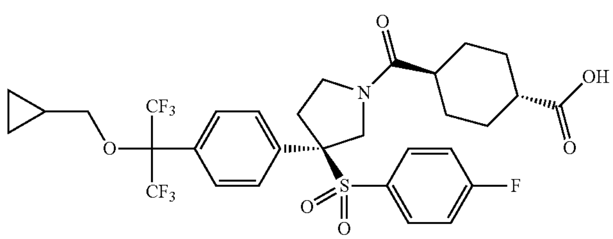 [SMILES: O=C(O)[C@H]1CC[C@H](C(=O)N2CC[C@](c3ccc(C(OCC4CC4)(C(F)(F)F)C(F)(F)F)cc3)(S(=O)(=O)c3ccc(F)cc3)C2)CC1] | 680.4 | 1.97 | B |
| 295 | 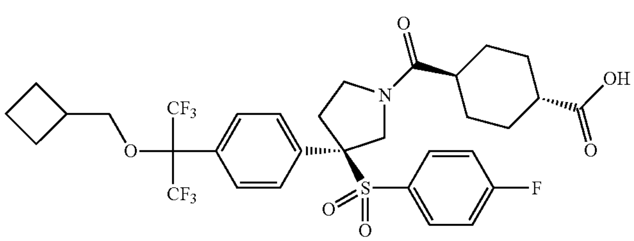 [SMILES: O=C(O)[C@H]1CC[C@H](C(=O)N2CC[C@](c3ccc(C(OCC4CCC4)(C(F)(F)F)C(F)(F)F)cc3)(S(=O)(=O)c3ccc(F)cc3)C2)CC1] | 694.5 | 2.11 | B |
| 296 | 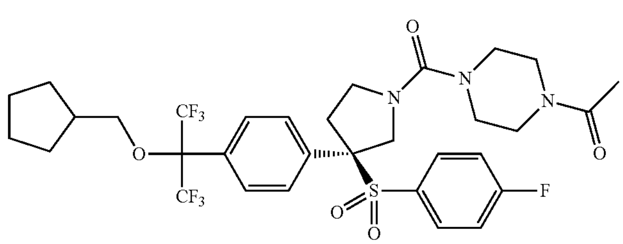 [SMILES: CC(=O)N1CCN(C(=O)N2CC[C@](c3ccc(C(OCC4CCCC4)(C(F)(F)F)C(F)(F)F)cc3)(S(=O)(=O)c3ccc(F)cc3)C2)CC1] | 708.3 | 2.39 | B |

TABLE 1-continued

| Ex. No. | Structure | MS (M + 1) | HPLC ret. time (min.) | HPLC method |
|---|---|---|---|---|
| 297 | 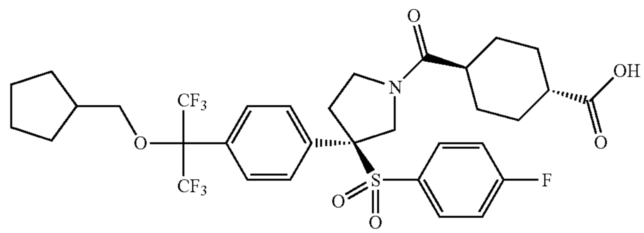 [SMILES: O=C(O)[C@H]1CC[C@H](C(=O)N2CC[C@](c3ccc(C(OCC4CCCC4)(C(F)(F)F)C(F)(F)F)cc3)(S(=O)(=O)c3ccc(F)cc3)C2)CC1] | 708.2 | 2.26 | B |
| 298 | (mixture of two diastereomers) | 809.5 | 4.556 | A |
| 299 | (mixture of two diastereomers) | 709.3 | 1.37 | B |
| 300 | 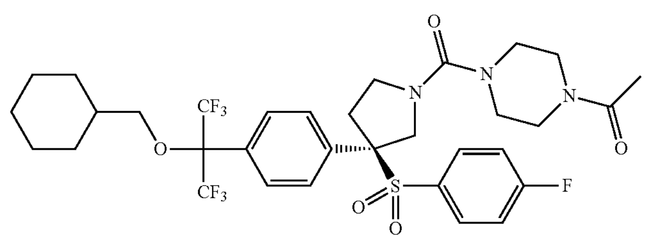 [SMILES: CC(=O)N1CCN(C(=O)N2CC[C@](c3ccc(C(OCC4CCCCC4)(C(F)(F)F)C(F)(F)F)cc3)(S(=O)(=O)c3ccc(F)cc3)C2)CC1] | 722.3 | 4.868 | A |
| 301 | 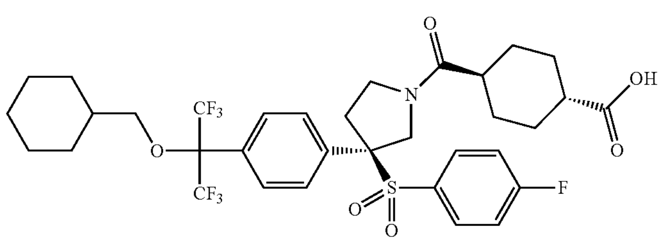 [SMILES: O=C(O)[C@H]1CC[C@H](C(=O)N2CC[C@](c3ccc(C(OCC4CCCCC4)(C(F)(F)F)C(F)(F)F)cc3)(S(=O)(=O)c3ccc(F)cc3)C2)CC1] | 722.3 | 2.33 | B |
| 302 | 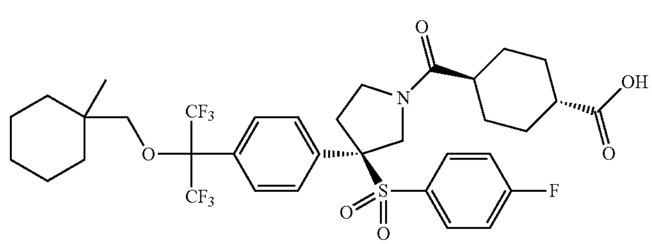 [SMILES: CC1(COC(c2ccc([C@]3(S(=O)(=O)c4ccc(F)cc4)CCN(C(=O)[C@H]4CC[C@H](C(=O)O)CC4)C3)cc2)(C(F)(F)F)C(F)(F)F)CCCCC1] | 736.2 | 2.479 | B |

TABLE 1-continued

| Ex. No. | Structure | MS (M + 1) | HPLC ret. time (min.) | HPLC method |
|---|---|---|---|---|
| 303 | (mixture of two diastereomers from cis and trans-4-(hydroxymethyl)cyclohexanol) | 737.4 | 1.68 | B |
| 304 | 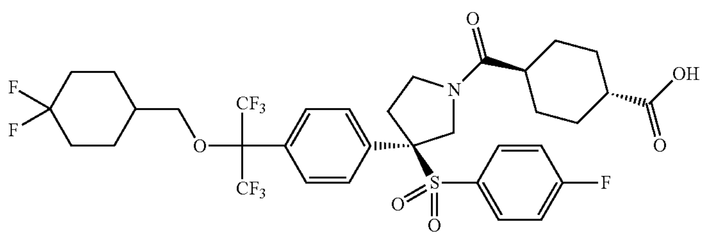 [SMILES: O=C(O)[C@H]1CC[C@H](C(=O)N2CC[C@](c3ccc(C(OCC4CCC(F)(F)CC4)(C(F)(F)F)C(F)(F)F)cc3)(S(=O)(=O)c3ccc(F)cc3)C2)CC1] | 758.4 | 4.641 | A |
| 305 | 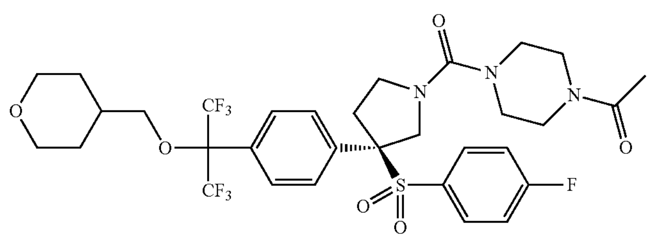 [SMILES: CC(=O)N1CCN(C(=O)N2CC[C@](c3ccc(C(OCC4CCOCC4)(C(F)(F)F)C(F)(F)F)cc3)(S(=O)(=O)c3ccc(F)cc3)C2)CC1] | 724.3 | 1.98 | B |
| 306 | 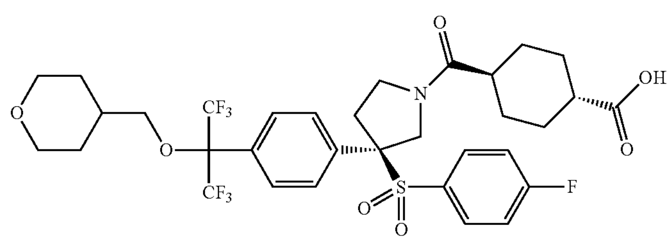 | 724.5 | 1.81 | B |
| 307 | (mixture of two diastereomers) | 734.4 | 2.49 | B |
| 308 | 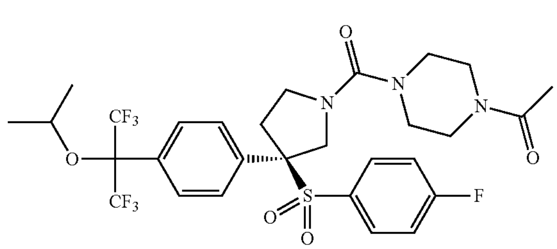 [SMILES: CC(=O)N1CCN(C(=O)N2CC[C@](c3ccc(C(OC(C)C)(C(F)(F)F)C(F)(F)F)cc3)(S(=O)(=O)c3ccc(F)cc3)C2)CC1] | 668.2 | 4.428 | A |

TABLE 1-continued

| Ex. No. | Structure | MS (M + 1) | HPLC ret. time (min.) | HPLC method |
|---|---|---|---|---|
| 309 | 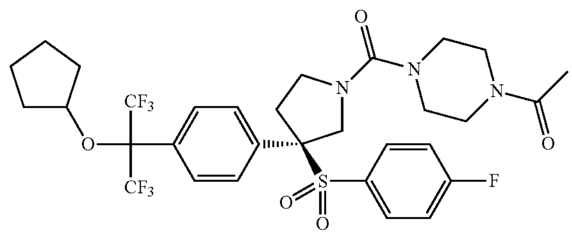 [SMILES: CC(=O)N1CCN(C(=O)N2CC[C@](c3ccc(C(OC4CCCC4)(C(F)(F)F)C(F)(F)F)cc3)(S(=O)(=O)c3ccc(F)cc3)C2)CC1] | 694.2 | 4.618 | A |
| 310 | 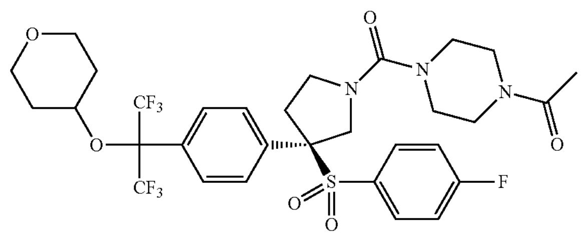 [SMILES: CC(=O)N1CCN(C(=O)N2CC[C@](c3ccc(C(OC4CCOCC4)(C(F)(F)F)C(F)(F)F)cc3)(S(=O)(=O)c3ccc(F)cc3)C2)CC1] | 710.2 | 4.241 | A |
| 311 | 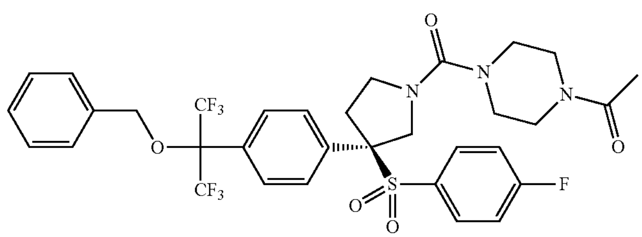 [SMILES: CC(=O)N1CCN(C(=O)N2CC[C@](c3ccc(C(OCc4ccccc4)(C(F)(F)F)C(F)(F)F)cc3)(S(=O)(=O)c3ccc(F)cc3)C2)CC1] | 716.3 | 2.09 | B |
| 312 | 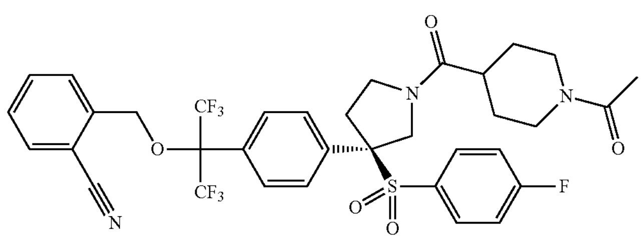 | 740.1 | 2.048 | B |
| 313 | 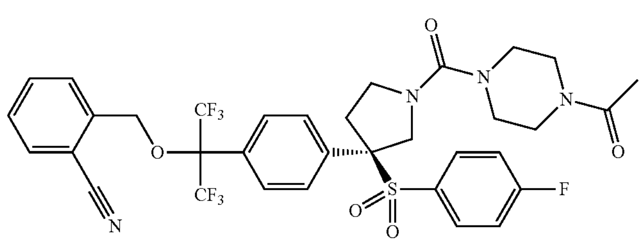 [SMILES: CC(=O)N1CCC(C(=O)N2CC[C@](c3ccc(C(OCc4ccccc4C#N)(C(F)(F)F)C(F)(F)F)cc3)(S(=O)(=O)c3ccc(F)cc3)C2)CC1] | 741.3 | 1.95 | B |
| 314 | 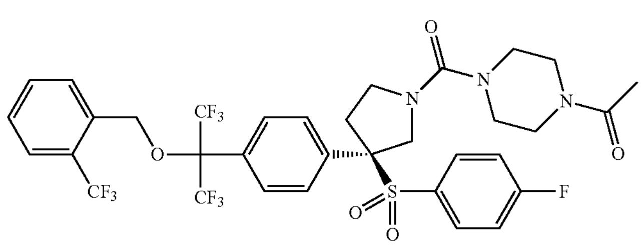 [SMILES: CC(=O)N1CCN(C(=O)N2CC[C@](c3ccc(C(OCc4ccccc4C(F)(F)F)(C(F)(F)F)C(F)(F)F)cc3)(S(=O)(=O)c3ccc(F)cc3)C2)CC1] | 784.2 | 2.39 | B |

TABLE 1-continued

| Ex. No. | Structure | MS (M + 1) | HPLC ret. time (min.) | HPLC method |
|---|---|---|---|---|
| 315 | 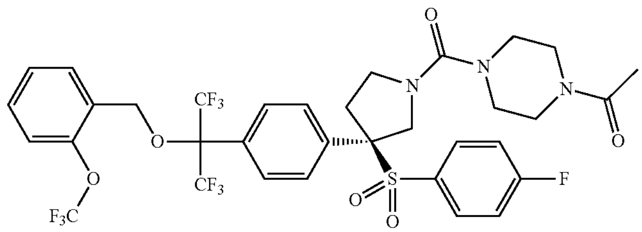 [SMILES: CC(=O)N1CCN(C(=O)N2CC[C@](c3ccc(C(OCc4ccccc4OC(F)(F)F)(C(F)(F)F)C(F)(F)F)cc3)(S(=O)(=O)c3ccc(F)cc3)C2)CC1] | 800.2 | 2.23 | B |
| 316 | 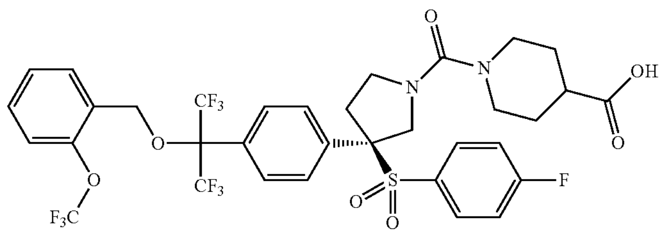 | 801.0 | 2.072 | B |
| 317 | 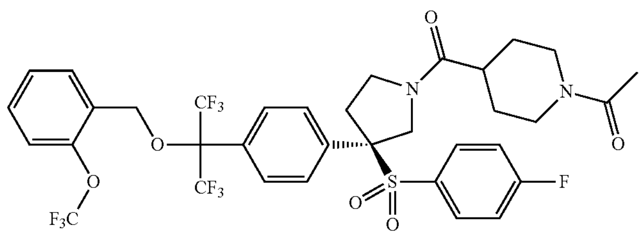 | 799.0 | 2.327 | B |
| 318 | 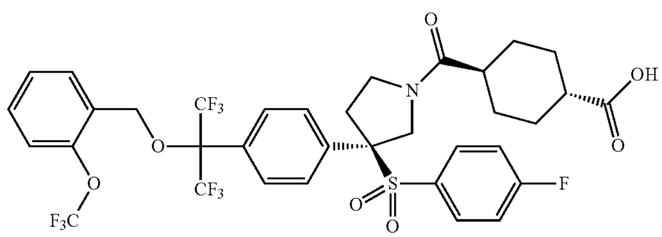 [SMILES: O=C(O)[C@H]1CC[C@H](C(=O)N2CC[C@](c3ccc(C(OCc4ccccc4OC(F)(F)F)(C(F)(F)F)C(F)(F)F)cc3)(S(=O)(=O)c3ccc(F)cc3)C2)CC1] | 800.3 | 2.16 | B |
| 319 | 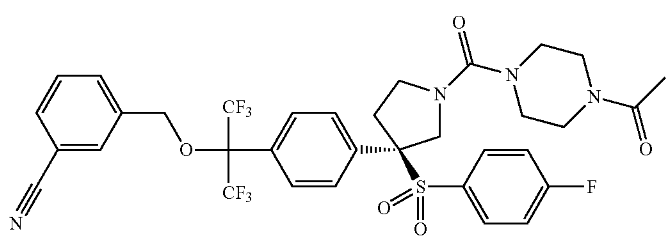 [SMILES: CC(=O)N1CCN(C(=O)N2CC[C@](c3ccc(C(OCc4cccc(C#N)c4)(C(F)(F)F)C(F)(F)F)cc3)(S(=O)(=O)c3ccc(F)cc3)C2)CC1] | 741.0 | 1.98 | B |
| 320 | 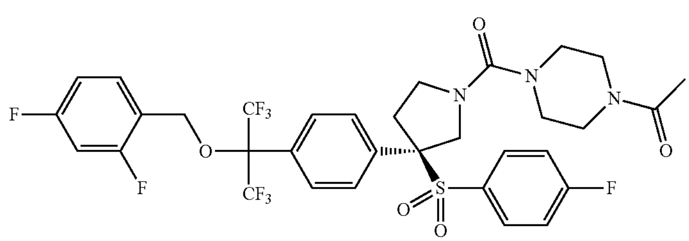 [SMILES: CC(=O)N1CCN(C(=O)N2CC[C@](c3ccc(C(OCc4ccc(F)cc4F)(C(F)(F)F)C(F)(F)F)cc3)(S(=O)(=O)c3ccc(F)cc3)C2)CC1] | 752.2 | 2.11 | B |

TABLE 1-continued

| Ex. No. | Structure | MS (M + 1) | HPLC ret. time (min.) | HPLC method |
|---|---|---|---|---|
| 321 | 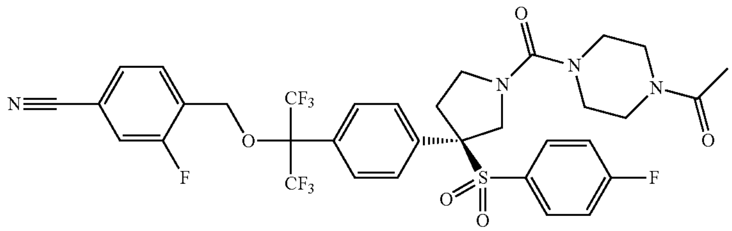 [SMILES: CC(=O)N1CCN(C(=O)N2CC[C@](c3ccc(C(OCc4ccc(C#N)cc4F)(C(F)(F)F)C(F)(F)F)cc3)(S(=O)(=O)c3ccc(F)cc3)C2)CC1] | 759.2 | 2.00 | B |
| 322 | 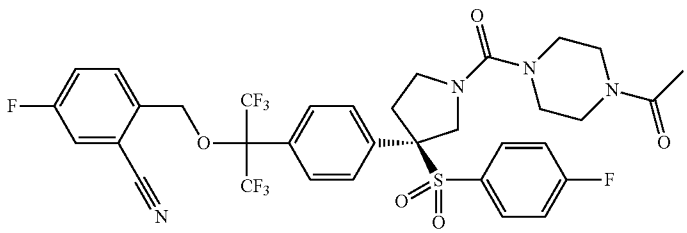 [SMILES: CC(=O)N1CCN(C(=O)N2CC[C@](c3ccc(C(OCc4ccc(F)cc4C#N)(C(F)(F)F)C(F)(F)F)cc3)(S(=O)(=O)c3ccc(F)cc3)C2)CC1] | 759.2 | 1.98 | B |
| 323 | 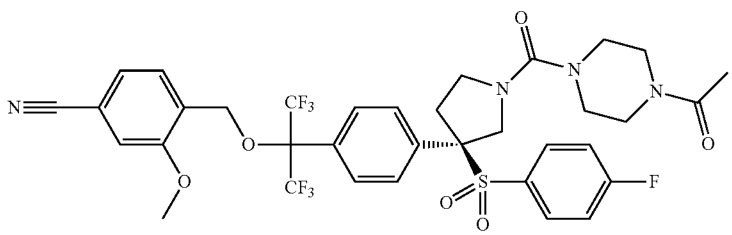 [SMILES: COc1cc(C#N)ccc1COC(c1ccc([C@]2(S(=O)(=O)c3ccc(F)cc3)CCN(C(=O)N3CCN(C(C)=O)CC3)C2)cc1)(C(F)(F)F)C(F)(F)F] | 771.3 | 2.06 | B |
| 324 | 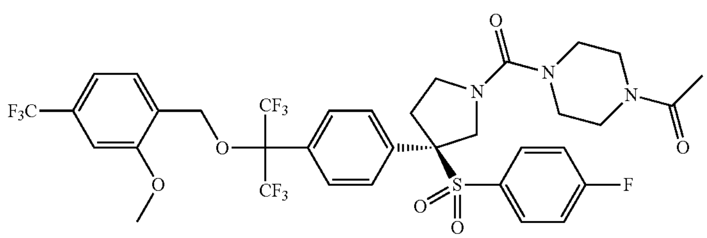 [SMILES: COc1cc(C(F)(F)F)ccc1COC(c1ccc([C@]2(S(=O)(=O)c3ccc(F)cc3)CCN(C(=O)N3CCN(C(C)=O)CC3)C2)cc1)(C(F)(F)F)C(F)(F)F] | 814.3 | 2.44 | B |
| 325 | 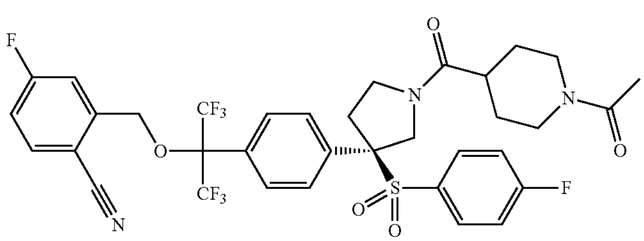 [SMILES: CC(=O)N1CCC(C(=O)N2CC[C@](c3ccc(C(OCc4cc(F)ccc4C#N)(C(F)(F)F)C(F)(F)F)cc3)(S(=O)(=O)c3ccc(F)cc3)C2)CC1] | 758.2 | 2.18 | B |
| 326 | 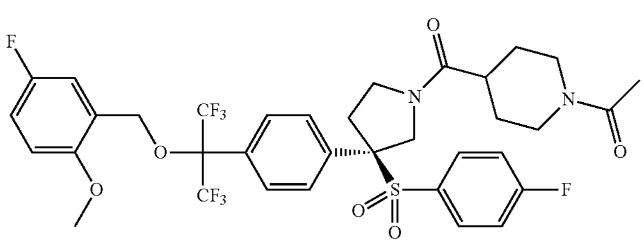 [SMILES: COc1ccc(F)cc1COC(c1ccc([C@]2(S(=O)(=O)c3ccc(F)cc3)CCN(C(=O)C3CCN(C(C)=O)CC3)C2)cc1)(C(F)(F)F)C(F)(F)F] | 763.1 | 2.235 | B |

TABLE 1-continued

| Ex. No. | Structure | MS (M + 1) | HPLC ret. time (min.) | HPLC method |
|---|---|---|---|---|
| 327 | 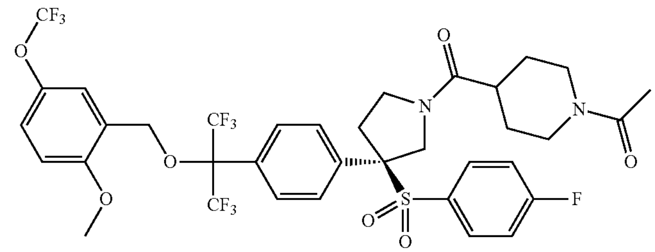 [SMILES: COc1ccc(OC(F)(F)F)cc1COC(c1ccc([C@]2(S(=O)(=O)c3ccc(F)cc3)CCN(C(=O)C3CCN(C(C)=O)CC3)C2)cc1)(C(F)(F)F)C(F)(F)F] | 829.3 | 2.47 | B |
| 328 | 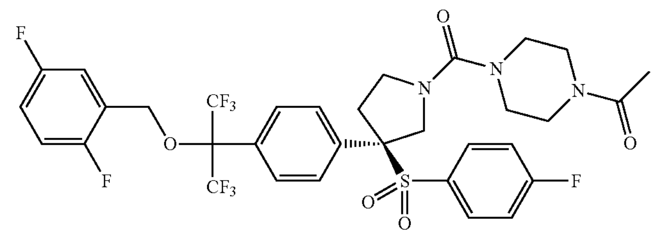 | 752.2 | 2.10 | B |
| 329 | 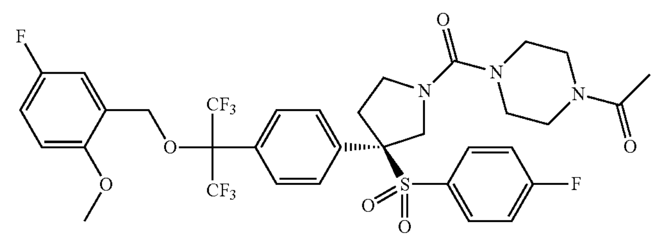 [SMILES: COc1ccc(F)cc1COC(c1ccc([C@]2(S(=O)(=O)c3ccc(F)cc3)CCN(C(=O)N3CCN(C(C)=O)CC3)C2)cc1)(C(F)(F)F)C(F)(F)F] | 764.2 | 2.29 | B |
| 330 | 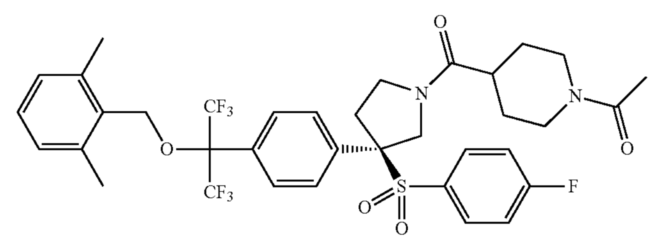 [SMILES: CC(=O)N1CCC(C(=O)N2CC[C@](c3ccc(C(OCc4c(C)cccc4C)(C(F)(F)F)C(F)(F)F)cc3)(S(=O)(=O)c3ccc(F)cc3)C2)CC1] | 743.5 | 2.31 | B |
| 331 | 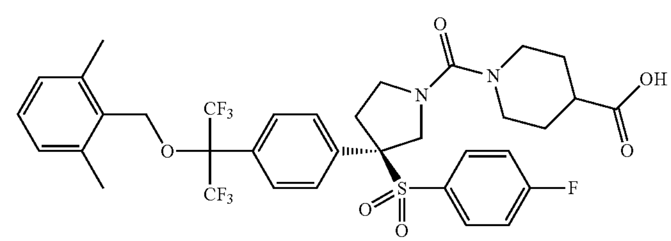 [SMILES: Cc1cccc(C)c1COC(c1ccc([C@]2(S(=O)(=O)c3ccc(F)cc3)CCN(C(=O)N3CCC(C(=O)O)CC3)C2)cc1)(C(F)(F)F)C(F)(F)F] | 745.4 | 2.08 | B |
| 332 | 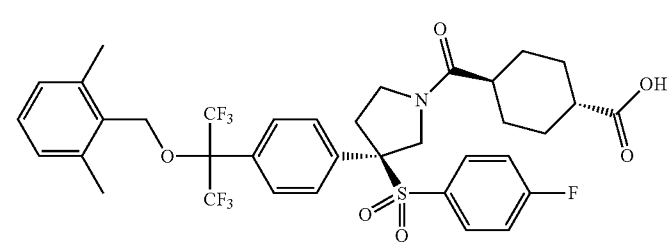 | 744.3 | 2.16 | B |

| Ex. No. | Structure | MS (M + 1) | HPLC ret. time (min.) | HPLC method |
|---|---|---|---|---|
| 333 | 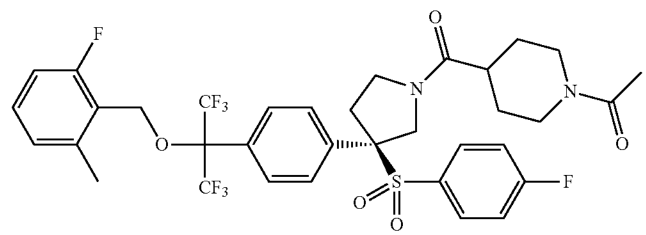 | 747.4 | 2.23 | B |
| 334 | 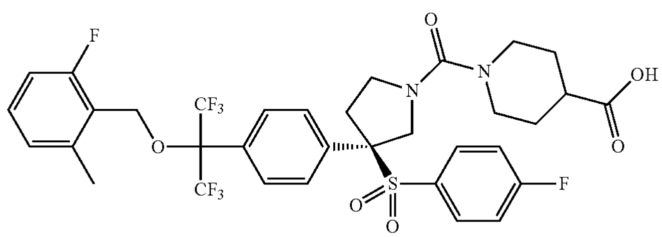 | 749.4 | 1.99 | B |
| 335 | 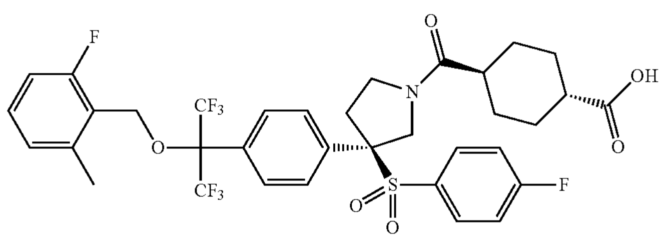 [SMILES: Cc1cccc(C)c1COC(c1ccc([C@]2(S(=O)(=O)c3ccc(F)cc3)CCN(C(=O)[C@H]3CC[C@H](C(=O)O)CC3)C2)cc1)(C(F)(F)F)C(F)(F)F] | 748.5 | 2.06 | B |
| 336 | 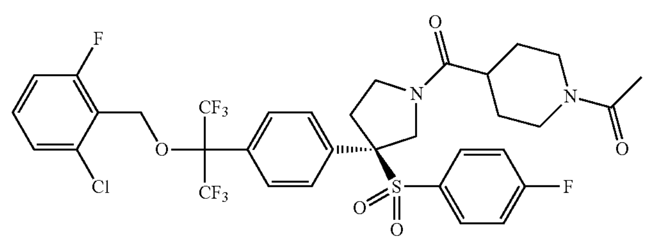 | 767.2 | 2.30 | B |
| 337 | 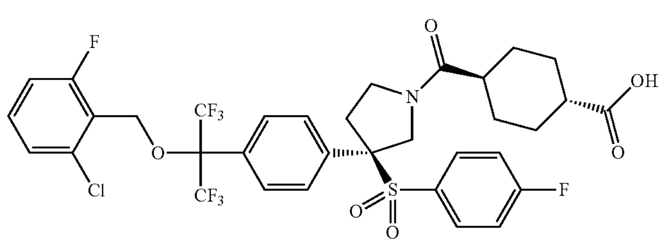 [SMILES: O=C(O)[C@H]1CC[C@H](C(=O)N2CC[C@](c3ccc(C(OCc4c(F)cccc4Cl)(C(F)(F)F)C(F)(F)F)cc3)(S(=O)(=O)c3ccc(F)cc3)C2)CC1] | 768.2 | 2.06 | B |
| 338 | 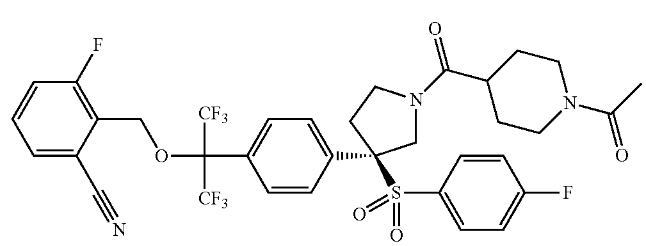 | 758.1 | 2.010 | B |

TABLE 1-continued

| Ex. No. | Structure | MS (M + 1) | HPLC ret. time (min.) | HPLC method |
|---|---|---|---|---|
| 339 | 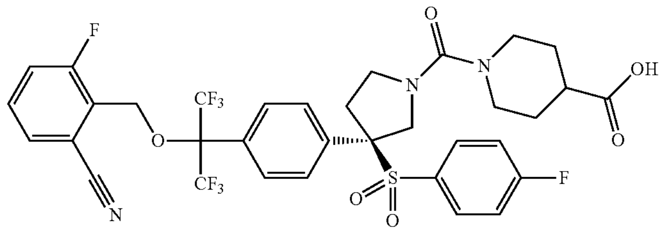 [SMILES: N#Cc1cccc(F)c1COC(c1ccc([C@]2(S(=O)(=O)c3ccc(F)cc3)CCN(C(=O)N3CCC(C(=O)O)CC3)C2)cc1)(C(F)(F)F)C(F)(F)F] | 760.2 | 1.87 | B |
| 340 | 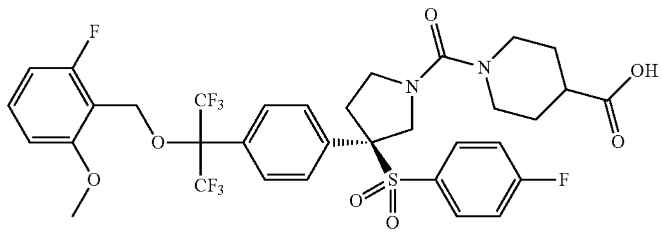 [SMILES: COc1cccc(F)c1COC(c1ccc([C@]2(S(=O)(=O)c3ccc(F)cc3)CCN(C(=O)N3CCC(C(=O)O)CC3)C2)cc1)(C(F)(F)F)C(F)(F)F] | 765.1 | 1.923 | B |
| 341 | 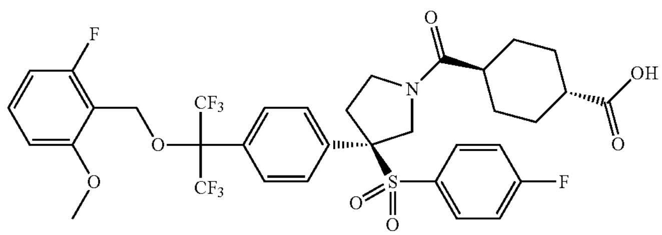 | 764.2 | 2.01 | B |
| 342 | 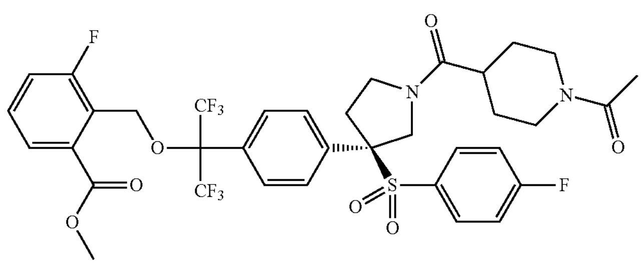 [SMILES: COC(=O)c1cccc(F)c1COC(c1ccc([C@]2(S(=O)(=O)c3ccc(F)cc3)CCN(C(=O)C3CCN(C(C)=O)CC3)C2)cc1)(C(F)(F)F)C(F)(F)F] | 791.0 | 4.441 | A |
| 343 | 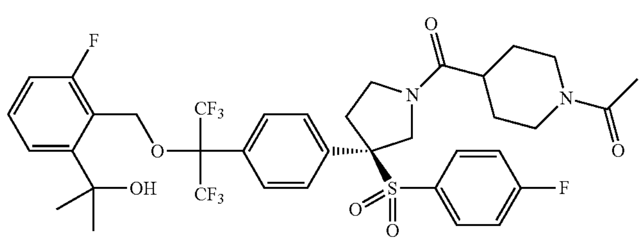 [SMILES: CC(=O)N1CCC(C(=O)N2CC[C@](c3ccc(C(OCc4c(F)cccc4C(C)(C)O)(C(F)(F)F)C(F)(F)F)cc3)(S(=O)(=O)c3ccc(F)cc3)C2)CC1] | 791.2 | 2.080 | B |
| 344 | 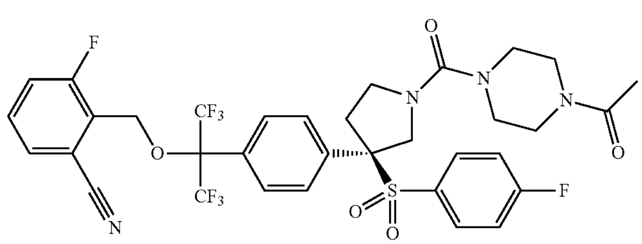 [SMILES: CC(=O)N1CCN(C(=O)N2CC[C@](c3ccc(C(OCc4c(F)cccc4C#N)(C(F)(F)F)C(F)(F)F)cc3)(S(=O)(=O)c3ccc(F)cc3)C2)CC1] | 759.2 | 2.06 | B |

TABLE 1-continued

| Ex. No. | Structure | MS (M + 1) | HPLC ret. time (min.) | HPLC method |
|---|---|---|---|---|
| 345 | 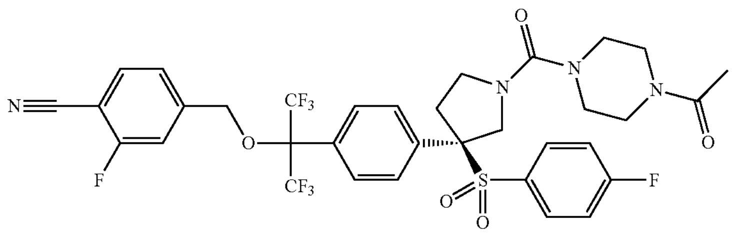 | 759.2 | 2.16 | B |
| 346 | 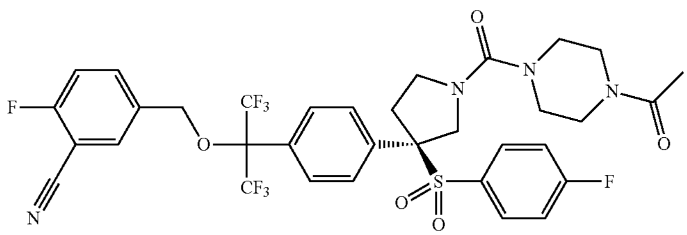 [SMILES: CC(=O)N1CCN(C(=O)N2CC[C@](c3ccc(C(OCc4ccc(F)c(C#N)c4)(C(F)(F)F)C(F)(F)F)cc3)(S(=O)(=O)c3ccc(F)cc3)C2)CC1] | 759.2 | 2.15 | B |
| 347 | 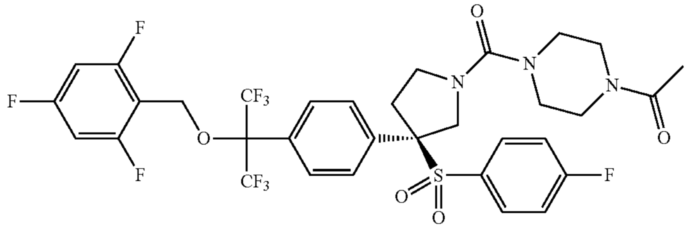 [SMILES: CC(=O)N1CCN(C(=O)N2CC[C@](c3ccc(C(OCc4c(F)cc(F)cc4F)(C(F)(F)F)C(F)(F)F)cc3)(S(=O)(=O)c3ccc(F)cc3)C2)CC1] | 770.0 | 2.11 | B |
| 348 | 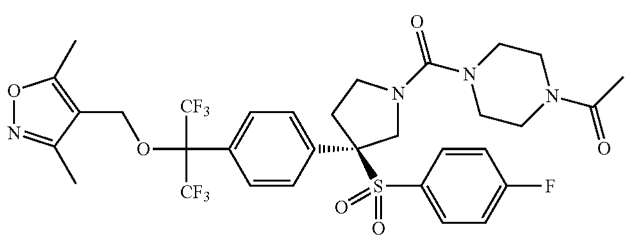 [SMILES: CC(=O)N1CCN(C(=O)N2CC[C@](c3ccc(C(OCc4c(C)noc4C)(C(F)(F)F)C(F)(F)F)cc3)(S(=O)(=O)c3ccc(F)cc3)C2)CC1] | 735.3 | 1.88 | B |
| 349 | 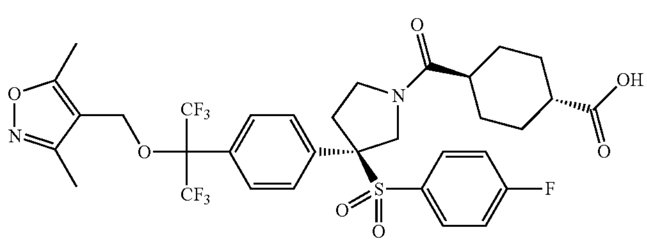 [SMILES: Cc1noc(C)c1COC(c1ccc([C@]2(S(=O)(=O)c3ccc(F)cc3)CCN(C(=O)[C@H]3CC[C@H](C(=O)O)CC3)C2)cc1)(C(F)(F)F)C(F)(F)F] | 735.3 | 1.77 | B |
| 350 | 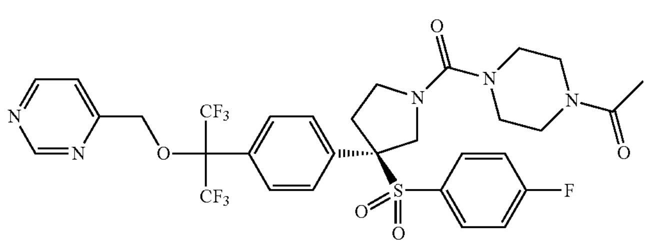 [SMILES: CC(=O)N1CCN(C(=O)N2CC[C@](c3ccc(C(OCc4ccncn4)(C(F)(F)F)C(F)(F)F)cc3)(S(=O)(=O)c3ccc(F)cc3)C2)CC1] | 718.2 | 1.67 | B |

TABLE 1-continued

| Ex. No. | Structure | MS (M + 1) | HPLC ret. time (min.) | HPLC method |
|---|---|---|---|---|
| 351 | 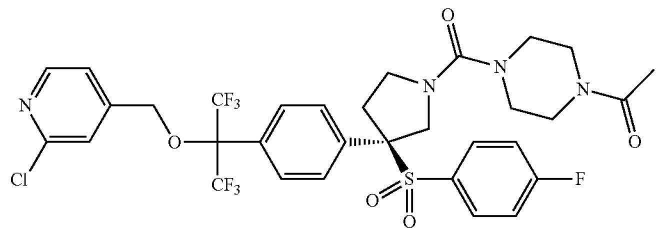 [SMILES: CC(=O)N1CCN(C(=O)N2CC[C@](c3ccc(C(OCc4ccnc(Cl)c4)(C(F)(F)F)C(F)(F)F)cc3)(S(=O)(=O)c3ccc(F)cc3)C2)CC1] | 751.2 | 2.10 | B |
| 352 | (mixture of two diastereomers) | 729.3 | 2.19 | B |
| 353 | (mixture of two diastereomers) | 730.2 | 2.35 | B |
| 354 | 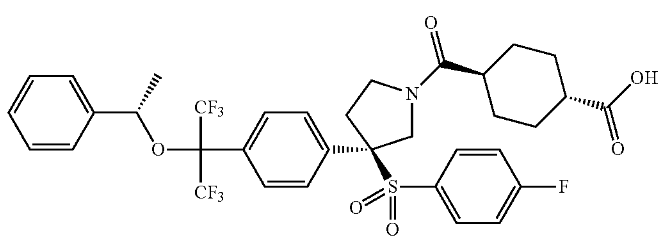 [SMILES: C[C@H](OC(c1ccc([C@]2(S(=O)(=O)c3ccc(F)cc3)CCN(C(=O)[C@H]3CC[C@H](C(=O)O)CC3)C2)cc1)(C(F)(F)F)C(F)(F)F)c1ccccc1] | 730.2 | 2.02 | B |
| 355 | 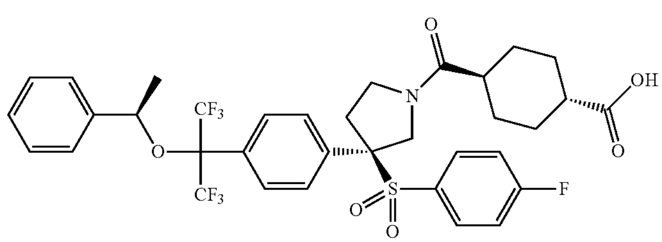 [SMILES: C[C@@H](OC(c1ccc([C@]2(S(=O)(=O)c3ccc(F)cc3)CCN(C(=O)[C@H]3CC[C@H](C(=O)O)CC3)C2)cc1)(C(F)(F)F)C(F)(F)F)c1ccccc1] | 730.2 | 2.01 | B |
| 356 | (mixture of two diastereomers) | 765.2 | 2.18 | B |

TABLE 1-continued

| Ex. No. | Structure | MS (M + 1) | HPLC ret. time (min.) | HPLC method |
|---|---|---|---|---|
| 357 | (mixture of two diastereomers) | 736.6 | 4.958 | A |
| 358 | 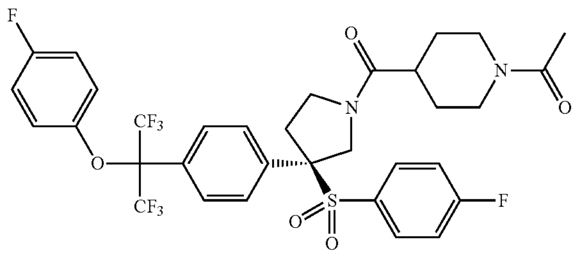 [SMILES: CC(=O)N1CCC(C(=O)N2CC[C@](c3ccc(C(Oc4ccc(F)cc4)(C(F)(F)F)C(F)(F)F)cc3)(S(=O)(=O)c3ccc(F)cc3)C2)CC1] | 719.2 | 2.08 | B |
| 359 | 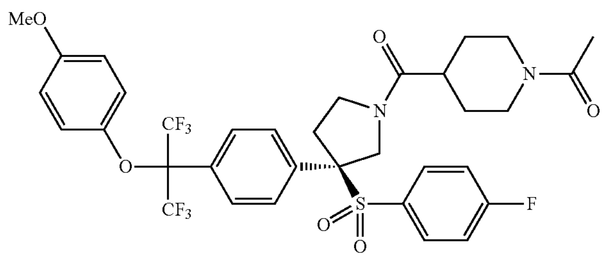 [SMILES: COc1ccc(OC(c2ccc([C@]3(S(=O)(=O)c4ccc(F)cc4)CCN(C(=O)C4CCN(C(C)=O)CC4)C3)cc2)(C(F)(F)F)C(F)(F)F)cc1] | 731.2 | 2.07 | B |
| 360 | 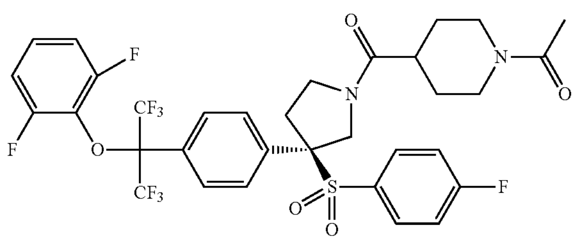 [SMILES: CC(=O)N1CCC(C(=O)N2CC[C@](c3ccc(C(Oc4c(F)cccc4F)(C(F)(F)F)C(F)(F)F)cc3)(S(=O)(=O)c3ccc(F)cc3)C2)CC1] | 737.2 | 2.22 | B |
| 361 | 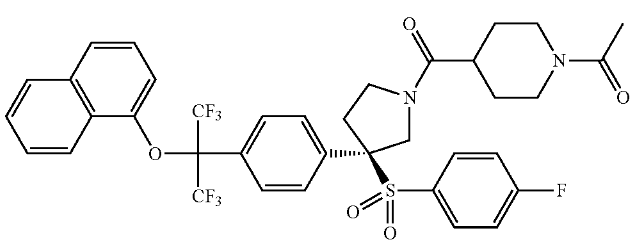 [SMILES: CC(=O)N1CCC(C(=O)N2CC[C@](c3ccc(C(Oc4cccc5ccccc45)(C(F)(F)F)C(F)(F)F)cc3)(S(=O)(=O)c3ccc(F)cc3)C2)CC1] | 751.3 | 2.29 | B |
| 362 | mixture of 2 diastereomers | 532.2 | 1.29 | B |

TABLE 1-continued

| Ex. No. | Structure | MS (M + 1) | HPLC ret. time (min.) | HPLC method |
|---|---|---|---|---|
| 363 | mixture of 2 diastereomers | 572.1 | 1.42 | B |
| 364 | 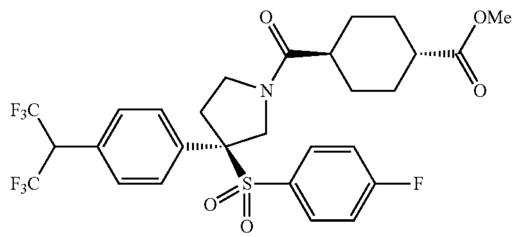 [SMILES: COC(=O)[C@H]1CC[C@H](C(=O)N2CC[C@](c3ccc(C(C(F)(F)F)C(F)(F)F)cc3)(S(=O)(=O)c3ccc(F)cc3)C2)CC1] | 624.3 | 4.190 | A |
| 365 | mixture of two diastereomers | 798.4 | 4.233 | B |
| 366 | 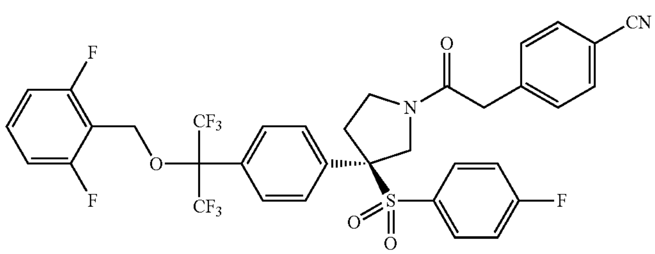 [SMILES: N#Cc1ccc(CC(=O)N2CC[C@](c3ccc(C(OCc4c(F)cccc4F)(C(F)(F)F)C(F)(F)F)cc3)(S(=O)(=O)c3ccc(F)cc3)C2)cc1] | 741.2 | 2.28 | B |

Example 367

(R)-1-benzyl-3-((4-fluoro-3-methylphenyl)sulfonyl)-3-(4-(perfluoropropan-2-yl)phenyl)pyrrolidine Step A: 1,1,1,3,3,3-hexafluoro-2-(4-(((4-fluoro-3-methylphenyl)thio)methyl)phenyl)propan-2-ol

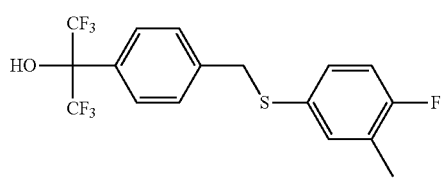 [SMILES: Cc1cc(SCc2ccc(C(O)(C(F)(F)F)C(F)(F)F)cc2)ccc1F]

Potassium carbonate (14.61 g, 106 mmol) was added to a solution of 4-fluoro-3-methylbenzenethiol (5.01 g, 35.2 mmol) and 2-(4-(bromomethyl)phenyl)-1,1,1,3,3,3-hexafluoropropan-2-ol (17.81 g, 52.9 mmol) in THF (60 mL). After 15 h at ambient temperature, the mixture was diluted with ethyl acetate (500 mL), washed with water (200 mL), brine (100 mL), dried (magnesium sulfate), filtered and concentrated under reduced pressure. The mixture was stirred at room temperature for 15 h. It was diluted with ethyl acetate (300 ml), washed with water, brine, dried (MgSO$_4$) and concentrated to give crude product (19.5 g). It was used without further purification. LC/MS (M−1): 397.3.

Step B: 1,1,1,3,3,3-hexafluoro-2-(4-(((4-fluoro-3-methylphenyl)sulfonyl)methyl)phenyl)propan-2-ol

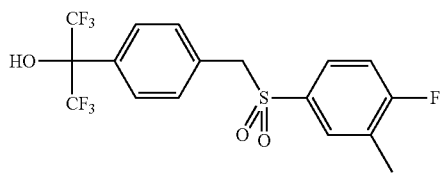 [SMILES: Cc1cc(S(=O)(=O)Cc2ccc(C(O)(C(F)(F)F)C(F)(F)F)cc2)ccc1F]

mCPBA (17.36 g, 77 mmol) was added to a solution of 1,1,1,3,3,3-hexafluoro-2-(4-((4-fluoro-3-methylphenyl)thio)methyl)phenyl)propan-2-ol (14.02 g, 35.2 mmol) in dichloromethane (100 mL). After 5 h at ambient temperature, the mixture was quenched with saturated sodium bicarbonate (100 mL), diluted with ethyl acetate (500 mL), washed with water (100 mL), brine (100 mL), dried (magnesium sulfate), filtered and concentrated under reduced pressure. Silica gel chromatography, eluting with 0-30% ethyl acetate in hexanes, gave the desired 1,1,1,3,3,3-hexafluoro-2-(4-(((4-fluoro-3-methylphenyl)sulfonyl)methyl)phenyl)propan-2-ol (10.3 g, 68% yield over 2 steps). LC/MS (M−1): 429.3; LC retention time: 1.11 min (analytical HPLC Method C); $^1$H NMR (400 MHz, CDCl$_3$) δ ppm 7.65 (d, J=8.1 Hz, 2H), 7.50-7.44 (m, 1H), 7.34 (d, J=2.0 Hz, 1H), 7.21 (d, J=8.6 Hz, 2H), 7.12-6.95 (m, 1H), 4.34 (s, 2H), 2.21 (s, 3H).

Step C: 1-fluoro-2-methyl-4-((4-(perfluoropropan-2-yl)benzyl)sulfonyl)benzene

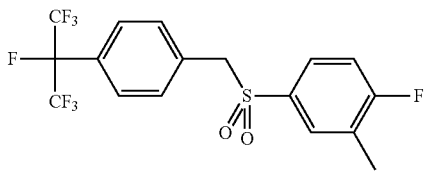 [SMILES: Cc1cc(S(=O)(=O)Cc2ccc(C(F)(C(F)(F)F)C(F)(F)F)cc2)ccc1F]

(Diethylamino)sulfur trifluoride (4.61 mL, 34.9 mmol) was added to a mixture of 1,1,1,3,3,3-hexafluoro-2-(4-(((4-fluoro-3-methylphenyl)sulfonyl)methyl)phenyl)propan-2-ol (2.50 g, 5.81 mmol) in dichloromethane (6 mL). The resultant mixture was heated to 50° C. in a sealed vial for 15 h. It was cooled down to 0° C. with an ice water bath. The reaction was carefully quenched with Methanol (5 mL) at 0° C. The mixture was diluted with ethyl acetate (400 mL), washed with water (100 mL), brine (100 mL), dried (magnesium sulfate), filtered and concentrated under reduced pressure. Silica gel chromatography, eluting with 0-30% ethyl acetate in hexanes, gave the desired 1-fluoro-2-methyl-4-((4-(perfluoropropan-2-yl)benzyl)sulfonyl)benzene (2.05 g, 82% yield). LC/MS (M+18): 450.1; LC retention time: 1.21 min (analytical HPLC Method C); $^1$H NMR (400 MHz, CDCl$_3$) δ ppm 7.63-7.51 (m, 2H), 7.48 (ddd, J=8.4, 4.8, 2.4 Hz, 1H), 7.42-7.31 (m, 1H), 7.31-7.18 (m, 2H), 7.08 (t, J=8.7 Hz, 1H), 4.35 (s, 2H), 2.23 (s, 3H).

Step D: 1-fluoro-2-methyl-4-((1-(4-(perfluoropropan-2-yl)phenyl)vinyl)sulfonyl)benzene

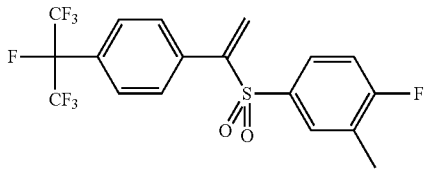 [SMILES: C=C(c1ccc(C(F)(C(F)(F)F)C(F)(F)F)cc1)S(=O)(=O)c1ccc(F)c(C)c1]

N,N,N',N'-tetramethylmethanediamine (5.70 g, 55.8 mmol) and acetic anhydride (5.26 mL, 55.8 mmol) were added to a solution of 1-fluoro-2-methyl-4-((4-(perfluoropropan-2-yl)benzyl)sulfonyl)benzene (4.02 g, 9.30 mmol) in N,N-dimethylformamide (30 mL) at room temperature. The mixture was stirred at room temperature in a sealed viral for 1 h and heated to 65° C. for 15 h. The mixture was cooled down to room temperature, diluted with ethyl acetate (400 mL), washed with saturated sodium bicarbonate (3×80 mL), water (80 mL), brine (80 mL), dried (magnesium sulfate), filtered and concentrated under reduced pressure. Silica gel chromatography, eluting with 0-15% ethyl acetate in hexanes, gave the desired 1-fluoro-2-methyl-4-((1-(4-(perfluoropropan-2-yl)phenyl)vinyl)sulfonyl)benzene (1.95 g, 47% yield). LC/MS (M+1): 445.2; LC retention time: 1.12 min (analytical HPLC Method C); 1H NMR (400 MHz, CDCl$_3$) δ ppm 7.62-7.40 (m, 6H), 7.03 (t, J=8.7 Hz, 1H), 6.66 (s, 1H), 6.01 (s, 1H), 2.21 (d, J=2.0 Hz, 3H).

Step E: (R)-1-benzyl-3-((4-fluoro-3-methylphenyl)sulfonyl)-3-(4-(perfluoropropan-2-yl)phenyl)pyrrolidine

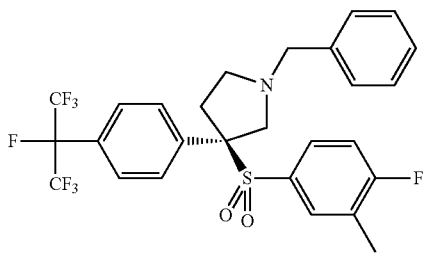 [SMILES: Cc1cc(S(=O)(=O)[C@@]2(c3ccc(C(F)(C(F)(F)F)C(F)(F)F)cc3)CCN(Cc3ccccc3)C2)ccc1F]

A 0.2 M dichloromethane solution of trifluoroacetic acid (0.878 mL, 0.176 mmol) was added dropwise to a solution of 1-fluoro-2-methyl-4-((1-(4-(perfluoropropan-2-yl)phenyl)vinyl)sulfonyl)benzene (1.95 g, 4.39 mmol) and N-benzyl-1-methoxy-N-((trimethylsilyl)methyl)methanamine (3.13 g, 13.17 mmol) in dichloromethane (30 mL) at 0° C. After stirring under nitrogen at 0° C. for 10 min and at room temperature for 1 h, the resulting mixture was diluted with ethyl acetate (300 mL), washed with saturated sodium bicarbonate (2×50 mL) and brine (50 mL), dried (magnesium sulfate), filtered and concentrated under reduced pressure. Silica gel chromatography, eluting with 0-30% ethyl acetate in hexanes, gave the desired product as racemic material (1.90 g). It was separated into its homochiral components using a chiral Lux Cellulose-4 (3×25 cm, 5 μm), CO$_2$/methanol (65/35), 40° C., 100 bars to afford the desired Example 367 (410 mg, 15% yield) as the second eluent off the column. LC/MS (M+1): 578.3; LC retention time: 4.01 min (analytical HPLC Method A); 1H NMR (400 MHz, CDCl$_3$) δ ppm 7.55-7.41 (m, 2H), 7.36-7.13 (m, 8H), 7.02-6.72 (m, 2H), 3.78-3.62 (m, 3H), 3.28 (d, J=10.8 Hz, 1H), 3.12-2.88 (m, 2H), 2.88-2.68 (m, 1H), 2.57-2.46 (m, 1H), 2.17-1.92 (m, 3H). The first eluent off the column was assigned as (S)-1-benzyl-3-((4-fluoro-3-methylphenyl)sulfonyl)-3-(4-(perfluoropropan-2-yl)phenyl)pyrrolidine (705 mg, 25% yield). LC/MS (M+1): 578.3; LC retention time: 4.01 min (analytical HPLC Method A); 1H NMR (400 MHz, CDCl$_3$) δ ppm 7.55-7.41 (m, 2H), 7.36-7.13 (m, 8H), 7.02-6.72 (m, 2H), 3.78-3.62 (m, 3H), 3.28 (d, J=10.8 Hz, 1H), 3.12-2.88 (m, 2H), 2.88-2.68 (m, 1H), 2.57-2.46 (m, 1H), 2.17-1.92 (m, 3H).

Example 368

(R)-1-(4-(3-((4-fluoro-3-methylphenyl)sulfonyl)-3-(4-(perfluoropropan-2-yl)phenyl)pyrrolidine-1-carbonyl)piperazin-1-yl)ethanone Step A: (R)-3-((4-fluoro-3-methylphenyl)sulfonyl)-3-(4-(perfluoropropan-2-yl)phenyl)pyrrolidine

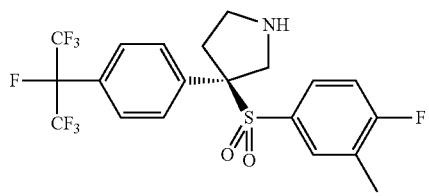 [SMILES: Cc1cc(S(=O)(=O)[C@@]2(c3ccc(C(F)(C(F)(F)F)C(F)(F)F)cc3)CCNC2)ccc1F]

A mixture of (R)-1-benzyl-3-((4-fluoro-3-methylphenyl)sulfonyl)-3-(4-(perfluoropropan-2-yl)phenyl)pyrrolidine (530 mg, 0.918 mmol, from Example 367) and 10% palladium on carbon (98 mg, 0.092 mmol) in methanol (10 mL) was hydrogenated under 40 psi hydrogen using a Parr Shaker for 5 h. The mixture was filtered to remove the catalyst. The filtrate was concentrated to give the desired (R)-3-((4-fluoro-3-methylphenyl)sulfonyl)-3-(4-(perfluoropropan-2-yl)phenyl)pyrrolidine (440 mg, 98% yield). LC/MS (M+1): 488.3; LC retention time: 0.88 min (analytical HPLC Method C); 1H NMR (400 MHz, CD$_3$OD) δ ppm 7.63 (d, J=8.4 Hz, 2H), 7.47-7.26 (m, 3H), 7.15 (t, J=8.9 Hz, 1H), 7.11-6.93 (m, 1H), 4.54 (d, J=13.4 Hz, 1H), 4.08-3.94 (m, 1H), 3.94-3.84 (m, 1H), 3.74-3.57 (m, 1H), 3.47-3.37 (m, 1H), 2.95-2.61 (m, 1H), 2.15 (d, 3H).

Step B: (R)-1-(4-(3-((4-fluoro-3-methylphenyl)sulfonyl)-3-(4-(perfluoropropan-2-yl)phenyl)pyrrolidine-1-carbonyl)piperazin-1-yl)ethanone

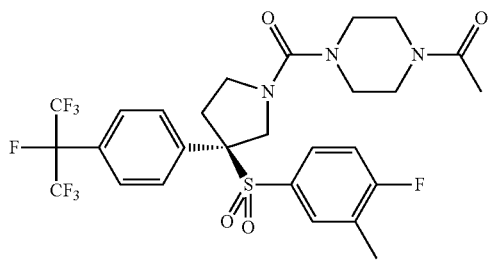 [SMILES: CC(=O)N1CCN(C(=O)N2CC[C@](c3ccc(C(F)(C(F)(F)F)C(F)(F)F)cc3)(S(=O)(=O)c3ccc(F)c(C)c3)C2)CC1]

Hunig's Base (0.011 mL, 0.063 mmol) was added dropwise to a mixture of (R)-3-((4-fluoro-3-methylphenyl)sulfonyl)-3-(4-(perfluoropropan-2-yl)phenyl)pyrrolidine (10 mg, 0.021 mmol) and 4-acetylpiperazine-1-carbonyl chloride (5.87 mg, 0.031 mmol) in dichloromethane (1 mL). After 1 h at room temperature, the mixture was concentrated under reduced pressure. The residue was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-100% B over 25 minutes, then a 5-minute hold at 100% B; Flow: 20 mL/min. Fractions containing the desired product were combined and dried via centrifugal evaporation to give Example 368 (7.0 mg, 53% yield). LC/MS (M+1): 642.3; LC retention time: 2.08 min (analytical HPLC Method B); 1H NMR (500 MHz, DMSO-d$_6$) δ ppm 7.63 (d, J=8.4 Hz, 2H), 7.49-7.35 (m, 3H), 7.35-7.26 (m, 1H), 7.11 (d, J=4.7 Hz, 1H), 4.53 (d, J=12.8 Hz, 1H), 3.96 (d, J=12.8 Hz, 1H), 3.75-3.56 (m, 1H), 3.58-3.29 (m, 3H), 3.27-2.94 (m, 7H), 2.70-2.56 (m, 1H), 2.13 (s, 3H), 2.03 (s, 3H).

Example 369

(S)-1-(4-(3-((4-fluoro-3-methylphenyl)sulfonyl)-3-(4-(perfluoropropan-2-yl)phenyl)pyrrolidine-1-carbonyl)piperazin-1-yl)ethanone Step A: (S)-3-((4-fluoro-3-methylphenyl)sulfonyl)-3-(4-(perfluoropropan-2-yl)phenyl)pyrrolidine

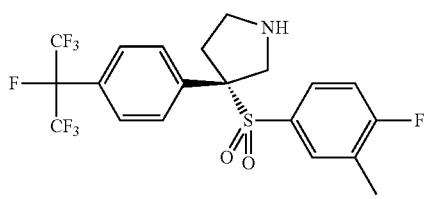 [SMILES: Cc1cc(S(=O)(=O)[C@]2(c3ccc(C(F)(C(F)(F)F)C(F)(F)F)cc3)CCNC2)ccc1F]

A mixture of (S)-1-benzyl-3-((4-fluoro-3-methylphenyl)sulfonyl)-3-(4-(perfluoropropan-2-yl)phenyl)pyrrolidine (705 mg, 1.22 mmol, from Example 367) and 10% palladium on carbon (130 mg, 0.122 mmol) in methanol (10 mL) was hydrogenated under 40 psi hydrogen using a Parr Shaker for 5 h. The mixture was filtered to remove the catalyst. The filtrate was concentrated to give the desired (R)-3-((4-fluoro-3-methylphenyl)sulfonyl)-3-(4-(perfluoropropan-2-yl)phenyl)pyrrolidine (590 mg, 99% yield). LC/MS (M+1): 488.3; LC retention time: 0.88 min (analytical HPLC Method C); 1H NMR (400 MHz, CD$_3$OD) δ ppm 7.63 (d, J=8.4 Hz, 2H), 7.47-7.26 (m, 3H), 7.15 (t, J=8.9 Hz, 1H), 7.11-6.93 (m, 1H), 4.54 (d, J=13.4 Hz, 1H), 4.08-3.94 (m, 1H), 3.94-3.84 (m, 1H), 3.74-3.57 (m, 1H), 3.47-3.37 (m, 1H), 2.95-2.61 (m, 1H), 2.15 (d, 3H).

Step B: (S)-1-(4-(3-((4-fluoro-3-methylphenyl)sulfonyl)-3-(4-(perfluoropropan-2-yl)phenyl)pyrrolidine-1-carbonyl)piperazin-1-yl)ethanone

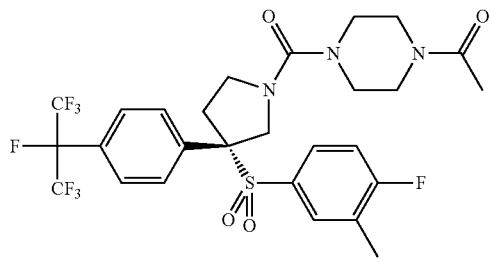 [SMILES: CC(=O)N1CCN(C(=O)N2CC[C@@](c3ccc(C(F)(C(F)(F)F)C(F)(F)F)cc3)(S(=O)(=O)c3ccc(F)c(C)c3)C2)CC1]

Hunig's Base (0.011 mL, 0.063 mmol) was added dropwise to a mixture of (R)-3-((4-fluoro-3-methylphenyl)sulfonyl)-3-(4-(perfluoropropan-2-yl)phenyl)pyrrolidine (10 mg, 0.021 mmol) and 4-acetylpiperazine-1-carbonyl chloride (5.87 mg, 0.031 mmol) in dichloromethane (1 mL).

After 1 h at room temperature, the mixture was concentrated under reduced pressure. The residue was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-100% B over 25 minutes, then a 5-minute hold at 100% B; Flow: 20 mL/min. Fractions containing the desired product were combined and dried via centrifugal evaporation to give Example 369 (9.3 mg, 71% yield). LC/MS (M+1): 642.3; LC retention time: 2.08 min (analytical HPLC Method B); 1HNMR (500 MHz, DMSO-$d_6$) δ ppm 7.63 (d, J=8.4 Hz, 2H), 7.49-7.35 (m, 3H), 7.35-7.26 (m, 1H), 7.11 (d, J=4.7 Hz, 1H), 4.53 (d, J=12.8 Hz, 1H), 3.96 (d, J=12.8 Hz, 1H), 3.75-3.56 (m, 1H), 3.58-3.29 (m, 3H), 3.27-2.94 (m, 7H), 2.70-2.56 (m, 1H), 2.13 (s, 3H), 2.03 (s, 3H).

The Examples in TABLE 2 below were prepared in the same manner as outlined in examples above.

TABLE 2

| Ex. No. | Structure | MS (M + 1) | HPLC ret. time (min.) | HPLC method |
|---|---|---|---|---|
| 370 | 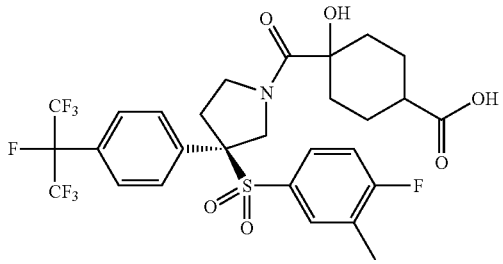<br>diastereomer A | 658.2 | 4.343 | A |
| 371 | 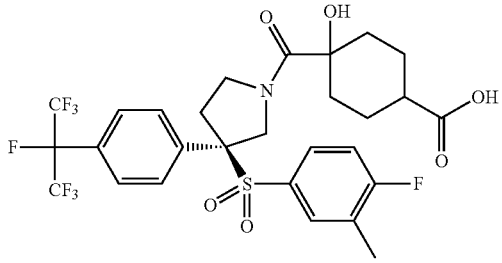<br>diastereomer B | 658.3 | 4.356 | A |
| 372 | 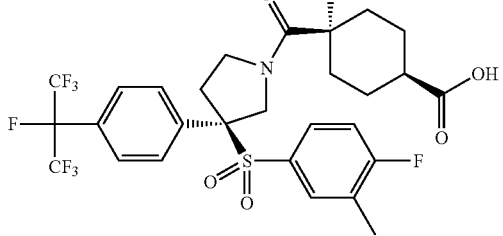 | 656.2 | 4.466 | A |
| 373 | 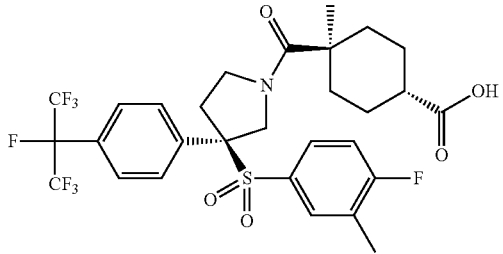 [SMILES: Cc1cc(S(=O)(=O)[C@@]2(c3ccc(C(F)(C(F)(F)F)C(F)(F)F)cc3)CCN(C(=O)[C@]3(C)CC[C@@H](C(=O)O)CC3)C2)ccc1F] | 656.2 | 4.450 | A |

TABLE 2-continued

| Ex. No. | Structure | MS (M + 1) | HPLC ret. time (min.) | HPLC method |
|---|---|---|---|---|
| 374 | 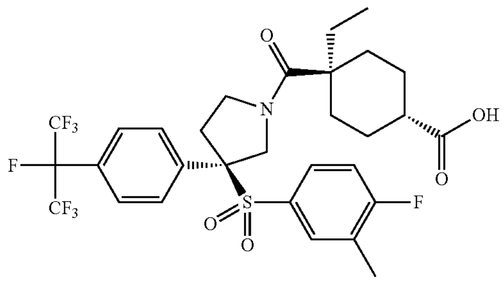 [SMILES: CC[C@]1(C(=O)N2CC[C@](c3ccc(C(F)(C(F)(F)F)C(F)(F)F)cc3)(S(=O)(=O)c3ccc(F)c(C)c3)C2)CC[C@H](C(=O)O)CC1] | 670.1 | 4.511 | A |
| 375 | 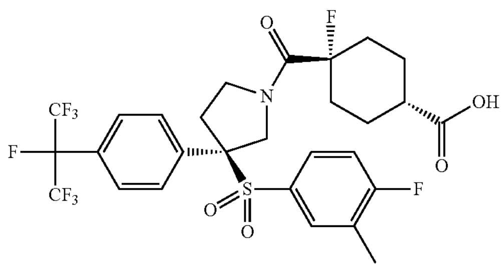 [SMILES: Cc1cc(S(=O)(=O)[C@@]2(c3ccc(C(F)(C(F)(F)F)C(F)(F)F)cc3)CCN(C(=O)[C@]3(F)CC[C@@H](C(=O)O)CC3)C2)ccc1F] | 660.1 | 4.498 | A |
| 376 | 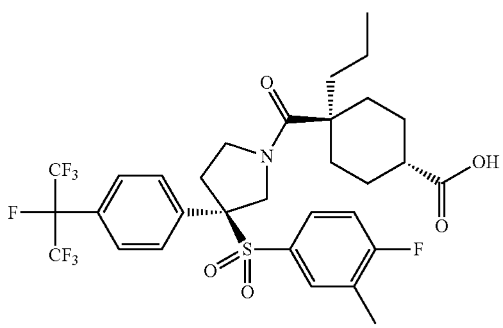 [SMILES: CCC[C@]1(C(=O)N2CC[C@](c3ccc(C(F)(C(F)(F)F)C(F)(F)F)cc3)(S(=O)(=O)c3ccc(F)c(C)c3)C2)CC[C@H](C(=O)O)CC1] | 684.3 | 2.249 | B |
| 377 | 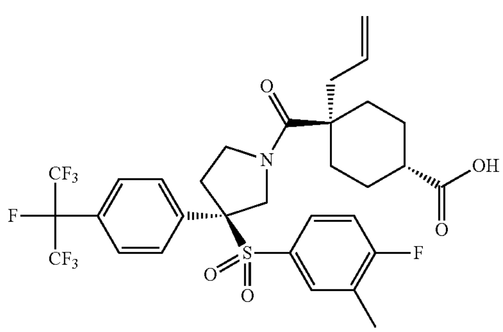 | 682.3 | 2.543 | D |
| 378 | 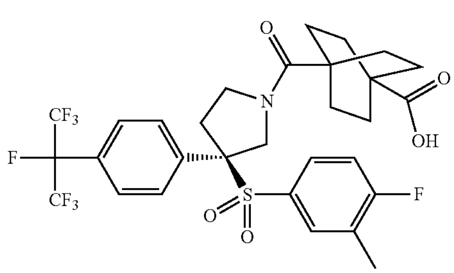 [SMILES: Cc1cc(S(=O)(=O)[C@@]2(c3ccc(C(F)(C(F)(F)F)C(F)(F)F)cc3)CCN(C(=O)C34CCC(C(=O)O)(CC3)CC4)C2)ccc1F] | 668.3 | 2.089 | B |

TABLE 2-continued

| Ex. No. | Structure | MS (M + 1) | HPLC ret. time (min.) | HPLC method |
|---|---|---|---|---|
| 379 | 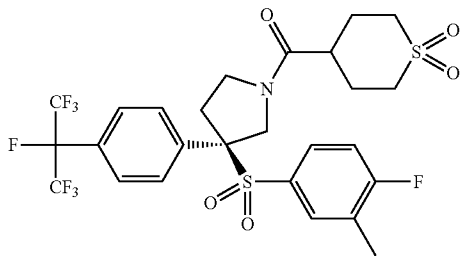 [SMILES: Cc1cc(S(=O)(=O)[C@@]2(c3ccc(C(F)(C(F)(F)F)C(F)(F)F)cc3)CCN(C(=O)C3CCS(=O)(=O)CC3)C2)ccc1F] | 648.1 | 2.078 | B |
| 380 | 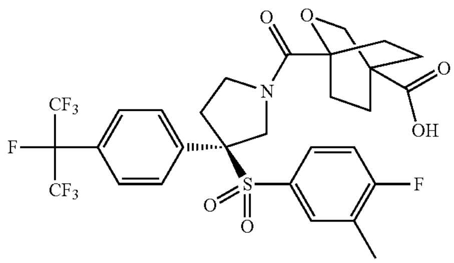 [SMILES: Cc1cc(S(=O)(=O)[C@@]2(c3ccc(C(F)(C(F)(F)F)C(F)(F)F)cc3)CCN(C(=O)C34CCC(C(=O)O)(CC3)CO4)C2)ccc1F] | 670.2 | 1.974 | B |
| 381 | 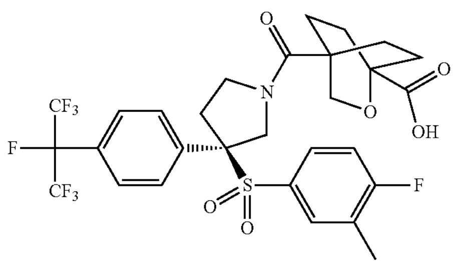 | 670.2 | 1.717 | B |
| 382 | 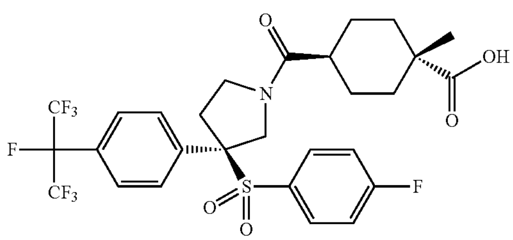 [SMILES: C[C@]1(C(=O)O)CC[C@H](C(=O)N2CC[C@](c3ccc(C(F)(C(F)(F)F)C(F)(F)F)cc3)(S(=O)(=O)c3ccc(F)cc3)C2)CC1] | 642.3 | 2.027 | B |
| 383 | 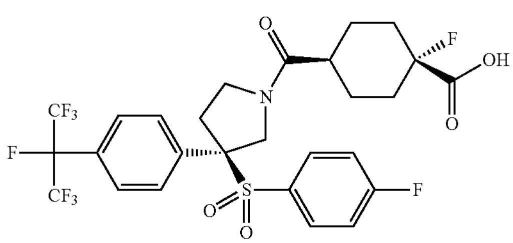 [SMILES: O=C([C@H]1CC[C@@](F)(C(=O)O)CC1)N1CC[C@](c2ccc(C(F)(C(F)(F)F)C(F)(F)F)cc2)(S(=O)(=O)c2ccc(F)cc2)C1] | 646.3 | 4.25 | A |
| 384 | 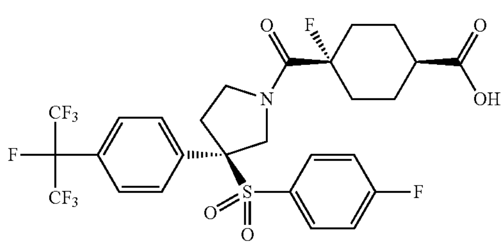 [SMILES: O=C(O)[C@H]1CC[C@@](F)(C(=O)N2CC[C@](c3ccc(C(F)(C(F)(F)F)C(F)(F)F)cc3)(S(=O)(=O)c3ccc(F)cc3)C2)CC1] | 646.3 | 4.44 | A |

TABLE 2-continued

| Ex. No. | Structure | MS (M + 1) | HPLC ret. time (min.) | HPLC method |
|---|---|---|---|---|
| 385 | 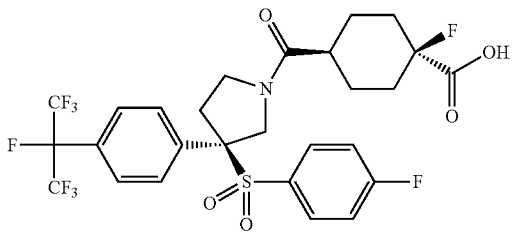 [SMILES: O=C([C@H]1CC[C@](F)(C(=O)O)CC1)N1CC[C@](c2ccc(C(F)(C(F)(F)F)C(F)(F)F)cc2)(S(=O)(=O)c2ccc(F)cc2)C1] | 646.3 | 4.19 | A |
| 386 | 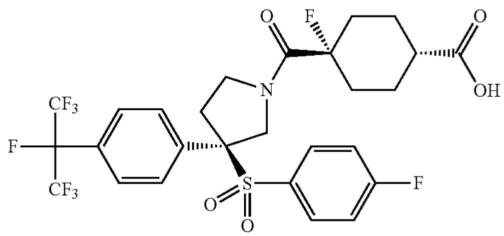 [SMILES: O=C(O)[C@H]1CC[C@](F)(C(=O)N2CC[C@](c3ccc(C(F)(C(F)(F)F)C(F)(F)F)cc3)(S(=O)(=O)c3ccc(F)cc3)C2)CC1] | 646.3 | 4.35 | A |
| 387 | 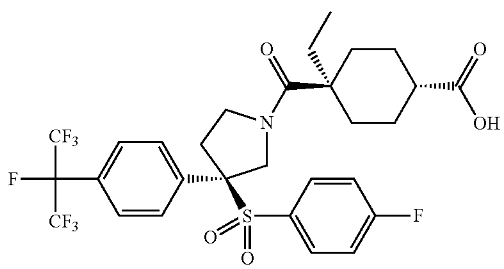 [SMILES: CC[C@]1(C(=O)N2CC[C@](c3ccc(C(F)(C(F)(F)F)C(F)(F)F)cc3)(S(=O)(=O)c3ccc(F)cc3)C2)CC[C@H](C(=O)O)CC1] | 656.1 | 4.40 | A |
| 388 | 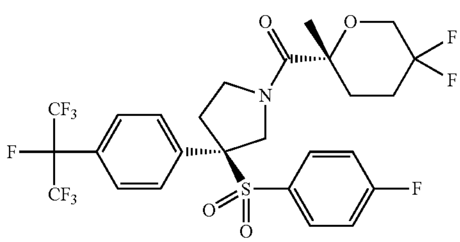 [SMILES: C[C@]1(C(=O)N2CC[C@](c3ccc(C(F)(C(F)(F)F)C(F)(F)F)cc3)(S(=O)(=O)c3ccc(F)cc3)C2)CCC(F)(F)CO1] | 636.1 | 2.405 | B |
| 389 | 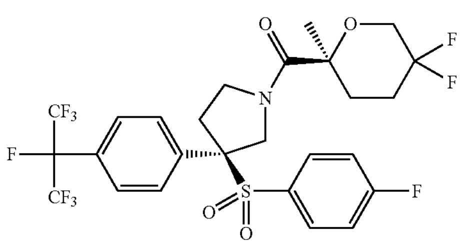 [SMILES: C[C@@]1(C(=O)N2CC[C@](c3ccc(C(F)(C(F)(F)F)C(F)(F)F)cc3)(S(=O)(=O)c3ccc(F)cc3)C2)CCC(F)(F)CO1] | 636.1 | 2.399 | B |
| 390 | 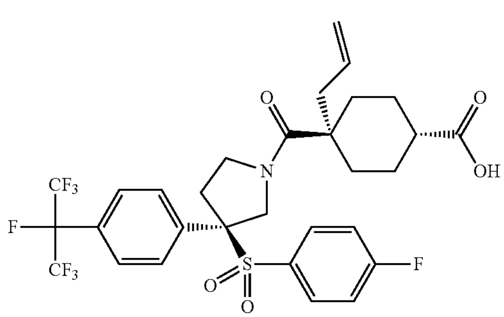 [SMILES: C=CC[C@]1(C(=O)N2CC[C@](c3ccc(C(F)(C(F)(F)F)C(F)(F)F)cc3)(S(=O)(=O)c3ccc(F)cc3)C2)CC[C@H](C(=O)O)CC1] | 668.1 | 2.226 | B |

TABLE 2-continued

| Ex. No. | Structure | MS (M + 1) | HPLC ret. time (min.) | HPLC method |
|---|---|---|---|---|
| 391 | 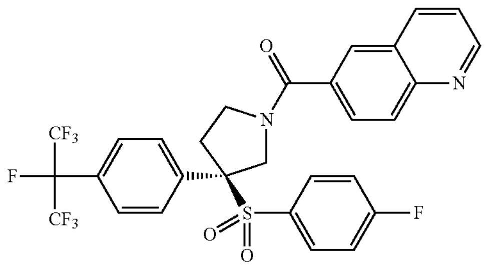 [SMILES: O=C(c1ccc2ncccc2c1)N1CC[C@](c2ccc(C(F)(C(F)(F)F)C(F)(F)F)cc2)(S(=O)(=O)c2ccc(F)cc2)C1] | 629.1 | 0.92 | C |
| 392 | 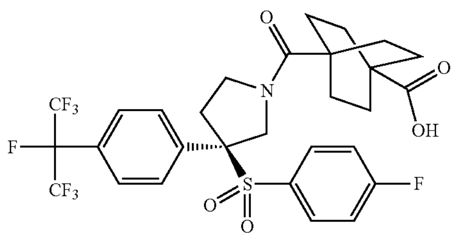 | 654.2 | 1.872 | B |
| 393 | 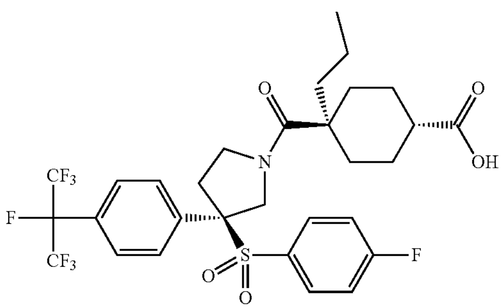 [SMILES: CCC[C@]1(C(=O)N2CC[C@](c3ccc(C(F)(C(F)(F)F)C(F)(F)F)cc3)(S(=O)(=O)c3ccc(F)cc3)C2)CC[C@H](C(=O)O)CC1] | 670.1 | 1.07 | C |
| 394 | 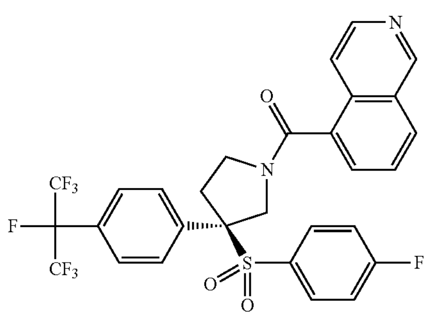 [SMILES: O=C(c1cccc2cnccc12)N1CC[C@](c2ccc(C(F)(C(F)(F)F)C(F)(F)F)cc2)(S(=O)(=O)c2ccc(F)cc2)C1] | 629.1 | 2.122 | B |
| 395 | 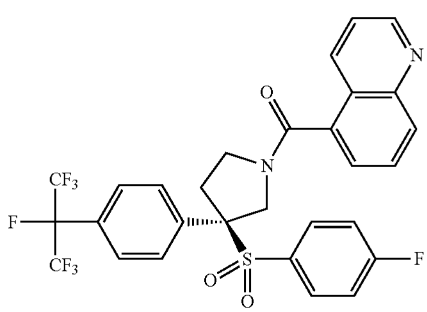 [SMILES: O=C(c1cccc2ncccc12)N1CC[C@](c2ccc(C(F)(C(F)(F)F)C(F)(F)F)cc2)(S(=O)(=O)c2ccc(F)cc2)C1] | 629.1 | 2.139 | B |

TABLE 2-continued

| Ex. No. | Structure | MS (M + 1) | HPLC ret. time (min.) | HPLC method |
|---|---|---|---|---|
| 396 | 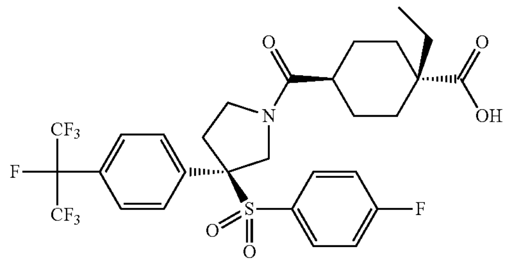 [SMILES: CC[C@]1(C(=O)O)CC[C@H](C(=O)N2CC[C@](c3ccc(C(F)(C(F)(F)F)C(F)(F)F)cc3)(S(=O)(=O)c3ccc(F)cc3)C2)CC1] | 656.3 | 2.047 | B |
| 397 | 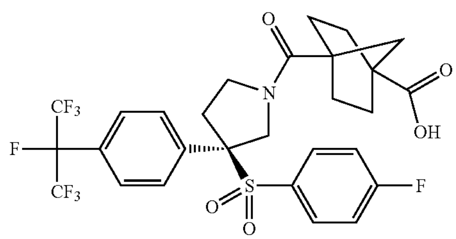 [SMILES: O=C(O)C12CCC(C(=O)N3CC[C@](c4ccc(C(F)(C(F)(F)F)C(F)(F)F)cc4)(S(=O)(=O)c4ccc(F)cc4)C3)(CC1)C2] | 640.4 | 1.868 | B |
| 398 | 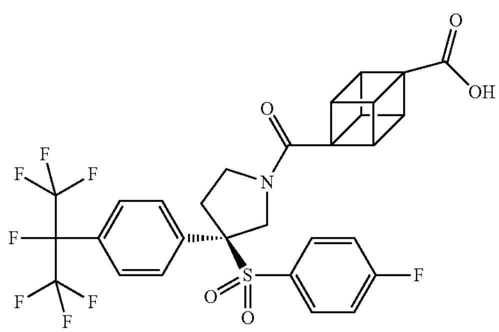 [SMILES: O=C(O)C12C3C4C1C1C2C3C41C(=O)N1CC[C@](c2ccc(C(F)(C(F)(F)F)C(F)(F)F)cc2)(S(=O)(=O)c2ccc(F)cc2)C1] | 648.4 | 4.25 | A |
| 399 | 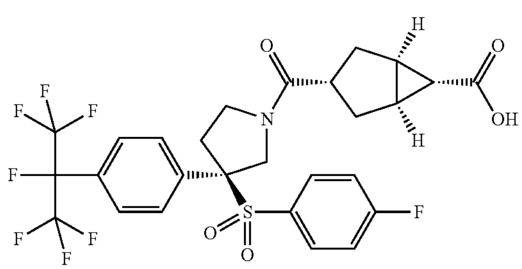 [SMILES: O=C(O)[C@H]1[C@@H]2C[C@@H](C(=O)N3CC[C@](c4ccc(C(F)(C(F)(F)F)C(F)(F)F)cc4)(S(=O)(=O)c4ccc(F)cc4)C3)C[C@@H]21] | 626.2 | 1.733 | B |
| 400 | 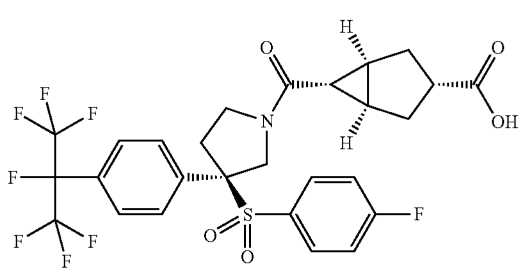 [SMILES: O=C(O)[C@@H]1C[C@@H]2[C@H](C1)[C@H]2C(=O)N1CC[C@](c2ccc(C(F)(C(F)(F)F)C(F)(F)F)cc2)(S(=O)(=O)c2ccc(F)cc2)C1] | 626.1 | 4.20 | A |

TABLE 2-continued

| Ex. No. | Structure | MS (M + 1) | HPLC ret. time (min.) | HPLC method |
|---|---|---|---|---|
| 401 | 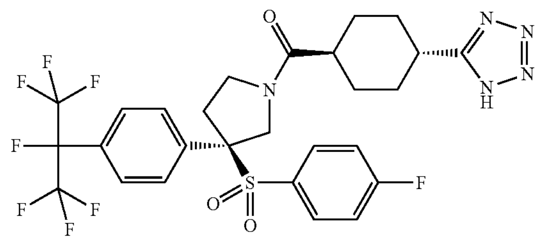 [SMILES: O=C([C@H]1CC[C@H](c2nnn[nH]2)CC1)N1CC[C@](c2ccc(C(F)(C(F)(F)F)C(F)(F)F)cc2)(S(=O)(=O)c2ccc(F)cc2)C1] | 652.1 | 1.698 | B |
| 402 | 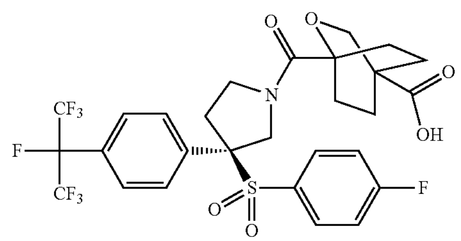 [SMILES: O=C(O)C12CCC(C(=O)N3CC[C@](c4ccc(C(F)(C(F)(F)F)C(F)(F)F)cc4)(S(=O)(=O)c4ccc(F)cc4)C3)(CC1)OC2] | 656.2 | 1.655 | B |
| 403 | 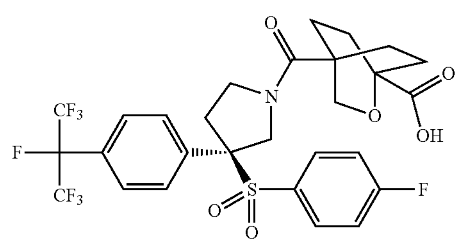 [SMILES: O=C(N1CC[C@](c2ccc(C(F)(C(F)(F)F)C(F)(F)F)cc2)(S(=O)(=O)c2ccc(F)cc2)C1)C12CCC(C(=O)O)(CC1)OC2] | 656.1 | 1.585 | B |
| 404 | 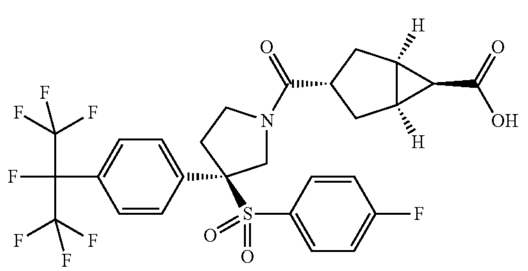 [SMILES: O=C(O)[C@@H]1[C@@H]2C[C@@H](C(=O)N3CC[C@](c4ccc(C(F)(C(F)(F)F)C(F)(F)F)cc4)(S(=O)(=O)c4ccc(F)cc4)C3)C[C@@H]21] | 626.1 | 1.690 | B |
| 405 | Diastereomer A | 668.1 | 4.13 | A |

TABLE 2-continued

| Ex. No. | Structure | MS (M + 1) | HPLC ret. time (min.) | HPLC method |
|---|---|---|---|---|
| 405 | Diastereomer B | 668.1 | 4.20 | A |
| 407 | 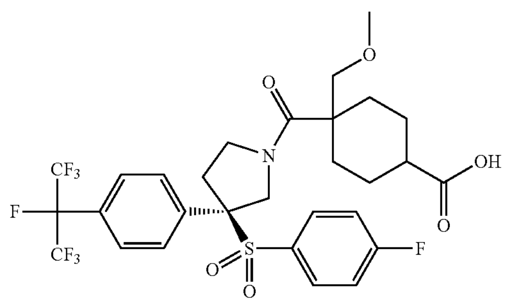 [SMILES: COCC1(C(=O)N2CC[C@](c3ccc(C(F)(C(F)(F)F)C(F)(F)F)cc3)(S(=O)(=O)c3ccc(F)cc3)C2)CCC(C(=O)O)CC1] | 672.1 | 4.33 | A |
| | Diastereomer A | 660.1 | 4.26 | A |
| 409 | Diastereomer B | 660.1 | 4.28 | A |
| 410 | 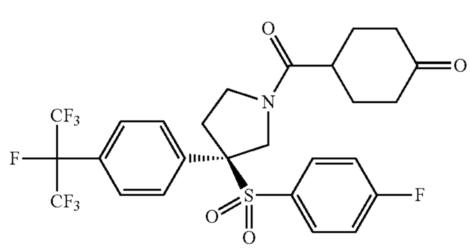 [SMILES: O=C1CCC(C(=O)N2CC[C@](c3ccc(C(F)(C(F)(F)F)C(F)(F)F)cc3)(S(=O)(=O)c3ccc(F)cc3)C2)CC1] | 598.1 | 4.18 | A |

TABLE 2-continued

| Ex. No. | Structure | MS (M + 1) | HPLC ret. time (min.) | HPLC method |
|---|---|---|---|---|
| 411 | 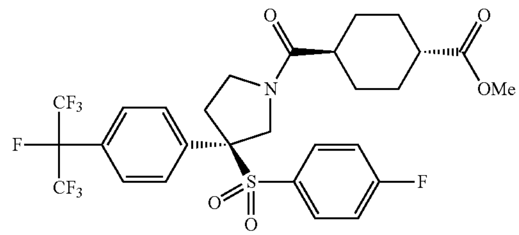 [SMILES: COC(=O)[C@H]1CC[C@H](C(=O)N2CC[C@](c3ccc(C(F)(C(F)(F)F)C(F)(F)F)cc3)(S(=O)(=O)c3ccc(F)cc3)C2)CC1] | 642.2 | 4.37 | A |

Example 412

1-((1R,4r)-4-((R)-3-((4-fluorophenyl)sulfonyl)-3-(4-(perfluoropropan-2-yl)phenyl)pyrrolidone-1-carbonyl)bicyclo[2.2.1]heptan-1-yl)ethanone Step A: 4-((R)-3-((4-fluorophenyl)sulfonyl)-3-(4-(perfluoropropan-2-yl)phenyl)pyrrolidine-1-carbonyl)-N-methoxy-N-methylbicyclo[2.2.1]heptane-1-carboxamide

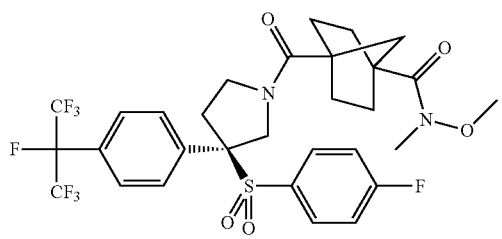 [SMILES: CON(C)C(=O)C12CCC(C(=O)N3CC[C@](c4ccc(C(F)(C(F)(F)F)C(F)(F)F)cc4)(S(=O)(=O)c4ccc(F)cc4)C3)(CC1)C2]

Hunig's Base (0.021 mL, 0.119 mmol) was added to a mixture of (1R,4r)-4-((R)-3-((4-fluorophenyl)sulfonyl)-3-(4-(perfluoropropan-2-yl)phenyl)pyrrolidine-1-carbonyl)bicyclo[2.2.1]heptane-1-carboxylic acid (19 mg, 0.030 mmol), 1-[bis(dimethylamino)methylene]-1H-1,2,3-triazolo[4,5-b]pyridinium 3-oxid hexafluorophosphate (16.94 mg, 0.045 mmol) and N,O-dimethylhydroxylamine hydrogen chloride salt (4.35 mg, 0.045 mmol) in N,N-dimethylformamide (1 mL). After stirring at ambient temperature for 2 h, the mixture was diluted with ethyl acetate (60 mL), washed with water (5 mL), brine (5 mL), dried (magnesium sulfate), filtered and concentrated under reduced pressure. Silica gel chromatography, eluting with 10-60% ethyl acetate in hexanes, gave the desired 4-((R)-3-(4-fluorophenyl)sulfonyl)-3-(4-(perfluoropropan-2-yl)phenyl)pyrrolidine-1-carbonyl)-N-methoxy-N-methylbicyclo[2.2.1]heptane-1-carboxamide (7.0 mg, 35% yield). LC/MS (M+1): 682.4; LC retention time: 1.04 min (analytical HPLC Method C).

Step B: 1-((1R,4r)-4-((R)-3-((4-fluorophenyl)sulfonyl)-3-(4-(perfluoropropan-2-yl)phenyl)pyrrolidine-1-carbonyl)bicyclo[2.2.1]heptan-1-yl)ethanone

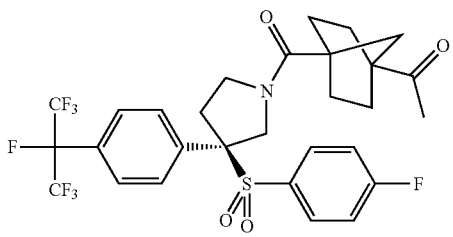 [SMILES: CC(=O)C12CCC(C(=O)N3CC[C@](c4ccc(C(F)(C(F)(F)F)C(F)(F)F)cc4)(S(=O)(=O)c4ccc(F)cc4)C3)(CC1)C2]

A 3.0 M diethyl ether solution of methylmagnesium bromide (10.25 µl, 0.031 mmol) was added to a mixture of (1R,4r)-4-((R)-3-((4-fluorophenyl)sulfonyl)-3-(4-(perfluoropropan-2-yl)phenyl)pyrrolidine-1-carbonyl)-N-methoxy-N-methylbicyclo[2.2.1]heptane-1-carboxamide (7 mg, 10.25 µmol) in tetrahydrofuran (1 mL) at 0° C. and stirred for 30 min. After quenching with saturated ammonium chloride (1 mL), the mixture was diluted with ethyl acetate (50 mL), washed with water (5 mL), brine (5 mL), dried (magnesium sulfate), filtered and concentrated under reduced pressure. Silica gel chromatography, eluting with 10-70% ethyl acetate in hexanes, gave Example 412 (3.5 mg, 48% yield). LC/MS (M+1): 638.3; LC retention time: 4.32 min (analytical HPLC Method A); 1H NMR (400 MHz, CD$_3$OD) δ ppm 7.66-7.51 (m, 2H), 7.47-7.30 (m, 4H), 7.16 (t, J=8.6 Hz, 2H), 5.12-4.91 (m, 1H), 4.24-4.01 (m, 1H), 3.99-3.83 (m, 2H), 3.22-2.97 (m, 1H), 2.82-2.53 (m, 1H), 2.26-2.17 (m, 3H), 2.13-1.64 (m, 10H).

Example 413

((R)-3-((4-fluorophenyl)sulfonyl)-3-(4-(perfluoropropan-2-yl)phenyl)pyrrolidin-1-yl)(4-(2-hydroxypropan-2-yl)bicyclo[2.2.1]heptan-1-yl)methanone Step A: methyl 4-((R)-3-((4-fluorophenyl)sulfonyl)-3-(4-(perfluoropropan-2-yl)phenyl)pyrrolidine-1-carbonyl)bicyclo[2.2.1]heptane-1-carboxylate

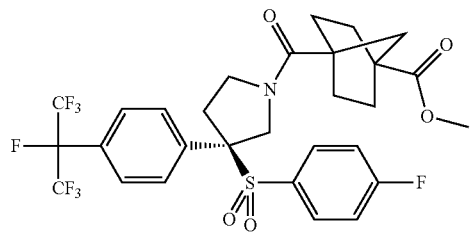 [SMILES: COC(=O)C12CCC(C(=O)N3CC[C@](c4ccc(C(F)(C(F)(F)F)C(F)(F)F)cc4)(S(=O)(=O)c4ccc(F)cc4)C3)(CC1)C2]

Hunig's Base (0.054 mL, 0.306 mmol) was added to a mixture of (R)-3-(4-fluorophenyl)sulfonyl)-3-(4-(perfluoropropan-2-yl)phenyl)pyrrolidine trifluoroacetic acid salt (45 mg, 0.077 mmol), 1-[bis(dimethylamino)methylene]-1H-1,2,3-triazolo[4,5-b]pyridinium 3-oxid hexafluorophosphate (43.7 mg, 0.115 mmol) and (1r,4r)-4-(methoxycarbonyl)bicyclo[2.2.1]heptane-1-carboxylic acid (22.78 mg, 0.115 mmol) in N,N-dimethylformamide (1 mL). After stirring at ambient temperature for 2 h, the mixture was diluted with ethyl acetate (60 mL), washed with water (5 mL), brine (5 mL), dried (magnesium sulfate), filtered and concentrated under reduced pressure. Silica gel chromatography, eluting with 10-60% ethyl acetate in hexanes, gave the desired methyl 4-((R)-3-((4-fluorophenyl)sulfonyl)-3-(4-(perfluoropropan-2-yl)phenyl)pyrrolidine-1-carbonyl)bicyclo[2.2.1]heptane-1-carboxylate (30.0 mg, 60% yield). LC/MS (M+1): 654.4; LC retention time: 1.09 min (analytical HPLC Method C); 1H NMR (400 MHz, CDCl$_3$) δ ppm 7.50 (d, J=8.1 Hz, 2H), 7.33-7.17 (m, 4H), 7.04-6.83 (m, 2H), 4.81 (d, J=14.1 Hz, 1H), 4.17-4.01 (m, 1H), 4.07-3.87 (m, 1H), 3.79 (t, J=9.1 Hz, 1H), 3.72 (s, 3H), 3.53-3.31 (m, 1H), 2.64-2.55 (m, 1H), 2.19-1.61 (m, 10H).

Step B: ((R)-3-((4-fluorophenyl)sulfonyl)-3-(4-(perfluoropropan-2-yl)phenyl)pyrrolidin-1-yl)(4-(2-hydroxypropan-2-yl)bicyclo[2.2.1]heptan-1-yl)methanone

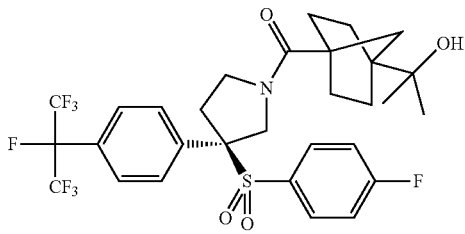 [SMILES: CC(C)(O)C12CCC(C(=O)N3CC[C@](c4ccc(C(F)(C(F)(F)F)C(F)(F)F)cc4)(S(=O)(=O)c4ccc(F)cc4)C3)(CC1)C2]

A 1.6 M diethyl ether solution of methylmagnesium bromide (0.026 mL, 0.038 mmol) was added to a mixture of (1R,4r)-methyl 4-((R)-3-((4-fluorophenyl)sulfonyl)-3-(4-(perfluoropropan-2-yl)phenyl)pyrrolidine-1-carbonyl)bicyclo[2.2.1]heptane-1-carboxylate (10 mg, 0.015 mmol) in tetrahydrofuran (1 mL) at −78° C. and stirred for 30 min. After quenching with methanol (0.2 mL), the mixture was warmed to room temperature. The crude material was purified via preparative LC/MS with the following conditions: Column: Waters XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-100% B over 20 minutes, then a 5-minute hold at 100% B; Flow: 20 mL/min. Fractions containing the desired product were combined and dried via centrifugal evaporation to give Example 413 (5.1 mg, 50% yield). LC/MS (M+1): 648.2; HPLC RT=2.334 min (analytical HPLC Method B). 1H NMR (500 MHz, DMSO-d$_6$) δ ppm 7.71-7.50 (m, 2H), 7.56-7.35 (m, 4H), 7.35-7.21 (m, 2H), 5.02-4.64 (m, 1H), 4.22-3.95 (m, 1H), 3.88-3.65 (m, 1H), 3.51 (d, J=9.8 Hz, 1H), 3.22-2.90 (m, 1H), 2.85-2.60 (m, 1H), 2.05-1.44 (m, 8H), 1.40-1.18 (m, 2H), 1.16-1.02 (m, 6H).

Example 414

(1R,4r)-4-((R)-3-((4-azidophenyl)sulfonyl)-3-(4-(perfluoropropan-2-yl)phenyl)pyrrolidine-1-carbonyl)cyclohexanecarboxylic acid

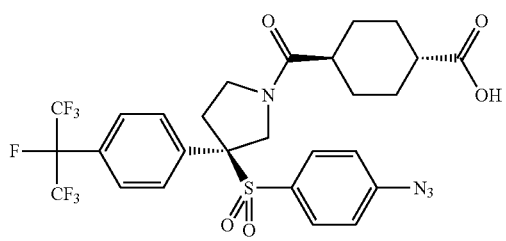

A mixture of (1R,4r)-4-((R)-3-((4-fluorophenyl)sulfonyl)-3-(4-(perfluoropropan-2-yl)phenyl)pyrrolidine-1-carbonyl)cyclohexanecarboxylic acid (20 mg, 0.032 mmol, Example 95) and sodium azide (20.72 mg, 0.319 mmol) in N,N-dimethylformamide (0.5 mL) was stirred at 80° C. for 15 h and cooled down to room temperature. The crude material was purified via preparative LC/MS with the following conditions: Column: Waters XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-100% B over 20 minutes, then a 5-minute hold at 100% B; Flow: 20 mL/min. Fractions containing the desired product were combined and dried via centrifugal evaporation to give Example 414 (16.0 mg, 73% yield). LC/MS (M+1): 651.1; HPLC RT=4.32 min (analytical HPLC Method A). 1H NMR (400 MHz, CD$_3$OD) δ ppm 7.59 (d, J=8.4 Hz, 2H), 7.50-7.16 (m, 4H), 7.10-6.85 (m, 2H), 5.07-4.93 (m, 1H), 4.16-3.75 (m, 2H), 3.78-3.58 (m, 1H), 2.83-2.52 (m, 1H), 2.53-2.20 (m, 2H), 2.20-1.76 (m, 4H), 1.68-1.44 (m, 4H).

Example 415

(1R,4r)-4-((R)-3-((4-chlorophenyl)sulfonyl)-3-(4-(perfluoropropan-2-yl)phenyl)pyrrolidine-1-carbonyl)cyclohexanecarboxylic acid Step A: (1R,4r)-4-((R)-3-((4-aminophenyl)sulfonyl)-3-(4-(perfluoropropan-2-yl)phenyl)pyrrolidine-1-carbonyl)cyclohexanecarboxylic acid

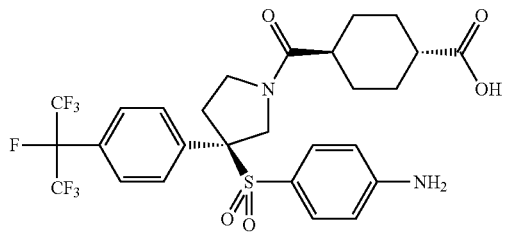

A mixture of (1R,4r)-4-((R)-3-((4-azidophenyl)sulfonyl)-3-(4-(perfluoropropan-2-yl)phenyl)pyrrolidine-1-carbonyl)cyclohexanecarboxylic acid (20 mg, 0.031 mmol) and 10% palladium on carbon (6.54 mg, 0.0062 mmol) in methanol (10 mL) was hydrogenated under 40 psi hydrogen using a Parr Shaker for 4 h. The mixture was filtered to remove the catalyst. The filtrate was concentrated to give the desired (1R,4r)-4-((R)-3-((4-aminophenyl)sulfonyl)-3-(4-(perfluoropropan-2-yl)phenyl)pyrrolidine-1-carbonyl)cyclohexanecarboxylic acid (18 mg, 93% yield). LC/MS (M+1): 652.1; LC retention time: 3.89 min (analytical HPLC Method A); 1H NMR (400 MHz, CD$_3$OD) δ ppm 7.60 (d, J=8.4 Hz, 2H), 7.49-7.29 (m, 2H), 7.12-6.88 (m, 2H), 6.69-6.32 (m, 2H), 4.80-4.58 (m, 1H), 3.83 (m, 2H), 3.26-3.07 (m, 1H), 2.77-2.32 (m, 2H), 2.02 (m, 5H), 1.65-1.33 (m, 5H).

Step B: (1R,4r)-4-((R)-3-((4-chlorophenyl)sulfonyl)-3-(4-(perfluoropropan-2-yl)phenyl)pyrrolidine-1-carbonyl)cyclohexanecarboxylic acid

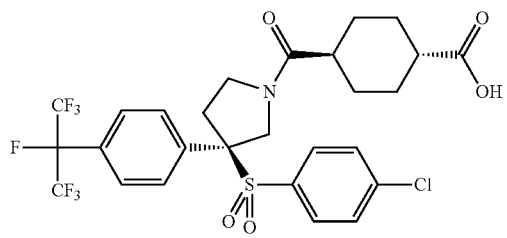 [SMILES: O=C(O)[C@H]1CC[C@H](C(=O)N2CC[C@](c3ccc(C(F)(C(F)(F)F)C(F)(F)F)cc3)(S(=O)(=O)c3ccc(Cl)cc3)C2)CC1]

A solution of (1R,4r)-4-((R)-3-((4-aminophenyl)sulfonyl)-3-(4-(perfluoropropan-2-yl)phenyl)pyrrolidine-1-carbonyl)cyclohexanecarboxylic acid (10 mg, 0.016 mmol) in acetonitrile (0.5 mL) was added to a mixture of tert-butyl nitrite (2.477 mg, 0.024 mmol) and copper(I) chloride (2.378 mg, 0.024 mmol) in acetonitrile (0.5 mL) at 65° dropwise over 3 min. After stirring at 65° C. for 15 min, the mixture was cooled to room temperature and added 1 N aqueous hydrogen chloride (0.1 mL). The crude material was purified via preparative LC/MS with the following conditions: Column: Waters XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-100% B over 20 minutes, then a 5-minute hold at 100% B; Flow: 20 mL/min. Fractions containing the desired product were combined and dried via centrifugal evaporation to give Example 415 (3.0 mg, 26% yield). LC/MS (M+1): 644.0; HPLC RT=4.39 min (analytical HPLC Method A). 1H NMR (400 MHz, CD$_3$OD) δ ppm 7.69-7.49 (m, 2H), 7.49-7.19 (m, 6H), 5.05-4.88 (m, 1H), 4.25-3.89 (m, 2H), 3.88-3.51 (m, 2H), 2.79-2.56 (m, 1H), 2.56-2.19 (m, 2H), 2.16-1.79 (m, 4H), 1.67-1.45 (m, 4H).

Example 416

(1R,4r)-4-((R)-3-((4-bromophenyl)sulfonyl)-3-(4-(perfluoropropan-2-yl)phenyl)pyrrolidine-1-carbonyl)cyclohexanecarboxylic acid

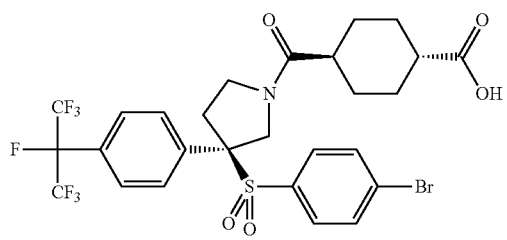 [SMILES: O=C(O)[C@H]1CC[C@H](C(=O)N2CC[C@](c3ccc(C(F)(C(F)(F)F)C(F)(F)F)cc3)(S(=O)(=O)c3ccc(Br)cc3)C2)CC1]

A solution of (1R,4r)-4-((R)-3-((4-aminophenyl)sulfonyl)-3-(4-(perfluoropropan-2-yl)phenyl)pyrrolidine-1-carbonyl)cyclohexanecarboxylic acid (50 mg, 0.080 mmol) in acetonitrile (1 mL) was added to a mixture of tert-butyl nitrite (12.4 mg, 0.120 mmol) and copper(II) bromide (26.8 mg, 0.120 mmol) in acetonitrile (1 mL) at 65° dropwise over 5 min. After stirring at 65° C. for 15 min, the mixture was cooled to room temperature and added 1 N aqueous hydrogen chloride (0.2 mL). The crude material was purified via preparative LC/MS with the following conditions: Column: Waters XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-100% B over 20 minutes, then a 5-minute hold at 100% B; Flow: 20 mL/min. Fractions containing the desired product were combined and dried via centrifugal evaporation to give Example 416 (22.0 mg, 36% yield). LC/MS (M+1): 690.0; HPLC RT=4.38 min (analytical HPLC Method A). 1H NMR (400 MHz, CDCl$_3$) δ ppm 7.59-7.44 (m, 4H), 7.21 (d, J=8.4 Hz, 2H), 7.18-7.06 (m, 2H), 4.82 (d, J=13.9 Hz, 1H), 4.17-4.00 (m, 1H), 3.94-3.83 (m, 1H), 3.83-3.72 (m, 1H), 3.48 (d, J=5.7 Hz, 1H), 2.67 (dt, J=14.2, 9.5 Hz, 1H), 2.48-2.31 (m, 2H), 2.28-2.10 (m, 2H), 2.05 (d, J=13.4 Hz, 1H), 1.84 (d, J=12.7 Hz, 1H), 1.72-1.57 (m, 2H), 1.57-1.35 (m, 2H).

It also gave a side product: (1R,4r)-4-((R)-3-((3,4-dibromophenyl)sulfonyl)-3-(4-(perfluoropropan-2-yl)phenyl)pyrrolidine-1-carbonyl)cyclohexanecarboxylic acid (8.0 mg, 13% yield). LC/MS (M+1): 768.0; HPLC RT=1.09 min (analytical HPLC Method C); 1H NMR (400 MHz, CDCl$_3$) δ ppm 7.74-7.48 (m, 3H), 7.32-7.13 (m, 4H), 4.85-4.66 (m, 1H), 4.14-3.99 (m, 1H), 3.87 (d, J=14.1 Hz, 1H), 3.83-3.64 (m, 1H), 3.43 (dd, J=13.8, 6.7 Hz, 1H), 2.65 (dt, J=14.2, 9.4 Hz, 1H), 2.47-2.27 (m, 2H), 2.15 (t, J=15.5 Hz, 2H), 2.02 (d, J=13.0 Hz, 1H), 1.80 (d, J=11.9 Hz, 1H), 1.70-1.57 (m, 2H), 1.57-1.37 (m, 2H).

Example 417

(1R,4r)-4-((R)-3-(4-(perfluoropropan-2-yl)phenyl)-3-tosylpyrrolidine-1-carbonyl)cyclohexanecarboxylic acid

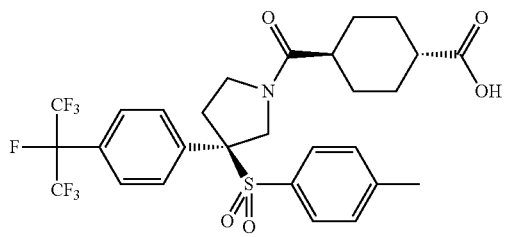 [SMILES: Cc1ccc(S(=O)(=O)[C@@]2(c3ccc(C(F)(C(F)(F)F)C(F)(F)F)cc3)CCN(C(=O)[C@H]3CC[C@H](C(=O)O)CC3)C2)cc1]

A mixture of (1R,4r)-4-((R)-3-((4-bromophenyl)sulfonyl)-3-(4-(perfluoropropan-2-yl)phenyl)pyrrolidine-1-carbonyl)cyclohexanecarboxylic acid (13 mg, 0.019 mmol), 2,4,6-trimethyl-1,3,5,2,4,6-trioxatriborinane (3.56 mg, 0.028 mmol), palladium tetrakis (4.36 mg, 3.78 μmol) and 2.0 M aqueous potassium phosphate (0.019 mL, 0.038 mmol) in N,N-dimethylformamide (0.5 mL) was degassed with nitrogen in a sealed vial and heated to 90° C. for 2 h. The mixture was cooled down to room temperature and purified via preparative LC/MS with the following conditions: Column: Waters XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-100% B over 20 minutes, then a 5-minute hold at 100% B; Flow: 20 mL/min. Fractions containing the desired product were combined and dried via centrifugal evaporation to give Example 417 (5.0 mg, 40% yield). LC/MS (M+1): 624.1; HPLC RT=4.25 min (analytical HPLC Method A). 1H NMR (400 MHz, CD₃OD) δ ppm 7.58 (d, J=8.4 Hz, 2H), 7.45-7.29 (m, 2H), 7.29-7.14 (m, 4H), 4.96 (d, J=12.5 Hz, 1H), 4.26-3.57 (m, 3H), 3.17 (d, J=16.8 Hz, 1H), 2.86-2.58 (m, 1H), 2.44-2.38 (m, 3H), 2.37-2.24 (m, 2H), 2.20-1.99 (m, 2H), 1.99-1.74 (m, 2H), 1.72-1.42 (m, 4H).

Example 418

(1R,4r)-4-((R)-3-((3,4-dimethylphenyl)sulfonyl)-3-(4-(perfluoropropan-2-yl)phenyl)pyrrolidine-1-carbonyl)cyclohexanecarboxylic acid

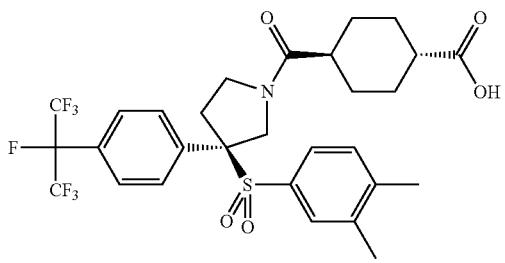 [SMILES: Cc1ccc(S(=O)(=O)[C@@]2(c3ccc(C(F)(C(F)(F)F)C(F)(F)F)cc3)CCN(C(=O)[C@H]3CC[C@H](C(=O)O)CC3)C2)cc1C]

Following similar procedure as Example 417, (1R,4r)-4-((R)-3-((3,4-dibromophenyl)sulfonyl)-3-(4-(perfluoropropan-2-yl)phenyl)pyrrolidine-1-carbonyl)cyclohexanecarboxylic acid (8.0 mg, 0.00104 mmol, the side product from Example 416) was converted to Example 418 (3.5 mg, 50% yield). LC/MS (M+1): 638.2; HPLC RT=4.36 min (analytical HPLC Method A). 1H NMR (400 MHz, CD₃OD) δ ppm 7.72-7.54 (m, 2H), 7.42-7.28 (m, 2H), 7.27-7.12 (m, 2H), 7.03-6.84 (m, 1H), 5.08-4.93 (m, 1H), 4.22-3.92 (m, 1H), 3.90-3.56 (m, 1H), 3.14 (m, 1H), 2.84-2.56 (m, 1H), 2.51-2.41 (m, 1H), 2.34 (s, 3H), 2.16 (s, 3H), 2.15-2.03 (m, 3H), 2.00-1.75 (m, 2H), 1.68-1.42 (m, 4H).

Example 419

(1R,4r)-4-((R)-3-(4-(perfluoropropan-2-yl)phenyl)-3-((4-vinylphenyl)sulfonyl)pyrrolidine-1-carbonyl)cyclohexanecarboxylic acid

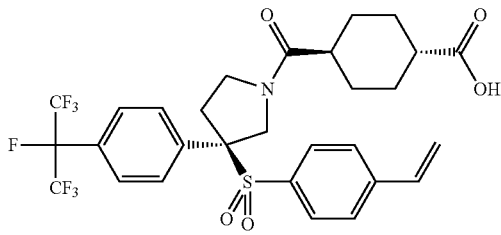

A mixture of (1R,4r)-4-((R)-3-((4-bromophenyl)sulfonyl)-3-(4-(perfluoropropan-2-yl)phenyl)pyrrolidine-1-carbonyl)cyclohexanecarboxylic acid (20 mg, 0.029 mmol), potassium trifluoro(vinyl)borate (7.78 mg, 0.058 mmol), [1,1'-bis(diphenylphosphino)ferrocene]dichloropalladium (II) (4.25 mg, 5.81 μmol) and 2.0 M aqueous potassium phosphate (0.019 mL, 0.038 mmol) in N,N-dimethylformamide (0.5 mL) was degassed with nitrogen in a sealed vial and heated to 90° C. for 2 h. The mixture was cooled down to room temperature and purified via preparative LC/MS with the following conditions: Column: Waters XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-100% B over 20 minutes, then a 5-minute hold at 100% B; Flow: 20 mL/min. Fractions containing the desired product were combined and dried via centrifugal evaporation to give Example 419 (12 mg, 62% yield). LC/MS (M+1): 636.2; HPLC RT=4.34 min (analytical HPLC Method A). 1H NMR (400 MHz, CD₃OD) δ ppm 7.71-7.52 (m, 2H), 7.53-7.41 (m, 2H), 7.41-7.21 (m, 4H), 6.91-6.67 (m, 1H), 6.14-5.89 (m, 1H), 5.66-5.38 (m, 1H), 5.12-4.90 (m, 1H), 4.27-3.58 (m, 3H), 3.23-3.03 (m, 1H), 2.81-2.56 (m, 2H), 2.50-2.22 (m, 2H), 2.18-1.98 (m, 2H), 1.95-1.76 (m, 2H), 1.59-1.47 (m, 3H).

Example 420

(1R,4r)-4-((R)-3-([1,1'-biphenyl]-4-ylsulfonyl)-3-(4-(perfluoropropan-2-yl)phenyl)pyrrolidine-1-carbonyl)cyclohexanecarboxylic acid

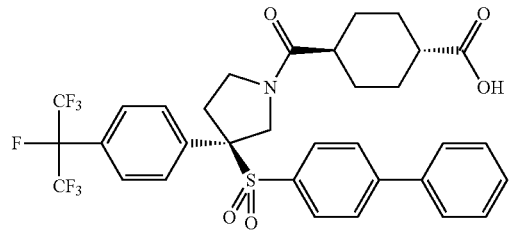 [SMILES: O=C(O)[C@H]1CC[C@H](C(=O)N2CC[C@](c3ccc(C(F)(C(F)(F)F)C(F)(F)F)cc3)(S(=O)(=O)c3ccc(-c4ccccc4)cc3)C2)CC1]

Following similar procedure as Example 417, (1R,4r)-4-((R)-3-((4-bromophenyl)sulfonyl)-3-(4-(perfluoropropan-2-yl)phenyl)pyrrolidine-1-carbonyl)cyclohexanecarboxylic acid (13 mg, 0.019 mmol) was converted to Example 420 (7.0 mg, 54% yield). LC/MS (M+1): 686.2; HPLC RT=2.744 min (analytical HPLC Method B). 1H NMR (400 MHz, DMSO-d₆) δ ppm 7.85-7.66 (m, 4H), 7.68-7.57 (m, 2H), 7.57-7.31 (m, 7H), 4.97-4.65 (m, 1H), 4.21-3.82 (m, 1H), 3.79 (d, J=13.8 Hz, 1H), 3.71-3.52 (m, 1H), 3.45-2.96 (m, 1H), 2.83-2.57 (m, 1H), 2.26-1.92 (m, 2H), 1.92-1.74 (m, 2H), 1.73-1.36 (m, 3H), 1.36-1.11 (m, 3H).

Example 421

((1R,4r)-4-((R)-3-((4-cyclopropylphenyl)sulfonyl)-3-(4-(perfluoropropan-2-yl)phenyl)pyrrolidine-1-carbonyl)cyclohexanecarboxylic acid

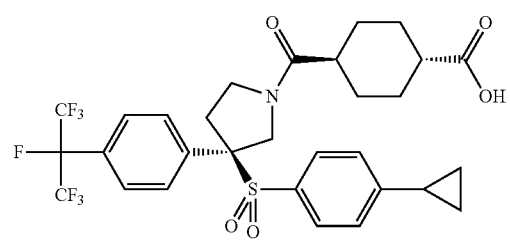 [SMILES: O=C(O)[C@H]1CC[C@H](C(=O)N2CC[C@](c3ccc(C(F)(C(F)(F)F)C(F)(F)F)cc3)(S(=O)(=O)c3ccc(C4CC4)cc3)C2)CC1]

Following similar procedure as Example 417, (1R,4r)-4-((R)-3-((4-bromophenyl)sulfonyl)-3-(4-(perfluoropropan-2-yl)phenyl)pyrrolidine-1-carbonyl)cyclohexanecarboxylic acid (13 mg, 0.019 mmol) was converted to Example 421 (6.7 mg, 52% yield). LC/MS (M+1): 650.2; HPLC RT=2.972 min (analytical HPLC Method B); 1H NMR (400 MHz, DMSO-d$_6$) δ ppm 7.74-7.52 (m, 2H), 7.51-7.32 (m, 2H), 7.21 (t, J=8.1 Hz, 2H), 7.17-6.99 (m, 2H), 4.95-4.59 (m, 1H), 4.15-3.52 (m, 4H), 3.18-2.94 (m, 1H), 2.57-2.42 (m, 1H), 2.27-2.05 (m, 2H), 2.05-1.77 (m, 4H), 1.77-1.41 (m, 2H), 1.37-1.25 (m, 3H), 1.08 (d, J=8.1 Hz, 2H), 0.74 (d, J=4.4 Hz, 2H).

Example 422

(1R,4r)-4-((R)-3-(4-(perfluoropropan-2-yl)phenyl)-3-((4-vinylphenyl)sulfonyl)pyrrolidine-1-carbonyl)cyclohexanecarboxylic acid

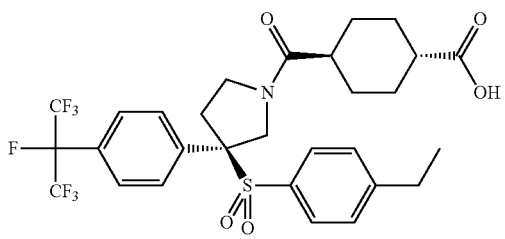 [SMILES: CCc1ccc(S(=O)(=O)[C@@]2(c3ccc(C(F)(C(F)(F)F)C(F)(F)F)cc3)CCN(C(=O)[C@H]3CC[C@H](C(=O)O)CC3)C2)cc1]

A mixture of (1R,4r)-4-((R)-3-(4-(perfluoropropan-2-yl)phenyl)-3-((4-vinylphenyl)sulfonyl)pyrrolidine-1-carbonyl)cyclohexanecarboxylic acid (6 mg, 9.44 mmol, from Example 419) and 10% palladium on carbon (5.02 mg, 0.0047 mmol) in methanol (10 mL) was hydrogenated under 40 psi hydrogen using a Parr Shaker for 4 h. The mixture was filtered to remove the catalyst. The filtrate was concentrated to give Example 422 (5.5 mg, 87% yield). LC/MS (M+1): 638.3; LC retention time: 4.40 min (analytical HPLC Method A); 1H NMR (400 MHz, CD$_3$OD) δ ppm 7.67-7.51 (m, 2H), 7.46-7.33 (m, 2H), 7.33-7.16 (m, 4H), 5.00-4.89 (m, 1H), 4.24-3.54 (m, 3H), 3.23-3.05 (m, 1H), 2.84-2.54 (m, 3H), 2.41 (m, 1H), 2.22-1.94 (m, 2H), 1.89-1.68 (m, 2H), 1.67-1.39 (m, 5H), 1.27-1.16 (m, 3H).

Examples 423 & 424

(R)-(3-((4-fluorophenyl)sulfonyl)-3-(4-(perfluoropropan-2-yl)phenyl)pyrrolidin-1-yl)(4-(hydroxymethyl)-1-methoxycyclohexyl)methanone

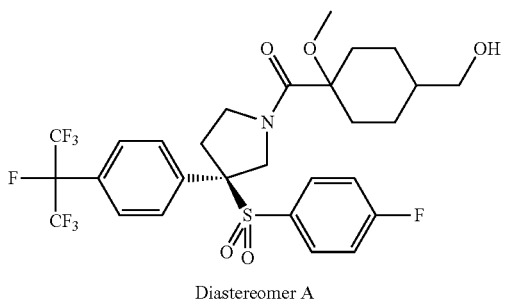

Diastereomer A

-continued

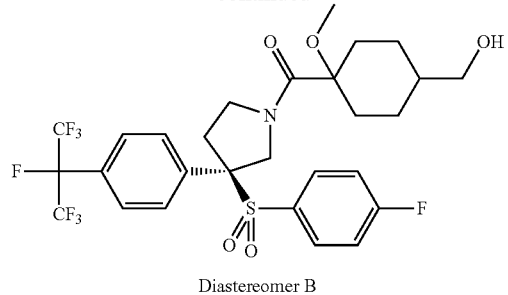

Diastereomer B

Step A: 4-(hydroxymethyl)-1-vinylcyclohexanol

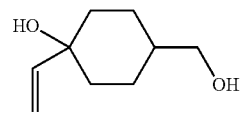

A 1.0 M tetrahydrofuran solution of lithium aluminum hydride (9.99 mL, 9.99 mmol) was added to a mixture of ethyl 4-hydroxy-4-vinylcyclohexanecarboxylate (1.98 g, 9.99 mmol) in tetrahydrofuran (60 mL) at 0° C. and stirred at room temperature for 2 h. After quenching with saturated ammonium chloride (10 mL), the mixture was diluted with ethyl acetate (300 mL), washed with water (30 mL), brine (30 mL), dried (magnesium sulfate), filtered and concentrated under reduced pressure. Silica gel chromatography, eluting with 50-100% ethyl acetate in hexanes, gave the desired 4-(hydroxymethyl)-1-vinylcyclohexanol as a 2 to 3 mixture of two isomers (1.10 g, 71% yield). 1H NMR showed two sets of signals for the cis and trans isomers.

Step B: 4-(((tert-butyldimethylsilyl)oxy)methyl)-1-vinylcyclohexanol

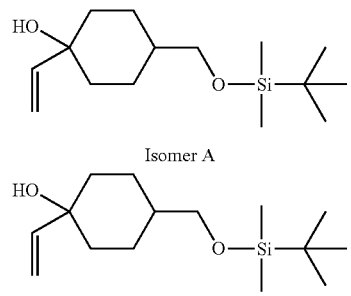

Isomer A

Isomer B tert-Butyldimethylsilyl chloride (1.167 g, 7.75 mmol) was added to a solution of 4-(hydroxymethyl)-1-vinylcyclohexanol (1.10 g, 7.04 mmol) and imidazole (1.198 g, 17.60 mmol) in N,N-dimethylformamide (10 mL) at 0° C. After stirring at ambient temperature for 3 h, the mixture was quenched with saturated ammonium chloride (20 mL), diluted with ethyl acetate (200 mL), washed with water (20 mL), brine (20 mL), dried (magnesium sulfate), filtered and concentrated under reduced pressure. Silica gel chromatography, eluting with 0-10% ethyl acetate in hexanes, gave the desired 4-(((tert-butyldimethylsilyl)oxy)methyl)-1-vinylcyclohexanol isomer A as the first eluent off the column (560 mg, 29% yield). 1H NMR (400 MHz, CDCl₃) δ ppm 5.91 (dd, J=17.4, 10.8 Hz, 1H), 5.20 (dd, J=17.4, 1.1 Hz, 1H), 4.98 (dd, J=10.8, 1.1 Hz, 1H), 3.42 (d, J=6.2 Hz, 2H), 1.61 (d, J=9.5 Hz, 4H), 1.53-1.23 (m, 5H), 0.87 (s, 9H), 0.02 (s, 6H). It also gave the desired 4-(((tert-butyldimethylsilyl)oxy)methyl)-1-vinylcyclohexanol isomer B as the second eluent off the column (650 mg, 34% yield). 1H NMR (400 MHz, CDCl₃) δ ppm 6.13-5.98 (m, 1H), 5.29 (dd, J=17.5, 1.2 Hz, 1H), 5.12 (dd, J=10.9, 1.2 Hz, 1H), 3.41 (d, J=6.4 Hz, 2H), 1.89-1.67 (m, 4H), 1.56-1.35 (m, 3H), 1.16-1.03 (m, 2H), 0.87 (s, 9H), 0.01 (s, 6H).

Step C: tert-butyl((4-methoxy-4-vinylcyclohexyl)methoxy)dimethylsilane

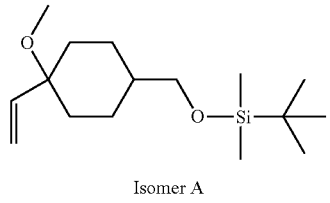 [SMILES: C=CC1(OC)CCC(CO[Si](C)(C)C(C)(C)C)CC1]

Isomer A

60% NaH (78 mg, 1.941 mmol) in mineral oil was added to a solution of 4-(((tert-butyldimethylsilyl)oxy)methyl)-1-vinylcyclohexanol (350 mg, 1.294 mmol, isomer A) in N,N-dimethylformamide (5 mL). After stirring at ambient temperature for 30 min, methyl iodide (0.121 mL, 1.941 mmol) was added. The resultant mixture was stirred for 15 h. The mixture was quenched with saturated ammonium chloride (5 mL), diluted with ethyl acetate (100 mL), washed with water (10 mL), brine (10 mL), dried (magnesium sulfate), filtered and concentrated under reduced pressure. Silica gel chromatography, eluting with 0-15% ethyl acetate in hexanes, gave the desired tert-butyl((4-methoxy-4-vinylcyclohexyl)methoxy)dimethylsilane isomer A (330 mg, 90% yield). 1H NMR (400 MHz, CDCl₃) δ ppm 5.70 (dd, J=17.6, 11.0 Hz, 1H), 5.20-4.97 (m, 2H), 3.40 (d, J=6.4 Hz, 2H), 3.06 (s, 3H), 1.85 (dd, J=14.1, 2.4 Hz, 2H), 1.65-1.49 (m, 2H), 1.49-1.36 (m, 1H), 1.36-1.11 (m, 4H), 0.86 (s, 9H), 0.00 (s, 6H).

Step D: 4-(((tert-butyldimethylsilyl)oxy)methyl)-1-methoxycyclohexanecarbaldehyde

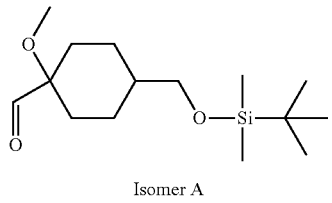 [SMILES: COC1(C=O)CCC(CO[Si](C)(C)C(C)(C)C)CC1]

Isomer A

Ozone was bubbled into a solution of tert-butyl((4-methoxy-4-vinylcyclohexyl)methoxy)dimethylsilane (330 mg, 1.160 mmol, isomer A) in dichloromethane (10 mL) at −78° C. until the mixture turned into blue color. Ozone was removed and bubbled with nitrogen until the blue color disappeared. The mixture was added dimethyl sulfide (0.214 mL, 2.90 mmol) and stirred at room temperature for 15 h. After evaporation of organic solvents, the residue was purified by silica gel chromatography, eluting with 0-15% ethyl acetate in hexanes, to give the desired 4-(((tert-butyldimethylsilyl)oxy)methyl)-1-methoxycyclohexanecarbaldehyde isomer A (170 mg, 51% yield). 1H NMR (400 MHz, CDCl₃) δ ppm 9.56 (s, 1H), 3.40 (d, J=6.4 Hz, 2H), 3.25 (s, 3H), 1.85 (dd, J=14.6, 2.8 Hz, 2H), 1.65 (dd, J=13.2, 3.3 Hz, 2H), 1.53-1.23 (m, 3H), 1.19 (d, J=3.1 Hz, 2H), 0.86 (s, 9H), 0.18-−0.13 (m, 6H).

Step E: 4-(((tert-butyldimethylsilyl)oxy)methyl)-1-methoxycyclohexanecarboxylic acid

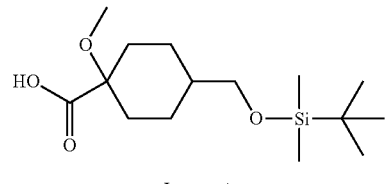

Isomer A

Sodium dihydrogen phosphate (107 mg, 0.890 mmol) and sodium chlorite (161 mg, 1.78 mmol) were added to a mixture of 4-(((tert-butyldimethylsilyl)oxy)methyl)-1-methoxycyclohexanecarbaldehyde (170 mg, 0.593 mmol, isomer A) and 2.0 M tetrahydrofuran solution of 2-methylbut-2-ene (2.97 mL, 5.94 mmol) in tert-butanol (5 mL) and water (1 mL). The resultant mixture was stirred at room temperature for 15 h. After evaporation of organic solvents, the residue was treated with ethyl acetate (100 mL), washed with brine (10 mL), dried (magnesium sulfate), filtered and concentrated under reduced pressure to provide the desired 4-(((tert-butyldimethylsilyl)oxy)methyl)-1-methoxycyclohexanecarboxylic acid isomer A as crude material (173 mg). It was used without further purification. LC/MS (M−1): 301.0; LC retention time: 1.25 min (analytical HPLC Method I); ¹HNMR (400 MHz, CDCl₃) δ ppm 3.39 (d, J=6.4 Hz, 2H), 3.25 (s, 3H), 2.00 (d, J=13.0 Hz, 2H), 1.75-1.56 (m, 4H), 1.56-1.37 (m, 1H), 1.31-1.02 (m, 2H), 0.85 (s, 9H), 0.01 (s, 6H).

Step F: (R)-(4-(((tert-butyldimethylsilyl)oxy)methyl)-1-methoxycyclohexyl)(3-((4-fluorophenyl)sulfonyl)-3-(4-(perfluoropropan-2-yl)phenyl)pyrrolidin-1-yl)methanone

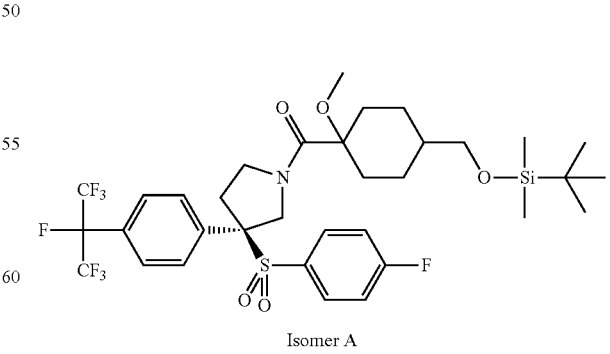

Isomer A

Hunig's Base (0.036 mL, 0.204 mmol) was added to a mixture of (R)-3-(4-fluorophenyl)sulfonyl)-3-(4-(perfluoropropan-2-yl)phenyl)pyrrolidine trifluoroacetic acid salt (30 mg, 0.051 mmol), 1-[bis(dimethylamino)methylene]-1H-1,2,3-triazolo[4,5-b]pyridinium 3-oxid hexafluorophosphate (22.5 mg, 0.061 mmol) and 4-(((tert-butyldimethylsilyl)oxy)methyl)-1-methoxycyclohexanecarboxylic acid (18.54 mg, 0.061 mmol, isomer A) in N,N-dimethylformamide (1 mL). After stirring at ambient temperature for 2 h, the mixture was diluted with ethyl acetate (60 mL), washed with water (5 mL), brine (5 mL), dried (magnesium sulfate), filtered and concentrated under reduced pressure. Silica gel chromatography, eluting with 10-60% ethyl acetate in hexanes, gave the desired (R)-(4-(((tert-butyldimethylsilyl)oxy)methyl)-1-methoxycyclohexyl)(3-((4-fluorophenyl)sulfonyl)-3-(4-(perfluoropropan-2-yl)phenyl)pyrrolidin-1-yl)methanone isomer A (24.0 mg, 62% yield). LC/MS (M+1): 758.2; LC retention time: 1.38 min (analytical HPLC Method C); 1H NMR (400 MHz, CDCl₃) δ ppm 7.61-7.37 (m, 2H), 7.27-7.07 (m, 4H), 6.98-6.88 (m, 2H), 5.36-4.59 (m, 1H), 4.28-3.81 (m, 2H), 3.48-3.24 (m, 3H), 3.20-3.08 (m, 3H), 2.71-2.33 (m, 1H), 2.33-1.88 (m, 2H), 1.88-1.39 (m, 6H), 1.30-1.04 (m, 2H), 0.95-0.83 (m, 9H), 0.01 (s, 6H).

Step G: (R)-(3-((4-fluorophenyl)sulfonyl)-3-(4-(perfluoropropan-2-yl)phenyl)pyrrolidin-1-yl)(4-(hydroxymethyl)-1-methoxycyclohexyl)methanone

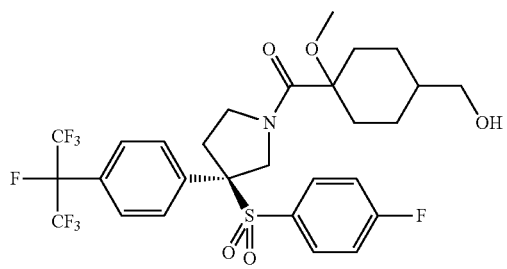

Isomer A

A 1.0 M tetrahydrofuran solution of tetrabutylammonium fluoride (0.058 mL, 0.058 mmol) was added to a mixture of (R)-(4-(((tert-butyldimethylsilyl)oxy)methyl)-1-methoxycyclohexyl)(3-((4-fluorophenyl)sulfonyl)-3-(4-(perfluoropropan-2-yl)phenyl)pyrrolidin-1-yl)methanone (22 mg, 0.029 mmol, isomer A) in tetrahydrofuran (1 mL). After stirring at ambient temperature for 4 h, the crude mixture was purified via preparative LC/MS with the following conditions: Column: Waters XBridge C18, 19×250 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 30-100% B over 25 minutes, then a 5-minute hold at 100% B; Flow: 20 mL/min. Fractions containing the desired product were combined and dried via centrifugal evaporation to give Example 423 (8.0 mg, 41% yield). LC/MS (M+1): 644.2; LC retention time: 4.20 min (analytical HPLC Method A); ¹HNMR (500 MHz, CDCl₃) δ ppm 7.55-7.42 (m, 2H), 7.36-7.09 (m, 4H), 6.98 (t, J=8.5 Hz, 2H), 5.44-4.66 (m, 1H), 4.36-4.14 (m, 1H), 4.14-3.96 (m, 1H), 3.85-3.34 (m, 2H), 3.29-3.08 (m, 3H), 2.69-2.34 (m, 1H), 2.36-2.09 (m, 1H), 2.01-1.65 (m, 8H), 1.41-1.19 (m, 2H).

Step H: (R)-(3-((4-fluorophenyl)sulfonyl)-3-(4-(perfluoropropan-2-yl)phenyl)pyrrolidin-1-yl)(4-(hydroxymethyl)-1-methoxycyclohexyl)methanone

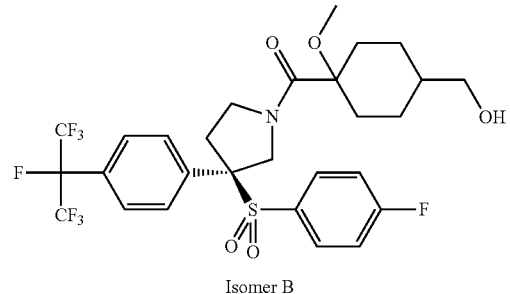 [SMILES: COC1(C(=O)N2CC[C@](c3ccc(C(F)(C(F)(F)F)C(F)(F)F)cc3)(S(=O)(=O)c3ccc(F)cc3)C2)CCC(CO)CC1]

Isomer B

Following similar procedures from Step C to G, 4-(((tert-butyldimethylsilyl)oxy)methyl)-1-vinylcyclohexanol (50 mg, 0.136 mmol, isomer B from Step B) was converted to Example 424 (11 mg, 12% yield). LC/MS (M+1): 644.1; LC retention time: 4.39 min (analytical HPLC Method A); ¹HNMR (500 MHz, CDCl₃) δ ppm 7.56-7.43 (m, 2H), 7.26-7.14 (m, 4H), 6.98 (t, J=8.5 Hz, 2H), 5.38-4.61 (m, 1H), 4.27-3.95 (m, 3H), 3.77-3.51 (m, 2H), 3.27-3.19 (m, 3H), 2.68-2.12 (m, 3H), 1.90-1.72 (m, 2H), 1.65-1.24 (m, 6H).

Examples 425 & 426

(R)-4-(3-((4-fluorophenyl)sulfonyl)-3-(4-(perfluoropropan-2-yl)phenyl)pyrrolidine-1-carbonyl)-4-methoxycyclohexanecarboxylic acid

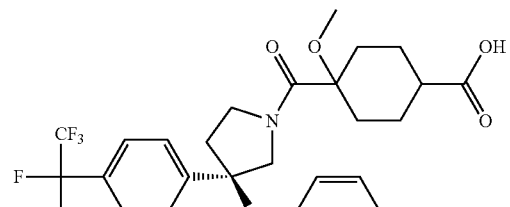

Diastereomer A

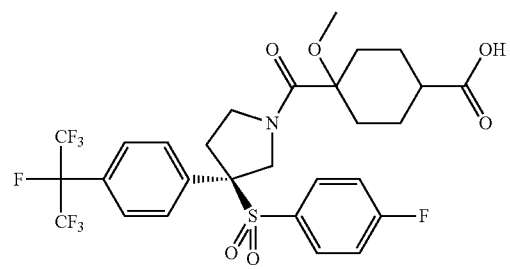

Diastereomer B

Step A: (R)-4-(3-((4-fluorophenyl)sulfonyl)-3-(4-(perfluoropropan-2-yl)phenyl)pyrrolidine-1-carbonyl)-4-methoxycyclohexanecarbaldehyde

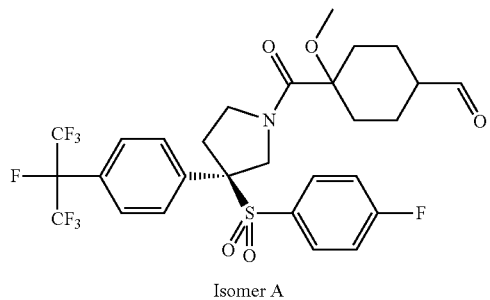 [SMILES: COC1(C(=O)N2CC[C@](c3ccc(C(F)(C(F)(F)F)C(F)(F)F)cc3)(S(=O)(=O)c3ccc(F)cc3)C2)CCC(C=O)CC1]

Isomer A

Dess-Martin periodinane (26.4 mg, 0.062 mmol) was added to a solution of (R)-(3-((4-fluorophenyl)sulfonyl)-3-(4-(perfluoropropan-2-yl)phenyl)pyrrolidin-1-yl)(4-(hydroxymethyl)-1-methoxycyclohexyl)methanone (20 mg, 0.031 mmol, Example 423) in dichloromethane (5 mL). After stirring at ambient temperature for 4 h, the mixture was quenched with saturated sodium bicarbonate (5 mL), diluted with ethyl acetate (100 mL), washed with water (10 mL), brine (10 mL), dried (magnesium sulfate), filtered and concentrated under reduced pressure. Silica gel chromatography, eluting with 10-50% ethyl acetate in hexanes, gave the (R)-4-(3-((4-fluorophenyl)sulfonyl)-3-(4-(perfluoropropan-2-yl)phenyl)pyrrolidine-1-carbonyl)-4-methoxycyclohexanecarbaldehyde isomer A (15 mg, 75% yield). LC/MS (M+1): 642.2; LC retention time: 1.12 min (analytical HPLC Method C); $^1$HNMR (500 MHz, CDCl$_3$) δ ppm 10.05-9.46 (m, 1H), 7.62-7.44 (m, 2H), 7.31-7.13 (m, 4H), 7.06-6.89 (m, 2H), 5.61-4.74 (m, 1H), 4.32-3.91 (m, 2H), 3.83-3.35 (m, 1H), 3.27-3.16 (m, 3H), 3.00 (dt, J=12.2, 4.6 Hz, 1H), 2.70-2.39 (m, 1H), 2.39-2.18 (m, 2H), 1.98-1.52 (m, 7H).

Step B: (R)-4-(3-((4-fluorophenyl)sulfonyl)-3-(4-(perfluoropropan-2-yl)phenyl)pyrrolidine-1-carbonyl)-4-methoxycyclohexanecarboxylic acid

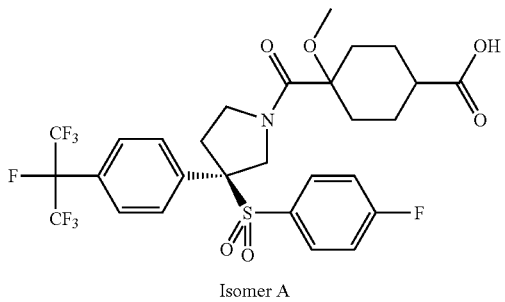 [SMILES: COC1(C(=O)N2CC[C@](c3ccc(C(F)(C(F)(F)F)C(F)(F)F)cc3)(S(=O)(=O)c3ccc(F)cc3)C2)CCC(C(=O)O)CC1]

Isomer A

Sodium dihydrogen phosphate (4.21 mg, 0.035 mmol) and sodium chlorite (6.34 mg, 0.070 mmol) were added to a mixture of (R)-4-(3-((4-fluorophenyl)sulfonyl)-3-(4-(perfluoropropan-2-yl)phenyl)pyrrolidine-1-carbonyl)-4-methoxycyclohexanecarbaldehyde isomer A (15 mg, 0.023 mmol) and 2.0 M tetrahydrofuran solution of 2-methylbut-2-ene (0.117 mL, 0.234 mmol) in tert-butanol (0.5 mL) and water (0.1 mL). After stirring at ambient temperature for 2 h, the mixture was diluted with ethyl acetate (60 mL), washed with water (5 mL), brine (5 mL), dried (magnesium sulfate), filtered and concentrated under reduced pressure.

The residue was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-100% B over 25 minutes, then a 5-minute hold at 100% B; Flow: 20 mL/min. Fractions containing the desired product were combined and dried via centrifugal evaporation to give Example 425 (9.6 mg, 59% yield). LC/MS (M+1): 658.2; LC retention time: 2.02 min (analytical HPLC Method B); $^1$HNMR (500 MHz, DMSO-d$_6$) δ ppm 7.60 (d, J=6.1 Hz, 2H), 7.45-7.08 (m, 6H), 5.40-4.60 (m, 1H), 4.26-3.85 (m, 2H), 3.83-3.35 (m, 1H), 3.21-3.00 (m, 3H), 3.00-2.93 (m, 1H), 2.68-2.57 (m, 1H), 2.28-2.07 (m, 1H), 2.05-1.90 (m, 2H), 1.84-1.39 (m, 6H).

Step C: (R)-4-(3-((4-fluorophenyl)sulfonyl)-3-(4-(perfluoropropan-2-yl)phenyl)pyrrolidine-1-carbonyl)-4-methoxycyclohexanecarboxylic acid

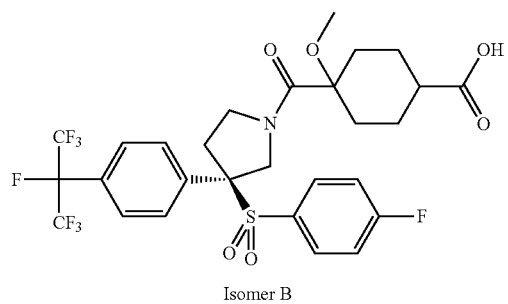 [SMILES: COC1(C(=O)N2CC[C@](c3ccc(C(F)(C(F)(F)F)C(F)(F)F)cc3)(S(=O)(=O)c3ccc(F)cc3)C2)CCC(C(=O)O)CC1]

Isomer B

Following similar procedures from Step A and B, (R)-(3-((4-fluorophenyl)sulfonyl)-3-(4-(perfluoropropan-2-yl)phenyl)pyrrolidin-1-yl)(4-(hydroxymethyl)-1-methoxycyclohexyl)methanone (14 mg, 0.022 mmol, Example 424) was converted to Example 426 (3.0 mg, 25% yield). LC/MS (M+1): 658.1; LC retention time: 4.43 min (analytical HPLC Method A); $^1$HNMR (500 MHz, CD$_3$OD) δ ppm 7.58 (d, J=7.0 Hz, 2H), 7.43-7.27 (m, 4H), 7.12 (q, J=8.9 Hz, 2H), 5.60-4.88 (m, 1H), 4.27-3.62 (m, 4H), 3.26-3.12 (m, 3H), 2.77-2.54 (m, 1H), 2.47-2.11 (m, 2H), 1.92-1.65 (m, 3H), 1.65-1.37 (m, 4H).

Examples 427 & 428

(R)-4-(3-((4-fluoro-3-methylphenyl)sulfonyl)-3-(4-(perfluoropropan-2-yl)phenyl)pyrrolidine-1-carbonyl)-4-methoxycyclohexanecarboxylic acid

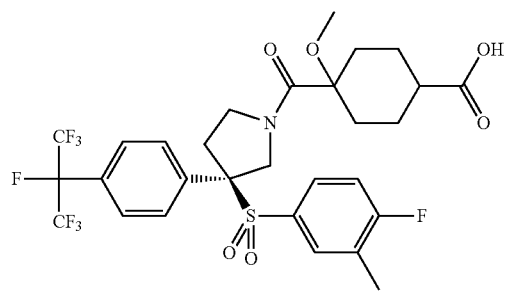

Diastereomer A

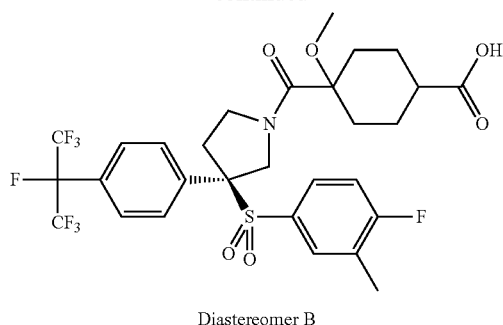

Diastereomer B

Step A: (R)-(4-(((tert-butyldimethylsilyl)oxy)methyl)-1-methoxycyclohexyl)(3-((4-fluoro-3-methylphenyl)sulfonyl)-3-(4-(perfluoropropan-2-yl)phenyl)pyrrolidin-1-yl)methanone

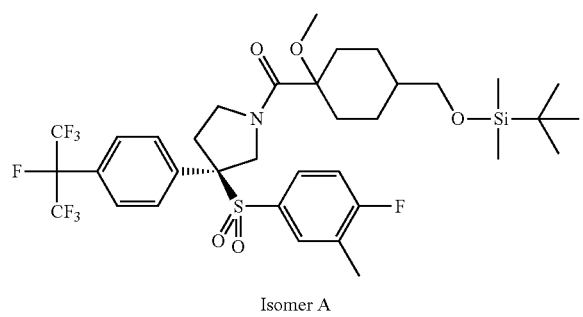 [SMILES: COC1(C(=O)N2CC[C@](c3ccc(C(F)(C(F)(F)F)C(F)(F)F)cc3)(S(=O)(=O)c3ccc(F)c(C)c3)C2)CCC(CO[Si](C)(C)C(C)(C)C)CC1]

Isomer A

Hunig's Base (0.058 mL, 0.333 mmol) was added to a mixture of (R)-3-((4-fluoro-3-methylphenyl)sulfonyl)-3-(4-(perfluoropropan-2-yl)phenyl)pyrrolidine trifluoroacetic acid salt (50 mg, 0.083 mmol), 1-[bis(dimethylamino)methylene]-1H-1,2,3-triazolo[4,5-b]pyridinium 3-oxid hexafluorophosphate (44.1 mg, 0.100 mmol) and 4-(((tert-butyldimethylsilyl)oxy)methyl)-1-methoxycyclohexanecarboxylic acid (25.1 mg, 0.083 mmol, isomer A from Step E of Example 423) in N,N-dimethylformamide (1 mL). After stirring at ambient temperature for 2 h, the mixture was diluted with ethyl acetate (60 mL), washed with water (5 mL), brine (5 mL), dried (magnesium sulfate), filtered and concentrated under reduced pressure. Silica gel chromatography, eluting with 0-50% ethyl acetate in hexanes, gave the desired (R)-(4-(((tert-butyldimethylsilyl)oxy)methyl)-1-methoxycyclohexyl)(3-((4-fluoro-3-methylphenyl)sulfonyl)-3-(4-(perfluoropropan-2-yl)phenyl)pyrrolidin-1-yl)methanone isomer A (40 mg, 62% yield). LC/MS (M+1): 772.3; LC retention time: 1.39 min (analytical HPLC Method C); 1H NMR (400 MHz, CDCl$_3$) δ ppm 7.53-7.39 (m, 2H), 7.26-7.09 (m, 3H), 6.91 (t, J=8.7 Hz, 2H), 5.24-4.61 (m, 1H), 4.24-3.54 (m, 3H), 3.47-3.31 (m, 2H), 3.18-3.09 (m, 3H), 2.62-2.16 (m, 2H), 2.11-2.03 (m, 3H), 1.97-1.73 (m, 2H), 1.71-1.41 (m, 5H), 1.26-1.09 (m, 2H), 0.89-0.81 (m, 6H).

Step B: (R)-(3-((4-fluoro-3-methylphenyl)sulfonyl)-3-(4-(perfluoropropan-2-yl)phenyl)pyrrolidine-1-yl)(4-(hydroxymethyl)-1-methoxycyclohexyl)methanone

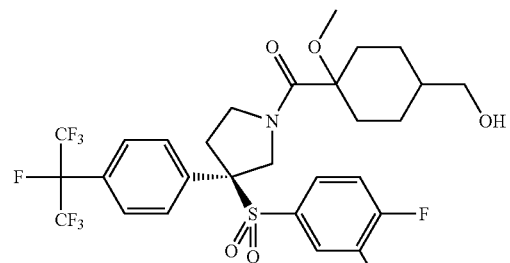

Isomer A

A 1.0 M tetrahydrofuran solution of tetrabutylammonium fluoride (0.104 mL, 0.104 mmol) was added to a mixture of (R)-(4-(((tert-butyldimethylsilyl)oxy)methyl)-1-methoxycyclohexyl)(3-((4-fluoro-3-methylphenyl)sulfonyl)-3-(4-(perfluoropropan-2-yl)phenyl)pyrrolidin-1-yl)methanone (40 mg, 0.052 mmol, isomer A) in tetrahydrofuran (1 mL). After stirring at ambient temperature for 4 h, the mixture was quenched with saturated sodium bicarbonate (5 mL), diluted with ethyl acetate (100 mL), washed with water (10 mL), brine (10 mL), dried (magnesium sulfate), filtered and concentrated under reduced pressure to provide the desired (R)-(3-((4-fluoro-3-methylphenyl)sulfonyl)-3-(4-(perfluoropropan-2-yl)phenyl)pyrrolidin-1-yl)(4-(hydroxymethyl)-1-methoxycyclohexyl)methanone as crude material (35 mg). LCMS (M+1): 644.1; 1.07 min (analytical HPLC Method C). It was used without further purification.

Step C: (R)-4-(3-((4-fluoro-3-methylphenyl)sulfonyl)-3-(4-(perfluoropropan-2-yl)phenyl)pyrrolidine-1-carbonyl)-4-methoxycyclohexanecarboxylic acid

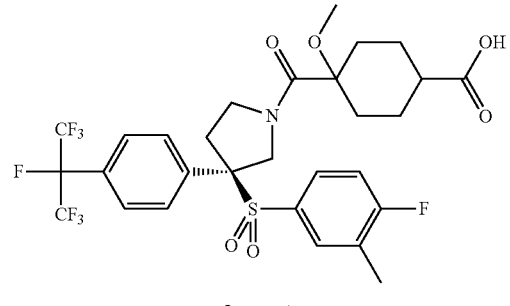

Isomer A

Dess-Martin periodinane (58.0 mg, 0.137 mmol) was added to a solution of (R)-(3-((4-fluoro-3-methylphenyl)sulfonyl)-3-(4-(perfluoropropan-2-yl)phenyl)pyrrolidin-1-yl)(4-(hydroxymethyl)-1-methoxycyclohexyl)methanone (30 mg, 0.046 mmol, isomer A) in dichloromethane (5 mL). After stirring at ambient temperature for 4 h, the mixture was quenched with saturated sodium bicarbonate (5 mL), diluted with ethyl acetate (100 mL), washed with water (10 mL), brine (10 mL), dried (magnesium sulfate), filtered and concentrated under reduced pressure. The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-100% B over 25 minutes, then a 5-minute hold at 100% B; Flow: 20 mL/min. Fractions containing the desired product were combined and dried via centrifugal evaporation to give Example 427 (9.7 mg, 32% yield). LC/MS (M+1): 672.2; LC retention time: 2.14 min (analytical HPLC Method B); $^1$HNMR (500 MHz, DMSO-$d_6$) δ ppm 7.61 (d, J=8.1 Hz, 2H), 7.42-7.12 (m, 4H), 7.08-6.87 (m, 1H), 5.36-4.45 (m, 1H), 4.19-3.88 (m, 2H), 3.83-3.32 (m, 1H), 3.16-3.03 (m, 3H), 2.94-2.66 (m, 1H), 2.36-2.15 (m, 1H), 2.16-2.04 (m, 3H), 2.04-1.87 (m, 2H), 1.82-1.39 (m, 7H).

Step D: (R)-4-(3-((4-fluoro-3-methylphenyl)sulfonyl)-3-(4-(perfluoropropan-2-yl)phenyl)pyrrolidine-1-carbonyl)-4-methoxycyclohexanecarboxylic acid

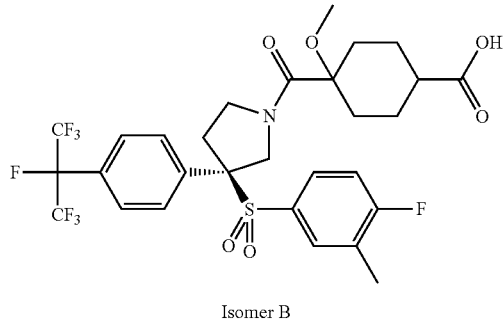 [SMILES: COC1(C(=O)N2CC[C@](c3ccc(C(F)(C(F)(F)F)C(F)(F)F)cc3)(S(=O)(=O)c3ccc(F)c(C)c3)C2)CCC(C(=O)O)CC1]

Isomer B

Following similar procedures from Step A to C, 4-(((tert-butyldimethylsilyl)oxy)methyl)-1-vinylcyclohexanol (24 mg, 0.080 mmol, isomer B from Step B of Example 423) was converted to Example 428 (6.0 mg, 23% yield). LC/MS (M+1): 672.1; LC retention time: 4.54 min (analytical HPLC Method A); 1HNMR (500 MHz, CD$_3$OD) δ ppm 7.60 (d, J=8.4 Hz, 2H), 7.45-7.21 (m, 3H), 7.17-6.82 (m, 2H), 5.50 (d, J=13.2 Hz, 1H), 4.32-3.86 (m, 3H), 3.29-3.16 (m, 3H), 3.11-2.66 (m, 1H), 2.66-2.43 (m, 1H), 2.31-2.04 (m, 3H), 2.17-1.61 (m, 9H).

Example 429

4-((R)-3-((4-fluorophenyl)sulfonyl)-3-(4-(perfluoropropan-2-yl)phenyl)pyrrolidine-1-carbonyl)cyclohex-3-enecarboxylic acid Step A: (R)-ethyl 4-(3-((4-fluorophenyl)sulfonyl)-3-(4-(perfluoropropan-2-yl)phenyl)pyrrolidine-1-carbonyl)-4-hydroxycyclohexanecarboxylate

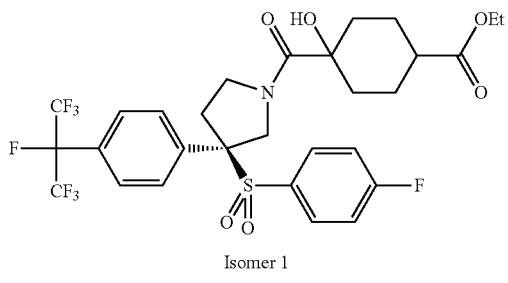 [SMILES: CCOC(=O)C1CCC(O)(C(=O)N2CC[C@](c3ccc(C(F)(C(F)(F)F)C(F)(F)F)cc3)(S(=O)(=O)c3ccc(F)cc3)C2)CC1]

Isomer 1

Hunig's Base (0.059 mL, 0.338 mmol) was added to a mixture of (R)-3-((4-fluorophenyl)sulfonyl)-3-(4-(perfluoropropan-2-yl)phenyl)pyrrolidine (40 mg, 0.084 mmol), 1-[bis(dimethylamino)methylene]-1H-1,2,3-triazolo[4,5-b]pyridinium 3-oxid hexafluorophosphate (56.1 mg, 0.124 mmol) and 4-(ethoxycarbonyl)-1-hydroxycyclohexanecarboxylic acid (27.4 mg, 0.124 mmol, intermediate 1) in N,N-dimethylformamide (1 mL). After stirring at ambient temperature for 2 h, the mixture was diluted with ethyl acetate (60 mL), washed with water (5 mL), brine (5 mL), dried (magnesium sulfate), filtered and concentrated under reduced pressure. Silica gel chromatography, eluting with 50-100% ethyl acetate in hexanes, gave the desired (R)-ethyl 4-(3-((4-fluorophenyl)sulfonyl)-3-(4-(perfluoropropan-2-yl)phenyl)pyrrolidine-1-carbonyl)-4-hydroxycyclohexanecarboxylate isomer 1 (38 mg, 67% yield). LC/MS (M+1): 672.3; LC retention time: 1.05 min (analytical HPLC Method C); 1H NMR (400 MHz, CDCl$_3$) δ ppm 7.50 (d, J=8.4 Hz, 2H), 7.35-7.11 (m, 4H), 6.98 (t, J=8.6 Hz, 2H), 4.82 (m, 1H), 4.44-4.24 (m, 1H), 4.15 (q, J=7.0 Hz, 2H), 4.10-3.89 (m, 2H), 3.48-3.19 (m, 1H), 2.52-2.24 (m, 3H), 2.11-1.58 (m, 8H), 1.27 (t, J=7.0 Hz, 3H).

Step B: ethyl 4-((R)-3-((4-fluorophenyl)sulfonyl)-3-(4-(perfluoropropan-2-yl)phenyl)pyrrolidine-1-carbonyl)cyclohex-3-enecarboxylate

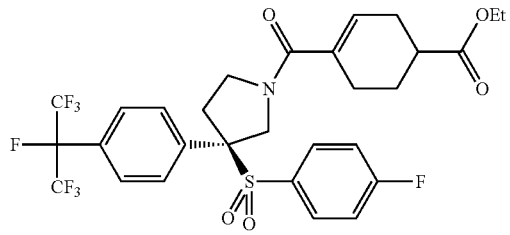 [SMILES: CCOC(=O)C1CC=C(C(=O)N2CC[C@](c3ccc(C(F)(C(F)(F)F)C(F)(F)F)cc3)(S(=O)(=O)c3ccc(F)cc3)C2)CC1]

(Diethylamino)sulfur trifluoride (0.018 mL, 0.027 mmol) was added to a mixture of (R)-ethyl 4-(3-((4-fluorophenyl)sulfonyl)-3-(4-(perfluoropropan-2-yl)phenyl)pyrrolidine-1-carbonyl)-4-hydroxycyclohexanecarboxylate (18 mg, 0.027 mmol) in dichloromethane (1 mL) at −78° C. and stirred for 30 min. The mixture was quenched with methanol (0.5 mL) at −78° C. and warmed to room temperature. The mixture was diluted with ethyl acetate (100 mL), washed with water (10 mL), brine (10 mL), dried (magnesium sulfate), filtered and concentrated under reduced pressure. Silica gel chromatography, eluting with 10-60% ethyl acetate in hexanes, gave the desired ethyl 4-((R)-3-((4-fluorophenyl)sulfonyl)-3-(4-(perfluoropropan-2-yl)phenyl)pyrrolidine-1-carbonyl)cyclohex-3-enecarboxylate (9.0 mg, 51% yield). LC/MS (M+1): 654.3; LC retention time: 1.10 min (analytical HPLC Method C); $^1$H NMR (400 MHz, CDCl$_3$) δ ppm 7.52 (d, J=8.4 Hz, 2H), 7.35-7.24 (m, 2H), 7.18 (d, J=8.4 Hz, 2H), 7.00 (t, J=8.4 Hz, 2H), 6.24-5.96 (m, 1H), 4.97-4.69 (m, 1H), 4.31-4.15 (m, 2H), 4.15-3.85 (m, 2H), 3.76 (t, J=9.1 Hz, 1H), 3.54-3.35 (m, 1H), 2.69-2.52 (m, 2H), 2.52-2.24 (m, 3H), 2.17-2.00 (m, 1H), 1.83 (m, 1H), 1.41-1.15 (m, 3H).

Step C: 4-((R)-3-((4-fluorophenyl)sulfonyl)-3-(4-(perfluoropropan-2-yl)phenyl)pyrrolidine-1-carbonyl)cyclohex-3-enecarboxylic acid

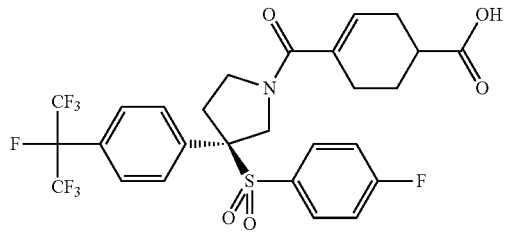 [SMILES: O=C(O)C1CC=C(C(=O)N2CC[C@](c3ccc(C(F)(C(F)(F)F)C(F)(F)F)cc3)(S(=O)(=O)c3ccc(F)cc3)C2)CC1]

A 1 N aqueous solution of lithium hydroxide (0.183 mL, 0.183 mmol) was added to a mixture of ethyl 4-((R)-3-((4-fluorophenyl)sulfonyl)-3-(4-(perfluoropropan-2-yl)phenyl)pyrrolidine-1-carbonyl)cyclohex-3-enecarboxylate (9 mg, 0.014 mmol) in tetrahydrofuran (0.5 mL). After stirring at ambient temperature for 15 h, the mixture was acidified to pH 2-3 with 1 N aqueous hydrochloric acid. The crude material was purified via preparative LC/MS with the following conditions: Column: Waters XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 25-100% B over 20 minutes, then a 5-minute hold at 100% B; Flow: 20 mL/min. Fractions containing the desired product were combined and dried via centrifugal evaporation to give Example 429 (6.0 mg, 70% yield). LC/MS (M+1): 626.2; HPLC RT=4.26 min (analytical HPLC Method A). 1H NMR (500 MHz, CD$_3$OD) δ ppm 7.80-7.46 (m, 2H), 7.35 (d, J=8.4 Hz, 4H), 7.24-6.94 (m, 2H), 6.22-5.96 (m, 1H), 5.02-4.92 (m, 1H), 4.03-3.85 (m, 2H), 3.85-3.50 (m, 1H), 2.84-2.57 (m, 2H), 2.57-2.23 (m, 4H), 2.19-2.01 (m, 2H), 2.00-1.67 (m, 1H).

Example 430

(R)-1-benzyl-3-((3-fluoro-4-methylphenyl)sulfonyl)-3-(4-(perfluoropropan-2-yl)phenyl)pyrrolidine Step A: δ 1-(bromomethyl)-4-(perfluoropropan-2-yl)benzene

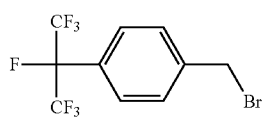

(Diethylamino)sulfur trifluoride (8.82 mL, 66.8 mmol) was added to a mixture of 2-(4-(bromomethyl)phenyl)-1,1,1,3,3,3-hexafluoropropan-2-ol (15.0 g, 44.5 mmol) in dichloromethane (20 mL). After stirring at ambient temperature for 15 h, the mixture was cooled down to 0° C. with an ice water bath and carefully quenched with methanol (8 mL). The mixture was diluted with ethyl acetate (400 mL), washed with water (100 mL), brine (100 mL), dried (magnesium sulfate), filtered and concentrated under reduced pressure. Silica gel chromatography, eluting with 0-10% ethyl acetate in hexanes, gave the desired 1-(bromomethyl)-4-(perfluoropropan-2-yl)benzene (7.6 g, 50% yield). $^1$H NMR (400 MHz, CDCl$_3$) δ ppm 7.67-7.39 (m, 4H), 4.50 (s, 2H).

Step B: 2-fluoro-1-methyl-4-((4-(perfluoropropan-2-yl)benzyl)sulfonyl)benzene

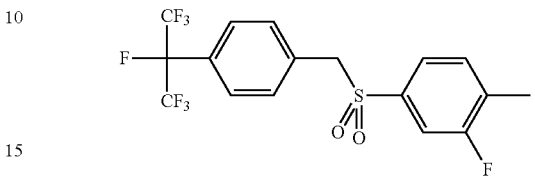

Sodium phosphate dibasic (2.144 g, 15.10 mmol) and sodium sulfite (3.57 g, 28.3 mmol) were dissolved in water (100 mL) at 30° C. This solution was then added to 3-fluoro-4-methylbenzene-1-sulfonyl chloride (2.95 g, 14.16 mmol) resulting in the formation of a creamy suspension. The resultant mixture was heated to 60° C. for 15 h. Subsequently, a solution of 1-(bromomethyl)-4-(perfluoropropan-2-yl)benzene (3.20 g, 9.44 mmol) in acetone (10 mL) was added dropwise over 10 min. After stirring at 60° C. for 15 h, the mixture was cooled down to room temperature and extracted with ethyl acetate (3×200 mL). The combined organic extract was washed with water (100 mL), brine (100 mL), dried (magnesium sulfate), filtered and concentrated under reduced pressure. Silica gel chromatography, eluting with 0-20% ethyl acetate in hexanes, gave the desired 2-fluoro-1-methyl-4-((4-(perfluoropropan-2-yl)benzyl)sulfonyl)benzene (2.90 g, 71% yield). LC/MS (M+18): 450.0; LC retention time: 1.11 min (analytical HPLC Method C); $^1$H NMR (400 MHz, CDCl$_3$) δ ppm 7.55 (d, J=8.3 Hz, 2H), 7.38-7.18 (m, 5H), 4.34 (s, 2H), 2.34 (d, J=2.1 Hz, 3H).

Step C: 1,1,1,3,3,3-hexafluoro-2-(4-(((4-fluoro-3-methylphenyl)sulfonyl)methyl)phenyl)propan-2-ol

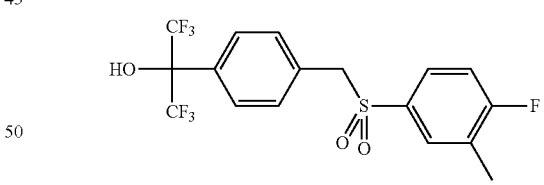

mCPBA (17.36 g, 77 mmol) was added to a solution of 1,1,1,3,3,3-hexafluoro-2-(4-((4-fluoro-3-methylphenyl)thio)methyl)phenyl)propan-2-ol (14.02 g, 35.2 mmol) in dichloromethane (100 mL). After 5 h at ambient temperature, the mixture was quenched with saturated sodium bicarbonate (100 mL), diluted with ethyl acetate (500 mL), washed with water (100 mL), brine (100 mL), dried (magnesium sulfate), filtered and concentrated under reduced pressure. Silica gel chromatography, eluting with 0-30% ethyl acetate in hexanes, gave the desired 1,1,1,3,3,3-hexafluoro-2-(4-(((4-fluoro-3-methylphenyl)sulfonyl)methyl)phenyl)propan-2-ol (10.3 g, 68% yield over 2 steps). LC/MS (M−1): 429.3; LC retention time: 1.09 min (analytical HPLC Method C); $^1$H NMR (400 MHz, CDCl$_3$) δ ppm 7.65 (d, J=8.1 Hz, 2H), 7.50-7.44 (m, 1H), 7.34 (d, J=2.0 Hz, 1H), 7.21 (d, J=8.6 Hz, 2H), 7.12-6.95 (m, 1H), 4.34 (s, 2H), 2.21 (s, 3H).

Step D: 2-fluoro-1-methyl-4-((1-(4-(perfluoropropan-2-yl)phenyl)vinyl)sulfonyl)benzene

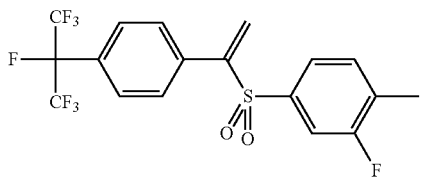 [SMILES: C=C(c1ccc(C(F)(C(F)(F)F)C(F)(F)F)cc1)S(=O)(=O)c1ccc(C)c(F)c1]

N,N,N',N'-tetramethylmethanediamine (1.70 g, 16.7 mmol) and acetic anhydride (1.57 mL, 16.7 mmol) were added to a solution of 2-fluoro-1-methyl-4-((4-(perfluoropropan-2-yl)benzyl)sulfonyl)benzene (1.20 g, 2.78 mmol) in N,N-dimethylformamide (8 mL) at room temperature. The mixture was stirred at room temperature in a sealed viral for 1 h and heated to 65° C. for 3 h. The mixture was cooled down to room temperature, diluted with ethyl acetate (300 mL), washed with saturated sodium bicarbonate (3×50 mL), water (50 mL), brine (50 mL), dried (magnesium sulfate), filtered and concentrated under reduced pressure. Silica gel chromatography, eluting with 0-15% ethyl acetate in hexanes, gave the desired 2-fluoro-1-methyl-4-((1-(4-(perfluoropropan-2-yl)phenyl)vinyl)sulfonyl)benzene (340 mg, 28% yield). LC/MS (M+1): 445.0; LC retention time: 1.15 min (analytical HPLC Method C); 1H NMR (400 MHz, CDCl$_3$) δ ppm 7.67-7.43 (m, 4H), 7.40-7.27 (m, 2H), 7.27-7.11 (m, 1H), 6.68 (s, 1H), 6.05 (s, 1H), 2.30 (d, J=1.8 Hz, 3H).

Step E: (R)-1-benzyl-3-((3-fluoro-4-methylphenyl)sulfonyl)-3-(4-(perfluoropropan-2-yl)phenyl)pyrrolidine

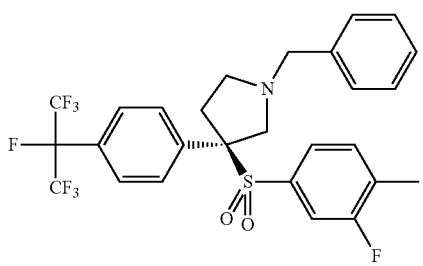 [SMILES: Cc1ccc(S(=O)(=O)[C@@]2(c3ccc(C(F)(C(F)(F)F)C(F)(F)F)cc3)CCN(Cc3ccccc3)C2)cc1F]

A 0.2 M dichloromethane solution of trifluoroacetic acid (0.189 mL, 0.038 mmol) was added dropwise to a solution of 2-fluoro-1-methyl-4-(1-(4-(perfluoropropan-2-yl)phenyl)vinyl)sulfonyl)benzene (420 mg, 0.945 mmol) and N-benzyl-1-methoxy-N-((trimethylsilyl)methyl)methanamine (449 mg, 1.89 mmol) in dichloromethane (10 mL) at 0° C. After stirring under nitrogen at 0° C. for 10 min and at room temperature for 1 h, the resulting mixture was diluted with ethyl acetate (200 mL), washed with saturated sodium bicarbonate (2×20 mL) and brine (20 mL), dried (magnesium sulfate), filtered and concentrated under reduced pressure. Silica gel chromatography, eluting with 0-20% ethyl acetate in hexanes, gave the desired product as racemic material (490 mg). It was separated into its homochiral components using a chiral ODH column (5×25 cm, 5 μm), CO$_2$/isopropanol (90/10), 35° C., 100 bars to afford the desired Example 430 (195 mg, 34% yield) as the second eluent off the column. LC/MS (M+1): 578.2; LC retention time: 4.02 min (analytical HPLC Method A); 1H NMR (400 MHz, CDCl$_3$) δ ppm 7.49 (d, J=8.4 Hz, 2H), 7.41-7.26 (m, 8H), 7.19-7.05 (m, 1H), 6.98 (dd, J=7.9, 1.8 Hz, 1H), 6.93 (dd, J=8.8, 1.7 Hz, 1H), 3.75-3.57 (m, 3H), 3.27 (d, J=11.0 Hz, 1H), 3.10-2.99 (m, 1H), 2.99-2.89 (m, 1H), 2.78 (td, J=8.2, 4.6 Hz, 1H), 2.60-2.48 (m, 1H), 2.30 (d, J=1.7 Hz, 3H).

Example 431

(1R,4r)-4-((R)-3-((4-hydroxyphenyl)sulfonyl)-3-(4-(perfluoropropan-2-yl)phenyl)pyrrolidine-1-carbonyl)cyclohexanecarboxylic acid

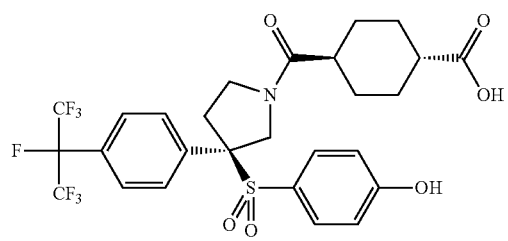 [SMILES: O=C(O)[C@H]1CC[C@H](C(=O)N2CC[C@](c3ccc(C(F)(C(F)(F)F)C(F)(F)F)cc3)(S(=O)(=O)c3ccc(O)cc3)C2)CC1]

A mixture of (1R,4r)-4-((R)-3-((4-fluorophenyl)sulfonyl)-3-(4-(perfluoropropan-2-yl)phenyl)pyrrolidine-1-carbonyl)cyclohexanecarboxylic acid (20 mg, 0.032 mmol, Example 95) and potassium hydroxide (8.94 mg, 0.159 mmol) in dimethylsulfoxide (0.5 mL) was stirred at 80° C. for 5 h, cooled down to room temperature and quenched with 1N aqueous hydrogen chloride (0.2 mL). The crude material was purified via preparative LC/MS with the following conditions: Column: Waters XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-100% B over 20 minutes, then a 5-minute hold at 100% B; Flow: 20 mL/min. Fractions containing the desired product were combined and dried via centrifugal evaporation to give Example 431 (2.0 mg, 10% yield). LC/MS (M+1): 636.3; HPLC RT=1.585 min (analytical HPLC Method B). 1H NMR (500 MHz, DMSO-d$_6$) δ ppm 7.68-7.54 (m, 2H), 7.46 (d, J=8.4 Hz, 1H), 7.37 (d, J=8.4 Hz, 1H), 7.20-7.04 (m, 2H), 6.80-6.61 (m, 2H), 4.92-4.57 (m, 1H), 4.16-3.72 (m, 1H), 3.71-3.25 (m, 2H), 3.15-2.92 (m, 1H), 2.79-2.62 (m, 1H), 2.30-2.06 (m, 2H), 2.04-1.79 (m, 3H), 1.73-1.60 (m, 2H), 1.48-1.30 (m, 3H).

The Examples in TABLE 3 below were prepared in the same manner as outlined in examples above.

TABLE 3
| ExNo | Structure | MS (M + 1) | HPLC ret. time (min.) | HPLC method |
|---|---|---|---|---|
| 432 | 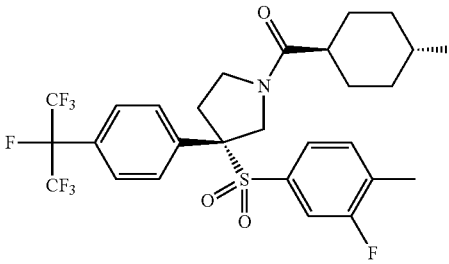 | 642.2 | 4.331 | A |
| 433 | 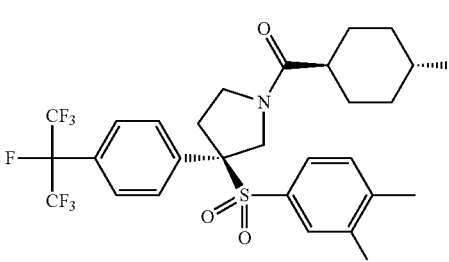 | 642.3 | — | — |
| 434 | 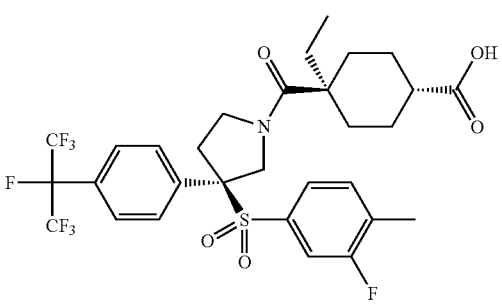 [SMILES: CC[C@]1(C(=O)N2CC[C@](c3ccc(C(F)(C(F)(F)F)C(F)(F)F)cc3)(S(=O)(=O)c3ccc(C)c(F)c3)C2)CC[C@H](C(=O)O)CC1] | 670.2 | 2.23 | E |
| 435 | 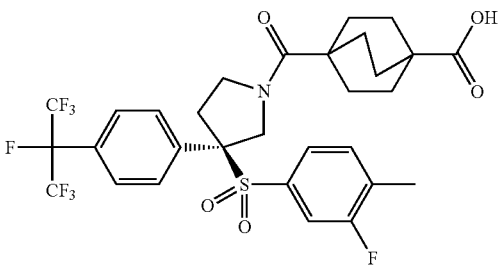 [SMILES: Cc1ccc(S(=O)(=O)[C@@]2(c3ccc(C(F)(C(F)(F)F)C(F)(F)F)cc3)CCN(C(=O)C34CCC(C(=O)O)(CC3)CC4)C2)cc1F] | 668.2 | 1.86 | E |
| 436 | 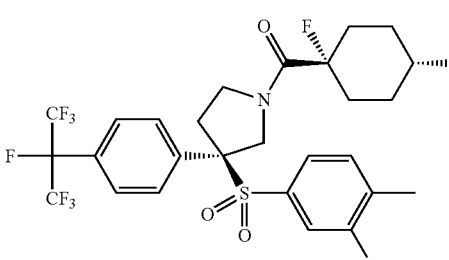 | 660.1 | 1.82 | E |

TABLE 3-continued

| ExNo | Structure | MS (M + 1) | HPLC ret. time (min.) | HPLC method |
|---|---|---|---|---|
| 437 | 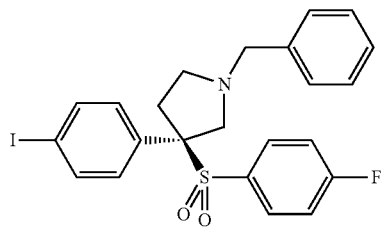 [SMILES: O=S(=O)(c1ccc(F)cc1)[C@@]1(c2ccc(I)cc2)CCN(Cc2ccccc2)C1] | 656.2 | 1.83 | E |
| 438 | 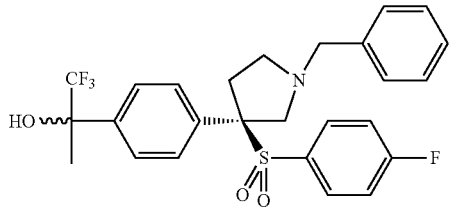 | 579.9 (M − 56 + 1) | 4.688 | A |

Example 439

(1R,4r)-4-((R)-3-(4-fluorophenylsulfonyl)-3-(4-(1,1,1,2-tetrafluoropropan-2-yl)phenyl)pyrrolidine-1-carbonyl)cyclohexanecarboxylic acid, mixture of two diastereomers Step A: (R)-1-benzyl-3-(4-fluorophenylsulfonyl)-3-(4-iodophenyl)pyrrolidine rac-1-Benzyl-3-(4-fluorophenylsulfonyl)-3-(4-iodophenyl)pyrrolidine (8.12 g, prepared in Step C of Examples 37 and 38) was separated into its homochiral components by preparative chiral SFC (Chiralpak AD-H 3×25 cm, 5 μm particles, 50% methanol in CO₂, 150 mL/min) to afford (R)-1-benzyl-3-(4-fluorophenylsulfonyl)-3-(4-iodophenyl) pyrrolidine (3.13 g, 43% yield) as the first eluent off the column and (S)-1-benzyl-3-(4-fluorophenylsulfonyl)-3-(4-iodophenyl)pyrrolidine (1.93 g, 26% yield) as the second eluent off the column. Analytical data for the R-isomer: LC/MS (M+1): 522.2; chiral HPLC retention time: 6.12 min (Chiralpak AD-H 0.46×25 cm, 5 μm particles, 35% methanol in CO₂, 3 mL/min); 1H NMR (400 MHz, CDCl₃) δ 7.60 (d, J=8.4 Hz, 2H), 7.44-7.37 (m, 2H), 7.36-7.21 (m, 5H), 7.08-7.00 (m, 2H), 6.90 (d, J=8.6 Hz, 2H), 3.72-3.60 (m, 3H), 3.16 (d, J=11.0 Hz, 1H), 3.03-2.87 (m, 2H), 2.72 (td, J=8.0, 4.6 Hz, 1H), 2.52-2.42 (m, 1H). Analytical data for S-isomer: LC/MS (M+1): 522.2; chiral HPLC retention time: 10.33 min (Chiralpak AD-H 0.46×25 cm, 5 μm particles, 35% methanol in CO₂, 3 mL/min); 1H NMR (400 MHz, CDCl₃) δ 7.63-7.57 (m, 2H), 7.44-7.37 (m, 2H), 7.36-7.21 (m, 5H), 7.09-6.99 (m, 2H), 6.93-6.87 (m, 2H), 3.72-3.60 (m, 3H), 3.16 (d, J=10.8 Hz, 1H), 3.02-2.86 (m, 2H), 2.72 (td, J=8.0, 4.5 Hz, 1H), 2.52-2.42 (m, 1H).

Step B: (R)-2-(4-(1-benzyl-3-(4-fluorophenylsulfonyl)pyrrolidin-3-yl)phenyl)-1,1,1-trifluoropropan-2-ol, mixture of two diastereomers mixture of two diastereomers 1.7 M tert-Butyllithium in pentane (0.427 mL, 0.726 mmol) was added dropwise to a stirred THF (2.5 mL) solution of (R)-1-benzyl-3-((4-fluorophenyl)sulfonyl)-3-(4-iodophenyl)pyrrolidine (172 mg, 0.330 mmol) at −78° C. under N2. After 5 minute, 1,1,1-trifluoropropan-2-one (0.059 mL, 0.660 mmol) was added. The mixture was stirred at −78° C. for 1 h then quenched by adding sat. NH4Cl (4 mL). The crude was separated into two phases after warmed up to ambient temperature. The aqueous phase was extracted with EtOAc (4 mL). The combined organic phase was concentrated. Silica gel chromatography, eluting with 0-50% ethyl acetate in hexanes, gave mixture of diastereomers of (R)-2-(4-(1-benzyl-3-(4-fluorophenylsulfonyl)pyrrolidin-3-yl)phenyl)-1,1,1-trifluoropropan-2-ol as white solid (43.9 mg, 26% yield). LC/MS (M+1): 508.2; 1H NMR (400 MHz, CDCl₃) δ 7.45 (dd, J=8.4, 3.1 Hz, 2H), 7.36-7.24 (m, 7H), 7.17 (dd, J=8.7, 1.6 Hz, 2H), 7.00-6.93 (m, 2H), 3.75-3.64 (m, 3H), 3.27 (dd, J=11.0, 1.6 Hz, 1H), 3.05-2.90 (m, 2H), 2.80-2.67 (m, 2H), 2.59-2.50 (m, 1H), 1.78-1.73 (m, 3H).

Step C: (R)-1,1,1-trifluoro-2-(4-(3-(4-fluorophenyl-sulfonyl)pyrrolidin-3-yl)phenyl)propan-2-ol, mixture of two diastereomers

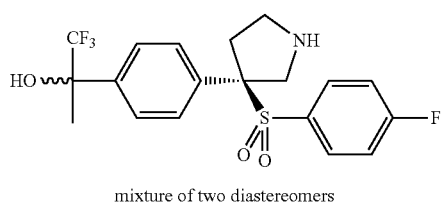 [SMILES: CC(O)(c1ccc([C@]2(S(=O)(=O)c3ccc(F)cc3)CCNC2)cc1)C(F)(F)F]

mixture of two diastereomers

A MeOH (1 mL) solution of mixture of diastereomers of (R)-2-(4-(1-benzyl-3-(4-fluorophenylsulfonyl)pyrrolidin-3-yl)phenyl)-1,1,1-trifluoropropan-2-ol (43 mg, 0.085 mmol) and Pearlman's catalyst (11.90 mg, 0.017 mmol) was stirred under 50 psi H2 at ambient temperature for 16 h. 1M HCl (185 uL, 0.185 mmol) and additional Pearlman's catalyst (35 mg) were added. The hydrogenation was resumed for additional 15 h. The mixture was filtered and the filtrate was concentrated to give crude mixture of diastereomers of (R)-1,1,1-trifluoro-2-(4-(3-(4-fluorophenylsulfonyl)pyrrolidin-3-yl)phenyl)propan-2-ol (30.6 mg) as white solid. It was used in Step D without further purification. LC/MS (M+1): 418.2

Step D: (1R,4r)-methyl 4-((R)-3-(4-fluorophenylsulfonyl)-3-(4-(1,1,1-trifluoro-2-hydroxypropan-2-yl)phenyl)pyrrolidine-1-carbonyl)cyclohexanecarboxylate, mixture of two diastereomers

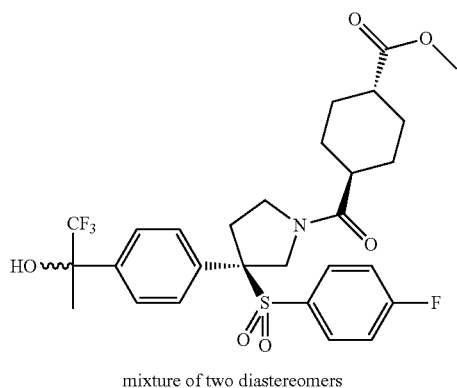 [SMILES: COC(=O)[C@H]1CC[C@H](C(=O)N2CC[C@](c3ccc(C(C)(O)C(F)(F)F)cc3)(S(=O)(=O)c3ccc(F)cc3)C2)CC1]

mixture of two diastereomers

An acetonitrile (0.5 mL) solution of crude mixture of diastereomers of (R)-1,1,1-trifluoro-2-(4-(3-(4-fluorophenylsulfonyl)pyrrolidin-3-yl)phenyl)propan-2-ol (30 mg, 0.072 mmol), (1r,4r)-4-(methoxycarbonyl)cyclohexanecarboxylic acid (20 mg, 0.107 mmol), BOP (34 mg, 0.077 mmol) and Hunig's base (0.063 mL, 0.359 mmol) was stirred at ambient temperature for 20 minute. The crude was purified via preparative HPLC with the following conditions: Column: Phenomenex 1-Phen Luna Axia C18, 30×100 mm, 5-μm particles; Mobile Phase A: 5:95 acetonitrile:water with 0.05% TFA; Mobile Phase B: 95:5 acetonitrile:water with 0.05% TFA; Gradient: 10-100% B over 10 minutes, then a 5-minute hold at 100% B; Flow: 20 mL/min. Fractions containing the desired product were combined and dried via centrifugal evaporation to give mixture of diastereomers of (1R,4r)-methyl 4-((R)-3-(4-fluorophenylsulfonyl)-3-(4-(1,1,1-trifluoro-2-hydroxypropan-2-yl)phenyl) pyrrolidine-1-carbonyl)cyclohexanecarboxylate (27.6 mg, 66% yield) as brown solid. LC/MS (M+1): 586.3; 1H NMR (400 MHz, 1:1 mixture of CDCl$_3$—CD$_3$OD) δ 7.55-7.45 (m, 2H), 7.29-7.21 (m, 2H), 7.12-6.97 (m, 4H), 4.86-4.73 (m, 1H), 4.12-3.96 (m, 1H), 3.88-3.74 (m, 2H), 3.69-3.63 (m, 3H), 3.06-2.30 (m, 3H), 2.15-1.94 (m, 3H), 1.84-1.74 (m, 1H), 1.69 (s, 3H), 1.63-1.38 (m, 4H).

Step E: (1R,4r)-methyl 4-((R)-3-(4-fluorophenylsulfonyl)-3-(4-(1,1,1,2-tetrafluoropropan-2-yl)phen 1)pyrrolidine-1-cyclohexanecarboxylate, mixture of two diastereomers

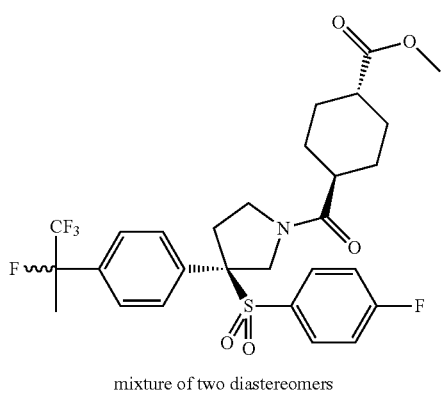 [SMILES: COC(=O)[C@H]1CC[C@H](C(=O)N2CC[C@](c3ccc(C(C)(F)C(F)(F)F)cc3)(S(=O)(=O)c3ccc(F)cc3)C2)CC1]

mixture of two diastereomers (Diethylamino)sulfur trifluoride (0.026 mL, 0.195 mmol) was added to a stirred ClCH$_2$CH$_2$Cl (0.5 mL) solution of mixture of diastereomers of (1R,4r)-methyl 4-((3R)-3-((4-fluorophenyl)sulfonyl)-3-(4-(1,1,1-trifluoro-2-hydroxypropan-2-yl)phenyl)pyrrolidine-1-carbonyl)cyclohexanecarboxylate (19 mg, 0.032 mmol). The mixture was stirred at ambient temperature for 40 minute then slowly added to MeOH (1 mL). The resulting solution was concentrated to give crude mixture of diastereomers of (1R,4r)-methyl 4-((R)-3-(4-fluorophenylsulfonyl)-3-(4-(1,1,1,2-tetrafluoropropan-2-yl)phenyl)pyrrolidine-1-carbonyl)cyclohexanecarboxylate (assuming 0.032 mmol). This material was used in Step F without further purification. LC/MS (M+1): 588.3.

Step F: (1R,4r)-4-((R)-3-(4-fluorophenylsulfonyl)-3-(4-(1,1,1,2-tetrafluoropropan-2-yl)phenyl)pyrrolidine-1-carbonyl)cyclohexanecarboxylic acid, mixture of two diastereomers

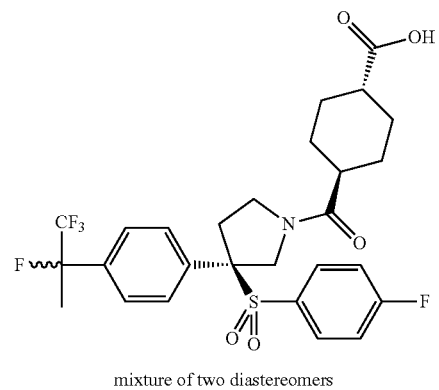 [SMILES: CC(F)(c1ccc([C@]2(S(=O)(=O)c3ccc(F)cc3)CCN(C(=O)[C@H]3CC[C@H](C(=O)O)CC3)C2)cc1)C(F)(F)F]

mixture of two diastereomers

The crude mixture of diastereomers of (1R,4r)-methyl 4-((R)-3-(4-fluorophenylsulfonyl)-3-(4-(1,1,1,2-tetrafluoropropan-2-yl)phenyl)pyrrolidine-1-carbonyl)cyclohexanecarboxylate (assuming 0.032 mmol) was dissolved in THF (0.5 mL) and DMSO (0.25 mL). To it was added 1 M NaOH (0.5 mL, 0.5 mmol). The mixture was stirred at ambient temperature for 19 h. The reaction was quenched by adding 1M HCl (0.5 mL, 0.5 mmol) and diluted with water (2 mL). A white solid precipitated out. The solid was further purified via preparative LC/MS with the following conditions: Column: Waters XBridge C18, 19×200 mm, 5-µm particles; Guard Column: Waters XBridge C18, 19×10 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 15-85% B over 15 minutes, then a 5-minute hold at 100% B; Flow: 20 mL/min. Fractions containing the desired product were combined and dried via centrifugal evaporation to give mixture of diastereomers of (1R,4r)-4-((R)-3-(4-fluorophenylsulfonyl)-3-(4-(1,1,1,2-tetrafluoropropan-2-yl)phenyl) pyrrolidine-1-carbonyl)cyclohexanecarboxylic acid (9.8 mg, 53%). LC/MS (M+1):574.3; LC retention time: 1.59 min (analytical HPLC Method B); 1H NMR (500 MHz, 1:1 mixture of CDCl$_3$—CD$_3$OD) δ 7.44-7.37 (m, 2H), 7.35-7.27 (m, 2H), 7.22-7.11 (m, 2H), 7.10-7.02 (m, 2H), 4.90-4.78 (m, 1H), 4.14-3.97 (m, 1H), 3.87-3.76 (m, 2H), 3.67-3.33 (m, 1H), 2.75-2.37 (m, 2H), 2.35-2.25 (m, 1H), 2.18-1.94 (m, 3H), 1.92-1.84 (m, 3H), 1.79 (d, J=13.0 Hz, 1H), 1.63-1.37 (m, 4H)

Example 440

(1R,4r)-4-((R)-3-(4-fluorophenylsulfonyl)-3-(4-(1,1,1-trifluoro-2-hydroxypropan-2-yl)phenyl)pyrrolidine-1-carbonyl)cyclohexanecarboxylic acid, mixture of two diastereomers

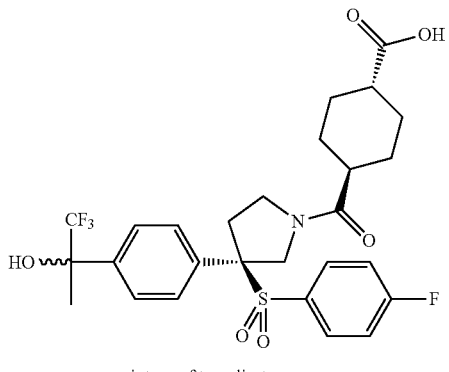

mixture of two diastereomers

A THF (0.25 mL) solution of (1R,4r)-methyl 4-((3R)-3-((4-fluorophenyl)sulfonyl)-3-(4-(1,1,1-trifluoro-2-hydroxypropan-2-yl)phenyl)pyrrolidine-1-carbonyl)cyclohexanecarboxylate (7.8 mg, 0.013 mmol from Step D of Example 439) and 1M LiOH (0.25 mL, 0.25 mmol) was stirred at ambient temperature for 4 h. After reaction completion, the crude was quenched with 1M HCl (0.25 mL, 0.25 mmol) and diluted with MeOH (1 mL). The resulting solution was purified via preparative LC/MS with the following conditions: Column: Waters XBridge C18, 19×200 mm, 5-µm particles; Guard Column: Waters XBridge C18, 19×10 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 0-100% B over 15 minutes, then a 3-minute hold at 100% B; Flow: 20 mL/min. Fractions containing the desired product were combined and dried via centrifugal evaporation to give (1R,4r)-4-((R)-3-(4-fluorophenylsulfonyl)-3-(4-(1,1,1-trifluoro-2-hydroxypropan-2-yl)phenyl)pyrrolidine-1-carbonyl)cyclohexanecarboxylic acid (6 mg, 74%). LC/MS (M+1): 572.3; LC retention time: 1.29 min (analytical HPLC Method B); 1H NMR (500 MHz, 1:1 mixture of CDCl$_3$—CD$_3$OD) δ 7.54-7.46 (m, 2H), 7.31-7.22 (m, 2H), 7.14-7.00 (m, 4H), 4.88-4.76 (m, 1H), 4.14-3.97 (m, 1H), 3.88-3.75 (m, 2H), 2.75-2.38 (m, 2H), 2.34-2.23 (m, 1H), 2.18-1.93 (m, 3H), 1.79 (d, J=12.5 Hz, 1H), 1.70 (s, 3H), 1.63-1.38 (m, 4H).

Example 441

Enantiomer 1 of 1-(3-(3-bromophenylsulfonyl)-3-(4-(perfluoropropan-2-yl)phenyl)pyrrolidin-1-yl)-2-(pyridin-4-yl)ethanone Step A: 2-(4-((3-bromophenylthio)methyl)phenyl)-1,1,1,3,3,3-hexafluoropropan-2-ol

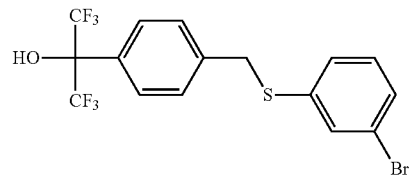 [SMILES: OC(c1ccc(CSc2cccc(Br)c2)cc1)(C(F)(F)F)C(F)(F)F]

A THF (87 ml) suspension of 2-(4-(bromomethyl)phenyl)-1,1,1,3,3,3-hexafluoropropan-2-ol (21.87 g, 43.5 mmol) from Step A of Example 1 and 3-bromobenzenethiol (8.33 g, 44.1 mmol) was stirred at ambient temperature for 20 h. The suspension was filtered through a short bed of Celite. The bed was washed with THF (50 mL). The combined filtrate was concentrated in vacuum. The crude 2-(4-(((3-bromophenyl)thio)methyl)phenyl)-1,1,1,3,3,3-hexafluoropropan-2-ol (assuming 43.5 mmol) was obtained as yellow oil and it was used in Step B without further purification.

Step B: 2-(4-((3-bromophenylsulfonyl)methyl)phenyl)-1,1,1,3,3,3-hexafluoropropan-2-ol

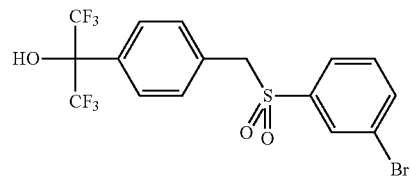 [SMILES: O=S(=O)(Cc1ccc(C(O)(C(F)(F)F)C(F)(F)F)cc1)c1cccc(Br)c1]

mCPBA (21.45 g, 96 mmol) was added in portion to a CH$_2$Cl$_2$ (124 mL) solution of 2-(4-(((3-bromophenyl)thio)methyl)phenyl)-1,1,1,3,3,3-hexafluoropropan-2-ol (assuming 43.5 mmol). The reaction was stirred at ambient temperature for 1 h. The suspension was filtered through a short bed of Celite to remove most of the excess mCPBA. The bed was washed with CH$_2$Cl$_2$ (200 mL). The combined filtrate was washed with sat. NaHCO₃ (200 mL), water (20 mL) and brine (20 mL), respectively. Silica gel chromatography, eluting with 0-30% ethyl acetate in hexanes, gave 2-(4-((3-bromophenylsulfonyl)methyl)phenyl)-1,1,1,3,3,3-hexafluoropropan-2-ol (15.89 g, 77%) as white solid. 1H NMR (400 MHz, CDCl₃) δ 7.77-7.72 (m, 2H), 7.67 (d, J=8.3 Hz, 2H), 7.56-7.51 (m, 1H), 7.35-7.29 (m, 1H), 7.25-7.21 (m, 2H), 4.36 (s, 2H).

Step C: 1-bromo-3-(4-(perfluoropropan-2-yl)benzylsulfonyl)benzene

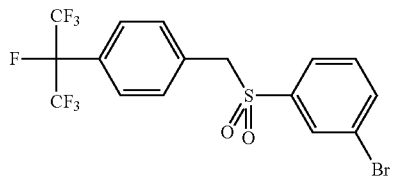 [SMILES: O=S(=O)(Cc1ccc(C(F)(C(F)(F)F)C(F)(F)F)cc1)c1cccc(Br)c1]

A stirred ClCH₂CH₂Cl (33.3 ml) solution of 2-(4-(((3-bromophenyl)sulfonyl)methyl)phenyl)-1,1,1,3,3,3-hexafluoropropan-2-ol (15.89 g, 33.3 mmol) and (diethylamino)sulfur trifluoride (24 mL, 182 mmol) was divided into four sealed safety vials and each vial was heated at 60° C. for 16 h. The reaction mixture was cooled to ambient temperature then added dropwise to cooled MeOH (0° C., 100 mL) with stirring. The resulting solution was concentrated. The residue was dissolved in Et₂O (50 mL). The Et₂O solution was basified with sat. NaHCO₃ (150 mL) and solid K₂CO₃ until no more CO2 released. The two phases were separated. The ether phase was washed with 0.5 M HCl (100 mL), water (50 mL) and brine (50 mL), respectively. Silica gel chromatography, eluting with 0-30% ethyl acetate in hexanes, gave 1-bromo-3-(4-(perfluoropropan-2-yl)benzylsulfonyl)benzene (13.85 g, 87%) as yellow solid. 1H NMR (400 MHz, CDCl₃) δ 7.78-7.72 (m, 2H), 7.60-7.54 (m, 3H), 7.36-7.32 (m, 1H), 7.30-7.27 (m, 2H), 4.37 (s, 2H).

Step D: 1-bromo-3-(1-(4-(perfluoropropan-2-yl)phenyl)vinylsulfonyl)benzene

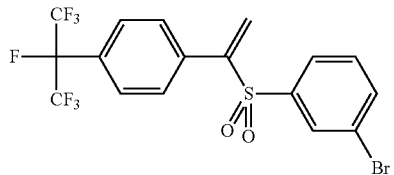 [SMILES: C=C(c1ccc(C(F)(C(F)(F)F)C(F)(F)F)cc1)S(=O)(=O)c1cccc(Br)c1]

Acetic anhydride (10.63 ml, 113 mmol) was added to a DMF (37.6 mL) solution of 1-bromo-3-((4-(perfluoropropan-2-yl)benzyl)sulfonyl)benzene (9 g, 18.78 mmol) and N,N,N',N'-tetramethylmethanediamine (15.56 ml, 113 mmol). The mixture was stirred at room temperature for 20 minute then warmed up to 60° C. for 2 h. Additional acetic anhydride (10.63 ml, 113 mmol) was added. The open flask was heated at 90° C. for 30 minute. After cooled to ambient temperature, the crude was slowly added to sat. NaHCO₃ (200 mL). Additional solid K₂CO₃ was added until the pH of the aqueous was tested as basic. The aqueous was extracted with EtOAc (2×300 mL). The combined EtOAc solution was washed with 10% LiCl (100 mL) and brine (100 mL), respectively. It was dried over Na2SO4, filtered and concentrated. Silica gel chromatography, eluting with 0-30% ethyl acetate in hexanes, gave 1-bromo-3-(1-(4-(perfluoropropan-2-yl)phenyl)vinylsulfonyl)benzene (6.4 g, 69%) as light yellow oil. 1H NMR (400 MHz, CDCl₃) δ 7.79 (t, J=1.8 Hz, 1H), 7.69 (ddd, J=8.0, 1.9, 1.0 Hz, 1H), 7.62-7.55 (m, 3H), 7.51-7.45 (m, 2H), 7.30 (t, J=7.9 Hz, 1H), 6.72 (d, J=0.4 Hz, 1H), 6.08 (d, J=0.4 Hz, 1H).

Step E: rac-1-benzyl-3-(3-bromophenylsulfonyl)-3-(4-(perfluoropropan-2-yl)phenyl)pyrrolidine

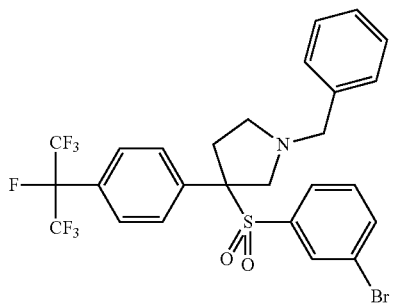 [SMILES: O=S(=O)(c1cccc(Br)c1)C1(c2ccc(C(F)(C(F)(F)F)C(F)(F)F)cc2)CCN(Cc2ccccc2)C1]

TFA (0.045 mL, 0.581 mmol) was added dropwise to a stirred CH₂Cl₂ (72.7 mL) solution of 1-bromo-3-((1-(4-(perfluoropropan-2-yl)phenyl)vinyl)sulfonyl)benzene (7.14 g, 14.5 mmol) and N-benzyl-1-methoxy-N-((trimethylsilyl)methyl)methanamine (10.35 g, 43.6 mmol). The mixture was stirred at ambient temperature for 17 h. The crude was quenched with sat. NaHCO₃ (50 mL) and stirred for 30 minute. The CH₂Cl₂ layer was separated and concentrated. Silica gel chromatography, eluting with 0-100% ethyl acetate in hexanes, gave rac-1-benzyl-3-((3-bromophenyl)sulfonyl)-3-(4-(perfluoropropan-2-yl)phenyl)pyrrolidine (10.37 g, 93%) as light yellow oil. LC/MS (M+1): 624.0, 626.0; 1H NMR (400 MHz, CDCl₃) δ 7.68 (ddd, J=7.9, 1.9, 1.1 Hz, 1H), 7.52 (d, J=8.6 Hz, 2H), 7.45 (t, J=1.7 Hz, 1H), 7.38-7.23 (m, 8H), 7.21-7.16 (m, 1H), 3.77-3.63 (m, 3H), 3.26 (d, J=11.0 Hz, 1H), 3.08-3.01 (m, 1H), 3.00-2.92 (m, 1H), 2.78 (td, J=8.2, 4.5 Hz, 1H), 2.59-2.50 (m, 1H).

Step F: rac-3-(3-bromophenylsulfonyl)-3-(4-(perfluoropropan-2-yl)phenyl)pyrrolidine

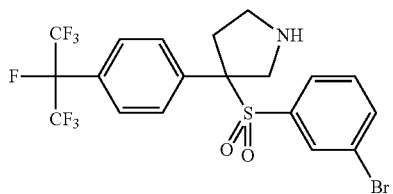 [SMILES: O=S(=O)(c1cccc(Br)c1)C1(c2ccc(C(F)(C(F)(F)F)C(F)(F)F)cc2)CCNC1]

1-chloroethyl carbonochloridate (0.832 mL, 7.64 mmol) was added to a stirred ClCH₂CH₂Cl (14 mL) solution of rac-1-benzyl-3-((3-bromophenyl)sulfonyl)-3-(4-(perfluoropropan-2-yl)phenyl)pyrrolidine (1.54 g, 2.47 mmol) at ambient temperature. The sealed safety vial containing the reaction mixture was heated at 90° C. for 24 h. Additional 1-chloroethyl carbonochloridate (0.536 mL) was added and the mixture was heated for additional 42 h. The solvent was evaporated, the residue was dissolved in MeOH (10 mL). The resulting solution was heated in the sealed safety vial for 9 h. Silica gel chromatography, eluting with 0-10% MeOH in CH₂Cl₂ with 10% NH4OH, gave rac-3-(3-bromophenylsulfonyl)-3-(4-(perfluoropropan-2-yl)phenyl)pyrrolidine (0.9522 g, 72% yield) as brown sticky solid. LC/MS (M+1): 534.1, 536.1; 1H NMR (400 MHz, 1:1 mixture of CDCl₃—CD₃OD) δ 7.76-7.71 (m, 1H), 7.52 (d, J=8.4 Hz, 2H), 7.32-7.18 (m, 5H), 4.12 (d, J=13.4 Hz, 1H), 3.47-3.37 (m, 1H), 3.26 (d, J=13.4 Hz, 1H), 3.12-2.94 (m, 2H), 2.54-2.44 (m, 1H).

Step G: Enantiomers 1 and 2 of 3-(3-bromophenylsulfonyl)-3-(4-(perfluoropropan-2-yl)phenyl)pyrrolidine

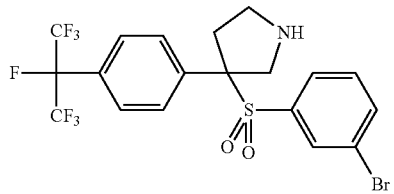 [SMILES: O=S(=O)(c1cccc(Br)c1)C1(c2ccc(C(F)(C(F)(F)F)C(F)(F)F)cc2)CCNC1]

rac-3-(3-bromophenylsulfonyl)-3-(4-(perfluoropropan-2-yl)phenyl)pyrrolidine (0.9522 g) was separated into its homochiral components by preparative chiral SFC (Chiralpak AD-H 5×25 cm, 5 μm particles, 35% methanol in CO₂ with 0.2% NH4OH, 150 mL/min) to afford the first eluent (enantiomer 1, 0.4863 g) and the second eluent (enantiomer 2, 0.3699 g) off the column.

Analytical data for the enantiomer 1: LC/MS (M+1): 534, 536; chiral HPLC retention time: 1.55 min (Chiralpak AD-H 0.46×25 cm, 5 μm particles, 35% methanol in CO₂ with 0.2% NH₄OH, 3 mL/min); 1H NMR (400 MHz, CDCl₃) δ 7.77-7.71 (m, 1H), 7.52 (d, J=8.4 Hz, 2H), 7.32-7.26 (m, 2H), 7.26-7.19 (m, 3H), 4.12 (d, J=13.4 Hz, 1H), 3.46-3.37 (m, 1H), 3.27 (d, J=13.4 Hz, 1H), 3.12-2.94 (m, 2H), 2.54-2.44 (m, 1H). Analytical data for the enantiomer 2: LC/MS (M+1): 534, 536; chiral HPLC retention time: 2.68 min (Chiralpak AD-H 0.46×25 cm, 5 μm particles, 35% methanol in CO₂ with 0.2% NH₄OH, 3 mL/min); 1H NMR (400 MHz, CDCl₃) δ 7.78-7.70 (m, 1H), 7.52 (d, J=8.4 Hz, 2H), 7.32-7.26 (m, 2H), 7.25-7.18 (m, 3H), 4.12 (d, J=13.4 Hz, 1H), 3.46-3.37 (m, 1H), 3.27 (d, J=13.4 Hz, 1H), 3.11-2.95 (m, 2H), 2.54-2.43 (m, 1H).

Step H: 1-(3-(3-bromophenylsulfonyl)-3-(4-(perfluoropropan-2-yl)phenyl)pyrrolidin-1-yl)-2-(pyridin-4-yl)ethanone, enantiomer 1

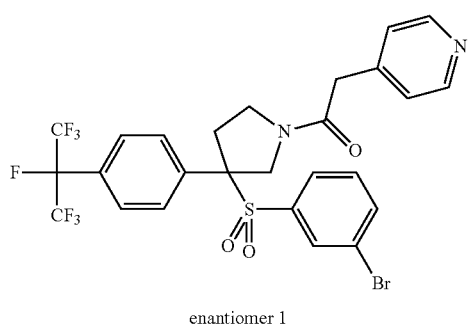 [SMILES: O=C(Cc1ccncc1)N1CCC(c2ccc(C(F)(C(F)(F)F)C(F)(F)F)cc2)(S(=O)(=O)c2cccc(Br)c2)C1]

enantiomer 1

Similar to the Step D of Example 439, the enantiomer 1 of 3-(3-bromophenylsulfonyl)-3-(4-(perfluoropropan-2-yl)phenyl)pyrrolidine (8 mg, 0.015 mmol), 2-(pyridin-4-yl)acetic acid, HCl (5 mg, 0.029 mmol), was converted to the enantiomer 1 of 1-(3-(3-bromophenylsulfonyl)-3-(4-(perfluoropropan-2-yl)phenyl)pyrrolidin-1-yl)-2-(pyridin-4-yl)ethanone (8 mg, 82%). LC/MS (M+1): 653.1, 655.1; LC retention time: 2.17 min (analytical HPLC Method B); 1H NMR (500 MHz, d6-DMSO) δ 8.48 (dd, J=15.1, 5.4 Hz, 2H), 7.98-7.87 (m, 1H), 7.68-7.58 (m, 2H), 7.56-7.37 (m, 4H), 7.34-7.10 (m, 3H), 4.83-4.67 (m, 1H), 4.25-3.40 (m, 5H), 3.24-2.99 (m, 1H), 2.82-2.57 (m, 1H).

Examples 442

1-(3-(3-bromophenylsulfonyl)-3-(4-(perfluoropropan-2-yl)phenyl)pyrrolidin-1-yl)-2-(pyridin-4-yl)ethanone, enantiomer 2

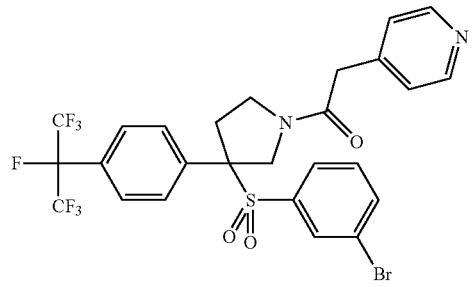

enantiomer 2

Similar to the Step D of Example 439, the enantiomer 2 of 3-(3-bromophenylsulfonyl)-3-(4-(perfluoropropan-2-yl)phenyl)pyrrolidine (8 mg, 0.015 mmol from Step G of Example 441) was converted to the enantiomer 2 of 1-(3-(3-bromophenylsulfonyl)-3-(4-(perfluoropropan-2-yl)phenyl)pyrrolidin-1-yl)-2-(pyridin-4-yl)ethanone (8.3 mg, 85%). LC/MS (M+1): 653.1, 655.1; LC retention time: 2.17 min (analytical HPLC Method B); 1H NMR (500 MHz, d6-DMSO) δ 8.50 (dd, J=14.8, 4.4 Hz, 2H), 7.94 (d, J=4.7 Hz, 1H), 7.68-7.57 (m, 2H), 7.55-7.37 (m, 4H), 7.35-7.11 (m, 3H), 4.82-4.68 (m, 1H), 4.25-3.56 (m, 4H), 3.49-3.38 (m, 1H), 3.24-3.01 (m, 1H), 2.82-2.57 (m, 1H).

Example 443

(1R,4r)-4-(3-(4-(perfluoropropan-2-yl)phenyl)-3-(m-tolylsulfonyl)pyrrolidine-1-carbonyl)cyclohexanecarboxylic acid, enantiomer 2

Step A: Enantiomer 2 of (1r,4r)-methyl 4-(3-(3-bromophenylsulfonyl)-3-(4-perfluoropropan-2-yl)phenyl)pyrrolidine-1-carbonyl)cyclohexanecarboxylate

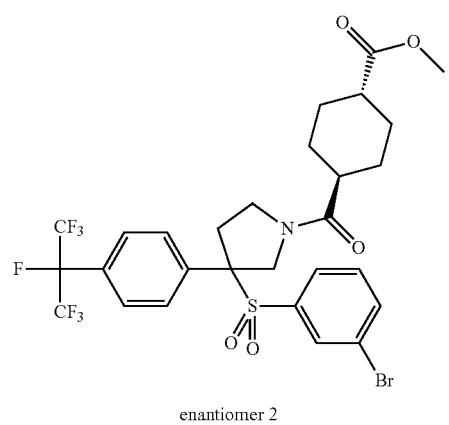 [SMILES: COC(=O)[C@H]1CC[C@H](C(=O)N2CCC(c3ccc(C(F)(C(F)(F)F)C(F)(F)F)cc3)(S(=O)(=O)c3cccc(Br)c3)C2)CC1]

enantiomer 2

Similar to the Step D of Example 439, enantiomer 2 of 3-(3-bromophenylsulfonyl)-3-(4-(perfluoropropan-2-yl) phenyl)pyrrolidine (125 mg, 0.234 mmol from Step G of Example 441) was converted to the enantiomer 2 of (1r,4r)-methyl 4-(3-(3-bromophenylsulfonyl)-3-(4-(perfluoropropan-2-yl)phenyl)pyrrolidine-1-carbonyl)cyclohexanecarboxylate (164 mg, 100%) as white solid. LC/MS (M+1): 702.3, 704.3; 1H NMR (400 MHz, CDCl$_3$) δ 7.75-7.68 (m, 1H), 7.59-7.50 (m, 2H), 7.39-7.31 (m, 1H), 7.26-7.16 (m, 4H), 4.77 (d, J=14.2 Hz, 1H), 4.16-4.01 (m, 1H), 3.89 (d, J=13.9 Hz, 1H), 3.78-3.63 (m, 4H), 3.44 (dd, J=14.2, 6.1 Hz, 1H), 2.70-2.59 (m, 1H), 2.43-2.30 (m, 2H), 2.07-1.97 (m, 2H), 1.82-1.74 (m, 1H), 1.69-1.37 (m, 5H).

Step B: (1r,4r)-4-(3-(4-(perfluoropropan-2-yl)phenyl)-3-(m-tolylsulfonyl)pyrrolidine-1-carbonyl)cyclohexanecarboxylic acid, enantiomer 2

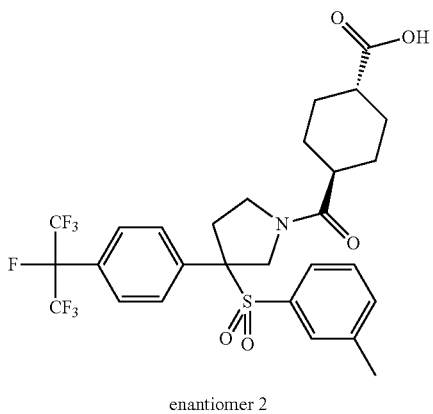 [SMILES: Cc1cccc(S(=O)(=O)C2(c3ccc(C(F)(C(F)(F)F)C(F)(F)F)cc3)CCN(C(=O)[C@H]3CC[C@H](C(=O)O)CC3)C2)c1]

enantiomer 2

A mixture of enantiomer 2 of (1r,4r)-methyl 4-(3-((3-bromophenyl)sulfonyl)-3-(4-(perfluoropropan-2-yl)phenyl) pyrrolidine-1-carbonyl)cyclohexanecarboxylate (15 mg, 0.021 mmol), 2,4,6-trimethyl-1,3,5,2,4,6-trioxatriborinane (8.2 mg, 0.065 mmol), Pd$_2$(dba)3.CHCl$_3$ (1.955 mg, 2.135 μmol), X-Phos (2.036 mg, 4.27 μmol) and 2 M potassium phosphate tribasic (0.032 mL, 0.064 mmol) was dissolved in dioxane (0.5 mL). The vial was degassed by vacuum-N$_2$ refill cycle twice. The sealed tube was heated at 95° C. for 75 minute then cooled to ambient temperature. 1M LiOH (0.5 mL) was added and the mixture was stirred at ambient temperature for 80 minute. The crude was neutralized by adding 1M HCl (0.5 mL) and filtered. The filtrate was purified via preparative LC/MS with the following conditions: Column: Waters XBridge C18, 19×200 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-100% B over 15 minutes, then a 5-minute hold at 100% B; Flow: 20 mL/min. Fractions containing the desired product were combined and dried via centrifugal evaporation to give enantiomer 2 of (1r,4r)-4-(3-(4-(perfluoropropan-2-yl) phenyl)-3-(m-tolylsulfonyl)pyrrolidine-1-carbonyl)cyclohexanecarboxylic acid (10 mg, 71% yield). LC/MS (M+1): 624.3; LC retention time: 1.80 min (analytical HPLC Method B); 1H NMR (500 MHz, 1:1 mixture of CDCl$_3$—CD$_3$OD) δ 7.57-7.41 (m, 3H), 7.35-7.16 (m, 4H), 6.98-6.89 (m, 1H), 4.92-4.78 (m, 1H), 4.15-3.98 (m, 1H), 3.88-3.76 (m, 2H), 3.68-3.33 (m, 1H), 2.76-2.52 (m, 1H), 2.47-2.26 (m, 2H), 2.22 (s, 3H), 2.16-1.93 (m, 3H), 1.78 (d, J=13.1 Hz, 1H), 1.63-1.37 (m, 4H).

The Examples in Table 4 below were prepared in the same manner as outlined in the Example 443 above, substituting with the appropriate boronic acids or ester reagents.

TABLE 4

| Ex | Structure | MS observed (M + 1) | HPLC ret. time (min.) | HPLC method |
| --- | --- | --- | --- | --- |
| 444 | | 636.2 | 1.85 | B | enantiomer 2

TABLE 4-continued
| Ex | Structure | MS observed (M + 1) | HPLC ret. time (min.) | HPLC method |
|---|---|---|---|---|
| 445 | 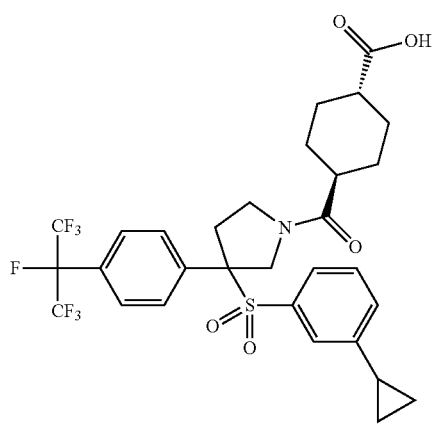 enantiomer 2 | 650.2 | 1.74 | B |
| 446 | 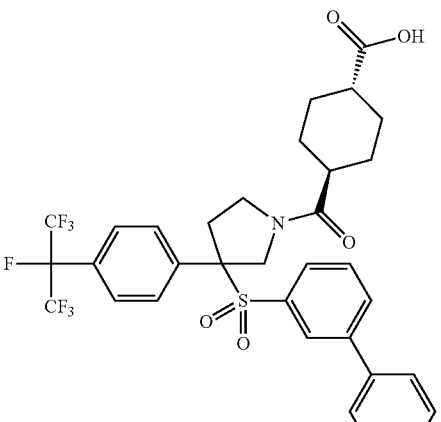 enantiomer 2 | 686.3 | 2.02 | B |
| 447 | 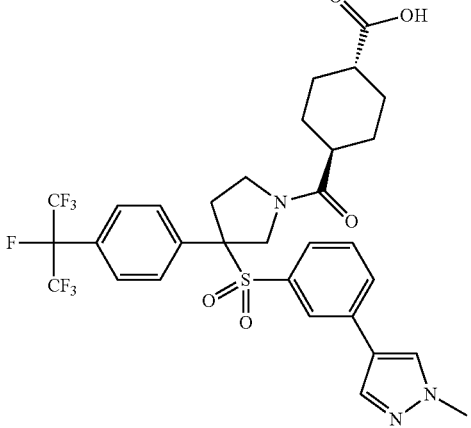 enantiomer 2 | 690.3 | 1.67 | B |

TABLE 4-continued
| Ex | Structure | MS observed (M + 1) | HPLC ret. time (min.) | HPLC method |
|---|---|---|---|---|
| 448 | 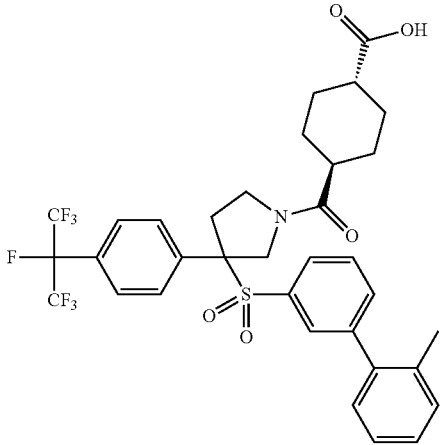 enantiomer 2 | 700.2 | 2.09 | B |
| 449 | 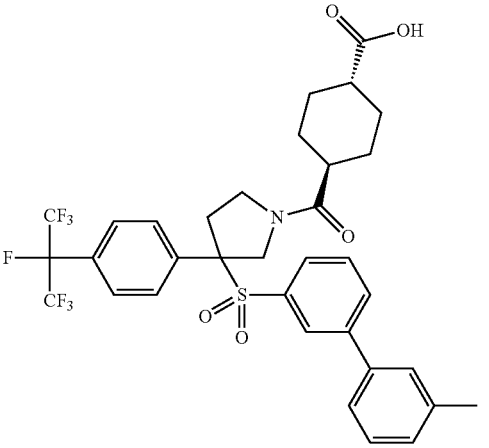 enantiomer 2 | 700.1 | 2.12 | B |
| 450 | 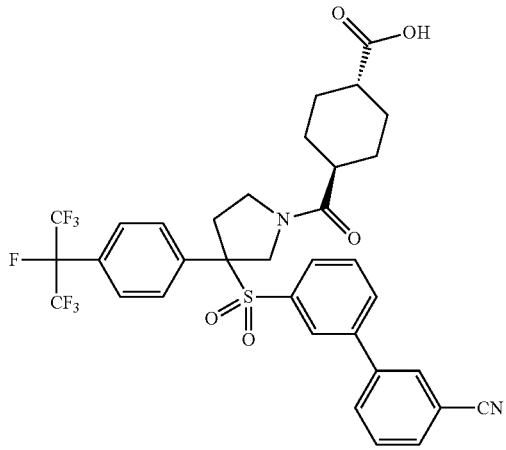 enantiomer 2 | 711.2 | 1.84 | B |

TABLE 4-continued
| Ex | Structure | MS observed (M + 1) | HPLC ret. time (min.) | HPLC method |
|---|---|---|---|---|
| 451 | 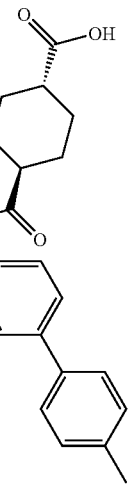 enantiomer 2 | 700.2 | 2.11 | B |
| 452 | 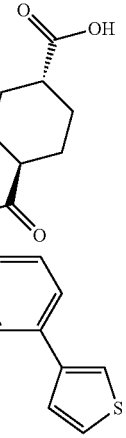 enantiomer 2 | 692.2 | 1.99 | B |
| 453 |  enantiomer 2 | 687.3 | 1.65 | B |

Example 454

(1r,4r)-4-(3-(4-(perfluoropropan-2-yl)phenyl)-3-(3-(pyridin-2-yl)phenylsulfonyl)pyrrolidone-1-carbonyl)cyclohexanecarboxylic acid, enantiomer 2

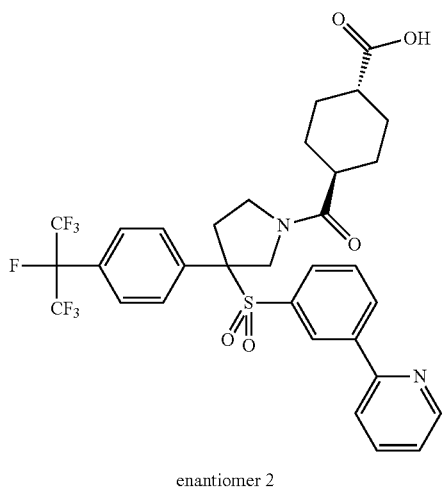 [SMILES: O=C(O)[C@H]1CC[C@H](C(=O)N2CCC(c3ccc(C(F)(C(F)(F)F)C(F)(F)F)cc3)(S(=O)(=O)c3cccc(-c4ccccn4)c3)C2)CC1]

enantiomer 2

A mixture of enantiomer 2 of (1r,4r)-methyl 4-(3-((3-bromophenyl)sulfonyl)-3-(4-(perfluoropropan-2-yl)phenyl)pyrrolidine-1-carbonyl)cyclohexanecarboxylate (15 mg, 0.021 mmol from Step A of Example 443), 2-(tributylstannyl)pyridine (15.7 mg, 0.043 mmol) and bis(triphenylphosphine)palladium(II) chloride (1.5 mg, 2.1 µmol) was dissolved in dioxane (0.5 mL). The vial was degassed by vacuum-$N_2$ refill cycle twice. The sealed tube was then heated at 90° C. for 3 h. After cooled to ambient temperature, 1M NaOH (0.25 mL) was added and the mixture was stirred for 40 minute. The crude was neutralized by adding 1M HCl (0.25 mL), diluted with MeOH (1 mL) and filtered. The filtrate was purified via preparative LC/MS with the following conditions: Column: Waters XBridge C18, 19×200 mm, 5-µm particles; Guard Column: Waters XBridge C18, 19×10 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 25-65% B over 20 minutes, then a 5-minute hold at 100% B; Flow: 20 mL/min. Fractions containing the desired product were combined and dried via centrifugal evaporation to give enantiomer 2 of (1r,4r)-4-(3-(4-(perfluoropropan-2-yl)phenyl)-3-(3-(pyridin-2-yl)phenylsulfonyl)pyrrolidine-1-carbonyl)cyclohexanecarboxylic acid (7.1 mg, 47% yield). LC/MS (M+1):687.3; LC retention time: 1.79 min (analytical HPLC Method B); 1H NMR (500 MHz, 1:1 mixture of $CDCl_3$—$CD_3OD$) δ 8.67-8.58 (m, 1H), 8.27-8.17 (m, 1H), 7.87-7.78 (m, 2H), 7.65-7.58 (m, 2H), 7.53-7.23 (m, 6H), 4.97-4.85 (m, 1H), 4.16-4.01 (m, 1H), 3.91-3.76 (m, 2H), 3.68-3.34 (m, 1H), 2.76-2.54 (m, 1H), 2.46-2.18 (m, 2H), 2.14-1.93 (m, 3H), 1.82-1.71 (m, 1H), 1.62-1.37 (m, 4H).

Example 455

(1r,4r)-4-(3-(4-(perfluoropropan-2-yl)phenyl)-3-(phenylsulfonyl)pyrrolidine-1-carbonyl)cyclohexanecarboxylic acid, enantiomer 2

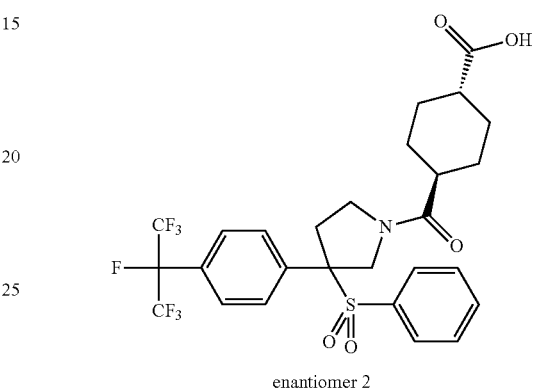

enantiomer 2

A MeOH (0.5 mL) suspension of enantiomer 2 of (1r,4r)-methyl 4-((R)-3-((3-bromophenyl)sulfonyl)-3-(4-(perfluoropropan-2-yl)phenyl)pyrrolidine-1-carbonyl)cyclohexanecarboxylate (15 mg, 0.021 mmol from Step A of Example 443) and Pearlman's catalyst (20 wt % on carbon, 3.7 mg, 5.27 µmol) was hydrogenated under 50 psi H2 at ambient temperature. After 4 h, 1M LiOH (0.5 mL) was added and the mixture was stirred for 16 h. The crude was diluted with MeOH (1 mL) and filtered. The filtrate was purified via preparative LC/MS with the following conditions: Column: Waters XBridge C18, 19×200 mm, 5-µm particles; Guard Column: Waters XBridge C18, 19×10 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 25-100% B over 20 minutes, then a 5-minute hold at 100% B; Flow: 20 mL/min. Fractions containing the desired product were combined and dried via centrifugal evaporation to give enantiomer 2 of (1r,4r)-4-(3-(4-(perfluoropropan-2-yl)phenyl)-3-(phenylsulfonyl)pyrrolidine-1-carbonyl)cyclohexanecarboxylic acid (11.4 mg, 87% yield). LC/MS (M+1):610.3; LC retention time: 1.71 min (analytical HPLC Method B); 1H NMR (500 MHz, 1:1 mixture of $CDCl_3$—$CD_3OD$) δ 7.63-7.60 (m, 1H), 7.54-7.47 (m, 2H), 7.39-7.32 (m, 2H), 7.32-7.26 (m, 2H), 7.22 (d, J=8.4 Hz, 1H), 4.93-4.81 (m, 1H), 4.16-3.95 (m, 1H), 3.89-3.77 (m, 2H), 3.66-3.33 (m, 1H), 2.76-2.53 (m, 1H), 2.45-2.24 (m, 2H), 2.16-1.92 (m, 4H), 1.79 (d, J=13.6 Hz, 1H), 1.64-1.39 (m, 4H).

The examples in Table 5 below were prepared in the same 2-step manner as outlined in the Examples 443 and 455 above, substituting with the appropriate boronic acids or esters.

TABLE 5
| Example number | Structure | MS observed (M + 1) | HPLC ret. time (min.) | HPLC method |
|---|---|---|---|---|
| 456 | 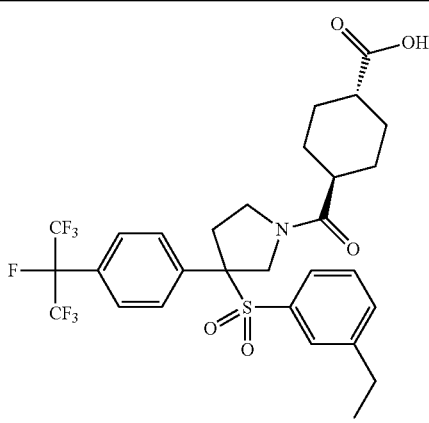 enantiomer 2 | 638.3 | 1.89 | B |
| 457 | 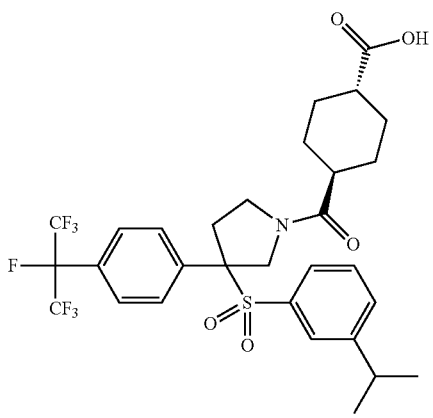 enantiomer 2 | 652.3 | 2.04 | B |
| 458 | 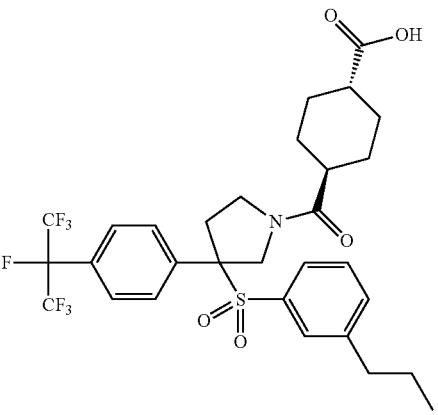 enantiomer 2 | 652.3 | 2.09 | B |

TABLE 5-continued
| Example number | Structure | MS observed (M + 1) | HPLC ret. time (min.) | HPLC method |
|---|---|---|---|---|
| 459 | 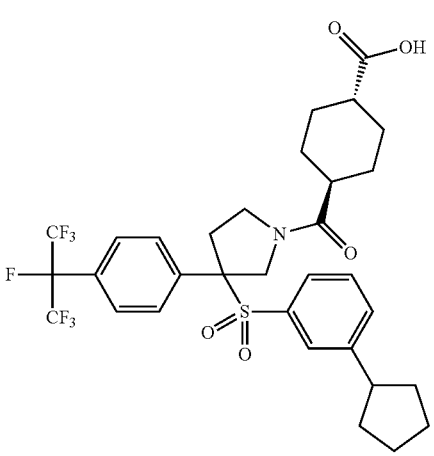<br>enantiomer 2 | 678.2 | 2.08 | B |
| 460 | 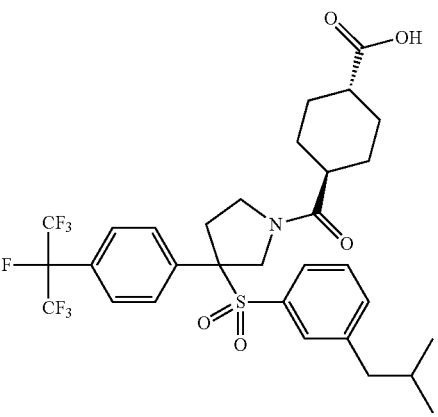<br>enantiomer 2 | 666.2 | 2.14 | B |
| 461 | 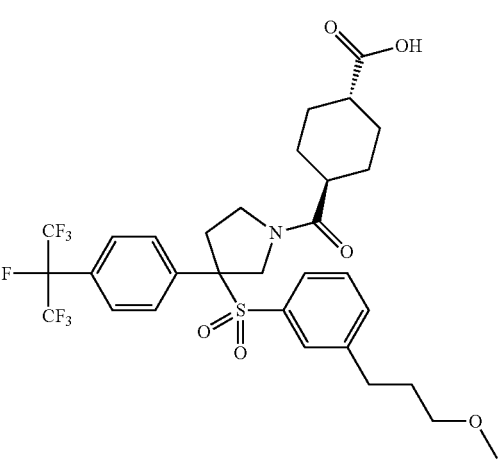<br>enantiomer 2 | 682.3 | 1.82 | B |

TABLE 5-continued

| Example number | Structure | MS observed (M + 1) | HPLC ret. time (min.) | HPLC method |
|---|---|---|---|---|
| 462 | 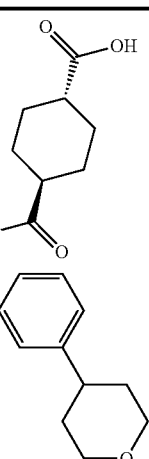<br>enantiomer 2 | 694.2 | 1.66 | B |
| 463 | 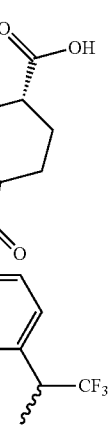<br>enantiomer 2 | 706.3 | 1.97 | B |

Example 464

(1r,4r)-4-(3-(3-bromophenylsulfonyl)-3-(4-(perfluoropropan-2-yl)phenyl)pyrrolidine-1-carbonyl)cyclohexanecarboxylic acid, enantiomer 2

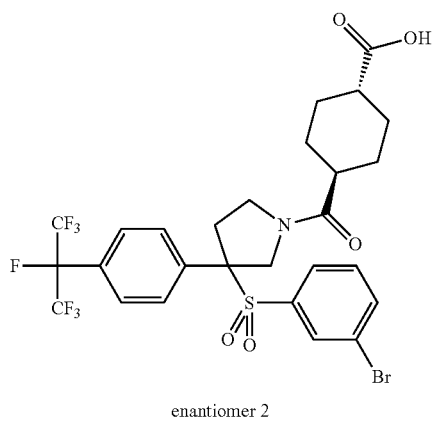 [SMILES: O=C(O)[C@H]1CC[C@H](C(=O)N2CCC(c3ccc(C(F)(C(F)(F)F)C(F)(F)F)cc3)(S(=O)(=O)c3cccc(Br)c3)C2)CC1]
enantiomer 2

1M NaOH (0.5 mL, 0.5 mmol) was added to a stirred dioxane (0.5 mL) solution of enantiomer 2 of (1r,4r)-methyl 4-(3-((3-bromophenyl)sulfonyl)-3-(4-(perfluoropropan-2-yl)phenyl)pyrrolidine-1-carbonyl)cyclohexanecarboxylate (9.3 mg, 0.013 mmol from Step A of Example 443) at ambient temperature. After 1 h, the crude was neutralized by adding 1 M HCl (0.5 mL), diluted with MeOH (0.5 mL) and filtered. The filtrate was purified via preparative LC/MS with the following conditions: Column: Waters XBridge C18, 19×200 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-100% B over 12 minutes, then a 5-minute hold at 100% B; Flow: 20 mL/min. Fractions containing the desired product were combined and dried via centrifugal evaporation to give enantiomer 2 of (1r,4r)-4-(3-(3-bromophenylsulfonyl)-3-(4-(perfluoropropan-2-yl) phenyl)pyrrolidine-1-carbonyl)cyclohexanecarboxylic acid (3 mg, 31% yield). LC/MS (M+1): 688.1, 690.1; LC retention time: 1.64 min (analytical HPLC Method B); 1H NMR (500 MHz, 1:1 mixture of CDCl$_3$—CD$_3$OD) δ 7.82-7.75 (m, 1H), 7.61-7.52 (m, 2H), 7.41-7.21 (m, 5H), 4.93-4.80 (m, 1H), 4.17-3.99 (m, 1H), 3.91-3.78 (m, 2H), 3.68-3.34 (m, 1H), 2.77-2.54 (m, 1H), 2.49-2.26 (m, 2H), 2.19-1.93 (m, 3H), 1.79 (d, J=13.6 Hz, 1H), 1.65-1.35 (m, 4H).

Example 465

(1r,4r)-4-(3-(3-chlorophenylsulfonyl)-3-(4-(perfluoropropan-2-yl)phenyl)pyrrolidine-1-carbonyl)cyclohexanecarboxylic acid, enantiomer 2

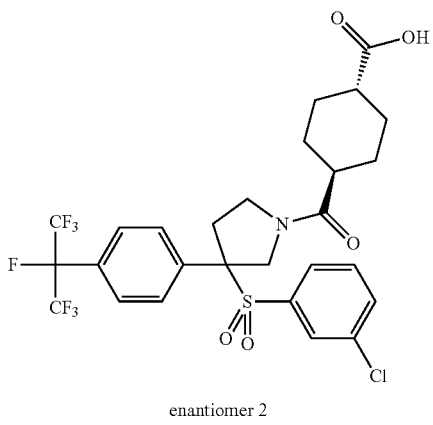 [SMILES: O=C(O)[C@H]1CC[C@H](C(=O)N2CCC(c3ccc(C(F)(C(F)(F)F)C(F)(F)F)cc3)(S(=O)(=O)c3cccc(Cl)c3)C2)CC1]

enantiomer 2

A dimethylacetamide (0.5 mL) solution of enantiomer 2 of (1r,4r)-methyl 4-(3-((3-bromophenyl)sulfonyl)-3-(4-(perfluoropropan-2-yl)phenyl)pyrrolidine-1-carbonyl)cyclohexanecarboxylate (15 mg, 0.021 mmol from Step A of Example 443) and copper(I) chloride (6.34 mg, 0.064 mmol) was heated by microwave at 220° C. (max power=400 W) for 20 min. After cooled to ambient temperature, 1 M NaOH (0.5 mL) and MeOH (0.5 mL) were added and the mixture was stirred for 40 minute. The crude was diluted with MeOH (0.5 mL) and filtered. The filtrate was purified via preparative LC/MS with the following conditions: Column: Waters XBridge C18, 19×200 mm, 5-µm particles; Guard Column: Waters XBridge C18, 19×10 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 25-100% B over 12 minutes, then a 5-minute hold at 100% B; Flow: 20 mL/min. Fractions containing the desired product were combined and dried via centrifugal evaporation to give enantiomer 2 of (1r,4r)-4-(3-(3-chlorophenylsulfonyl)-3-(4-(perfluoropropan-2-yl)phenyl)pyrrolidine-1-carbonyl)cyclohexanecarboxylic acid (7.9 mg, 54% yield). LC/MS (M+1): 644.2; LC retention time: 1.69 min (analytical HPLC Method B); 1H NMR (500 MHz, 1:1 mixture of CDCl$_3$—CD$_3$OD) δ 7.65-7.52 (m, 3H), 7.42-7.24 (m, 4H), 7.17-7.06 (m, 1H), 4.92-4.81 (m, 1H), 4.16-3.99 (m, 1H), 3.88-3.79 (m, 2H), 3.68-3.33 (m, 1H), 2.77-2.55 (m, 1H), 2.48-2.26 (m, 2H), 2.17-1.95 (m, 3H), 1.82-1.76 (m, 1H), 1.65-1.38 (m, 4H).

Example 466

(1r,4r)-4-(3-(3-cyanophenylsulfonyl)-3-(4-(perfluoropropan-2-yl)phenyl)pyrrolidine-1-carbonyl)cyclohexanecarboxylic acid, enantiomer 2

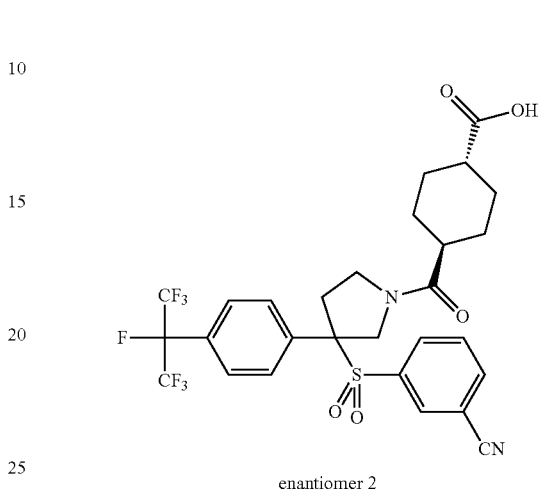

enantiomer 2

A DMF (0.5 mL) suspension of enantiomer 2 of (1r,4r)-methyl 4-(3-((3-bromophenyl)sulfonyl)-3-(4-(perfluoropropan-2-yl)phenyl)pyrrolidine-1-carbonyl)cyclohexanecarboxylate (12 mg, 0.017 mmol from Step A of Example 443), zinc powder (0.112 mg, 1.708 µmol), Pd(Ph$_3$P)$_4$ (3.95 mg, 3.42 µmol) and zinc cyanide (6.02 mg, 0.051 mmol) was degassed by vacuum-N2 refill cycle twice. The sealed safety vial was heated at 120° C. for 2 h. After cooled to ambient temperature, 1M NaOH (0.5 mL) and MeOH (0.5 mL) were added and the mixture was stirred for 1 h. The crude was diluted with MeOH (0.5 mL) and filtered. The filtrate was purified via preparative LC/MS with the following conditions: Column: Waters XBridge C18, 19×200 mm, 5-µm particles; Guard Column: Waters XBridge C18, 19×10 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 25-100% B over 20 minutes, then a 7-minute hold at 100% B; Flow: 20 mL/min. Fractions containing the desired product were combined and dried via centrifugal evaporation to give enantiomer 2 of (1r,4r)-4-(3-(3-cyanophenylsulfonyl)-3-(4-(perfluoropropan-2-yl)phenyl)pyrrolidine-1-carbonyl) cyclohexanecarboxylic acid (3.1 mg, 27% yield). LC/MS (M+1): 635.2; LC retention time: 1.64 min (analytical HPLC Method B); 1H NMR (500 MHz, 1:1 mixture of CDCl$_3$—CD$_3$OD) δ 7.98-7.92 (m, 1H), 7.62-7.51 (m, 5H), 7.38-7.23 (m, 2H), 4.97-4.81 (m, 1H), 4.17-4.02 (m, 1H), 3.91-3.80 (m, 2H), 3.68-3.35 (m, 1H), 2.78-2.56 (m, 1H), 2.48-2.27 (m, 2H), 2.17-1.95 (m, 3H), 1.80 (d, J=12.4 Hz, 1H), 1.65-1.39 (m, 4H).

Example 467

(1r,4r)-4-(3-(3-hydroxyphenylsulfonyl)-3-(4-(perfluoropropan-2-yl)phenyl)pyrrolidine-1-carbonyl)cyclohexanecarboxylic acid, enantiomer 2

Step A: Enantiomer 2 of (1r,4r)-methyl 4-(3-(4-(perfluoropropan-2-yl)phenyl)-3-(3-(4,4,5,5-tetramethyl-1,3,2-dioxaborolan-2-yl)phenylsulfonyl)pyrrolidine-1-carbonyl)cyclohexanecarboxylate

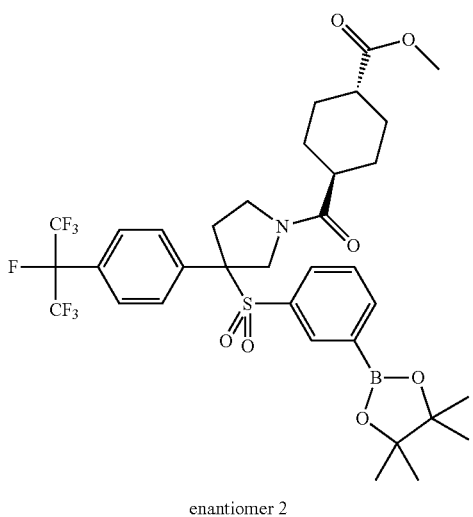 [SMILES: COC(=O)[C@H]1CC[C@H](C(=O)N2CCC(c3ccc(C(F)(C(F)(F)F)C(F)(F)F)cc3)(S(=O)(=O)c3cccc(B4OC(C)(C)C(C)(C)O4)c3)C2)CC1]

enantiomer 2

A stirred dioxane (0.25 mL) solution of enantiomer 2 of (1r,4r)-methyl 4-(3-((3-bromophenyl)sulfonyl)-3-(4-(perfluoropropan-2-yl)phenyl)pyrrolidine-1-carbonyl)cyclohexanecarboxylate (15 mg, 0.021 mmol from Step A of Example 443), 4,4,4',4',5,5,5',5'-octamethyl-2,2'-bi(1,3,2-dioxaborolane) (6.7 mg, 0.026 mmol), potassium acetate (6.2 mg, 0.063 mmol) and $PdCl_2(dppf)-CH_2Cl_2$ adduct (0.5 mg, 0.6 mmol) was degassed by vacuum-$N_2$ refill cycle twice. The sealed safety vial was then heated at 80° C. for 16 h. After cooled to ambient temperature, the crude was diluted with MeOH (1.5 mL) and filtered. The filtrate was concentrated. The resulting residue (assuming 0.021 mmol) was dissolved in MeOH (0.5 mL) and used in the Step B.

Step B: Enantiomer 2 of (1r,4r)-4-(3-(3-hydroxyphenylsulfonyl)-3-(4-(perfluoropropan-2-yl)phenyl)pyrrolidine-1-carbonyl)cyclohexanecarboxylic acid

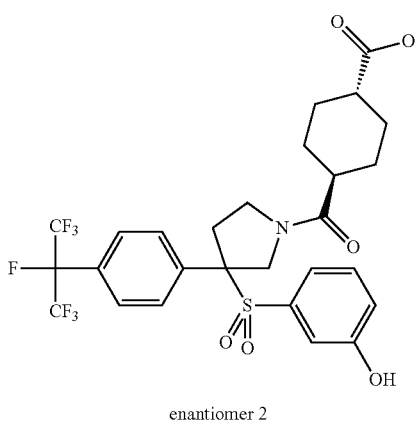

enantiomer 2

To the stirred MeOH (0.5 mL) solution of crude enantiomer 2 of (1r,4r)-methyl 4-(3-(4-(perfluoropropan-2-yl)phenyl)-3-((3-(4,4,5,5-tetramethyl-1,3,2-dioxaborolan-2-yl)phenyl)sulfonyl)pyrrolidine-1-carbonyl)cyclohexanecarboxylate (assuming 0.021 mmol) was added 1M NaOH (0.5 mL) and 30 wt % hydrogen peroxide (0.5 mL, 4.41 mmol) at ambient temperature. The mixture was stirred for 70 minute, diluted with MeOH (2 mL) then filtered. Half of the filtrate (1.75 mL, assuming 0.0105 mmol) was purified via preparative LC/MS with the following conditions: Column: Waters XBridge C18, 19×200 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-85% B over 20 minutes, then a 5-minute hold at 85% B; Flow: 20 mL/min. Fractions containing the desired product were combined and dried via centrifugal evaporation to give enantiomer 2 of (1r,4r)-4-(3-(3-hydroxyphenylsulfonyl)-3-(4-(perfluoropropan-2-yl)phenyl)pyrrolidine-1-carbonyl)cyclohexanecarboxylic acid (2.7 mg, 41%). LC/MS (M+1): 626.3; LC retention time: 1.62 min (analytical HPLC Method B); 1H NMR (500 MHz, 1:1 mixture of $CDCl_3$—$CD_3OD$) δ 7.95 (s, 1H), 7.57-7.48 (m, 2H), 7.36-7.22 (m, 2H), 7.16-7.09 (m, 1H), 7.02 (dd, J=8.2, 2.4 Hz, 1H), 6.88-6.83 (m, 1H), 6.65 (d, J=7.8 Hz, 1H), 4.91-4.82 (m, 1H), 4.15-3.90 (m, 1H), 3.88-3.74 (m, 2H), 3.64-3.34 (m, 1H), 2.76-2.52 (m, 1H), 2.44-2.23 (m, 2H), 2.18-1.91 (m, 3H), 1.77 (d, J=13.4 Hz, 1H), 1.64-1.38 (m, 4H).

Example 468

(1r,4r)-4-(3-(3-methoxyphenylsulfonyl)-3-(4-(perfluoropropan-2-yl)phenyl)pyrrolidine-1-carbonyl)cyclohexanecarboxylic acid, enantiomer 2

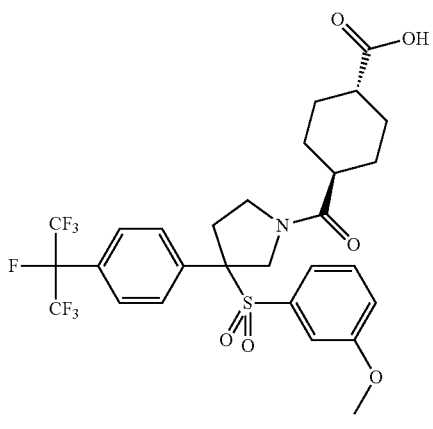

enantiomer 2

Half of the filtrate containing enantiomer 2 of (1r,4r)-4-(3-(3-hydroxyphenylsulfonyl)-3-(4-(perfluoropropan-2-yl)phenyl)pyrrolidine-1-carbonyl)cyclohexanecarboxylic acid (1.75 mL, assuming 0.0105 mmol from Step A of Example 467) was concentrated. To the residue was added DMF (0.5 mL), potassium carbonate (50 mg, 0.362 mmol) and iodomethane (50 uL, 0.800 mmol). The mixture was stirred at ambient temperature for 1 h. 1M NaOH (0.36 mL) was added and the mixture was stirred for 3 h. 1M HCl (0.36 mL) was added to neutralize the solution. The resulting solution was diluted with MeOH (1 mL) then filtered. The filtrate was purified via preparative LC/MS with the following conditions: Column: Waters XBridge C18, 19×200 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-70% B over 25 minutes, then a 5-minute hold at 100% B; Flow: 20 mL/min. Fractions containing the desired product were combined and dried via centrifugal evaporation to give enantiomer 2 of (1r,4r)-4-(3-(3-methoxyphenylsulfonyl)-3-(4-(perfluoropropan-2-yl)phenyl)pyrrolidine-1-carbonyl)cyclohexanecarboxylic acid (4.2 mg, 63%). LC/MS (M+1): 640.3; LC retention time: 1.79 min (analytical HPLC Method B); 1H NMR (500 MHz, 1:1 mixture of CDCl$_3$—CD$_3$OD) δ 7.57-7.50 (m, 2H), 7.36-7.24 (m, 3H), 7.16 (dd, J=8.3, 2.5 Hz, 1H), 7.02-6.96 (m, 1H), 6.71 (d, J=1.7 Hz, 1H), 4.93-4.84 (m, 1H), 4.15-3.94 (m, 1H), 3.88-3.76 (m, 2H), 3.65 (s, 3H), 3.62-3.34 (m, 1H), 2.76-2.54 (m, 1H), 2.46-2.24 (m, 2H), 2.17-1.92 (m, 3H), 1.78 (d, J=13.4 Hz, 1H), 1.63-1.38 (m, 4H).

Example 469

(1r,4r)-4-ethyl-4-(3-(4-(perfluoropropan-2-yl)phenyl)-3-(m-tolylsulfonyl)pyrrolidine-1-carbonyl)cyclohexanecarboxylic acid, enantiomer 2

Step A: Enantiomer 2 of (1r,4r)-tert-butyl 4-(3-(3-bromophenylsulfonyl)-3-(4-(perfluoropropan-2-yl)phenyl)pyrrolidin-1-carbonyl)-4-ethylcyclohexanecarboxylate

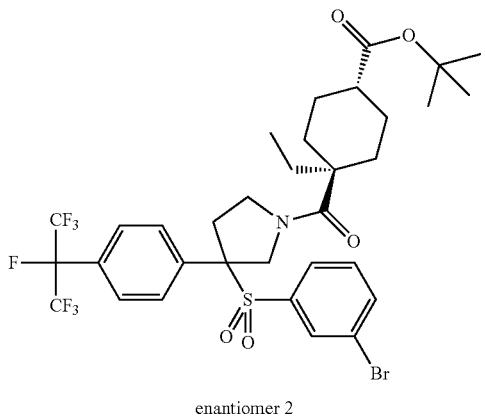 [SMILES: CC[C@]1(C(=O)N2CCC(c3ccc(C(F)(C(F)(F)F)C(F)(F)F)cc3)(S(=O)(=O)c3cccc(Br)c3)C2)CC[C@H](C(=O)OC(C)(C)C)CC1]

enantiomer 2

Similar to Step D of Example 439, enantiomer 2 of 3-(3-bromophenylsulfonyl)-3-(4-(perfluoropropan-2-yl)phenyl)pyrrolidine (20 mg, 0.037 mmol from Step G of Example 441) and (1r,4r)-4-(tert-butoxycarbonyl)-1-ethylcyclohexanecarboxylic acid (9.60 mg, 0.037 mmol) were coupled to give enantiomer 2 of (1r,4r)-tert-butyl 4-(3-(3-bromophenylsulfonyl)-3-(4-(perfluoropropan-2-yl)phenyl)pyrrolidine-1-carbonyl)-4-ethylcyclohexanecarboxylate (16.7 mg, 58%) as yellow solid. LC/MS (M+1): 772.1, 774.1; 1H NMR (400 MHz, CDCl$_3$) δ 7.70 (dt, J=7.9, 1.5 Hz, 1H), 7.54 (d, J=8.4 Hz, 2H), 7.33-7.28 (m, 2H), 7.23 (d, J=8.1 Hz, 3H), 4.89-4.73 (m, 1H), 4.17-4.06 (m, 2H), 3.84 (br. s., 1H), 2.63 (br. s., 1H), 2.39-2.24 (m, 1H), 1.92-1.54 (m, 11H), 1.47-1.44 (m, 9H), 0.80 (t, J=7.5 Hz, 3H).

Step B: Enantiomer 2 of (1r,4r)-tert-butyl 4-ethyl-4-(3-(4-(perfluoropropan-2-yl)phenyl)-3-(m-tolylsulfonyl)pyrrolidine-1-carbonyl)cyclohexanecarboxylate

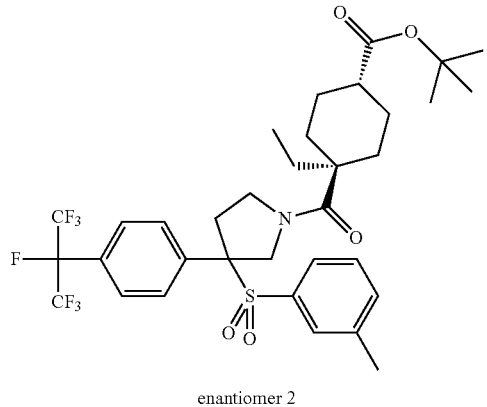 [SMILES: CC[C@]1(C(=O)N2CCC(c3ccc(C(F)(C(F)(F)F)C(F)(F)F)cc3)(S(=O)(=O)c3cccc(C)c3)C2)CC[C@H](C(=O)OC(C)(C)C)CC1]

enantiomer 2

Similar to the Step B of Example 443, enantiomer 2 of (1r,4r)-tert-butyl 4-(3-((3-bromophenyl)sulfonyl)-3-(4-(perfluoropropan-2-yl)phenyl)pyrrolidine-1-carbonyl)-4-ethylcyclohexanecarboxylate (16.7 mg, 0.022 mmol) was converted to enantiomer 2 of (1r,4r)-tert-butyl 4-ethyl-4-(3-(4-(perfluoropropan-2-yl)phenyl)-3-(m-tolylsulfonyl)pyrrolidine-1-carbonyl)cyclohexanecarboxylate (16 mg) as yellow oil. LC/MS (M+1):708.2.

Step C: Enantiomer 2 of (1r,4r)-methyl 4-ethyl-4-(3-(4-(perfluoropropan-2-yl)phenyl)-3-m-tolylsulfonyl)pyrrolidin-1-carbonyl)cyclohexanecarboxylate enantiomer 2

4 M HCl in dioxane (0.18 mL, 0.72 mmol) was added to enantiomer 2 of (1r,4r)-tert-butyl 4-ethyl-4-(3-(4-(perfluoropropan-2-yl)phenyl)-3-(m-tolylsulfonyl)pyrrolidine-1-carbonyl)cyclohexanecarboxylate (16 mg) and the mixture was stirred at ambient temperature for 18 h. Additional 4 M HCl in dioxane (0.18 mL, 0.72 mmol) was added and the mixture was stirred for additional 4 h. The crude was diluted with MeOH (1 mL) and purified via preparative HPLC with the following conditions: Column: Phenomenex Luna Axia C18, 30×200 mm, 5-μm particles; Mobile Phase A: 5:95 acetonitrile:water with 0.05% TFA; Mobile Phase B: 95:5 acetonitrile:water with 0.05% TFA; Gradient: 0-100% B over 10 minutes, then a 5-minute hold at 100% B; Flow: 20 mL/min. Fractions containing the title compound were combined and dried via centrifugal evaporation to give enantiomer 2 of (1r,4r)-methyl 4-ethyl-4-(3-(4-(perfluoropropan-2-yl)phenyl)-3-(m-tolylsulfonyl)pyrrolidine-1-carbonyl)cyclohexanecarboxylate. LC/MS (M+1): 666.2.

Step D: Enantiomer 2 of (1r,4r)-4-ethyl-4-(3-(4-(perfluoropropan-2-yl)phenyl)-3-(m-tolylsulfonyl)pyrrolidine-1-carbonyl)cyclohexanecarboxylic acid

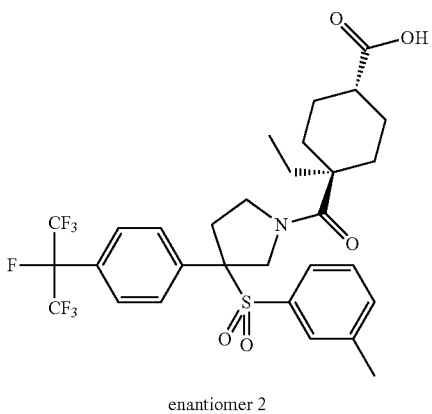 [SMILES: CC[C@]1(C(=O)N2CCC(c3ccc(C(F)(C(F)(F)F)C(F)(F)F)cc3)(S(=O)(=O)c3cccc(C)c3)C2)CC[C@H](C(=O)O)CC1]

enantiomer 2

The enantiomer 2 of (1r,4r)-methyl 4-ethyl-4-(3-(4-(perfluoropropan-2-yl)phenyl)-3-(m-tolylsulfonyl)pyrrolidine-1-carbonyl)cyclohexanecarboxylate was hydrolyzed in MeOH (0.2 mL) and 1M NaOH (0.2 mL) at ambient temperature for 2 hr then 60° C. for 1 hr. The crude was neutralized with 1 M HCl (0.2 mL) then diluted with MeOH (1 mL) and purified via preparative HPLC with the following conditions: Column: Phenomenex Luna Axia C18, 30×200 mm, 5-μm particles; Mobile Phase A: 5:95 acetonitrile:water with 0.05% TFA; Mobile Phase B: 95:5 acetonitrile:water with 0.05% TFA; Gradient: 20-100% B over 10 minutes, then a 5-minute hold at 100% B; Flow: 20 mL/min. Fractions containing the desired product were combined and dried via centrifugal evaporation to give enantiomer 2 of (1r,4r)-4-ethyl-4-(3-(4-(perfluoropropan-2-yl)phenyl)-3-(m-tolylsulfonyl)pyrrolidine-1-carbonyl)cyclohexanecarboxylic acid (2.6 mg, 18%). LC/MS (M+1): 652.1; LC retention time: 1.07 min (analytical HPLC Method I); 1H NMR (500 MHz, CD$_3$OD) δ 7.57 (d, J=8.5 Hz, 2H), 7.48 (d, J=7.5 Hz, 1H), 7.37-7.29 (m, 3H), 7.22 (d, J=7.9 Hz, 1H), 6.95 (s, 1H), 4.23-3.54 (m, 3H), 2.80-2.49 (m, 1H), 2.39 (d, J=5.2 Hz, 1H), 2.23 (s, 3H), 2.00-1.62 (m, 10H), 0.81 (t, J=7.5 Hz, 3H)

Example 470

(1r,4r)-4-(3-(3-benzylphenylsulfonyl)-3-(4-(perfluoropropan-2-yl)phenyl)pyrrolidine-1-carbonyl)cyclohexanecarboxylic acid, enantiomer 2

Step A: Enantiomers 1 and 2 of 1-benzyl-3-(3-bromophenylsulfonyl)-3-(4-(perfluoropropan-2-yl)phenyl)pyrrolidine

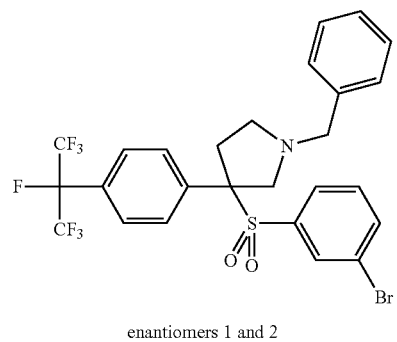 [SMILES: O=S(=O)(c1cccc(Br)c1)C1(c2ccc(C(F)(C(F)(F)F)C(F)(F)F)cc2)CCN(Cc2ccccc2)C1]

enantiomers 1 and 2 rac-1-benzyl-3-(3-bromophenylsulfonyl)-3-(4-(perfluoropropan-2-yl)phenyl)pyrrolidine (9 g from Step E of Example 441) was separated into its homochiral components by preparative chiral SFC (OD-H 5×25 cm, 5 μm particles, 15% methanol in CO2, 250 mL/min) to afford the first eluent off the column as the enantiomer 1 (4.25 g, 51% yield) and the second eluent as the enantiomer 2 (3.97 g, 47% yield). Analytical data for the enantiomer 1: LC/MS (M+1): 624.0, 626.0; chiral HPLC retention time: 2.75 min (OD-H 0.46×25 cm, 5 μm particles, 15% methanol in CO$_2$, 3 mL/min); 1H NMR (400 MHz, CDCl$_3$) δ 7.72-7.65 (m, 1H), 7.52 (d, J=8.6 Hz, 2H), 7.45 (t, J=1.7 Hz, 1H), 7.38-7.23 (m, 8H), 7.22-7.15 (m, 1H), 3.74-3.63 (m, 3H), 3.26 (d, J=11.1 Hz, 1H), 3.10-2.91 (m, 2H), 2.78 (td, J=8.2, 4.5 Hz, 1H), 2.60-2.50 (m, 1H). Analytical data for the enantiomer 2: LC/MS (M+1): 624.0, 626.0; chiral HPLC retention time: 3.27 min (OD-H 0.46×25 cm, 5 μm particles, 15% methanol in CO$_2$, 3 mL/min); 1H NMR (400 MHz, CDCl$_3$) δ 7.71-7.65 (m, 1H), 7.52 (d, J=8.6 Hz, 2H), 7.45 (t, J=1.7 Hz, 1H), 7.38-7.23 (m, 8H), 7.21-7.15 (m, 1H), 3.77-3.65 (m, 3H), 3.26 (d, J=11.1 Hz, 1H), 3.09-2.92 (m, 2H), 2.78 (td, J=8.2, 4.4 Hz, 1H), 2.61-2.50 (m, 1H).

Step B: Enantiomer 2 of 1-benzyl-3-(3-benzylphenylsulfonyl)-3-(4-(perfluoropropan-2-yl)phenyl)pyrrolidine

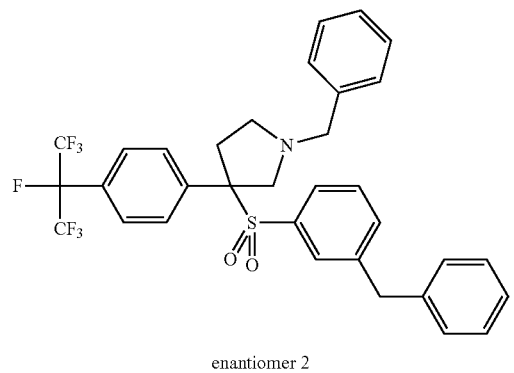 [SMILES: O=S(=O)(c1cccc(Cc2ccccc2)c1)C1(c2ccc(C(F)(C(F)(F)F)C(F)(F)F)cc2)CCN(Cc2ccccc2)C1]

enantiomer 2

A stirred dioxane (0.5 mL) solution of enantiomer 2 of 1-benzyl-3-((3-bromophenyl)sulfonyl)-3-(4-(perfluoropropan-2-yl)phenyl)pyrrolidine (25 mg, 0.040 mmol) and bis(triphenylphosphine)palladium(II) chloride (2.81 mg, 4.00 μmol) was degassed with N2 purge. 0.5M benzylzinc(II) bromide in THF (0.160 mL, 0.080 mmol) was added dropwise under N2. The mixture was stirred at ambient temperature for 2 h. The crude was acidified by adding 1M HCl (0.54 mL) and diluted with MeOH (1 mL). The solution was filtered and the filtrate (assuming 0.040 mmol) was used in the Step C without further purification. LC/MS (M+1): 636.1.

Step C: Enantiomer 2 of 3-(3-benzylphenylsulfonyl)-3-(4-(perfluoropropan-2-yl)phenyl)pyrrolidine

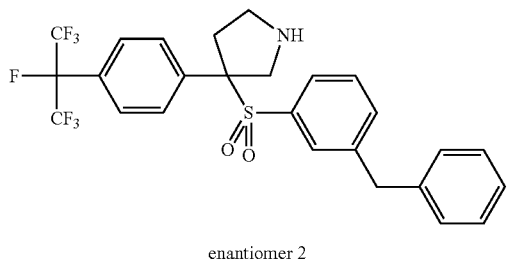 [SMILES: O=S(=O)(c1cccc(Cc2ccccc2)c1)C1(c2ccc(C(F)(C(F)(F)F)C(F)(F)F)cc2)CCNC1]

enantiomer 2

Pearlman's catalyst (15 mg, 20 wt %) was added to the filtrate (assuming 0.040 mmol) from Step B. The mixture was hydrogenated under 50 psi H2 at ambient temperature for 19 h. The crude was filtered. The filtrate was concentrated to give a brown oil (11 mg, 50%). The crude material was used in Step D without further purification. LC/MS (M+1): 546.1.

Step D: Enantiomer 2 of (1r,4r)-4-(3-(3-benzylphenylsulfonyl)-3-(4-(perfluoropropan-2-yl)phenyl)pyrrolidine-1-carbonyl)cyclohexanecarboxylic acid

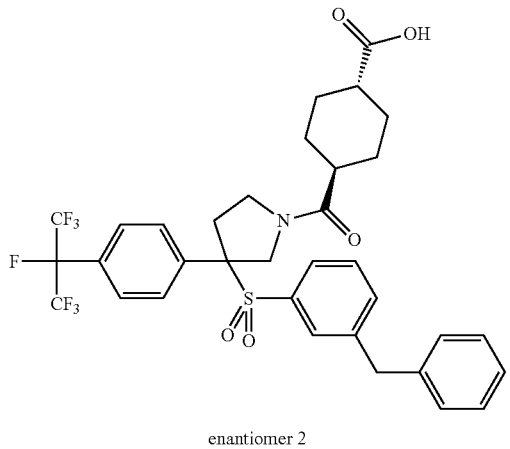 [SMILES: O=C(O)[C@H]1CC[C@H](C(=O)N2CCC(c3ccc(C(F)(C(F)(F)F)C(F)(F)F)cc3)(S(=O)(=O)c3cccc(Cc4ccccc4)c3)C2)CC1]

enantiomer 2

Similar to Step D of Example 439, enantiomer 2 of 3-((3-benzylphenyl)sulfonyl)-3-(4-(perfluoropropan-2-yl)phenyl)pyrrolidine (11 mg, 0.020 mmol) was converted to 2 of (1r,4r)-4-(3-(3-benzylphenylsulfonyl)-3-(4-(perfluoropropan-2-yl)phenyl)pyrrolidine-1-carbonyl)cyclohexanecarboxylic acid (7 mg, 48%). LC/MS (M+1): 700.2; LC retention time: 1.98 min (analytical HPLC Method B); 1H NMR (500 MHz, 1:1 mixture of CDCl$_3$—CD$_3$OD) δ 7.52-7.46 (m, 2H), 7.44-7.39 (m, 1H), 7.31-7.15 (m, 7H), 7.15-7.11 (m, 1H), 7.07 (d, J=7.5 Hz, 2H), 4.85-4.78 (m, 1H), 4.09-3.91 (m, 1H), 3.88-3.71 (m, 4H), 3.30-3.25 (m, 1H), 2.70-2.23 (m, 3H), 2.17-1.90 (m, 3H), 1.81-1.72 (m, 1H), 1.62-1.37 (m, 4H).

Example 471

(1r,4r)-4-(3-(3-(hydroxymethyl)phenylsulfonyl)-3-(4-(perfluoropropan-2-yl)phenyl)pyrrolidine-1-carbonyl)cyclohexanecarboxylic acid, enantiomer 2

Step A: Enantiomer 2 of (1r,4r)-methyl 4-(3-(3-formylphenylsulfonyl)-3-(4-perfluoropropan-2-yl)phenyl)pyrrolidine-1-carbonyl)cyclohexanecarboxylate

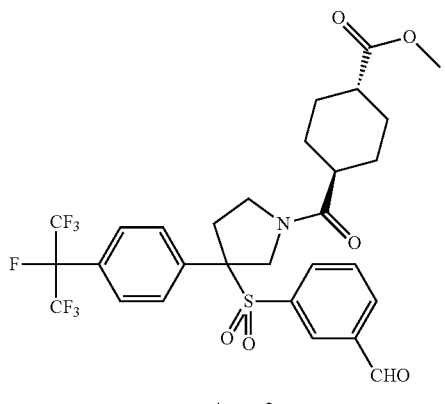

enantiomer 2

Enantiomer 2 of (1r,4r)-methyl 4-(3-(4-(perfluoropropan-2-yl)phenyl)-3-((3-vinylphenyl)sulfonyl)pyrrolidine-1-carbonyl)cyclohexanecarboxylate (28.7 mg, 0.044 mmol from the precursor of Example 444) was ozonolysized in CH$_2$Cl$_2$ (0.5 mL) at −78° C. while blue solution color persisted for 10 min. Oxygen was then blew in to remove the excess ozone. After the solution color changed to colorless, triphenylphosphine on polystyrene (200 mg, 0.200 mmol) was added and the stirred mixture was slowly warmed up to ambient temperature in 1 h. The crude was filtered. The filtrate was concentrated to give enantiomer 2 of (1r,4r)-methyl 4-(3-(3-formylphenylsulfonyl)-3-(4-(perfluoropropan-2-yl)phenyl)pyrrolidine-1-carbonyl)cyclohexanecarboxylate (29 mg, 100%) as colorless oil. LC/MS (M+1): 652.1.

311

Step B: Enantiomer 2 of (1r,4r)-methyl 4-((3-(3-(hydroxymethyl)phenylsulfonyl)-3-(4-perfluoropropan-2-yl)phenyl)pyrrolidine-1-carbonyl)cyclohexanecarboxylate

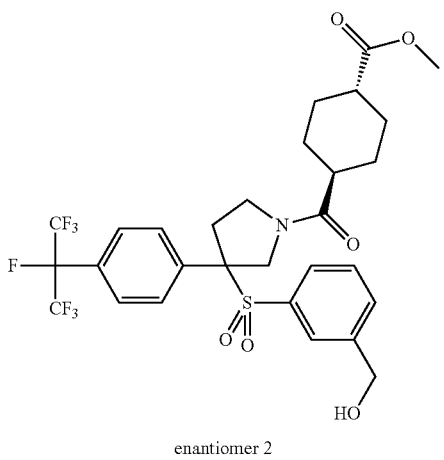 [SMILES: COC(=O)[C@H]1CC[C@H](C(=O)N2CCC(c3ccc(C(F)(C(F)(F)F)C(F)(F)F)cc3)(S(=O)(=O)c3cccc(CO)c3)C2)CC1]

enantiomer 2

Enantiomer 2 of (1r,4r)-methyl 4-(3-(3-formylphenylsulfonyl)-3-(4-(perfluoropropan-2-yl)phenyl)pyrrolidine-1-carbonyl)cyclohexanecarboxylate (29 mg, 0.044 mmol) was dissolved in THF (0.5 mL) and MeOH (0.18 mL). To it was added sodium borohydride (2.4 mg, 0.063 mmol). The mixture was stirred at ambient temperature for 30 minute. One third of the crude solution (assuming 0.014 mmol) was used in Step C. LC/MS (M+1): 654.1.

Step C: Enantiomer 2 of (1r,4r)-4-(3-(3-(hydroxymethyl)phenylsulfonyl)-3-(4-perfluoropropan-2-yl)phenyl)pyrrolidine-1-carbonyl)cyclohexanecarboxylic acid

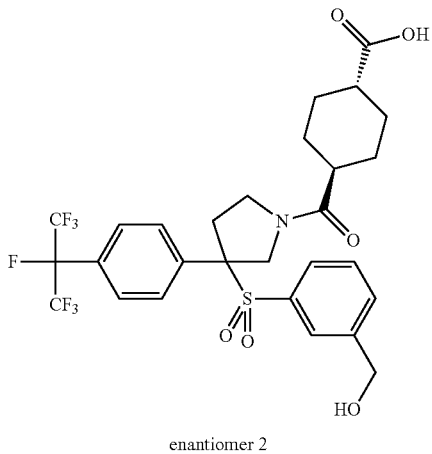 [SMILES: O=C(O)[C@H]1CC[C@H](C(=O)N2CCC(c3ccc(C(F)(C(F)(F)F)C(F)(F)F)cc3)(S(=O)(=O)c3cccc(CO)c3)C2)CC1]

enantiomer 2

1M NaOH (0.18 mL, 0.18 mmol) was added to the crude enantiomer 2 of (1r,4r)-methyl 4-(3-(3-(hydroxymethyl)phenylsulfonyl)-3-(4-(perfluoropropan-2-yl)phenyl)pyrrolidine-1-carbonyl)cyclohexanecarboxylate solution (assuming 0.014 mmol). The mixture was stirred at ambient temperature for 75 minute. The crude was neutralized with 1M HCl (0.18 mL) and diluted with MeOH (1.5 mL). The mixture was filtered and the filtrate was purified via preparative LC/MS with the following conditions: Column: Waters XBridge C18, 19×200 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-100% B over 20 minutes, then a 5-minute hold at 100% B; Flow: 20 mL/min. Fractions containing the desired product were combined and dried via centrifugal evaporation to give enantiomer 2 of (1r,4r)-4-(3-(3-(hydroxymethyl)phenylsulfonyl)-3-(4-(perfluoropropan-2-yl)phenyl)pyrrolidine-1-carbonyl)cyclohexanecarboxylic acid (4.3 mg, 48%). LC/MS (M+1): 640.2; LC retention time: 1.525 min (analytical HPLC Method B); 1H NMR (500 MHz, 1:1 mixture of CDCl$_3$—CD$_3$OD) δ 7.66-7.60 (m, 1H), 7.55-7.48 (m, 2H), 7.36-7.21 (m, 4H), 7.13-7.05 (m, 1H), 4.93-4.82 (m, 1H), 4.56-4.50 (m, 2H), 4.15-3.96 (m, 1H), 3.88-3.77 (m, 2H), 3.67-3.33 (m, 1H), 2.76-2.53 (m, 1H), 2.47-2.26 (m, 2H), 2.20-1.91 (m, 3H), 1.85-1.75 (m, 1H), 1.65-1.38 (m, 4H).

Example 472

(1r,4r)-4-(3-(3-(methoxymethyl)phenylsulfonyl)-3-(4-(perfluoropropan-2-yl)phenyl)pyrrolidine-1-carbonyl)cyclohexanecarboxylic acid, enantiomer 2

Step A: Enantiomer 2 of (1r,4r)-methyl 4-((3-(3-(chloromethyl)phenylsulfonyl)-3-(4-(perfluoropropan-2-yl)phenyl)pyrrolidine-1-carbonyl)cyclohexanecarboxylate

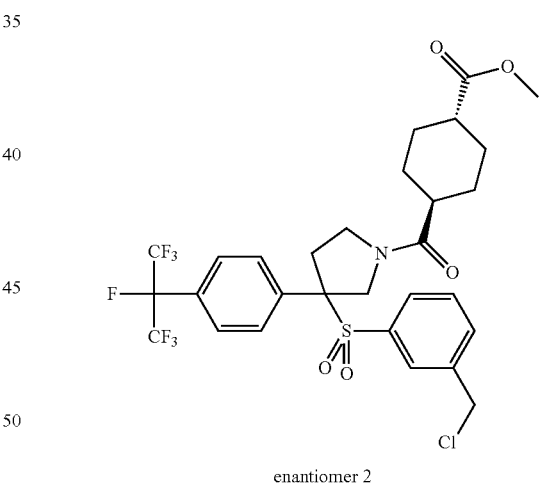

enantiomer 2

The remaining crude enantiomer 2 of (1r,4r)-methyl 4-(3-(3-(hydroxymethyl)phenylsulfonyl)-3-(4-(perfluoropropan-2-yl)phenyl)pyrrolidine-1-carbonyl)cyclohexanecarboxylate solution (assuming 0.028 mmol from Step B of Example 471) was concentrated and azeotroped with toluene (2 mL). The resulting white solid was dissolved in CH$_2$Cl$_2$ (0.5 mL). Thionyl chloride (2.95 μL, 0.040 mmol) was added and the solution was stirred at ambient temperature for 18 h. Additional thionyl chloride (38.4 μL) was added and the solution was stirred for additional 30 h. The reaction was quenched by adding MeOH (0.54 mL) and stirred for 30 minute at ambient temperature. The solution was concentrated and the residue (assuming 0.028 mmol) was used in Step B without further purification. LC/MS (M+1): 672.1.

Step B: Enantiomer 2 of (1r,4r)-4-(3-(3-(methoxymethyl)phenylsulfonyl)-3-(4-perfluoropropan-2-yl)phenyl)pyrrolidine-1-carbonyl)cyclohexanecarboxylic acid

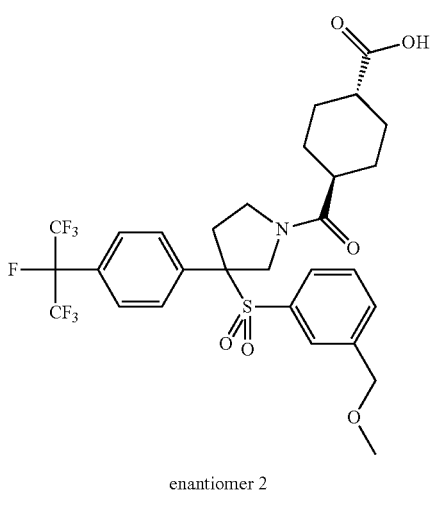 [SMILES: COCc1cccc(S(=O)(=O)C2(c3ccc(C(F)(C(F)(F)F)C(F)(F)F)cc3)CCN(C(=O)[C@H]3CC[C@H](C(=O)O)CC3)C2)c1]

enantiomer 2

25 wt % Sodium methoxide in MeOH (0.5 mL, 2.187 mmol) was added to the crude enantiomer 2 of (1r,4r)-methyl 4-(3-(3-(chloromethyl)phenylsulfonyl)-3-(4-(perfluoropropan-2-yl)phenyl)pyrrolidine-1-carbonyl)cyclohexanecarboxylate (assuming 0.028 mmol) and the resulting suspension was stirred at ambient temperature for 52 h. The crude was neutralized with 2M HCl (1 mL) and diluted with MeOH (2.5 mL). The mixture was filtered. The filtrate was purified via preparative HPLC with the following conditions: Column: Phenomenex Luna Axia C18, 21×100 mm, 5-μm particles; Mobile Phase A: 5:95 acetonitrile:water with 0.05% TFA; Mobile Phase B: 95:5 acetonitrile:water with 0.05% TFA; Gradient: 0-100% B over 8 minutes, then a 7-minute hold at 100% B; Flow: 20 mL/min. Fractions containing the desired product were combined and dried via centrifugal evaporation to give enantiomer 2 of (1r,4r)-4-(3-(3-(methoxymethyl)phenylsulfonyl)-3-(4-(perfluoropropan-2-yl)phenyl)pyrrolidine-1-carbonyl)cyclohexanecarboxylic acid (6.1 mg, 33%) as white lypholized powder. LC/MS (M+1): 654.1; LC retention time: 1.00 min (analytical HPLC Method I); 1H NMR (400 MHz, CDCl$_3$) δ 7.62-7.47 (m, 3H), 7.37-7.30 (m, 1H), 7.26-7.13 (m, 3H), 4.88-4.77 (m, 1H), 4.36-4.28 (m, 2H), 4.15-4.03 (m, 1H), 3.89 (d, J=13.9 Hz, 1H), 3.76 (td, J=9.5, 2.5 Hz, 1H), 3.47 (dd, J=14.8, 6.6 Hz, 1H), 3.40-3.34 (m, 3H), 2.64 (dt, J=14.1, 9.4 Hz, 1H), 2.55-2.33 (m, 2H), 2.25-2.02 (m, 3H), 1.87-1.76 (m, 1H), 1.72-1.57 (m, 2H), 1.56-1.41 (m, 2H).

Example 473

(1r,4r)-4-(3-(3-(difluoromethyl)phenylsulfonyl)-3-(4-(perfluoropropan-2-yl)phenyl)pyrrolidine-1-carbonyl)cyclohexanecarboxylic acid, enantiomer 2

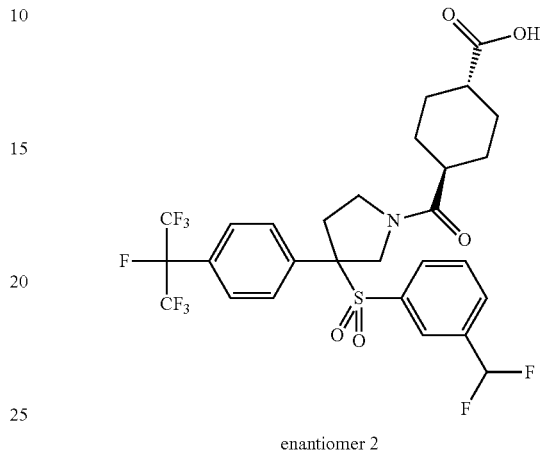

enantiomer 2

(Diethylamino)sulfur trifluoride (0.021 mL, 0.157 mmol) was added to a stirred CH$_2$Cl$_2$ (0.5 mL) solution of enantiomer 2 of (1r,4r)-methyl 4-(3-(3-formylphenylsulfonyl)-3-(4-(perfluoropropan-2-yl)phenyl)pyrrolidine-1-carbonyl)cyclohexanecarboxylate (17 mg, 0.026 mmol, from Step A of Example 471). The mixture was stirred at ambient temperature for 1 h. Additional (diethylamino)sulfur trifluoride (0.04 mL) was added and the mixture was stirred for additional 19 h. The solution was concentrated. The resulting residue was dissolved in MeOH (0.9 mL). To it was added 1M NaOH (1.08 mL) and the resulting solution was stirred at ambient temperature for 21 h. The crude was concentrated, neutralized with 1M HCl (1.08 mL) and diluted with water (5 mL). The suspension was filtered. The solid was dissolved in MeCN (2 mL). The solution was purified via preparative LC/MS with the following conditions: Column: Waters XBridge C18, 19×200 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-75% B over 20 minutes, then a 5-minute hold at 100% B; Flow: 20 mL/min. Fractions containing the desired product were combined and dried via centrifugal evaporation to give enantiomer 2 of (1r,4r)-4-(3-(3-(difluoromethyl)phenylsulfonyl)-3-(4-(perfluoropropan-2-yl)phenyl)pyrrolidine-1-carbonyl)cyclohexanecarboxylic acid (4.1 mg, 22%). LC/MS (M+1): 660.3; LC retention time: 2.47 min (analytical HPLC Method B); 1H NMR (500 MHz, 1:1 mixture of CDCl$_3$—CD$_3$OD) δ 7.82-7.75 (m, 1H), 7.56-7.46 (m, 4H), 7.39-7.18 (m, 3H), 6.71-6.41 (m, 1H), 4.90-4.79 (m, 1H), 4.14-4.01 (m, 1H), 3.91-3.77 (m, 2H), 3.68-3.33 (m, 1H), 2.76-2.52 (m, 1H), 2.46-2.25 (m, 2H), 2.18-1.94 (m, 3H), 1.84-1.74 (m, 1H), 1.63-1.37 (m, 4H).

Example 474

(1r,4r)-4-(3-(3-(2,2-difluoroethyl)phenylsulfonyl)-3-(4-(perfluoropropan-2-yl)phenyl)pyrrolidine-1-carbonyl)cyclohexanecarboxylic acid, enantiomer 2

Step A: Enantiomer 2 of (1r,4r)-methyl 4-(3-(3-allylphenylsulfonyl)-3-(4-perfluoropropan-2-yl)phenyl)pyrrolidine-1-carbonyl)cyclohexanecarboxylate

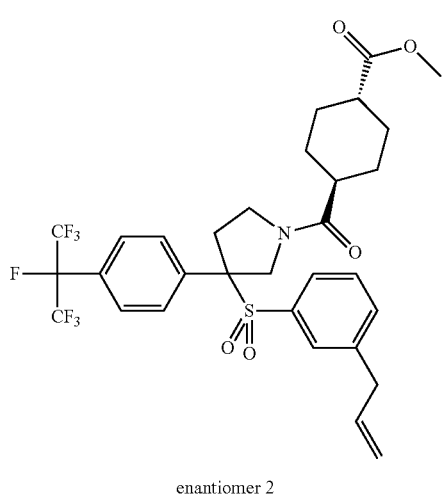 [SMILES: C=CCc1cccc(S(=O)(=O)C2(c3ccc(C(F)(C(F)(F)F)C(F)(F)F)cc3)CCN(C(=O)[C@H]3CC[C@H](C(=O)OC)CC3)C2)c1]

enantiomer 2

A mixture of enantiomer 2 of (1r,4r)-methyl 4-(3-((3-bromophenyl)sulfonyl)-3-(4-(perfluoropropan-2-yl)phenyl) pyrrolidine-1-carbonyl)cyclohexanecarboxylate (50 mg, 0.071 mmol from Step A of Example 443), allyltributylstannane (47.1 mg, 0.142 mmol) and bis(triphenylphosphine) palladium(II) chloride (5 mg, 7.12 µmol) was dissolved in dioxane (0.5 mL). The vial was degassed by vacuum-$N_2$ refill cycle twice. The sealed tube was then heated at 90° C. for 90 minute. Additional allyltributylstannane (47 mg) and bis(triphenylphosphine)palladium(II) chloride (5 mg) were added. The heating was continued for additional 90 minute. Silica gel chromatography, eluting with 0-100% ethyl acetate in hexanes, gave enantiomer 2 of (1r,4r)-methyl 4-(3-(3-allylphenylsulfonyl)-3-(4-(perfluoropropan-2-yl) phenyl)pyrrolidine-1-carbonyl)cyclohexanecarboxylate (42.4 mg, 90%) as white solid. LC/MS (M+1): 664.2; 1H NMR (400 MHz, $CDCl_3$) δ 7.56-7.46 (m, 2H), 7.45-7.38 (m, 1H), 7.32-7.22 (m, 2H), 7.18 (d, J=8.3 Hz, 2H), 7.00 (s, 1H), 5.88-5.72 (m, 1H), 5.15-4.96 (m, 2H), 4.82-4.73 (m, 1H), 3.88 (d, J=13.8 Hz, 1H), 3.75-3.60 (m, 4H), 3.49-3.38 (m, 1H), 3.30-3.21 (m, 2H), 2.63 (dt, J=14.1, 9.2 Hz, 1H), 2.42-2.28 (m, 2H), 2.15-1.97 (m, 3H), 1.82-1.73 (m, 1H), 1.68-1.40 (m, 5H).

Step B: Enantiomer 2 of (1r,4r)-methyl 4-((3-(3-(2-oxoethyl)phenylsulfonyl)-3-(4-perfluoropropan-2-yl) phenyl)pyrrolidine-1-carbonyl)cyclohexanecarboxylate

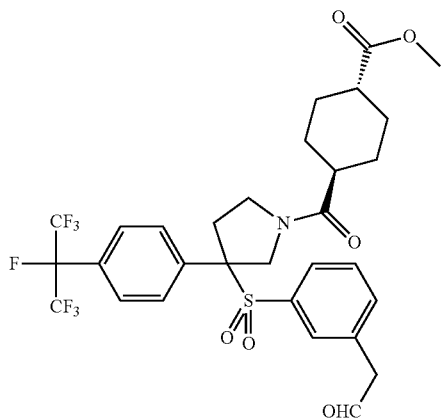

enantiomer 2

Enantiomer 2 of (1r,4r)-Methyl 4-((3-((3-allylphenyl)sulfonyl)-3-(4-(perfluoropropan-2-yl)phenyl)pyrrolidine-1-carbonyl)cyclohexanecarboxylate (11.7 mg, 0.018 mmol) was ozonolysized in $CH_2Cl_2$ (0.5 mL) at −78° C. while blue solution color persisted for 10 min. Oxygen was then blew in to remove the excess ozone. After the solution color changed to colorless, triphenylphosphine on polystyrene (Nova Biochem) (75 mg, 0.075 mmol) was added and the stirred mixture was slowly warmed up to ambient temperature in 1 h. The crude was filtered to give $CH_2Cl_2$ solution of enantiomer 2 of (1r,4r)-methyl 4-(3-(3-(2-oxoethyl)phenylsulfonyl)-3-(4-(perfluoropropan-2-yl)phenyl)pyrrolidine-1-carbonyl)cyclohexanecarboxylate (assuming 0.018 mmol). LC/MS (M+1): 666.2.

Step C: Enantiomer 2 of (1r,4r)-4-(3-(3-(2,2-difluoroethyl)phenylsulfonyl)-3-(4-perfluoropropan-2-yl) phenyl)pyrrolidin-1-carbonyl)cyclohexanecarboxylic acid

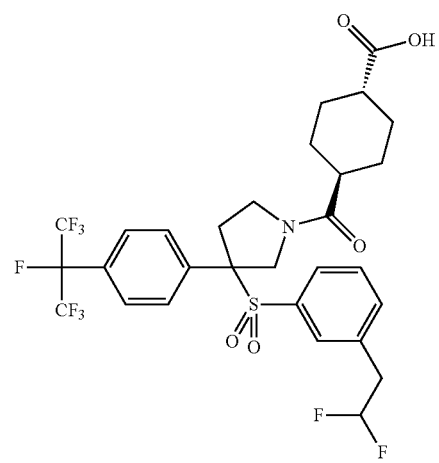 [SMILES: O=C(O)[C@H]1CC[C@H](C(=O)N2CCC(c3ccc(C(F)(C(F)(F)F)C(F)(F)F)cc3)(S(=O)(=O)c3cccc(CC(F)F)c3)C2)CC1]

(Diethylamino)sulfur trifluoride (0.014 mL, 0.106 mmol) was added to a stirred CH₂Cl₂ (0.5 mL) solution of enantiomer 2 (1r,4r)-methyl 4-(3-(3-(2-oxoethyl)phenylsulfonyl)-3-(4-(perfluoropropan-2-yl)phenyl)pyrrolidine-1-carbonyl)cyclohexanecarboxylate (assuming 0.018 mmol). The mixture was stirred at ambient temperature for 45 minute. The solvent was evaporated. The residue was dissolved in MeOH (0.18 mL). To it was added 1M NaOH (0.18 mL). The mixture was stirred at ambient temperature for 19 h. Additional MeOH (0.9 mL) and 1M NaOH (0.54 mL) were added and the mixture was stirred for additional 7 h. The crude was neutralized with 1M HCl (0.54 mL) and diluted with water (5 mL). The suspension was filtered. The solid was dissolved in MeCN (2 mL). The solution was purified via preparative LC/MS with the following conditions: Column: Waters XBridge C18, 19×200 mm, 5-µm particles; Guard Column: Waters XBridge C18, 19×10 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 25-70% B over 20 minutes, then a 5-minute hold at 100% B; Flow: 20 mL/min. Fractions containing the desired product were combined and dried via centrifugal evaporation to give enantiomer 2 of (1r,4r)-4-(3-(3-(2,2-difluoroethyl)phenylsulfonyl)-3-(4-(perfluoropropan-2-yl)phenyl)pyrrolidine-1-carbonyl)cyclohexanecarboxylic acid (3.5 mg, 28%). LC/MS (M+1): 674.3; LC retention time: 2.49 min (analytical HPLC Method B); 1H NMR (500 MHz, 1:1 mixture of CDCl₃—CD₃OD) δ 7.57-7.47 (m, 3H), 7.39-7.30 (m, 1H), 7.30-7.17 (m, 4H), 6.07-5.75 (m, 1H), 4.90-4.79 (m, 1H), 4.14-3.97 (m, 1H), 3.89-3.75 (m, 2H), 3.66-3.34 (m, 1H), 3.14-3.00 (m, 2H), 2.69 (dt, J=14.3, 9.4 Hz, 1H), 2.62-2.24 (m, 2H), 2.18-1.91 (m, 3H), 1.77 (d, J=13.4 Hz, 1H), 1.64-1.37 (m, 4H).

Example 475

(1r,4r)-4-(3-(3-(1-hydroxycyclobutyl)phenylsulfonyl)-3-(4-(perfluoropropan-2-yl)phenyl)pyrrolidine-1-carbonyl)cyclohexanecarboxylic acid, enantiomer 2

Step A: Enantiomer 2 of 1-(3-(1-benzyl-3-(4-(perfluoropropan-2-yl)phenyl)pyrrolidin-3-ylsulfonyl)phenyl)cyclobutanol

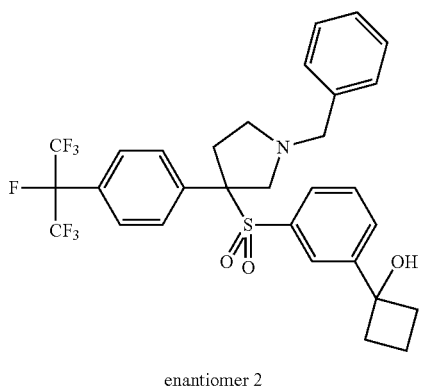 [SMILES: O=S(=O)(c1cccc(C2(O)CCC2)c1)C1(c2ccc(C(F)(C(F)(F)F)C(F)(F)F)cc2)CCN(Cc2ccccc2)C1]

enantiomer 2

2.5 M n-Butyllithium in hexane (47.4 µL, 0.119 mmol) was added to a stirred THF (593 µL) solution of enantiomer 2 of 1-benzyl-3-((3-bromophenyl)sulfonyl)-3-(4-(perfluoropropan-2-yl)phenyl)pyrrolidine (37 mg, 0.059 mmol from Step A of Example 470) at −78° C. under N2. After 11 minute, cyclobutanone (18 mg, 0.257 mmol) was added at −78° C. The mixture was stirred at −78° C. for additional 50 minute. The reaction was quenched by adding sat. NH₄Cl (2 mL) at −78° C. then warmed up to ambient temperature. The THF layer was separated and concentrated. The resulting oil (assuming 0.059 mmol) was dissolved in MeOH (2 mL) and used in Step B without further purification. LC/MS (M+1): 616.2.

Step B: Enantiomer 2 of 1-(3-(3-(4-(perfluoropropan-2-yl)phenyl)pyrrolidin-3-ylsulfonyl)phenyl)cyclobutanol

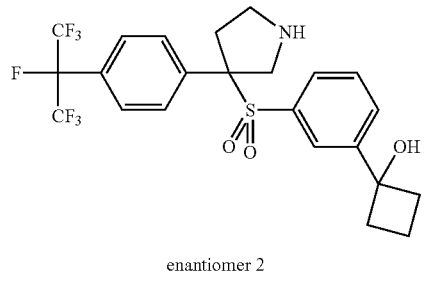 [SMILES: O=S(=O)(c1cccc(C2(O)CCC2)c1)C1(c2ccc(C(F)(C(F)(F)F)C(F)(F)F)cc2)CCNC1]

enantiomer 2

To the MeOH (2 mL) solution of enantiomer 2 of 1-(3-(1-benzyl-3-(4-(perfluoropropan-2-yl)phenyl)pyrrolidin-3-ylsulfonyl)phenyl)cyclobutanol (assuming 0.059 mmol) was added Pearlman's catalyst (11 mg). The mixture was hydrogenated under 50 psi H2 at ambient temperature for 65 h. Additional Pearlman's catalyst (11 mg) was added followed by 1M HCl (0.18 mL). The mixture was hydrogenated under 50 psi H2 for additional 23 h. The mixture was filtered. The filtrate was purified via preparative HPLC with the following conditions: Column: Phenomenex Luna Axia C18, 30×100 mm, 5-µm particles; Mobile Phase A: 5:95 acetonitrile:water with 0.05% TFA; Mobile Phase B: 95:5 acetonitrile:water with 0.05% TFA; Gradient: 0-100% B over 10 minutes, then a 5-minute hold at 100% B; Flow: 20 mL/min. Fractions containing the desired product were combined and dried via centrifugal evaporation to give impure enantiomer 2 of 1-(3-(3-(4-(perfluoropropan-2-yl)phenyl)pyrrolidin-3-ylsulfonyl)phenyl)cyclobutanol (19.7 mg). LC/MS (M+1): 526.1.

Step C: Enantiomer 2 of (1r,4r)-methyl 4-((3-(3-(1-hydroxycyclobutyl)phenylsulfonyl)-3-(4-(perfluoropropan-2-yl)phenyl)pyrrolidine-1-carbonyl)cyclohexanecarboxylate

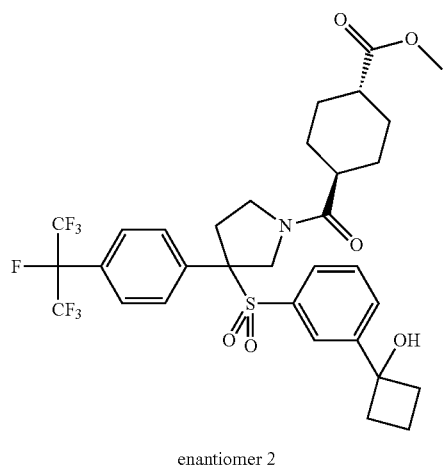 [SMILES: COC(=O)[C@H]1CC[C@H](C(=O)N2CCC(c3ccc(C(F)(C(F)(F)F)C(F)(F)F)cc3)(S(=O)(=O)c3cccc(C4(O)CCC4)c3)C2)CC1]

enantiomer 2

Similar to the Step D of Example 1, the impure enantiomer 2 of 1-(3-((3-(4-(perfluoropropan-2-yl)phenyl)pyrrolidin-3-yl)sulfonyl)phenyl)cyclobutanol (19.7 mg, assuming 0.031 mmol) was converted to the enantiomer 2 of (1r,4r)-methyl 4-(3-(3-(1-hydroxycyclobutyl)phenylsulfonyl)-3-(4-(perfluoropropan-2-yl)phenyl)pyrrolidine-1-carbonyl)cyclohexanecarboxylate (12.5 mg, 59%) as white solid. LC/MS (M+1): 694.2.

Step D: Enantiomer 2 of (1r,4r)-4-(3-(3-(1-hydroxycyclobutyl)phenylsulfonyl)-3-(4-perfluoropropan-2-yl)phenyl)pyrrolidine-1-carbonyl)cyclohexanecarboxylic acid

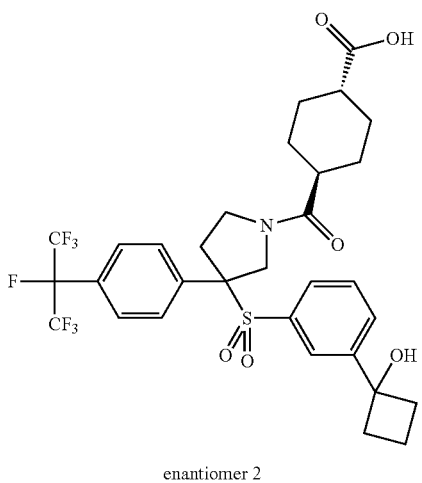 [SMILES: O=C(O)[C@H]1CC[C@H](C(=O)N2CCC(c3ccc(C(F)(C(F)(F)F)C(F)(F)F)cc3)(S(=O)(=O)c3cccc(C4(O)CCC4)c3)C2)CC1]

enantiomer 2

A MeOH (0.4 mL) solution of enantiomer 2 of (1r,4r)-methyl 4-(3-((3-(1-hydroxycyclobutyl)phenyl)sulfonyl)-3-(4-(perfluoropropan-2-yl)phenyl)pyrrolidine-1-carbonyl)cyclohexanecarboxylate (5 mg, 7.21 μmol) and 1M NaOH (180 μL, 0.180 mmol) was stirred at ambient temperature for 70 minute. The crude was purified via preparative HPLC with the following conditions: Column: Phenomenex Luna C18, 21×100 mm, 5-μm particles; Mobile Phase A: 5:95 acetonitrile:water with 0.05% TFA; Mobile Phase B: 95:5 acetonitrile:water with 0.05% TFA; Gradient: 0-100% B over 10 minutes, then a 5-minute hold at 100% B; Flow: 20 mL/min. Fractions containing the desired product were combined and dried via centrifugal evaporation to give enantiomer 2 of (1r,4r)-4-(3-(3-(1-hydroxycyclobutyl)phenylsulfonyl)-3-(4-(perfluoropropan-2-yl)phenyl)pyrrolidine-1-carbonyl)cyclohexanecarboxylic acid (2.8 mg, 54%). LC/MS (M+1): 680.2. LC retention time: 0.96 min (analytical HPLC Method I); 1H NMR (500 MHz, 1:1 mixture of $CDCl_3$—$CD_3OD$) δ 7.83-7.62 (m, 2H), 7.51 (d, J=8.4 Hz, 2H), 7.38-7.20 (m, 3H), 7.15-7.00 (m, 1H), 4.89-4.78 (m, 1H), 4.12-3.96 (m, 1H), 3.88-3.72 (m, 2H), 3.27-3.05 (m, 1H), 2.76-2.49 (m, 1H), 2.44-2.24 (m, 5H), 2.16-1.92 (m, 4H), 1.84-1.71 (m, 1H), 1.67-1.36 (m, 6H).

Example 476

(1r,4r)-4-((3-(3-(1-fluorocyclobutyl)phenylsulfonyl)-3-(4-(perfluoropropan-2-yl)phenyl)pyrrolidine-1-carbonyl)cyclohexanecarboxylic acid, enantiomer 2

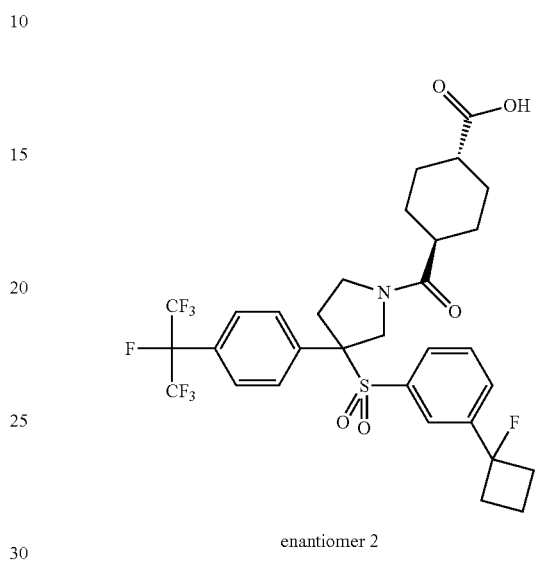

enantiomer 2

(Diethylamino)sulfur trifluoride (0.01 mL, 0.076 mmol) was added to a stirred $CH_2Cl$ (0.4 mL) solution of enantiomer 2 of (1r,4r)-methyl 4-(3-((3-(1-hydroxycyclobutyl)phenyl)sulfonyl)-3-(4-(perfluoropropan-2-yl)phenyl)pyrrolidine-1-carbonyl)cyclohexanecarboxylate (3.2 mg, 4.61 μmol from Step C of Example 475). The mixture was stirred at ambient temperature for 90 minute. The solvent was evaporated. The residue was dissolved in MeOH (0.18 mL). To it was added 1M NaOH (0.1 mL). The mixture was stirred at ambient temperature for 17 h. Additional MeOH (0.54 mL) and 1M NaOH (0.28 mL) and the mixture was stirred for additional 7 h. The crude was neutralized with 1M HCl (0.38 mL). The crude was purified via preparative HPLC with the following conditions: Column: Phenomenex Luna C18, 21×100 mm, 5-μm particles; Mobile Phase A: 5:95 acetonitrile:water with 0.05% TFA; Mobile Phase B: 95:5 acetonitrile:water with 0.05% TFA; Gradient: 0-100% B over 10 minutes, then a 5-minute hold at 100% B; Flow: 20 mL/min. Fractions containing the desired product were combined and dried via centrifugal evaporation to give enantiomer 2 of (1r,4r)-4-(3-(3-(1-fluorocyclobutyl)phenylsulfonyl)-3-(4-(perfluoropropan-2-yl)phenyl)pyrrolidine-1-carbonyl)cyclohexanecarboxylic acid (1.5 mg, 45%). LC/MS (M+1): 682.2; LC retention time: 1.05 min (analytical HPLC Method I); 1H NMR (500 MHz, 1:1 mixture of $CDCl_3$—$CD_3OD$) δ 7.75 (dd, J=8.2, 1.1 Hz, 1H), 7.56-7.35 (m, 4H), 7.33-7.20 (m, 3H), 4.89-4.79 (m, 1H), 4.14-3.99 (m, 1H), 3.90-3.74 (m, 2H), 3.67-3.33 (m, 1H), 2.77-2.47 (m, 3H), 2.44-2.24 (m, 4H), 2.18-1.95 (m, 4H), 1.80-1.41 (m, 6H).

Example 477

(1r,4r)-4-((3-(3-(2-fluoropropan-2-yl)phenylsulfonyl)-3-(4-(perfluoropropan-2-yl)phenyl)pyrrolidine-1-carbonyl)cyclohexanecarboxylic acid, enantiomer 2

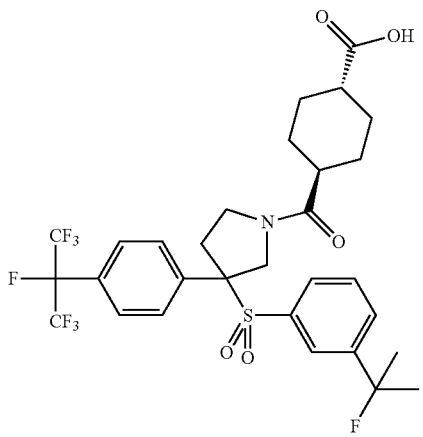

enantiomer 2

Similar to the synthesis of Examples 475 and 476, enantiomer 2 of 1-benzyl-3-((3-bromophenyl)sulfonyl)-3-(4-(perfluoropropan-2-yl)phenyl)pyrrolidine was converted to enantiomer 2 of (1r,4r)-4-(3-(3-(2-fluoropropan-2-yl)phenylsulfonyl)-3-(4-(perfluoropropan-2-yl)phenyl)pyrrolidine-1-carbonyl)cyclohexanecarboxylic acid in five steps. LC/MS (M+1): 670.3; LC retention time: 1.87 min (analytical HPLC Method B); 1H NMR (500 MHz, 1:1 mixture of CDCl₃—CD₃OD) δ 7.70-7.64 (m, 1H), 7.58-7.50 (m, 2H), 7.48-7.38 (m, 2H), 7.36-7.17 (m, 3H), 4.88-4.80 (m, 1H), 4.15-3.99 (m, 1H), 3.87-3.59 (m, 2H), 2.75-2.50 (m, 1H), 2.46-2.24 (m, 2H), 2.17-1.94 (m, 4H), 1.85-1.73 (m, 1H), 1.62-1.38 (m, 10H).

Example 478

(1r,4r)-4-((3-(4-(perfluoropropan-2-yl)phenyl)-3-(3-(2,2,2-trifluoroethyl)phenylsulfonyl)pyrrolidine-1-carbonyl)cyclohexanecarboxylic acid, enantiomer 2

Step A: Enantiomer 2 of (1r,4r)-methyl 4-(3-(4-(perfluoropropan-2-yl)phenyl)-3-(3-(2,2,2-trifluoroethyl)phenylsulfonyl)pyrrolidine-1-carbonyl)cyclohexanecarboxylate

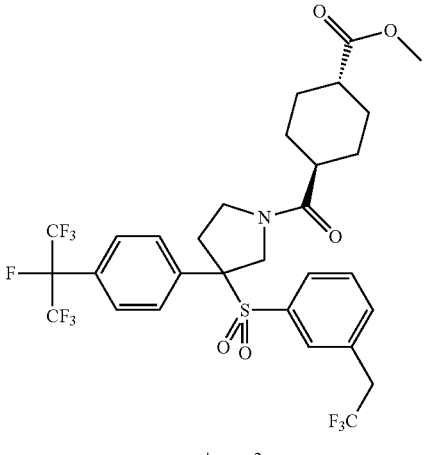

enantiomer 2

A stirred dioxane (1 mL) solution of enantiomer 2 of (1r,4r)-methyl 4-(3-(4-(perfluoropropan-2-yl)phenyl)-3-((3-(4,4,5,5-tetramethyl-1,3,2-dioxaborolan-2-yl)phenyl)sulfonyl)pyrrolidine-1-carbonyl)cyclohexanecarboxylate (58.5 mg, 0.039 mmol from Step A of Example 467), 4,5-bis(diphenylphosphino)-9,9-dimethylxanthene (24 mg, 0.041 mmol), Pd₂(dba)₃ (14.5 mg, 0.016 mmol) and cesium carbonate (130 mg, 0.399 mmol) was degassed by vacuum-N2 refill cycle twice. 1,1,1-Trifluoro-2-iodoethane (124.5 mg, 0.593 mmol) and water (25 mg, 1.388 mmol) were added. The sealed tube was degassed by vacuum-N2 refill cycle twice again then heated at 90° C. for 2 h. Silica gel chromatography, eluting with 0-100% ethyl acetate in hexanes, gave enantiomer 2 of (1r,4r)-methyl 4-(3-(4-(perfluoropropan-2-yl)phenyl)-3-(3-(2,2,2-trifluoroethyl)phenylsulfonyl)pyrrolidine-1-carbonyl)cyclohexanecarboxylate (24.5 mg, 85%) as off-white solid. LC/MS (M+1): 706.6.

Step B: Enantiomer 2 of (1r,4r)-4-(3-(4-(perfluoropropan-2-yl)phenyl)-3-(3-(2,2,2-trifluoroethyl)phenylsulfonyl)pyrrolidine-1-carbonyl)cyclohexanecarboxylic acid

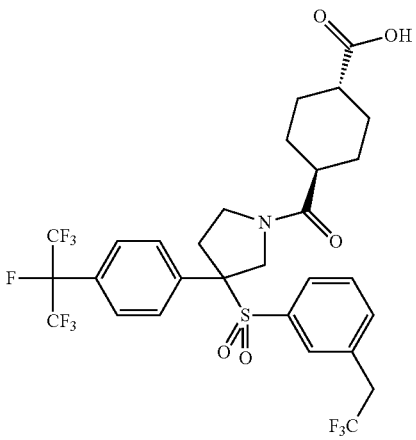

enantiomer 2

Enantiomer 2 of (1r,4r)-methyl 4-(3-(4-(perfluoropropan-2-yl)phenyl)-3-(3-(2,2,2-trifluoroethyl)phenylsulfonyl)pyrrolidine-1-carbonyl)cyclohexanecarboxylate (24.5 mg, 0.035 mmol) was dissolved in THF (0.18 mL). To it was added 1M NaOH (0.18 mL) and MeOH (0.18 mL). The mixture was stirred at ambient temperature for 70 minute. The crude was neutralized by adding 1M HCl (0.18 mL) then concentrated. The resulting aqueous suspension was diluted with water (2 mL) then filtered. The solid was washed with water (2 mL) and dried in vacuo overnight to give enantiomer 2 of (1r,4r)-4-(3-(4-(perfluoropropan-2-yl)phenyl)-3-(3-(2,2,2-trifluoro ethyl)phenylsulfonyl)pyrrolidine-1-carbonyl)cyclohexanecarboxylic acid (15.2 mg, 63%) as white solid. LC/MS (M+1): 692.2; LC retention time: 1.03 min (analytical HPLC Method I); 1H NMR (500 MHz, 1:1 mixture of CDCl₃—CD₃OD) δ 7.60 (d, J=7.7 Hz, 1H), 7.55-7.47 (m, 2H), 7.42-7.17 (m, 5H), 4.90-4.79 (m, 1H), 4.14-3.97 (m, 1H), 3.90-3.74 (m, 2H), 3.39-3.33 (m, 3H), 2.76-2.48 (m, 1H), 2.45-2.24 (m, 2H), 2.19-2.03 (m, 2H), 1.99-1.92 (m, 1H), 1.78 (d, J=12.1 Hz, 1H), 1.64-1.36 (m, 4H).

Example 479

(1r,4r)-4-(3-(3-(2-hydroxy-2-methylpropyl)phenyl-sulfonyl)-3-(4-(perfluoropropan-2-yl)phenyl)pyrrolidine-1-carbonyl)cyclohexanecarboxylic acid, enantiomer 2

Step A: Diastereomer mixture of (1r,4r)-methyl 4-(3-(3-(3,3-dimethyloxiran-2-yl)phenylsulfonyl)-3-(4-(perfluoropropan-2-yl)phenyl)pyrrolidine-1-carbonyl)cyclohexanecarboxylate

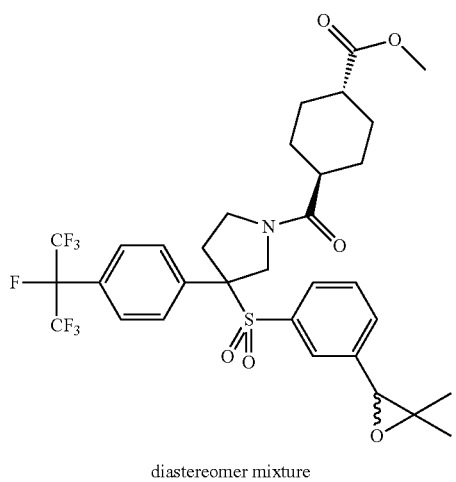 [SMILES: COC(=O)[C@H]1CC[C@H](C(=O)N2CCC(c3ccc(C(F)(C(F)(F)F)C(F)(F)F)cc3)(S(=O)(=O)c3cccc(C4OC4(C)C)c3)C2)CC1]

diastereomer mixture

A CHCl$_3$ (0.5 mL) solution of mCPBA (19 mg, 77 wt %, 0.085 mmol) and enantiomer 2 of (1r,4r)-methyl 4-(3-((3-(2-methylprop-1-en-1-yl)phenyl)sulfonyl)-3-(4-(perfluoropropan-2-yl)phenyl)pyrrolidine-1-carbonyl)cyclohexanecarboxylate (48.5 mg, 0.072 mmol from the precursor of Example 463) was stirred at ambient temperature for 1 h. Sat. NaHCO$_3$ (2 mL) was added and stirred vigorously for 10 min. After phase separation, the organic layer was washed with 10% LiCl (2 mL) then concentrated. Silica gel chromatography, eluting with 0-100% ethyl acetate in hexanes, gave diastereomer mixture of (1r,4r)-methyl 4-(3-(3-(3,3-dimethyloxiran-2-yl)phenylsulfonyl)-3-(4-(perfluoropropan-2-yl)phenyl)pyrrolidine-1-carbonyl)cyclohexanecarboxylate (31 mg, 62%) as white solid. LC/MS (M+1): 694.2; 1H NMR (400 MHz, CDCl$_3$) δ 7.57-7.46 (m, 3H), 7.38-7.28 (m, 2H), 7.26-7.11 (m, 3H), 4.88-4.72 (m, 1H), 4.11-3.99 (m, 1H), 3.94-3.85 (m, 1H), 3.78-3.66 (m, 4H), 3.52-3.36 (m, 1H), 2.64 (dtd, J=14.0, 9.2, 4.7 Hz, 1H), 2.44-2.28 (m, 2H), 2.16-1.98 (m, 2H), 1.84-1.37 (m, 10H), 1.01-0.95 (m, 3H).

Step B: Enantiomer 2 of (1r,4r)-methyl 4-((3-(3-(2-hydroxy-2-methylpropyl)phenylsulfonyl)-3-(4-(perfluoropropan-2-yl)phenyl)pyrrolidine-1-carbonyl)cyclohexanecarboxylate

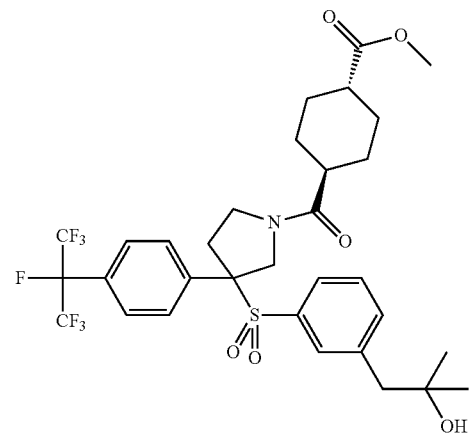

enantiomer 2

10 wt % Palladium on carbon (5 mg, 4.47 μmol) was added to a stirred ethyl acetate (0.5 mL) suspension of diastereomer mixture of (1r,4r)-methyl 4-(3-((3-(3,3-dimethyloxiran-2-yl)phenyl)sulfonyl)-3-(4-(perfluoropropan-2-yl)phenyl)pyrrolidine-1-carbonyl)cyclohexanecarboxylate (31 mg, 0.045 mmol), formic acid (6.86 μL, 0.179 mmol) and triethylamine (0.025 mL, 0.179 mmol). The mixture was stirred at ambient temperature for 19 h. Additional formic acid (0.343 mL), triethylamine (0.25 mL) and palladium on carbon (15 mg) were added. The mixture was stirred for additional 27 h. The crude was filtered. The filtrate was concentrated. The resulting residue was diluted with 10% LiCl (2 mL) and a white solid precipitated out. The solid was collected by filtration and washed with water (4 mL). The solid was dried in vacuo to give enantiomer 2 of (1r,4r)-methyl 4-(3-(3-(2-hydroxy-2-methylpropyl)phenylsulfonyl)-3-(4-(perfluoropropan-2-yl)phenyl)pyrrolidine-1-carbonyl)cyclohexanecarboxylate (21.8 mg, 70%). LC/MS (M+1): 696.2; 1H NMR (500 MHz, CDCl$_3$) δ 7.53-7.43 (m, 3H), 7.37-7.31 (m, 1H), 7.26-7.14 (m, 3H), 7.13-7.02 (m, 1H), 4.85-4.77 (m, 1H), 4.09-4.01 (m, 1H), 3.91-3.81 (m, 1H), 3.75-3.64 (m, 4H), 2.72-2.58 (m, 2H), 2.42-2.29 (m, 2H), 2.18-1.97 (m, 3H), 1.80-1.73 (m, 1H), 1.70-1.34 (m, 7H), 1.24-1.13 (m, 6H).

325

Step C: Enantiomer 2 of (1r,4r)-4-(3-(3-(2-hydroxy-2-methylpropyl)phenylsulfonyl)-3-(4-(perfluoropropan-2-yl)phenyl)pyrrolidine-1-carbonyl)cyclohexanecarboxylic acid

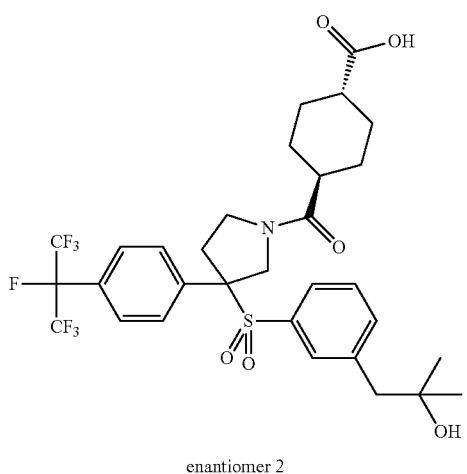 [SMILES: CC(C)(O)Cc1cccc(S(=O)(=O)C2(c3ccc(C(F)(C(F)(F)F)C(F)(F)F)cc3)CCN(C(=O)[C@H]3CC[C@H](C(=O)O)CC3)C2)c1]

enantiomer 2

Enantiomer 2 of (1r,4r)-methyl 4-(3-(3-(2-hydroxy-2-methylpropyl)phenylsulfonyl)-3-(4-(perfluoropropan-2-yl)phenyl)pyrrolidine-1-carbonyl)cyclohexanecarboxylate (8 mg, 0.011 mmol) was dissolved in MeOH (0.5 mL). To it was added 1M NaOH (0.18 mL). The mixture was stirred at ambient temperature for 18 h. The crude was neutralized by adding 1M HCl (0.18 mL). The solution was purified via preparative LC/MS with the following conditions: Column: Waters XBridge C18, 19×200 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-100% B over 25 minutes, then a 5-minute hold at 100% B; Flow: 20 mL/min. Fractions containing the desired product were combined and dried via centrifugal evaporation to give enantiomer 2 of (1r,4r)-4-(3-(3-(2-fluoro-2-methylpropyl)phenylsulfonyl)-3-(4-(perfluoropropan-2-yl)phenyl)pyrrolidine-1-carbonyl) cyclohexanecarboxylic acid (7.9 mg, 59%). LC/MS (M+1): 682.3; LC retention time: 1.70 min (analytical HPLC Method B); 1H NMR (500 MHz, 1:1 mixture of CDCl$_3$—CD$_3$OD) δ 7.51-7.44 (m, 3H), 7.39-7.15 (m, 4H), 7.02-6.94 (m, 1H), 4.91-4.80 (m, 1H), 4.13-3.96 (m, 1H), 3.88-3.74 (m, 2H), 3.65-3.32 (m, 1H), 2.73-2.50 (m, 3H), 2.44-2.24 (m, 2H), 2.16-1.91 (m, 3H), 1.77 (d, J=13.3 Hz, 1H), 1.64-1.37 (m, 4H), 1.17-1.09 (m, 6H).

326

Example 480

(1r,4r)-4-((3-(3-(2-fluoro-2-methylpropyl)phenylsulfonyl)-3-(4-(perfluoropropan-2-yl)phenyl)pyrrolidine-1-carbonyl)cyclohexanecarboxylic acid, enantiomer 2

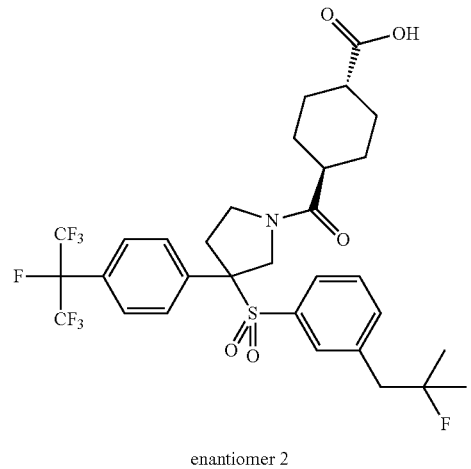 [SMILES: CC(C)(F)Cc1cccc(S(=O)(=O)C2(c3ccc(C(F)(C(F)(F)F)C(F)(F)F)cc3)CCN(C(=O)[C@H]3CC[C@H](C(=O)O)CC3)C2)c1]

enantiomer 2

(Diethylamino)sulfur trifluoride (2.5 μL, 0.019 mmol) was added to a stirred CH$_2$Cl$_2$ (0.5 mL) solution of enantiomer 2 of (1r,4r)-methyl 4-(3-((3-(2-hydroxy-2-methylpropyl)phenyl)sulfonyl)-3-(4-(perfluoropropan-2-yl)phenyl)pyrrolidine-1-carbonyl)cyclohexanecarboxylate (13 mg, 0.019 mmol from Step B of Example 479). The mixture was stirred at ambient temperature for 40 minute. The solvent was evaporated. The residue was dissolved in MeOH (0.5 mL) and THF (0.2 mL). To it was added 1M NaOH (0.18 mL). The mixture was stirred at ambient temperature for 19 h. The crude was neutralized with 1M HCl (0.18 mL). The solution was purified via preparative LC/MS with the following conditions: Column: Waters XBridge C18, 19×200 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-85% B over 20 minutes, then a 5-minute hold at 100% B; Flow: 20 mL/min. Fractions containing the desired product were combined and dried via centrifugal evaporation to give enantiomer 2 of (1r,4r)-4-(3-(3-(2-fluoro-2-methylpropyl)phenylsulfonyl)-3-(4-(perfluoropropan-2-yl)phenyl)pyrrolidine-1-carbonyl)cyclohexanecarboxylic acid (7.9 mg, 59%). LC/MS (M+1): 684.3; LC retention time: 1.94 min (analytical HPLC Method B); 1H NMR (500 MHz, 1:1 mixture of CDCl$_3$—CD$_3$OD) δ 7.53-7.44 (m, 3H), 7.37-7.12 (m, 5H), 4.88-4.80 (m, 1H), 4.13-3.96 (m, 1H), 3.89-3.74 (m, 2H), 3.64-3.32 (m, 1H), 2.93-2.50 (m, 3H), 2.44-2.25 (m, 2H), 2.18-1.91 (m, 3H), 1.77 (d, J=13.4 Hz, 1H), 1.64-1.40 (m, 4H), 1.32-1.20 (m, 6H).

Example 481

(1r,4r)-4-(3-(4-(perfluoropropan-2-yl)phenyl)-3-(3-(trifluoromethyl)phenylsulfonyl)pyrrolidine-1-carbonyl)cyclohexanecarboxylic acid, enantiomer 1

Step A: rac-1-benzyl-3-(4-(perfluoropropan-2-yl)phenyl)-3-(3-(trifluoromethyl)phenylsulfonyl)pyrrolidine

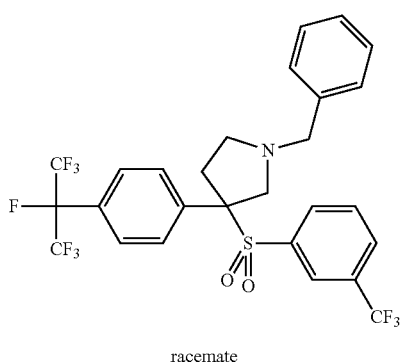 [SMILES: O=S(=O)(c1cccc(C(F)(F)F)c1)C1(c2ccc(C(F)(C(F)(F)F)C(F)(F)F)cc2)CCN(Cc2ccccc2)C1]

racemate

Similar to the synthesis of Example 441, rac-1-benzyl-3-(4-(perfluoropropan-2-yl)phenyl)-3-(3-(trifluoromethyl)phenylsulfonyl)pyrrolidine (434 mg) was prepared from 2-(4-(bromomethyl)phenyl)-1,1,1,3,3,3-hexafluoropropan-2-ol and sodium 3-(trifluoromethyl)benzenesulfinate in four steps. LC/MS (M+1): 614.1; 1H NMR (400 MHz, CDCl$_3$) δ 7.86-7.80 (m, 1H), 7.61 (d, J=7.9 Hz, 1H), 7.57-7.46 (m, 4H), 7.38-7.27 (m, 7H), 3.80-3.67 (m, 3H), 3.27 (d, J=11.0 Hz, 1H), 3.13-3.04 (m, 1H), 3.03-2.95 (m, 1H), 2.80 (td, J=8.2, 4.6 Hz, 1H), 2.62-2.51 (m, 1H).

Step B: rac-3-(4-(perfluoropropan-2-yl)phenyl)-3-(3-(trifluoromethyl)phenylsulfonyl)pyrrolidine

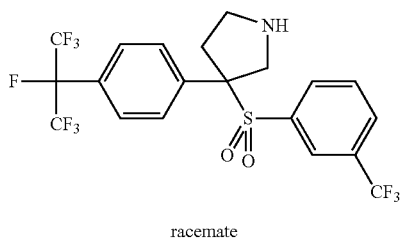 [SMILES: O=S(=O)(c1cccc(C(F)(F)F)c1)C1(c2ccc(C(F)(C(F)(F)F)C(F)(F)F)cc2)CCNC1]

racemate

A stirred MeOH (5 mL) solution of rac-1-benzyl-3-(4-(perfluoropropan-2-yl)phenyl)-3-((3-(trifluoromethyl)phenyl)sulfonyl)pyrrolidine (434 mg, 0.707 mmol), Pearlman's catalyst (49.7 mg, 20 wt %, 0.071 mmol) and 1M HCl (0.707 mL, 0.707 mmol) was hydrogenated under 50 psi H2 at ambient temperature for 18 h. The crude was filtered. The filtrate was concentrated to give rac-3-(4-(perfluoropropan-2-yl)phenyl)-3-(3-(trifluoromethyl)phenylsulfonyl)pyrrolidine (390 mg) as white solid. LC/MS (M+1): 524.1.

Step C: Enantiomers 1 and 2 of 3-(4-(perfluoropropan-2-yl)phenyl)-3-(3-(trifluoromethyl)phenylsulfonyl)pyrrolidine

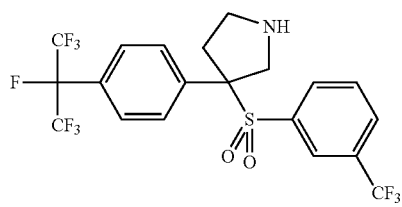

enantiomers 1 and 2 rac-3-(4-(perfluoropropan-2-yl)phenyl)-3-(3-(trifluoromethyl)phenylsulfonyl)pyrrolidine (390 mg) was separated into its homochiral components by preparative chiral SFC (Chiralpak AD-H 5×25 cm, 5 μm particles, 10% methanol in CO$_2$ with 0.2% NH$_4$OH, 150 mL/min) to afford the first eluent off the column as enantiomer 1 (0.1477 g, 39% yield) and the second eluent as enantiomer 2 (0.1610 g, 42% yield). Analytical data for the enantiomer 1: LC/MS (M+1): 524.3; chiral HPLC retention time: 2.46 min (Chiralpak AD-H 0.46×25 cm, 5 μm particles, 10% methanol in CO$_2$ with 0.2% NH$_4$OH, 3 mL/min); 1H NMR (500 MHz, CDCl$_3$) δ 7.84 (d, J=7.6 Hz, 1H), 7.61-7.56 (m, 1H), 7.55-7.49 (m, 3H), 7.37 (s, 1H), 7.18 (d, J=8.4 Hz, 2H), 4.20 (d, J=13.6 Hz, 1H), 3.58-3.49 (m, 1H), 3.31 (d, J=13.6 Hz, 1H), 3.16-3.05 (m, 2H), 2.52-2.43 (m, 1H). Analytical data for the enantiomer 2: LC/MS (M+1): 524.2; chiral HPLC retention time: 3.22 min (Chiralpak AD-H 0.46×25 cm, 5 μm particles, 10% methanol in CO$_2$ with 0.2% NH4OH, 3 mL/min); 1H NMR (400 MHz, CDCl$_3$) δ 7.85 (d, J=7.8 Hz, 1H), 7.71 (d, J=7.6 Hz, 1H), 7.59-7.49 (m, 3H), 7.36 (s, 1H), 7.17 (d, J=8.5 Hz, 2H), 4.31 (d, J=13.4 Hz, 1H), 3.70-3.62 (m, 1H), 3.45 (d, J=13.4 Hz, 1H), 3.29-3.15 (m, 2H), 2.57-2.51 (m, 1H).

Step D: Enantiomer 1 of (1r,4r)-4-(3-(4-(perfluoropropan-2-yl)phenyl)-3-(3-(trifluoromethyl)phenylsulfonyl)pyrrolidine-1-carbonyl)cyclohexanecarboxylic acid

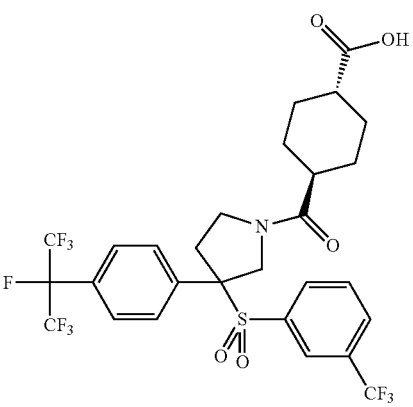

enantiomer 1

Hunig's base (30 µL, 0.172 mmol) was added to an acetonitrile (0.5 mL) solution of enantiomer 1 of 3-(4-(perfluoropropan-2-yl)phenyl)-3-((3-(trifluoromethyl)phenyl)sulfonyl)pyrrolidine (14 mg, 0.027 mmol), (1r,4r)-4-(methoxycarbonyl)cyclohexanecarboxylic acid (14 mg, 0.075 mmol) and BOP (27 mg, 0.061 mmol). The mixture was stirred at ambient temperature for 1 h. M NaOH (0.18 mL) was added. The mixture was stirred for 17 h. Additional 1M NaOH (0.54 mL) was added. The mixture was stirred for additional 3 h then diluted with MeOH (1 mL). The solution was purified via preparative LC/MS with the following conditions: Column: Waters XBridge C18, 19×200 mm, 5-µm particles; Guard Column: Waters XBridge C18, 19×10 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 25-100% B over 20 minutes, then a 5-minute hold at 100% B; Flow: 20 mL/min. Fractions containing the desired product were combined and dried via centrifugal evaporation to give Enantiomer 1 of (1r,4r)-4-(3-(4-(perfluoropropan-2-yl)phenyl)-3-(3-(trifluoromethyl)phenylsulfonyl)pyrrolidine-1-carbonyl)cyclohexanecarboxylic acid (16.6 mg, 92%). LC/MS (M+1): 678.0; LC retention time: 1.928 min (analytical HPLC Method B); 1H NMR (400 MHz, 1:1 mixture of $CDCl_3$—$CD_3OD$) δ 7.91 (d, J=7.8 Hz, 1H), 7.80-7.62 (m, 2H), 7.57-7.50 (m, 2H), 7.35-7.19 (m, 3H), 4.92-4.79 (m, 1H), 4.15-4.05 (m, 1H), 3.90-3.77 (m, 2H), 3.69-3.33 (m, 1H), 2.58-2.38 (m, 1H), 2.35-2.24 (m, 1H), 2.16-1.95 (m, 3H), 1.78 (d, J=10.0 Hz, 1H), 1.64-1.38 (m, 4H).

Examples 482-484 in Table 6 below were prepared in the same manner as outlined in the Step D of Example 481 above. Examples 485-516 were synthesized using conditions described for previous examples.

TABLE 6

| Example number | Structure | MS observed (M + 1) | HPLC ret. time (min.) | HPLC method |
|---|---|---|---|---|
| 482 | 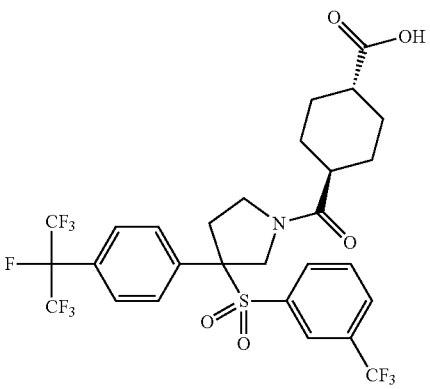<br>enantiomer 2 | 678.2 | 1.78 | B |
| 483 | 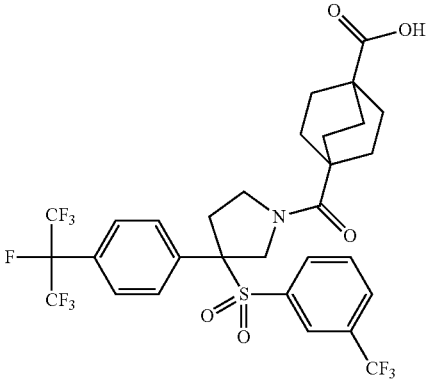<br>enantiomer 2 | 704.2 | 1.89 | B |

TABLE 6-continued
| Example number | Structure | MS observed (M + 1) | HPLC ret. time (min.) | HPLC method |
|---|---|---|---|---|
| 484 | 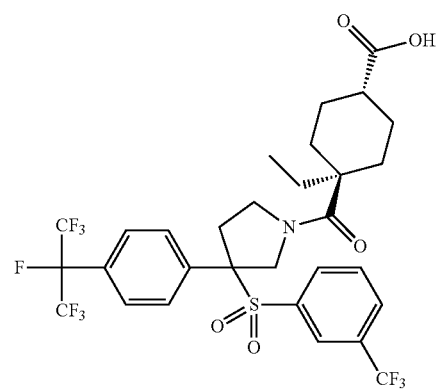 enantiomer 2 | 706.2 | 2.00 | B |
| 485 | 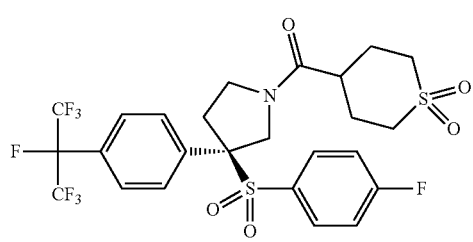 [SMILES: O=C(C1CCS(=O)(=O)CC1)N1CC[C@](c2ccc(C(F)(C(F)(F)F)C(F)(F)F)cc2)(S(=O)(=O)c2ccc(F)cc2)C1] | 634.7 | 11.3 | J |
| 486 | 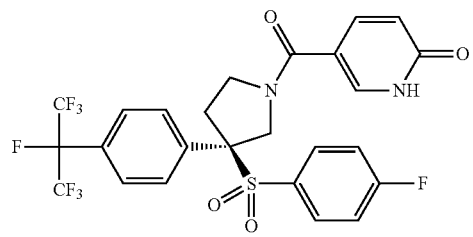 | 595.2 | 1.76 | B |
| 487 | 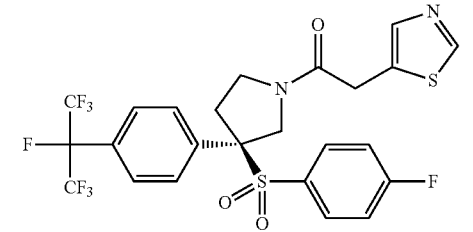 [SMILES: O=C(Cc1cncs1)N1CC[C@](c2ccc(C(F)(C(F)(F)F)C(F)(F)F)cc2)(S(=O)(=O)c2ccc(F)cc2)C1] | 599.1 | 1.95 | B |
| 488 | 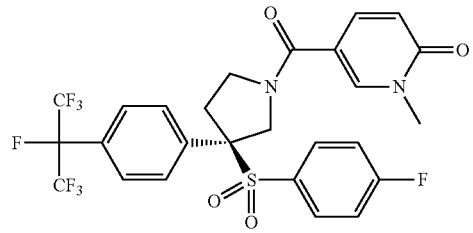 [SMILES: Cn1cc(C(=O)N2CC[C@](c3ccc(C(F)(C(F)(F)F)C(F)(F)F)cc3)(S(=O)(=O)c3ccc(F)cc3)C2)ccc1=O] | 609.2 | 1.83 | B |

TABLE 6-continued
| Example number | Structure | MS observed (M + 1) | HPLC ret. time (min.) | HPLC method |
|---|---|---|---|---|
| 489 | 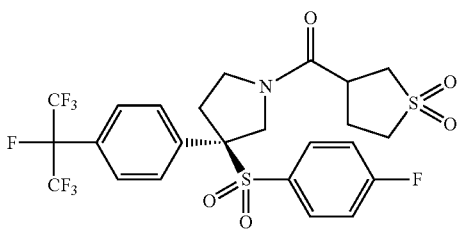<br>diastereomer 1 | 620.4 | 11.5 | J |
| 490 | 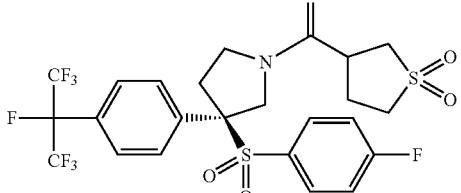<br>diastereomer 2 | 620.4 | 11.5 | J |
| 491 | 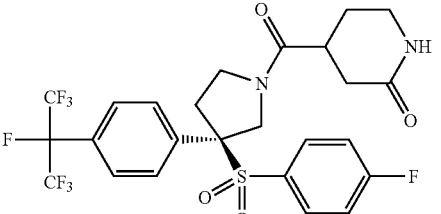<br>diastereomer 1 | 599.2 | 1.145 | K |
| 492 | 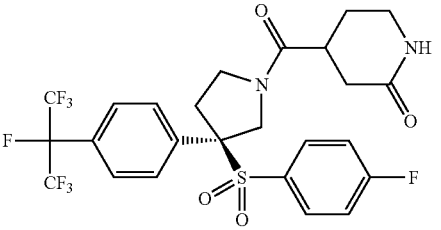<br>diastereomer 2 | 599.1 | 1.148 | K |
| 493 | 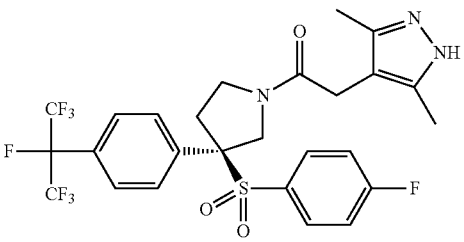 [SMILES: Cc1n[nH]c(C)c1CC(=O)N1CC[C@](c2ccc(C(F)(C(F)(F)F)C(F)(F)F)cc2)(S(=O)(=O)c2ccc(F)cc2)C1] | 610.4 | 10.3 | J |

TABLE 6-continued
| Example number | Structure | MS observed (M + 1) | HPLC ret. time (min.) | HPLC method |
|---|---|---|---|---|
| 494 | 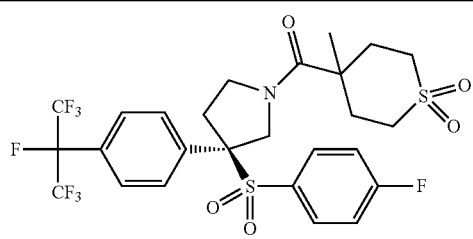 | 648.1 | 11.8 | J |
| 495 | 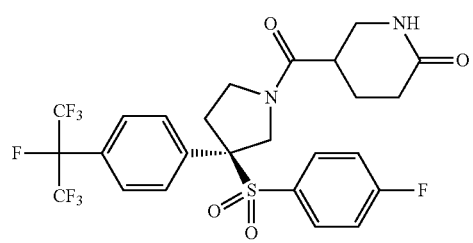 diastereomer 1 | 599.1 | 1.13 | K |
| 496 | 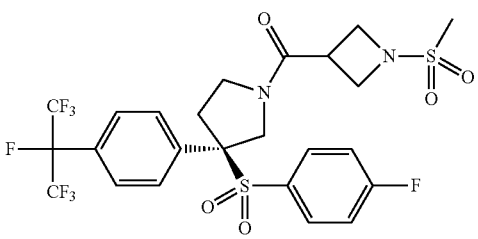 [SMILES: CS(=O)(=O)N1CC(C(=O)N2CC[C@](c3ccc(C(F)(C(F)(F)F)C(F)(F)F)cc3)(S(=O)(=O)c3ccc(F)cc3)C2)C1] | 635.3 | 1.96 | B |
| 497 | 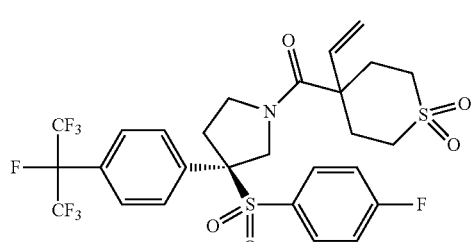 | 660.3 | 2.09 | B |
| 498 | 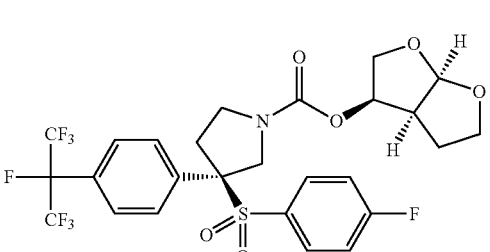 | 647.3 (M + 18) | 2.11 | B |
| 499 | 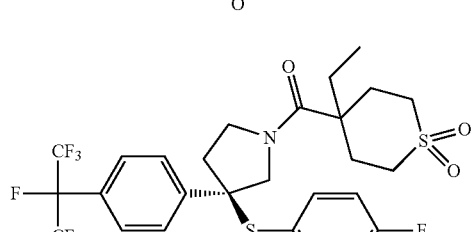 | 662.4 | 12.1 | J |

TABLE 6-continued

| Example number | Structure | MS observed (M + 1) | HPLC ret. time (min.) | HPLC method |
|---|---|---|---|---|
| 500 | diastereomer 1 | 649.4 | 11.6 | J |
| 501 | diastereomer 2 | 649.4 | 11.6 | J |
| 502 | 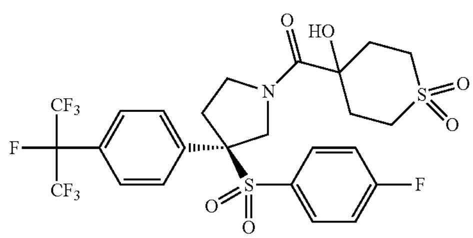 [SMILES: O=C(N1CC[C@](c2ccc(C(F)(C(F)(F)F)C(F)(F)F)cc2)(S(=O)(=O)c2ccc(F)cc2)C1)C1(O)CCS(=O)(=O)CC1] | 650.3 | 1.95 | B |
| 503 | 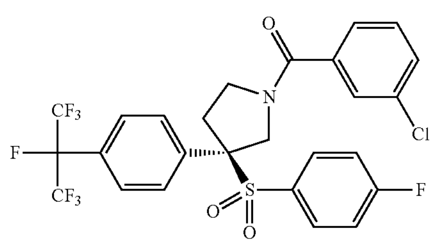 [SMILES: O=C(c1cccc(Cl)c1)N1CC[C@](c2ccc(C(F)(C(F)(F)F)C(F)(F)F)cc2)(S(=O)(=O)c2ccc(F)cc2)C1] | 612.2 | 2.41 | B |
| 504 | 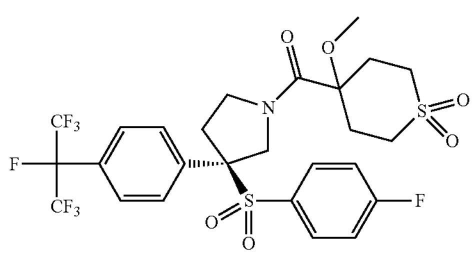 [SMILES: COC1(C(=O)N2CC[C@](c3ccc(C(F)(C(F)(F)F)C(F)(F)F)cc3)(S(=O)(=O)c3ccc(F)cc3)C2)CCS(=O)(=O)CC1] | 664.1 | 2.04 | B |
| 505 | 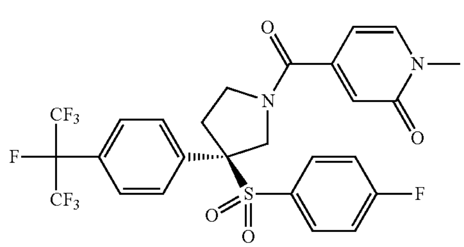 [SMILES: Cn1ccc(C(=O)N2CC[C@](c3ccc(C(F)(C(F)(F)F)C(F)(F)F)cc3)(S(=O)(=O)c3ccc(F)cc3)C2)cc1=O] | 609.3 | 1.85 | C |

TABLE 6-continued

| Example number | Structure | MS observed (M + 1) | HPLC ret. time (min.) | HPLC method |
|---|---|---|---|---|
| 506 | 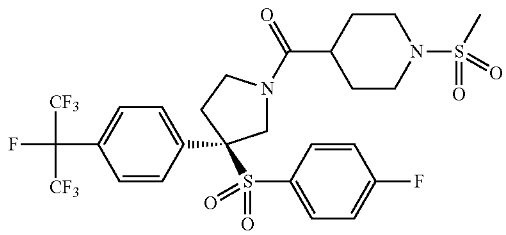 [SMILES: CS(=O)(=O)N1CCC(C(=O)N2CC[C@](c3ccc(C(F)(C(F)(F)F)C(F)(F)F)cc3)(S(=O)(=O)c3ccc(F)cc3)C2)CC1] | 663.1 | 1.98 | C |
| 507 | 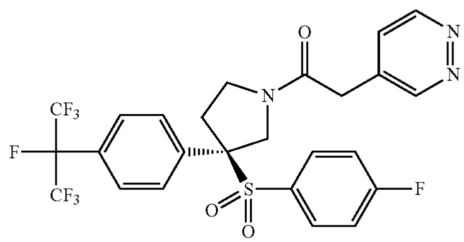 [SMILES: O=C(Cc1ccnnc1)N1CC[C@](c2ccc(C(F)(C(F)(F)F)C(F)(F)F)cc2)(S(=O)(=O)c2ccc(F)cc2)C1] | 593.9 | 1.88 | B |
| 508 | 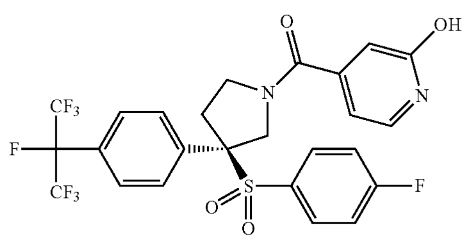 [SMILES: O=C(c1ccnc(O)c1)N1CC[C@](c2ccc(C(F)(C(F)(F)F)C(F)(F)F)cc2)(S(=O)(=O)c2ccc(F)cc2)C1] | 595.3 | 1.77 | C |
| 509 | 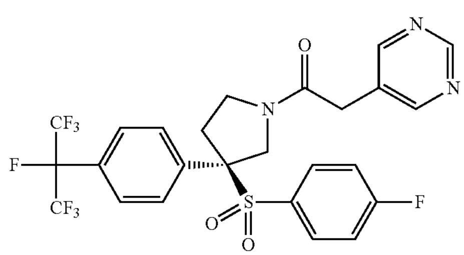 [SMILES: O=C(Cc1cncnc1)N1CC[C@](c2ccc(C(F)(C(F)(F)F)C(F)(F)F)cc2)(S(=O)(=O)c2ccc(F)cc2)C1] | 594.1 | 1.83 | C |
| 510 | 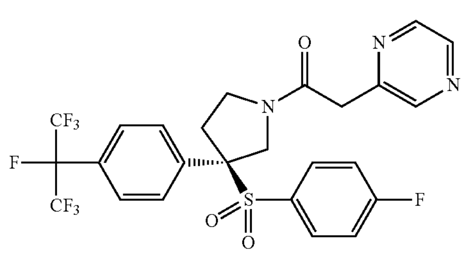 [SMILES: O=C(Cc1cnccn1)N1CC[C@](c2ccc(C(F)(C(F)(F)F)C(F)(F)F)cc2)(S(=O)(=O)c2ccc(F)cc2)C1] | 594.2 | 1.91 | C |
| 511 | 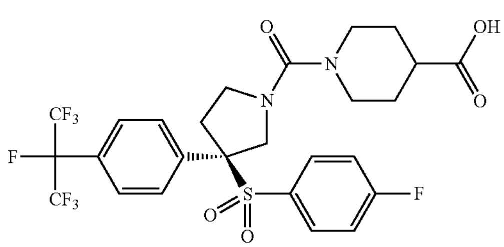 [SMILES: O=C(O)C1CCN(C(=O)N2CC[C@](c3ccc(C(F)(C(F)(F)F)C(F)(F)F)cc3)(S(=O)(=O)c3ccc(F)cc3)C2)CC1] | 629.2 | 1.65 | B |

TABLE 6-continued

| Example number | Structure | MS observed (M + 1) | HPLC ret. time (min.) | HPLC method |
|---|---|---|---|---|
| 512 | 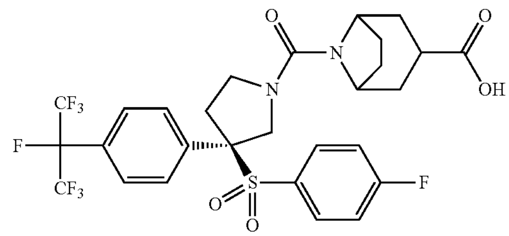 [SMILES: O=C(O)C1CC2CCC(C1)N2C(=O)N1CC[C@](c2ccc(C(F)(C(F)(F)F)C(F)(F)F)cc2)(S(=O)(=O)c2ccc(F)cc2)C1] | 655.1 | 1.85 | B |
| 513 | 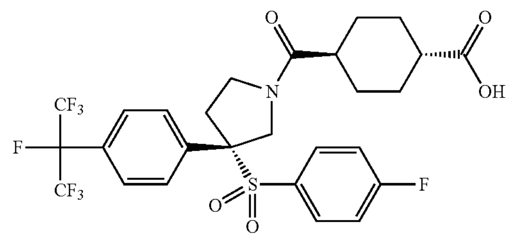 [SMILES: O=C(O)[C@H]1CC[C@H](C(=O)N2CC[C@@](c3ccc(C(F)(C(F)(F)F)C(F)(F)F)cc3)(S(=O)(=O)c3ccc(F)cc3)C2)CC1] | 628.5 | 12.94 | L |
| 514 | 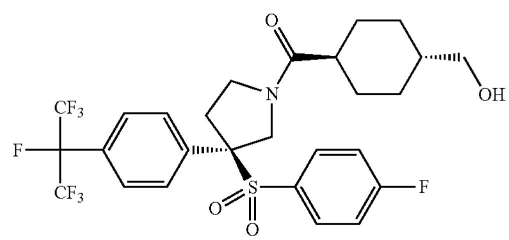 [SMILES: O=C([C@H]1CC[C@H](CO)CC1)N1CC[C@](c2ccc(C(F)(C(F)(F)F)C(F)(F)F)cc2)(S(=O)(=O)c2ccc(F)cc2)C1] | 614.2 | 1.98 | B |
| 515 | 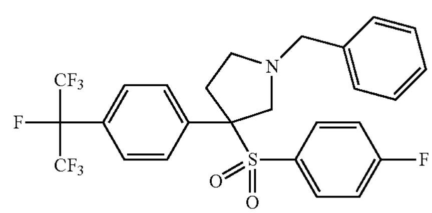 [SMILES: O=S(=O)(c1ccc(F)cc1)C1(c2ccc(C(F)(C(F)(F)F)C(F)(F)F)cc2)CCN(Cc2ccccc2)C1] | 564.3 | 11.30 | J |
| 516 | 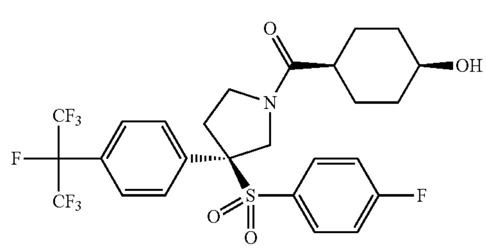 [SMILES: O=C([C@H]1CC[C@@H](O)CC1)N1CC[C@](c2ccc(C(F)(C(F)(F)F)C(F)(F)F)cc2)(S(=O)(=O)c2ccc(F)cc2)C1] | 600.5 | 1.228 | K |

Examples 517 and 518

((R)-3-((4-fluorophenyl)sulfonyl)-3-(4-(perfluoropropan-2-yl)phenyl)pyrrolidin-1-yl)(1r,4R)-4-hydroxycyclohexyl)methanone and cyclohex-3-en-1-yl (R)-3-((4-fluorophenyl)sulfonyl)-3-(4-(perfluoropropan-2-yl)phenyl)pyrrolidin-1-yl)methanone, respectively

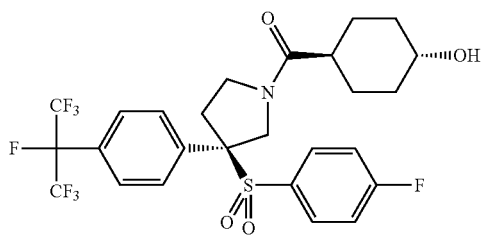

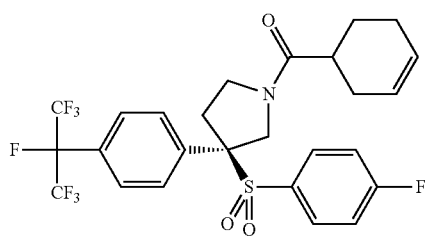

A flask was charged with ((R)-3-((4-fluorophenyl)sulfonyl)-3-(4-(perfluoropropan-2-yl)phenyl)pyrrolidin-1-yl)((1s,4S)-4-hydroxycyclohexyl)methanone (70 mg, 0.117 mmol) from Example 516, 4-nitrobenzoic acid (78 mg, 0.467 mmol), triphenylphosphine (119 mg, 0.455 mmol), and anhydrous tetrahydrofuran (3 ml). Diisopropyl azodicarboxylate (0.091 ml, 0.461 mmol) was added dropwise at 0° C. under nitrogen. Upon completion of the addition, the solution was stirred at room temperature overnight. The solvent and other volatile reaction components were removed under reduced pressure. Flash chromatography purification (12 g silica gel column, gradient elution from 5 to 100% of ethyl acetate in hexanes) afforded a crude ester product.

The ester was dissolved in methanol (2 mL) and diethyl ether (1 mL). 2M aq NaOH (0.2 mL, 0.400 mmol) was added. The mixture was stirred at RT for 2 h. The mixture was neutralized with acetic acid and concentrated. The crude material was purified via preparative LC/MS with the following conditions: Column: Waters XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-95% B over 20 minutes, then a 6-minute hold at 100% B; Flow: 20 mL/min. Fractions containing the desired product were combined and dried via centrifugal evaporation. ((R)-3-((4-fluorophenyl)sulfonyl)-3-(4-(perfluoropropan-2-yl)phenyl)pyrrolidin-1-yl)((1r,4R)-4-hydroxycyclohexyl)methanone (5.3 mg, 0.0088 mmol, 7.6% yield) and cyclohex-3-en-1-yl((R)-3-((4-fluorophenyl)sulfonyl)-3-(4-(perfluoropropan-2-yl)phenyl)pyrrolidin-1-yl)methanone (15.7 mg, 0.027 mmol, 23% yield) were obtained.

Analytical Data for ((R)-3-(4-fluorophenyl)sulfonyl)-3-(4-(perfluoropropan-2-yl)phenyl)pyrrolidin-1-yl)((1r,4R)-4-hydroxycyclohexyl)methanone: LC/MS (M+1): 600.2; LC retention time: 1.89 min (analytical HPLC Method B); $^1$H NMR (500 MHz, DMSO-$d_6$) δ 7.59 (d, J=7.2 Hz, 2H), 7.49-7.33 (m, 4H), 7.32-7.24 (m, 2H), 4.85-4.66 (m, 2H), 4.13-3.27 (m, 4H), 3.22-2.93 (m, 1H), 2.77-2.53 (m, 1H), 2.22-1.54 (m, 5H), 1.41-1.06 (m, 4H).

Analytical Data for cyclohex-3-en-1-yl((R)-3-((4-fluorophenyl)sulfonyl)-3-(4-(perfluoropropan-2-yl)phenyl)pyrrolidin-1-yl)methanone: LC/MS (M+1): 582.2; LC retention time: 2.27 min (analytical HPLC Method B); $^1$H NMR (500 MHz, DMSO-$d_6$) δ 7.64-7.54 (m, 2H), 7.50-7.33 (m, 4H), 7.33-7.22 (m, 2H), 5.78-5.61 (m, 2H), 4.87-4.68 (m, 1H), 4.17-3.28 (m, 3H), 3.22-2.53 (m, 3H), 2.29-1.83 (m, 4H), 1.81-1.34 (m, 2H).

Example 519

(R)-(4-fluoro-1,1-dioxidotetrahydro-2H-thiopyran-4-yl)(3-((4-fluorophenyl)sulfonyl)-3-(4-(perfluoropropan-2-yl)phenyl)pyrrolidin-1-yl)methanone

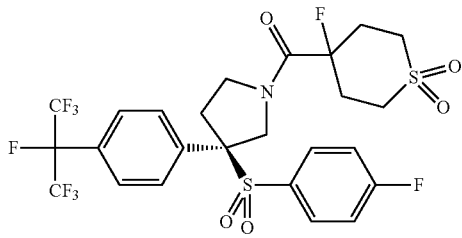 [SMILES: O=C(N1CC[C@](c2ccc(C(F)(C(F)(F)F)C(F)(F)F)cc2)(S(=O)(=O)c2ccc(F)cc2)C1)C1(F)CCS(=O)(=O)CC1]

DAST (0.012 mL, 0.092 mmol) was added to a stirred CH$_2$Cl$_2$ (1 mL) solution of (R)-3-((4-fluorophenyl)sulfonyl)-3-(4-(perfluoropropan-2-yl)phenyl)pyrrolidin-1-yl)(4-hydroxy-1,1-dioxidotetrahydro-2H-thiopyran-4-yl)methanone (20 mg, 0.031 mmol) at RT under nitrogen. The solution was stirred at RT overnight. The reaction was quenched with saturated aqueous sodium bicarbonate solution (1.5 mL). The aqueous layer was extracted with EtOAc (2×1 mL). The combined organic solutions were dried over sodium sulfate and concentrated. The crude material was purified via preparative LC/MS with the following conditions: Column: Waters XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 35-75% B over 25 minutes, then a 5-minute hold at 75% B; Flow: 20 mL/min. Fractions containing the desired product were combined and dried via centrifugal evaporation. (R)-(4-fluoro-1,1-dioxidotetrahydro-2H-thiopyran-4-yl)(3-((4-fluorophenyl)sulfonyl)-3-(4-(perfluoropropan-2-yl)phenyl)pyrrolidin-1-yl)methanone (9.4 mg, 47% yield). LC/MS (M+1): 652.1; LC retention time: 2.03 min (analytical HPLC Method B); $^1$H NMR (500 MHz, DMSO-$d_6$) γ 7.64-7.56 (m, 2H), 7.46-7.33 (m, 4H), 7.33-7.25 (m, 2H), 5.09-4.76 (m, 1H), 4.27-3.83 (m, 2H), 3.62-3.10 (m, 6H), 3.06-2.68 (m, 1H), 2.62-2.35 (m, 4H).

Example 520

(4-(1,2-dihydroxyethyl)-1,1-dioxidotetrahydro-2H-thiopyran-4-yl)((R)-3-((4-fluorophenyl)sulfonyl)-3-(4-(perfluoropropan-2-yl)phenyl)pyrrolidin-1-yl)methanone Step A: (R)-(1,1-dioxido-4-vinyltetrahydro-2H-thiopyran-4-yl)(3-((4-fluorophenyl)sulfonyl)-3-(4-(perfluoropropan-2-yl)phenyl)pyrrolidin-1-yl)methanone

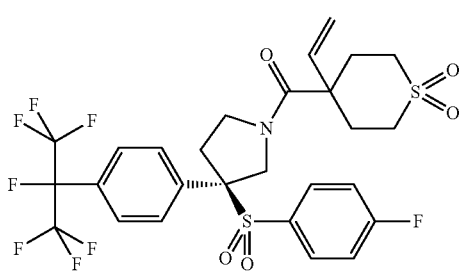 [SMILES: C=CC1(C(=O)N2CC[C@](c3ccc(C(F)(C(F)(F)F)C(F)(F)F)cc3)(S(=O)(=O)c3ccc(F)cc3)C2)CCS(=O)(=O)CC1]

To a stirred mixture of (R)-3-((4-fluorophenyl)sulfonyl)-3-(4-(perfluoropropan-2-yl)phenyl)pyrrolidine (300 mg, 0.634 mmol),4-vinyltetrahydro-2H-thiopyran-4-carboxylic acid 1,1-dioxide (155 mg, 0.760 mmol) [PCT Int. Appl., 20131850931], Hunig's Base (0.332 mL, 1.901 mmol) and anhydrous DMF (3 mL) was added HATU (361 mg, 0.951 mmol) at RT under nitrogen. The mixture as stirred at room temperature for 1 h before being concentrated. The residue was treated with saturated aqueous sodium bicarbonate solution (5 mL) and extracted with ethyl acetate (3×3 mL). The combined organic solutions were dried over anhydrous sodium sulfate and concentrated. Flash chromatography purification (12 g silica gel column, gradient elution from 0 to 100% of ethyl acetate in hexanes) afforded (R)-(1,1-dioxido-4-vinyltetrahydro-2H-thiopyran-4-yl)(3-((4-fluorophenyl)sulfonyl)-3-(4-(perfluoropropan-2-yl)phenyl)pyrrolidin-1-yl)methanone (360 mg, 0.546 mmol, 86% yield). LC/MS (M+1): 660.4; LC retention time: 1.32 min (analytical HPLC Method K).

Step B: (4-(1,2-dihydroxyethyl)-1,1-dioxidotetrahydro-2H-thiopyran-4-yl)((R)-3-((4-fluorophenyl)sulfonyl)-3-(4-(perfluoropropan-2-yl)phenyl)pyrrolidin-1-yl)methanone and (R)-4-(3-((4-fluorophenyl)sulfonyl)-3-(4-(perfluoropropan-2-yl)phenyl)pyrrolidine-1-carbonyl)tetrahydro-2H-thiopyran-4-carbaldehyde 1,1-dioxide

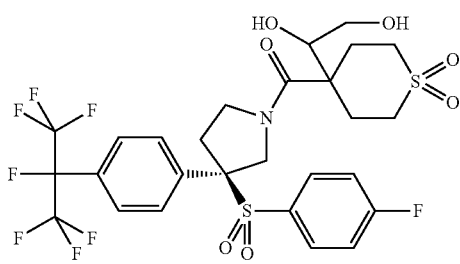

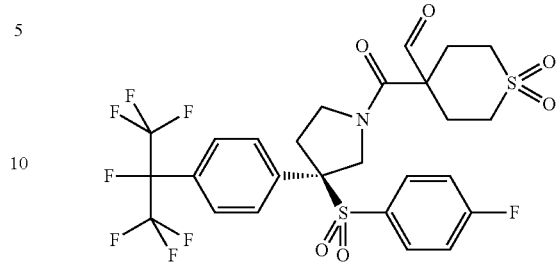

To a clear solution of (R)-(1,1-dioxido-4-vinyltetrahydro-2H-thiopyran-4-yl)(3-((4-fluorophenyl)sulfonyl)-3-(4-(perfluoropropan-2-yl)phenyl)pyrrolidin-1-yl)methanone (335 mg, 0.508 mmol) in THF (3 mL) were sequentially added 50% NMO in water (0.316 mL, 1.524 mmol) and 2.5% tert-butanol solution of osmium tetroxide (0.191 mL, 0.015 mmol) at RT. The solution was vigorously stirred at RT for 2 hr. More 50% NMO in water (0.316 mL, 1.524 mmol) and 2.5% tert-butanol solution of osmium tetroxide (0.4 mL) were added at RT. The mixture was stirred at RT overnight. More 2.5% tert-butanol solution of osmium tetroxide (0.4 mL) were added at RT. The mixture was stirred at RT overnight and at 60° C. for 4 h.

6% of the mixture was purified via preparative LC/MS with the following conditions: Column: Waters XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-85% B over 20 minutes, then a 5-minute hold at 100% B; Flow: 20 mL/min. Fractions containing the desired product were combined and dried via centrifugal evaporation. (4-(1,2-dihydroxyethyl)-1,1-dioxidotetrahydro-2H-thiopyran-4-yl)((R)-3-((4-fluorophenyl)sulfonyl)-3-(4-(perfluoropropan-2-yl)phenyl)pyrrolidin-1-yl)methanone (20 mg, 0.029 mmol, 5.7% yield). LC/MS (M+1): 694.2; LC retention time: 1.78 min (analytical HPLC Method B). To the rest of the mixture, a solution of sodium periodate (435 mg, 2.032 mmol) in H2O (4 mL) was added. The mixture was stirred vigorously at RT under nitrogen for 30 min. The mixture was extracted with ethyl acetate (3×3 mL). The combined organic solutions were dried over anhydrous sodium sulfate and concentrated. Flash chromatography purification (12 g silica gel column, gradient elution from 20 to 80% of ethyl acetate in hexanes) afforded (R)-4-(3-((4-fluorophenyl)sulfonyl)-3-(4-(perfluoropropan-2-yl)phenyl)pyrrolidine-1-carbonyl)tetrahydro-2H-thiopyran-4-carbaldehyde 1,1-dioxide (280 mg, 0.423 mmol, 83% yield) as a solid. LC/MS (M+1): 662.5; LC retention time: 1.28 min (analytical HPLC Method K).

Example 521

(R)-4-(3-((4-fluorophenyl)sulfonyl)-3-(4-(perfluoropropan-2-yl)phenyl)pyrrolidine-1-carbonyl)-N-methyltetrahydro-2H-thiopyran-4-carboxamide 1,1-dioxide

Step A: (R)-4-(3-((4-fluorophenyl)sulfonyl)-3-(4-(perfluoropropan-2-yl)phenyl)pyrrolidine-1-carbonyl)tetrahydro-2H-thiopyran-4-carboxylic acid 1,1-dioxide

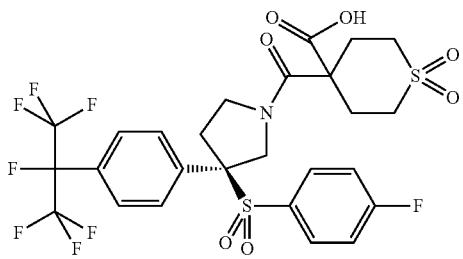 [SMILES: O=C(O)C1(C(=O)N2CC[C@](c3ccc(C(F)(C(F)(F)F)C(F)(F)F)cc3)(S(=O)(=O)c3ccc(F)cc3)C2)CCS(=O)(=O)CC1]

A mixture of (R)-4-(3-((4-fluorophenyl)sulfonyl)-3-(4-(perfluoropropan-2-yl)phenyl)pyrrolidine-1-carbonyl)tetrahydro-2H-thiopyran-4-carbaldehyde 1,1-dioxide (100 mg, 0.151 mmol), sodium chlorite (42.7 mg, 0.378 mmol), potassium dihydrogen phosphate (123 mg, 0.907 mmol), 2-methyl-2-butene (0.227 ml, 0.453 mmol), THF (3 mL), t-BuOH (1 mL), and H$_2$O (4 mL) was vigorously stirred at 0° C. for 3 h. AcOH (0.078 mL, 1.360 mmol) was added. The mixture was then diluted with hexanes (4 mL). The aqueous layer was separated and extracted with ethyl acetate (3×2 mL). The combined organic solutions were washed with brine (1 mL), dried over sodium sulfate, filtered, and concentrated under reduced pressure to give crude (R)-4-(3-((4-fluorophenyl)sulfonyl)-3-(4-(perfluoropropan-2-yl)phenyl)pyrrolidine-1-carbonyl)tetrahydro-2H-thiopyran-4-carboxylic acid 1,1-dioxide (120 mg, 0.177 mmol, 117% yield) as a solid. The crude product was used as such in the following step. LC/MS (M+1): 678.5; LC retention time: 1.19 min (analytical HPLC Method K).

Step B: (R)-4-(3-((4-fluorophenyl)sulfonyl)-3-(4-(perfluoropropan-2-yl)phenyl)pyrrolidine-1-carbonyl)-N-methyltetrahydro-2H-thiopyran-4-carboxamide 1,1-dioxide

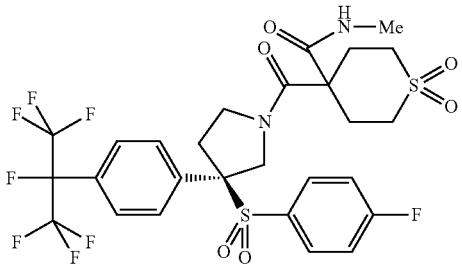 [SMILES: CNC(=O)C1(C(=O)N2CC[C@](c3ccc(C(F)(C(F)(F)F)C(F)(F)F)cc3)(S(=O)(=O)c3ccc(F)cc3)C2)CCS(=O)(=O)CC1]

To a stirred mixture of (R)-4-(3-((4-fluorophenyl)sulfonyl)-3-(4-(perfluoropropan-2-yl)phenyl)pyrrolidine-1-carbonyl)tetrahydro-2H-thiopyran-4-carboxylic acid 1,1-dioxide (23 mg, 0.034 mmol), Hunig's Base (0.024 mL, 0.136 mmol) and anhydrous CH$_2$Cl$_2$ (1 mL) was added BOP (30.0 mg, 0.068 mmol) at RT under nitrogen. The mixture was stirred at room temperature for 1 h before 2M THF solution of methylamine (0.170 mL, 0.339 mmol) was added. The mixture was stirred at RT overnight and concentrated. The crude material was purified via preparative LC/MS with the following conditions: Column: Waters XBridge C18, 19×200 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 25-100% B over 20 minutes, then a 5-minute hold at 100% B; Flow: 20 mL/min. Fractions containing the desired product were combined and dried via centrifugal evaporation. (R)-4-(3-((4-fluorophenyl)sulfonyl)-3-(4-(perfluoropropan-2-yl)phenyl)pyrrolidine-1-carbonyl)-N-methyltetrahydro-2H-thiopyran-4-carboxamide 1,1-dioxide (17 mg, 0.024 mmol, 72% yield) was obtained. LC/MS (M+1): 691.2; LC retention time: 1.90 min (analytical HPLC Method B).

The examples in Table 7 below were prepared in the same manner as outlined in examples above.

TABLE 7

| Ex. No | Structure | MS (M + 1) | HPLC ret. time (min.) | HPLC method |
|---|---|---|---|---|
| 522 | 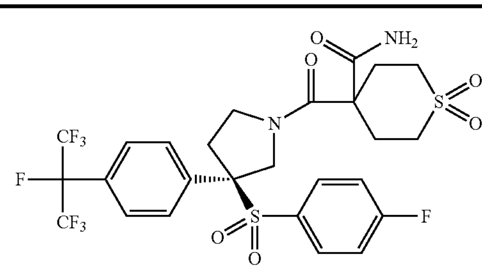 | 677.3 | 1.82 | B |

TABLE 7-continued

| Ex. No | Structure | MS (M + 1) | HPLC ret. time (min.) | HPLC method |
|---|---|---|---|---|
| 523 | 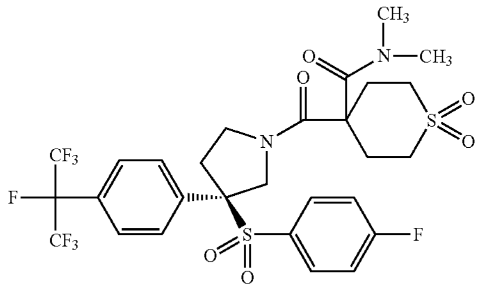 [SMILES: CN(C)C(=O)C1(C(=O)N2CC[C@](c3ccc(C(F)(C(F)(F)F)C(F)(F)F)cc3)(S(=O)(=O)c3ccc(F)cc3)C2)CCS(=O)(=O)CC1] | 705.2 | 1.99 | B |
| 524 | 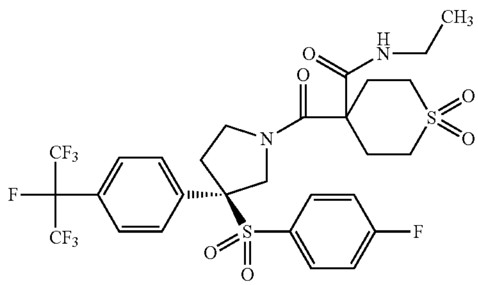 [SMILES: CCNC(=O)C1(C(=O)N2CC[C@](c3ccc(C(F)(C(F)(F)F)C(F)(F)F)cc3)(S(=O)(=O)c3ccc(F)cc3)C2)CCS(=O)(=O)CC1] | 705.2 | 1.98 | B |

Examples 525 and 526

(R)-(4-((ethylamino)methyl)-1,1-dioxidotetrahydro-2H-thiopyran-4-yl)(3-((4-fluorophenyl)sulfonyl)-3-(4-(perfluoropropan-2-yl)phenyl)pyrrolidin-1-yl)methanone and (R)-(3-((4-fluorophenyl)sulfonyl)-3-(4-(perfluoropropan-2-yl)phenyl)pyrrolidin-1-yl)(4-(hydroxymethyl)-1,1-dioxidotetrahydro-2H-thiopyran-4-yl)methanone,

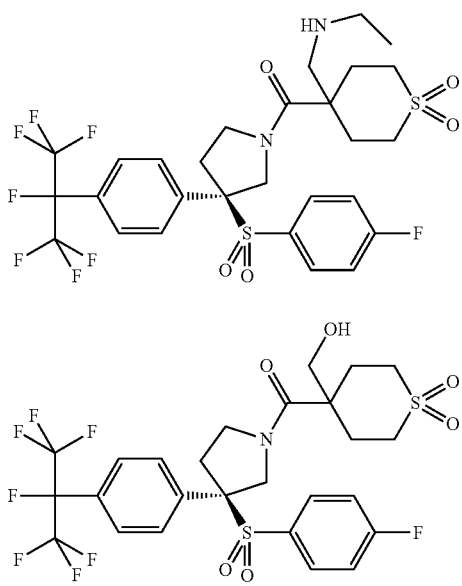

To a mixture of (R)-4-(3-((4-fluorophenyl)sulfonyl)-3-(4-(perfluoropropan-2-yl)phenyl)pyrrolidine-1-carbonyl)tetrahydro-2H-thiopyran-4-carbaldehyde 1,1-dioxide (20 mg, 0.030 mmol), ethylamine hydrochloride (12.33 mg, 0.151 mmol) and potassium acetate (29.7 mg, 0.302 mmol) in DCE (1.0 ml) was added sodium triacetoxyborohydride (12.81 mg, 0.060 mmol). The reaction was stirred at RT overnight. More Sodium triacetoxyborohydride was added till the completion of the reaction. Aq NaOH (1N, 1 mL) and water (1 mL) was added. The aqueous layer was separated and extracted with ethyl acetate (2×1 mL). The combined organic solutions were concentrated under reduced pressure. The crude material was purified via preparative LC/MS with the following conditions: Column: Waters XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 30-80% B over 19 minutes, then a 5-minute hold at 100% B; Flow: 20 mL/min. Fractions containing the desired product were combined and dried via centrifugal evaporation. (R)-(4-((ethylamino)methyl)-1,1-dioxidotetrahydro-2H-thiopyran-4-yl)(3-((4-fluorophenyl)sulfonyl)-3-(4-(perfluoropropan-2-yl)phenyl)pyrrolidin-1-yl)methanone (13 mg, 60% yield) and (R)-(3-((4-fluorophenyl)sulfonyl)-3-(4-(perfluoropropan-2-yl)phenyl)pyrrolidin-1-yl)(4-(hydroxymethyl)-1,1-dioxidotetrahydro-2H-thiopyran-4-yl)methanone (8.9 mg, 40% yield) were obtained.

Analytical data for (R)-(4-((ethylamino)methyl)-1,1-dioxidotetrahydro-2H-thiopyran-4-yl)(3-((4-fluorophenyl)sulfonyl)-3-(4-(perfluoropropan-2-yl)phenyl)pyrrolidin-1-yl)methanone: LC/MS (M+1): 691.3; LC retention time: 1.95 min (analytical HPLC Method B).

Analytical data for (R)-(3-((4-fluorophenyl)sulfonyl)-3-(4-(perfluoropropan-2-yl)phenyl)pyrrolidin-1-yl)(4-(hydroxymethyl)-1,1-dioxidotetrahydro-2H-thiopyran-4-yl)methanone: LC/MS (M+1): 664.2; LC retention time: 1.87 min (analytical HPLC Method B).

The Examples in Table 8 below were prepared in the similar manner as outlined in examples above.

TABLE 8

| Ex. No. | Structure | MS (M + 1) | HPLC ret. time (min.) | HPLC method |
|---|---|---|---|---|
| 527 | 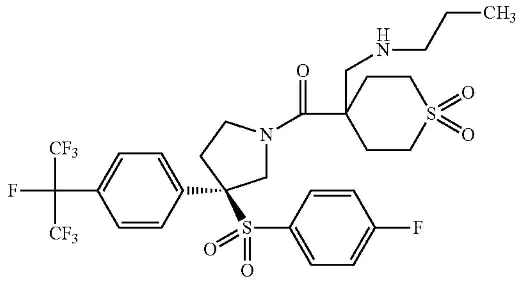 [SMILES: CCCNCC1(C(=O)N2CC[C@](c3ccc(C(F)(C(F)(F)F)C(F)(F)F)cc3)(S(=O)(=O)c3ccc(F)cc3)C2)CCS(=O)(=O)CC1] | 705.3 | 2.11 | B |
| 528 | 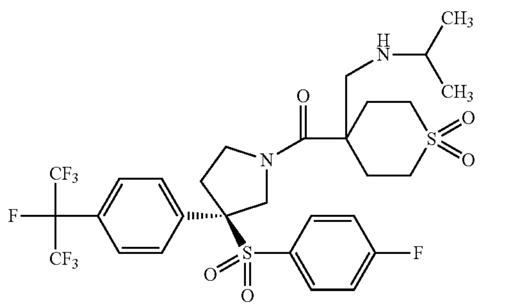 [SMILES: CC(C)NCC1(C(=O)N2CC[C@](c3ccc(C(F)(C(F)(F)F)C(F)(F)F)cc3)(S(=O)(=O)c3ccc(F)cc3)C2)CCS(=O)(=O)CC1] | 705.2 | 2.06 | B |
| 529 | 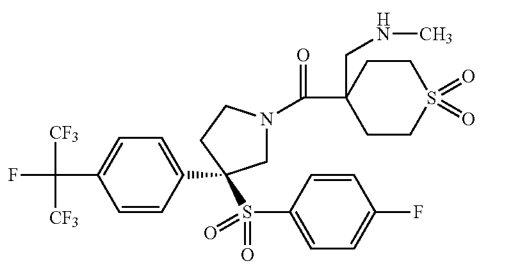 [SMILES: CNCC1(C(=O)N2CC[C@](c3ccc(C(F)(C(F)(F)F)C(F)(F)F)cc3)(S(=O)(=O)c3ccc(F)cc3)C2)CCS(=O)(=O)CC1] | 677.2 | 1.86 | B |
| 530 | 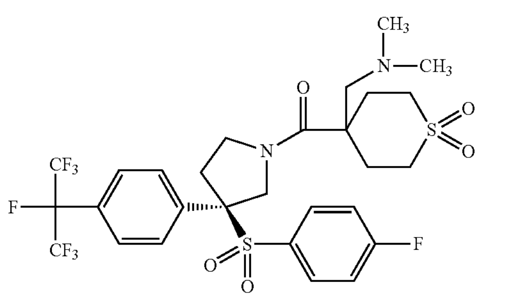 [SMILES: CN(C)CC1(C(=O)N2CC[C@](c3ccc(C(F)(C(F)(F)F)C(F)(F)F)cc3)(S(=O)(=O)c3ccc(F)cc3)C2)CCS(=O)(=O)CC1] | 691.2 | 2.11 | B |
| 531 | 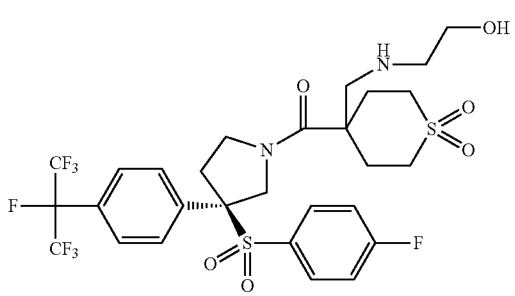 [SMILES: O=C(N1CC[C@](c2ccc(C(F)(C(F)(F)F)C(F)(F)F)cc2)(S(=O)(=O)c2ccc(F)cc2)C1)C1(CNCCO)CCS(=O)(=O)CC1] | 707.2 | 1.80 | B |

Example 532

(R)-methyl (4-(3-((4-fluorophenyl)sulfonyl)-3-(4-(perfluoropropan-2-yl)phenyl)pyrrolidine-1-carbonyl)-1,1-dioxidotetrahydro-2H-thiopyran-4-yl)carbamate

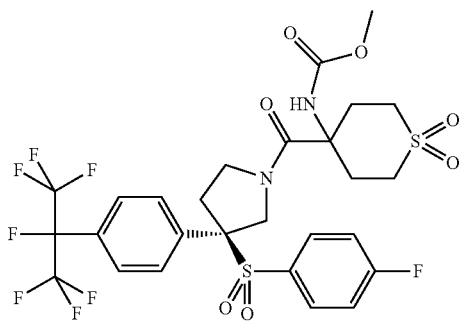 [SMILES: COC(=O)NC1(C(=O)N2CC[C@](c3ccc(C(F)(C(F)(F)F)C(F)(F)F)cc3)(S(=O)(=O)c3ccc(F)cc3)C2)CCS(=O)(=O)CC1]

Hunig's Base (9.67 µA, 0.055 mmol) was added to a stirred mixture of (R)-4-(3-((4-fluorophenyl)sulfonyl)-3-(4-(perfluoropropan-2-yl)phenyl)pyrrolidine-1-carbonyl)tetrahydro-2H-thiopyran-4-carboxylic acid 1,1-dioxide (25 mg, 0.037 mmol), diphenylphosphoryl azide (0.016 mL, 0.074 mmol), and anhydrous Toluene (0.5 mL) at RT under a nitrogen atmosphere. The mixture was stirred at 80° C. for 2 hr. MeOH (0.5 mL) was added. The resultant mixture was stirred at 65° C. overnight. The solvent was removed under reduced pressure. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 25-85% B over 20 minutes, then a 5-minute hold at 100% B; Flow: 20 mL/min. Fractions containing the desired product were combined and dried via centrifugal evaporation.

The material was further purified via preparative LC/MS with the following conditions: Column: XBridge C18, 19×200 mm, 5-µm particles; Mobile Phase A: 5:95 acetonitrile:water with 0.1% trifluoroacetic acid; Mobile Phase B: 95:5 acetonitrile: water with 0.1% trifluoroacetic acid; Gradient: 35-75% B over 20 minutes, then a 5-minute hold at 100% B; Flow: 20 mL/min. Fractions containing the desired product were combined and dried via centrifugal evaporation.

(R)-methyl (4-(3-((4-fluorophenyl)sulfonyl)-3-(4-(perfluoropropan-2-yl)phenyl)pyrrolidine-1-carbonyl)-1,1-dioxidotetrahydro-2H-thiopyran-4-yl)carbamate (1.7 mg, 5% yield) was obtained. LC/MS (M+1): 707.1; LC retention time: 1.91 min (analytical HPLC Method B).

Examples 533 and 534

(R)-(3-((4-fluorophenyl)sulfonyl)-3-(4-(perfluoropropan-2-yl)phenyl)pyrrolidin-1-yl)(4-(methylsulfonyl)cyclohexyl)methanone, diastereomers one and two

Step A: methyl 4-(methylthio)cyclohexanecarboxylate

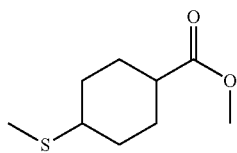

To a stirred solution of ethyl 4-hydroxycyclohexanecarboxylate (1.873 ml, 11.61 mmol) in anhydrous pyridine (8 ml) was added p-toluenesulfonyl chloride (2.214 g, 11.61 mmol) in one portion at RT under nitrogen. The mixture was stirred at RT under nitrogen for 2 h and at 40° C. for 2 h. Water (6 mL) was added to quench the reaction. The mixture was basified with $K_2CO_3$ solid (2.8 g) slowly. The aqueous layer was separated and extracted with ethyl acetate (2×2 mL). The combined organic solutions were dried over sodium sulfate, filtered, and concentrated under reduced pressure.

The residue was mixed with sodium thiomethoxide (0.977 g, 13.94 mmol), acetone (20 ml) and methanol (5 ml). The mixture was stirred at RT for 3 days. The solid was filtered and washed with diethyl ether. The filtrate was concentrated. The residue was mixed with water (3 mL) and extracted with ether (3×3 mL). The combined organic solutions were dried over sodium sulfate, filtered, and concentrated under reduced pressure. Flash chromatography purification (40 g silica gel column, gradient elution from 0 to 20% of diethyl ether in hexanes) afforded methyl 4-(methylthio)cyclohexanecarboxylate (0.23 g, 1.222 mmol, 10.52% yield) as liquids.

Step B: 4-(methylthio)cyclohexanecarboxylic acid

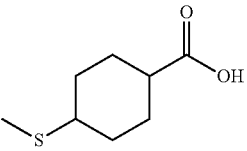

A mixture of methyl 4-(methylthio)cyclohexanecarboxylate (230 mg, 1.222 mmol), 2N aq NaOH (1.832 mL, 3.66 mmol), and THF (4 mL) was vigorously stirred at 60° C. under nitrogen for 3 h. The mixture was concentrated. The aqueous residue was washed with hexanes (3 mL) and acidified with 6N aqueous HCl to pH=1. Extraction with EtOAc (3×2 mL) gave 4-(methylthio)cyclohexanecarboxylic acid (210 mg, 1.205 mmol, 99% yield). LC/MS (M+1): 175.2.

Step C: (R)-(3-((4-fluorophenyl)sulfonyl)-3-(4-(perfluoropropan-2-yl)phenyl)pyrrolidin-1-yl)(4-(methylsulfonyl)cyclohexyl)methanone

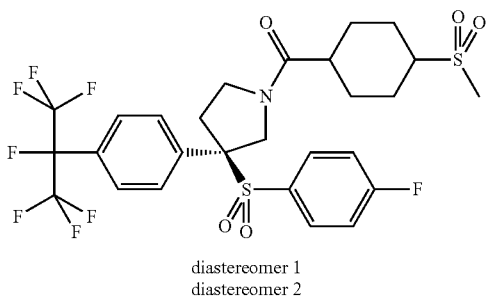 [SMILES: CS(=O)(=O)C1CCC(C(=O)N2CC[C@](c3ccc(C(F)(C(F)(F)F)C(F)(F)F)cc3)(S(=O)(=O)c3ccc(F)cc3)C2)CC1]

diastereomer 1
diastereomer 2

BOP (67.3 mg, 0.152 mmol) was added to a solution of (R)-3-((4-fluorophenyl)sulfonyl)-3-(4-(perfluoropropan-2-yl)phenyl)pyrrolidine (60 mg, 0.127 mmol) and 4-(methylthio)cyclohexanecarboxylic acid (22.09 mg, 0.127 mmol) in anhydrous $CH_2Cl_2$ (1 mL) at RT under nitrogen. Hunig's Base (0.044 mL, 0.253 mmol) was then added. The mixture was stirred at RT for 2 h. Flash chromatography purification (4 g silica gel column, gradient elution from 10 to 100% of ethyl acetate in hexanes) afforded (R)-(3-((4-fluorophenyl)sulfonyl)-3-(4-(perfluoropropan-2-yl)phenyl)pyrrolidin-1-yl)(4-(methylthio)cyclohexyl)methanone (70 mg, 0.111 mmol, 88% yield) as a white solid.

The amide was dissolved in DCM (3 mL). mCPBA (94 mg, 0.380 mmol) was added at RT. The mixture was stirred at RT for 2 h. The mixture was concentrated. Purification using reverse phase HPLC (Phen Luna 5 u 30×100 mm (Axia); gradient over 7 min from 40 to 100% of solvent B; solvent A: 10% MeOH: 90% $H_2O$: 0.1% TFA; solvent B: 90% MeOH, 10% $H_2O$, 0.1% TFA), concentration, basification with $K_2CO_3$, and EtOAc extraction gave (R)-(3-((4-fluorophenyl)sulfonyl)-3-(4-(perfluoropropan-2-yl)phenyl)pyrrolidin-1-yl)(4-(methylsulfonyl)cyclohexyl)methanone. SFC separation (Column: Lux Cell-4 (3×25 cm, 5 μm; Column Temp.: 35° C.; Flow rate: 150/min; Mobile Phase: $CO_2$/MeOH=55/45; Injection Vol. 2.5 mL (10 mg/ml); Detector Wavelength: 220 nm) gave peak 1 (13 mg, 15% yield) and peak 2 (36 mg, 42% yield) as solids.

Analytical data for peak 1: LC/MS (M+1): 662.1; LC retention time: 11.84 min (analytical HPLC Method L); $^1$H NMR (400 MHz, CHLOROFORM-d) δ ppm 7.56-7.48 (m, 2H), 7.30-7.11 (m, 4H), 7.05-6.94 (m, 2H), 4.88-4.76 (m, 1H), 4.10-4.00 (m, 1H), 3.87 (d, J=13.8 Hz, 1H), 3.79-3.67 (m, 1H), 3.48 (dd, J=14.1, 6.6 Hz, 1H), 2.85 (s, 3H), 2.81-2.46 (m, 2H), 2.36-2.03 (m, 6H), 1.81-1.19 (m, 3H)

Analytical data for peak 2: LC/MS (M+1): 662.1; LC retention time: 11.59 min (analytical HPLC Method L); $^1$H NMR (400 MHz, CHLOROFORM-d) δ ppm 7.57-7.47 (m, 2H), 7.31-7.12 (m, 4H), 7.03-6.94 (m, 2H), 4.87-4.77 (m, 1H), 4.12-4.01 (m, 1H), 3.84 (d, J=13.8 Hz, 1H), 3.76 (td, J=9.5, 2.3 Hz, 1H), 3.47 (dd, J=14.2, 7.1 Hz, 1H), 3.05-2.89 (m, 1H), 2.87 (s, 3H), 2.65 (dt, J=14.2, 9.5 Hz, 1H), 2.51-2.12 (m, 4H), 2.00-1.90 (m, 1H), 1.80-1.59 (m, 4H).

The Examples in TABLE 9 below were prepared in the same manner as outlined in examples above.

TABLE 9

| Ex. No. | Structure | MS (M + 1) | HPLC ret. time (min.) | HPLC method |
|---|---|---|---|---|
| 535 | diastereomer 1 | 634.5 | 13.52 | L |
| 536 | diastereomer 2 | 634.5 | 13.24 | L |

Example 537

(1S,4r)-4-((2S)-4-((4-fluorophenyl)sulfonyl)-2-(hydroxymethyl)-4-(4-(perfluoropropan-2-yl)phenyl)pyrrolidine-1-carbonyl)cyclohexanecarboxylic acid

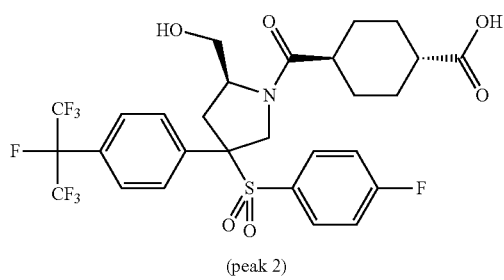 [SMILES: O=C(O)[C@H]1CC[C@H](C(=O)N2CC(c3ccc(C(F)(C(F)(F)F)C(F)(F)F)cc3)(S(=O)(=O)c3ccc(F)cc3)C[C@H]2CO)CC1]

(peak 2)

Step A: 2-(4-bromophenyl)-1,1,1,3,3,3-hexafluoropropan-2-ol

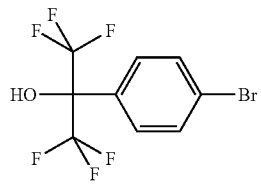 [SMILES: OC(c1ccc(Br)cc1)(C(F)(F)F)C(F)(F)F]

To a stirred solution of copper(II) bromide (1.293 g, 5.79 mmol) in acetonitrile (15 mL) was added tert-butyl nitrite (0.764 mL, 5.79 mmol) in one portion at 60° C. A solution of 2-(4-aminophenyl)-1,1,1,3,3,3-hexafluoropropan-2-ol (1 g, 3.86 mmol) in acetonitrile (3 mL) was then added dropwise at 60° C. After stirring for 15 min at 60° C., the mixture was concentrated. The residue was diluted with water (20 mL) and extracted with EtOAc (10 mL, 2×4 mL). The combined organic solutions were dried over anhydrous sodium sulfate and concentrated. Flash chromatography purification using (24 g silica gel column, gradient elution from 0 to 30% of ethyl acetate in hexanes) afforded 2-(4-bromophenyl)-1,1,1,3,3,3-hexafluoropropan-2-ol (1.3 g, 4.02 mmol, 104% yield) as a liquid.

Step B: 1-bromo-4-(perfluoropropan-2-yl)benzene

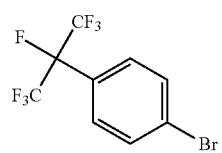

DAST (0.798 mL, 6.04 mmol) was added to a stirred ClCH₂CH₂Cl (4 mL) solution of 2-(4-bromophenyl)-1,1,1,3,3,3-hexafluoropropan-2-ol (1.3 g, 4.02 mmol) at RT under nitrogen. The solution was stirred at 50° C. in a safety sealed vials for 3 h. MeOH (0.081 mL, 2.012 mmol) was added dropwise at 0° C. The mixture was stirred at RT for 5 min before water (5 mL) was added at 0° C. with vigorously stirring. The mixture was stirred at RT for 15 min. The aqueous layer was separated and extracted with DCM (1 mL) and then hexanes (2×3 mL). The combined organic solutions were dried over sodium sulfate. Flash chromatography purification (24 g silica gel column, gradient elution from 0 to 20% of ethyl acetate in hexanes) afforded 1-bromo-4-(perfluoropropan-2-yl)benzene (0.7 g, 53.5% yield) as a liquid. LC retention time: 1.47 min (analytical HPLC Method K); ¹H NMR (400 MHz, CHLOROFORM-d) δ ppm 7.66 (d, J=8.4 Hz, 2H), 7.49 (d, J=8.4 Hz, 2H).

Step C: (2S)-di-tert-butyl 4-hydroxy-4-(4-(perfluoropropan-2-yl)phenyl)pyrrolidine-1,2-dicarboxylate

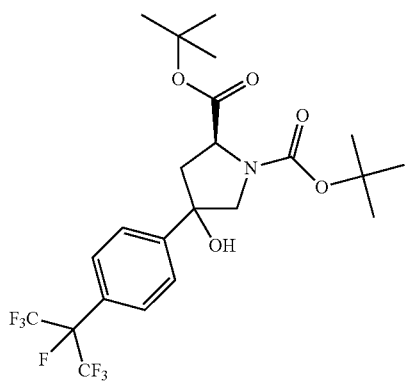 [SMILES: CC(C)(C)OC(=O)[C@@H]1CC(O)(c2ccc(C(F)(C(F)(F)F)C(F)(F)F)cc2)CN1C(=O)OC(C)(C)C]

To a stirred solution of 1-bromo-4-(perfluoropropan-2-yl)benzene (0.7 g, 2.154 mmol) in anhydrous tetrahydrofuran (4 mL) was added 1.6M hexanes solution of BuLi (1.346 mL, 2.154 mmol) dropwise at −78° C. under nitrogen. The mixture was stirred at −78° C. for 1 hour before magnesium bromide (0.397 g, 2.154 mmol) was added. The temperature was raised to RT and stirred at RT for 1 min. n-boc-4-oxo-1-proline tert-butyl ester (0.615 g, 2.154 mmol) was added at −78° C. and the mixture was stirred at −78° C. for 30 min. The temperature was raised to RT over 30 min. The mixture was stirred at RT for 1 h before a saturated aqueous NH₄Cl solution (3 mL) was added at 0° C. to quench the reaction. Water (1 mL) and hexanes (4 mL) were added. The mixture was filtered and the filtrate was separated. The aqueous layer was extracted with EtOAc (3×3 mL). The combined organic solutions were dried over sodium sulfate, filtered, and concentrated under reduced pressure. Flash chromatography purification (24 g silica gel column, gradient elution from 0 to 50% of ethyl acetate in hexanes) afforded (2S)-di-tert-butyl 4-hydroxy-4-(4-(perfluoropropan-2-yl)phenyl)pyrrolidine-1,2-dicarboxylate (0.38 g, 33.2% yield) as foam solid. LC/MS (M+1): 532.5; LC retention time: 1.55 min (analytical HPLC Method K).

Step D: (2S)-4-((4-fluorophenyl)thio)-4-(4-(perfluoropropan-2-yl)phenyl)pyrrolidine-2-carboxylic acid

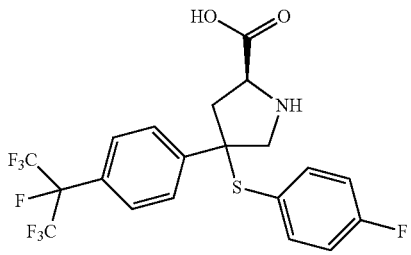 [SMILES: O=C(O)[C@@H]1CC(Sc2ccc(F)cc2)(c2ccc(C(F)(C(F)(F)F)C(F)(F)F)cc2)CN1]

To a stirred mixture of (2S)-di-tert-butyl 4-hydroxy-4-(4-(perfluoropropan-2-yl)phenyl)pyrrolidine-1,2-dicarboxylate (230 mg, 0.433 mmol) and 4-fluorobenzenethiol (1 mL, 9.39 mmol) was added methanesulfonic acid (0.6 mL, 9.24 mmol) dropwise at 0° C. The mixture was stirred at 60° C. for 5 hr and RT overnight. A mixture of EtOAc and hexanes (1:2; 5 mL) were added. Aqueous KOAc was added to neutralized the mixture. The solid formed was filtered, washed with water (3×0.5 mL) and a mixture of EtOAc and hexanes (1:1; 3×0.5 mL), and dried to give (2S)-4-((4-fluorophenyl)thio)-4-(4-(perfluoropropan-2-yl)phenyl)pyrrolidine-2-carboxylic acid (140 mg, 66.6% yield) as a white solid. LC/MS (M+1): 486.4; LC retention time: 1.05 min (analytical HPLC Method K).

Step E: ((2S)-4-((4-fluorophenyl)thio)-4-(4-(perfluoropropan-2-yl)phenyl)pyrrolidin-2-yl)methanol

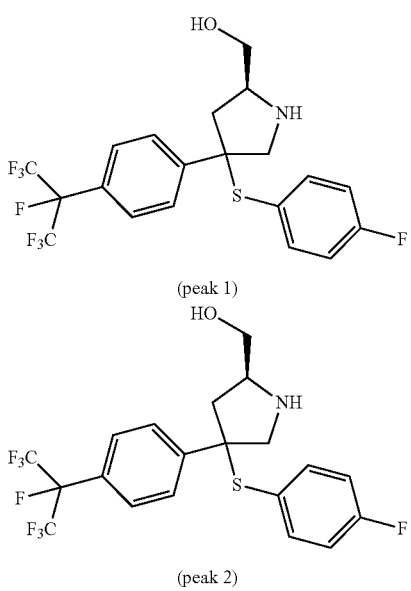

1M THF solution of borane-tetrahydrofuran complex (1.2 mL, 1.200 mmol) was added dropwise to a mixture of (2S)-4-((4-fluorophenyl)thio)-4-(4-(perfluoropropan-2-yl)phenyl)pyrrolidine-2-carboxylic acid (140 mg, 0.288 mmol) and anhydrous tetrahydrofuran (5 mL) at 0° C. under nitrogen. The solution was stirred at RT for 1 h and at 65° C. overnight. After cooling, 3 ml of MeOH and 0.15 ml of $H_2SO_4$ were added. After 30 min at RT and 1 h at reflux, 2M aqueous NaOH was added at RT to basify the mixture. The mixture was stirred at RT for 1 hr. The mixture was concentrated to remove organic solvents. The aqueous residue was extracted with EtOAc (3×4 mL). The combined organic solutions were dried over sodium sulfate, filtered, and concentrated under reduced pressure. Purification using reverse phase HPLC (Waters Xbridge C18 19×100 mm; gradient over 9 min from 30 to 100% of solvent B; solvent A: 10% MeOH: 90% $H_2O$: 0.1% TFA; solvent B: 90% MeOH, 10% $H_2O$, 0.1% TFA), concentration, basification with 2M aqueous NaOH, and extraction with EtOAc gave ((2S)-4-((4-fluorophenyl)thio)-4-(4-(perfluoropropan-2-yl)phenyl)pyrrolidin-2-yl)methanol (91 mg, 66.9% yield) as a white solid. LC/MS (M+1): 472.6; LC retention time: 1.04 min (analytical HPLC Method K); $^1$H NMR (500 MHz, DMSO-$d_6$) γ 7.50 (t, J=7.7 Hz, 2H), 7.30-7.15 (m, 2H), 7.05-6.91 (m, 4H), 3.75-3.48 (m, 2H), 3.46-3.13 (m, 3H), 2.53-2.40 (m, 1H), 2.18-1.94 (m, 1H).

Chiral SFC separation (Column: Whelko(rr) 3×25 cm, 10 um; Column Temp.: 30° C.; Flow rate: 250/min; Mobile Phase: $CO_2$/MeOH w/0.1% $NH_4OH$=90/10; Injection Vol.: 0.4 mL (10 mg/mL); Detector Wavelength: 220 nm) gave peak 1 (36 mg) and peak 2 (26 mg) as solids.

Step F: (1S,4r)-4-((2S)-4-((4-fluorophenyl)thio)-2-(hydroxymethyl)-4-(4-(perfluoropropan-2-yl)phenyl)pyrrolidine-1-carbonyl)cyclohexanecarboxylic acid

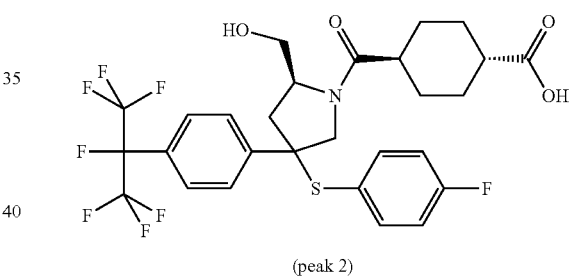

(peak 2)

To a stirred solution of trans-4-(methoxycarbonyl)cyclohexanecarboxylic acid (14.81 mg, 0.080 mmol) and Hunig's Base (27.8 μl, 0.159 mmol) in anhydrous $CH_2Cl_2$ (1 mL) was added BOP (35.2 mg, 0.080 mmol) at RT under nitrogen. The mixture as stirred at room temperature for 1 h before (2S)-4-((4-fluorophenyl)thio)-4-(4-(perfluoropropan-2-yl)phenyl)pyrrolidin-2-yl)methanol (peak 2, 25 mg, 0.053 mmol) was added. The mixture was stirred at RT for 1 h. Saturated aqueous sodium bicarbonate solution (2 mL) was added to quench the reaction. The aqueous layer was separated and extracted with ethyl acetate (3×1 mL). The combined organic solutions were dried over sodium sulfate, filtered, and concentrated under reduced pressure.

The residue was mixed with lithium hydroxide monohydrate (8.90 mg, 0.212 mmol), water (0.2 mL), and THF (1 mL). The mixture was stirred at RT for 2 h and 60° C. for 1.5 h. The reaction was cooled to RT and quenched with AcOH (40 μA, 0.699 mmol). the mixture was concentrated. One third of the material was purified and characterized. LC/MS (M+1): 626.2; LC retention time: 1.78 min (analytical HPLC Method B).

361

Step G: (1S,4r)-4-((2S)-4-((4-fluorophenyl)sulfonyl)-2-(hydroxymethyl)-4-(4-perfluoropropan-2-yl)phenyl)pyrrolidin-1-carbonyl)cyclohexanecarboxylic acid

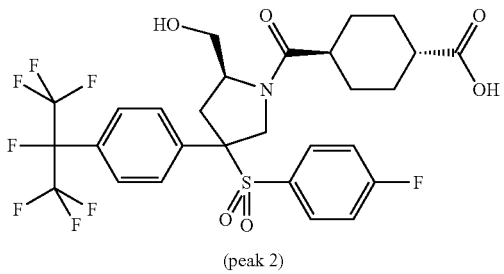 [SMILES: O=C(O)[C@H]1CC[C@H](C(=O)N2CC(c3ccc(C(F)(C(F)(F)F)C(F)(F)F)cc3)(S(=O)(=O)c3ccc(F)cc3)C[C@H]2CO)CC1]

(peak 2)

(1S,4r)-4-((2S)-4-((4-fluorophenyl)thio)-2-(hydroxymethyl)-4-(4-(perfluoropropan-2-yl)phenyl)pyrrolidine-1-carbonyl)cyclohexanecarboxylic acid (21.89 mg, 0.035 mmol, from peak 2) was dissolved in dichloromethane (1 mL). m-CPBA (34.5 mg, 0.140 mmol, 70% pure) was added at RT. The mixture was stirred at RT for 1 h before DMSO (20 μl, 0.282 mmol) was added to quench the reaction. The mixture was concentrated. The crude material was purified via preparative LC/MS with the following conditions: Column: Waters XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 minutes, then a 5-minute hold at 100% B; Flow: 20 mL/min. Fractions containing the desired product were combined and dried via centrifugal evaporation. (1S,4r)-4-((2S)-4-((4-fluorophenyl)sulfonyl)-2-(hydroxymethyl)-4-(4-(perfluoropropan-2-yl)phenyl)pyrrolidine-1-carbonyl)cyclohexanecarboxylic acid (17.0 mg, 70% yield) was obtained. LC/MS (M+1): 658.3; LC retention time: 1.52 min (analytical HPLC Method B).

Example 538

(1S,4r)-4-((2S)-4-((4-fluorophenyl)sulfonyl)-2-(isopropylcarbamoyl)-4-(4-perfluoropropan-2-yl)phenyl)pyrrolidine-1-carbonyl)cyclohexanecarboxylic acid

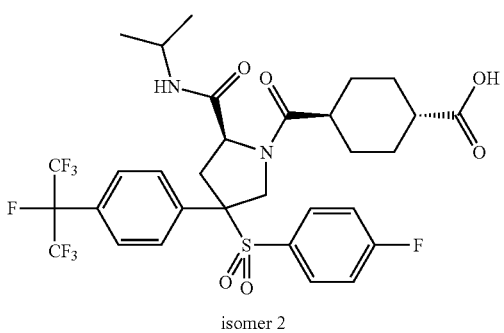 [SMILES: CC(C)NC(=O)[C@@H]1CC(c2ccc(C(F)(C(F)(F)F)C(F)(F)F)cc2)(S(=O)(=O)c2ccc(F)cc2)CN1C(=O)[C@H]1CC[C@H](C(=O)O)CC1]

isomer 2

362

Step A: (2S)-4-((4-fluorophenyl)thio)-1-(trans-4-(methoxycarbonyl)cyclohexanecarbonyl)-4-(4-(perfluoropropan-2-yl)phenyl)pyrrolidine-2-carboxylic acid

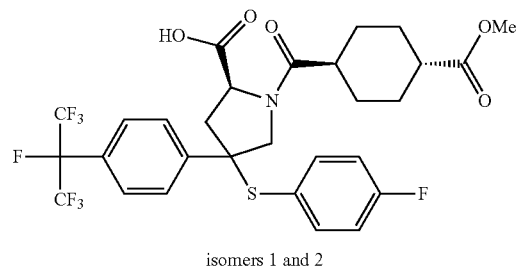 [SMILES: COC(=O)[C@H]1CC[C@H](C(=O)N2CC(Sc3ccc(F)cc3)(c3ccc(C(F)(C(F)(F)F)C(F)(F)F)cc3)C[C@H]2C(=O)O)CC1]

isomers 1 and 2

BOP (109 mg, 0.247 mmol) was added to a solution of trans-1,4-cyclohexanedicarboxylic acid monomethyl ester (46.0 mg, 0.247 mmol) and Hunig's Base (0.06 mL) in anhydrous DMF (0.5 mL) at RT under nitrogen. The mixture was stirred at RT for 1.5 h. The obtained solution was added to a stirred mixture of (2S)-4-((4-fluorophenyl)thio)-4-(4-(perfluoropropan-2-yl)phenyl)pyrrolidine-2-carboxylic acid (60 mg, 0.124 mmol), Hunig's Base (0.06 mL) and anhydrous DMF (0.5 mL). The mixture was stirred at RT for 2 hr. Purification using reverse phase HPLC (Phen Luna 5 u 30×100 mm (Axia); gradient over 6 min from 50 to 100% of solvent B; solvent A: 10% MeOH: 90% H₂O: 0.1% TFA; solvent B: 90% MeOH, 10% H₂O, 0.1% TFA) and concentration gave 2 isomers of (2S)-4-((4-fluorophenyl)thio)-1-(trans-4-(methoxycarbonyl)cyclohexanecarbonyl)-4-(4-(perfluoropropan-2-yl)phenyl)pyrrolidine-2-carboxylic acids. Isomer 1 (3.5 mg, 5.36 μmol, 4.33% yield): LC/MS (M+1): 654.5; LC retention time: 1.41 min (analytical HPLC Method K). Isomer 2 (2.3 mg, 3.52 μmol, 2.85% yield): LC/MS (M+1): 654.5; LC retention time: 1.38 min (analytical HPLC Method K).

Step B: (1S,4r)-4-((2S)-4-((4-fluorophenyl)sulfonyl)-2-(isopropylcarbamoyl)-4-(4-perfluoropropan-2-yl)phenyl)pyrrolidine-1-carbonyl)cyclohexanecarboxylic acid

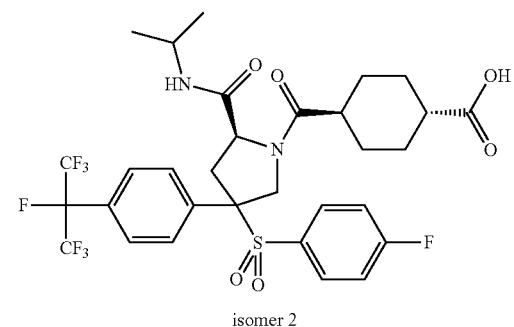 [SMILES: CC(C)NC(=O)[C@@H]1CC(c2ccc(C(F)(C(F)(F)F)C(F)(F)F)cc2)(S(=O)(=O)c2ccc(F)cc2)CN1C(=O)[C@H]1CC[C@H](C(=O)O)CC1]

isomer 2

BOP (3.11 mg, 7.04 μmol) was added to a solution of (2S,4S)-4-((4-fluorophenyl)thio)-1-((1r,4S)-4-(methoxycarbonyl)cyclohexanecarbonyl)-4-(4-(perfluoropropan-2-yl)phenyl)pyrrolidine-2-carboxylic acid (2.3 mg, 3.52 μmol, isomer 2) and isopropylamine (2 μl, 0.023 mmol) in anhydrous CH$_2$Cl$_2$ (2 mL) at RT under nitrogen. The mixture was stirred at RT for 1 hr and then concentrated. THF (1 mL) and 1N aqueous NaOH (200 µl, 0.200 mmol) were added and the mixture was stirred at 50° C. for 1.5 h. The mixture was cooled to RT before AcOH (50 µl, 0.873 mmol) was added. m-CPBA (1.735 mg, 7.04 µmol) was added at RT. After stirred at RT for 1 h, The mixture was concentrated. Purification using reverse phase HPLC (Waters Xbridge C18 19×100 mm; gradient over 7 min from 40 to 100% of solvent B; solvent A: 10% MeOH: 90% H$_2$O: 0.1% TFA; solvent B: 90% MeOH, 10% H$_2$O, 0.1% TFA), concentration, and lyophilization gave (1S,4r)-4-((2S)-4-((4-fluorophenyl)sulfonyl)-2-(isopropylcarbamoyl)-4-(4-(perfluoropropan-2-yl)phenyl)pyrrolidine-1-carbonyl)cyclohexanecarboxylic acid (0.56 mg, 0.747 µmol, 21% yield) as a solid. LC/MS (M+1): 713.6; LC retention time: 12.12 min (analytical HPLC Method J).

Example 539

(1R,4r)-4-((R)-3-(4-bromo-3-fluorophenyl)-3-((4-fluorophenyl)sulfonyl)pyrrolidine-1-carbonyl)cyclohexanecarboxylic acid

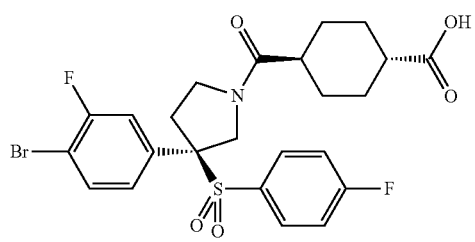 [SMILES: O=C(O)[C@H]1CC[C@H](C(=O)N2CC[C@](c3ccc(Br)c(F)c3)(S(=O)(=O)c3ccc(F)cc3)C2)CC1]

Step A: 1-bromo-4-(bromomethyl)-2-fluorobenzene

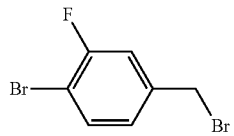

A suspension of 1-bromo-2-fluoro-4-methylbenzene (20.00 g, 106 mmol), NBS (18.83 g, 106 mmol) and AIBN (0.087 g, 0.529 mmol) in CCl$_4$ (100 mL) was stirred under nitrogen for 15 h at reflux. The mixture was cooled to rt and filtered. The filter cake was rinsed with ether. The filtrate was concentrated. The residue was treated with a 1:1 mixture of Et$_2$O-hexanes (400 mL), stirred for 10 min and filtered. The filtrate was concentrated and again treated with a 1:1 mixture of Et$_2$O-hexanes (100 mL), stirred for 10 min and filtered. The filtrate was concentrated to give the product mixture as pale yellow liquid (28.21 g). 1H NMR indicated a mixture of 1-bromo-4-(bromomethyl)-2-fluorobenzene, a,a-dibromo product and unreacted starting material in a molar ratio of 67%:16%:17% (by integration of CH$_2$Br at 4.41 ppm, CHBr$_2$ at 6.56 ppm and CH$_3$ at 2.32 ppm). The weight percentage of desired product is 67%.

Step B: 1-bromo-2-fluoro-4-(((4-fluorophenyl)sulfonyl)methyl)benzene

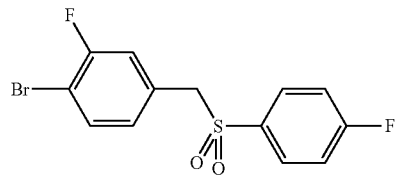 [SMILES: O=S(=O)(Cc1ccc(Br)c(F)c1)c1ccc(F)cc1]

Sodium 4-fluorobenzenesulfinate (15.42 g, 85 mmol) was added in several portions to a stirred solution of impure 1-bromo-4-(bromomethyl)-2-fluorobenzene (28.21 g, 70.5 mmol, ~67% pure) in DMF (80 mL). The mixture warmed up slightly during the addition. The mixture was stirred at ambient temperature for 1 h and at 70° C. for 2 h. After cooling to rt, the mixture was diluted with EtOAc (500 mL), washed with water (2×250 mL), brine (50 mL), dried (MgSO4) and concentrated. The white residue was treated with CH$_2$Cl$_2$ (20 mL) and hexanes (200 mL), sonicated to break up solid chunks, stirred for 30 min, and filtered. The filter cake was washed with hexanes (200 mL) and dried under vacuum to give the desired product as white solid (22.95 g). 1H NMR (400 MHz, CHLOROFORM-d) δ ppm 7.73-7.64 (m, 2H), 7.47 (dd, J=8.1, 7.0 Hz, 1H), 7.22-7.14 (m, 2H), 6.93 (dd, J=8.9, 2.0 Hz, 1H), 6.76 (dd, J=8.2, 1.6 Hz, 1H), 4.25 (s, 2H).

Step C: 1-bromo-2-fluoro-4-(1-((4-fluorophenyl)sulfonyl)vinyl)benzene

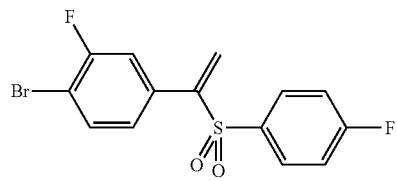 [SMILES: C=C(c1ccc(Br)c(F)c1)S(=O)(=O)c1ccc(F)cc1]

Ac$_2$O (37.4 mL, 396 mmol) was added dropwise to a stirred solution of 1-bromo-2-fluoro-4-((4-fluorophenyl)sulfonyl)methyl)benzene (22.94 g, 66.1 mmol) and N,N,N',N'-tetramethyldiaminomethane (40.5 g, 396 mmol) in DMF (120 mL) under nitrogen in a rt water bath. The mixture warmed up slightly. The resulting solution was stirred at 60° C. under nitrogen for 13 h. Additional Ac$_2$O (12.5 mL, 2 eq) was added to facilitate the NMe$_2$ elimination. After stirring for 1 h at 60° C., additional Ac$_2$O (6.25 mL) was added. After another 4 h at 70° C., the mixture was diluted with EtOAc (500 mL), washed with sat NaHCO$_3$ (3×200 mL), then 2 N K$_3$PO$_4$ (2×100 mL), dried (MgSO4) and concentrated. The crude material was purified with silica gel chromatography, eluting with 5-80% EtOAc in hexanes, gave impure product. The material was re-purified with silica gel chromatography, eluting with 5-25% EtOAc in hexanes, gave the desired product as viscous yellow liquid (10.50 g). 1H NMR (400 MHz, CHLOROFORM-d) δ ppm 7.76-7.65 (m, 2H), 7.48 (dd, J=8.3, 7.1 Hz, 1H), 7.22-7.17 (m, 1H), 7.16-7.08 (m, 2H), 7.02 (ddd, J=8.3, 2.0, 0.7 Hz, 1H), 6.67 (s, 1H), 6.01 (s, 1H); LC retention time: 4.038 min (analytical HPLC Method A).

Step D: (R)-1-benzyl-3-(4-bromo-3-fluorophenyl)-3-((4-fluorophenyl)sulfonyl)pyrrolidine

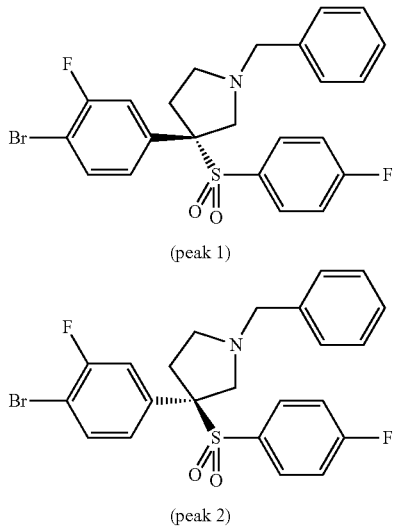

(peak 1)

(peak 2)

A solution of TFA (1.255 mL, 16.29 mmol) in CH₂Cl₂ (20 mL) was added dropwise to a stirred solution of 1-bromo-2-fluoro-4-(1-((4-fluorophenyl)sulfonyl)vinyl)benzene (14.63 g, 40.7 mmol) and N-benzyl-1-methoxy-N-((trimethylsilyl)methyl)methanamine (19.34 g, 81 mmol) in CH₂Cl₂ (100 mL) at 0° C. The resulting solution was stirred at 0° C. for 30 min and at ambient temperature for 2 h. The mixture was washed with sat NaHCO₃ (2×50 mL), dried (MgSO₄), and concentrated. Silica gel chromatography, eluting with 5-25% EtOAc in hexanes, gave partial separation. The mixture fractions were combined and re-purified using similar conditions. All pure fractions were combined to give the desired product as tan viscous oil (18.18 g, impure). The two enantiomers were separated chiral SFC LUX Cell-4 column to give (S)-1-benzyl-3-(4-bromo-3-fluorophenyl)-3-((4-fluorophenyl)sulfonyl)pyrrolidine (1st peak off column, 8.120 g) and (R)-1-benzyl-3-(4-bromo-3-fluorophenyl)-3-((4-fluorophenyl)sulfonyl)pyrrolidine (2nd peak off column, 8.110 g), both as tan solids. Analytical data for (R)-1-benzyl-3-(4-bromo-3-fluorophenyl)-3-((4-fluorophenyl)sulfonyl) pyrrolidine: LC/MS (M+1): 494.0; LC retention time: 3.401 min (analytical HPLC Method A); 1H NMR (500 MHz, CHLOROFORM-d) δ ppm 7.48-7.40 (m, 3H), 7.35-7.24 (m, 3H), 7.23-7.18 (m, 2H), 7.10-7.03 (m, 2H), 6.96 (dd, J=9.9, 2.3 Hz, 1H), 6.84 (dd, J=8.5, 1.8 Hz, 1H), 3.70-3.57 (m, 3H), 3.13 (d, J=11.0 Hz, 1H), 2.97 (ddd, J=13.6, 7.6, 5.0 Hz, 1H), 2.91-2.83 (m, 1H), 2.72 (td, J=8.3, 4.9 Hz, 1H), 2.44 (ddd, J=13.8, 7.5, 6.7 Hz, 1H).

Step E: (R)-3-(4-bromo-3-fluorophenyl)-3-((4-fluorophenyl)sulfonyl)pyrrolidine

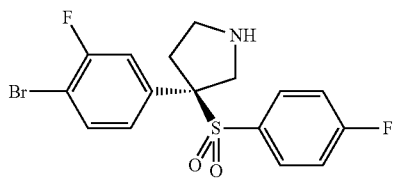 [SMILES: O=S(=O)(c1ccc(F)cc1)[C@@]1(c2ccc(Br)c(F)c2)CCNC1]

1-chloroethyl chloroformate (495 mg, 3.46 mmol) was added to a solution of (R)-1-benzyl-3-(4-bromo-3-fluorophenyl)-3-((4-fluorophenyl)sulfonyl)pyrrolidine (426 mg, 0.865 mmol) in 1,2-dichloroethane (6 mL). The reaction vial was sealed and stirred at 90° C. for 18 h. The mixture was concentrated, treated with MeOH (10 mL) and stirred at reflux for 1 h. The mixture was concentrated. Silica gel chromatography, eluting with 20-80% solvent B gradient (solvent A: CH₂Cl₂, solvent B: MeOH—CH₂Cl₂—NH4OH ratio of 10:90:1) to give the desired product as white solid (303 mg, 87% yield). LC/MS (M+1): 403.9; LC retention time: 3.023 min (analytical HPLC Method A); 1H NMR (500 MHz, METHANOL-d4) δ ppm 7.51 (dd, J=8.4, 7.5 Hz, 1H), 7.47-7.39 (m, 2H), 7.28-7.17 (m, 2H), 7.03 (dd, J=10.2, 2.3 Hz, 1H), 6.85 (dt, J=8.5, 1.1 Hz, 1H), 4.05 (d, J=13.3 Hz, 1H), 3.38-3.25 (m, 2H), 3.06-2.94 (m, 2H), 2.50-2.37 (m, 1H).

Step F: (1R,4r)-methyl 4-((R)-3-(4-bromo-3-fluorophenyl)-3-((4-fluorophenyl)sulfonyl)pyrrolidine-1-carbonyl)cyclohexanecarboxylate

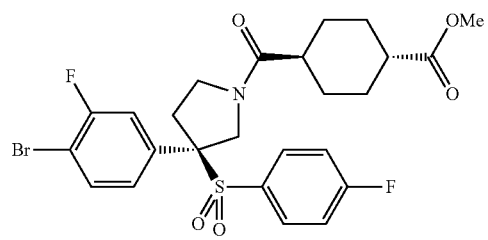 [SMILES: COC(=O)[C@H]1CC[C@H](C(=O)N2CC[C@](c3ccc(Br)c(F)c3)(S(=O)(=O)c3ccc(F)cc3)C2)CC1]

HATU (336 mg, 0.883 mmol) and DIEA (0.386 mL, 2.208 mmol) were added to a stirred mixture of (R)-3-(4-bromo-3-fluorophenyl)-3-((4-fluorophenyl)sulfonyl)pyrrolidine (296 mg, 0.736 mmol) and trans-1,4-cyclohexanedicarboxylic acid monomethyl ester (164 mg, 0.883 mmol) in DMF (5 mL). After stirring for 1 h at rt, the mixture was diluted with EtOAc (75 mL), washed with water (2×15 mL), brine (10 mL), dried (MgSO₄) and concentrated. Silica gel chromatography, loading with CH₂Cl₂-toluene and eluting with 20-50% EtOAc in hexanes (product insoluble) then 0-10% MeOH in CH₂Cl₂, gave the desired product as white solid (421 mg). LC/MS (M+1): 572.0; LC retention time: 4.021 min (analytical HPLC Method A).

Step G: (1R,4r)-4-((R)-3-(4-bromo-3-fluorophenyl)-3-((4-fluorophenyl)sulfonyl)pyrrolidine-1-carbonyl)cyclohexanecarboxylic acid

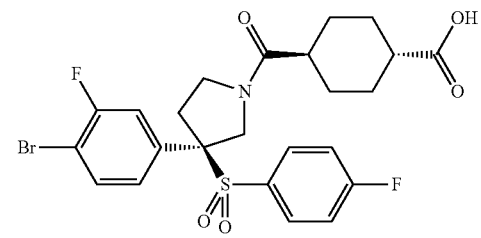 [SMILES: O=C(O)[C@H]1CC[C@H](C(=O)N2CC[C@](c3ccc(Br)c(F)c3)(S(=O)(=O)c3ccc(F)cc3)C2)CC1]

A mixture of (1R,4r)-methyl 4-((R)-3-(4-bromo-3-fluorophenyl)-3-((4-fluorophenyl)sulfonyl)pyrrolidine-1-carbonyl)cyclohexanecarboxylate (15.8 mg) in 1 N NaOH (0.5 mL), MeOH (0.5 mL) and THF (1 mL) was stirred at rt for 2 h. The mixture was adjusted to pH 3-4 with 1 N HCl. The organic solvents were evaporated in vacuo. The residue was diluted with water (5 mL), stirred for 10 min and filtered. The filter cake was washed with water (10 mL) and dried under vacuum to give the desired product as white solid (12.9 mg, 84% yield). LC/MS (M+1): 556.0, 558.0; LC retention time: 3.828 min (analytical HPLC Method A).

Example 540

(1R,4r)-4-((R)-3-(3-fluoro-4-methylphenyl)-3-((4-fluorophenyl)sulfonyl)pyrrolidine-1-carbonyl)cyclohexanecarboxylic acid

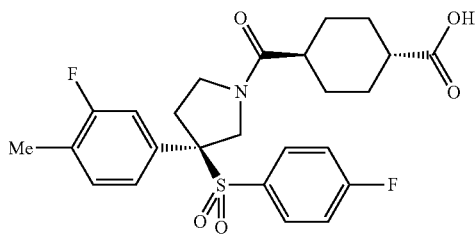 [SMILES: Cc1ccc([C@]2(S(=O)(=O)c3ccc(F)cc3)CCN(C(=O)[C@H]3CC[C@H](C(=O)O)CC3)C2)cc1F]

A mixture of (1R,4r)-methyl 4-((R)-3-(4-bromo-3-fluorophenyl)-3-((4-fluorophenyl)sulfonyl)pyrrolidine-1-carbonyl)cyclohexanecarboxylate (18 mg, 0.032 mmol), trimethylboroxine (7.92 mg, 0.063 mmol) and PdCl$_2$(dppf)-CH$_2$Cl$_2$ Adduct (5.15 mg, 6.31 µmol) was pumped under vacuum and backfilled with nitrogen three times. Potassium phosphate tribasic (2 M) (0.047 mL, 0.095 mmol) and 1,4-dioxane (1 mL) were quickly added. The mixture was immediately pumped under vacuum and backfilled with nitrogen three times, sealed and stirred at 100° C. for 15 h.

The mixture was cooled to rt. 1 N NaOH (1 mL) and MeOH (1 mL) were added. After stirring for 1 h, the mixture was acidified to pH 2-3 with 1 N HCl. The organic solvents were evaporated in vacuo. The residue was diluted with EtOAc (15 mL), washed with water (2×3 mL), brine (3 mL), dried (MgSO$_4$) and concentrated. The crude material was purified via preparative LC/MS with the following conditions: Column: Waters XBridge C18, 19×200 mm, 5-µm particles; Mobile Phase A: 5:95 acetonitrile: water with 10-mM ammonium acetate; Mobile Phase B: 95:5 acetonitrile:water with 10-mM ammonium acetate; Gradient: 10-50% B over 25 minutes, then a 5-minute hold at 50% B; Flow: 20 mL/min. Fractions containing the desired product were combined and dried via centrifugal evaporation to give the desired product (10.2 mg, 63% yield). LC/MS (M+1): 492.2; LC retention time: 1.43 min (analytical HPLC Method B).

Example 541

(R)-2-(4-(1-benzyl-3-((4-fluorophenyl)sulfonyl)pyrrolidin-3-yl)-2-fluorophenyl)-1,1,1,3,3,3-hexafluoropropan-2-ol

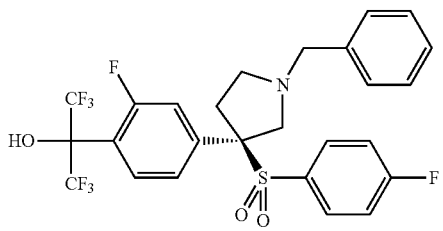 [SMILES: O=S(=O)(c1ccc(F)cc1)[C@@]1(c2ccc(C(O)(C(F)(F)F)C(F)(F)F)c(F)c2)CCN(Cc2ccccc2)C1]

A 1.6 M hexane solution of N-butyllithium (1.655 mL, 2.65 mmol) was added dropwise over 6 min to a stirred solution of (R)-1-benzyl-3-(4-bromo-3-fluorophenyl)-3-((4-fluorophenyl)sulfonyl)pyrrolidine (1.630 g, 3.31 mmol) in THF (60 mL) under nitrogen at −78° C. The resulting yellow solution was stirred for 15 min at −78° C. After removing the nitrogen inlet, gaseous CF$_3$C(O)CF$_3$ (~1.53 g) was slowly added via a needle by placing the tip of the needle just above the cold solution to allow CF$_3$C(O)CF$_3$ to condense. The weight of CF$_3$C(O)CF$_3$ was estimated by weighing the CF$_3$C(O)CF$_3$ cylinder before and after the addition. The resulting colorless solution was stirred under nitrogen for 30 min at −78° C. and at ambient temperature for 30 min. The mixture was quenched with sat NH$_4$Cl (50 mL). After evaporation of organic solvent under reduced pressure, the aqueous residue was extracted with EtOAc (3×50 mL). The combine extracts were washed with brine (10 mL), dried (MgSO$_4$) and concentrated. Silica gel chromatography, eluting with 10-40% EtOAc in hexanes, gave the desired product (862 mg, 45% yield). LC/MS (M+1): 580.0; LC retention time: 3.618 min (analytical HPLC Method A); 1H NMR (500 MHz, CHLOROFORM-d) δ ppm 7.63 (t, J=8.4 Hz, 1H), 7.38-7.30 (m, 4H), 7.30-7.22 (m, 3H), 7.05 (dd, J=8.5, 2.0 Hz, 1H), 7.02-6.93 (m, 3H), 4.31 (br. s., 1H), 3.75-3.59 (m, 3H), 3.22 (d, J=11.0 Hz, 1H), 3.04-2.96 (m, 1H), 2.95-2.87 (m, 1H), 2.79 (td, J=8.2, 4.4 Hz, 1H), 2.54-2.42 (m, 1H).

Example 542

(R)-tert-butyl 3-(3-fluoro-4-(1,1,1,3,3,3-hexafluoro-2-hydroxypropan-2-yl)phenyl)-3-((4-fluorophenyl)sulfonyl)pyrrolidine-1-carboxylate Step A: (R)-1,1,1,3,3,3-hexafluoro-2-(2-fluoro-4-(3-((4-fluorophenyl)sulfonyl)pyrrolidin-3-yl)phenyl)propan-2-ol

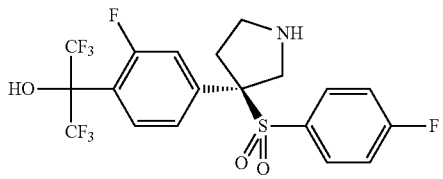 [SMILES: O=S(=O)(c1ccc(F)cc1)[C@@]1(c2ccc(C(O)(C(F)(F)F)C(F)(F)F)c(F)c2)CCNC1]

A mixture of (R)-2-(4-(1-benzyl-3-((4-fluorophenyl)sulfonyl)pyrrolidin-3-yl)-2-fluorophenyl)-1,1,1,3,3,3-hexafluoropropan-2-ol (862 mg, 1.487 mmol), 20% palladium hydroxide on carbon (522 mg, 0.744 mmol) and 1 N hydrochloric acid (3.72 mL, 3.72 mmol) in MeOH (30 mL)

was hydrogenated under 40 psi H2 using a Parr Shaker for 15 h. The catalyst was removed by filtration. The filter cake was rinsed with MeOH (50 mL). The filtrate was concentrated to give the desired product HCl salt as white solid (745 mg, 95% yield). LC/MS (M+1): 490.0; LC retention time: 3.385 min (analytical HPLC Method A); 1H NMR (500 MHz, METHANOL-d4) δ ppm 7.85 (t, J=8.2 Hz, 1H), 7.47-7.37 (m, 2H), 7.24-7.14 (m, 2H), 7.09 (dd, J=8.4, 2.0 Hz, 1H), 7.00 (dd, J=13.0, 1.8 Hz, 1H), 4.51 (d, J=13.6 Hz, 1H), 3.95 (d, J=13.6 Hz, 1H), 3.87 (ddd, J=11.6, 9.7, 7.9 Hz, 1H), 3.65 (ddd, J=11.7, 9.4, 3.5 Hz, 1H), 3.37-3.32 (m, 1H), 2.77 (dt, J=14.8, 9.6 Hz, 1H).

Step B: (R)-tert-butyl 3-(3-fluoro-4-(1,1,1,3,3,3-hexafluoro-2-hydroxypropan-2-yl)phenyl)-3-((4-fluorophenyl)sulfonyl)pyrrolidine-1-carboxylate

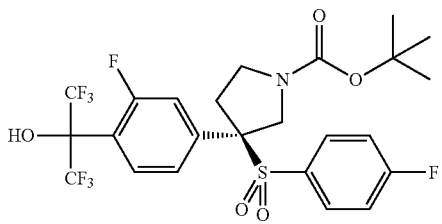 [SMILES: CC(C)(C)OC(=O)N1CC[C@](c2ccc(C(O)(C(F)(F)F)C(F)(F)F)c(F)c2)(S(=O)(=O)c2ccc(F)cc2)C1]

Hunig's Base (0.742 mL, 4.25 mmol) was added to a stirred solution of (R)-1,1,1,3,3,3-hexafluoro-2-(2-fluoro-4-(3-((4-fluorophenyl)sulfonyl)pyrrolidin-3-yl)phenyl)propan-2-ol HCl salt (0.745 g, 1.417 mmol) and BOC-Anhydride (0.464 g, 2.125 mmol) in CH$_2$Cl$_2$ (15 mL) at rt. After 2 h at rt, the mixture was diluted with EtOAc (50 mL), washed with water (2×15 mL), brine (10 mL), dried (MgSO$_4$) and concentrated. Silica gel chromatography, eluting with 20-40% EtOAc in hexanes, gave the desired product as white solid (773 mg, 91% yield). LC/MS (M−56+1): 534.0; LC retention time: 4.318 min (analytical HPLC Method A); 1H NMR (500 MHz, METHANOL-d4) δ ppm 7.81 (td, J=8.2, 2.6 Hz, 1H), 7.53-7.42 (m, 2H), 7.22-7.14 (m, 2H), 7.09 (dt, J=8.4, 2.3 Hz, 1H), 6.98 (dd, J=13.1, 1.8 Hz, 1H), 4.71-4.60 (m, 1H), 3.91-3.77 (m, 1H), 3.69-3.58 (m, 1H), 3.54-3.43 (m, 1H), 3.24-3.05 (m, 1H), 2.62 (tt, J=13.3, 9.3 Hz, 1H), 1.58-1.42 (m, 9H), t-butyl groups (1.58-1.42) showed two single peaks.

Example 543

(R)-tert-butyl 3-(3-fluoro-4-(1,1,1,3,3,3-hexafluoro-2-methoxypropan-2-yl)phenyl)-3-((4-fluorophenyl)sulfonyl)pyrrolidine-1-carboxylate

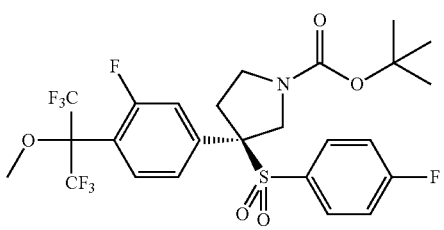 [SMILES: COC(c1ccc([C@]2(S(=O)(=O)c3ccc(F)cc3)CCN(C(=O)OC(C)(C)C)C2)cc1F)(C(F)(F)F)C(F)(F)F]

Iodomethane (0.113 mL, 1.815 mmol) was added to a stirred mixture of (R)-tert-butyl 3-(3-fluoro-4-(1,1,1,3,3,3-hexafluoro-2-hydroxypropan-2-yl)phenyl)-3-((4-fluorophe-nyl)sulfonyl)pyrrolidine-1-carboxylate (107 mg, 0.182 mmol) and potassium carbonate (125 mg, 0.908 mmol) in DMF (1.5 mL). The reaction vial was stirred at rt for 18 h, diluted with EtOAc (30 mL), washed with water (2×5 mL), brine (5 mL), dried (MgSO$_4$) and concentrated. Silica gel chromatography, eluting with 10-30% EtOAc in hexanes, gave the desired product as white solid (104 mg, 95% yield). LC/MS (M−56+1): 548.0; LC retention time: 4.523 min (analytical HPLC Method A).

Example 544

(1R,4r)-4-((R)-3-(3-fluoro-4-(1,1,1,3,3,3-hexafluoro-2-methoxypropan-2-yl)phenyl)-3-((4-fluorophenyl)sulfonyl)pyrrolidine-1-carbonyl)cyclohexanecarboxylic acid Step A: (R)-3-(3-fluoro-4-(1,1,1,3,3,3-hexafluoro-2-methoxypropan-2-yl)phenyl)-3-((4-fluorophenyl)sulfonyl)pyrrolidine

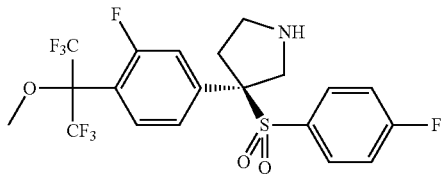 [SMILES: COC(c1ccc([C@]2(S(=O)(=O)c3ccc(F)cc3)CCNC2)cc1F)(C(F)(F)F)C(F)(F)F]

A solution of (R)-tert-butyl 3-(3-fluoro-4-(1,1,1,3,3,3-hexafluoro-2-methoxypropan-2-yl)phenyl)-3-((4-fluorophenyl)sulfonyl)pyrrolidine-1-carboxylate (101 mg, 0.167 mmol) in CH$_2$Cl$_2$ (3 mL) and 4 N HCl in dioxane (3 mL) was stirred at rt for 1 h. The mixture was concentrated and dried under vacuum to give the desired product as white solid (101 mg, 12% over theoretical weight). The material was used without purification, assuming purity of 89%. LC/MS (M+1): 504.0; LC retention time: 3.708 min (analytical HPLC Method A). 1H NMR (500 MHz, METHANOL-d4) δ ppm 7.59 (t, J=8.2 Hz, 1H), 7.50-7.43 (m, 2H), 7.26-7.18 (m, 2H), 7.15-7.08 (m, 2H), 4.54 (d, J=13.6 Hz, 1H), 3.97 (d, J=13.6 Hz, 1H), 3.88 (ddd, J=11.6, 9.8, 7.9 Hz, 1H), 3.70-3.62 (m, 1H), 3.50 (s, 3H), 3.40-3.32 (m, 1H), 2.78 (dt, J=14.8, 9.6 Hz, 1H).

Step B: (1R,4r)-4-((R)-3-(3-fluoro-4-(1,1,1,3,3,3-hexafluoro-2-methoxypropan-2-yl)phenyl)-3-((4-fluorophenyl)sulfonyl)pyrrolidine-1-carbonyl)cyclohexanecarboxylic acid

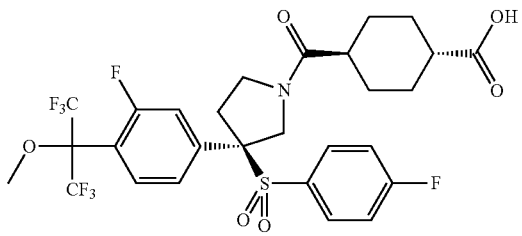 [SMILES: COC(c1ccc([C@]2(S(=O)(=O)c3ccc(F)cc3)CCN(C(=O)[C@H]3CC[C@H](C(=O)O)CC3)C2)cc1F)(C(F)(F)F)C(F)(F)F]

Hunig's Base (0.022 mL, 0.124 mmol) was added to a mixture of (R)-3-(3-fluoro-4-(1,1,1,3,3,3-hexafluoro-2-methoxypropan-2-yl)phenyl)-3-((4-fluorophenyl)sulfonyl)

pyrrolidine HCl salt (15 mg, 0.025 mmol, 89% pure), TRANS-1,4-cyclohexanedicarboxylic acid monomethyl ester (6.91 mg, 0.037 mmol) and HATU (14.10 mg, 0.037 mmol) in THF (1 mL). The reaction vial was sealed and stirred at 70° C. for 1 h. Additional trans-1,4-cyclohexanedicarboxylic acid monomethyl ester (6.91 mg, 0.037 mmol), HATU (14.10 mg, 0.037 mmol) and Hunig's Base (0.022 mL, 0.124 mmol) were added. After another hour at 70° C., the mixture was cooled to rt, 1 N NaOH (1 mL) and MeOH (1 mL) were added. After 1 h at rt, the mixture was acidified to pH3-4 with 1 N HCl. The organic solvents were evaporated. The residue was treated with EtOAc (15 mL), washed with water (2×5 mL), brine (5 mL), dried (MgSO$_4$) and concentrated. The crude material was purified via preparative LC/MS with the following conditions: Column: Waters XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-75% B over 15 minutes, then a 3-minute hold at 100% B; Flow: 20 mL/min. Fractions containing the desired product were combined and dried via centrifugal evaporation to give the desired product (11.8 mg, 73% yield). LC/MS (M+1): 658.2; LC retention time: 1.66 min (analytical HPLC Method B).

Example 545

(R)-4-(3-(3-fluoro-4-(perfluoropropan-2-yl)phenyl)-3-((4-fluorophenyl)sulfonyl)pyrrolidine-1-carbonyl)bicyclo[2.2.2]octane-1-carboxylic acid Step A: (R)-tert-butyl 3-(3-fluoro-4-(perfluoropropan-2-yl)phenyl)-3-((4-fluorophenyl)sulfonyl)pyrrolidine-1-carboxylate

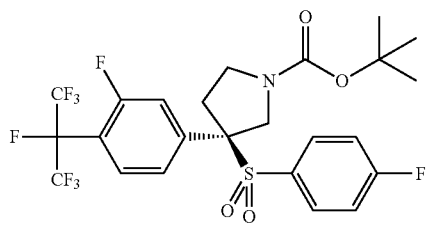 [SMILES: CC(C)(C)OC(=O)N1CC[C@](c2ccc(C(F)(C(F)(F)F)C(F)(F)F)c(F)c2)(S(=O)(=O)c2ccc(F)cc2)C1]

DAST (2.036 mL, 15.41 mmol) was added to a stirred suspension of (R)-tert-butyl 3-(3-fluoro-4-(1,1,1,3,3,3-hexafluoro-2-hydroxypropan-2-yl)phenyl)-3-((4-fluorophenyl)sulfonyl)pyrrolidine-1-carboxylate (0.757 g, 1.284 mmol) in 1,2-dichloroethane (10 mL). The reaction vial was sealed and stirred at 60° C. for 15 h. LCMS analysis showed the desired product was formed as a minor peak. The mixture was cooled to rt, carefully quenched with MeOH (0.5 mL), diluted with EtOAc (60 mL) and washed with sat NaHCO$_3$ (caution: CO$_2$ release!). The aqueous phase was separated and extracted with EtOAc (20 mL). The combined organic phase was washed with brine (10 mL), dried (MgSO$_4$) and concentrated. Silica gel chromatography, eluting with 5-40% EtOAc in hexanes, gave the desired product as white solid (132 mg, 17% yield). LC/MS (M−56+1): 536.0; LC retention time: 4.558 min (analytical HPLC Method A). The unreacted starting material was also recovered (612 mg).

Step B: (R)-3-(3-fluoro-4-(perfluoropropan-2-yl)phenyl)-3-((4-fluorophenyl)sulfonyl)pyrrolidine

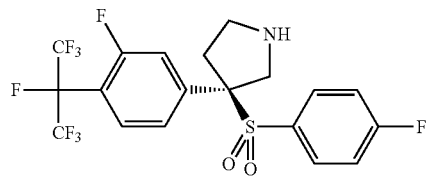 [SMILES: O=S(=O)(c1ccc(F)cc1)[C@@]1(c2ccc(C(F)(C(F)(F)F)C(F)(F)F)c(F)c2)CCNC1]

A solution of (R)-tert-butyl 3-(3-fluoro-4-(perfluoropropan-2-yl)phenyl)-3-((4-fluorophenyl)sulfonyl)pyrrolidine-1-carboxylate (132 mg, 0.223 mmol) in CH$_2$Cl$_2$ (3 mL) and 4 N HCl in dioxane (3 mL) was stirred at rt for 1 h. The mixture was concentrated and dried under vacuum to give the desired product as off-white solid (125 mg, 6% over theoretical weight). The material was used without purification, assuming purity of 94%. LC/MS (M+1): 492.0; LC retention time: 3.740 min (analytical HPLC Method A); $^1$H NMR (500 MHz, METHANOL-d4) δ ppm 7.67 (t, J=8.0 Hz, 1H), 7.51-7.43 (m, 2H), 7.27-7.15 (m, 4H), 4.54 (d, J=13.6 Hz, 1H), 3.96 (d, J=13.6 Hz, 1H), 3.89 (ddd, J=11.6, 9.7, 7.8 Hz, 1H), 3.70-3.62 (m, 1H), 3.40-3.32 (m, 1H), 2.78 (dt, J=14.8, 9.6 Hz, 1H).

Step C: (R)-methyl 4-(3-(3-fluoro-4-(perfluoropropan-2-yl)phenyl)-3-((4-fluorophenyl)sulfonyl)pyrrolidine-1-carbonyl)bicyclo[2.2.2]octane-1-carboxylate

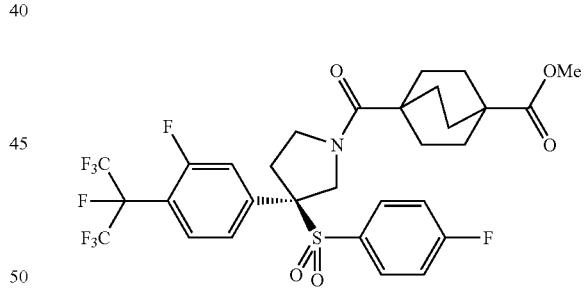

HATU (20.31 mg, 0.053 mmol) and DIEA (0.031 mL, 0.178 mmol) were added to a stirred mixture of (R)-3-(3-fluoro-4-(perfluoropropan-2-yl)phenyl)-3-((4-fluorophenyl)sulfonyl)pyrrolidine, HCl (20 mg, 0.036 mmol, 94% pure) and 4-(methoxycarbonyl)bicyclo[2.2.2]octane-1-carboxylic acid (11.34 mg, 0.053 mmol) in DMF (1 mL). The reaction vial was sealed and stirred at rt for 30 min and at 70° C. for 1 h. The mixture was diluted with EtOAc (20 mL), washed with water (2×5 mL), brine (5 mL), dried (MgSO$_4$) and concentrated. Silica gel chromatography, eluting with 0-10% MeOH in CH$_2$Cl$_2$ give impure product as white solid. LC/MS (M+1): 686.2; LC retention time: 4.481 min (analytical HPLC Method A).

Step D: (R)-4-(3-(3-fluoro-4-(perfluoropropan-2-yl)phenyl)-3-((4-fluorophenyl)sulfonyl)pyrrolidine-1-carbonyl)bicyclo[2.2.2]octane-1-carboxylic acid

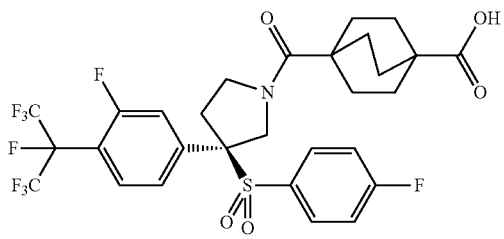 [SMILES: O=C(O)C12CCC(C(=O)N3CC[C@](c4ccc(C(F)(C(F)(F)F)C(F)(F)F)c(F)c4)(S(=O)(=O)c4ccc(F)cc4)C3)(CC1)CC2]

A mixture of the impure (R)-methyl 4-(3-(3-fluoro-4-(perfluoropropan-2-yl)phenyl)-3-((4-fluorophenyl)sulfonyl)pyrrolidine-1-carbonyl)bicyclo[2.2.2]octane-1-carboxylate, THF (1 mL), 1 N NaOH (1 mL) and THF (1 mL) was stirred at rt for 4.5 h. The mixture was acidified to pH 3-4 with 1 N HCl. The organic solvents were evaporated in vacuo. The residue was diluted with EtOAc (20 mL), washed with water (2×5 mL), brine (5 mL), dried (MgSO$_4$) and concentrated. The residue was purified via preparative HPLC with the following conditions: Column: Phenomenex LUNA 5μ C18, 21.2×100 mm; Mobile Phase A: 10:90 MeOH:water with 0.1% TFA; Mobile Phase B: 90:10 MeOH:water with 0.1% TFA; Gradient: 70-100% B over 10 minutes, then a 2-minute hold at 100% B; Flow: 20 mL/min. The desired product was obtained as white solid (15.1 mg, 63% yield over 2 steps). LC/MS (M+1): 672.5; LC retention time: 4.348 min (analytical HPLC Method A).

Example 546

(3-((2,3-dihydro-1H-inden-5-yl)sulfonyl)-3-(4-(perfluoropropan-2-yl)phenyl)pyrrolidin-1-yl)(1,1-dioxidotetrahydro-2H-thiopyran-4-yl)methanone Step A: 2-(4-(((2,3-dihydro-1H-inden-5-yl)sulfonyl)methyl)phenyl)-1,1,1,3,3,3-hexafluoropropan-2-ol

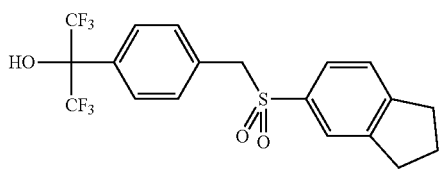 [SMILES: O=S(=O)(Cc1ccc(C(O)(C(F)(F)F)C(F)(F)F)cc1)c1ccc2c(c1)CCC2]

To a stirred solution of 2-(4-(bromomethyl)phenyl)-1,1,1,3,3,3-hexafluoropropan-2-ol (2.063 g, 4.90 mmol) in DMF (20 mL) was added sodium 2,3-dihydro-1H-indene-5-sulfinate (1.0 g, 4.90 mmol) in three equal portion (in a interval of 10 min). Resulting pale yellow colored reaction mixture was stirred at room temperature for 4 h. After completion of the reaction, water was added (50 mL) and extracted with ethyl acetate (2×50 mL). Combined organic layers was washed with brine solution (50 mL), dried over anhydrous Na$_2$SO$_4$, filtered and concentrated to get the crude compound as pale yellow gummy liquid (3.1 gm). The crude was purified by column ISCO Comb flash chromatogram (eluted with 30% ethyl acetate in pet-ether and 40 gm Red-Sep silica column was used) to yield 2-(4-(((2,3-dihydro-1H-inden-5-yl)sulfonyl)methyl)phenyl)-1,1,1,3,3,3-hexa fluoropropan-2-ol (1.0 g, 2.281 mmol, 46.6% yield) as a crystalline white solid. LCMS: Method Info Acquity BEH C18 (2.1×50 mm)1.7μ); Buffer: 5 mM Ammonium Acetate pH 3.5; Mphase A: Buffer:ACN (95:5); Mphase B: Buffer:ACN (5:95); Method: % B: O min-5%:1.1 min-95%:1.7 min-95%; Flow=0.8 ML/MIN; RT=1.15 min; 94.69% product @ 220 nm; m/z=456.1 [m+18]. $^1$HNMR (400 MHz, DMSO-d$_6$): δ 8.73 (s, 1H), 7.64 (s, 2H), 7.55-7.26 (m, 5H), 4.68 (s, 2H), 2.95 (t, J=7.53 Hz, 2H), 2.87 (t, J=7.53 Hz, 2H), 2.12-1.82 (m, 2H). $^{19}$F NMR (376 MHz): δ −74.17.

Step B: 5-((4-(perfluoropropan-2-yl)benzyl)sulfonyl)-2,3-dihydro-1H-indene

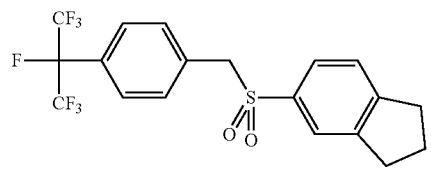 [SMILES: O=S(=O)(Cc1ccc(C(F)(C(F)(F)F)C(F)(F)F)cc1)c1ccc2c(c1)CCC2]

A solution of 2-(4-(((2,3-dihydro-1H-inden-5-yl)sulfonyl)methyl)phenyl)-1,1,1,3,3,3-hexafluoro propan-2-ol (2.1 g, 4.79 mmol) in DCM (30 ml) was cooled to −78° C. under inert atmosphere. To the mixture was added DAST (2.53 ml, 19.16 mmol) drop wise over a period of 15 min. The reaction mixture was then slowly allowed to reach room temperature and stirred for another 4 h. The reaction was cooled to 0° C. and carefully quenched the reaction by 10% sodium bicarbonate solution (~20-25 mL). Extracted with DCM (2×50 mL), combined organic layers was washed with brine solution, dried over anhydrous sodium sulphate, filtered and concentrated under reduced pressure to get crude product as pale yellow gummy liquid. The crude was purified by ISCO comb-flash chromatogram (using 40 gm red-sep silica column and eluted with 20% ethyl acetate in pet-ether) to yield 5-((4-(perfluoropropan-2-yl)benzyl)sulfonyl)-2,3-dihydro-1H-indene (1.7 g, 3.86 mmol, 81% yield) as a crystalline white solid. 1H NMR (400 MHz, CDCl$_3$): δ 7.52 (d, J=8.26 Hz, 2H), 7.44-7.39 (m, 1H), 7.37 (s, 1H), 7.30-7.26 (m, 3H), 4.32 (s, 2H), 2.96 (t, J=7.50 Hz, 2H), 2.85 (t, J=7.50 Hz, 2H), 2.13-2.09 (m, 2H). LCMS: Method Info: Acquity BEH C18 (2.1×50 mm) 1.7μ); Buffer: 5 mM Ammonium Acetate pH 3.5; Mphase A: Buffer:ACN (95:5); Mphase B: Buffer:ACN (5:95); Method: % B:Omin-5%:1.1 min-95%:1.7 min-95%; Flow=0.8 ML/MIN; RT=1.30 min; 94.69% product @ 220 nm; m/z=458.1 [m+18].

Step C: 5-((1-(4-(perfluoropropan-2-yl)phenyl)vinyl)sulfonyl)-2,3-dihydro-1H-indene

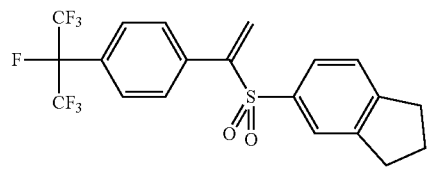 [SMILES: C=C(c1ccc(C(F)(C(F)(F)F)C(F)(F)F)cc1)S(=O)(=O)c1ccc2c(c1)CCC2]

To a solution of 5-((4-(perfluoropropan-2-yl)benzyl)sulfonyl)-2,3-dihydro-1H-indene (1.7 g, 3.86 mmol) in DMF (15 mL) was added N,N,N',N'-tetramethyl diaminomethane (3.16 mL, 23.16 mmol) followed by Ac$_2$O (2.185 mL, 23.16 mmol) at ambient temperature. The resulting reaction mixture was stirred at 60° C. for 14 h. Reaction mixture was quenched/diluted with water (50 mL) and extracted with ethyl acetate (2×50 mL). Combined ethyl acetate layer was washed with brine solution (50 mL), dried over anhydrous sodium sulphate, filtered and concentrated to get crude compound as red color liquid. Crude product was purified by ISCO comb-flash chromatogram (Using 40 gm red-sep silica column and eluted with 30% ethyl acetate in pet-ether) to generate transparent gummy liquid of 5-((1-(4-(perfluoropropan-2-yl)phenyl)vinyl)sulfonyl)-2,3-dihydro-1H-indene (1.0 g, 0.884 mmol, 22.90% yield). $^1$H NMR (400 MHz, CDCl$_3$): δ 7.58-7.52 (m, 2H), 7.52-7.41 (m, 4H), 7.23 (d, J=8.07 Hz, 1H), 6.63 (s, 1H), 5.98 (s, 1H), 2.92 (t, J=7.54 Hz, 2H), 2.85 (t, J=7.50 Hz, 2H), 2.11-2.07 (m, 2H). $^{19}$F NMR (376 MHz): 6-75.85, −182.90. LCMS: Method Info: Acquity BEH C18 (2.1×50 mm) 1.7μ); Buffer: 5 mM Ammonium Acetate pH 3.5; Mphase A: Buffer:ACN (95:5); Mphase B: Buffer:ACN (5:95); Method: % B:0min-5%:1.1 min-95%:1.7 min-95%; Flow=0.8 ML/MIN; RT=1.35 min; 94.69% product @ 220 nm; m/z=470.1 [m+18].

Step D: 1-benzyl-3-((2,3-dihydro-1H-inden-5-yl)sulfonyl)-3-(4-(perfluoropropan-2-yl)phenyl)pyrrolidine

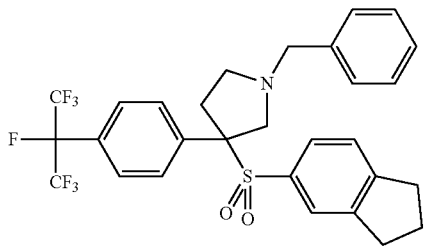 [SMILES: O=S(=O)(c1ccc2c(c1)CCC2)C1(c2ccc(C(F)(C(F)(F)F)C(F)(F)F)cc2)CCN(Cc2ccccc2)C1]

To a solution of 5-((1-(4-(perfluoropropan-2-yl)phenyl)vinyl)sulfonyl)-2,3-dihydro-1H-indene (0.6 g, 1.326 mmol) and N-(methoxymethyl)-N-(trimethylsilylmethyl)benzylamine (0.679 mL, 2.65 mmol) in DCM (50 mL) was added 2M solution of trifluoroacetic acid (4.09 μL, 0.053 mmol) in DCM at 0° C. under nitrogen atmosphere. Reaction was stirred at room temperature for 1 h. Reaction mixture was quenched with saturated 10% sodium bicarbonate solution (20 mL), extracted with ethyl acetate (2×20 mL). Combined organic layer was separated out, washed with brine solution, dried over anhydrous sodium sulphate and concentrated in rota-yap to get crude as pale yellow gummy liquid. The crude compound was purified by column chromatography using ISCO comb flash chromatogram (using 24 gm Red-sep silica column and eluted with 10% ethyl acetate in pet-ether) to get white solids of 1-benzyl-3-((2,3-dihydro-1H-inden-5-yl)sulfonyl)-3-(4-(perfluoropropan-2-yl)phenyl)pyrrolidine (0.55 g, 0.892 mmol, 67.3% yield).

1H NMR (400 MHz, CDCl$_3$): δ 7.45 (d, J=8.4 Hz, 1H), 7.39-7.17 (m, 9H), 7.12 (s, 2H), 3.83-3.59 (m, 3H), 3.30 (d, J=10.9 Hz, 1H), 3.13-2.88 (m, 4H), 2.85-2.70 (m, 3H), 2.55-2.43 (m, 1H), 2.15-1.99 (m, 2H). $^{19}$F NMR (376 MHz): δ −75.67, −182.80. LCMS: Method Info: Acquity BEH C18 (2.1×50 mm) 1.7μ); Buffer: 5 mM Ammonium Acetate pH 3.5; Mphase A: Buffer:ACN (95:5); Mphase B: Buffer:ACN (5:95); Method: % B:0min-5%:1.1 min-95%:1.7 min-95%; Flow=0.8 ML/MIN; RT=1.44 min; 94.69% product @ 220 nm; m/z=586.2 [m+1].

Step E: 3-((2,3-dihydro-1H-inden-5-yl)sulfonyl)-3-(4-(perfluoropropan-2-yl)phenyl)pyrrolidine

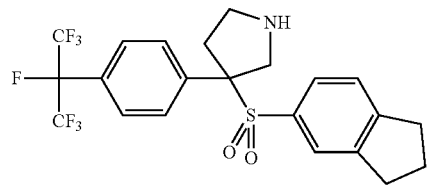 [SMILES: O=S(=O)(c1ccc2c(c1)CCC2)C1(c2ccc(C(F)(C(F)(F)F)C(F)(F)F)cc2)CCNC1]

To a Acetic Acid (15 mL) solution of 1-benzyl-3-((2,3-dihydro-1H-inden-5-yl)sulfonyl)-3-(4-(perfluoropropan-2-yl)phenyl)pyrrolidine (0.55 g, 0.892 mmol) was added Pd/C (20 mg, 0.019 mmol) at room temperature and was stirred at room temperature under hydrogen (balloon, atmospheric pressure) for 1 h. After completion, the reaction mixture was filtered through celite pad, washed with acetic acid (2×15 mL). The filtrate was concentrated under reduced pressure to get the crude product. Crude was purified by preparative HPLC. After concentration of the fractions it was obtained as gummy colorless liquid. The gummy residue thus obtained was dissolved in Acetonitrile (2 mL), added 1N HCl (10 mL). The mixture was finally lyophilized to produce white colored solids of 3-((2,3-dihydro-1H-inden-5-yl)sulfonyl)-3-(4-(perfluoropropan-2-yl)phenyl)pyrrolidine-.HCl (0.325 g, 0.605 mmol, 67.8% yield). 1H NMR (400 MHz, DMSO-d6): δ 7.60 (d, J=8.53 Hz, 2H), 7.38-7.27 (m, 3H), 7.16 (dd, J=7.7, 1.7 Hz, 1H), 6.85 (s, 1H), 4.29 (d, J=13.5 Hz, 1H), 3.93 (d, J=13.5 Hz, 1H), 3.67-3.55 (m, 1H), 3.50-3.39 (m, 1H), 3.16-3.04 (m, 1H), 2.91 (t, J=7.53 Hz, 2H), 2.76-2.61 (m, 3H), 2.07-1.88 (m, 2H). 19F NMR (376 MHz): δ −75.13, −182.04. HPLC Purity: Method info: Mobile Phase A: 0.05% TFA IN WATER:Acetonitrile (95:5); Mobile Phase B: Acetonitrile: 0.05% TFA IN WATER pH 2.5 (95:5); FLOW: 1 ml\min. XBridge-Phenyl (150×4.6 mm) 3.5 micron; RT=9.39 min, purity 99.45% @ 220 nm. Sunfire C18 3.5 μm, 4.6×150 mm: RT=8.06 min; purity 99.79% @220 mm. LCMS: Method Info: Column-Kinetex XB-C18 (75×3 mm-2.6 μm); Mphase A: 10 mM NH$_4$COOH in water: ACN (98:02); Mphase B: 10 mM NH$_4$COOH in water:ACN (02:98); Flow=1 ML/MIN; RT=3.46 min, 98.76% product @ 220 nm; MS (ES): m/z=496.0[M+1].

The two enantiomers were separated with chiral SFC Cellulose-4 column to give enantiomer 1 (1st peak off column, 104 mg) and enantiomer 2 (2nd peak off column, 93 mg).

Step F: (3-((2,3-dihydro-1H-inden-5-yl)sulfonyl)-3-(4-(perfluoropropan-2-yl)phenyl)pyrrolidin-1-yl)(1,1-dioxidotetrahydro-2H-thiopyran-4-yl)methanone

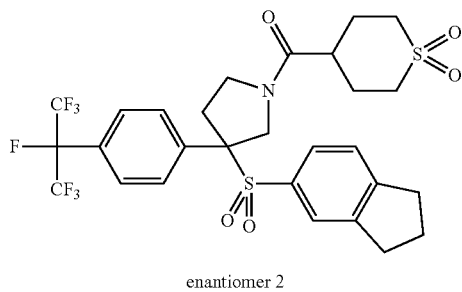 [SMILES: O=C(C1CCS(=O)(=O)CC1)N1CCC(c2ccc(C(F)(C(F)(F)F)C(F)(F)F)cc2)(S(=O)(=O)c2ccc3c(c2)CCC3)C1]

enantiomer 2

DIEA (0.026 mL, 0.151 mmol) was added to a stirred mixture of enantiomer 2 of 3-((2,3-dihydro-1H-inden-5-yl)sulfonyl)-3-(4-(perfluoropropan-2-yl)phenyl)pyrrolidine (15 mg, 0.030 mmol), tetrahydro-2H-thiopyran-4-carboxylic acid 1,1-dioxide (13.49 mg, 0.076 mmol) and HATU (28.8 mg, 0.076 mmol) in THF (1 mL). The reaction vial was sealed, stirred at 70° C. for 1 h and concentrated. The crude material was purified via preparative LC/MS with the following conditions: Column: Waters XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 30-100% B over 15 minutes, then a 5-minute hold at 100% B; Flow: 20 mL/min. Fractions containing the desired product were combined and dried via centrifugal evaporation to give the desired product (11.6 mg, 58% yield). LC/MS (M+1): 656.2; LC retention time: 2.10 min (analytical HPLC Method B).

The Examples in TABLE 10 below were prepared in the same manner as outlined in examples above.

TABLE 10

| Ex. No | Structure | MS (M + 1) | HPLC ret. time (min.) | HPLC method |
|---|---|---|---|---|
| 547 | 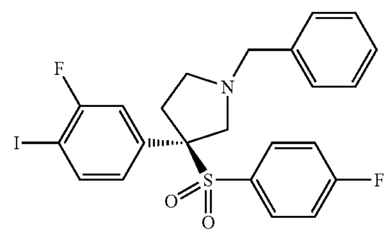 [SMILES: O=S(=O)(c1ccc(F)cc1)[C@@]1(c2ccc(I)c(F)c2)CCN(Cc2ccccc2)C1] | 540.0 | 3.390 | A |
| 548 | 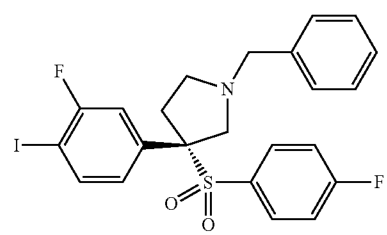 [SMILES: O=S(=O)(c1ccc(F)cc1)[C@]1(c2ccc(I)c(F)c2)CCN(Cc2ccccc2)C1] | 540.0 | 3.401 | A |
| 549 | 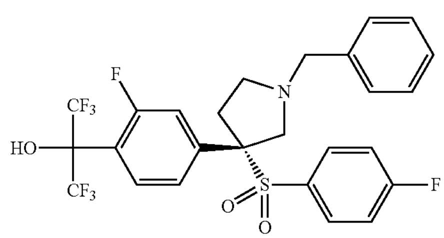 [SMILES: O=S(=O)(c1ccc(F)cc1)[C@]1(c2ccc(C(O)(C(F)(F)F)C(F)(F)F)c(F)c2)CCN(Cc2ccccc2)C1] | 580.1 | 3.631 | A |
| 550 | 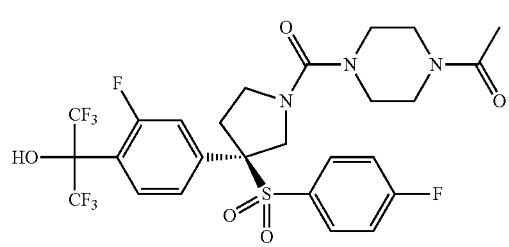 [SMILES: CC(=O)N1CCN(C(=O)N2CC[C@](c3ccc(C(O)(C(F)(F)F)C(F)(F)F)c(F)c3)(S(=O)(=O)c3ccc(F)cc3)C2)CC1] | 644.3 | 1.62 | B |

TABLE 10-continued

| Ex. No | Structure | MS (M + 1) | HPLC ret. time (min.) | HPLC method |
|---|---|---|---|---|
| 551 | 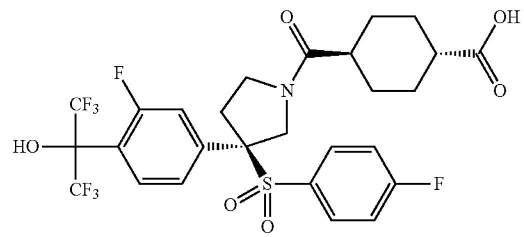 [SMILES: O=C(O)[C@H]1CC[C@H](C(=O)N2CC[C@](c3ccc(C(O)(C(F)(F)F)C(F)(F)F)c(F)c3)(S(=O)(=O)c3ccc(F)cc3)C2)CC1] | 644.3 | 1.38 | B |
| 552 | 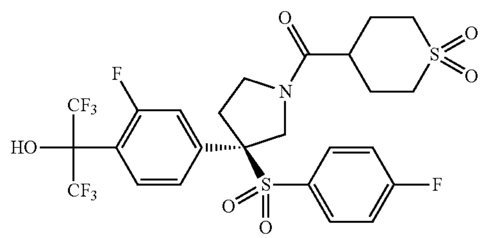 [SMILES: O=C(C1CCS(=O)(=O)CC1)N1CC[C@](c2ccc(C(O)(C(F)(F)F)C(F)(F)F)c(F)c2)(S(=O)(=O)c2ccc(F)cc2)C1] | 650.3 | 1.65 | B |
| 553 | 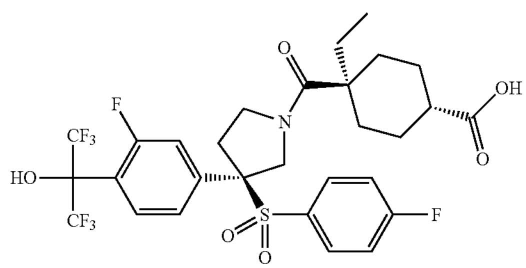 [SMILES: CC[C@]1(C(=O)N2CC[C@](c3ccc(C(O)(C(F)(F)F)C(F)(F)F)c(F)c3)(S(=O)(=O)c3ccc(F)cc3)C2)CC[C@H](C(=O)O)CC1] | 672.3 | 1.66 | B |
| 554 | 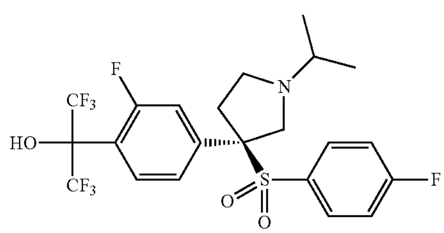 [SMILES: CC(C)N1CC[C@](c2ccc(C(O)(C(F)(F)F)C(F)(F)F)c(F)c2)(S(=O)(=O)c2ccc(F)cc2)C1] | 532.6 | 3.388 | A |
| 555 | 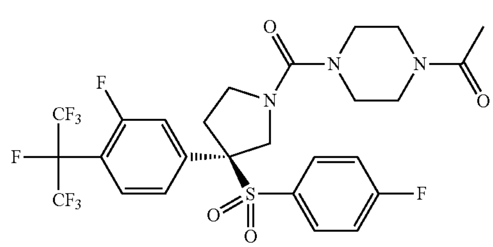 [SMILES: CC(=O)N1CCN(C(=O)N2CC[C@](c3ccc(C(F)(C(F)(F)F)C(F)(F)F)c(F)c3)(S(=O)(=O)c3ccc(F)cc3)C2)CC1] | 646.2 | 1.89 | B |
| 556 | 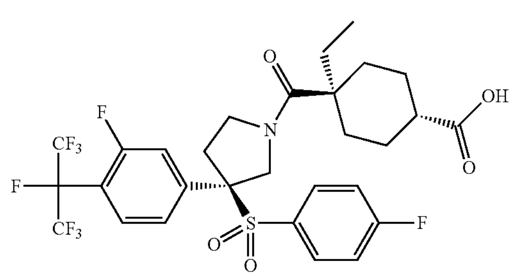 [SMILES: CC[C@]1(C(=O)N2CC[C@](c3ccc(C(F)(C(F)(F)F)C(F)(F)F)c(F)c3)(S(=O)(=O)c3ccc(F)cc3)C2)CC[C@H](C(=O)O)CC1] | 674.2 | 4.375 | A |

TABLE 10-continued

| Ex. No | Structure | MS (M + 1) | HPLC ret. time (min.) | HPLC method |
|---|---|---|---|---|
| 557 | 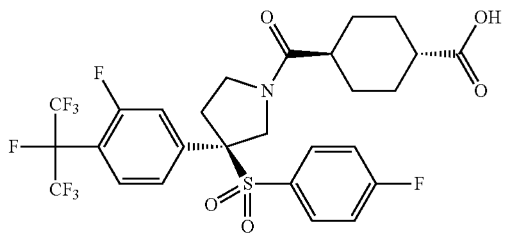 [SMILES: O=C(O)[C@H]1CC[C@H](C(=O)N2CC[C@](c3ccc(C(F)(C(F)(F)F)C(F)(F)F)c(F)c3)(S(=O)(=O)c3ccc(F)cc3)C2)CC1] | 646.1 | 1.66 | B |
| 558 | 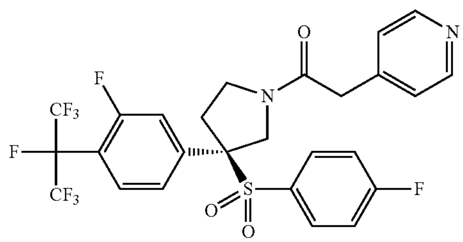 [SMILES: O=C(Cc1ccncc1)N1CC[C@](c2ccc(C(F)(C(F)(F)F)C(F)(F)F)c(F)c2)(S(=O)(=O)c2ccc(F)cc2)C1] | 611.1 | 1.94 | B |
| 559 | 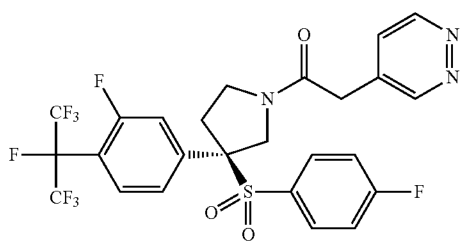 [SMILES: O=C(Cc1ccnnc1)N1CC[C@](c2ccc(C(F)(C(F)(F)F)C(F)(F)F)c(F)c2)(S(=O)(=O)c2ccc(F)cc2)C1] | 612.1 | 1.84 | B |
| 560 | 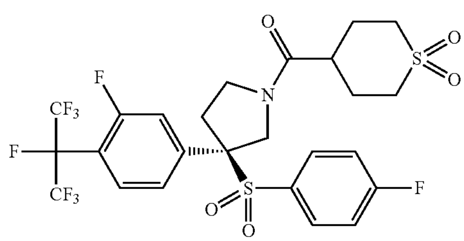 [SMILES: O=C(C1CCS(=O)(=O)CC1)N1CC[C@](c2ccc(C(F)(C(F)(F)F)C(F)(F)F)c(F)c2)(S(=O)(=O)c2ccc(F)cc2)C1] | 652.1 | 4.236 | A |
| 561 | 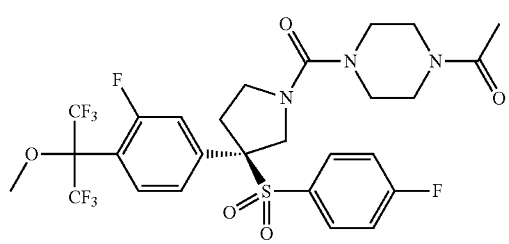 [SMILES: COC(c1ccc([C@]2(S(=O)(=O)c3ccc(F)cc3)CCN(C(=O)N3CCN(C(C)=O)CC3)C2)cc1F)(C(F)(F)F)C(F)(F)F] | 658.3 | 1.86 | B |
| 562 | 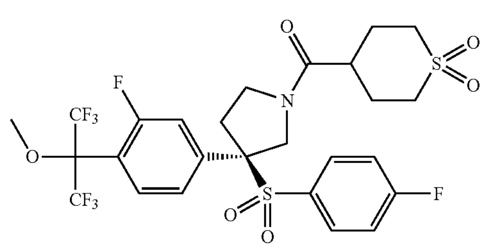 [SMILES: COC(c1ccc([C@]2(S(=O)(=O)c3ccc(F)cc3)CCN(C(=O)C3CCS(=O)(=O)CC3)C2)cc1F)(C(F)(F)F)C(F)(F)F] | 664.4 | 4.021 | A |

TABLE 10-continued

| Ex. No | Structure | MS (M + 1) | HPLC ret. time (min.) | HPLC method |
|---|---|---|---|---|
| 563 | 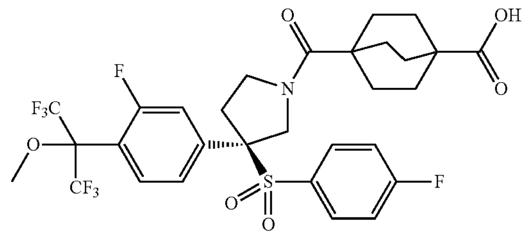 [SMILES: COC(c1ccc([C@]2(S(=O)(=O)c3ccc(F)cc3)CCN(C(=O)C34CCC(C(=O)O)(CC3)CC4)C2)cc1F)(C(F)(F)F)C(F)(F)F] | 684.2 | 1.85 | B |
| 564 | 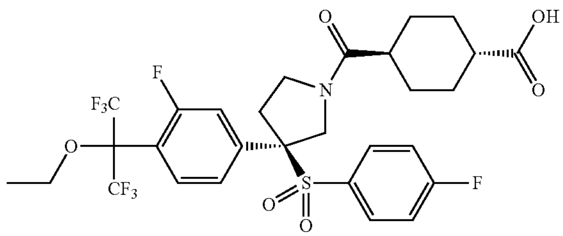 [SMILES: CCOC(c1ccc([C@]2(S(=O)(=O)c3ccc(F)cc3)CCN(C(=O)[C@H]3CC[C@H](C(=O)O)CC3)C2)cc1F)(C(F)(F)F)C(F)(F)F] | 672.3 | 1.74 | B |
| 565 | 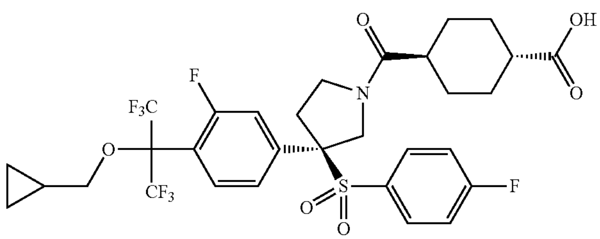 [SMILES: O=C(O)[C@H]1CC[C@H](C(=O)N2CC[C@](c3ccc(C(OCC4CC4)(C(F)(F)F)C(F)(F)F)c(F)c3)(S(=O)(=O)c3ccc(F)cc3)C2)CC1] | 698.2 | 1.83 | B |
| 566 | 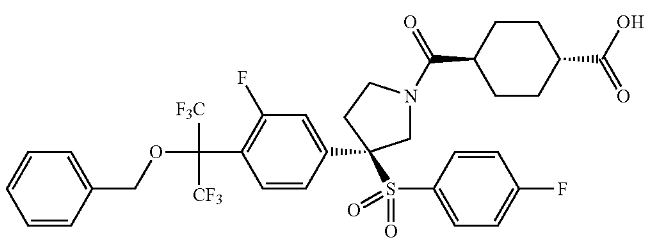 [SMILES: O=C(O)[C@H]1CC[C@H](C(=O)N2CC[C@](c3ccc(C(OCc4ccccc4)(C(F)(F)F)C(F)(F)F)c(F)c3)(S(=O)(=O)c3ccc(F)cc3)C2)CC1] | 734.2 | 1.92 | B |
| 567 | 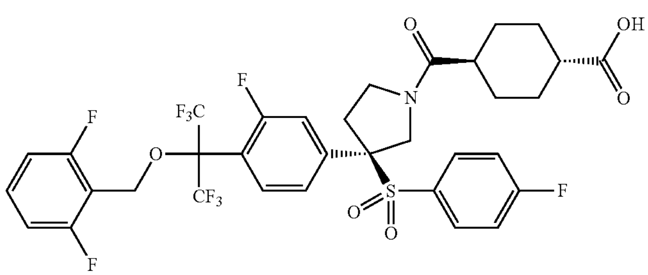 [SMILES: O=C(O)[C@H]1CC[C@H](C(=O)N2CC[C@](c3ccc(C(OCc4c(F)cccc4F)(C(F)(F)F)C(F)(F)F)c(F)c3)(S(=O)(=O)c3ccc(F)cc3)C2)CC1] | 770.2 | 1.89 | B |
| 568 | 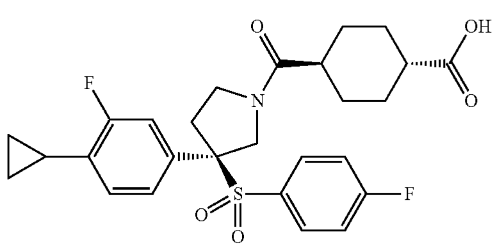 [SMILES: O=C(O)[C@H]1CC[C@H](C(=O)N2CC[C@](c3ccc(C4CC4)c(F)c3)(S(=O)(=O)c3ccc(F)cc3)C2)CC1] | 518.2 | 1.38 | B |

TABLE 10-continued

| Ex. No | Structure | MS (M + 1) | HPLC ret. time (min.) | HPLC method |
|---|---|---|---|---|
| 569 | (structure) | 554.2 | 1.52 | B |
| 570 | (structure) enantiomer 1 | 650.3 | 4.383 | A |
| 571 | (structure) enantiomer 2 | 650.2 | 4.390 | A |
| 572 | (structure) enantiomer 2 | 676.3 | 2.01 | B |

General RORγ SPA Binding Assay

The binding of potential ligands to RORγ is measured by competition with [$^3$H] 25-hydroxycholesterol (Perkin Elmer NET674250UC) using a scintillation proximity assay (SPA) binding assay. The ligand binding domain of human RORγ (A262-S507) with an N-terminal His tag is expressed in *E. coli* and purified using nickel affinity chromatography. 15 ug/well RORγ (A262-S507) is incubated with test compound at varying concentrations in 3-fold serial dilution, with final concentrations ranging from 16.6 μM to 0.28 nM for 10 min at room temperature in PBS buffer (Invitrogen #14190-144) containing 0.5% fatty acid free BSA (Gemini Bio-Products, Cat. #700-107P) and 0.1% Glycerol (Sigma Cat#G5516). 10 nM of [$^3$H] 25-hydroxycholesterol is then added, and the reaction is incubated for 10 min. 10 mg/mL of Copper-His Tag-PVT beads (Perkin Elmer cat #RPNQ0095) are added, and the mixture is incubated for 60 min. The reaction is read on a TopCount Microplate scintillation plate reader (Perkin Elmer). The competition data of the test compound over a range of concentrations was plotted as percentage inhibition of radioligand specifically bound in the absence of test compound (percent of total signal). After correcting for non-specific binding, IC$_{50}$ values were determined. The IC$_{50}$ value is defined as the concentration of test compound needed to reduce [$^3$H] 25-hydroxycholesterol specific binding by 50% and is calculated using the four parameter logistic equation to fit the normalized data.

IC$_{50}$ values of some of the compounds of the invention in the RORγ binding assay are provided below.

| Example # | RORγ Binding IC$_{50}$, uM |
|---|---|
| 1 | 2.753 |
| 2 | 1.947 |
| 3 | 0.035 |
| 4 | 0.227 |
| 5 | 0.194 |
| 6 | 0.704 |
| 7 | 0.103 |
| 8 | 0.047 |
| 9 | 0.048 |
| 10 | 0.059 |
| 11 | 0.142 |
| 12 | 0.044 |
| 13 | 0.289 |
| 14 | 0.149 |
| 15 | 0.129 |
| 16 | 0.079 |
| 17 | 0.074 |
| 18 | 0.129 |
| 19 | 0.058 |
| 20 | 0.068 |
| 21 | 0.149 |
| 22 | 0.106 |
| 23 | 0.071 |
| 24 | 0.050 |
| 25 | 0.031 |
| 26 | 0.114 |
| 27 | 0.951 |
| 28 | 1.876 |
| 29 | 0.217 |
| 30 | 0.031 |
| 31 | 0.120 |
| 32 | 2.156 |
| 33 | 0.503 |
| 34 | 0.021 |
| 35 | 0.227 |
| 36 | 0.213 |
| 37 | 0.360 |
| 38 | 4.991 |
| 39 | 0.072 |
| 40 | 0.050 |
| 41 | 0.046 |
| 42 | 0.049 |
| 43 | 0.945 |
| 44 | 0.460 |
| 45 | 1.222 |
| 46 | 0.925 |
| 47 | 2.931 |
| 48 | 0.317 |
| 49 | 0.281 |
| 50 | 0.114 |
| 51 | 0.234 |
| 52 | 0.096 |
| 53 | 0.027 |
| 54 | 1.702 |
| 55 | 0.046 |
| 56 | 0.052 |
| 57 | 0.085 |
| 58 | 0.091 |
| 59 | 3.904 |
| 60 | 0.485 |
| 61 | 0.054 |
| 62 | 0.169 |
| 63 | 0.204 |
| 64 | 0.615 |
| 65 | 0.381 |
| 66 | 0.148 |
| 67 | 0.079 |
| 68 | 0.151 |
| 69 | 1.558 |
| 70 | 0.674 |
| 71 | 0.249 |
| 72 | 0.173 |
| 73 | 0.125 |
| 74 | 0.231 |
| 75 | 0.113 |
| 76 | 0.135 |
| 77 | 0.037 |
| 78 | 0.141 |
| 79 | 0.166 |
| 80 | 0.230 |
| 81 | 0.456 |
| 82 | 0.245 |
| 83 | 4.819 |
| 84 | 0.031 |
| 85 | 0.223 |
| 86 | 0.785 |
| 87 | 1.414 |
| 88 | 0.934 |
| 89 | 0.355 |
| 90 | 0.958 |
| 91 | 0.843 |
| 92 | 0.173 |
| 93 | 0.645 |
| 94 | 0.063 |
| 95 | 0.049 |
| 96 | 0.151 |
| 97 | 0.190 |
| 98 | 0.545 |
| 99 | 0.059 |
| 100 | 0.758 |
| 101 | 0.017 |
| 102 | 0.074 |
| 103 | 0.148 |
| 104 | 0.048 |
| 105 | 0.059 |
| 106 | 0.049 |
| 107 | 0.111 |
| 108 | 0.053 |
| 109 | 0.051 |
| 110 | 0.559 |
| 111 | 0.287 |
| 112 | 0.055 |
| 113 | 0.287 |
| 114 | 0.033 |
| 115 | 0.040 |
| 116 | 0.032 |
| 117 | 0.016 |
| 118 | 0.870 |
| 119 | 0.042 |
| 120 | 0.141 |
| 121 | 0.119 |
| 122 | 0.192 |
| 123 | 0.024 |
| 124 | 0.051 |
| 125 | 0.106 |
| 126 | 0.076 |
| 127 | 0.035 |
| 128 | 0.047 |
| 129 | 0.041 |
| 130 | 0.365 |
| 131 | 0.172 |
| 132 | 0.097 |
| 133 | 0.150 |
| 134 | 0.092 |
| 135 | 0.461 |
| 136 | 0.152 |
| 137 | 0.036 |
| 138 | 0.052 |
| 139 | 0.142 |
| 140 | 0.116 |
| 141 | 0.073 |
| 142 | 0.074 |
| 143 | 1.359 |
| 144 | 0.060 |
| 145 | 0.074 |
| 146 | 0.140 |
| 147 | 0.069 |
| 148 | 0.032 |
| 149 | 0.032 |
| 150 | 0.157 |
| 151 | 0.121 |
| 152 | 0.090 |
| 153 | 0.241 |
| 154 | 0.042 |

| Example # | RORγ Binding IC$_{50}$, uM |
|---|---|
| 155 | 0.055 |
| 156 | 0.071 |
| 157 | 0.121 |
| 158 | 0.174 |
| 159 | 0.142 |
| 160 | 0.085 |
| 161 | 0.141 |
| 162 | 0.960 |
| 163 | 0.311 |
| 164 | 0.195 |
| 165 | 0.612 |
| 166 | 1.604 |
| 167 | 0.136 |
| 168 | 0.120 |
| 169 | 0.078 |
| 170 | 0.358 |
| 171 | 0.141 |
| 172 | 0.222 |
| 173 | 0.471 |
| 174 | 0.040 |
| 175 | 0.133 |
| 176 | 0.267 |
| 177 | 0.221 |
| 178 | 0.057 |
| 179 | 0.202 |
| 180 | 0.106 |
| 181 | 0.056 |
| 182 | 0.079 |
| 183 | 0.104 |
| 184 | 0.140 |
| 185 | 0.041 |
| 186 | 0.055 |
| 187 | 0.051 |
| 188 | 0.151 |
| 189 | 0.071 |
| 190 | 0.230 |
| 191 | 0.179 |
| 192 | 0.531 |
| 193 | 0.046 |
| 194 | 0.221 |
| 195 | 0.028 |
| 196 | 0.137 |
| 197 | 0.182 |
| 198 | 0.209 |
| 199 | 0.133 |
| 200 | 0.171 |
| 201 | 0.060 |
| 202 | 0.032 |
| 203 | 0.130 |
| 204 | 0.101 |
| 205 | 0.089 |
| 206 | 0.056 |
| 207 | 0.437 |
| 208 | 0.033 |
| 209 | 0.264 |
| 210 | 0.216 |
| 211 | 0.075 |
| 212 | 0.119 |
| 213 | 0.087 |
| 214 | 0.032 |
| 215 | 0.292 |
| 216 | 0.128 |
| 217 | 0.194 |
| 218 | 0.116 |
| 219 | 0.096 |
| 220 | 0.034 |
| 221 | 0.133 |
| 222 | 0.044 |
| 223 | 0.155 |
| 224 | 0.018 |
| 225 | 2.558 |
| 226 | 0.394 |
| 227 | 0.089 |
| 228 | 0.065 |
| 229 | 0.047 |
| 230 | 0.012 |
| 231 | 0.023 |
| 232 | 0.030 |
| 233 | 0.039 |
| 234 | 0.046 |
| 235 | 0.066 |
| 236 | 0.032 |
| 237 | 0.031 |
| 238 | 0.378 |
| 239 | 0.164 |
| 240 | 0.152 |
| 241 | 0.262 |
| 242 | 0.046 |
| 243 | 0.052 |
| 244 | 0.107 |
| 245 | 0.144 |
| 246 | 0.090 |
| 247 | 0.024 |
| 248 | 0.026 |
| 249 | 1.316 |
| 250 | 0.108 |
| 251 | 0.048 |
| 252 | 0.080 |
| 253 | 0.787 |
| 254 | 0.172 |
| 255 | 0.206 |
| 256 | 0.132 |
| 257 | 0.067 |
| 258 | 0.710 |
| 259 | 0.620 |
| 260 | 0.039 |
| 261 | 0.044 |
| 262 | 0.080 |
| 263 | 0.065 |
| 264 | 0.658 |
| 265 | 0.102 |
| 266 | 0.115 |
| 267 | 0.113 |
| 268 | 0.202 |
| 269 | 0.028 |
| 270 | 0.111 |
| 271 | 0.016 |
| 272 | 0.044 |
| 273 | 0.058 |
| 274 | 0.398 |
| 275 | 0.032 |
| 276 | 0.233 |
| 277 | 0.075 |
| 278 | 0.065 |
| 279 | 0.095 |
| 280 | 0.027 |
| 281 | 0.047 |
| 282 | 0.069 |
| 283 | 0.076 |
| 284 | 0.035 |
| 285 | 0.923 |
| 286 | 0.292 |
| 287 | 0.026 |
| 288 | 0.073 |
| 289 | 0.047 |
| 290 | 0.111 |
| 291 | 0.039 |
| 292 | 0.233 |
| 293 | 0.026 |
| 294 | 0.025 |
| 295 | 0.033 |
| 296 | 0.049 |
| 297 | 0.096 |
| 298 | 0.147 |
| 299 | 1.449 |
| 300 | 0.133 |
| 301 | 0.051 |
| 302 | 1.388 |
| 303 | 0.815 |
| 304 | 0.231 |
| 305 | 0.054 |
| 306 | 0.279 |

| Example # | RORγ Binding IC$_{50}$, uM |
|---|---|
| 307 | 0.099 |
| 308 | 0.039 |
| 309 | 0.038 |
| 310 | 0.051 |
| 311 | 0.050 |
| 312 | 0.076 |
| 313 | 0.121 |
| 314 | 0.078 |
| 315 | 0.135 |
| 316 | 0.047 |
| 317 | 0.168 |
| 318 | 0.072 |
| 319 | 0.177 |
| 320 | 0.263 |
| 321 | 0.396 |
| 322 | 0.106 |
| 323 | 0.383 |
| 324 | 0.169 |
| 325 | 0.084 |
| 326 | 0.254 |
| 327 | 0.707 |
| 328 | 0.073 |
| 329 | 0.093 |
| 330 | 0.188 |
| 331 | 0.075 |
| 332 | 0.081 |
| 333 | 0.221 |
| 334 | 0.181 |
| 335 | 0.166 |
| 336 | 0.211 |
| 337 | 0.054 |
| 338 | 0.078 |
| 339 | 0.075 |
| 340 | 0.056 |
| 341 | 0.155 |
| 342 | 0.153 |
| 343 | 0.041 |
| 344 | 0.070 |
| 345 | 0.206 |
| 346 | 0.446 |
| 347 | 0.216 |
| 348 | 0.096 |
| 349 | 0.074 |
| 350 | 0.243 |
| 351 | 0.155 |
| 352 | 0.220 |
| 353 | 0.187 |
| 354 | 0.102 |
| 355 | 0.046 |
| 356 | 0.044 |
| 357 | 0.182 |
| 358 | 0.208 |
| 359 | 0.295 |
| 360 | 0.086 |
| 361 | 0.196 |
| 362 | 0.365 |
| 363 | 0.115 |
| 364 | 1.300 |
| 365 | 0.079 |
| 366 | 0.048 |
| 367 | 3.443 |
| 368 | 0.024 |
| 369 | 1.819 |
| 370 | 0.080 |
| 371 | 0.068 |
| 372 | 0.553 |
| 373 | 0.061 |
| 374 | 0.041 |
| 375 | 0.051 |
| 376 | 0.071 |
| 377 | 0.069 |
| 378 | 0.079 |
| 379 | 0.044 |
| 380 | 0.186 |
| 381 | 0.171 |
| 382 | 0.057 |
| 383 | 1.599 |
| 384 | 0.370 |
| 385 | 0.024 |
| 386 | 0.043 |
| 387 | 0.028 |
| 388 | 0.311 |
| 389 | 0.323 |
| 390 | 0.080 |
| 391 | 1.435 |
| 392 | 0.060 |
| 393 | 0.142 |
| 394 | 2.393 |
| 395 | 2.816 |
| 396 | 0.171 |
| 397 | 1.344 |
| 398 | 0.106 |
| 399 | 0.082 |
| 400 | 0.159 |
| 401 | 0.109 |
| 402 | 0.051 |
| 403 | 0.040 |
| 404 | 1.283 |
| 405 | 1.265 |
| 406 | 0.259 |
| 407 | 0.066 |
| 408 | 0.955 |
| 409 | 0.080 |
| 410 | 0.089 |
| 411 | 1.186 |
| 412 | 0.266 |
| 413 | 0.320 |
| 414 | 0.062 |
| 415 | 0.092 |
| 416 | 0.079 |
| 417 | 0.121 |
| 418 | 0.074 |
| 419 | 0.055 |
| 420 | 4.621 |
| 421 | 0.166 |
| 422 | 0.110 |
| 423 | 0.426 |
| 424 | 0.140 |
| 425 | 0.053 |
| 426 | 0.514 |
| 427 | 0.066 |
| 428 | 0.292 |
| 429 | 0.338 |
| 430 | 3.771 |
| 431 | 4.222 |
| 432 | 1.860 |
| 433 | 0.310 |
| 434 | 0.670 |
| 435 | 0.107 |
| 436 | 0.254 |
| 437 | 0.072 |
| 438 | 0.609 |
| 439 | 0.174 |
| 440 | 0.583 |
| 441 | 2.356 |
| 442 | 0.225 |
| 443 | 0.088 |
| 444 | 0.220 |
| 445 | 0.047 |
| 446 | 0.051 |
| 447 | 0.606 |
| 448 | 1.288 |
| 449 | 1.526 |
| 450 | 2.390 |
| 451 | 0.825 |
| 452 | 0.086 |
| 453 | 0.152 |
| 454 | 0.405 |
| 455 | 0.103 |
| 456 | 0.059 |
| 457 | 0.043 |
| 458 | 0.074 |

| Example # | RORγ Binding IC$_{50}$, uM |
|---|---|
| 459 | 0.109 |
| 460 | 0.079 |
| 461 | 0.270 |
| 462 | 0.109 |
| 463 | 0.115 |
| 464 | 0.184 |
| 465 | 0.058 |
| 466 | 1.048 |
| 467 | 0.471 |
| 468 | 0.117 |
| 469 | 0.135 |
| 470 | 0.939 |
| 471 | 2.543 |
| 472 | 0.143 |
| 473 | 0.074 |
| 474 | 0.083 |
| 475 | 2.452 |
| 476 | 0.074 |
| 477 | 0.286 |
| 478 | 0.072 |
| 479 | 3.228 |
| 480 | 0.116 |
| 481 | 2.705 |
| 482 | 0.082 |
| 483 | 0.186 |
| 484 | 0.155 |
| 485 | 0.054 |
| 486 | 2.025 |
| 487 | 0.293 |
| 488 | 3.718 |
| 489 | 0.058 |
| 490 | 0.133 |
| 491 | 3.665 |
| 492 | 2.054 |
| 493 | 0.460 |
| 494 | 0.095 |
| 495 | 3.918 |
| 496 | 0.064 |
| 497 | 0.065 |
| 498 | 0.137 |
| 499 | 0.054 |
| 500 | 0.067 |
| 501 | 0.041 |
| 502 | 0.029 |
| 503 | 3.373 |
| 504 | 0.035 |
| 505 | 1.727 |
| 506 | 0.122 |
| 507 | 0.158 |
| 508 | 1.338 |
| 509 | 0.167 |
| 510 | 0.457 |
| 511 | 0.187 |
| 512 | 1.085 |
| 513 | 1.697 |
| 514 | 0.052 |
| 515 | 3.780 |
| 516 | 0.184 |
| 517 | 0.191 |
| 518 | 0.584 |
| 519 | 0.139 |
| 520 | 0.109 |
| 521 | 0.129 |
| 522 | 0.175 |
| 523 | 0.347 |
| 524 | 0.134 |
| 525 | 1.440 |
| 526 | 0.056 |
| 527 | 0.245 |
| 528 | 0.818 |
| 529 | 0.185 |
| 530 | 0.130 |
| 531 | 0.059 |
| 532 | 0.579 |
| 533 | 0.075 |
| 534 | 0.246 |
| 535 | 0.227 |
| 536 | 0.117 |
| 537 | 0.571 |
| 538 | 2.780 |
| 539 | 0.307 |
| 540 | 0.687 |
| 541 | 0.288 |
| 542 | 0.080 |
| 543 | 0.059 |
| 544 | 0.142 |
| 545 | 0.056 |
| 546 | 0.202 |
| 547 | 1.137 |
| 548 | 2.524 |
| 549 | 1.893 |
| 550 | 0.040 |
| 551 | 0.195 |
| 552 | 0.101 |
| 553 | 0.091 |
| 554 | 0.915 |
| 555 | 0.081 |
| 556 | 0.066 |
| 557 | 0.051 |
| 558 | 0.066 |
| 559 | 0.131 |
| 560 | 0.059 |
| 561 | 0.050 |
| 562 | 0.046 |
| 563 | 0.068 |
| 564 | 0.145 |
| 565 | 0.185 |
| 566 | 0.256 |
| 567 | 0.188 |
| 568 | 0.095 |
| 569 | 0.092 |
| 570 | 1.177 |
| 571 | 0.068 |
| 572 | 0.211 |

The invention claimed is:
1. A compound having the following formula (I):

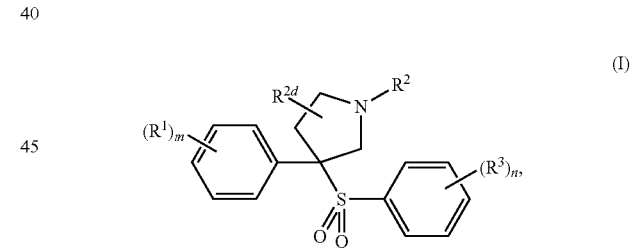

or a stereoisomer or pharmaceutically acceptable salt thereof, wherein:
R$^1$ is selected from H, halo, C$_{1-6}$ alkyl substituted with 0-3 R$^{1a}$ and —(CR$^{2e}$R$^{2f}$)r-3-14 membered carbocycle substituted with 0-3 R$^{1a}$;
R$^{1a}$ is, independently at each occurrence, hydrogen, =O, halo, CF$_3$, OCF$_3$, CN, NO$_2$, —(CR$^{2e}$R$^{2f}$)r-OR$^b$, —(CR$^{2e}$R$^{2f}$)r-S(O)$_p$R$^b$, —(CR$^{2e}$R$^{2f}$)r-C(O)R$^b$, —(CR$^{2e}$R$^{2f}$)r-C(O)OR$^b$, —(CR$^{2e}$R$^{2f}$)r-OC(O)R$^b$, —(CR$^{2e}$R$^{2f}$)r-NR$^{11}$R$^{11}$, —(CR$^{2e}$R$^{2f}$)r-C(O)NR$^{11}$R$^{11}$, —(CR$^{2e}$R$^{2f}$)r-NR$^b$C(O)R$^c$, —(CR$^{2e}$R$^{2f}$)r-NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, C$_{1-6}$ alkyl substituted with 0-3 R$^a$, C$_{1-6}$ haloalkyl, C$_{2-6}$ alkenyl substituted with 0-3 R$^a$, C$_{2-6}$ alkynyl substituted with 0-3 R$^a$, —(CR$^{2e}$R$^{2f}$)r-3-14membered carbocycle substituted with 0-3 R$^a$, or —(CR$^{2e}$R$^{2f}$)r-5-7 membered heterocycle comprising carbon atoms, and 1-4 heteroatoms selected from N, O, and $S(O)_p$ substituted with 0-3 $R^a$;

$R^2$ is selected from hydrogen, $-(CR^{2e}R^{2f})r\text{-}C(O)R^{2d}$, $-(CR^{2e}R^{2f})r\text{-}C(O)OR^{2b}$, $-(CR^{2e}R^{2f})r\text{-}C(O)NR^{11}R^{11}$, $-(CR^{2e}R^{2f})r\text{-}S(O)_2R^{2c}$, $C_{1-6}$ alkyl substituted with 0-3 $R^{2a}$, $C_{2-6}$ alkenyl substituted with 0-3 $R^{2a}$, $-(CR^{2e}R^{2f})$r-3-10 membered carbocycle substituted with 0-3 $R^a$, and $-(CR^{2e}R^{2f})$r-4-7 membered heterocycle comprising carbon atoms, and 1-4 heteroatoms selected from N, O, and $S(O)_p$ substituted with 0-3 $R^a$;

$R^{2a}$ is, independently at each occurrence, hydrogen, =O, halo, $OCF_3$, CN, $NO_2$, $-(CR^{2e}R^{2f})r\text{-}OR^b$, $-(CR^{2e}R^{2f})r\text{-}S(O)_pR^b$, $-(CR^{2e}R^{2f})r\text{-}C(O)R^b$, $-(CR^{2e}R^{2f})r\text{-}C(O)OR^b$, $-(CR^{2e}R^{2f})r\text{-}OC(O)R^b$, $-(CR^{2e}R^{2f})r\text{-}NR^{11}R^{11}$, $-(CR^{2e}R^{2f})r\text{-}C(O)NR^{11}R^{11}$, $-(CR^{2e}R^{2f})r\text{-}NR^bC(O)R^c$, $-(CR^{2e}R^{2f})r\text{-}NR^bC(O)OR^c$, $-NR^bC(O)NR^{11}R^{11}$, $-S(O)_pNR^{11}R^{11}$, $-NR^bS(O)_pR^c$, $C_{1-6}$ alkyl substituted with 0-3 $R^a$, $C_{1-6}$ haloalkyl, $C_{2-6}$ alkenyl substituted with 0-3 $R^a$, $C_{2-6}$ alkynyl substituted with 0-3 $R^a$, $-(CR^{2e}R^{2f})$r-3-14 membered carbocycle substituted with 0-3 $R^a$, or $-(CR^{2e}R^{2f})$r-4-7 membered heterocycle comprising carbon atoms, and 1-4 heteroatoms selected from N, O, and $S(O)_p$ substituted with 0-3 $R^a$;

$R^{2b}$ is, independently at each occurrence, hydrogen, $CF_3$, $-(CR^{2e}R^{2f})_qOR^b$, $-(CR^{2e}R^{2f})_qS(O)_pR^b$, $-(CR^{2e}R^{2f})r\text{-}C(O)R^{1d}$, $-(CR^{2e}R^{2f})r\text{-}C(O)OR^b$, $-(CR^{2e}R^{2f})_qOC(O)R^b$, $-(CR^{2e}R^{2f})_qNR^{11}R^{11}$, $-(CR^{2e}R^{2f})r\text{-}C(O)NR^{11}R^{11}$, $-(CR^{2e}R^{2f})_qNR^bC(O)R^{1c}$, $-(CR^{2e}R^{2f})_qNR^bC(O)OR^c$, $-(CR^{2e}R^{2f})_qNR^bC(O)NR^{11}R^{11}$, $-(CR^{2e}R^{2f})_qS(O)_2NR^{11}R^{11}$, $-(CR^{2e}R^{2f})_qNR^bS(O)_2R^c$, $C_{1-6}$ alkyl substituted with 0-2 $R^a$, $C_{1-6}$ haloalkyl, $-(CR^{2e}R^{2f})$r-3-14 membered carbocycle substituted with 0-3 $R^a$, or $-(CR^{2e}R^{2f})$r-5-7 membered heterocycle comprising carbon atoms and 1-4 heteroatoms selected from N, O, and $S(O)_p$ substituted with 0-2 $R^a$;

$R^{2c}$ is independently at each occurrence, hydrogen, $C_{1-6}$ alkyl substituted with 0-3 $R^a$, $C_{2-6}$ alkenyl substituted with 0-3 $R^a$, $C_{3-10}$ cycloalkyl substituted with 0-3 $R^a$, $C_{6-10}$ aryl substituted with 0-3 $R^a$, or $-(CR^{2e}R^{2f})$r-5-10 membered heterocycle containing 1-4 heteroatoms selected from N, O, and $S(O)_p$, substituted with 0-3 $R^a$;

$R^{2d}$ is, independently at each occurrence, $C_{1-6}$ alkyl substituted with 0-2 $R^d$, $C_{1-6}$ haloalkyl, $C(O)NR^{11}R^{11}$, $-(CR^{2e}R^{2f})r\text{-}C_{3-10}$ cycloalkyl substituted with 0-3 $R^d$, $-(CR^{2e}R^{2f})$r-phenyl substituted with 0-2 $R^a$, or a $-(CR^{2e}R^{2f})$r-4-10 membered heterocycle where the heterocycle may be fused, bridged or spirocyclic, containing 1-4 heteroatoms selected from N, O, and $S(O)_p$, substituted with 0-3 $R^a$;

$R^{2e}$ and $R^{2f}$ are, independently at each occurrence, hydrogen, halogen or $C_{1-6}$ alkyl;

$R^3$ is selected from hydrogen, halo, $N_3$, CN, $-(CR^{2e}R^{2f})r\text{-}OR^{3b}$, $-(CR^{2e}R^{2f})r\text{-}NR^{11}R^{11}$, $C_{1-6}$ alkyl substituted with 0-3 $R^{3a}$, $C_{3-10}$ cycloalkyl substituted with 0-3 $R^{3a}$; and phenyl substituted with 0-3 $R^{3a}$, or 4-10 membered heterocycle containing 1-4 heteroatoms selected from N, O, and $S(O)_p$, substituted with 0-3 $R^{1a}$, or two $R^3$ located on adjacent carbon atoms link to form a 5-7 membered carbocycle or a 5-7 membered heterocycle comprising carbon atoms and 1-4 heteroatom selected from N, O and $S(O)_p$, both optionally substituted with 0-3 $R^{3a}$;

$R^{3a}$ is, independently at each occurrence, hydrogen, =O, halo, $OCF_3$, $OCHF_2$, $CF_3$, $CHF_2$, CN, $NO_2$, $-(CR^{2e}R^{2f})r\text{-}OR^b$, $-(CR^{2e}R^{2f})r\text{-}S(O)_pR^b$, $-(CR^{2e}R^{2f})r\text{-}C(O)R^b$, $-(CR^{2e}R^{2f})r\text{-}C(O)OR^b$, $-(CR^{2e}R^{2f})r\text{-}OC(O)R^b$, $-(CR^{2e}R^{2f})r\text{-}NR^{11}R^{11}$, $-(CR^{2e}R^{2f})r\text{-}C(O)NR^{11}R^{11}$, $-(CR^{2e}R^{2f})r\text{-}NR^bC(O)R^c$, $-(CR^{2e}R^{2f})r\text{-}NR^bC(O)OR^c$, $-NR^bC(O)NR^{11}R^{11}$, $-S(O)_pNR^{11}R^{11}$, $-NR^bS(O)_pR^c$, $C_{1-6}$ alkyl substituted with 0-3 $R^a$, $C_{2-6}$ alkenyl substituted with 0-3 $R^a$, $C_{2-6}$ alkynyl substituted with 0-3 $R^a$, $C_{1-6}$ haloalkyl, $-(CR^{2e}R^{2f})$r-3-14 membered carbocycle substituted with 0-3 $R^a$, or $-(CR^{2e}R^{2f})$r-5-10 membered heterocycle comprising carbon atoms and 1-4 heteroatoms selected from N, O, and $S(O)_p$ substituted with 0-3 $R^a$;

$R^{3b}$ is, independently at each occurrence, hydrogen, $CF_3$, $-(CR^{2e}R^{2f})_qOR^b$, $-(CR^{2e}R^{2f})_qS(O)_pR^b$, $-(CR^{2e}R^{2f})r\text{-}C(O)R^{1d}$, $-(CR^{2e}R^{2f})r\text{-}C(O)OR^b$, $-(CR^{2e}R^{2f})_qOC(O)R^b$, $-(CR^{2e}R^{2f})_qNR^{11}R^{11}$, $-(CR^{2e}R^{2f})r\text{-}C(O)NR^{11}R^{11}$, $-(CR^{2e}R^{2f})_qNR^bC(O)R^{1c}$, $-(CR^{2e}R^{2f})_qNR^bC(O)OR^c$, $-(CR^{2e}R^{2f})_qNR^bC(O)NR^{11}R^{11}$, $-(CR^{2e}R^{2f})_qS(O)_2NR^{11}R^{11}$, $-(CR^{2e}R^{2f})_qNR^bS(O)_2R^c$, $C_{1-6}$ alkyl substituted with 0-3 $R^a$, $C_{1-6}$ haloalkyl, $-(CR^{2e}R^{2f})$r-3-14 membered carbocycle substituted with 0-3 $R^a$, or $-(CR^{2e}R^{2f})$r-5-7 membered heterocycle comprising carbon atoms and 1-4 heteroatoms selected from N, O, and $S(O)_p$ substituted with 0-3 $R^a$;

$R^{11}$ is, independently at each occurrence, hydrogen, $C_{1-6}$ alkyl substituted with 0-3 $R^f$, $CF_3$, $C_{3-10}$ cycloalkyl substituted with 0-3 $R^f$, $-(CR^{2e}R^{2f})$r-phenyl substituted with 0-3 $R^d$, or $-(CR^{2e}R^{2f})$r-5-7 membered heterocycle comprising carbon atoms and 1-4 heteroatoms selected from N, O, and $S(O)_p$ substituted with 0-3 $R^d$;

or one $R^{11}$ and a second $R^{11}$, both attached to the same nitrogen atom, combine to form a heterocycle comprising carbon atoms and 1-4 heteroatoms selected from N, O, and $S(O)_p$ substituted with 0-3 $R^d$;

$R^a$ is, independently at each occurrence, hydrogen, =O, halo, $OCF_3$, $CF_3$, $CHF_2$, CN, $NO_2$, $-(CR^{2e}R^{2f})r\text{-}OR^b$, $-(CR^{2e}R^{2f})r\text{-}S(O)_pR^b$, $-(CR^{2e}R^{2f})r\text{-}C(O)R^b$, $-(CR^{2e}R^{2f})r\text{-}C(O)OR^b$, $-(CR^{2e}R^{2f})r\text{-}OC(O)R^b$, $-(CR^{2e}R^{2f})r\text{-}NR^{11}R^{11}$, $-(CR^{2e}R^{2f})r\text{-}C(O)NR^{11}R^{11}$, $-(CR^{2e}R^{2f})r\text{-}NR^bC(O)R^c$, $-(CR^{2e}R^{2f})r\text{-}NR^bC(O)OR^c$, $-NR^bC(O)NR^{11}R^{11}$, $-S(O)_pNR^{11}R^{11}$, $-NR^bS(O)_pR^c$, $C_{1-6}$ alkyl substituted with 0-3 $R^f$, $C_{1-6}$ haloalkyl, $C_{2-6}$ alkenyl substituted with 0-3 $R^a$, $C_{2-6}$ alkynyl substituted with 0-3 $R^a$, $-(CR^{2e}R^{2f})$r-3-14 membered carbocycle, or $-(CR^{2e}R^{2f})$r-5-7 membered heterocycle comprising carbon atoms and 1-4 heteroatoms selected from N, O, and $S(O)_p$ substituted with 0-3 $R^f$;

$R^b$ is, independently at each occurrence, hydrogen, $C_{1-6}$ alkyl substituted with 0-3 $R^d$, $C_{1-6}$ haloalkyl, $C_{3-6}$ cycloalkyl substituted with 0-3 $R^d$, $-(CR^{2e}R^{2f})$r-5-7 membered heterocycle comprising carbon atoms and 1-4 heteroatoms selected from N, O, and $S(O)_p$ substituted with 0-3 $R^f$, or $-(CR^{2e}R^{2f})$r-6-10 membered carbocycle substituted with 0-3 $R^d$;

$R^c$ is, independently at each occurrence, hydrogen, $C_{1-6}$ alkyl substituted with 0-3 $R^f$, $-(CR^{2e}R^{2f})r\text{-}C_{3-6}$ cycloalkyl substituted with 0-3 $R^f$, or $-(CR^{2e}R^{2f})$r-phenyl substituted with 0-3 $R^f$;

$R^d$ is, independently at each occurrence, hydrogen, =O, halo, $OCF_3$, $CF_3$, CN, $NO_2$, $-OR^e$, $-(CR^{2e}R^{2f})r\text{-}C(O)R^c$, $-NR^eR^e$, $-NR^eC(O)OR^c$, $C(O)NR^eR^e$, $-NR^eC(O)R^c$, $CO_2R^c$, $-NR^eSO_2R^c$, $SO_2R^c$, $C_{1-6}$ alkyl substituted with 0-3 $R^f$, $C_{3-6}$ cycloalkyl substituted with 0-3 $R^f$, $-(CR^{2e}R^{2f})$r-phenyl substituted with 0-3 $R^f$ or $-(CR^{2e}R^{2f})$r-5-7 membered heterocycle comprising carbon atoms and 1-4 heteroatoms selected from N, O, and $S(O)_p$ substituted with 0-3 $R^f$;

$R^e$ is, independently at each occurrence, selected from hydrogen, $C(O)NR^fR^f$, $C_{1-6}$ alkyl, $C_{3-6}$ cycloalkyl, or —$(CR^{2e}R^{2f})$r-phenyl substituted with 0-3 $R^f$;

$R^f$ is, independently at each occurrence, hydrogen, =O, halo, CN, $NH_2$, $NH(C_{1-6}$ alkyl), $N(C_{1-6}$ alkyl)$_2$, $SO_2$ $(C_{1-6}$ alkyl), $CO_2H$, $CO_2(C_{1-6}$ alkyl), OH, $C_{3-6}$ cycloalkyl, $CF_3$ or $O(C_{1-6}$ alkyl);

or $R^f$ is, independently at each occurrence, an optionally substituted —$(CR^{2e}R^{2f})$r-5-10 membered heterocycle comprising carbon atoms and 1-4 heteroatoms selected from N, O, and $S(O)_p$, phenyl or $C_{3-6}$ cycloalkyl, each group optionally substituted with halo, CN, $CF_3$, $C_{1-6}$ alkyl or $O(C_{1-6}$ alkyl);

m and n are independently selected from 0, 1, 2 and 3;

p and q, independently at each occurrence, are 0, 1, or 2; and r is 0, 1, 2, 3, or 4.

2. The compound of claim 1, or a stereoisomer or pharmaceutically-acceptable salt thereof, wherein $R^1$ is halo, phenyl substituted with 0-3 $R^{1a}$, or $C_{1-6}$ alkyl substituted with 0-3 $R^{1a}$; and $R^{1a}$ is, independently at each occurrence, hydrogen, $CF_3$, halo, $C_{1-6}$ alkyl substituted with 0-3 $R^a$, —$(CR^{2e}R^{2f})$r-$OR^b$, and —$(CR^{2e}R^{2f})$r-phenyl substituted with 0-3 $R^a$.

3. The compound of claim 1, or a stereoisomer or pharmaceutically-acceptable salt thereof, wherein:

$R^2$ is hydrogen, $SO_2R^{2c}$, $C_{1-6}$ alkyl substituted with 0-3 $R^{2a}$, $CO_2R^{2b}$, —$C(O)R^{2d}$, —$C(O)NR^{11}R^{11}$; or a 5-7 membered heterocycle comprising carbon atoms, and 1-4 heteroatoms selected from N, O, and $S(O)_p$ substituted with 0-3 $R^a$, $R^{2a}$ is hydrogen or $C_{1-6}$ alkyl substituted with 0-3 $R^a$;

$R^{2b}$ is hydrogen, $C_{1-6}$ alkyl substituted with 0-3 $R^a$, $C_{3-6}$ cycloalkyl substituted with 0-3 $R^a$, —$(CR^{2e}R^{2f})$r-5-7 membered heterocycle comprising carbon atoms and 1-4 heteroatoms selected from N, O, and $S(O)_p$ substituted with 0-3 $R^a$, or —$(CR^{2e}R^{2f})$r-phenyl substituted with 0-3 $R^a$;

$R^{2c}$ is, independently at each occurrence, hydrogen, $C_{1-6}$ alkyl substituted with 0-3 $R^a$, $C_{2-6}$ alkenyl substituted with 0-3 $R^a$, $C_{3-10}$ cycloalkyl substituted with 0-3 $R^a$, $C_{6-10}$ aryl substituted with 0-3 $R^a$, or —$(CR^{2e}R^{2f})$r-5-10-membered heterocycle containing 1-4 heteroatoms selected from N, O, and $S(O)_p$, substituted with 0-3 $R^a$; and $R^{2d}$ is, independently at each occurrence, hydrogen, $C_{1-6}$ alkyl substituted with 0-3 $R^d$, $C_{1-6}$ haloalkyl, $C(O)NR^{11}R^{11}$, $C_{3-10}$ cycloalkyl substituted with 0-2 $R^d$, $(CR^{2e}R^{2f})$r-phenyl substituted with 0-2 $R^a$, or a 4-10 membered heterocycle containing 1-4 heteroatoms selected from N, O, and $S(O)_p$, substituted with 0-3 $R^a$.

4. The compound of claim 1, or a stereoisomer or pharmaceutically-acceptable salt thereof, wherein:

$R^3$ is hydrogen, halo, $N_3$, CN, $OR^{3b}$, —$NH_2$, $NH(C_{1-6}$ alkyl), $N(C_{1-6}$ alkyl)$_2$, $C_{1-6}$ alkyl substituted with 0-3 $R^{3a}$ or $C_{3-10}$ cycloalkyl substituted with 0-3 $R^{3a}$;

$R^{3a}$ is, independently at each occurrence, hydrogen, =O, halo, $OCF_3$, $OCHF_2$, $CF_3$, $CHF_2$, CN, $NO_2$, —$(CR^{2e}R^{2f})$r-$OR^b$, —$(CR^{2e}R^{2f})$r-$S(O)_pR^b$, —$(CR^{2e}R^{2f})$r-$C(O)R^b$, —$(CR^{2e}R^{2f})$r-$C(O)OR^b$, —$(CR^{2e}R^{2f})$r-$OC(O)R^b$, —$(CR^{2e}R^{2f})$r-$NR^{11}R^{11}$, —$(CR^{2e}R^{2f})$r-$C(O)NR^{11}R^{11}$, —$(CR^{2e}R^{2f})$r-$NR^bC(O)$ $R^c$, —$(CR^{2e}R^{2f})$r-$NR^bC(O)OR^c$, —$NR^bC(O)NR^{11}R^{11}$, —$S(O)_pNR^{11}R^{11}$, —$NR^bS(O)pR^c$, $C_{1-6}$ alkyl substituted with 0-3 $R^a$, $C_{2-6}$ alkenyl substituted with 0-3 $R^a$, $C_{2-6}$ alkynyl substituted with 0-3 $R^a$, $C_{1-6}$ haloalkyl, —$(CR^{2e}R^{2f})$r-3-14 membered carbocycle substituted with 0-3 $R^a$, or —$(CR^{2e}R^{2f})$r-5-10 membered heterocycle comprising carbon atoms and 1-4 heteroatoms selected from N, O, and $S(O)_p$ substituted with 0-3 $R^a$; and $R^{3b}$ is, independently at each occurrence, hydrogen, $C_{1-6}$ alkyl substituted with 0-3 $R^a$ or phenyl substituted with 0-3 $R^a$.

5. A compound according claim 1 having the following formula

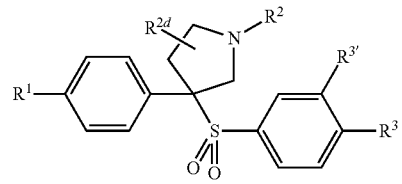

or a stereoisomer or pharmaceutically-acceptable salt thereof, wherein:

$R^1$ is halo, phenyl substituted with 0-3 $R^{1a}$, or $C_{1-6}$ alkyl substituted with 0-3 $R^{1a}$;

$R^{1a}$ is, independently at each occurrence, hydrogen, $CF_3$, halo, $C_{1-6}$ alkyl substituted with 0-3 $R^a$, —$(CR^{2e}R^{2f})$r-$OR^b$, and —$(CR^{2e}R^{2f})$r-phenyl substituted with 0-3 $R^a$;

$R^2$ is hydrogen, $SO_2R^{2c}$, $C_{1-6}$ alkyl substituted with 0-3 $R^{2a}$, $CO_2R^{2b}$, —$C(O)R^{2d}$, —$C(O)NR^{11}R^{11}$; or a 5-7 membered heterocycle comprising carbon atoms, and 1-4 heteroatoms selected from N, O, and $S(O)_p$ substituted with 0-3 $R^a$, $R^{2a}$ is hydrogen or $C_{1-6}$ alkyl substituted with 0-3 $R^a$, $R^{2b}$ is hydrogen, $C_{1-6}$ alkyl substituted with 0-3 $R^a$ (Me, Et, tBu), $C_{3-6}$ cycloalkyl substituted with 0-3 $R^a$, —$(CR^{2e}R^{2f})$r-5-7 membered heterocycle comprising carbon atoms and 1-4 heteroatoms selected from N, O, and $S(O)_p$ substituted with 0-3 $R^a$, or —$(CR^{2e}R^{2f})$r-phenyl substituted with 0-3 $R^a$;

$R^{2c}$ is independently at each occurrence hydrogen, $C_{1-6}$ alkyl substituted with 0-3 $R^a$, $C_{2-6}$ alkenyl substituted with 0-3 $R^a$, $C_{3-10}$ cycloalkyl substituted with 0-3 $R^a$, $C_{6-10}$ aryl substituted with 0-3 $R^a$, or a —$(CR^{2e}R^{2f})$r-5-10 membered heterocycle containing 1-4 heteroatoms selected from N, O, and $S(O)_p$, substituted with 0-3 $R^a$;

$R^{2d}$ is independently at each occurrence, hydrogen, $C_{1-6}$ alkyl substituted with 0-3 $R^d$ (Me), $C_{1-6}$ haloalkyl, $C(O)NR^{11}R^{11}$, $C_{3-6}$ cycloalkyl substituted with 0-2 $R^d$, —$(CR^{2e}R^{2f})$r-phenyl substituted with 0-2 $R^a$, or 5-10 membered heterocycle containing 1-4 heteroatoms selected from N, O, and $S(O)_p$, substituted with 0-3 $R^a$;

$R^3$ and $R^{3'}$ are, independently selected from hydrogen, halo, $N_3$, CN, $OR^{3b}$, —$NH_2$, $NH(C_{1-6}$ alkyl), $N(C_{1-6}$ alkyl)$_2$, $C_{1-6}$ alkyl substituted with 0-3 $R^{3a}$ and $C_{3-10}$ cycloalkyl substituted with 0-3 $R^{3a}$;

$R^{3a}$ is, independently at each occurrence, hydrogen, =O, halo, $OCF_3$, $OCHF_2$, $CF_3$, $CHF_2$, CN, $NO_2$, —$(CR^{2e}R^{2f})$r-$OR^b$, —$(CR^{2e}R^{2f})$r-$S(O)_pR^b$, —$(CR^{2e}R^{2f})$r-$C(O)R^b$, —$(CR^{2e}R^{2f})$r-$C(O)OR^b$, —$(CR^{2e}R^{2f})$r-$OC(O)R^b$, —$(CR^{2e}R^{2f})$r-$NR^{11}R^{11}$, —$(CR^{2e}R^{2f})$r-$C(O)NR^{11}R^{11}$, —$(CR^{2e}R^{2f})$r-$NR^bC(O)$ $R^c$, —$(CR^{2e}R^{2f})$r-$NR^bC(O)OR^c$, —$NR^bC(O)NR^{11}R^{11}$, —$S(O)_pNR^{11}R^{11}$, —$NR^bS(O)_pR^c$, $C_{1-6}$ alkyl substituted with 0-3 $R^a$, $C_{2-6}$ alkenyl substituted with 0-3 $R^a$, $C_{2-6}$ alkynyl substituted with 0-3 $R^a$, $C_{1-6}$ haloalkyl, —$(CR^{2e}R^{2f})_r$-3-14 membered carbocycle substituted with 0-3 $R^a$, or —$(CR^{2e}R^{2f})_r$-5-10 membered heterocycle comprising carbon atoms and 1-4 heteroatoms selected from N, O, and $S(O)_p$ substituted with 0-3 $R^a$; and $R^{3b}$ is, independently at each occurrence, hydrogen, $C_{1-6}$ alkyl substituted with 0-3 $R^a$ or phenyl substituted with 0-3 $R^a$;

$R^{11}$ is, independently at each occurrence, hydrogen, $C_{1-6}$ alkyl substituted with 0-3 $R^f$, $CF_3$, $C_{3-10}$ cycloalkyl substituted with 0-3 $R^f$, —$(CR^{2e}R^{2f})_r$-phenyl substituted with 0-3 $R^d$, or —$(CR^{2e}R^{2f})_r$-5-7 membered heterocycle comprising carbon atoms and 1-4 heteroatoms selected from N, O, and $S(O)_p$ substituted with 0-3 $R^d$;

or one $R^{11}$ and a second $R^{11}$, both attached to the same nitrogen atom, combine to form a heterocycle comprising carbon atoms and 1-4 heteroatoms selected from N, O, and $S(O)_p$ substituted with 0-3 $R^d$;

$R^a$ is, independently at each occurrence, hydrogen, =O, halo, $OCF_3$, $CF_3$, $CHF_2$, CN, $NO_2$, —$(CR^{2e}R^{2f})_r$-$OR^b$, —$(CR^{2e}R^{2f})_r$-$S(O)_pR^b$, —$(CR^{2e}R^{2f})_r$-$C(O)R^b$, —$(CR^{2e}R^{2f})_r$-$C(O)OR^b$, —$(CR^{2e}R^{2f})_r$-$OC(O)R^b$, —$(CR^{2e}R^{2f})_r$-$NR^{11}R^{11}$, —$(CR^{2e}R^{2f})_r$-$C(O)NR^{11}R^{11}$, —$(CR^{2e}R^{2f})_r$-$NR^bC(O)R^c$, —$(CR^{2e}R^{2f})_r$-$NR^bC(O)OR^c$, —$NR^bC(O)NR^{11}R^{11}$, —$S(O)_pNR^{11}R^{11}$, —$NR^bS(O)_pR^c$, $C_{1-6}$ alkyl substituted with 0-3 $R^f$, $C_{1-6}$ haloalkyl, $C_{2-6}$ alkenyl substituted with 0-3 $R^a$, $C_{2-6}$ alkynyl substituted with 0-3 $R^a$, —$(CR^{2e}R^{2f})_r$-3-14 membered carbocycle, or —$(CR^{2e}R^{2f})_r$-5-7 membered heterocycle comprising carbon atoms and 1-4 heteroatoms selected from N, O, and $S(O)_p$ substituted with 0-3 $R^f$;

$R^b$ is, independently at each occurrence, hydrogen, $C_{1-6}$ alkyl substituted with 0-3 $R^d$, $C_{1-6}$ haloalkyl, $C_{3-6}$ cycloalkyl substituted with 0-3 $R^d$, —$(CR^{2e}R^{2f})_r$-5-7 membered heterocycle comprising carbon atoms and 1-4 heteroatoms selected from N, O, and $S(O)_p$ substituted with 0-3 $R^f$, or —$(CR^{2e}R^{2f})_r$-6-10 carbocycle substituted with 0-3 $R^d$;

$R^c$ is, independently at each occurrence, hydrogen, $C_{1-6}$ alkyl substituted with 0-3 $R^f$, —$(CR^{2e}R^{2f})_r$-$C_{3-6}$ cycloalkyl substituted with 0-3 $R^f$, or —$(CR^{2e}R^{2f})_r$-phenyl substituted with 0-3 $R^f$;

$R^d$ is, independently at each occurrence, hydrogen, =O, halo, $OCF_3$, $CF_3$, CN, $NO_2$, —$OR^e$, —$(CR^{2e}R^{2f})_r$-$C(O)R^c$, —$NR^eR^e$, —$NR^eC(O)OR^c$, $C(O)NR^eR^e$, —$NR^eC(O)R^c$, $CO_2R^c$, —$NR^eSO_2R^c$, $SO_2R^c$, $C_{1-6}$ alkyl substituted with 0-3 $R^f$, $C_{3-6}$ cycloalkyl substituted with 0-3 $R^f$, —$(CR^{2e}R^{2f})_r$-phenyl substituted with 0-3 $R^f$ or —$(CR^{2e}R^{2f})_r$-5-7 membered heterocycle comprising carbon atoms and 1-4 heteroatoms selected from N, O, and $S(O)_p$ substituted with 0-3 $R^f$;

$R^e$ is, independently at each occurrence, selected from hydrogen, $C(O)NR^fR^f$, $C_{1-6}$ alkyl, $C_{3-6}$ cycloalkyl, and —$(CR^{2e}R^{2f})_r$-phenyl substituted with 0-3 $R^f$;

$R^f$ is, independently at each occurrence, hydrogen, =O, halo, CN, $NH_2$, $NH(C_{1-6}$ alkyl), $N(C_{1-6}$ alkyl)$_2$, $SO_2$($C_{1-6}$ alkyl), $CO_2H$, $CO_2(C_{1-6}$ alkyl), OH, $C_{3-6}$ cycloalkyl, $CF_3$, or $O(C_{1-6}$ alkyl);

or $R^f$ is, independently at each occurrence, an optionally substituted —$(CR^{2e}R^{2f})_r$-5-10 membered heteroaryl comprising carbon atoms and 1-4 heteroatoms selected from N, O, and S, phenyl or $C_{3-6}$ cycloalkyl, each group optionally substituted with halo, CN, $CF_3$, $C_{1-6}$ alkyl or $O(C_{1-6}$ alkyl);

p and q, independently at each occurrence, are 0, 1, or 2; and r is 0, 1, or 2.

6. A compound according to claim 5, or a stereoisomer or pharmaceutically-acceptable salt thereof, having the formula:

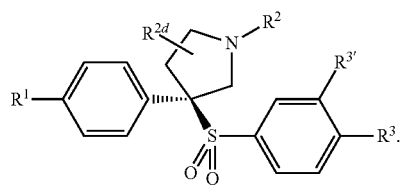

7. A compound according to claim 5, or a stereoisomer or pharmaceutically-acceptable salt thereof, wherein $R^1$ is

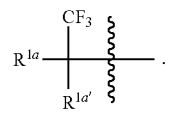

8. A compound according to claim 5, or a stereoisomer or pharmaceutically-acceptable salt thereof, wherein $R^1$ is

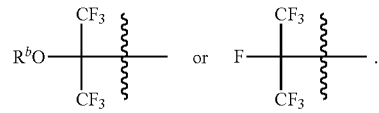

9. A compound according to claim 5, or a stereoisomer or pharmaceutically-acceptable salt thereof, wherein $R^1$ is

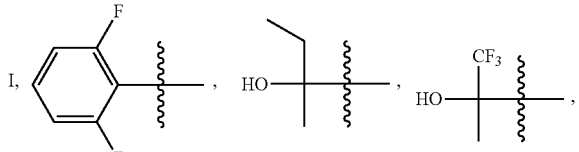

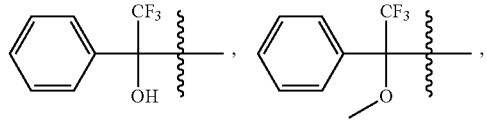

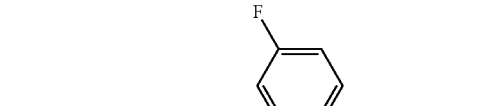

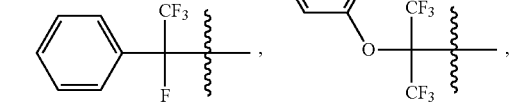

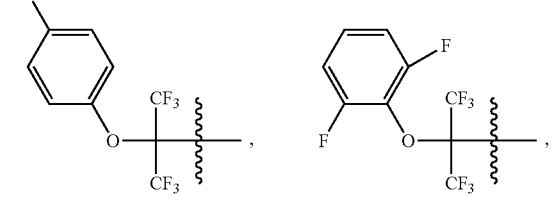

401
-continued
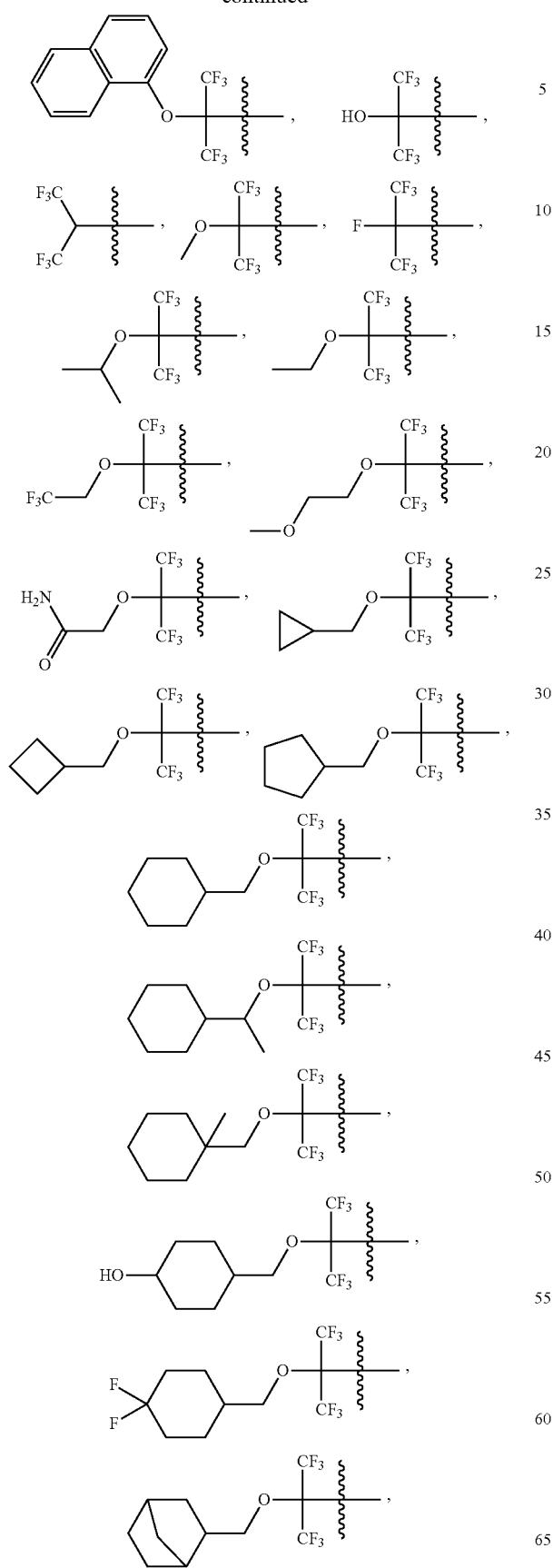
402
-continued
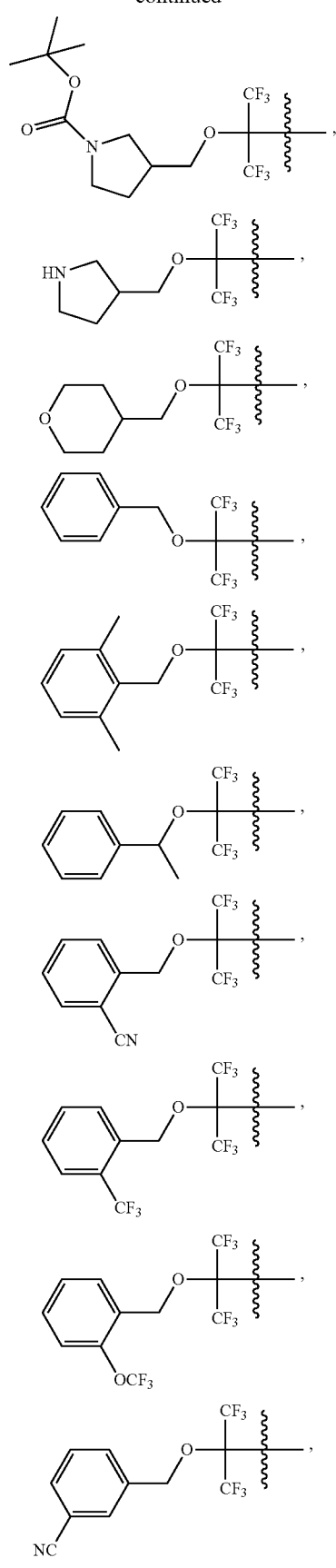

-continued
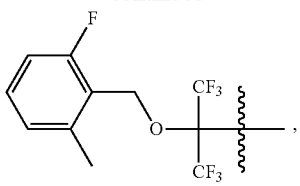
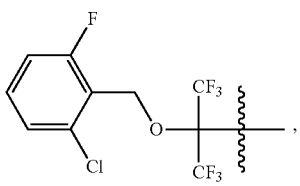
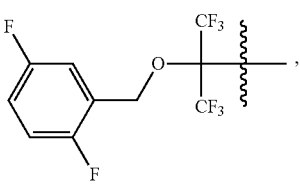
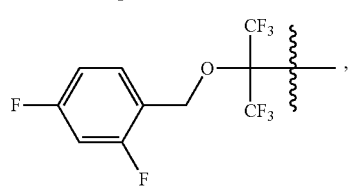
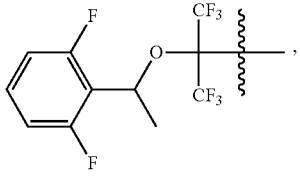
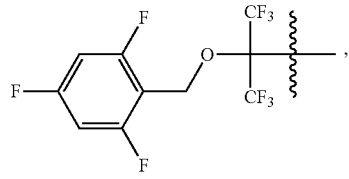
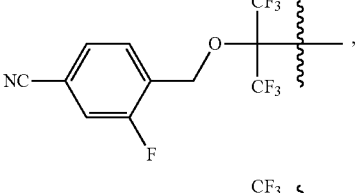
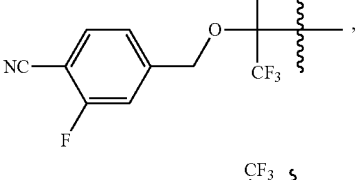
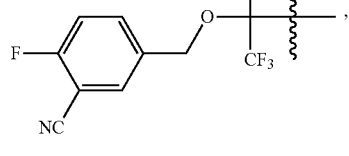
-continued
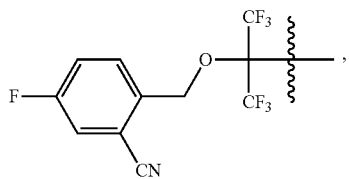
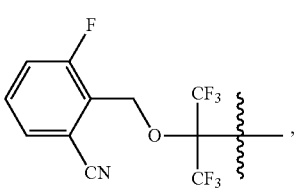
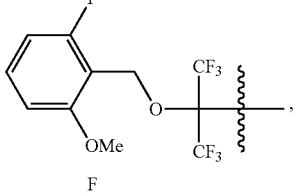
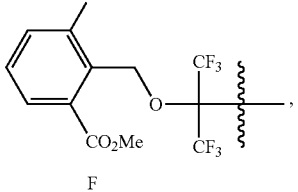
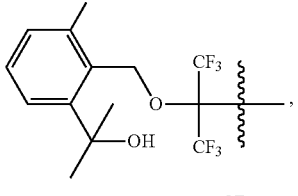
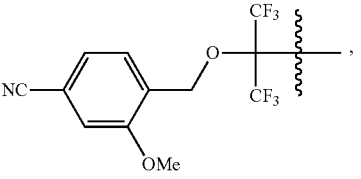
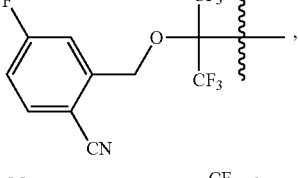
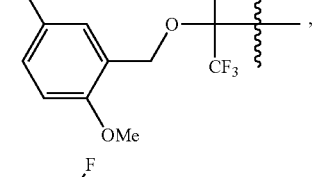
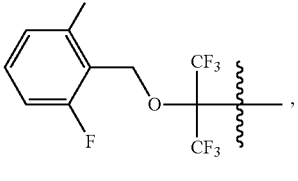

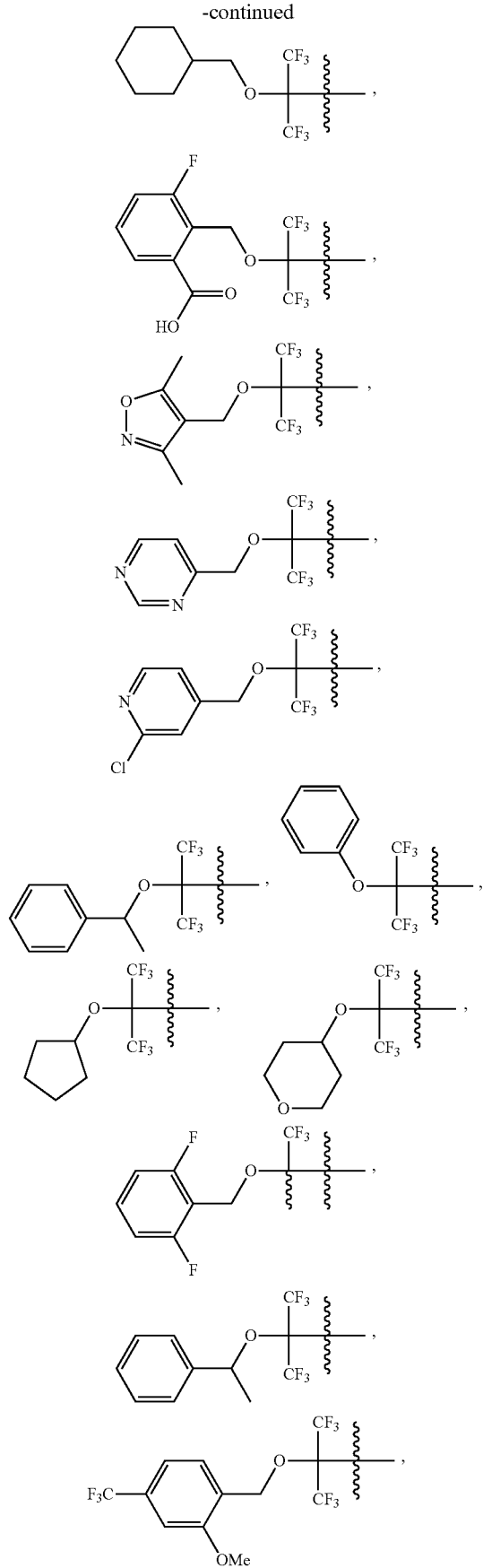
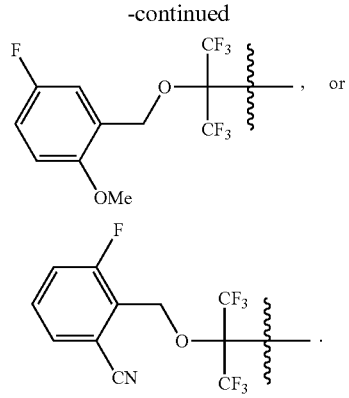
10. A compound of claim 5, or a stereoisomer or pharmaceutically-acceptable salt thereof, wherein $R^2$ is $CO_2R^{2b}$, —C(O)$R^{2d}$, or C(O)N$R^{11}R^{11}$.
11. A compound of claim 5, or a stereoisomer or pharmaceutically-acceptable salt thereof, wherein $R^2$ is:
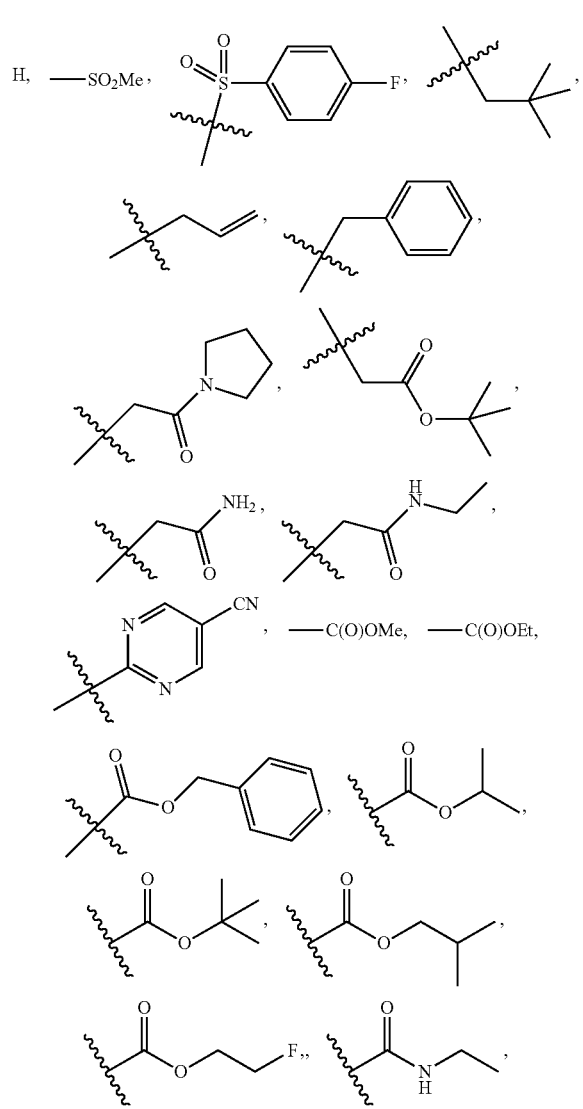

407
-continued
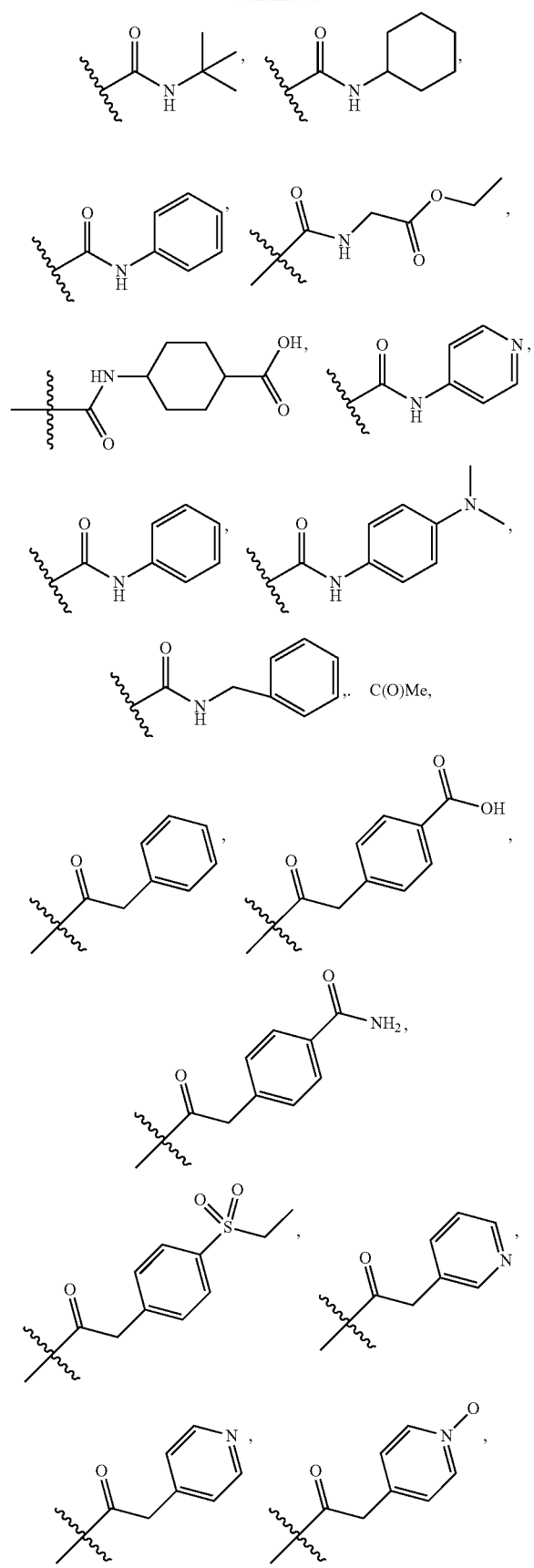
408
-continued
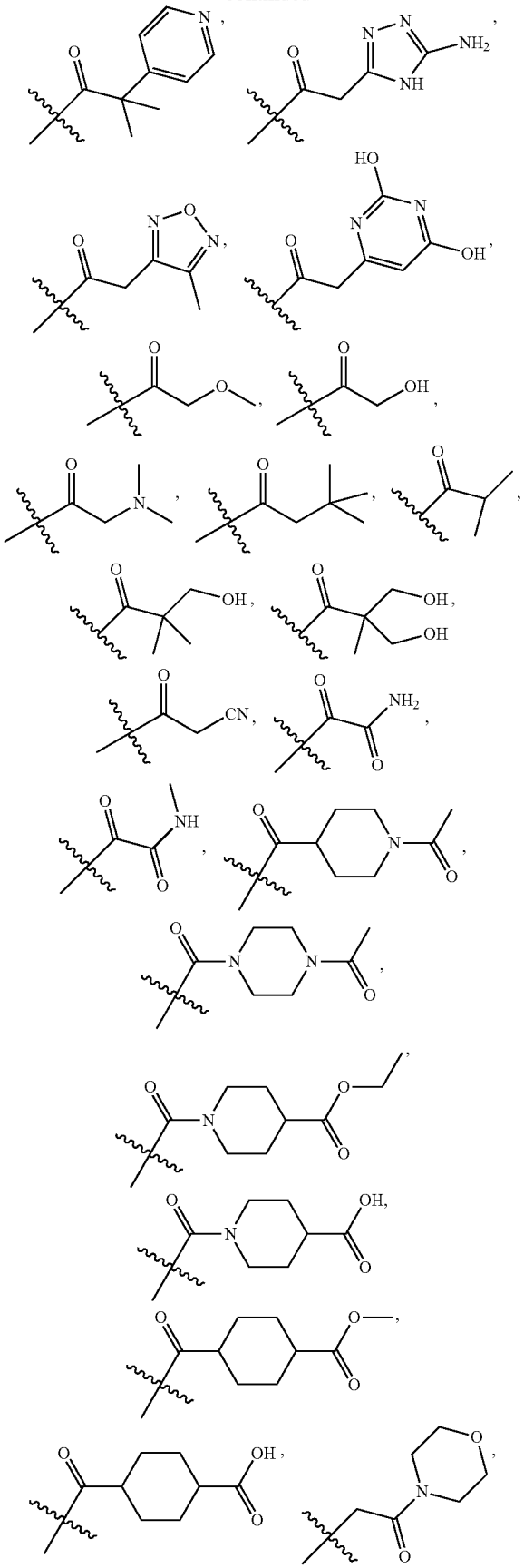

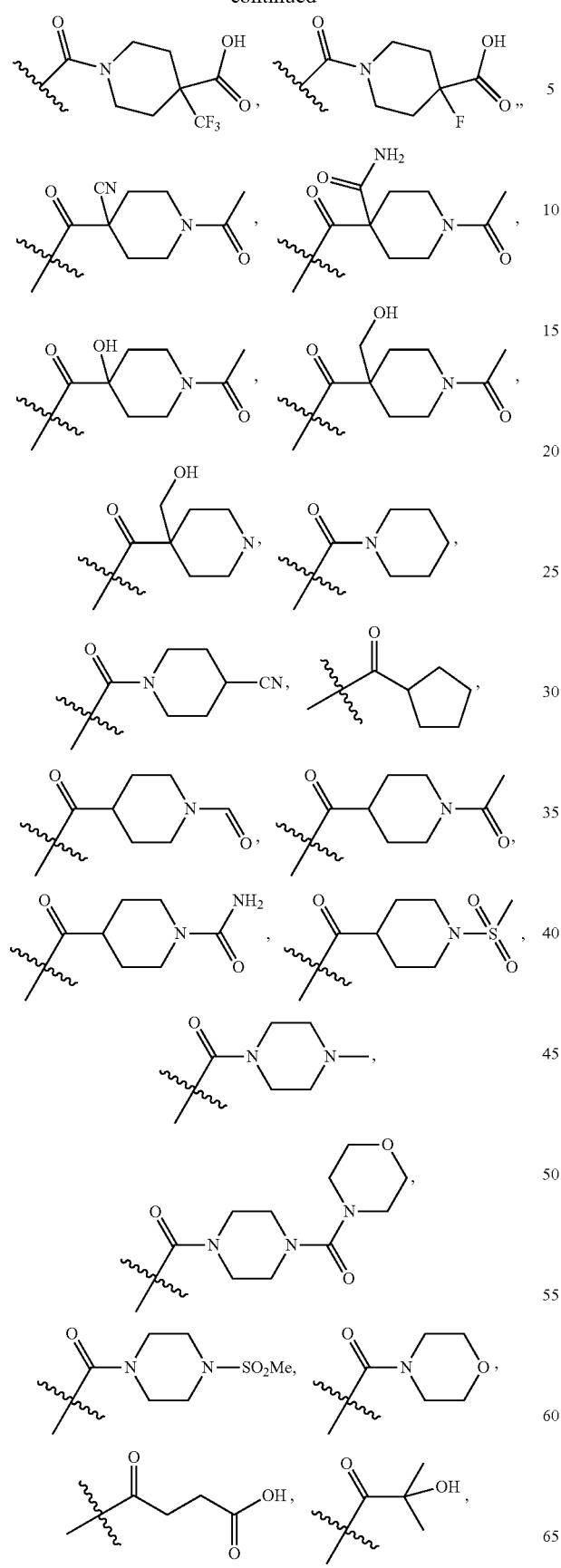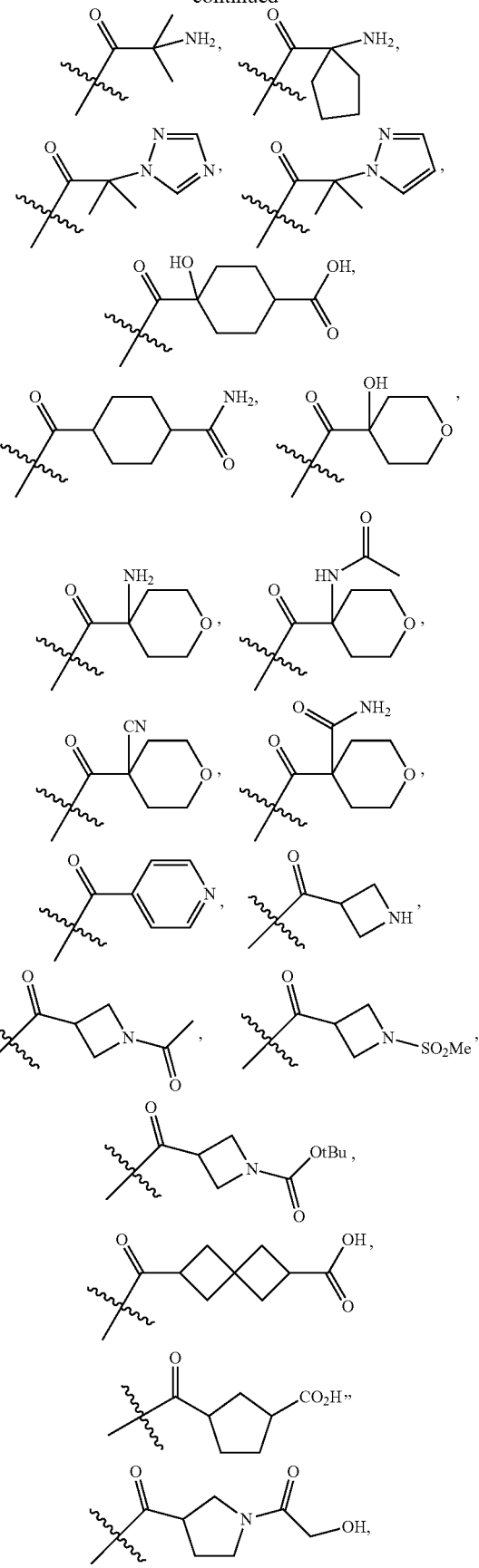

411
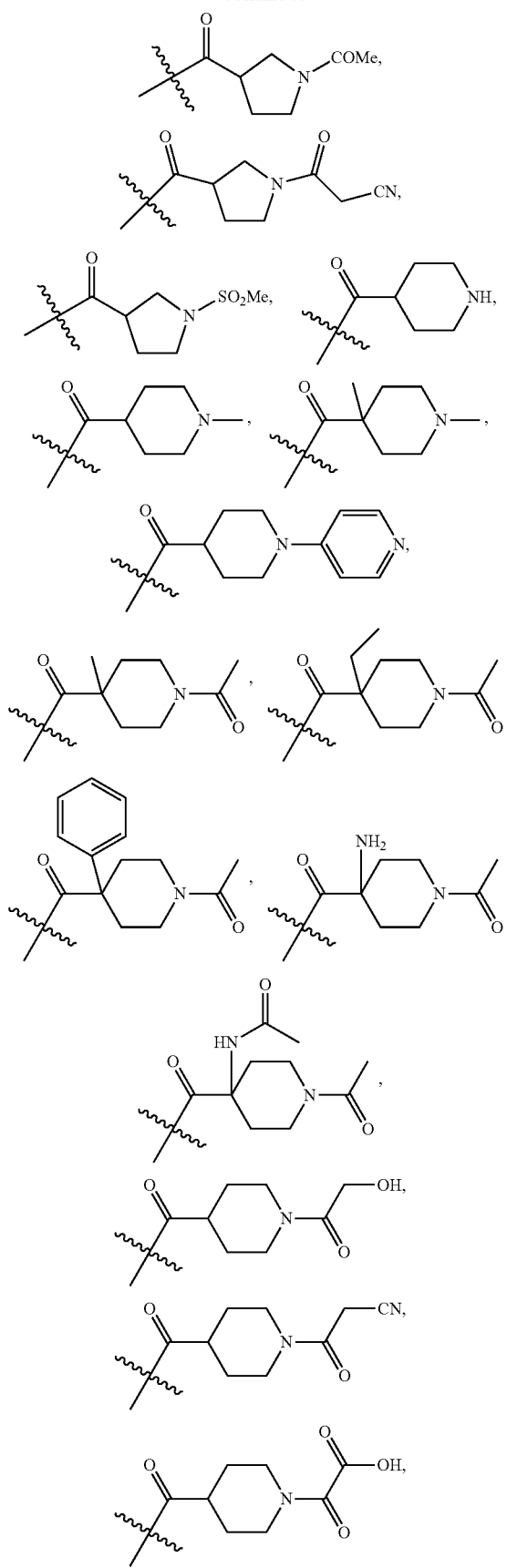
412
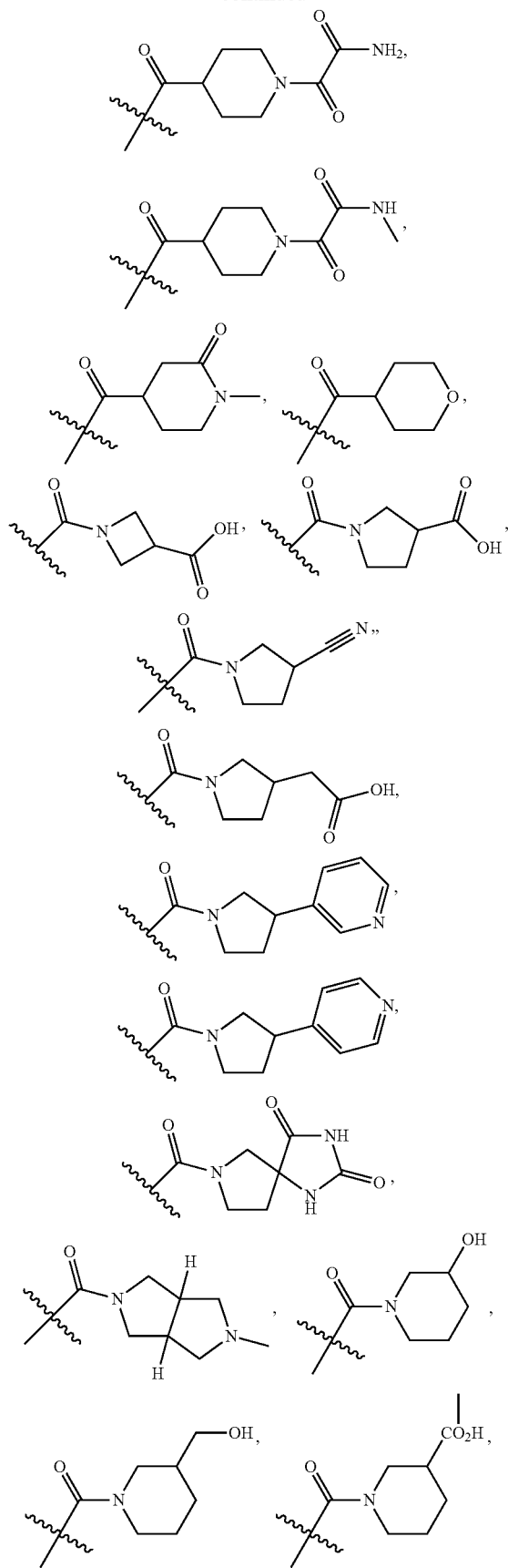

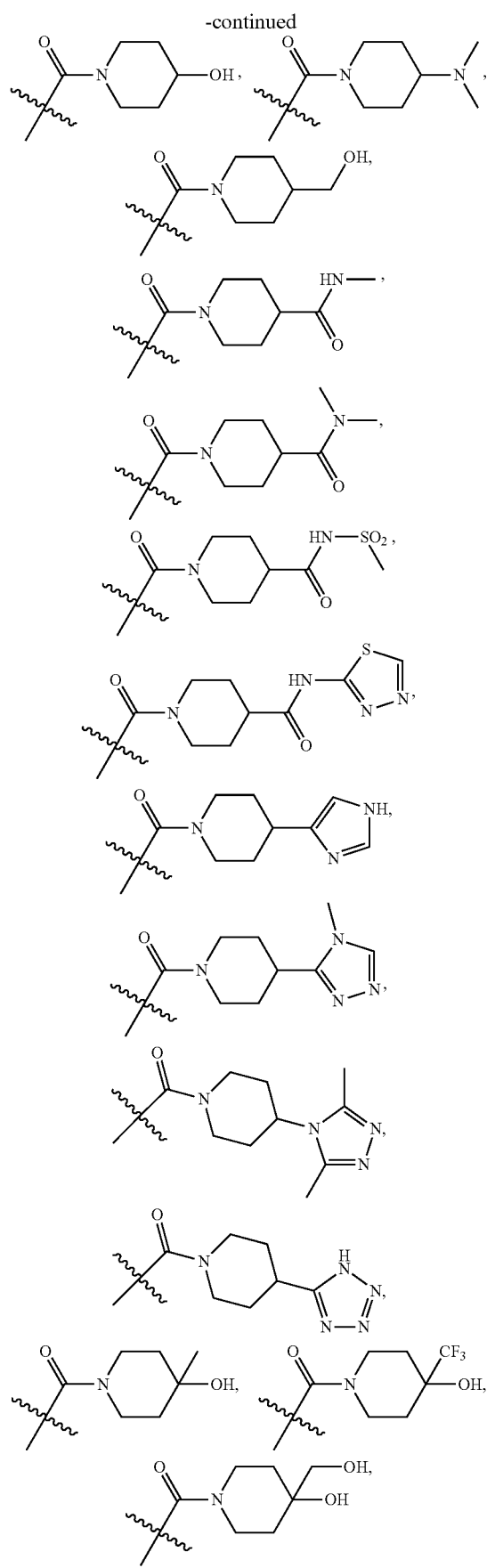
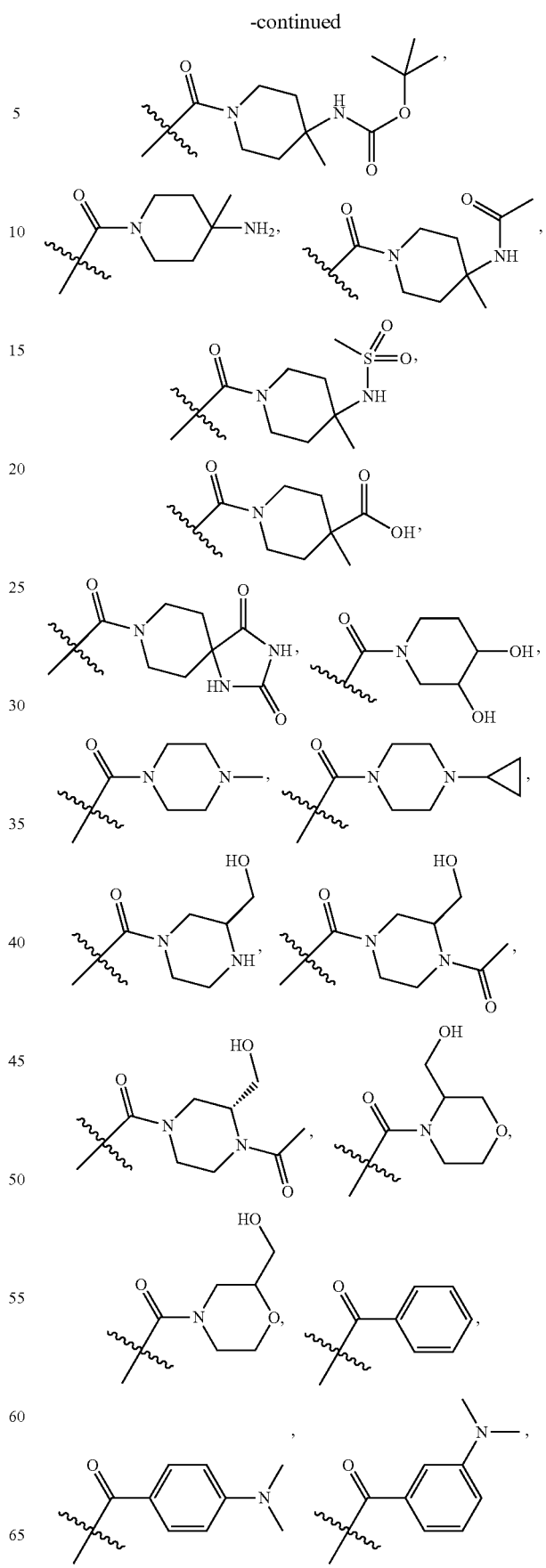

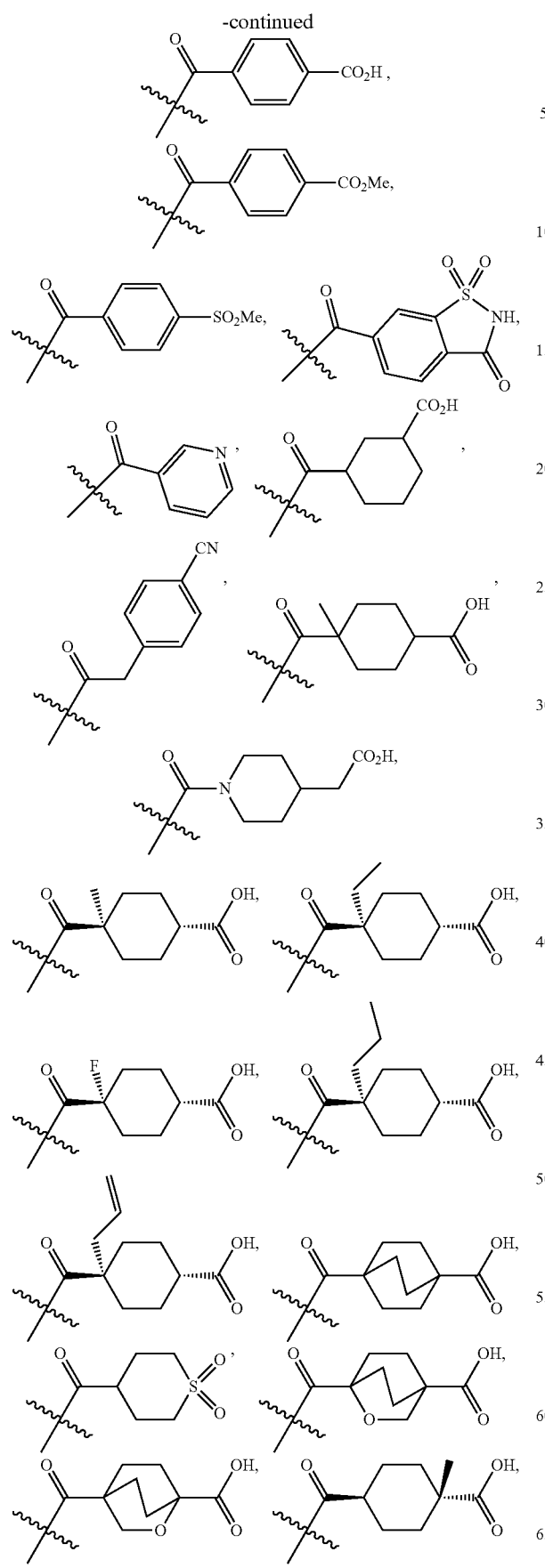
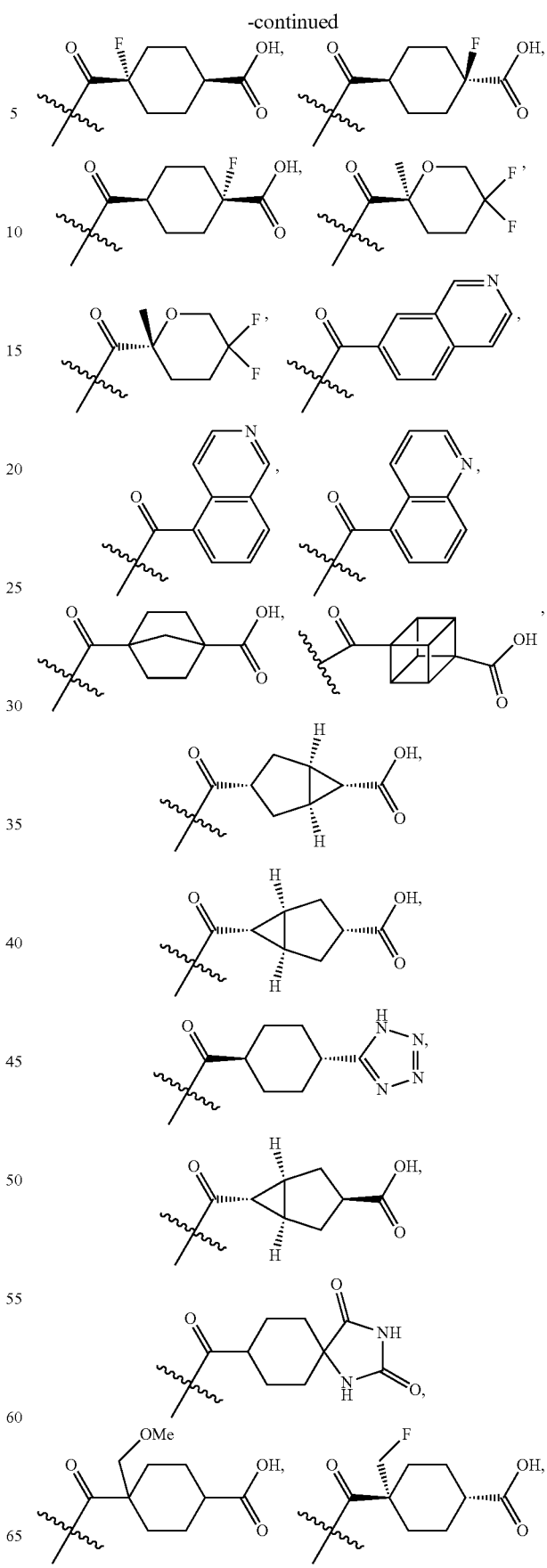

417
-continued
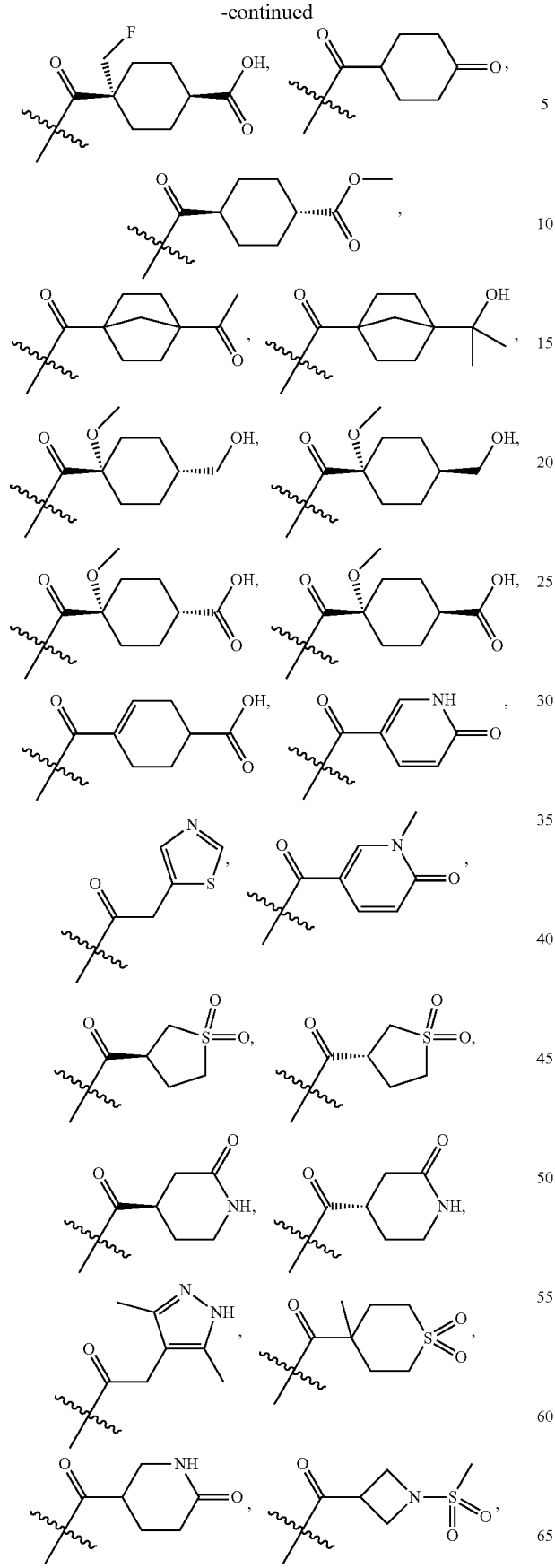
418
-continued
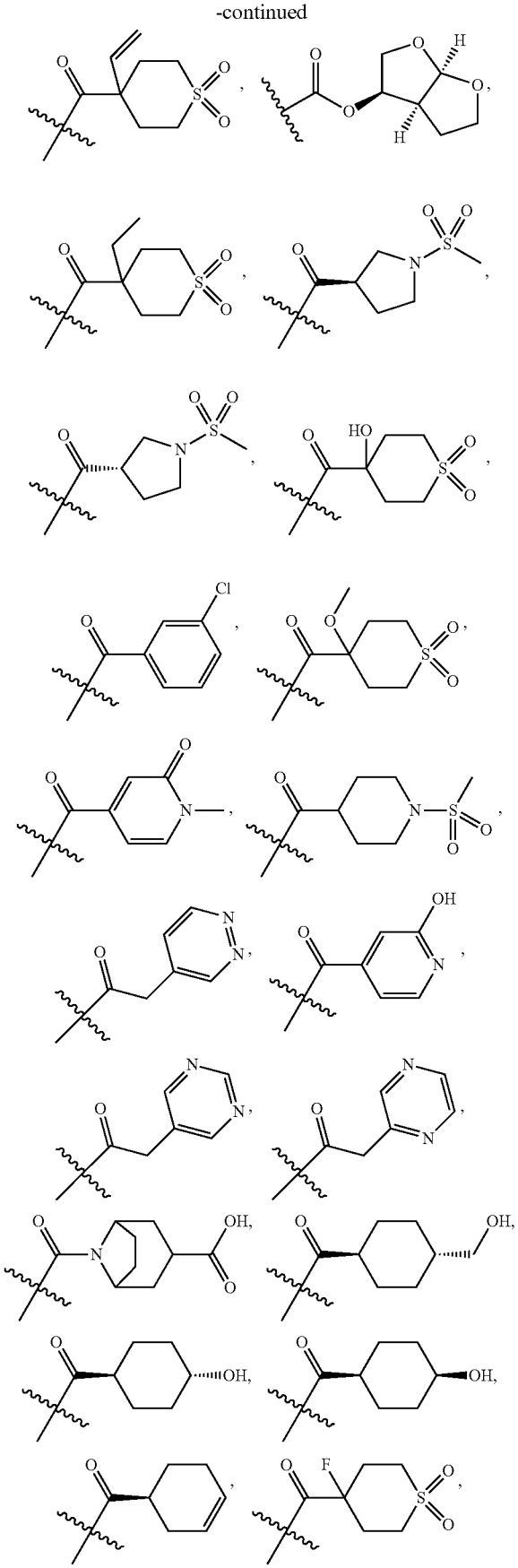

-continued

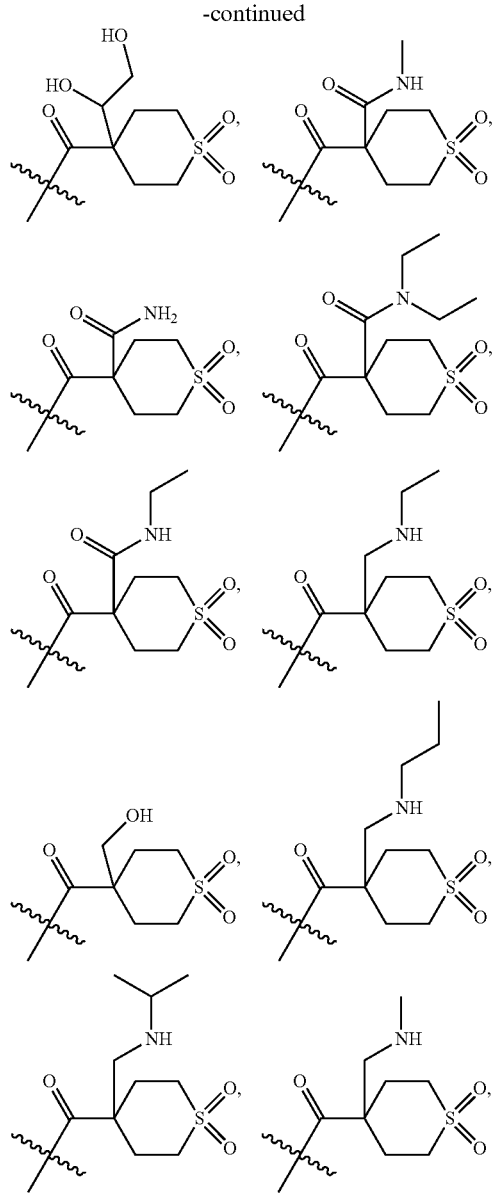

-continued

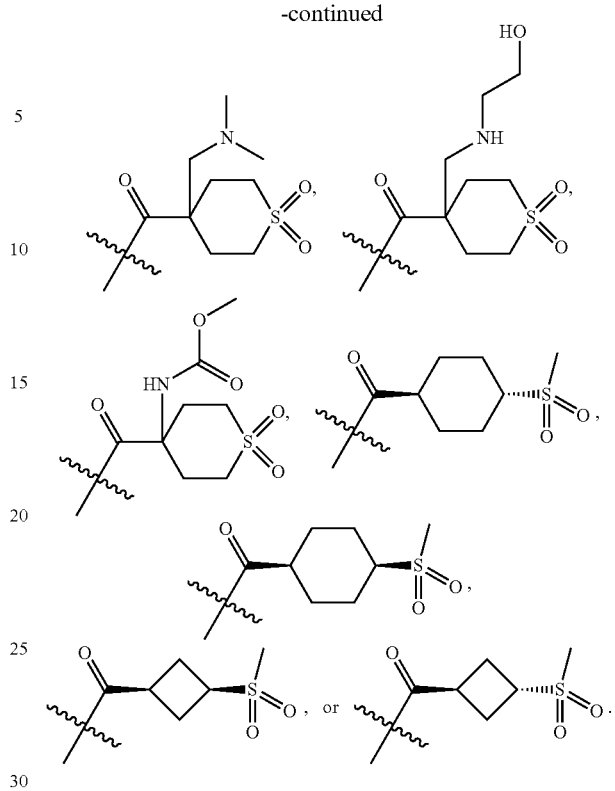

12. A compound of according to claim 5, or a stereoisomer or pharmaceutically-acceptable salt thereof, wherein $R^3$ and $R^{3'}$ are, independently, hydrogen, halo, $N_3$, CN, —O(phenyl), —$NH_2$, $NH(C_{1-6}$ alkyl), $N(C_{1-6}alkyl)_2$, $C_{1-6}$alkyl or $C_{3-6}$cycloalkyl.

13. A pharmaceutical composition comprising one or more compounds according to claim 1 and a pharmaceutically acceptable carrier or diluent.

14. A method of treating a disease or disorder selected from psoriasis, rheumatoid arthritis, inflammatory bowel disease, Crohn's disease, ulcerative colitis, acute graft-versus-host disease, psoriatic arthritis, ankylosing spondylitis and multiple sclerosis in a subject, the method comprising administering to the subject a therapeutically-effective amount of a compound according to claim 1.

* * * * *

UNITED STATES PATENT AND TRADEMARK OFFICE
CERTIFICATE OF CORRECTION

PATENT NO. : 9,458,171 B2
APPLICATION NO. : 14/590233
DATED : October 4, 2016
INVENTOR(S) : Jingwu Duan et al.

It is certified that error appears in the above-identified patent and that said Letters Patent is hereby corrected as shown below:

In the Claims

In Column 394, Line 39: In Claim 1, delete "having the following" and insert -- of --

In Column 394, Line 65-66: In Claim 1, delete "r-3-14membered" and insert -- r-3-14 membered --

In Column 395, Line 29: In Claim 1, delete "—$(CR^{2e}R^{2f})_qNR^bC(O)NR^{11}R^{11}$," and insert -- —$(CR^{2e}R^{2f})_qNR^bC(O)NR^{11}R^{11}$, --

In Column 395, Line 35: In Claim 1, delete "$S(O)_P$substituted" and insert -- $S(O)_P$ substituted --

In Column 395, Line 36: In Claim 1, delete "is" and insert -- is, --

In Column 395, Line 57: In Claim 1, delete "$R^{1a}$," and insert -- $R^{3a}$, --

In Column 396, Line 40: In Claim 1, delete "—$S(O)_{pNR}{}^{11}R^{11}$," and insert -- —$S(O)_PNR^{11}R^{11}$, --

In Column 396, Line 62: In Claim 1, delete "$CO_2R^C$," and insert -- $CO_2R^c$, --

In Column 398, Line 10: In Claim 5, after "according" insert -- to --

In Column 398, Line 10: In Claim 5, delete "having the following" and insert -- of the --

In Column 398, Line 49: In Claim 5, delete "is" and insert -- is, ---

In Column 398, Line 58: In Claim 5, delete "$R^{3a}$.;" and insert -- $R^{3a}$; --

Signed and Sealed this
Twenty-fifth Day of July, 2017

Joseph Matal
*Performing the Functions and Duties of the
Under Secretary of Commerce for Intellectual Property and
Director of the United States Patent and Trademark Office*

CERTIFICATE OF CORRECTION (continued)
U.S. Pat. No. 9,458,171 B2

In Column 399, Line 49: In Claim 5, delete "—NR$^e$SO$_2$R$^c$,SO$_2$R$^c$," and insert
-- —NR$^e$SO$_2$R$^c$, SO$_2$R$^c$, --

In Column 400, Line 5: In Claim 6, delete "having" and insert -- of --

In Column 406, Line 63-66:

In Claim 11, delete " 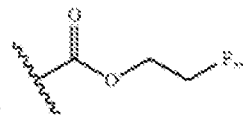 " and insert -- 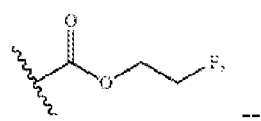 --

In Column 409, Line 1-7:

In Claim 11, delete "  " and insert --  --

In Column 409, Line 21-26:

In Claim 11, delete " 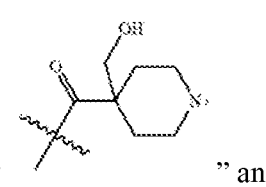 " and insert -- 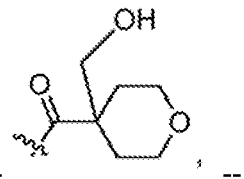 --

In Column 410, Line 57-61:

In Claim 11, delete " 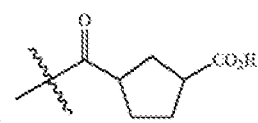 " and insert -- 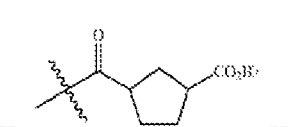 --

In Column 412, Line 26-31:

In Claim 11, delete " 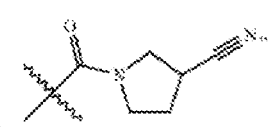 " and insert -- 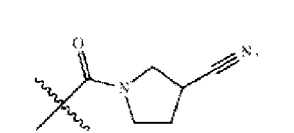 --